US008324216B2

(12) United States Patent
Pennell et al.

(10) Patent No.: US 8,324,216 B2
(45) Date of Patent: Dec. 4, 2012

(54) SUBSTITUTED PIPERAZINES

(75) Inventors: Andrew M. K. Pennell, San Francisco, CA (US); James B. Aggen, Burlingame, CA (US); J. J. Kim Wright, Redwood City, CA (US); Subhabrata Sen, Sunnyvale, CA (US); Brian E. McMaster, Mountain View, CA (US); Daniel Joseph Dairaghi, Palo Alto, CA (US); Wei Chen, Fremont, CA (US); Penglie Zhang, Foster City, CA (US)

(73) Assignee: Chemocentryx, Inc., Mountain View, CA (US)

( * ) Notice: Subject to any disclaimer, the term of this patent is extended or adjusted under 35 U.S.C. 154(b) by 59 days.

(21) Appl. No.: 12/555,650

(22) Filed: Sep. 8, 2009

(65) Prior Publication Data

US 2010/0240618 A1 Sep. 23, 2010

Related U.S. Application Data

(60) Division of application No. 11/008,774, filed on Dec. 8, 2004, now Pat. No. 7,589,199, which is a continuation-in-part of application No. 10/979,882, filed on Nov. 1, 2004, now abandoned, which is a continuation-in-part of application No. 10/732,897, filed on Dec. 9, 2003, now Pat. No. 7,842,693, which is a continuation-in-part of application No. 10/460,752, filed on Jun. 11, 2003, now Pat. No. 7,157,464.

(60) Provisional application No. 60/453,711, filed on Jun. 12, 2002.

(51) Int. Cl.
*A61K 31/496* (2006.01)
*C07D 233/61* (2006.01)
*C07D 249/14* (2006.01)
*C07D 257/04* (2006.01)

(52) U.S. Cl. .................. 514/254.05; 544/366; 544/370
(58) Field of Classification Search .................. None
See application file for complete search history.

(56) References Cited

U.S. PATENT DOCUMENTS

| | | | |
|---|---|---|---|
| 3,362,956 A | 1/1968 | Archer |
| 3,478,032 A | 11/1969 | Arya |
| 3,491,098 A | 1/1970 | Archer |
| 3,723,433 A | 3/1973 | Ueno et al. |
| 3,950,354 A | 4/1976 | Wenzelburger et al. |
| 3,994,890 A | 11/1976 | Fujimura et al. |
| 4,166,452 A | 9/1979 | Generales, Jr. |
| 4,174,393 A | 11/1979 | Van Daalen et al. |
| 4,256,108 A | 3/1981 | Theeuwes |
| 4,265,874 A | 5/1981 | Bonsen et al. |
| 4,310,429 A | 1/1982 | Lai |
| 4,442,102 A | 4/1984 | Heinemann et al. |
| 4,547,505 A | 10/1985 | Oepen et al. |
| 4,559,341 A | 12/1985 | Petersen et al. |
| 4,562,189 A | 12/1985 | Tomcufcik et al. |
| 4,672,063 A | 6/1987 | Jasserand et al. |
| 4,772,604 A | 9/1988 | Van Wijngaarden et al. |
| 4,880,809 A | 11/1989 | Sugihara et al. |
| 4,997,836 A | 3/1991 | Sugihara et al. |
| 5,011,928 A | 4/1991 | Venero et al. |
| 5,177,078 A | 1/1993 | Ward et al. |
| 5,215,989 A | 6/1993 | Baldwin et al. |
| 5,227,486 A | 7/1993 | Merce-Vidal et al. |
| 5,292,739 A | 3/1994 | Merce-Vidal et al. |
| 5,346,896 A | 9/1994 | Ward et al. |
| 5,382,586 A | 1/1995 | Merce-Vidal et al. |
| 5,464,788 A | 11/1995 | Bock et al. |
| 5,580,985 A | 12/1996 | Lee et al. |
| 5,607,936 A | 3/1997 | Chiang et al. |
| 5,646,151 A | 7/1997 | Kruse et al. |
| 5,681,954 A | 10/1997 | Yamamoto et al. |
| 5,719,156 A | 2/1998 | Shue et al. |
| 5,756,504 A | 5/1998 | Bock et al. |
| 5,760,028 A | 6/1998 | Jadhav et al. |
| 5,760,225 A | 6/1998 | Yuan |
| 5,780,475 A | 7/1998 | Baker et al. |
| 5,798,359 A | 8/1998 | Shue et al. |
| 5,968,938 A | 10/1999 | Williams et al. |
| 6,043,246 A | 3/2000 | Fukami et al. |
| 6,114,334 A | 9/2000 | Kerrigan et al. |
| 6,191,159 B1 | 2/2001 | Pinto |
| 6,207,665 B1 | 3/2001 | Bauman et al. |
| 6,288,083 B1 | 9/2001 | Luly et al. |
| 6,329,385 B1 | 12/2001 | Luly et al. |
| 6,384,035 B1 | 5/2002 | Hutchings et al. |
| 6,451,339 B2 | 9/2002 | Patel et al. |

(Continued)

FOREIGN PATENT DOCUMENTS

EP 0 255 217 A1 2/1988

(Continued)

OTHER PUBLICATIONS

CA Registry No. 663922-70-1, entered into the Registry File on Mar. 17, 2004.*
CA Registry No. 500867-39-0, entered into the Registry File on Mar. 28, 2003.*
CA Registry No. 313987-10-9, entered into the Registry File on Jan. 15, 2001.*
Anders, et al., A chemokine receptor CCR-1 antagonist reduces renal fibrosis after unilateral ureter ligation. J Clin Invest. (2002) 109(2):251-9.
Badran, M. et al., "Indazole derivatives (part III): synthesis of pyrazolo-[1,2-a]indazole-1,9-dione,[1,2,4]triazino[1,2-a]indazole-1,10-dione, 3-(Indazol-1-yl)propionic acid amides and hydrazides possessing potential biological activity" *Alex. J. Pharm. Sci.* (1999) 13(2):101-106.

(Continued)

Primary Examiner — Emily Bernhardt
(74) Attorney, Agent, or Firm — Kilpatrick Townsend & Stockton LLP

(57) ABSTRACT

Compounds are provided that act as potent antagonists of the CCR1 receptor, and have in vivo anti-inflammatory activity. The compounds are generally aryl piperazine derivatives and are useful in pharmaceutical compositions, methods for the treatment of CCR1-mediated diseases, and as controls in assays for the identification of competitive CCR1 antagonists.

8 Claims, 57 Drawing Sheets

U.S. PATENT DOCUMENTS

| | | | |
|---|---|---|---|
| 6,455,544 | B1 | 9/2002 | Friedhoff et al. |
| 6,469,041 | B2 | 10/2002 | Yuan |
| 6,492,375 | B2 | 12/2002 | Snutch |
| 6,518,273 | B1 | 2/2003 | Chapman et al. |
| 7,449,576 | B1 | 11/2008 | Pennell et al. |
| 7,589,199 | B2 | 9/2009 | Pennell et al. |
| 2002/0022624 | A1 | 2/2002 | Dinnell et al. |
| 2002/0040020 | A1 | 4/2002 | Breitenbucher et al. |
| 2002/0045613 | A1 | 4/2002 | Pauls et al. |
| 2002/0045749 | A1 | 4/2002 | Li |
| 2002/0049205 | A1 | 4/2002 | Li et al. |
| 2002/0077321 | A1 | 6/2002 | Khanna et al. |
| 2002/0107255 | A1 | 8/2002 | Bllumberg et al. |
| 2002/0119961 | A1 | 8/2002 | Blumberg et al. |
| 2003/0087917 | A1 | 5/2003 | Strack et al. |
| 2003/0139425 | A1 | 7/2003 | Bauman et al. |
| 2003/0149021 | A1 | 8/2003 | Li et al. |
| 2004/0162282 | A1 | 8/2004 | Pennell et al. |
| 2005/0256130 | A1 | 11/2005 | Pennell et al. |

FOREIGN PATENT DOCUMENTS

| | | | |
|---|---|---|---|
| EP | 0 479 546 A2 | 4/1992 | |
| EP | 1 006 110 A1 | 6/2000 | |
| JP | 58052256 | * | 3/1983 |
| JP | 04-257570 A | 9/1992 | |
| WO | WO 97/10219 A1 | 3/1997 | |
| WO | WO 97/44329 A1 | 11/1997 | |
| WO | WO 98/25617 A1 | 6/1998 | |
| WO | WO 98/39000 A1 | 9/1998 | |
| WO | WO 98/56771 A2 | 12/1998 | |
| WO | WO 99/07351 A2 | 2/1999 | |
| WO | WO 99/09984 A1 | 3/1999 | |
| WO | WO 99/25686 A1 | 5/1999 | |
| WO | WO 99/32468 A1 | 7/1999 | |
| WO | WO 99/37619 A1 | 7/1999 | |
| WO | WO 99/37651 A1 | 7/1999 | |
| WO | WO 00/31032 A1 | 6/2000 | |
| WO | WO 00/46195 A1 | 8/2000 | |
| WO | WO 00/46196 A1 | 8/2000 | |
| WO | WO 00/46197 A1 | 8/2000 | |
| WO | WO 00/46198 A1 | 8/2000 | |
| WO | WO 00/46199 A1 | 8/2000 | |
| WO | WO 00/47539 A1 | 8/2000 | |
| WO | WO 00/53600 A1 | 9/2000 | |
| WO | WO 00/69815 A1 | 11/2000 | |
| WO | WO 00/69820 A1 | 11/2000 | |
| WO | WO 00/69848 A1 | 11/2000 | |
| WO | WO 02/08221 A3 | 1/2002 | |
| WO | WO 02/14314 A2 | 2/2002 | |
| WO | WO 02/070523 A1 | 9/2002 | |
| WO | WO 03/008395 A1 | 1/2003 | |
| WO | WO 03/024450 A1 | 3/2003 | |
| WO | WO 03/051842 A2 | 6/2003 | |
| WO | WO 03/0581841 A2 | 6/2003 | |
| WO | WO 03/0581841 A3 | 6/2003 | |
| WO | WO 03/105853 A1 | 12/2003 | |
| WO | WO 2004/009550 A1 | 1/2004 | |
| WO | WO 2004/013130 A1 | 2/2004 | |
| WO | WO 2004/035556 A1 | 4/2004 | |

OTHER PUBLICATIONS

Bebernitz, G. et al., "The effect of 1,3-diaryl-[1H]-pyrazole-4-acetamides on glucose utilization in on/ob mice" *J. Med. Chem.* (2001) 44:2601-2611.

Bendele, et al., Animal models of arthritis: relevance to human disease, Toxicologic Pathol. (1999) 27:134-142.

Berge, S.M., et al., Pharmaceutical Salts, Journal of Pharmaceutical Sciences (1977) 66:1-19.

Chemcats Database, Chemical Abstracting Service, Accession No. 2003:2855298, Jan. 1, 2004 for CAS Registry No. 492422-98-7.

Chemcats Database, Chemical Abstracting Service, Accession No. 2001:2759474, Oct. 20, 2003 for CAS Registry No. 351986-92-0.

Czarnocka-Janowicz, A. et al., "Synthesis and pharmacological activity of 5-substituted-s-triazole-3-thiols" *Pharmazie* (1991) 46:109-112.

Database Crossfire Beilstein 'Online! Beilstein Institut zur Forderung der Chemischen Wissenschaften, Frankfurt am Main, DE; Database accession No. BRN 6982047 XP002254060 abstract & Varasi et al., *Farmaco Ed. Sci.* (1987) 42(6):425-436.

Database Crossfire Beilstein 'Online! Beilstein Institut zur Forderung der Chemischen Wissenschaften, Frankfurt am Main, DE; Database accession No. BRN 1159762 XP002254062 abstract & Zotta et al. *FARMACIA* (1977) 25:129-134.

Database Crossfire Beilstein 'Online! Beilstein Institut zur Forderung der Chemischen Wissenschaften, Frankfurt am Main, DE; Database accession No. BRN 6000843 XP002254061 abstract & Toja et al., *Heterocycles* (1987) 26(8):2129-2138.

Database Crossfire Beilstein 'Online! Beilstein Institut zur Forderung der Chemischen Wissenschaften, Frankfurt am Main, DE; Database accession No. BRN 9229443 XP002254063 abstract & Vovk, et al., *Russ. J. Org. Chem.* (2001) 37(12).

Devries, M. et al., "On the edge: the physiological and pathophysiological role of chemokines during inflammatory and immunological responses" *Sem. Immun.* (1999) 11:95-104.

Fischer, F. et al., "Modulation of experimental autoimmune encephalomyelitis: effect of altered peptide ligand on chemokine and chemokine receptor expression" *J. Neuroimmun.* (2000) 110:195208.

Foks, H. et al., "Synthesis of new 5-substituted 1,2,4-triazole-3-thione derivatives" *Phosphorus, Sulfur and Silicon* (2000) 164:67-81.

Gao, et al., Targeting of the chemokine receptor CCR1 suppresses development of acute and chronic cardiac allograft rejection, J Clin Invest. (2000) 105(1):35-44.

Hayao, S. et al., "New antihypertensive aminoalkyltetrazoles" *J. Med. Chem.* (1967) 10:400-402.

Hcaplus; Accession No. 1984:630511, Document No. 101:230511; Japanese Patent No. 59130890, issued Jul. 27, 1984; Abstract, 4 pages.

Hesselgesser, J. et al., "Identification and characterization of small molecule functional antagonists of the CCR1 chemokine receptor" *J. Biol. Chem.* (1998) 2373(25):15687-156952.

Izikson, L. et al., "Resistance to experimental autoimmune encephalomyelitis in mice lacking the CC chemokine receptor $(CCR)^2$" *J. Exp. Med.* (2000) 192(7):1075-1080.

Kennedy, K. et al., "Role of chemokines in the regulation of Th1/Th2 and autoimmune encephalomyelitis" *J. Clin. Immunol.* (1999) 19(5):273-279.

Liang, M. et al., "Species selectivity of a small molecule antagonist for the CCR1 chemokine receptor" *Eur. J. Pharmacol.* (2000) 389:41-49.

Liang, M. et al., "Identification and characterization of a potent, selective, and orally active antagonist of the CC chemokine receptor" *J. Biol. Chem.* (2000) 275(25):19000-19008.

Monteclaro, et al., The amino-terminal domain of CCR2 is both necessary and sufficient for high affinity binding of monocyte chemoattractant protein 1. Receptor activation by a pseudo-tethered ligand, J Biol Chem. (1997) 272(37):23186-90.

Ng, H. et al., "Discovery of novel non-peptide CCR1 receptor antagonists" *J. Med. Chem.* (1999) 42:4680-4694.

Nicolai, E. et al., "Synthesis and angiotensin II receptor antagonist activity of C-linkedpyrazole derivatives" *Chem. Pharm. Bull.* (1994) 42(8):1617-1630.

Patent Abstracts of Japan, vol. 007, No. 139 (C-171), Jun. 17, 1983 & JP 58 052256 A (Nippon Noyaku KK), Mar. 28, 1983 abstract.

Plater-Zyberk, C. et al., "Effect of a CC chemokine receptor antagonist on collagen induced arthritis in DBA/1 mice" *Ummun. Lett.* (1997) 57:117-120.

Podolin, et al., A potent and selective nonpeptide antagonist of CXCR2 inhibits acute and chronic models of arthritis in the rabbit, J. Immunol. (2002) 169(11):6435-6444.

Rossi, D., et al., The biology of chemokines and their receptors, Annu Rev Immunol. (2000) 18:217- 42.

Rottman, J. et al., "Leukocyte recruitment during onset of experimental allergic encephalomyelitis is CCR1 dependent" *Eur. J. Immunol.* (2000) 30:2372-2377.

Saeki, T., et al., CCR1 chemokine receptor antagonist, Curr Pharm Des. (2003) 9:1201-1208.

SciFinder Report; Piperazine, 1-[(4-nitro-1H-imidazol-1-y1)acetyl]-4-phenyl-(9C1); Registry No. 312707-74-7; Catalogs: STN Chemcats, Exploratory Library, Interchim Intermediates, AsinEx Express Gold Collection, and Pharma Library Collection; report dated Sep. 30, 2003; 7 pages.

SciFinder Report; Piperazine, 1-[(3,5-dimethyl-4-nitro-1H-pyrazol-1-yl)acetyl]-4-(4-fluorophenyl)-(9Cl); Registry No. 356039-23-1; Catalogs: STN Chemcats, Exploratory Library, ChemDiv, Inc. Product Library; report dated Sep. 30, 2003; 4 pages.

SciFinder Report; Piperazine, 1-[2-(3,5-dimethyl-4-nitro-1H-pyrazol-1-yl)-1-oxopropyl]-4-phenyl-; Registry No. 489449-56-1; Catalogs: Compounds for Screening, Interchim Intermediates; report dated Sep. 30, 2003; 3 pages.

SciFinder Report; Piperazine, 1-[(2,4-dinitro-1H-Imidazol-1-yl)acetyl]-4-(4-fluorophenyl)-; Registry No. 313987-12-1; Catalogs: Exploratory Library, Interchim Intermediates, ChemDiv, Inc. Product.Library, AsinEx Express Gold Collection, Pharma Library Collection; report dated Sep. 30, 2003; 7 pages.

SciFinder Report; Piperazine,1-[(2,4-dinitro-1H-imidazol-1-yl)acetyl]4-phenyl-; Registry no. 313987-13-2; Catalogs: Exploratory Library, Interchim Intermediates, Compounds for Screening, ChemDic, Inc. Product Library, AsinEx Express Gold Collection, Pharma Library Collection; report dated Sep. 30, 2003; 7 pages.

Trentham, et al., Autoimmunity to type II collagen an experimental model of arthritis, J. Exp Med. (1977) 146(3):857-868.

Tokuda, et al., Pivotal role of CCR1-positive leukocytes in bleomycin-induced lung fibrosis in mice, J Immunol. (2000) 164(5):2745-51.

Walsh, D. et al., "Synthesis and antiallergy activity of N-[2-(dimethylamino)ethyl]-4-aryl-1-piperazinecarboxamide derivatives" *J. Med. Chem.* (1990) 33:2028-2032.

Abouzid, K. et al., "Synthesis and Antihypertensive Activity of Novel Benzimidazole, Benzoxazole and Benzothiazole Derivatives," *Bull. Fac. Pharm. Cairo Univ.*, 2001, vol. 40, No. 1, pp. 7-13.

Supplementary Partial European Search Report mailed on Jun. 3, 2009, for EP Application No. 04813774.9, 5 pages.

* cited by examiner

SUBSTITUTED PIPERAZINES

CROSS-REFERENCES TO RELATED APPLICATIONS

This application is a divisional of U.S. Ser. No. 11/008,774 filed Dec. 8, 2004 now U.S. Pat. No. 7,589,199, which is a continuation in part of U.S. Ser. No. 10/979,882, filed Nov. 1, 2004 now abandoned, which is a continuation in part of U.S. Ser. No. 10/732,897, filed Dec. 9, 2003 now U.S. Pat. No. 7,842,693, which is a continuation in part of U.S. Ser. No. 10/460,752, filed Jun. 11, 2003 now U.S. Pat. No. 7,157,464, which claims the benefit of Provisional Application Ser. No. 60/453,711, filed Jun. 12, 2002, (originally U.S. Ser. No. 10/171,398, filed Jun. 12, 2002) the contents of each being incorporated herein by reference.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., Semin Immunol 11(2):95-104 (1999)). A hallmark of some demyelinating diseases such as multiple sclerosis is the chemokine-mediated monocyte/macrophage and T cell recruitment to the central nervous system (see, Kennedy, et al., J. Clin. Immunol. 19(5):273-279 (1999)). Chemokine recruitment of destructive WBCs to transplants has been implicated in their subsequent rejection. See, DeVries, M. E., et al., ibid. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 k.D), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., Ann. Rev. Immunol. 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., Current Pharmaceutical Design 9:1201-1208 (2003)) since they have been implicated in rheumkoid arthritis, transplant rejection (see, DeVries, M. E., et al., ibid.), and multiple sclerosis (see, Fischer, et al., J Neuroimmunol. 110 (1-2):195-208 (2000); Izikson, et al., J. Exp. Med. 192(7): 1075-1080 (2000); and Rottman, et al., Eur. J. Immunol. 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., ibid.). Notably, in an experimental model of rheumatoid arthritis, disease development is diminished when a signaling-blocking, modified-RANTES ligand is administered (see Plater-Zyberk, et al., Immunol Lett. 57(1-3):117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., J. Biol. Chem. 273(25):15687-15692 (1998); Ng, et al., J. Med. Chem. 42(22):4680-4694 (1999); Liang, et al., J. Biol. Chem. 275(25):19000-19008 (2000); and Liang, et al., Eur. J. Pharmacol. 389(1):41-49 (2000)). In view of the effectiveness demonstrated for treatment of disease in animal models (see, Liang, et al., J. Biol. Chem. 275(25):19000-19008 (2000)), the search has continued to identify additional compounds that can be used in the treatment of diseases mediated by CCR1 signaling.

BRIEF SUMMARY OF THE INVENTION

The present invention provides compounds having the formula:

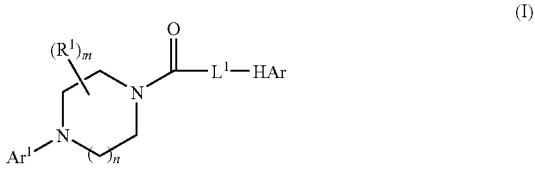

(I)

or a pharmaceutically acceptable salt or N-oxide thereof. In the formula above, the subscript n represents an integer of from 1 to 2, preferably 1. The subscript m represents an integer of from 0 to 10, limited by the number of available substituents positions on the piperazine or homopiperazine ring to which it is attached. For example, piperazine derivatives (n is 1) can have from 0 to 8 $R^1$ groups, preferably 0 to 4 $R^1$ groups, and more preferably 0, 1 or 2 $R^1$ groups. Each $R^1$ is a substituent independently selected from $C_{1-8}$ alkyl, $C_{1-8}$haloalkyl, $C_{3-6}$ cycloalkyl, $C_{2-8}$ alkenyl and $C_{2-8}$ alkynyl, —$COR^a$, —$CO_2R^a$, —$CONR^aR^b$, —$NR^aCOR^b$, —$SO_2R^a$, —$X^1COR^a$, —$X^1CO_2R^a$, —$X^1CONR^aR^b$, —$X^1NR^aCOR^b$, —$X^1SO_2R^a$, —$X^1SO_2NR^aR^b$, —$X^1NR^aR^b$, —$X^1OR^a$, wherein $X^1$ is a member selected from the group consisting of $C_{1-4}$ alkylene, $C_{2-4}$ alkenylene and $C_{2-4}$ alkynylene and each $R^a$ and $R^b$ is independently selected from the group consisting of hydrogen, $C_{1-8}$alkyl, $C_{1-8}$haloalkyl, $C_{3-6}$ cycloalkyl and aryl-$C_{1-4}$ alkyl, or optionally $R^a$ and $R^b$ when attached to the same nitrogen atom can be combined with the nitrogen atom to form a five or six-membered ring having from 0 to 2 additional heteroatoms as ring members, and wherein the aliphatic portions of each of the $R^1$ substituents is optionally substituted with from one to three members selected from the group consisting of —OH, —$OR^m$, —$OC(O)NHR^m$, —$OC(O)N(R^m)_2$, —SH, —$SR^m$, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl.

The symbol $Ar^1$ represents an optionally substituted aryl or heteroaryl group. Preferred aryl groups are phenyl and naphthyl. Preferred heteroaryl groups are those having from 5 to 10 ring vertices, at least one of which is a nitrogen atom (e.g., pyridyl, pyridazinyl, pyrazinyl, pyrimidinyl, triazinyl, quinolinyl, quinoxalinyl, purinyl and the like). Each of the $Ar^1$ rings is optionally substituted with from one to five $R^2$ substituents independently selected from halogen, —$OR^c$, —$OC(O)R^c$, —$NR^cR^d$, —$SR^c$, $R^e$, —CN, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —NH—$C(NH_2)$=NH, —$NR^eC(NH_2)$=NH, —NH—$C(NH_2)$=$NR^e$, —NH—C(NHR^e)=NH, —$NR^eC(NHR^e)$=NH, —$NR^eC(NH_2)$=$NR^e$, —NH—$C(NHR^e)$=$NR^e$, —NH—$C(NR^eR^e)$=NH, —$S(O)R^e$, —$S(O)_2R^e$, —$NR^eS(O)_2R^e$, —$S(O)_2NR^cR^d$, —$N_3$, —$C(NOR^c)R^d$, —$C(NR^cW)$=NW, —$N(W)C(R^c)$=NW, —$NR^cC(S)NR^cR^d$, —$X^2C(NOR^c)R^d$, —$X^2C(NR^cW)$=NW, —$X^2N(W)C(R^c)$=NW, —$X^2NR^cC(S)NR^cR^d$, —$X^2OR^c$, —O—$X^2OR^c$, —$X^2OC(O)R^c$, —$X^2NR^cR^d$, —O—$X^2NR^cR^d$, —$X^2SR^c$, —$X^2CN$, —$X^2NO_2$, —$X^2CO_2R^c$, —O—$X^2CO_2R^c$, —$X^2CONR^cR^d$, —O—$X^2CONR^cR^d$, —$X^2C(O)R^c$, —$X^2OC(O)NR^cR^d$, —$X^2NR^dC(O)_2R^e$, —$X^2NR^cC(O)NR^cR^d$, —$X^2NH$—C(NH_2)=NH, —$X^2NR^eC(NH_2)$=NH, —$X^2NH$—C(NH_2)=$NR^e$, —$X^2NH$—C(NHR^e)=NH, —$X^2S(O)R^e$, —$X^2S(O)_2R^e$, —$X^2NR^eS(O)_2R^e$, —$X^2S(O)_2NR^cR^d$, —$X^2N_3$, —$NR^d$—$X^2OR^c$, —$NR^d$—$X^2NR^cR^d$, —$NR^d$—$X^2CO_2R^e$, and —$NR^d$—$X^2CONR^cR^d$, wherein W is selected from $R^c$, —CN, —$CO_2R^e$ and —$NO_2$, and wherein $X^2$ is a member selected from the group consisting of $C_{1-4}$ alkylene, $C_{2-4}$ alkenylene and $C_{2-4}$ alkynylene and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or optionally $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of $R^c$, $R^d$ and $R^e$ is optionally further substituted with from one to three members selected from the group consisting of —OH, —$OR^n$, —$OC(O)NHR^n$, —$OC(O)N(R^n)_2$, —SH, —$SR^n$, —$S(O)R^n$, —$S(O)_2R^n$, —$SO_2NH_2$, —$S(O)_2NHR^n$, —$S(O)_2N(R^n)_2$, —$NHS(O)_2R^n$, —$NR^nS(O)_2R^n$, —$C(O)NH_2$, —$C(O)NHR^n$, —$C(O)N(R^n)_2$, —$C(O)R^n$, —$NHC(O)R^n$, —$NR^nC(O)R^n$, —$NHC(O)NH_2$, —$NR^nC(O)NH_2$, —$NR^nC(O)NHR^n$, —$NHC(O)NHR^n$, —$NR^nC(O)N(R^n)_2$, —$NHC(O)N(R^n)_2$, —$CO_2H$, —$CO_2R^n$, —$NHCO_2R^n$, —$NR^nCO_2R^n$, —CN, —$NO_2$, —$NH_2$, —$NHR^n$, —$N(R^n)_2$, —$NR^nS(O)NH_2$ and —$NR^nS(O)_2NHR^n$, wherein each $R^n$ is independently an unsubstituted $C_{1-6}$ alkyl. Optionally, two $R^2$ substituents on adjacent carbon atoms are combined to form a five or six-membered ring having 0-3 heteroatoms as ring members.

The symbol HAr represents an optionally substituted heteroaryl group. The heteroaryl groups for HAr can be the same or different from any of the heteroaryl groups used for $Ar^1$. Generally, the HAr groups are monocyclic, but can also be fused bicyclic systems having from 5 to 10 ring atoms, at least one of which is a nitrogen atom. Certain preferred heteroaryl groups are 5 or 6-membered rings having at least one nitrogen atom as a ring vertex and fused ring systems having a 5-membered ring fused to a benzene ring, for example pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzopyrazolyl and benzotriazolyl, each of which is substituted with from one to five $R^3$ substituents independently selected from the group consisting of halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —NH—$C(NH_2)$=NH, —$NR^hC(NH_2)$=NH, —NH—$C(NH_2)$=$NR^h$, —NH—C(NHR^h)=NH, —$NR^hC(NHR^h)$=NH, —$NR^hC(NH_2)$=$NR^h$, —NH—$C(NHR^h)$=$NR^h$, —NH—$C(NR^hR^h)$=NH, —$S(O)R^h$, —$S(O)_2R^h$, —$NR^fS(O)_2R^h$, —$S(O)_2NR^fR^g$, —$NR^fS(O)_2NR^fR^g$, —$N_3$, —$C(NOR^f)R^g$, —$C(NR^fW^a)$=$NW^a$, —$N(W^a)C(R^f)$=$NW^a$, —$X^3C(NOR^f)R^g$, —$X^3C(NR^fW^a)$=$NW^a$, —$X^3N(W^a)C(R^f)$=NW, —$NR^fC(S)NR^fR^g$, —$X^3NR^fC(S)NR^fR^g$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—$C(O)NR^fR^g$, —$X^3NH$—C(NH_2)=NH, —$X^3NR^hC(NH_2)$=NH, —$X^3NH$—C(NH_2)=$NR^h$, —$X^3NH$—C(NHR^h)=NH, —$X^3S(O)R^h$, —$X^3S(O)_2R^h$, —$X^3NR^fS(O)_2R^h$, —$X^3S(O)_2NR^fR^g$, —Y, —$SO_2Y$, —C(O)Y, —$X^3Y$, —$X^3N_3$, —O—$X^3OR^f$, —O—$X^3NR^fR^g$, —O—$X^3CO_2R^f$, —O—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$, wherein Y is a five to ten-membered aryl, heteroaryl or heterocyclic ring, optionally substituted with from one to three substituents selected from the group consisting of halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —S(O)$R^h$, —$S(O)_2R^h$, —$NR^fS(O)_2R^h$, —$S(O)_2NR^fR^g$, —$C(NOR^f)R^g$, —$C(NR^fW^a)$=$NW^a$, —$N(W^a)C(R^f)$=$NW^a$, —$X^3C(NOR^f)R^g$, —$X^3C(NR^fW^a)$=NW, —$X^3N(W^a)C(R^f)$=$NW^a$, —$X^3OR^f$, —$X^3NR^fR^g$, —$X^3NR^fS(O)_2R^h$ and —$X^3S(O)_2NR^fR^g$, and wherein $W^a$ is selected from $R^f$, —CN, —$CO_2R^h$ and —$NO_2$, and wherein each $X^3$ is independently selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $R^f$, $R^g$ and $R^h$ is optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl. Among the most preferred HAr groups are substituted or unsubstituted pyrazoles and benzopyrazoles as well as substituted or unsubstituted triazoles and benzotriazoles. Preferably, substituted or unsubstituted pyrazoles and benzopyrazoles are attached to the remainder of the molecule via a nitrogen atom of the pyrazole ring. Optionally, two $R^3$ substituents on adjacent carbon atoms are combined to form a five or six-membered ring having 0-3 heteroatoms as ring members. In other embodiments, HAr can be a furanyl or thienyl ring (e.g., having no ring nitrogen atom) and being optionally substituted as described above.

The symbol $L^1$ represents a linking group having from one to three main chain atoms selected from the group consisting of C, N, O and S and being optionally substituted with from one to three substituents selected from the group consisting of halogen, phenyl, —$OR^i$, —$OC(O)R^i$, —$NR^iR^j$, —$SR^i$, —$R^k$, —CN, —$NO_2$, —$CO_2R^i$, —$CONR^iR^j$, —$C(O)R^i$, —$OC(O)NR^iR^j$, —$NR^jC(O)R^i$, —$NR^jC(O)_2R^k$, —$X^4OR^i$, —$X^4OC(O)R^i$, —$X^4NR^iR^j$, —$X^4SR^i$, —$X^4CN$, —$X^4NO_2$, —$X^4CO_2R^i$, —$X^4CONR^iR^j$, —$X^4C(O)R^i$, —$X^4OC(O)NR^iR^j$, —$X^4NR^jC(O)R^i$ and —$X^4NR^jC(O)_2R^k$, wherein $X^4$ is selected from the group consisting of $C_{1-4}$ alkylene, $C_{2-4}$ alkenylene and $C_{2-4}$ alkynylene and each $R^i$ and $R^j$ is independently selected from hydrogen, $C_{1-8}$ galkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each $R^k$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl.

In certain preferred embodiments, the linking groups are unsubstituted, while in other preferred embodiments, substituents are present that can increase partitioning into selected solvents or into selected tissues. For example, addition of a hydroxy group to a propylene linkage will generally provide compounds having more favorable solubility in water. Preferably, $L^1$ is selected from —$CH_2$—, —$CH_2CH_2$—, —$CH_2CH_2CH_2$—, —$CH_2O$—, —$CH_2NH$—, —$CH_2OCH_2$— and —$CH_2NHCH_2$—. Most preferably, $L^1$ is —$CH_2$—.

In addition to the compounds provided herein, the present invention further provides pharmaceutical compositions containing one or more of these compounds, as well as methods for the use of these compounds in therapeutic methods, primarily to treat diseases associated with CCR1 signalling activity.

DETAILED DESCRIPTION OF THE INVENTION

I. Abbreviation and Definitions

Figure 1A:
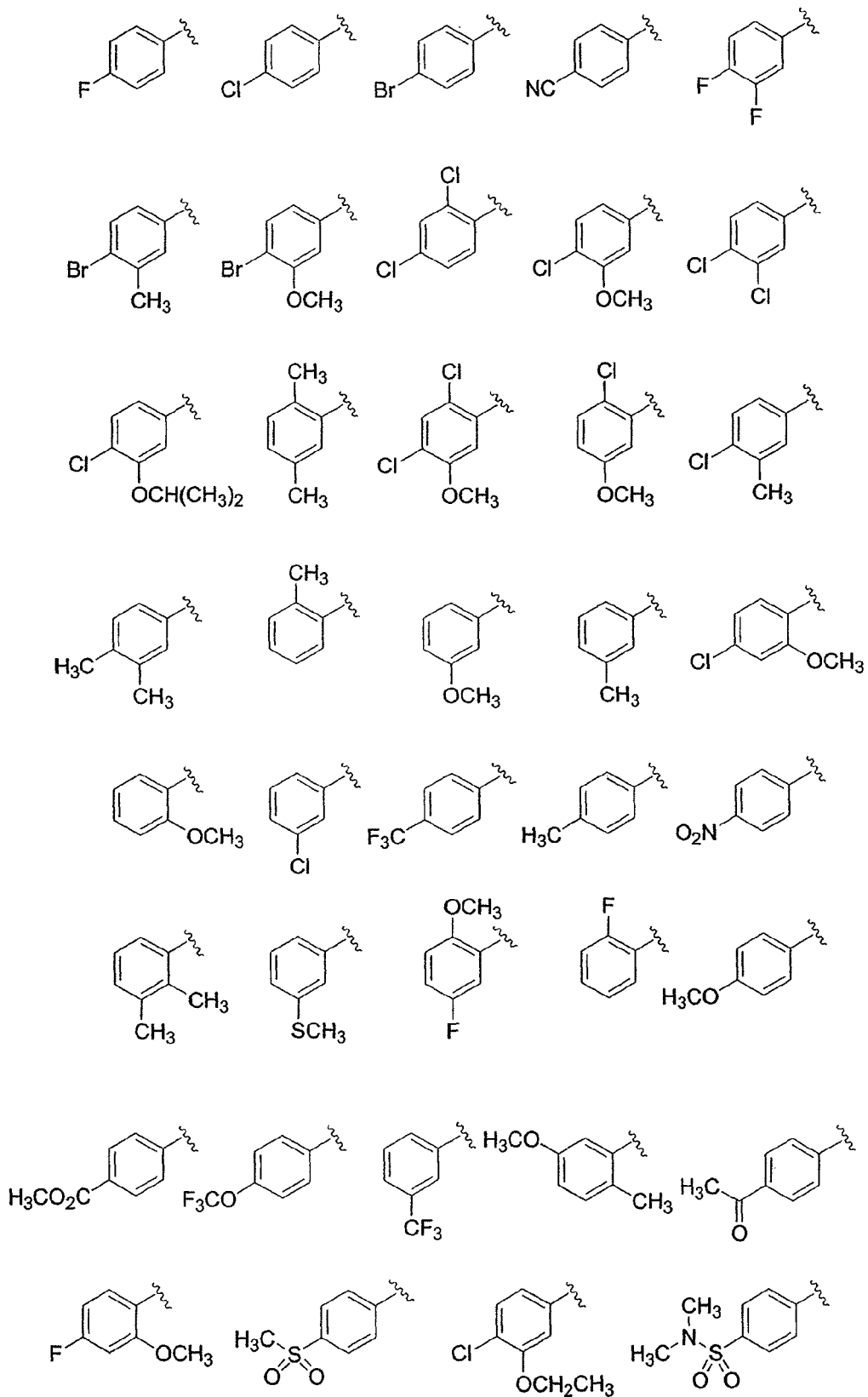
FIGS. 1A through 1G provides selected and preferred $Ar^1$ groups for compounds of formulae I, II and III.
Figure 1B:
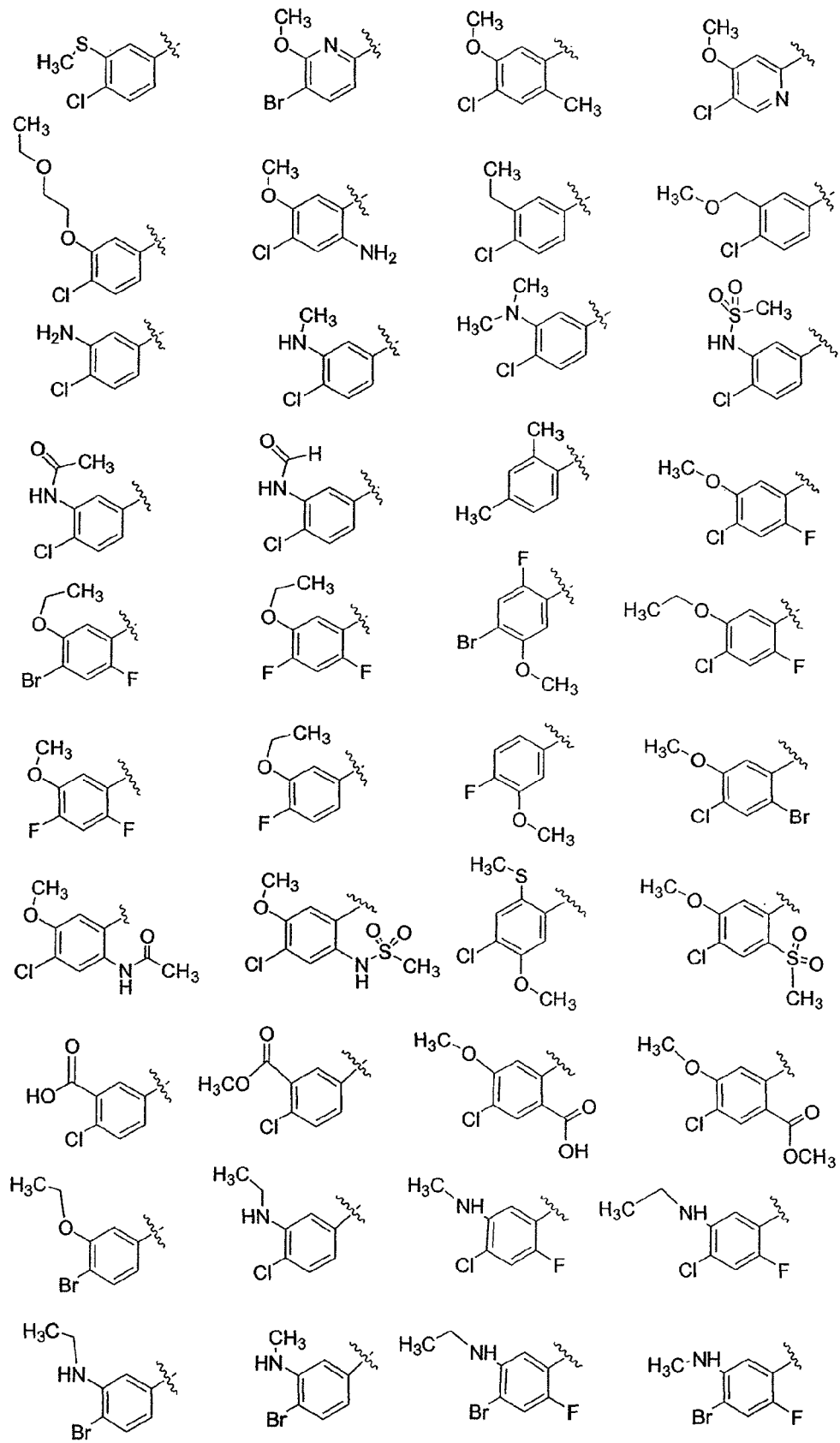
Figure 1C:
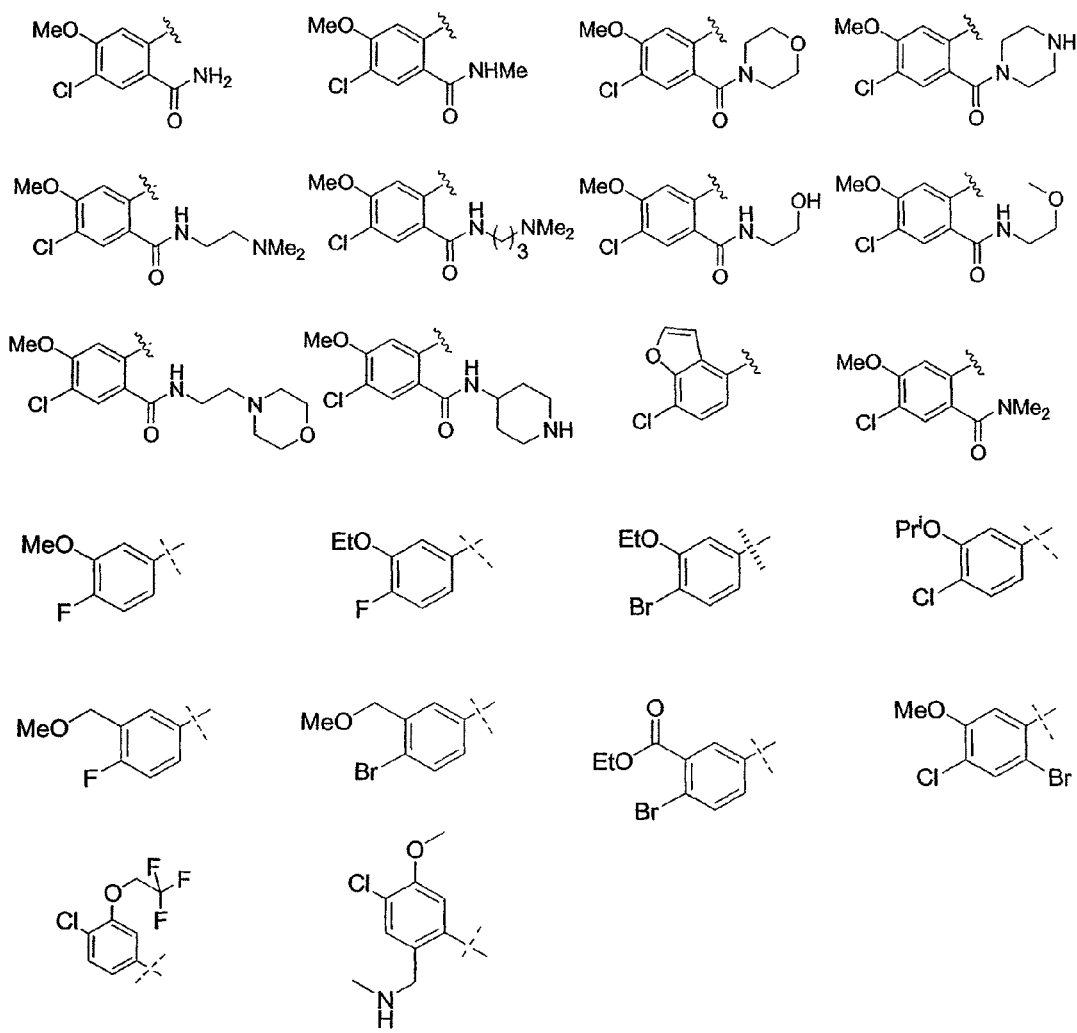
Figure 1D:
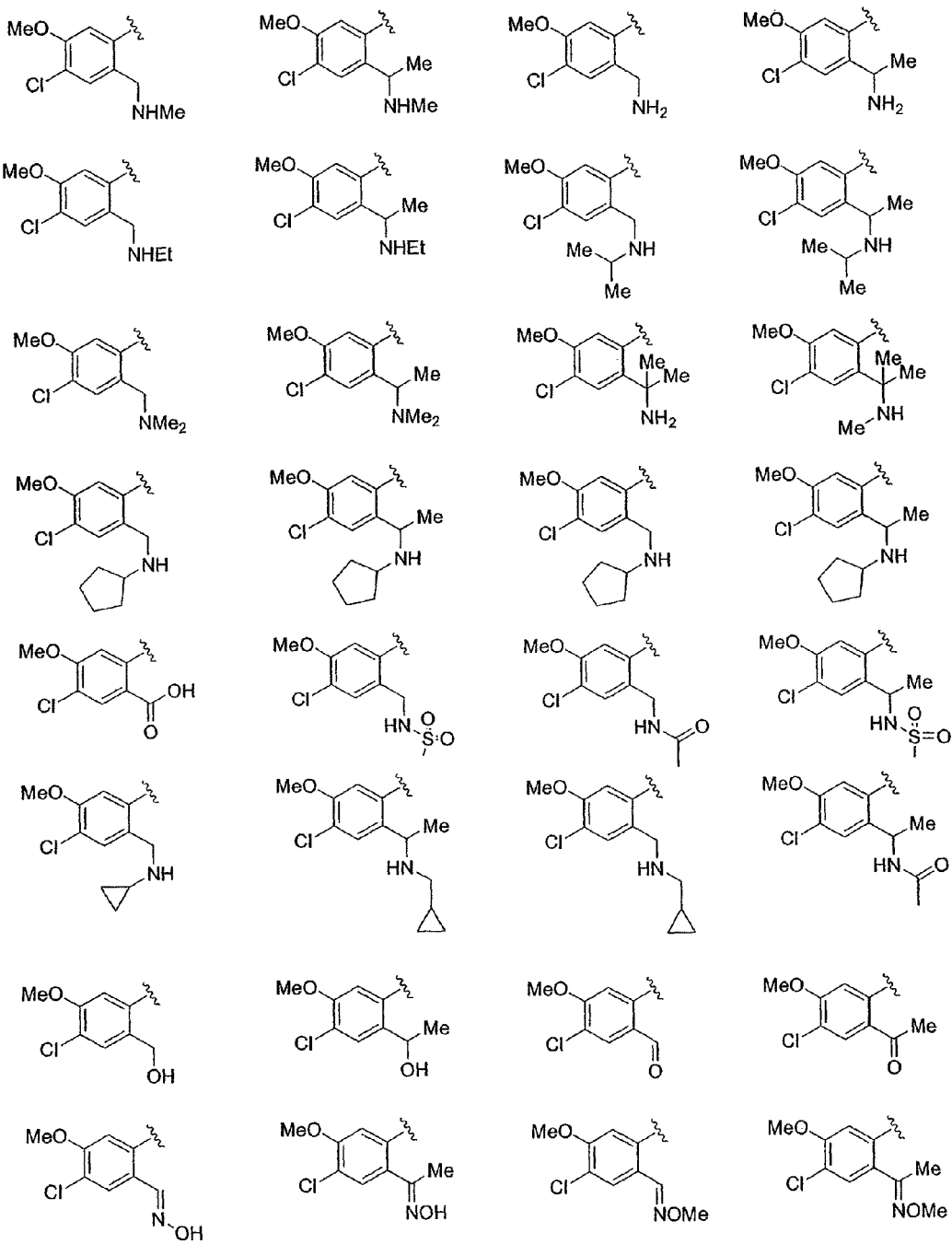
Figure 1E:
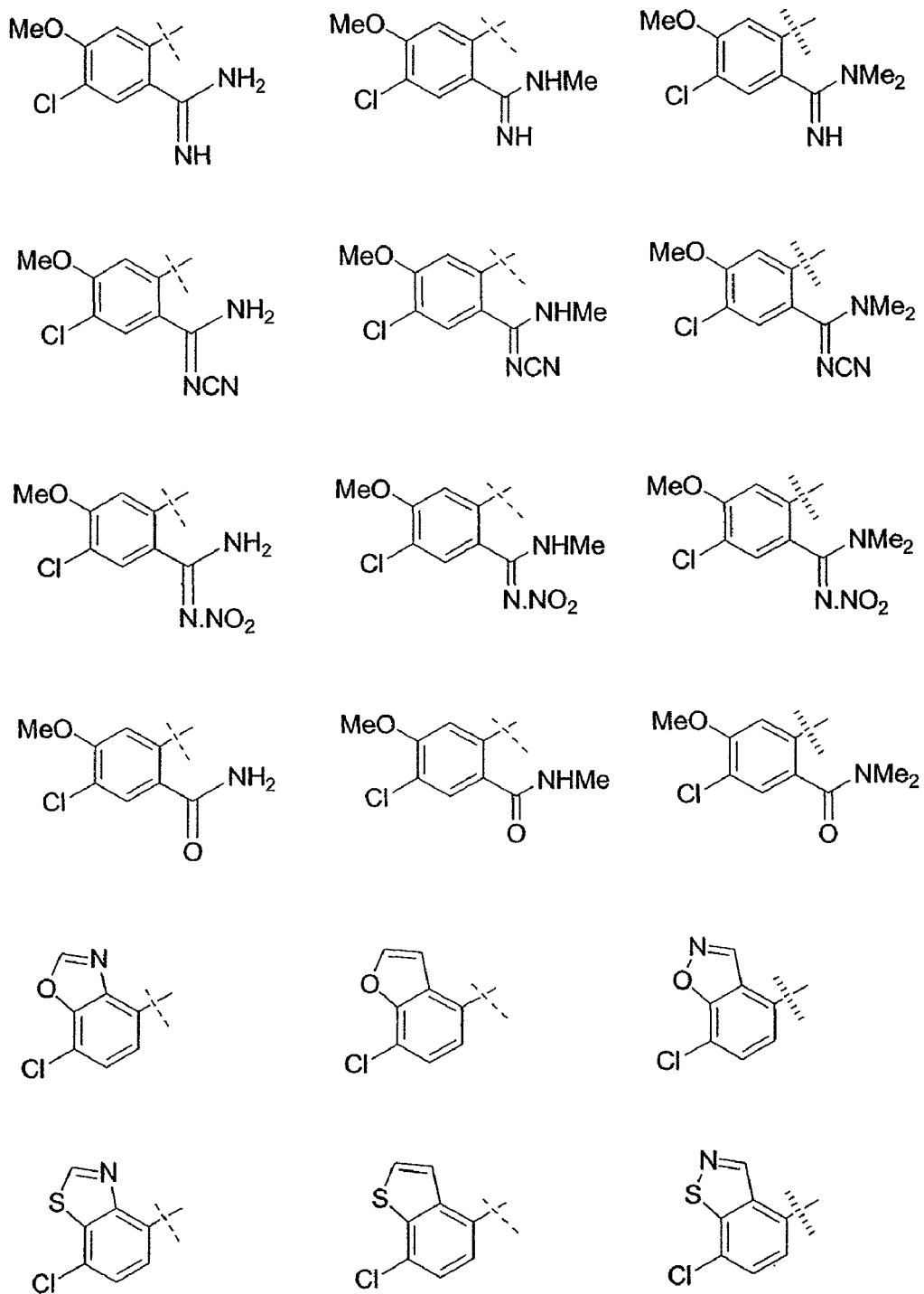
Figure 1F:
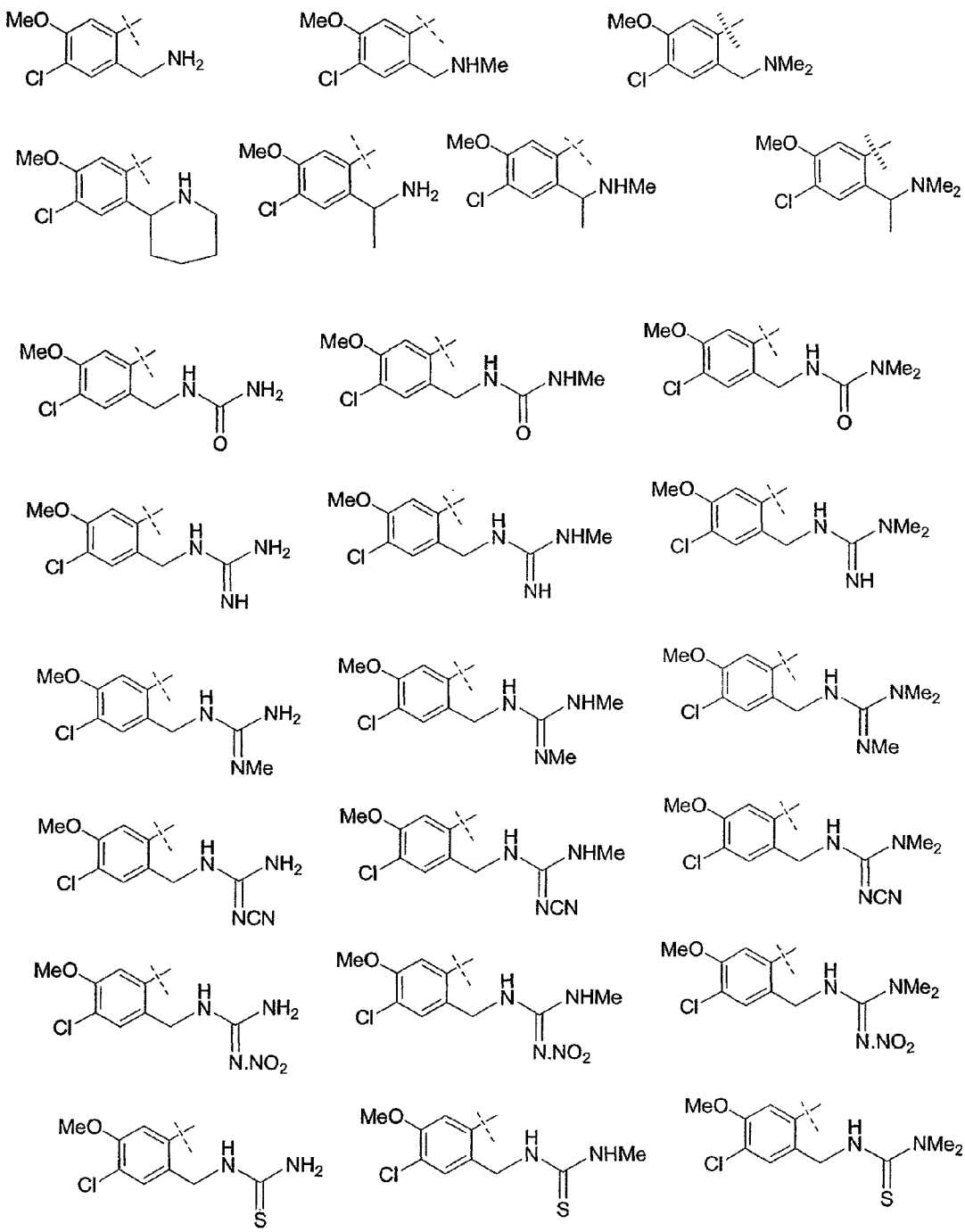
Figure 1G:
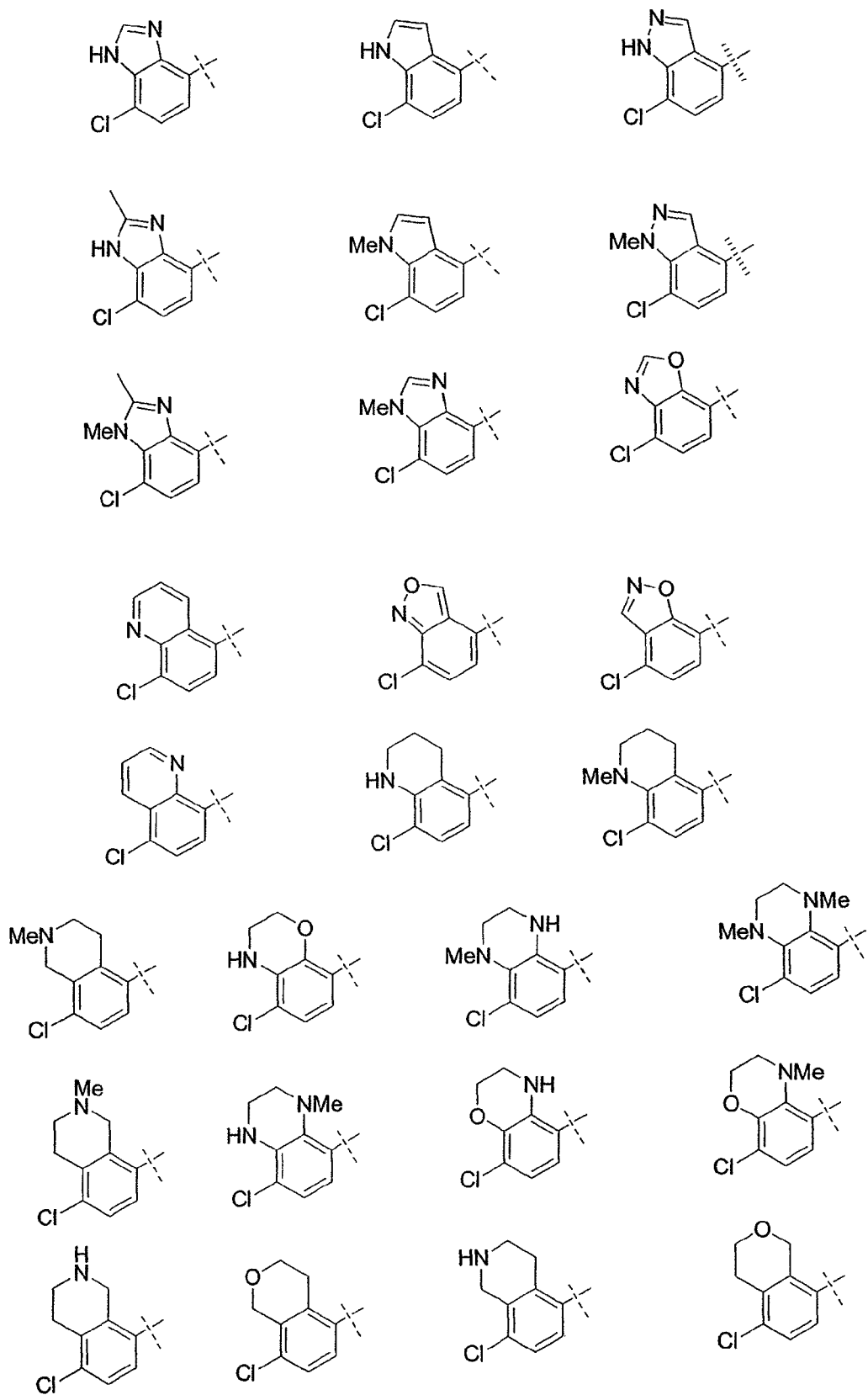

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R"' each independently refer to hydrogen, unsubstituted $C_{1-8}$ alkyl, unsubstituted heteroalkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of formula I (as well as the subgeneric formulae II, III and IV) act as potent antagonists of the CCR1 receptor. The compounds have in vivo anti-inflammatory activity. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides compounds having the formula:

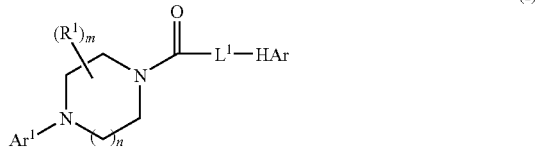

or a pharmaceutically acceptable salt or N-oxide thereof

In the formula above, the subscript n represents an integer of from 1 to 2, preferably 1. The subscript m represents an integer of from 0 to 10, limited by the number of available substituents positions on the piperazine or homopiperazine ring to which it is attached. For example, piperazine derivatives (n is 1) can have from 0 to 8 $R^1$ groups, preferably 0 to 4 $R^1$ groups, and more preferably 0, 1 or 2 $R^1$ groups.

The symbol $Ar^1$ represents an optionally substituted aryl or heteroaryl group. Preferred aryl groups are phenyl and naphthyl. Preferred heteroaryl groups are those having from 5 to 10 ring vertices, at least one of which is a nitrogen atom (e.g., pyridyl, pyridazinyl, pyrazinyl, pyrimidinyl, triazinyl, quinolinyl, quinoxalinyl, purinyl and the like). Each of the $Ar^1$ rings is optionally substituted with from one to five $R^2$ substituents independently selected from halogen, —$OR^c$, —$OC(O)R^c$, —$NR^cR^d$, —$SR^c$, —$R^e$, —CN, —$NO_2$, —$CO_2R^c$, —$CONR^cR^d$, —$C(O)R^c$, —$OC(O)NR^cR^d$, —$NR^dC(O)R^c$, —$NR^dC(O)_2R^e$, —$NR^c$—$C(O)NR^cR^d$, —NH—$C(NH_2)$=NH, —$NR^eC(NH_2)$=NH, —NH—$C(NH_2)$=$NR^e$, —NH—$C(NHR^e)$=NH, —$NR^eC(NHR^e)$=NH, —$NR^eC(NH_2)$=$NR^e$, —NH—$C(NHR^e)$=$NR^e$, —NH—$C(NR^eR^e)$=NH, —$S(O)R^e$, —$S(O)_2R^e$, —$NR^eS(O)_2R^e$, —$S(O)_2NR^cR^d$, —$N_3$, —$C(NOR^e)R^d$, —$C(NR^cW)$=NW, —$N(W)C(W)$=NW, —$NR^cC(S)NR^cR^d$, —$X^2C(NOR^c)R^d$, —$X^2C(NR^cW)$=NW, —$X^2N(W)C(R^c)$=NW, —$X^2NR^cC(S)NR^c$ $R^d$, —$X^2OR^c$, —O—$X^2OR^c$, —$X^2OC(O)R^c$, —$X^2NR^cR^d$, —O—$X^2NR^cR^d$, —$X^2SR^c$, —$X^2CN$, —$X^2NO_2$, —$X^2CO_2R^c$, —O—$X^2CO_2R^c$, —$X^2CONR^cR^d$, —O—$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^c$ $R^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^eS(O)_2R^e$, —$X^2S(O)_2NR^cR^d$, —$X^2N_3$, —$NR^d$—$X^2OR^c$, —$NR^d$—$X^2NR^cR^d$, —$NR^d$—$X^2CO_2R^c$, and —$NR^d$—$X^2CONR^cR^d$, wherein each W is selected from $R^e$, —CN, —$CO_2R^e$ and —$NO_2$, and wherein each $X^2$ is a member selected from the group consisting of $C_{1-4}$ alkylene, $C_{2-4}$ alkenylene and $C_{2-4}$ alkynylene and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or optionally $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, and each of $R^c$, $R^d$ and $R^e$ is optionally further substituted with from one to three members selected from the group consisting of —OH, —$OR''$, —$OC(O)NHR''$, —$OC(O)N(R'')_2$, —SH, —$SR''$, —$S(O)R''$, —$S(O)_2R''$, —$SO_2NH_2$, —$S(O)_2NHR''$, —$S(O)_2N(R'')_2$, —$NHS(O)_2R''$, —$NR''S(O)_2R''$, —$C(O)$ NH$_2$, —C(O)NHR″, —C(O)N(R″)$_2$, —C(O)R″, —NHC(O)R″, —NR″C(O)R″, —NHC(O)NH$_2$, —NR″C(O)NH$_2$, —NR″C(O)NHR″, —NHC(O)NHR″, —NR″C(O)N(R″)$_2$, —NHC(O)N(R″)$_2$, —CO$_2$H, —CO$_2$R″, —NHCO$_2$R″, —NR″CO$_2$R″, —CN, —NO$_2$, —NH$_2$, —NHR″, —N(R″)$_2$, —NR″S(O)NH$_2$ and —NR″S(O)$_2$NHR″, wherein each R″ is independently an unsubstituted C$_{1-6}$ alkyl. Optionally, two R$^2$ substituents on adjacent carbon atoms are combined to form a five or six-membered ring having 0-3 heteroatoms as ring members.

HAr is an optionally substituted heteroaryl group. The heteroaryl groups for HAr can be the same or different from any of the heteroaryl groups used for Ar$^1$. Generally, the HAr groups are monocyclic, but can also be fused bicyclic systems having from 5 to 10 ring atoms, at least one of which is a nitrogen atom. Certain preferred heteroaryl groups are 5 or 6-membered rings having at least one nitrogen atom as a ring vertex and fused ring systems having a 5-membered ring fused to a benzene ring, for example pyrazolyl, imidazolyl, triazolyl, tetrazolyl, oxazolyl, isoxazolyl, oxadiazolyl, oxathiadiazolyl, pyrrolyl, thiazolyl, isothiazolyl, benzimidazolyl, benzopyrazolyl and benzotriazolyl. Preferably, the fused bicyclic HAr moiety, when present, is attached to the remainder of the molecule through the 5-member ring. Additionally, each of the HAr groups is substituted with from one to five R$^3$ substituents independently selected from the group consisting of halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)=NH, —NR$^h$C(NH$_2$)=NH, —NH—C(NH$_2$)=NR$^h$, —NH—C(NHR$^h$)=NH, —NR$^h$C(NHR$^h$)=NH, —NR$^h$C(NH$_2$)=NR$^h$, —NH—C(NHR$^h$)=NR$^h$, —NH—C(NR$^h$R$^h$)=NH, —S(O)R$^h$, —S(O)$_2$R$^h$, —NR$^f$S(O)$_2$R$^h$, —S(O)$_2$NR$^f$R$^g$, —NR$^f$S(O)$_2$NR$^f$R$^g$, —C(NOR$^f$)R$^g$, —C(NR$^f$W$^a$)=NW$^a$, —N(W)C(R$^f$)=NW$^a$, —N$_3$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$C(NOR$^f$)R$^g$, —X$^3$C(NR$^f$W$^a$)=NW, —X$^3$N(W$^a$)C(R$^f$)=NW$^a$, —Y, —SO$_2$Y, —C(O)Y, —X$^3$Y, —X$^3$N$_3$, —O—X$^3$OR$^f$, —O—X$^3$NR$^f$R$^g$, —O—X$^3$CO$_2$R$^f$, —O—X$^3$CONR$^f$R$^g$, —NR$^g$—X$^3$OR$^f$, —NR$^g$—X$^3$NR$^f$R$^g$, —NR$^g$—X$^3$CO$_2$R$^f$, and —NR$^g$—X$^3$CONR$^f$R$^g$, wherein Y is a five to ten-membered aryl, heteroaryl or heterocyclic ring, optionally substituted with from one to three substituents selected from the group consisting of halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —C(NOR$^f$)R$^g$, —C(NR$^f$W$^a$)=NW$^a$, —N(W$^a$)C(R$^f$)=NW$^a$, —X$^3$C(NOR$^f$)R$^g$, —X$^3$C(NR$^f$W$^a$)=NW$^a$, —X$^3$N(W$^a$)C(R$^f$)=NW$^a$, —X$^3$OR$^f$, —X$^3$NR$^f$R$^g$, —X$^3$NR$^f$S(O)$_2$R$^h$ and —X$^3$S(O)$_2$NR$^f$R$^g$, wherein each W$^a$ is selected from R$^f$, —CN, —CO$_2$R$^h$ and —NO$_2$, and wherein each X$^3$ is independently selected from the group consisting of C$_{1-4}$ alkylene, C$_{2-4}$ alkenylene and C$_{2-4}$ alkynylene and each R$^f$ and R$^g$ is independently selected from hydrogen, C$_{1-8}$ alkyl, C$_{1-8}$haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, or when attached to the same nitrogen atom can be combined with the nitrogen atom to form a five or six-membered ring having from 0 to 2 additional heteroatoms as ring members, and each R$^h$ is independently selected from the group consisting of C$_{1-8}$ alkyl, C$_{1-8}$haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, wherein the aliphatic portions of R$^f$, R$^g$ and R$^h$ is optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$, wherein each R$^o$ is independently an unsubstituted C$_{1-6}$ alkyl. Optionally, two R$^3$ substituents on adjacent carbon atoms are combined to form a five or six-membered ring having 0-3 heteroatoms as ring members. Among the most preferred HAr groups are substituted or unsubstituted pyrazoles and benzopyrazoles and substituted or unsubstituted triazoles and benzotriazoles. Preferably, substituted or unsubstituted pyrazoles are attached to the remainder of the molecule via a nitrogen atom of the pyrazole ring.

The symbol L$^1$ represents a linking group having from one to three main chain atoms selected from the group consisting of C, N, O and S and being optionally substituted with from one to three substituents selected from the group consisting of halogen, phenyl, —OR$^i$, —OC(O)R$^i$, —NR$^i$R$^j$, —SR$^i$, —R$^k$, —CN, —NO$_2$, —CO$_2$R$^i$, —C(O)R$^i$, —OC(O)NR$^i$R$^j$, —NR$^i$C(O)R$^i$, —NR$^i$C(O)$_2$R$^k$, —X$^4$OR$^i$, —X$^4$OC(O)R$^i$, —X$^4$NR$^i$R$^j$, —X$^4$SR$^i$, —X$^4$CN, —X$^4$NO$_2$, —X$^4$CO$_2$R$^i$, —X$^4$CONR$^i$R$^j$, —X$^4$C(O)R$^i$, —X$^4$OC(O)NR$^i$R$^j$, —X$^4$NR$^i$C(O)R$^i$ and —X$^4$NR$^i$C(O)$_2$R$^k$, wherein X$^4$ is selected from the group consisting of C$_{1-4}$ alkylene, C$_{2-4}$ alkenylene and C$_{2-4}$ alkynylene and each R$^i$ and R$^j$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, and each R$^k$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl. In certain preferred embodiments, the linking groups are unsubstituted, while in other preferred embodiments, substituents are present that can increase partitioning into selected solvents or into selected tissues. For example, addition of a hydroxy group to a propylene linkage will generally provide compounds having more favorable solubility in water. Preferably, L$^1$ is selected from —CH$_2$—, —CH$_2$CH$_2$—, —CH$_2$CH$_2$CH$_2$—, —CH$_2$O—, —CH$_2$NH—, —CH$_2$OCH$_2$— and —CH$_2$NHCH$_2$—. More preferably, L$^1$ is —CH$_2$—.

Returning to the piperazine or homopiperazine portion of the compounds, each R$^1$ is a substituent independently selected from C$_{1-8}$ alkyl, C$_{1-8}$ haloalkyl, C$_{3-6}$ cycloalkyl, C$_{2-8}$ alkenyl and C$_{2-8}$ alkynyl, —COR$^a$, —CO$_2$R$^a$, —CONR$^a$R$^b$, —NR$^a$COR$^b$, —SO$_2$R$^a$, —X$^1$COR$^a$, —X$^1$CO$_2$R$^a$, —X$^1$CONR$^a$R$^b$, —X$^1$NR$^a$COR$^b$, —X$^1$SO$_2$R$^a$, —X$^1$SO$_2$NR$^a$R$^b$, —X$^1$NR$^a$R$^b$, —X$^1$OR$^a$, wherein X$^1$ is a member selected from the group consisting of C$_{1-4}$ alkylene, C$_{2-4}$ alkenylene and C$_{2-4}$ alkynylene and each R$^a$ and R$^b$ is independently selected from the group consisting of hydrogen, C$_{1-8}$ alkyl, C$_{1-8}$ haloalkyl, C$_{3-6}$ cycloalkyl and aryl-C$_{1-4}$ alkyl, or optionally R$^a$ and R$^b$ when attached to the same nitrogen atom can be combined with the nitrogen atom to form a five or six-membered ring having from 0 to 2 additional heteroatoms as ring members, and wherein the aliphatic portions of each of the R$^1$ substituents is optionally substituted with from one to three members selected from the group consisting of —OH, —OR$^m$, —OC(O)NHR$^m$, —OC (O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each Ie is independently an unsubstituted C$_{1-6}$ alkyl. In certain preferred embodiments, R$^I$, when present is selected from methyl, ethyl, isopropyl, —CH$_2$OH, —CH$_2$OCH$_3$, —CH$_2$OCH$_2$CH$_3$, —CH$_2$OCH(CH$_3$)$_2$, —CH(CH$_3$)OH and —CH(CH$_3$)OCH$_3$, or more preferably, methyl, —CH$_2$OH and —CH$_2$OCH$_3$.

Excluded from the above generic formula, as well as each of the formulae below, are those compounds that are either commercially available or known in the literature, including: CAS Reg. No. 492422-98-7, 1-[[4-bromo-5-methyl-3-(trifluoromethyl)-1H-pyrazol-1-yl]acetyl]-4-(5-chloro-2-methylphenyl)-piperazine; CAS Reg. No. 351986-92-0, 1-[[4-chloro-5-methyl-3-(trifluoromethyl)-1H-pyrazol-1-yl]acetyl]-4-(4-fluorophenyl)-piperazine; CAS Reg. No. 356039-23-1, 1-[(3,5-dimethyl-4-nitro-1H-pyrazol-1-yl)acetyl]-4-(4-fluorophenyl)-piperazine; 1-(2-{4-nitro-3,5-dimethyl-1H-pyrazol-1-yl}propanoyl)-4-phenylpiperazine; 2-(2,4-Dinitro-imidazol-1-yl)-1-[4-(4-fluorophenyl)-piperazin-1-yl]-ethanone; 2-(2,4-Dinitro-imidazol-1-yl)-1-(4-phenyl-piperazin-1-yl)-ethanone; 2-(4-nitro-imidazol-1-yl)-1-(4-phenyl-piperazin-1-yl)-ethanone; and CAS Reg. No. 492992-15-1, 3-[3-Fluoro-4-[4-[(1-pyrazolyl)acetyl]piperazine-1-yl]phenyl]-5-[[(isoxazol-3-yl)amino]methyl]isoxazole.

A number of groups of embodiments can be outlined as follows.

In a first group of embodiments, the compounds are represented by formula I in which Ar$^1$ is selected from
(i) phenyl, substituted with from 1 to 5 R$^2$ groups;
(ii) pyridinyl, substituted with from 1 to 4 R$^2$ groups; and
(iii) pyrimidinyl, substituted with from 1 to 3 R$^2$ groups;
(iv) pyrazinyl, substituted with from 1 to 3 R$^2$ groups; and
(v) pyridazinyl, substituted with from 1 to 3 R$^2$ groups;
wherein each R$^2$ is a member independently selected from the group consisting of halogen, —OC(O)R$^c$, —OC(O)R$^c$, —NR$^c$R$^d$, —SR$^c$, —R$^e$, —CN, —NO$_2$, —CO$_2$R$^c$, —CONR$^c$R$^d$, —C(O)R$^c$, —OC(O)NR$^c$R$^d$, —NR$^d$C(O)R$^c$, —NR$^d$C(O)$_2$R$^e$, —NR$^c$—C(O)NR$^c$R$^d$, —C(NOR$^c$)R$^d$, —C(NR$^c$W)=NW, —N(W)C(R$^c$)=NW, —S(O)R$^e$, —S(O)$_2$R$^e$, —NR$^c$S(O)$_2$R$^e$, —S(O)$_2$NR$^c$R$^d$ and —N$_3$, wherein each R$^c$ and R$^d$ is independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl, and each R$^e$ is independently selected from the group consisting of C$_{1-8}$ alkyl, C$_{1-8}$ haloalkyl, C$_{3-6}$ cycloalkyl, C$_{2-8}$ alkenyl and C$_{2-8}$ alkynyl, wherein the aliphatic portions of R$^c$, R$^d$ and R$^e$ are optionally further substituted with from one to three members selected from the group consisting of OH, O(C$_{1-8}$ alkyl), SH, S(C$_{1-8}$ alkyl), CN, NO$_2$, NH$_2$, NH(C$_{1-8}$ alkyl) and N(C$_{1-8}$ alkyl)$_2$. More preferably, Ar$^1$ is phenyl substituted with from 1 to 3 R$^2$ groups. Some preferred embodiments are those in which the Ar$^1$ groups are represented by:

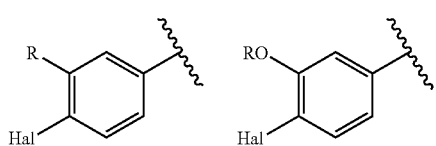

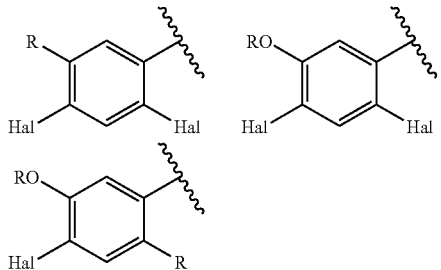

wherein Hal is F, Cl or Br and each R is independently C$_{1-6}$ alkyl or C$_{3-6}$ cycloalkyl.

In other preferred embodiments, L$^1$ is —CH$_2$— and is optionally substituted with phenyl, —R$^k$, —X$^4$OR$^i$, OC(O)R$^i$, —X$^4$NR$^i$R$^j$, —X$^4$SR$^i$, —X$^4$CN or —X$^4$NO$_2$. In still other preferred embodiments, HAr is selected from pyrazolyl and triazolyl, each of which is optionally substituted with from one to three R$^3$ groups independently selected from halogen, phenyl, thienyl, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —S(O)R$^h$, —S(O)$_2$R$^h$, —S(O)$_2$NR$^f$R$^g$, —NR$^f$S(O)$_2$R$^h$, —NR$^f$S(O)$_2$NR$^f$R$^g$, —N$_3$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$S(O)R$^h$, —X$^3$S(O)$_2$R$^h$, —X$^3$NR$^f$S(O)$_2$R$^h$, —X$^3$S(O)$_2$NR$^f$R$^g$ and —X$^3$N$_3$ wherein R$^f$ and R$^g$ are each independently selected from the group consisting of H, C$_{1-8}$ alkyl and C$_{1-8}$ haloalkyl, and each R$^h$ is independently selected from the group consisting of C$_{1-8}$ alkyl and C$_{1-8}$ haloalkyl. In still other preferred embodiments, the subscript n is 1, m is 0, 1 or 2, Ar$^1$ is phenyl substituted with from one to three R$^2$ groups, HAr is pyrazolyl which is substituted with three R$^3$ groups and L$^1$ is —CH$_2$—. In certain preferred embodiments in this group, Ar$^1$ is selected from those substituted phenyl moieties provided in FIGS. 1A through 1G.

In a second group of embodiments, the compounds are represented by formula I in which Ar$^1$ is selected from
(i) phenyl, substituted with from 1 to 5 R$^2$ groups;
(ii) pyridinyl, substituted with from 1 to 4 R$^2$ groups; and
(iii) pyrimidinyl, substituted with from 1 to 3 R$^2$ groups;
(iv) pyrazinyl, substituted with from 1 to 3 R$^2$ groups; and
(v) pyridazinyl, substituted with from 1 to 3 R$^2$ groups;
wherein each R$^2$ is a member independently selected from the group consisting of halogen, —X$^2$OR$^c$, —O—X$^2$OR$^c$, —X$^2$OC(O)R$^c$, —X$^2$NR$^c$R$^d$, —O—X$^2$NR$^c$R$^d$, —X$^2$SR$^c$, —X$^2$CN, —X$^2$NO$_2$, —X$^2$CO$_2$R$^c$, —O—X$^2$CO$_2$R$^c$, —X$^2$CONR$^c$R$^d$, —O—X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$C(NOR$^c$)R$^d$, —X$^2$C(NR$^c$W)=NW, —X$^2$N(W)C(R$^c$)=NW, —X$^2$S(O)R$^e$, —X$^2$S(O)$_2$R$^e$, —X$^2$NR$^c$S(O)$_2$R$^e$, —X$^2$S(O)$_2$NR$^c$R$^d$ and —X$^2$N$_3$.

In a third group of embodiments, the compounds are represented by formula I in which HAr is a member selected from the group consisting of pyrazolyl and triazolyl, which is optionally substituted with from one to three R$^3$ groups independently selected from the group consisting of halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)=NH, —NR$^h$C(NH$_2$)=NH, —NH—C(NH$_2$)=NR$^h$, —NH—C(NHR$^h$)=NH, —S(O)R$^h$, —S(O)$_2$R$^h$, —NR$^f$S(O)$_2$R$^h$, —S(O)$_2$NR$^f$R$^g$, —NR$^f$S(O)$_2$R$^h$, —NR$^f$S(O)$_2$NR$^f$R$^g$, —N$_3$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —Y, —X$^3$Y and —X$^3$N$_3$ wherein Y is a five to ten-membered aryl, heteroaryl or heterocyclic ring, optionally substituted with from one to three substitutents selected from the group consisting of halogen, —OR$^f$, —NR$^f$R$^g$, —R$^h$, —SR$^f$, —CN, —NO$_2$, —CO$_2$R$^f$, —CONR$^f$R$^g$, —C(O)R, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$NR$^f$R$^g$, and wherein each X$^3$ is independently selected from the group consisting of C$_{1-4}$ alkylene, C$_{2-4}$ alkenylene and C$_{2-4}$ alkynylene and each R$^f$ and R$^g$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, or when attached to the same nitrogen atom can be combined with the nitrogen atom to form a five or six-membered ring having from 0 to 2 additional heteroatoms as ring members, and each R$^h$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, wherein the aliphatic portions of R$^f$, R$^g$ and R$^h$ are optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R)$_2$, —NR$^o$S(O)NH$_2$ and —NR$^o$S(O)$_2$NHR$^o$, wherein R$^o$ is unsubstituted C$_{1-6}$ alkyl. Within this group of embodiments, preferred compounds are those in which n is 1, m is 0-2, Ar$^1$ is phenyl substituted with from one to three R$^2$ groups, HAr is pyrazolyl which is substituted with two to three R$^3$ groups, more preferably three R$^3$ groups and L$^1$ is —CH$_2$—. Optionally, two R$^2$ groups on Ar$^j$ are combined as noted above to form a five or six-membered ring having from 0-2 heteroatoms as ring members. Further preferred are those in which Ar$^1$ is selected from the substituted phenyl moieties provided in FIGS. 1A through 1G. In some preferred embodiments are those compounds in which one of the R$^3$ groups is selected from the group consisting of —Y and —X$^3$—Y. More preferably, those compounds wherein Y is selected from the group consisting of thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl and oxadiazolyl, which is optionally substituted, or phenyl or naphthyl which is substituted as set forth above, or more preferably, with from one to three substituents independently selected from the group consisting of halogen, —OR$^f$, —NR$^f$R$^g$, —COR$^f$, —CO$_2$R$^f$, —CONR$^f$R$^g$, —NO$_2$, —R$^h$, —CN, —X$^3$—OR$^f$, —X$^3$—NR$^f$R$^g$ and —X$^3$—NR$^f$S(O)$_2$R$^h$, wherein R$^f$ and R$^g$ are each independently selected from the group consisting of H, C$_{1-8}$ alkyl, C$_{3-6}$ cycloalkyl and C$_{1-8}$ haloalkyl, and each R$^h$ is independently selected from the group consisting of C$_{1-8}$ alkyl, C$_{3-6}$ cycloalkyl and C$_{1-8}$ haloalkyl.

In another group of embodiments, the compounds are represented by formula II:

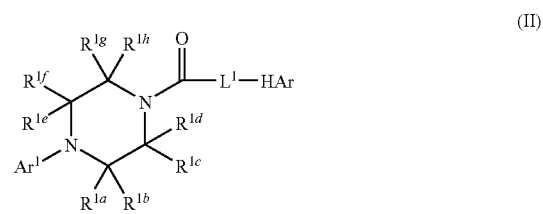

Figure 2A:
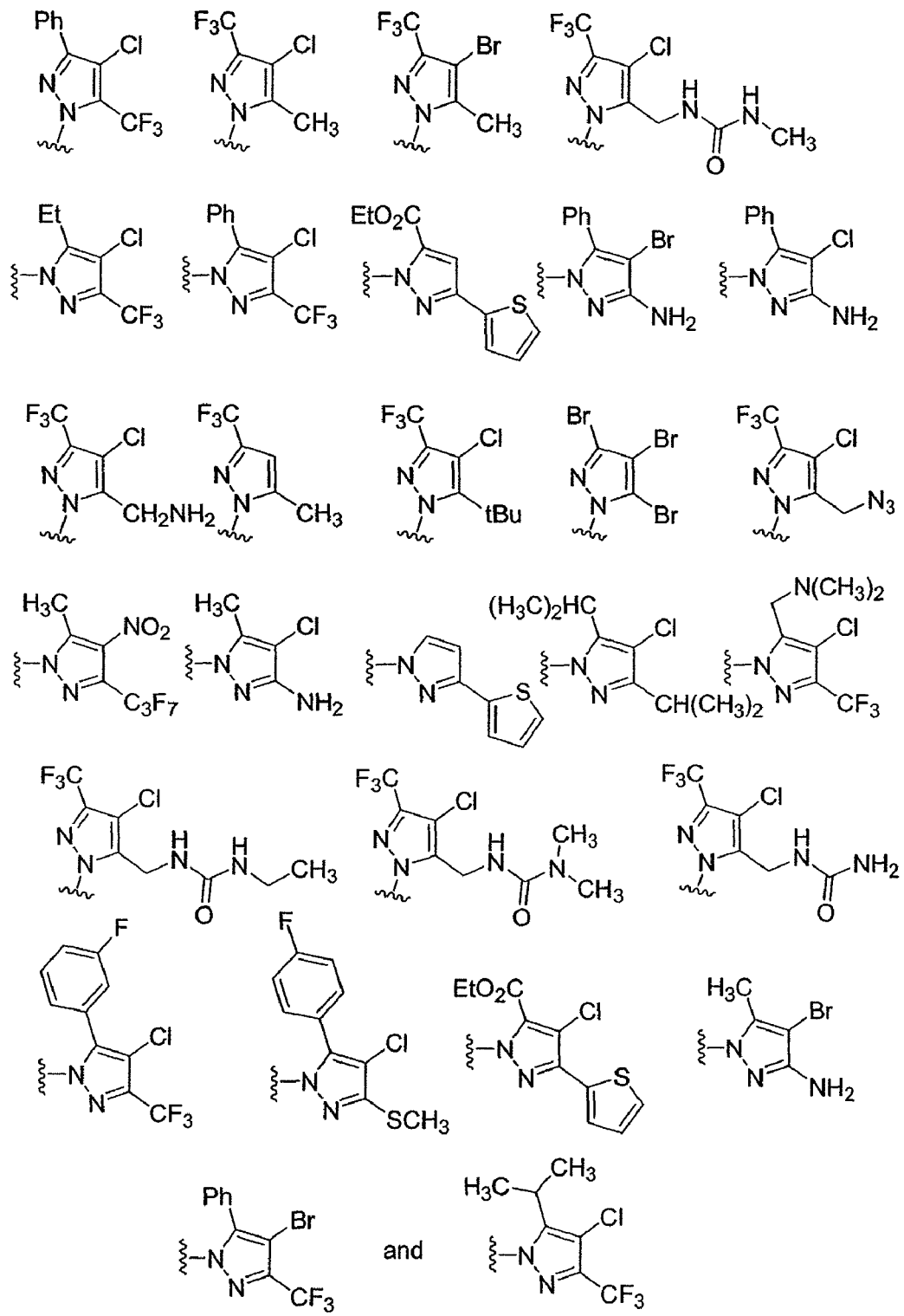
FIGS. 2A through 2Z, 2AA through 2HH and 3 provide selected and preferred HAr groups for compounds of formulae I, II, III and IV.
Figure 2B:
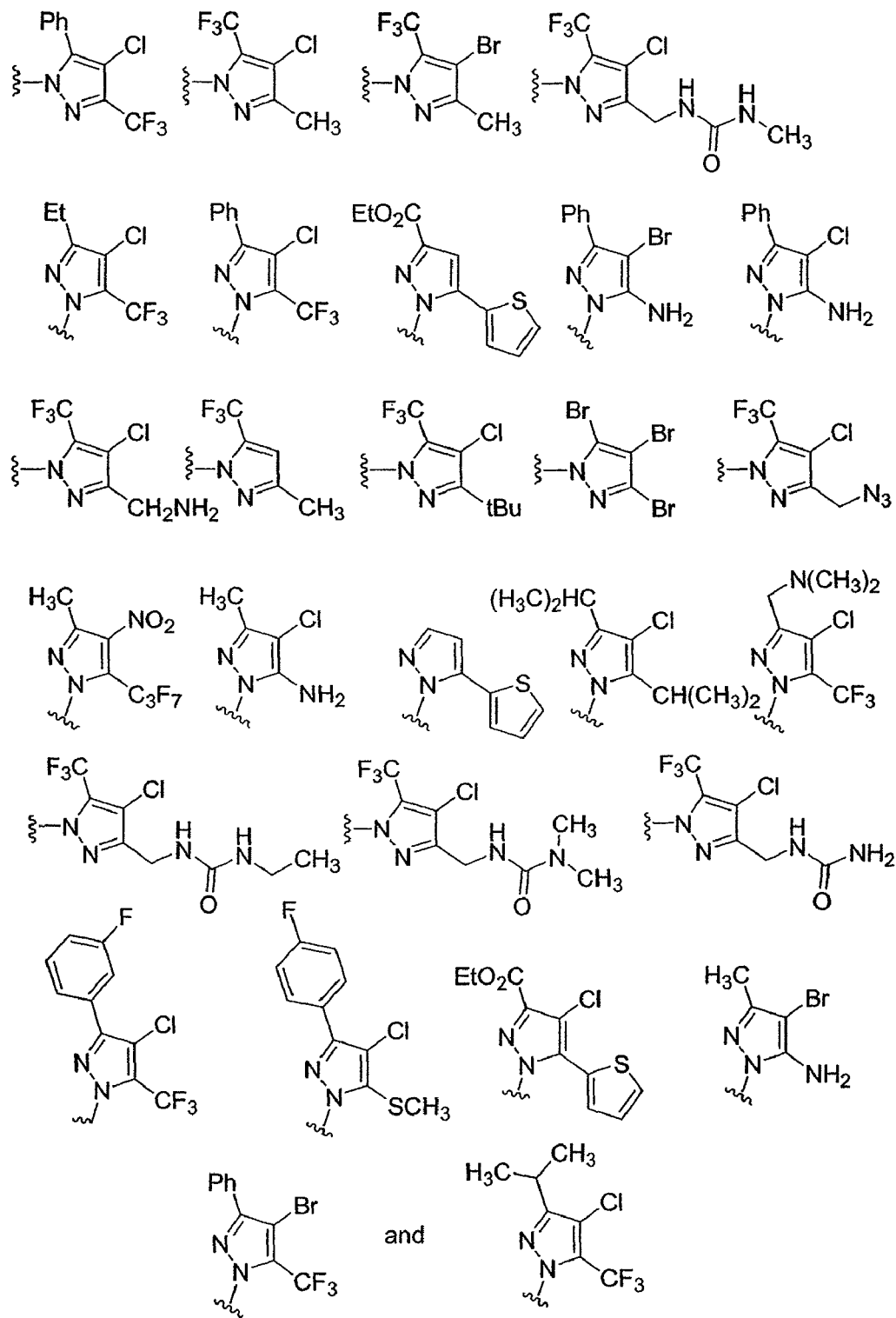
Figure 2C:
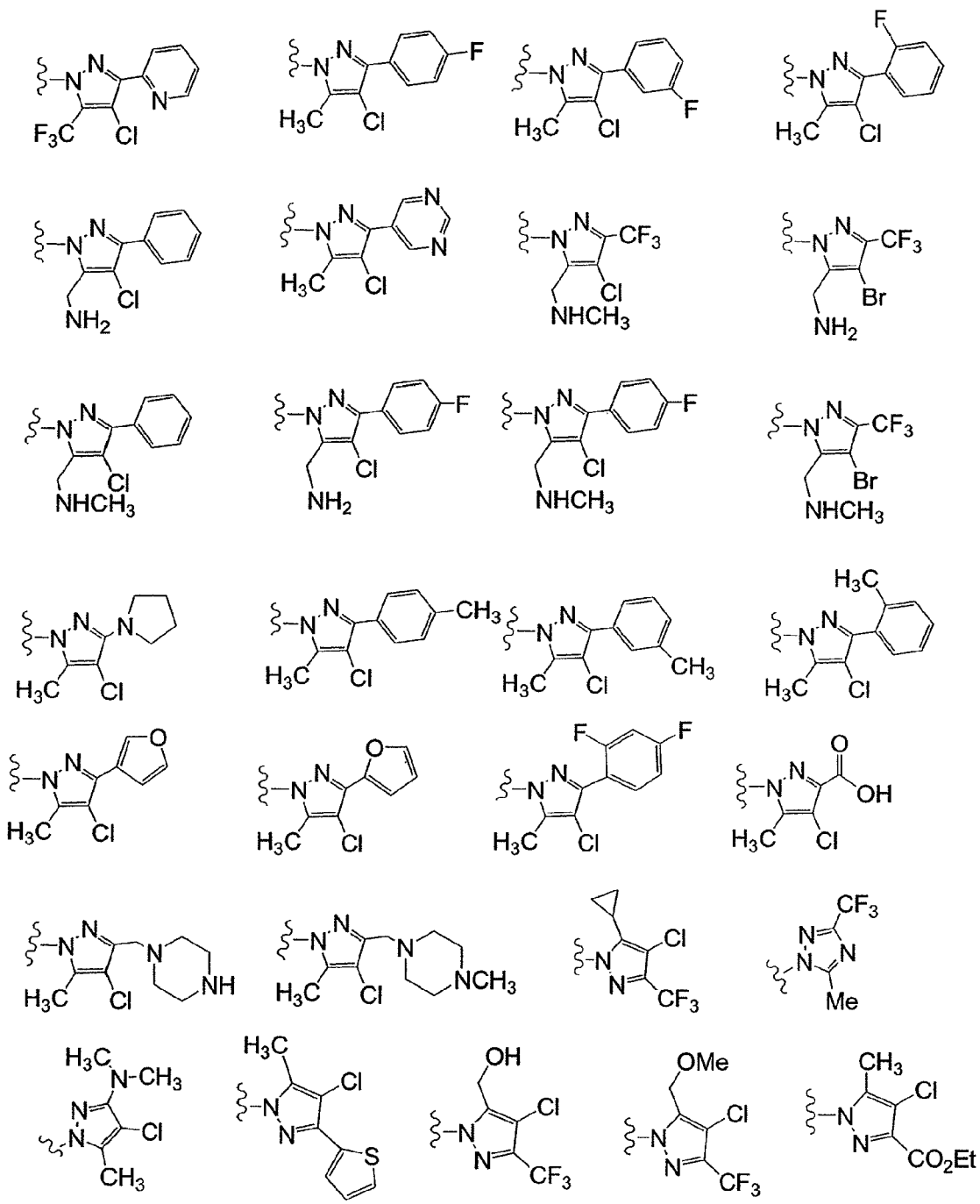
Figure 2D:
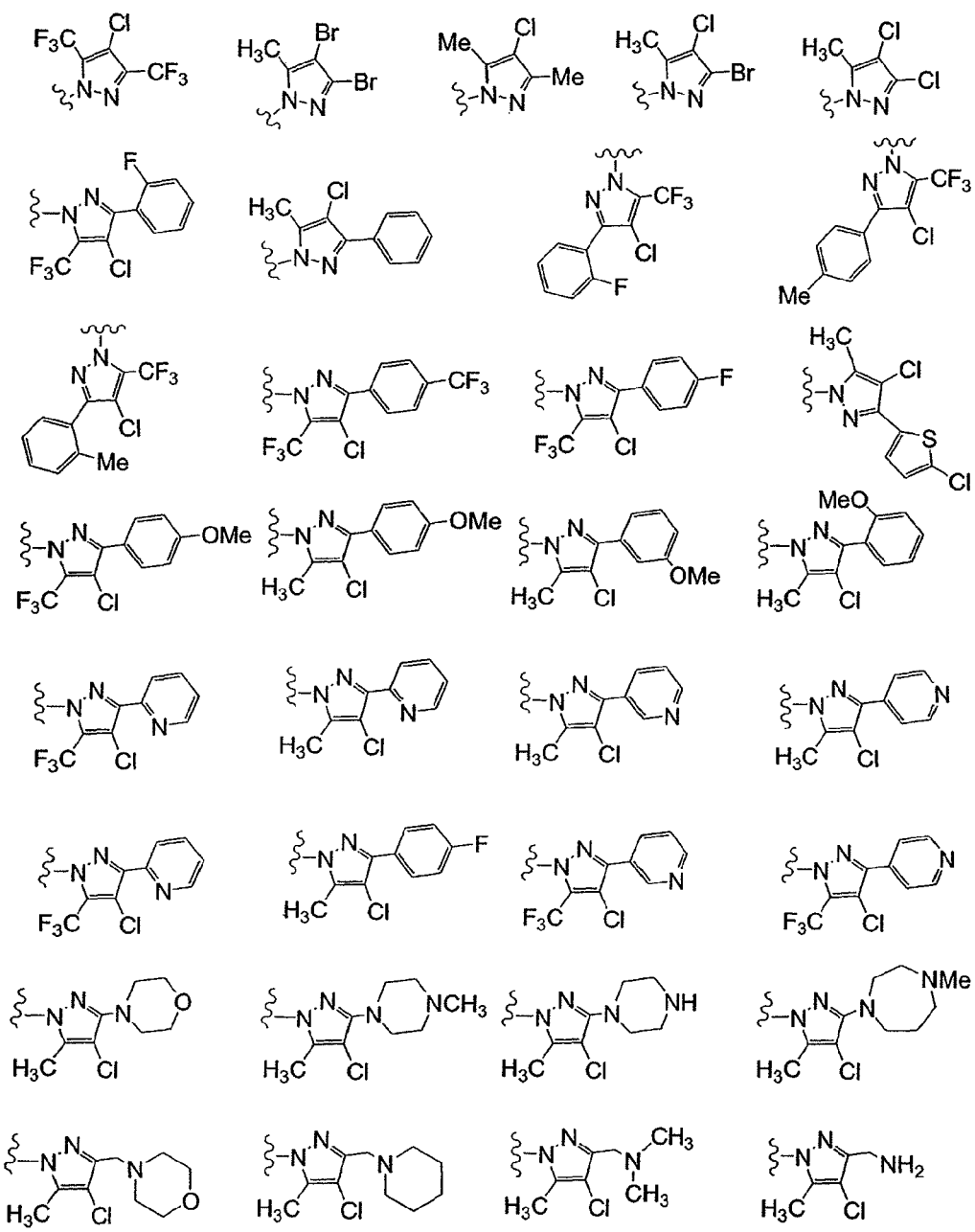
Figure 2E:
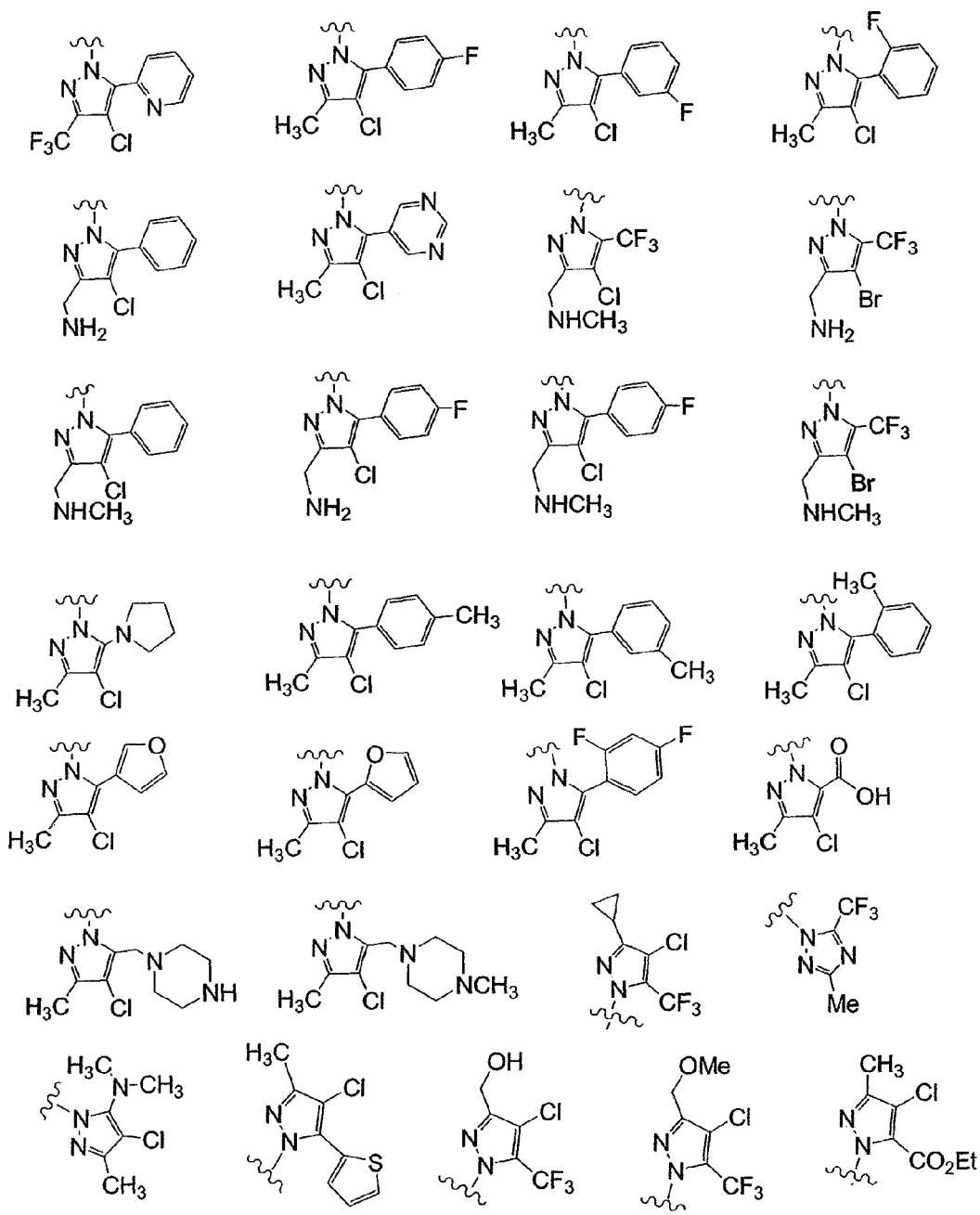
Figure 2F:
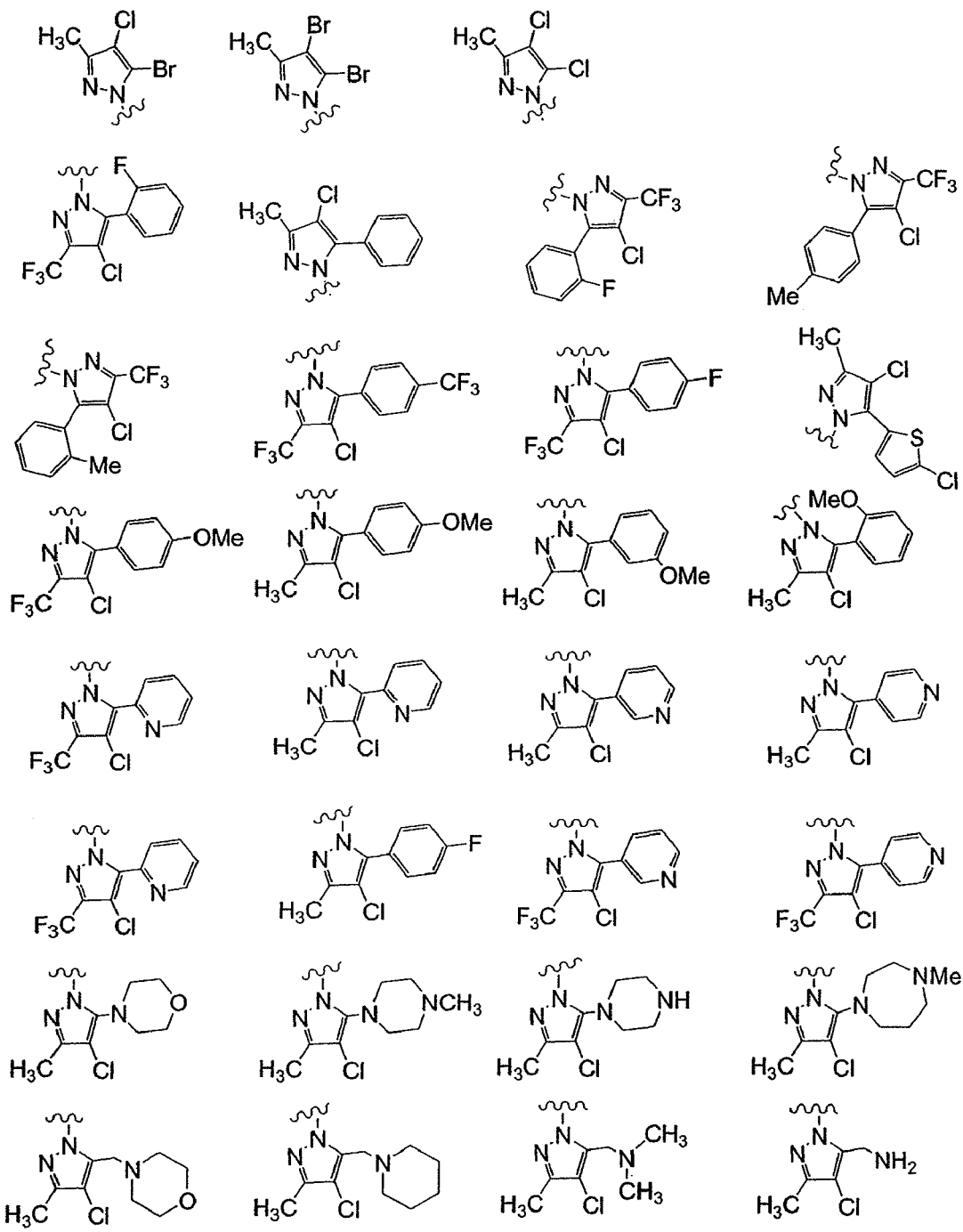
Figure 2G:
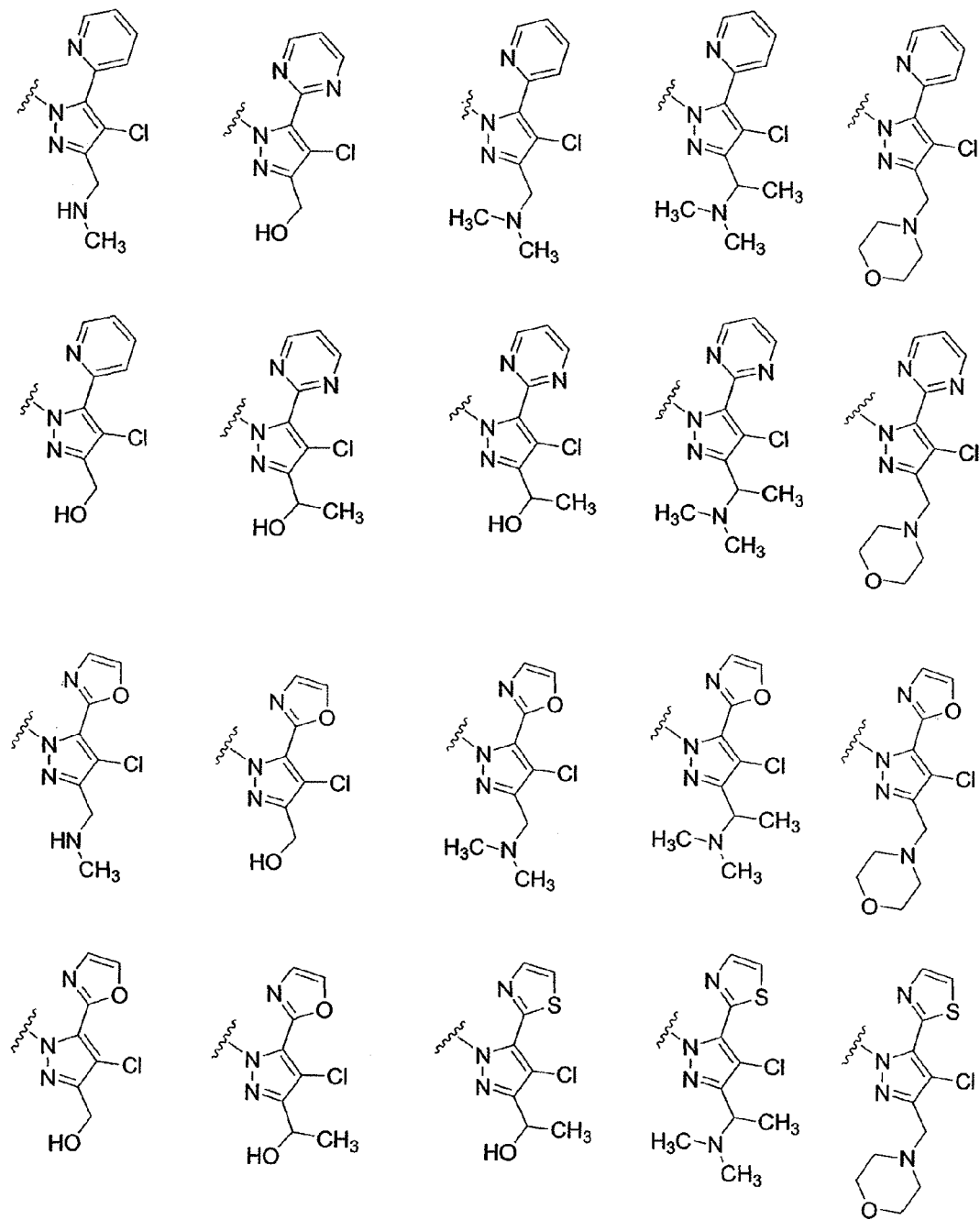
Figure 2H:
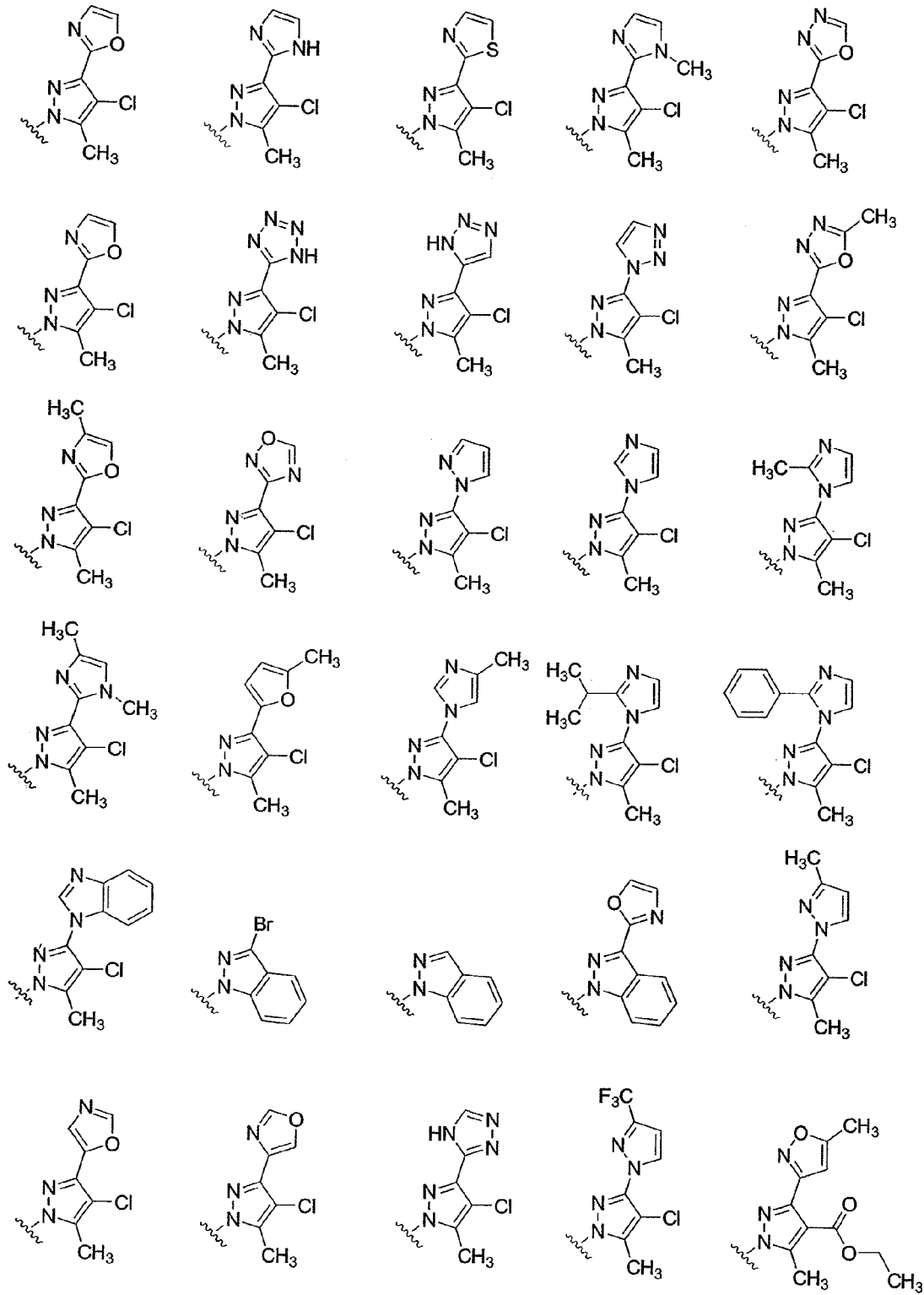
Figure 2I:
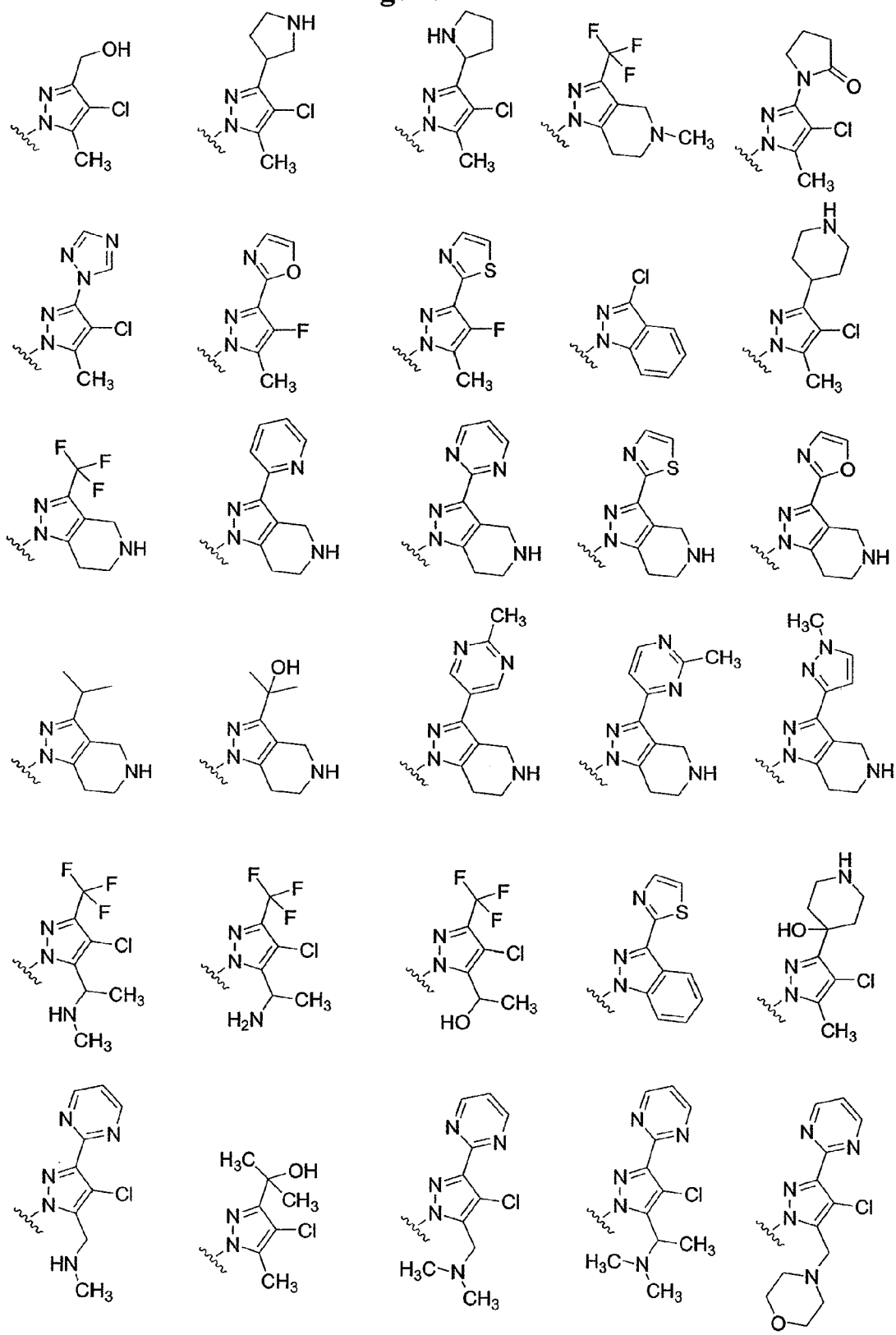
Figure 2J:
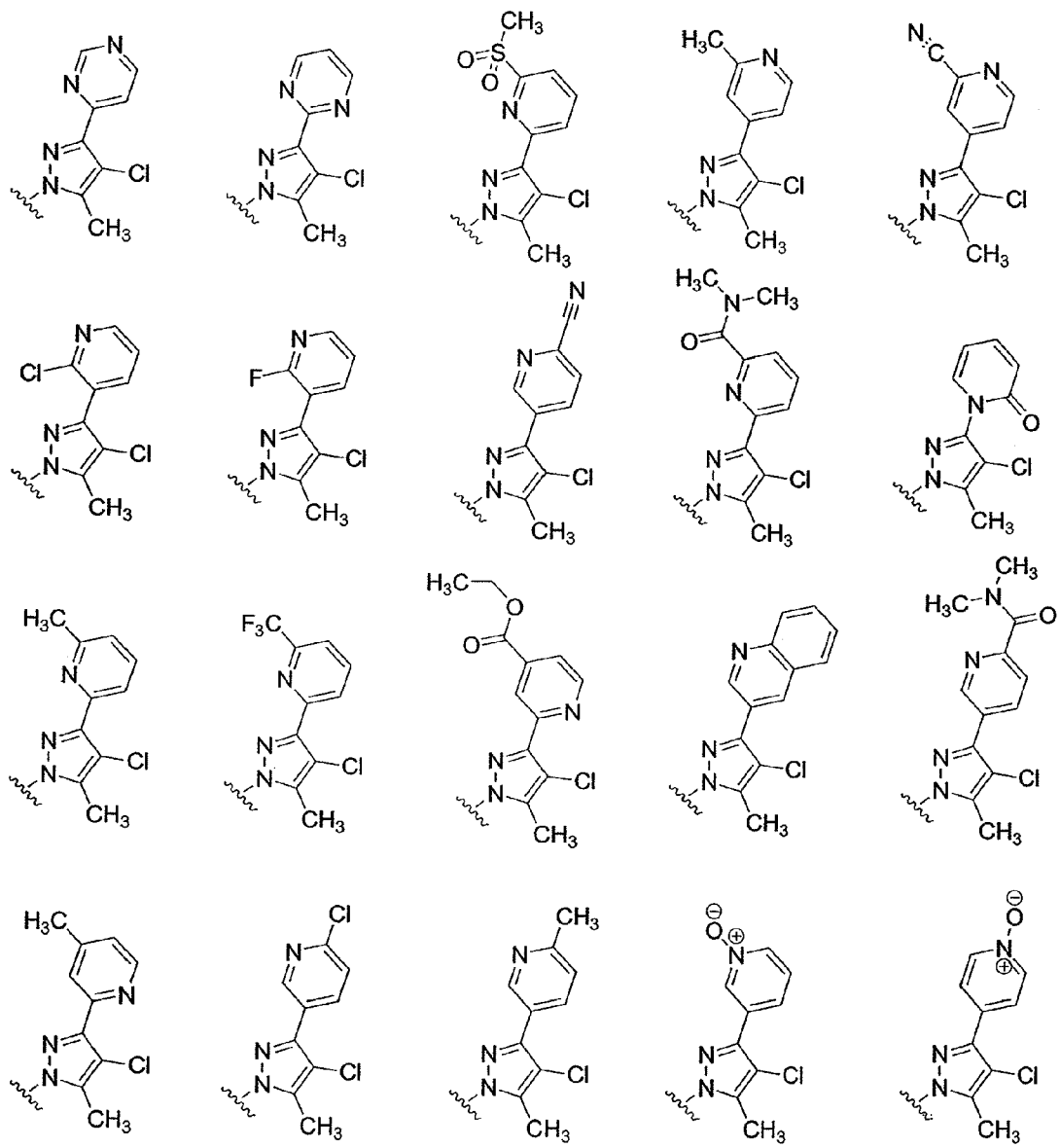
Figure 2K:
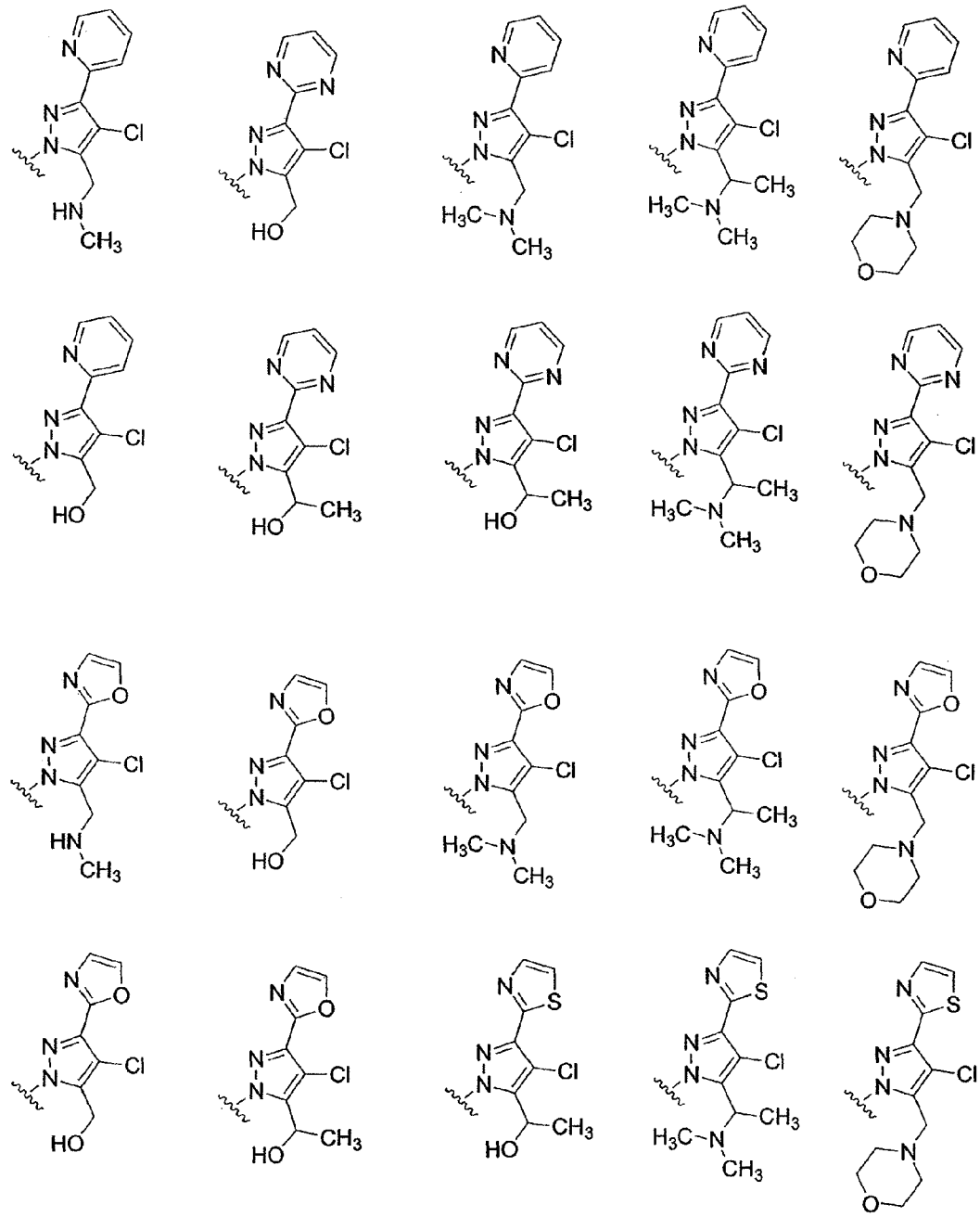
Figure 2L:
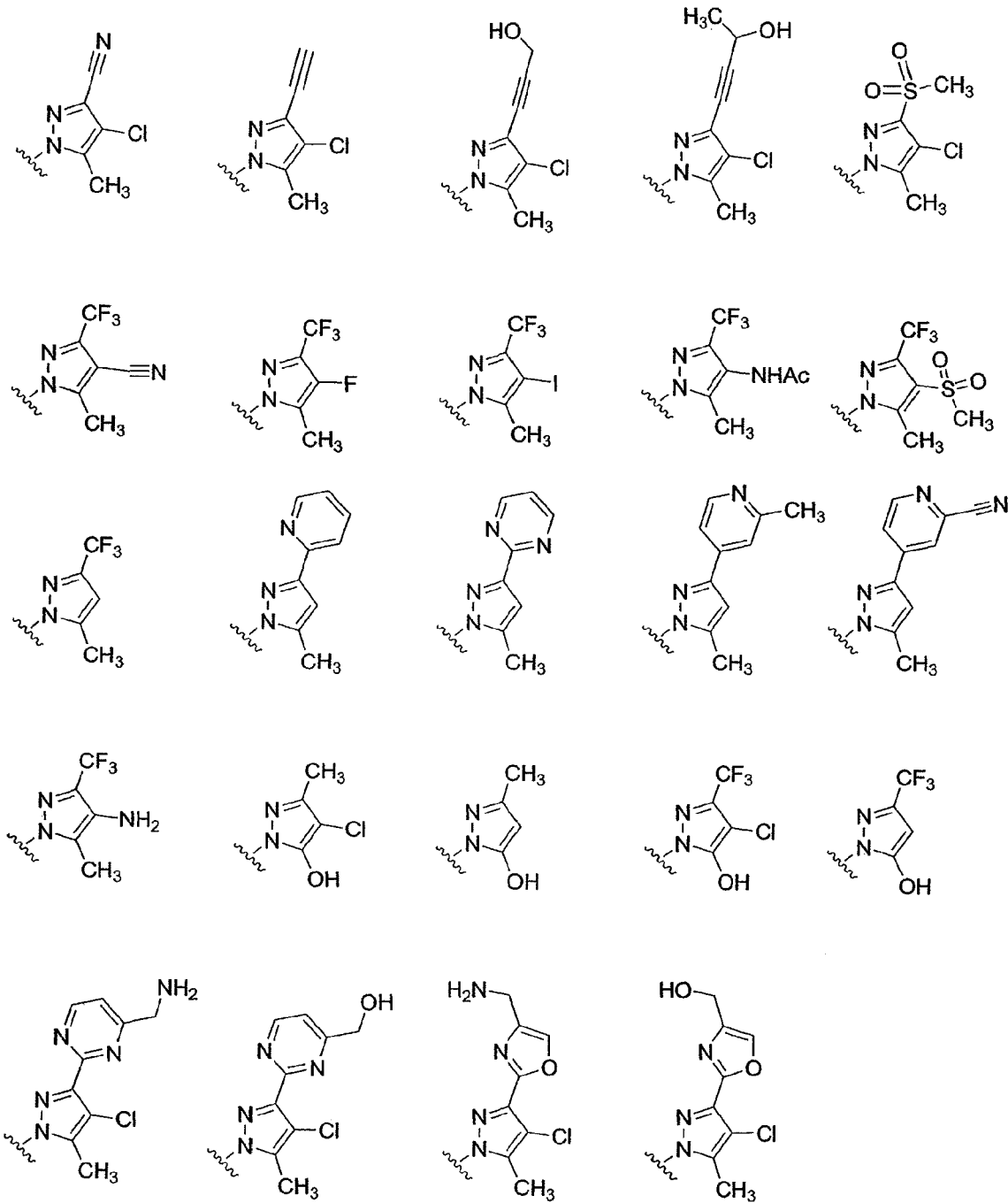
Figure 2M:
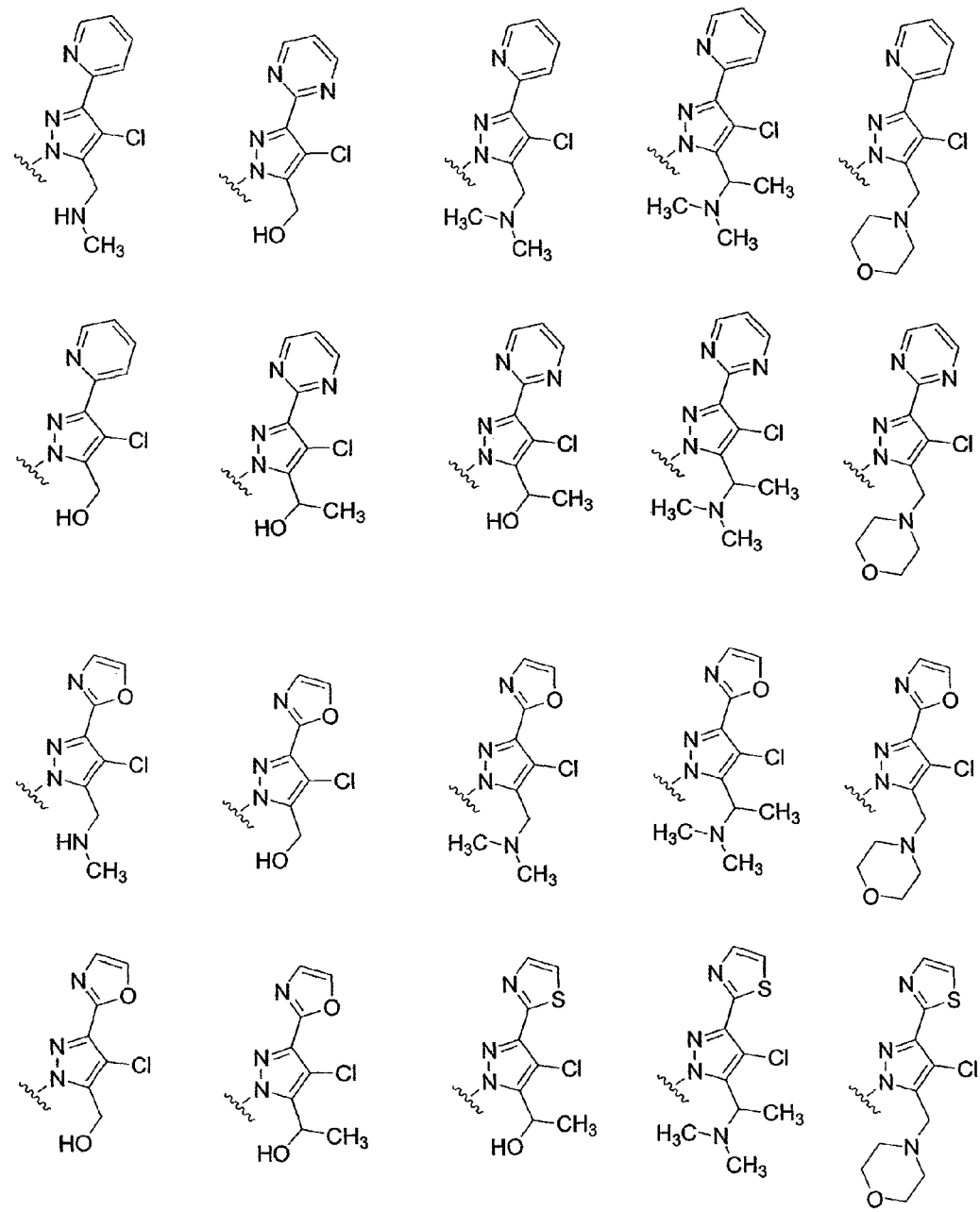
Figure 2N:
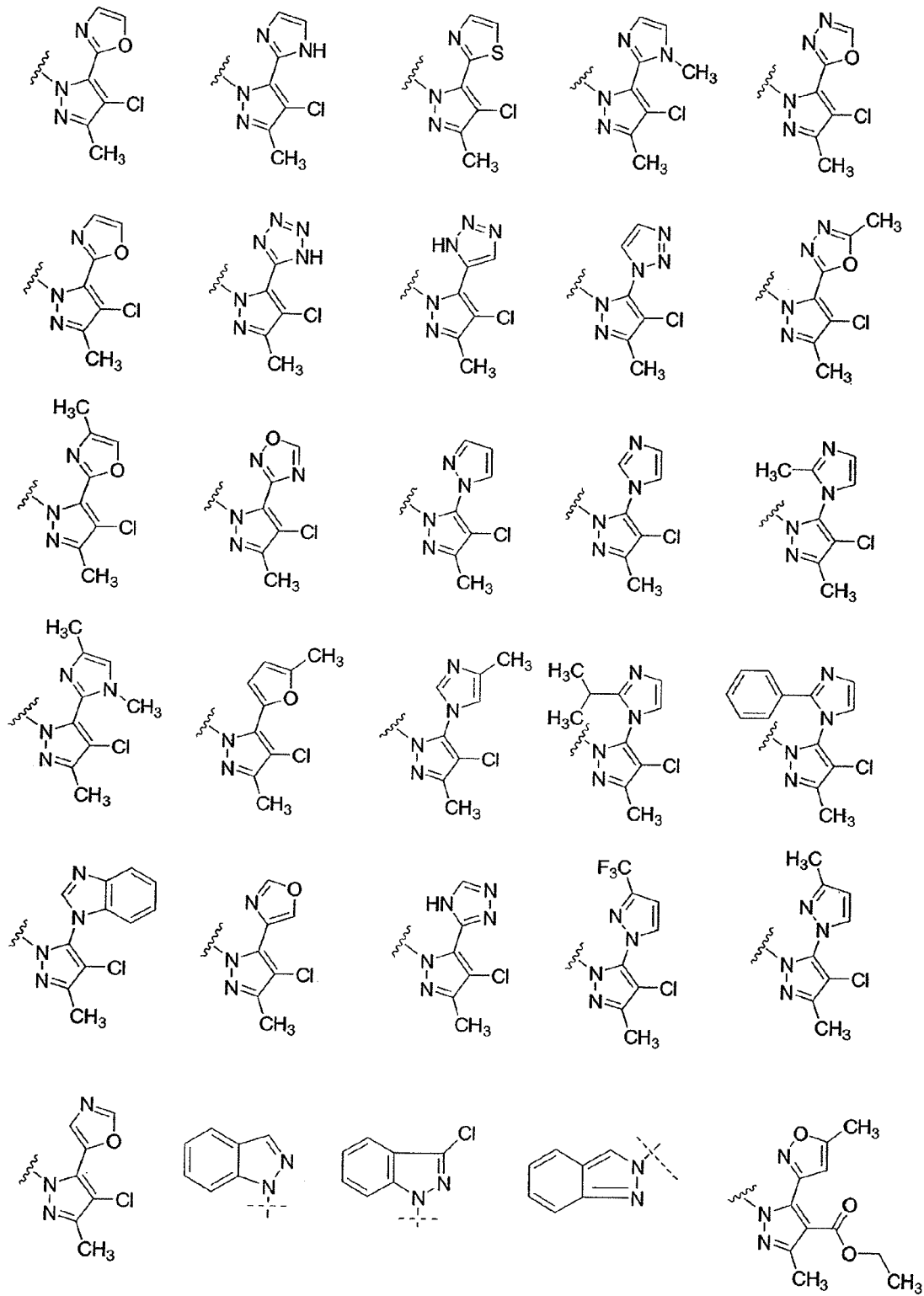
Figure 2O:
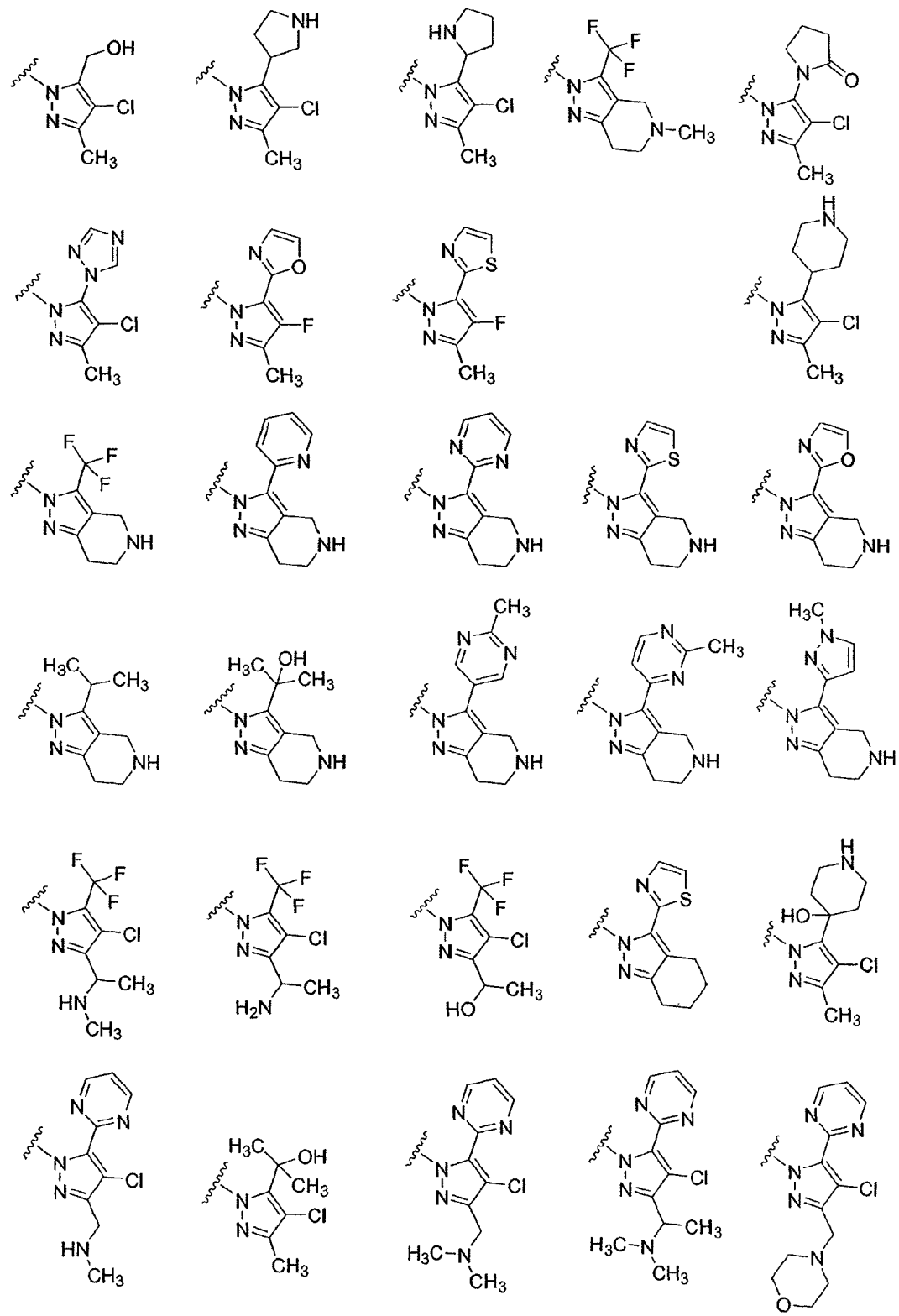
Figure 2P:
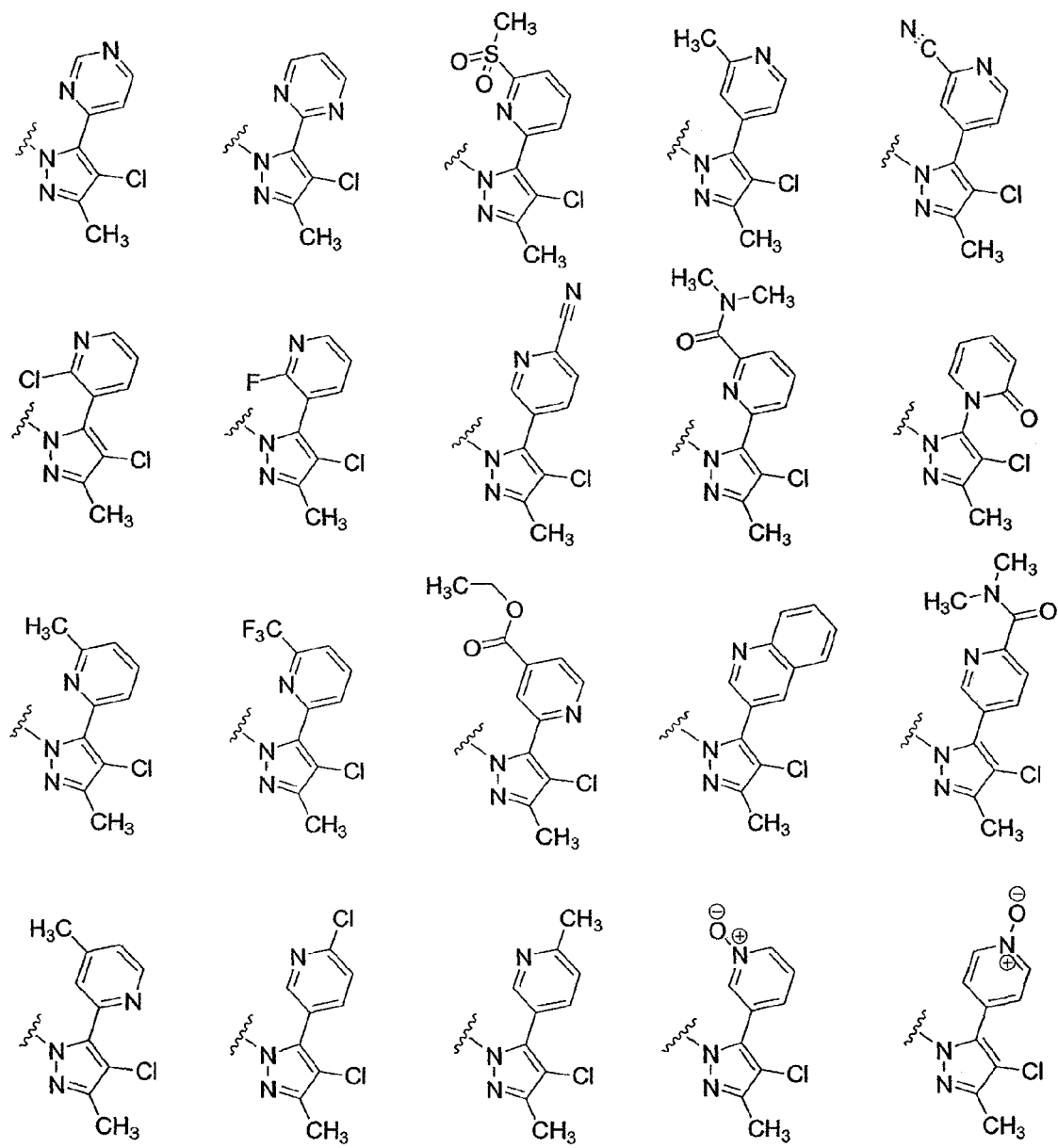
Figure 2Q:
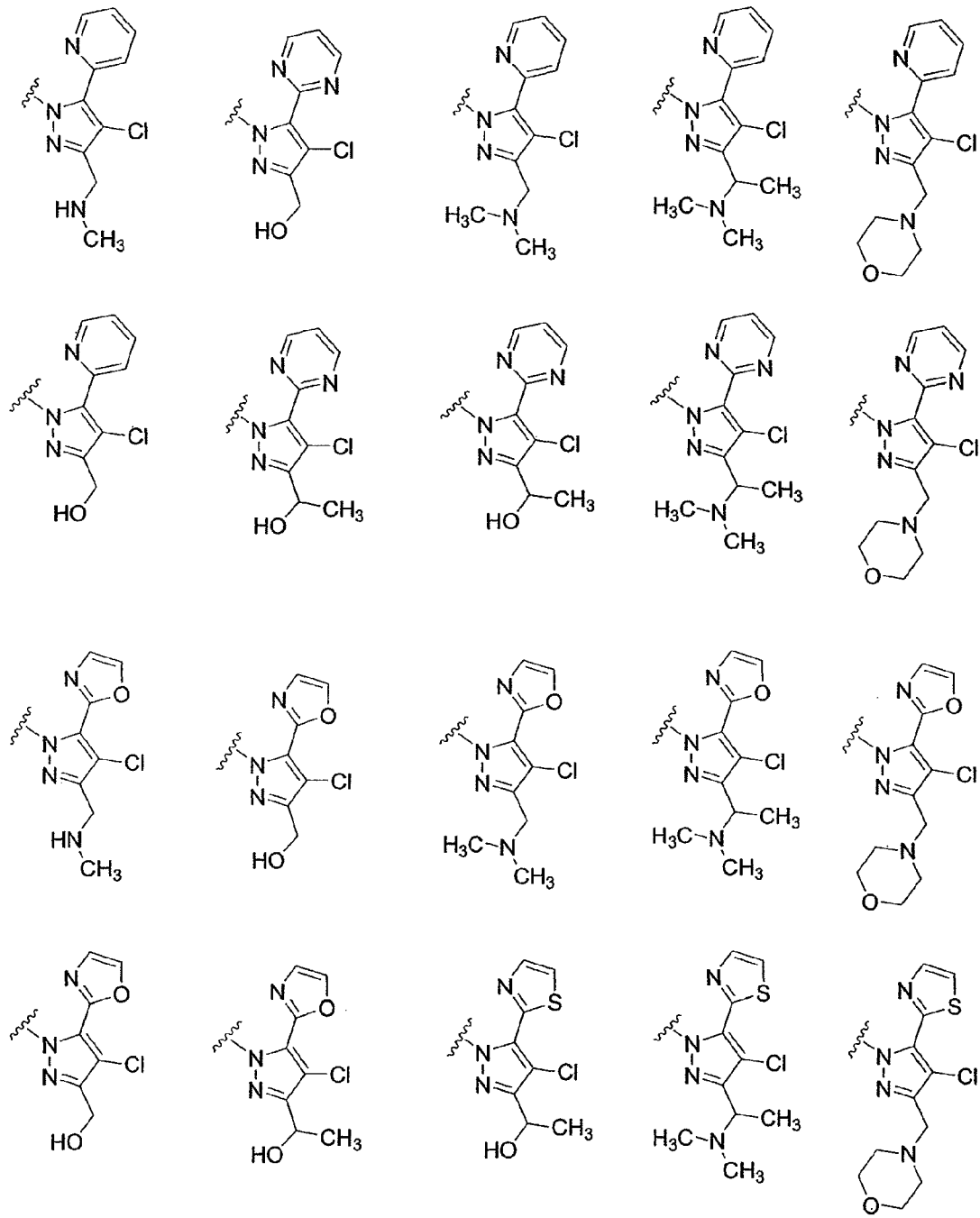
Figure 2R:
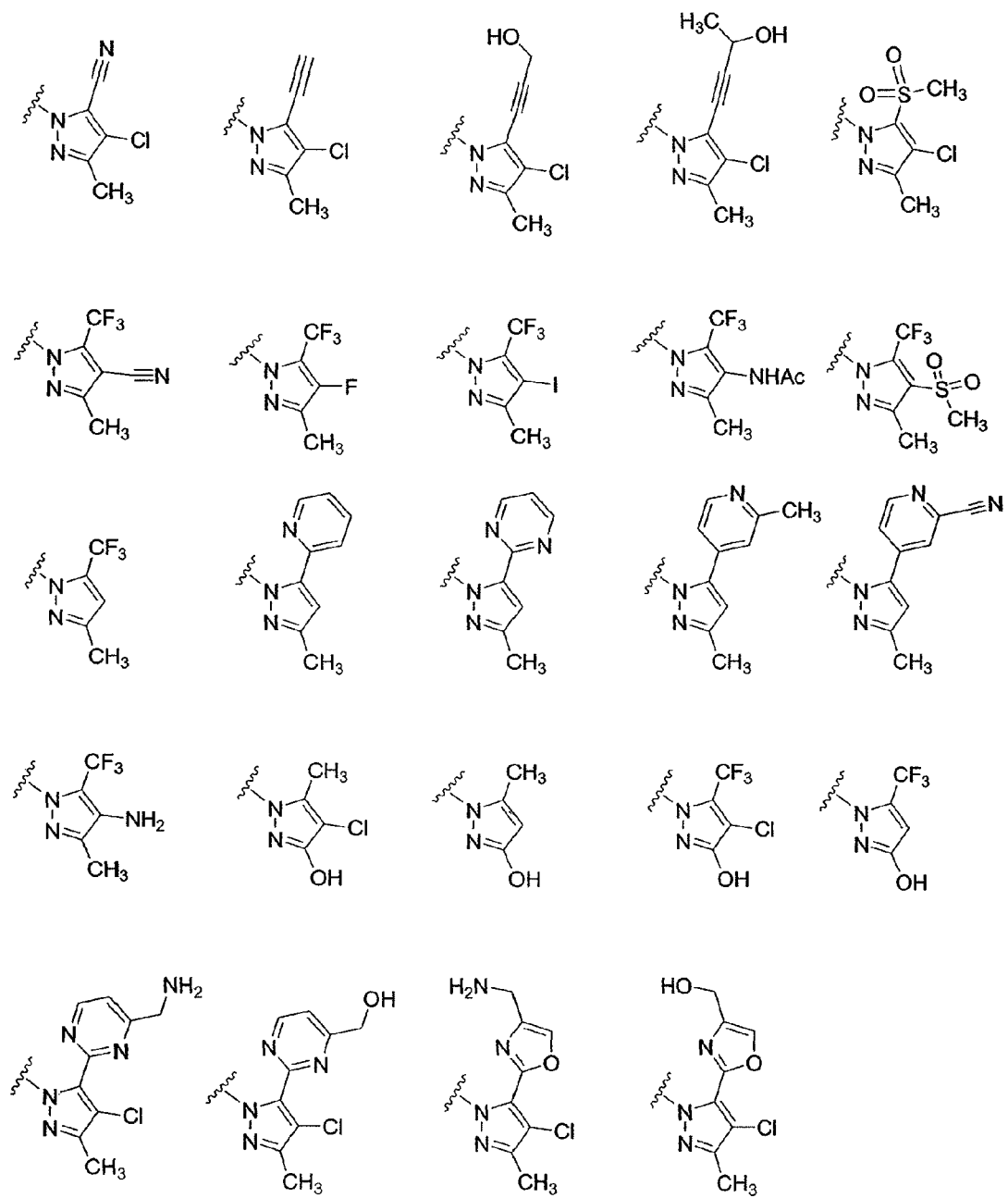
Figure 2S:
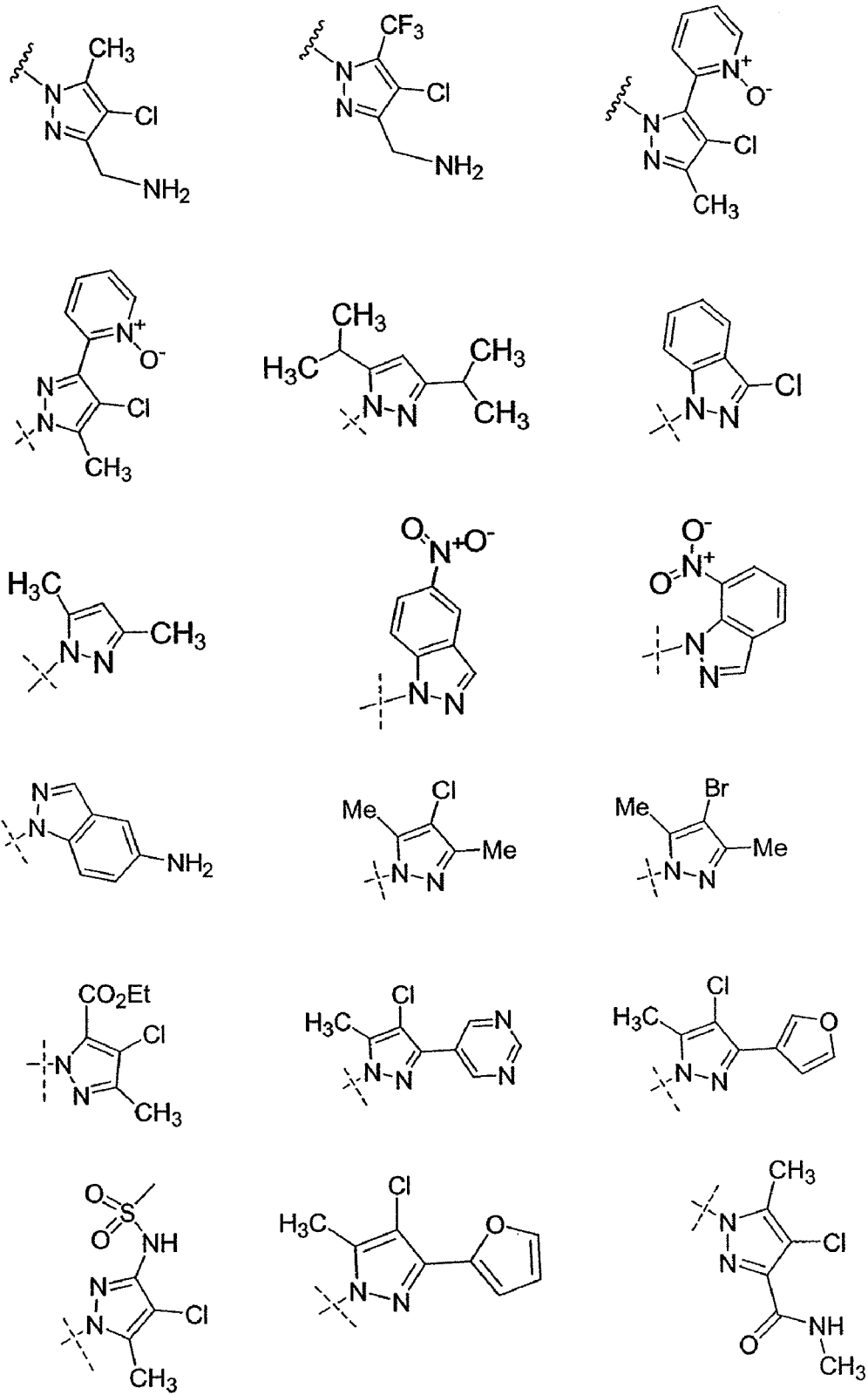
Figure 2T:
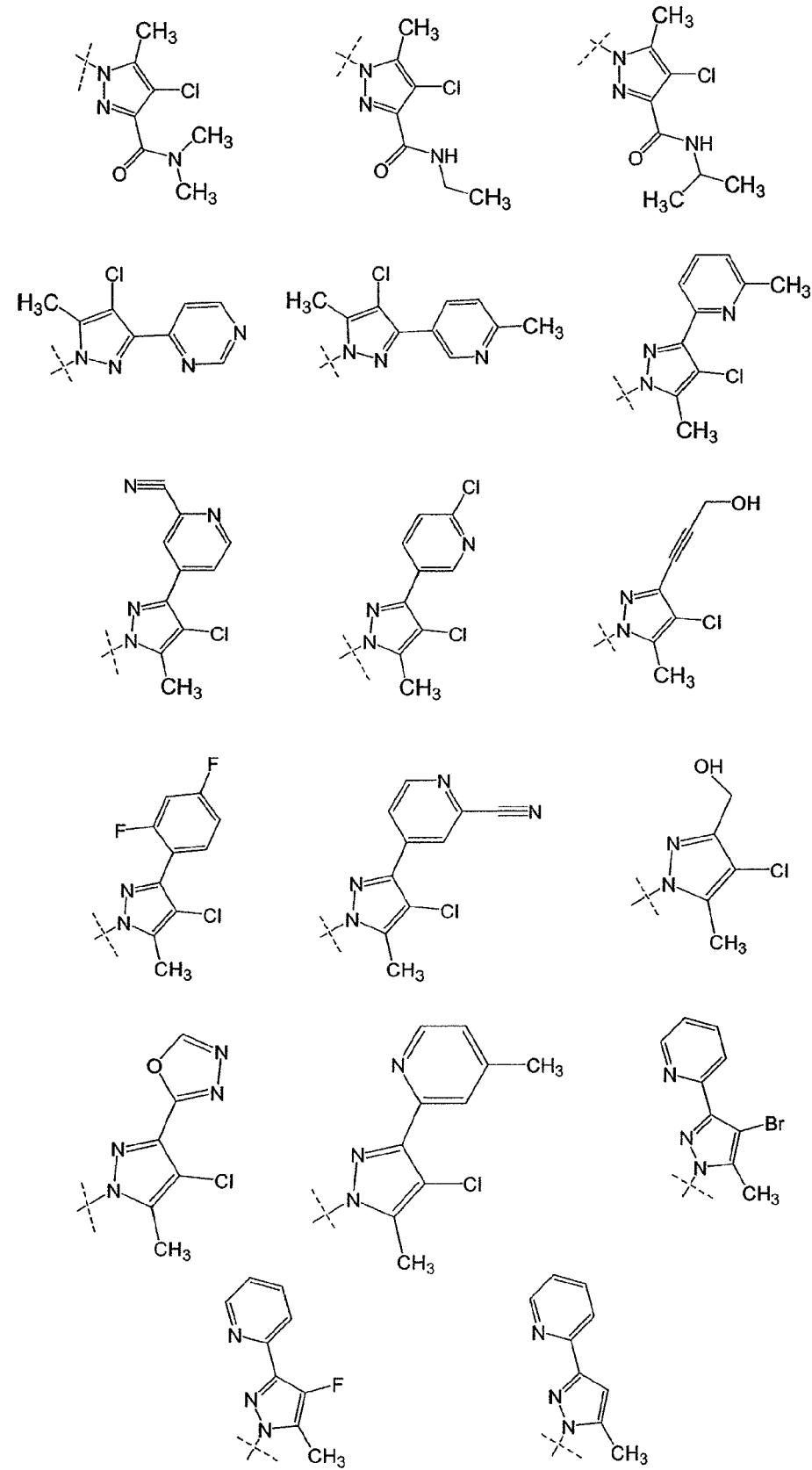
Figure 2U:
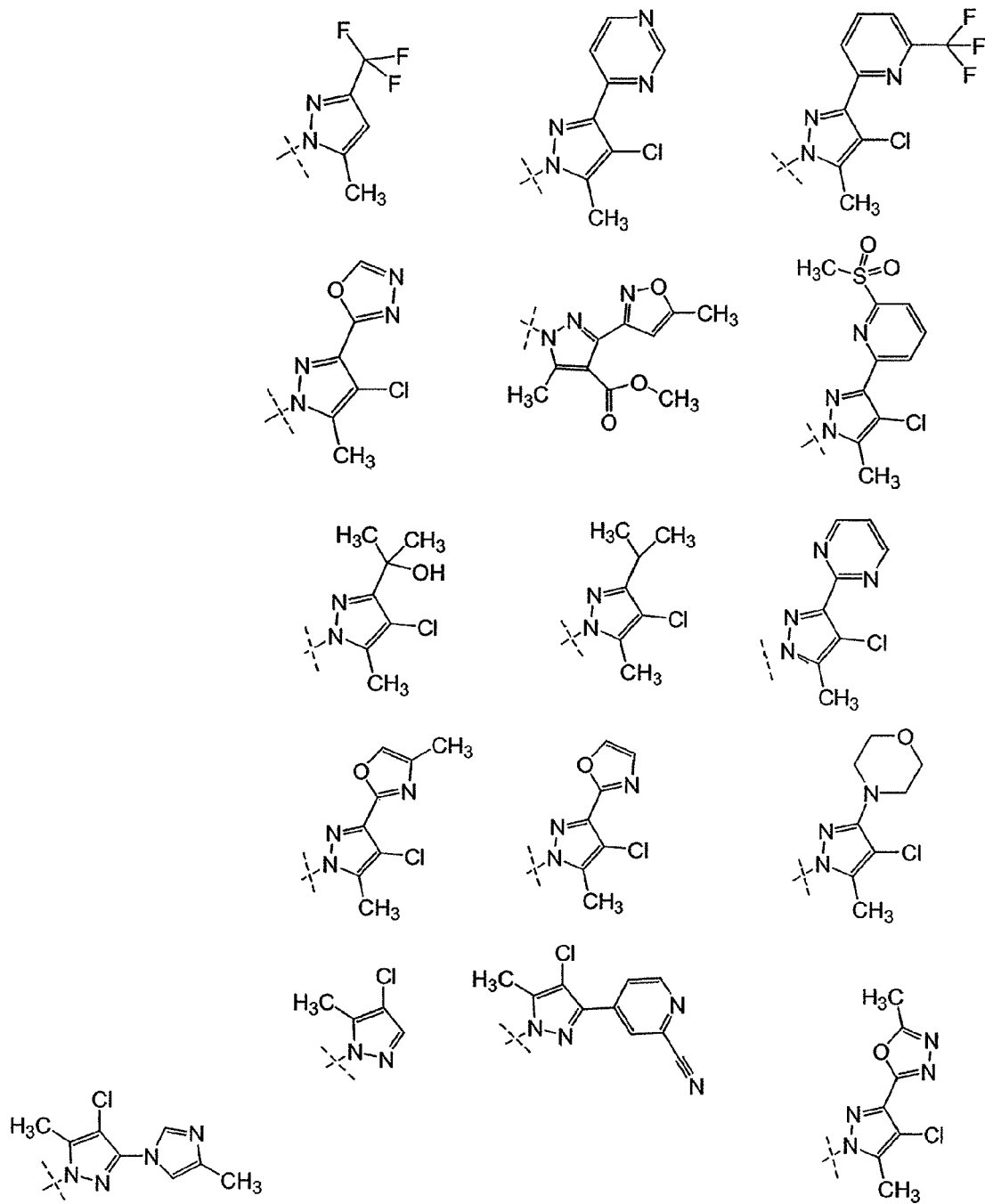
Figure 2V:
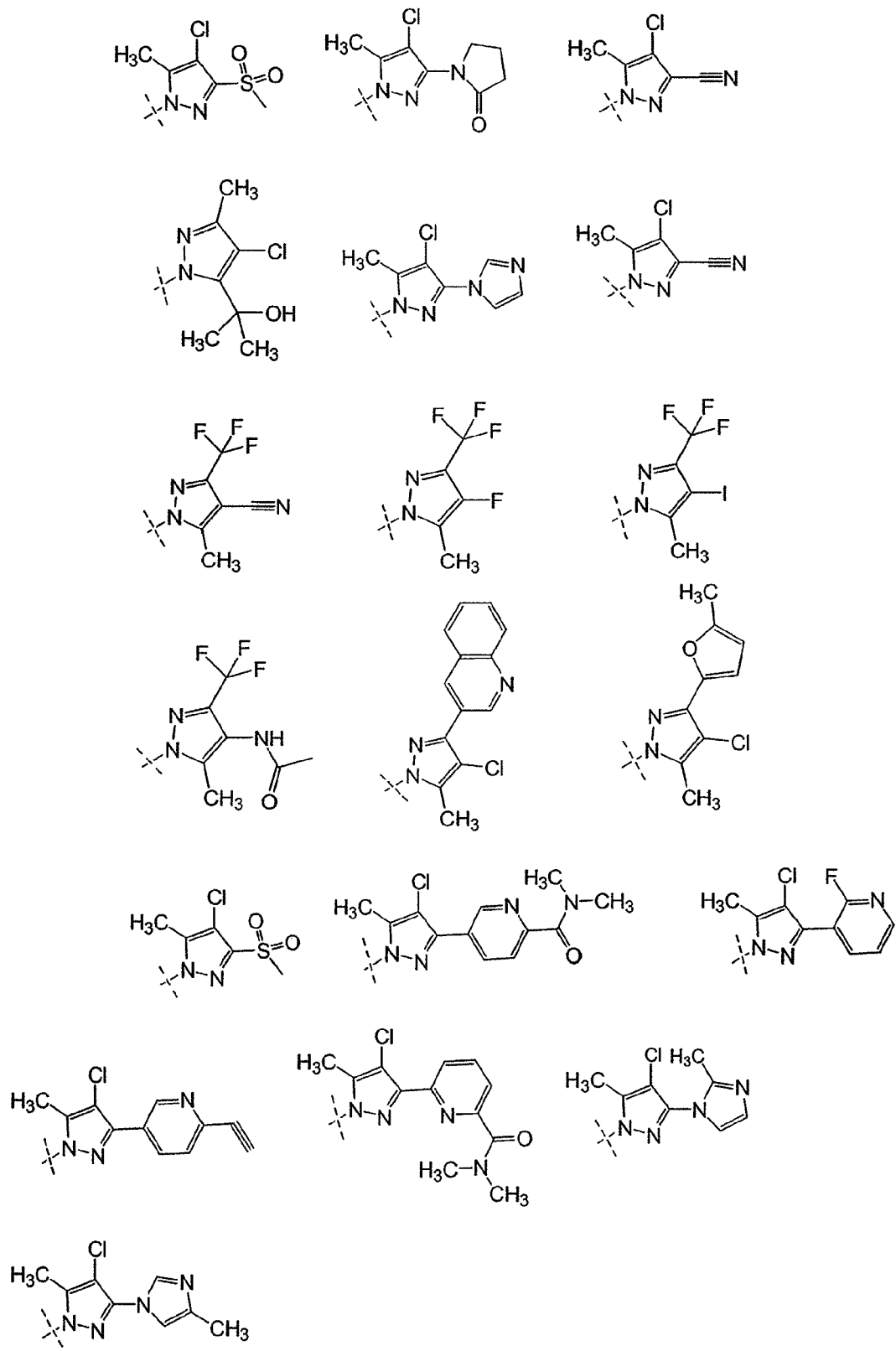
Figure 2W:
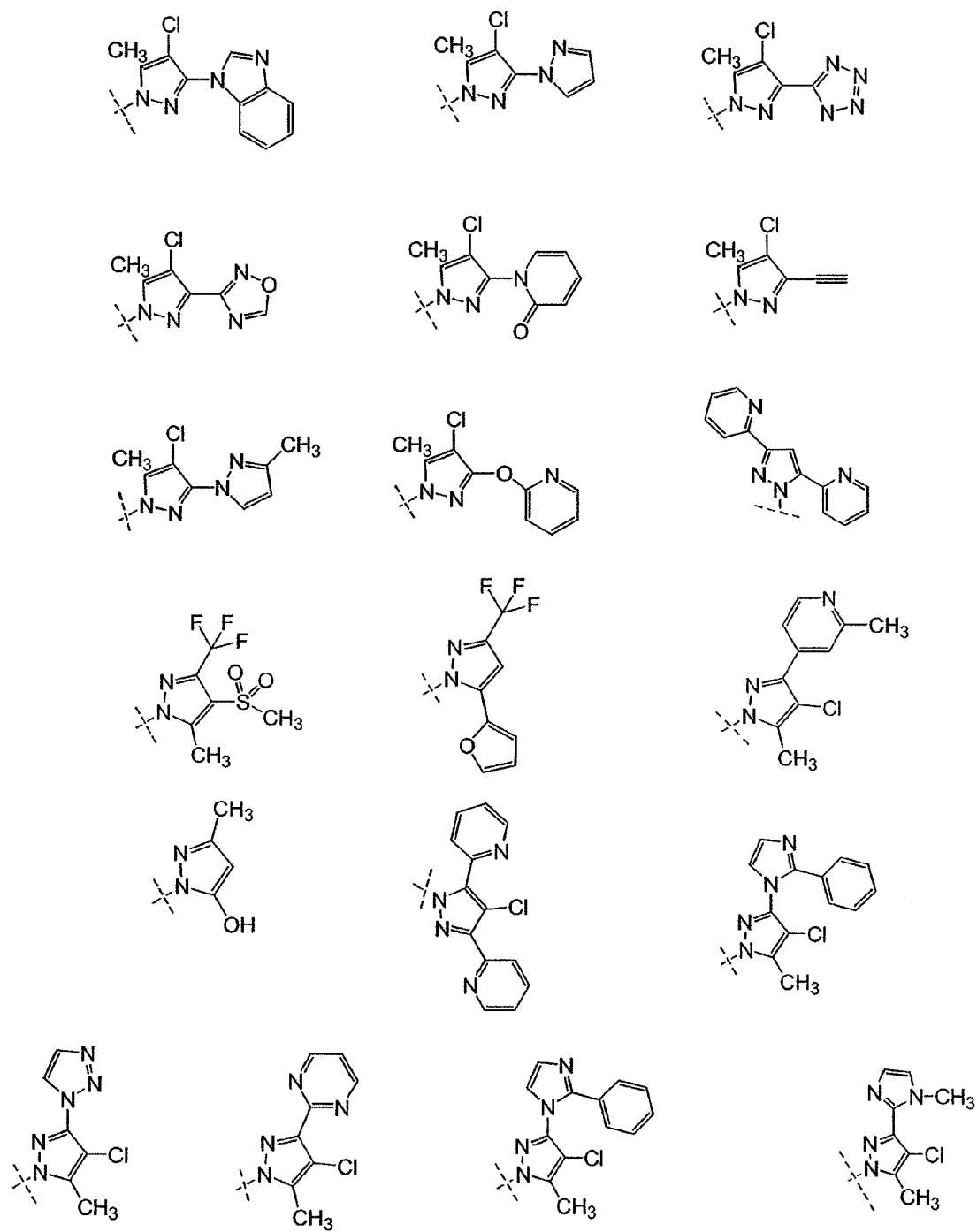
Figure 2X:
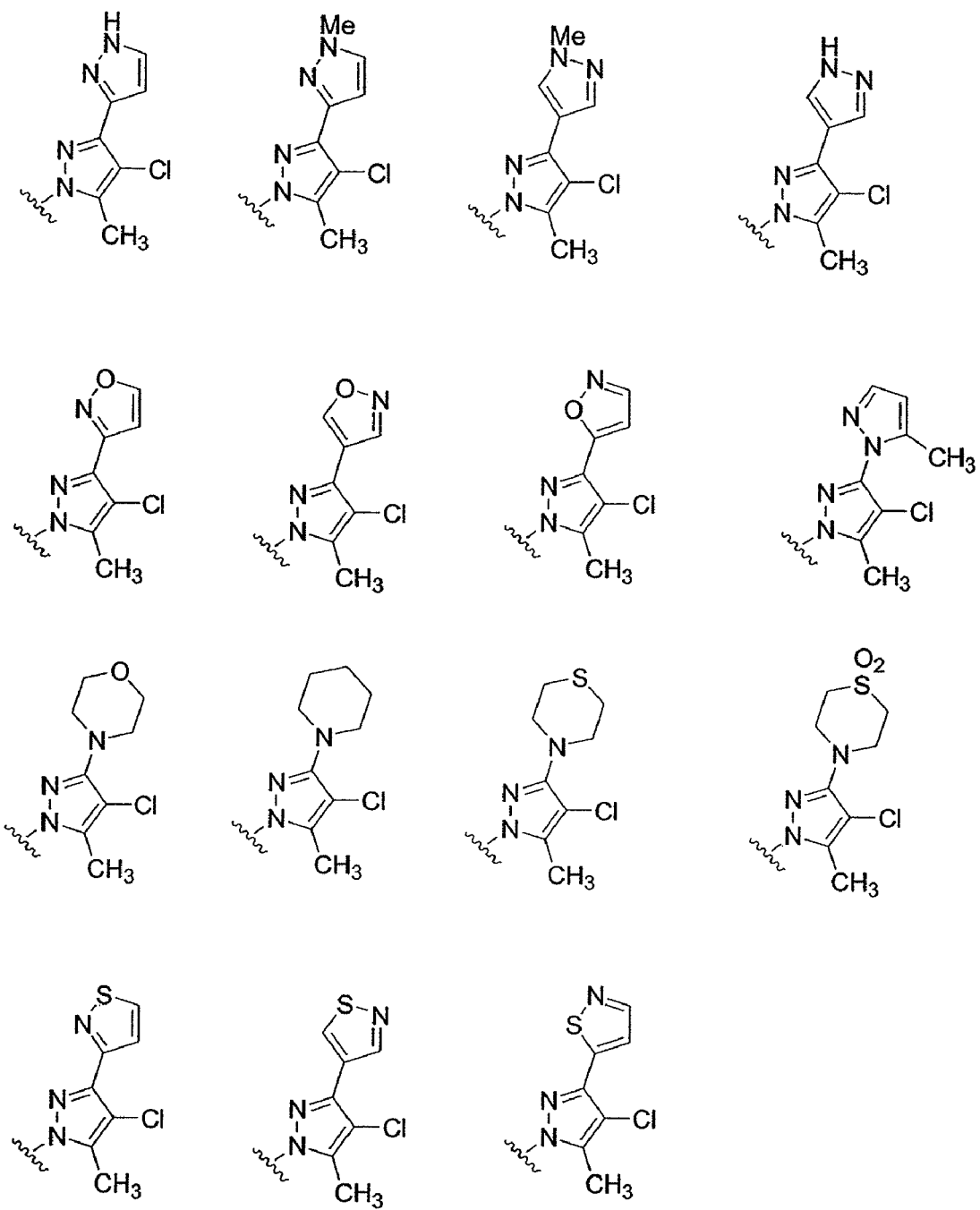
Figure 2Y:
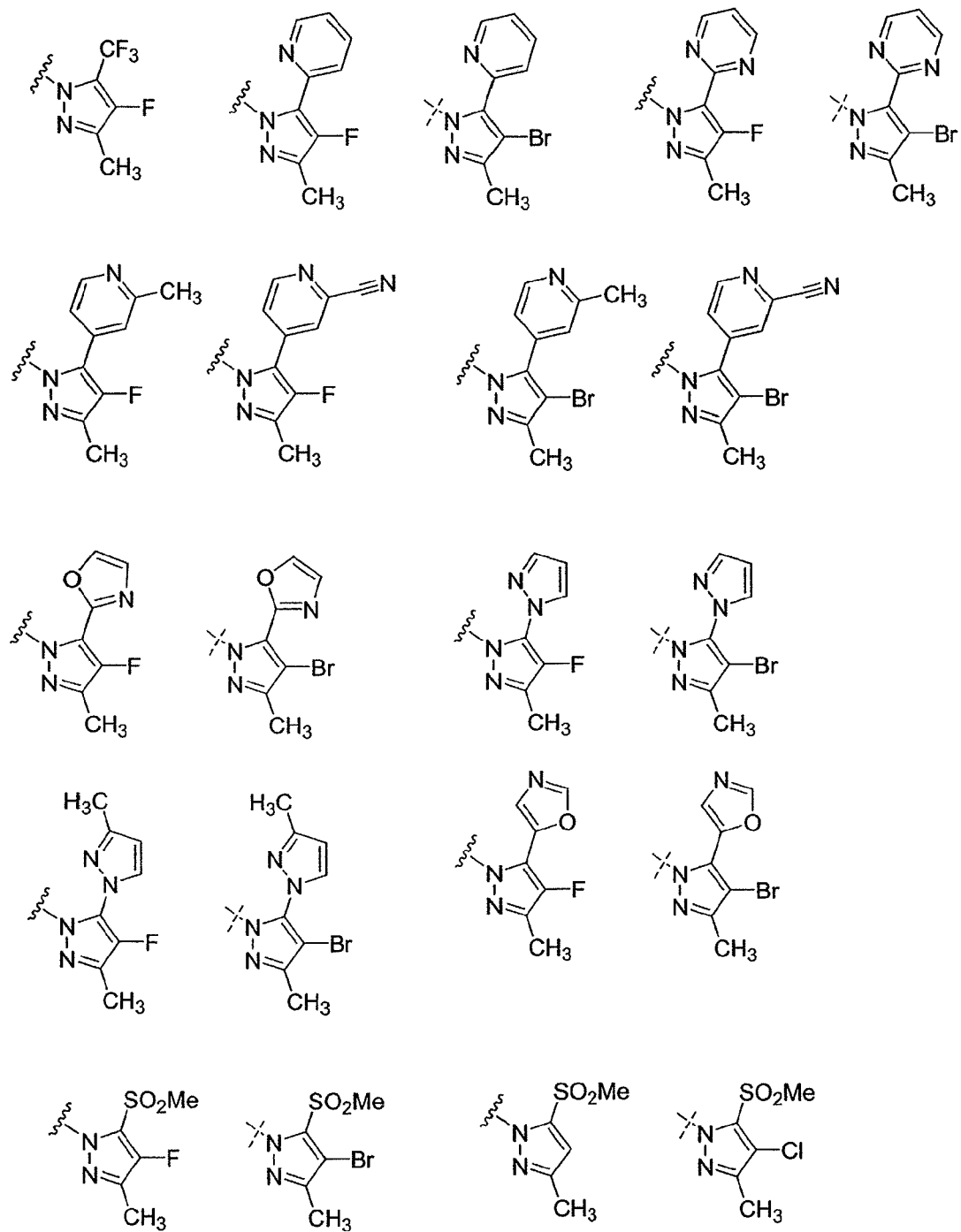
Figure 2Z:
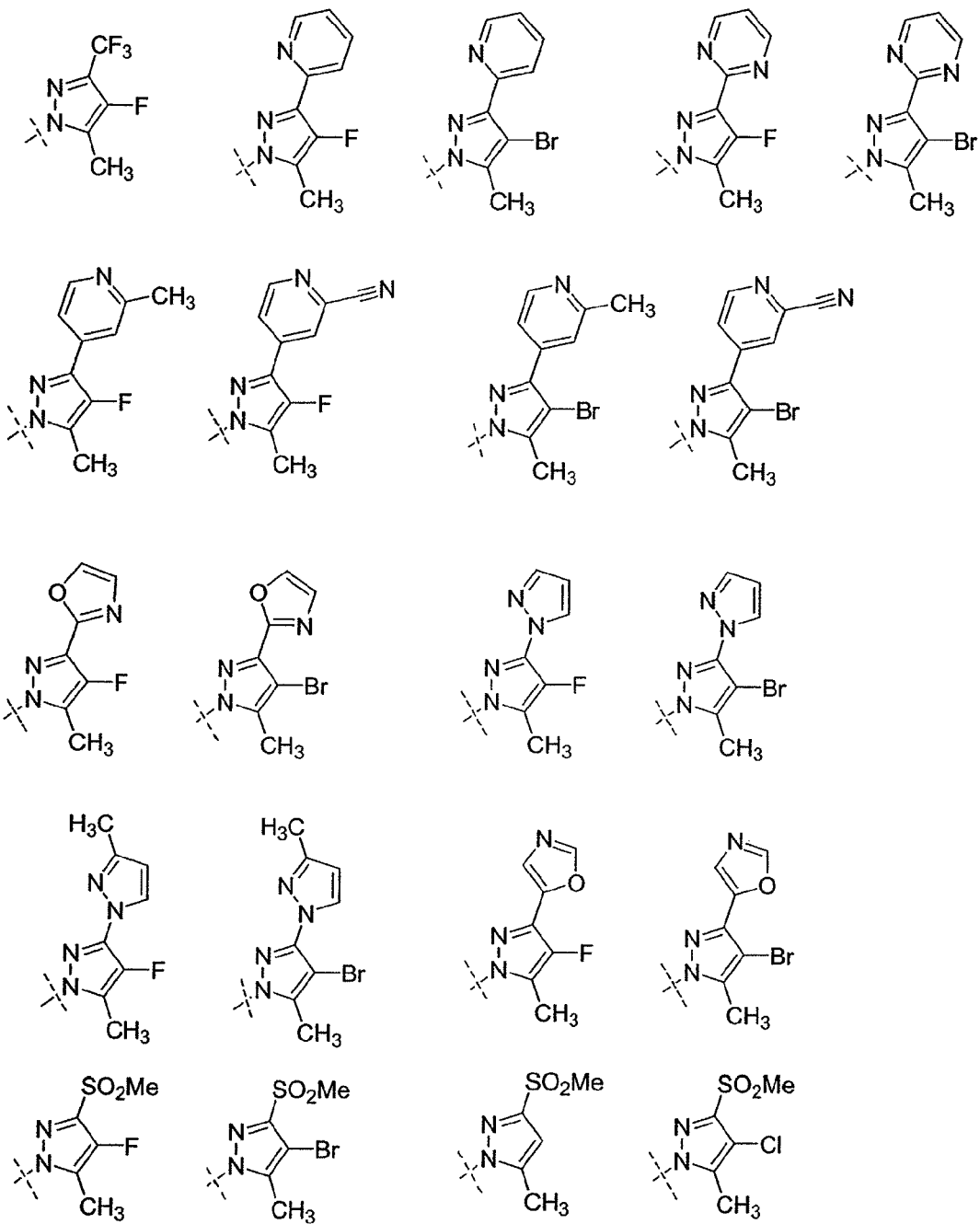
Figure 2A:
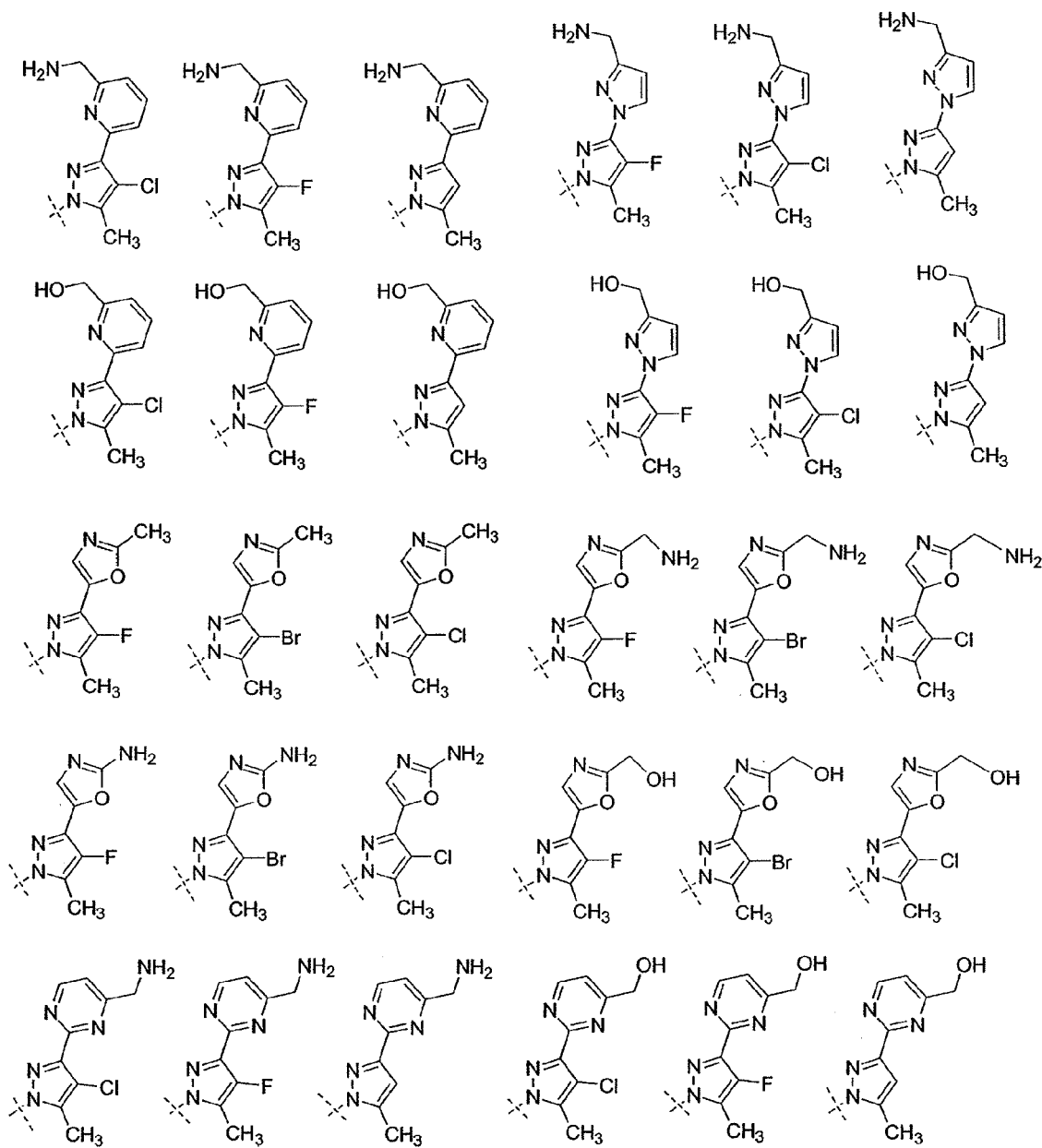
Figure 2B:
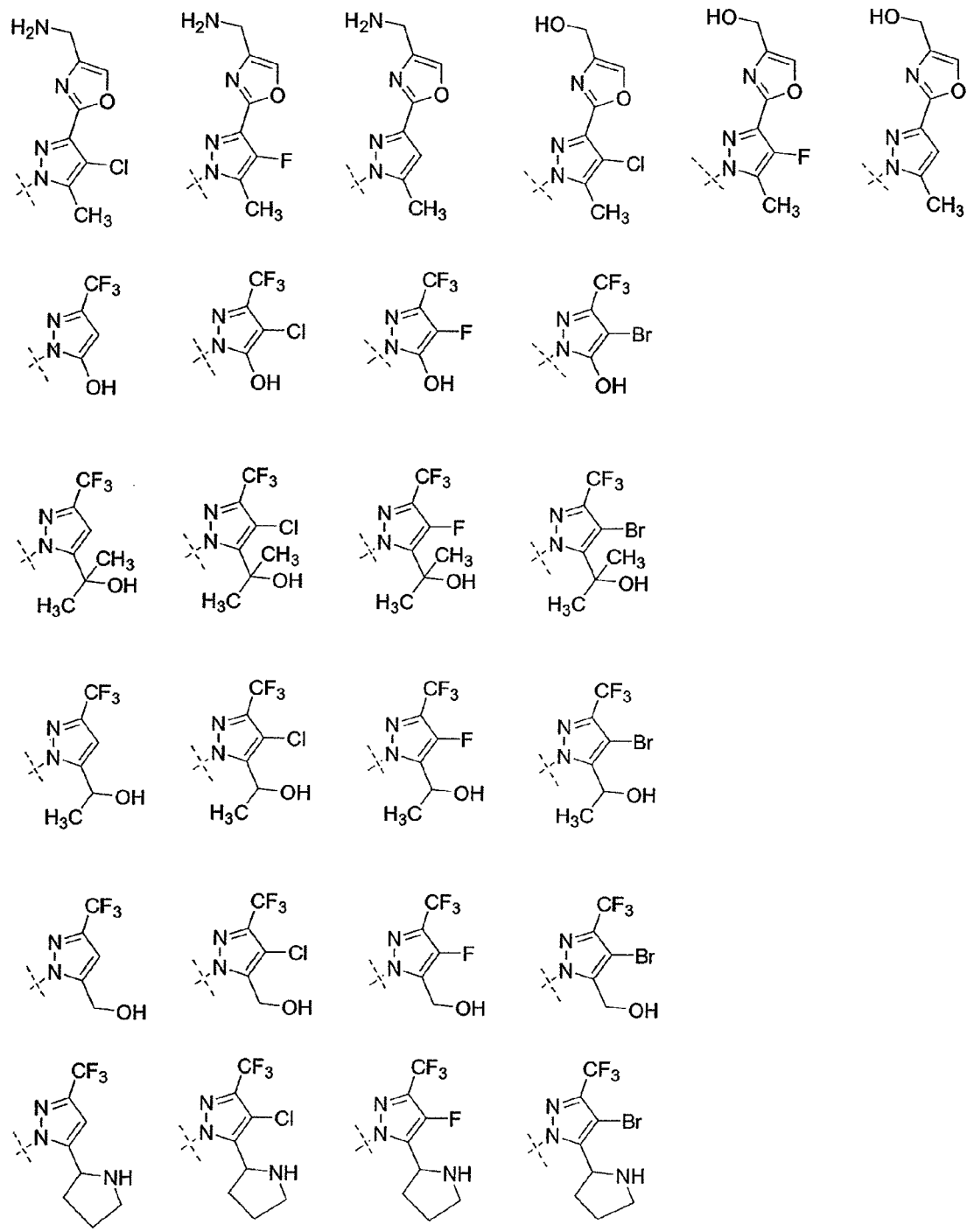
Figure 2C:
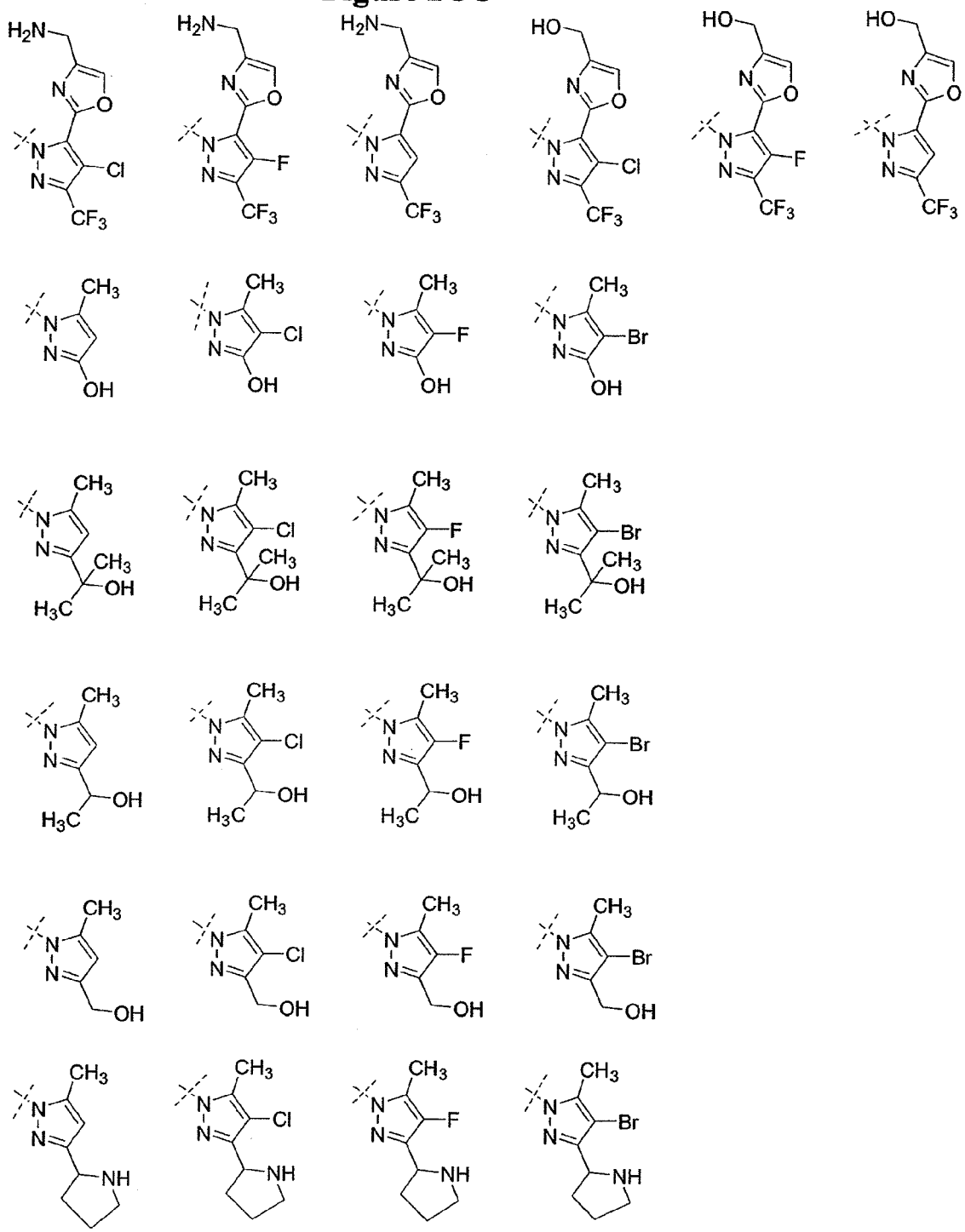
Figure 2D:
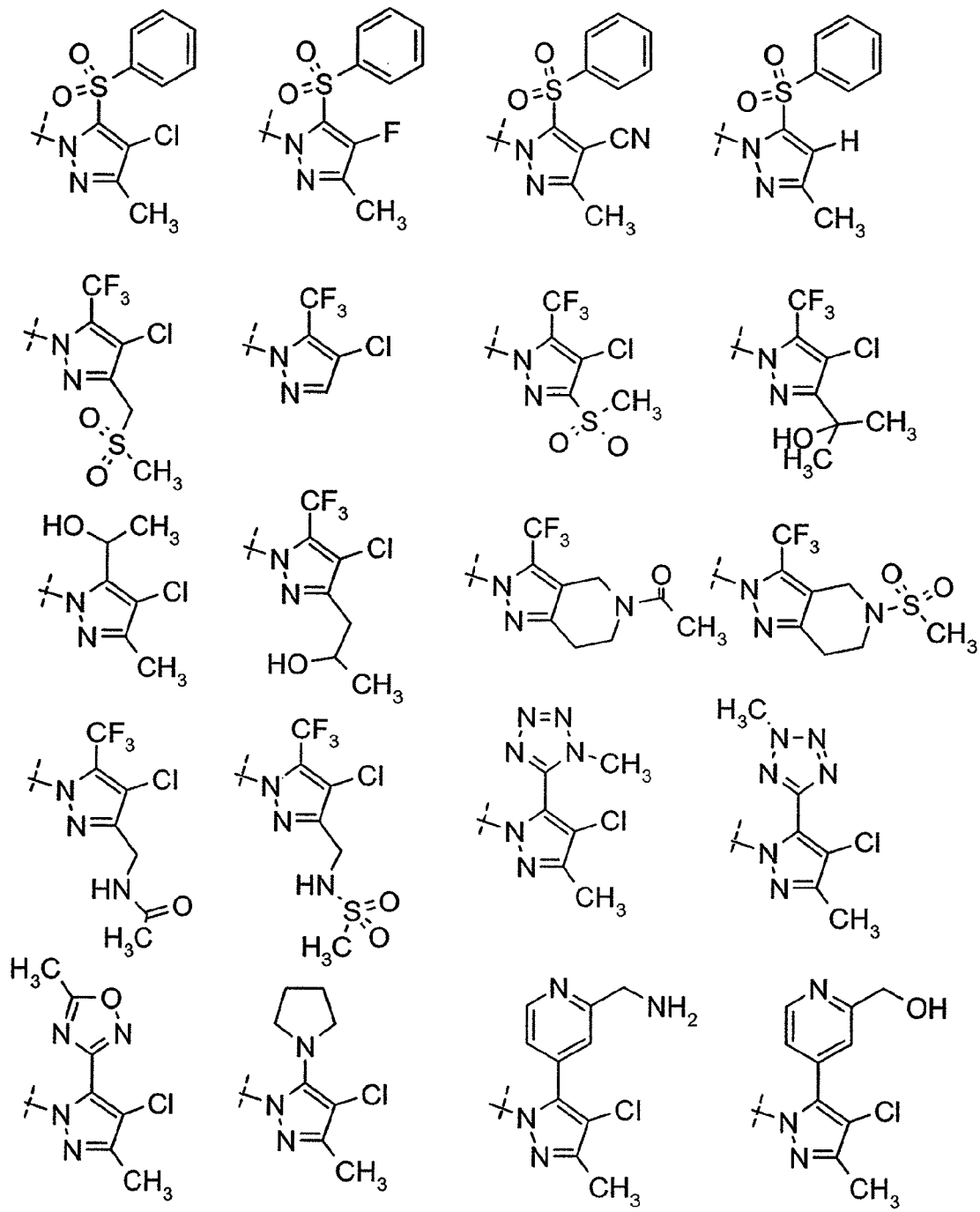
Figure 2E:
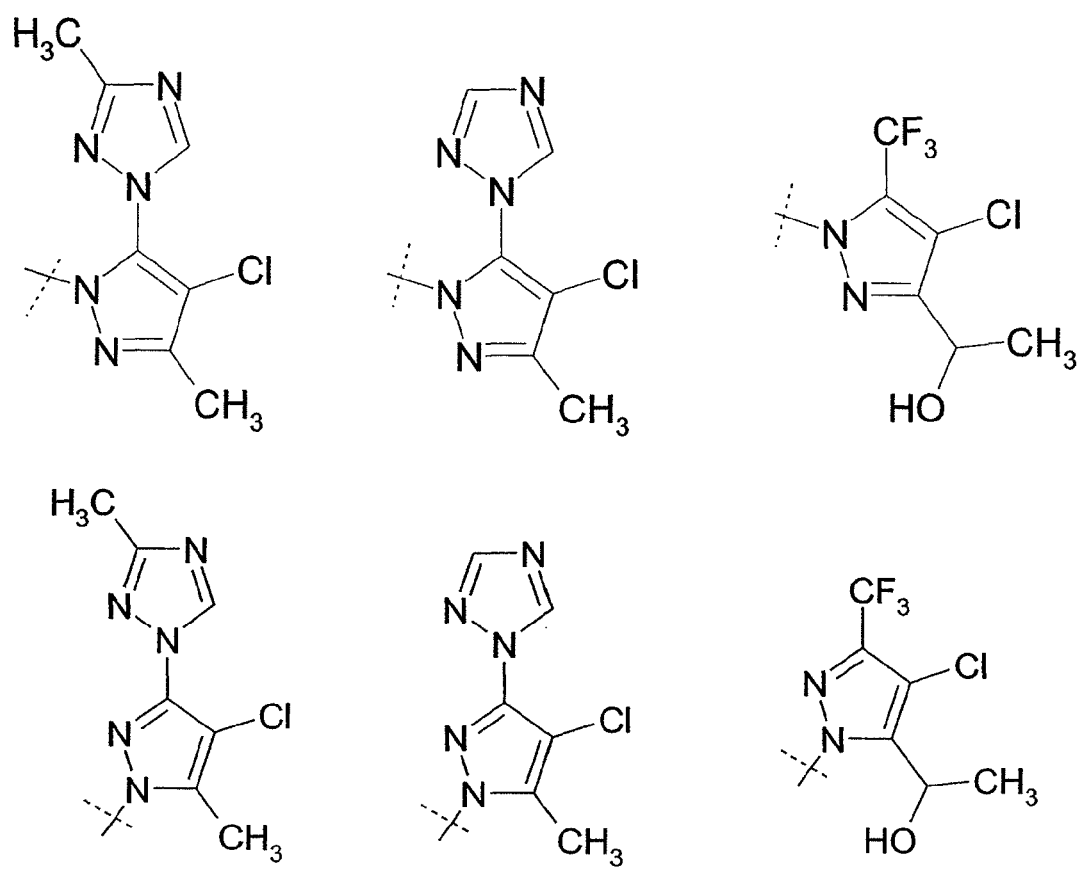
Figure 2F:
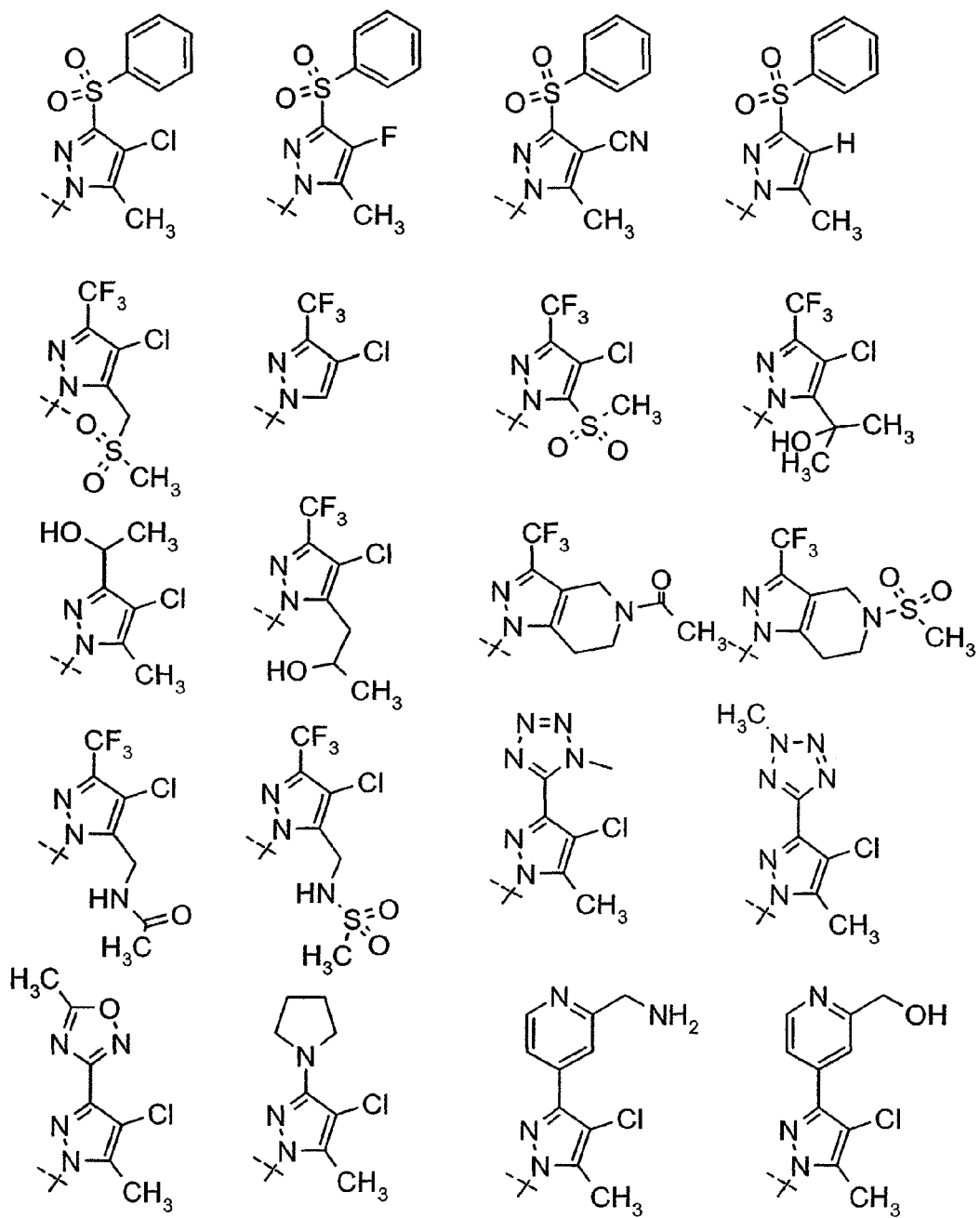
Figure 2G:
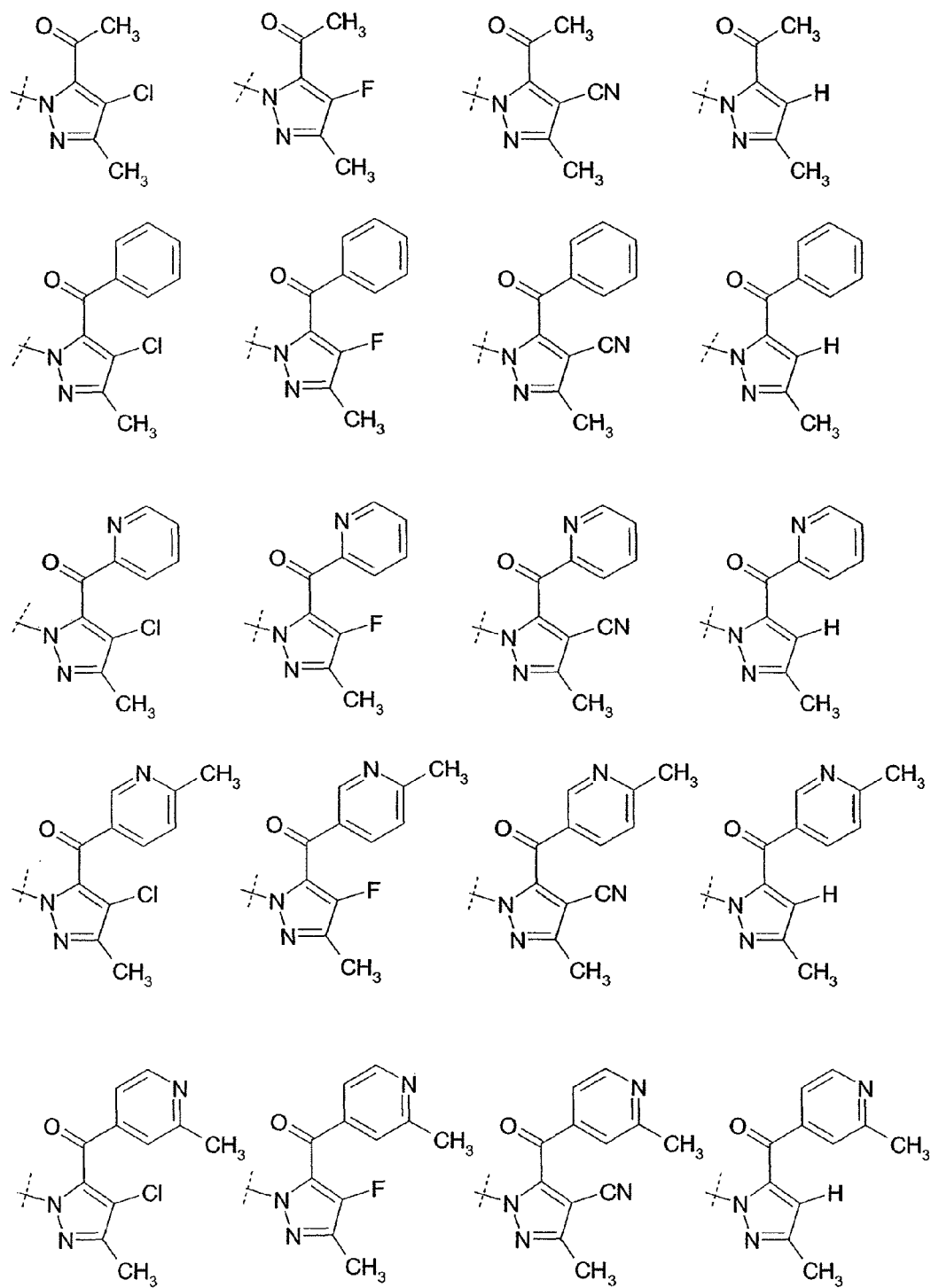
Figure 2H:
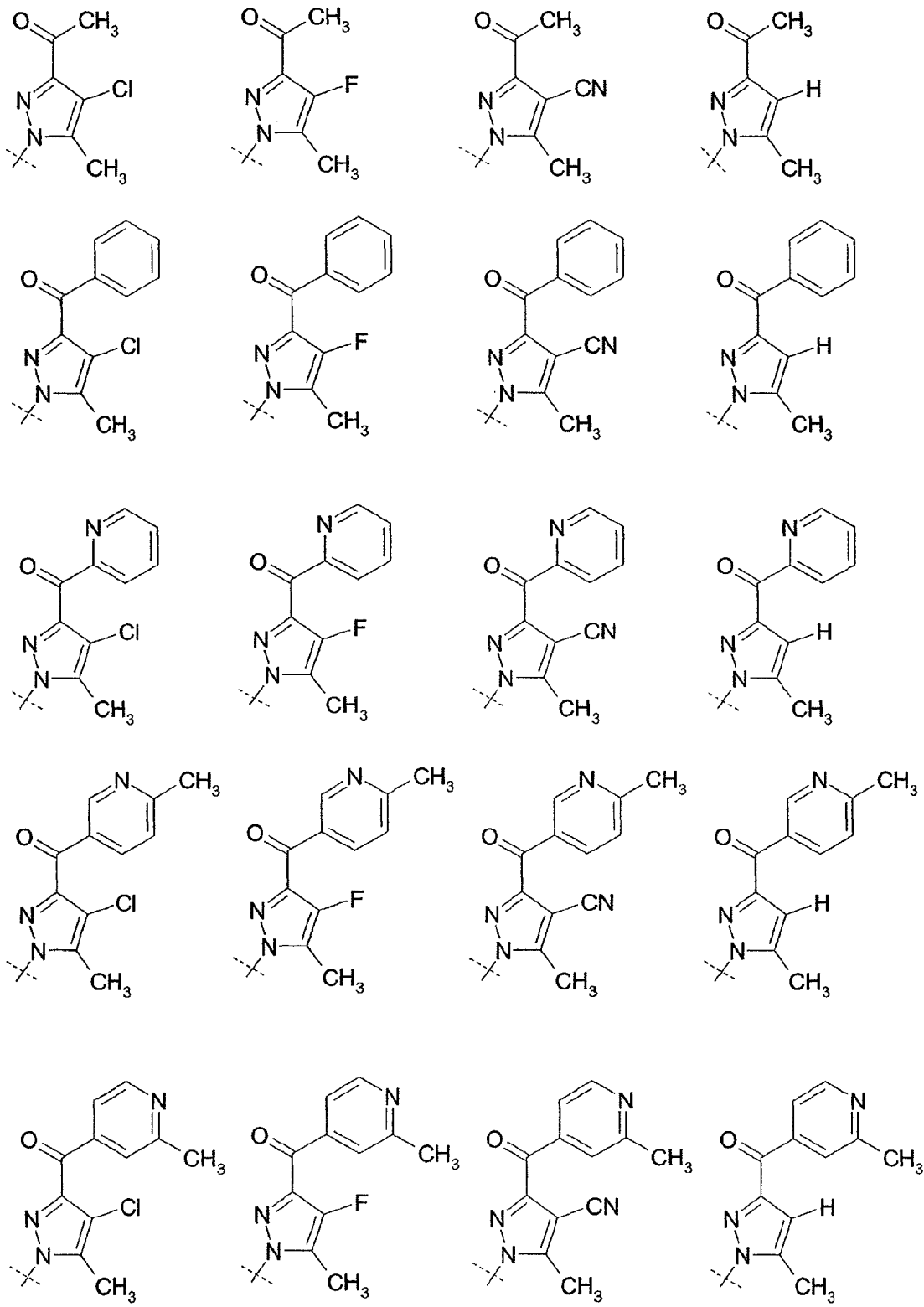
Figure 3:
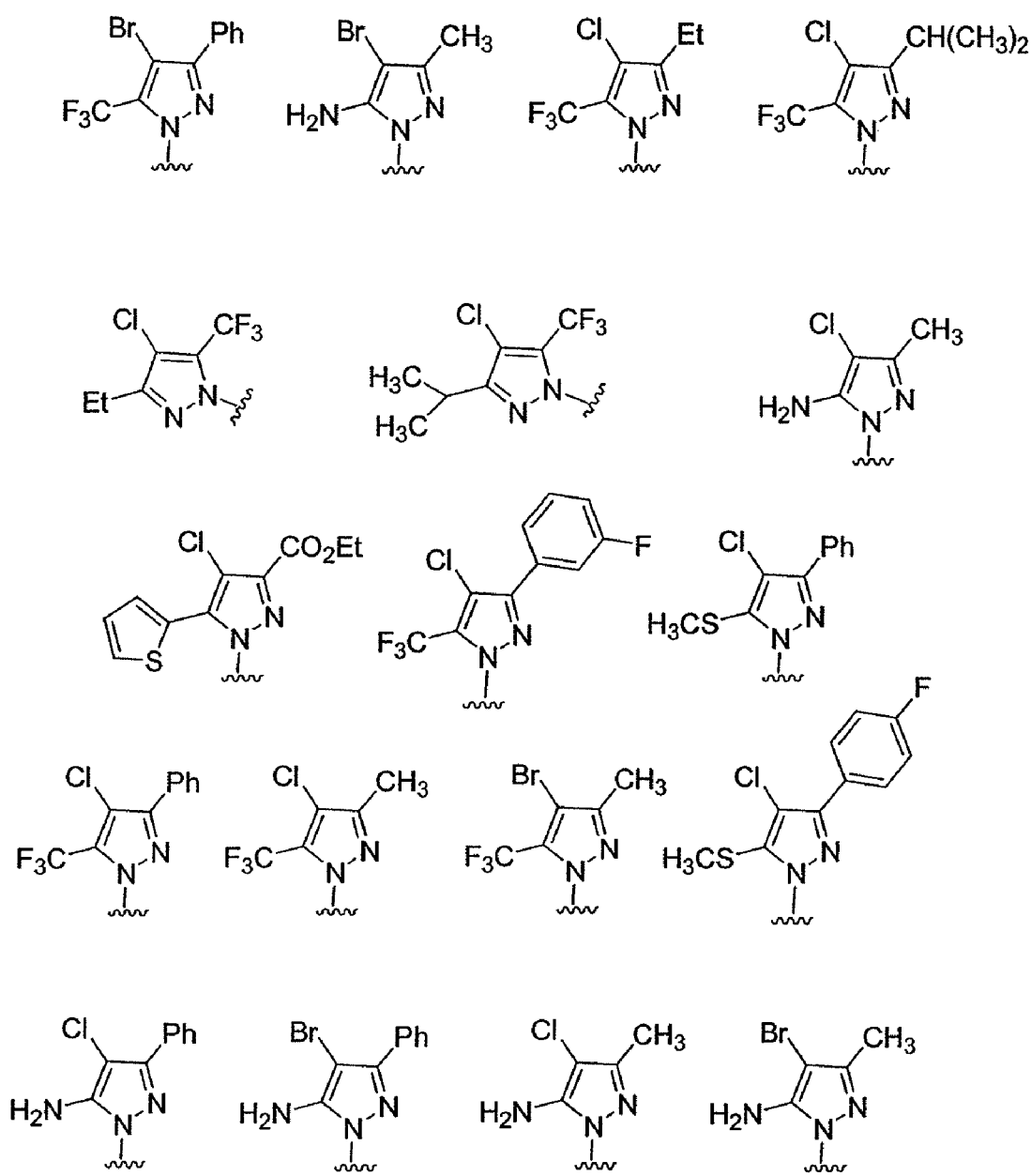

(II)

or a pharmaceutically acceptable salt or N-oxide thereof, wherein each of R$^{1a}$, R$^{1b}$, R$^{1c}$, R$^{1d}$, R$^{1e}$, R$^{1f}$, R$^{1g}$ and R$^{1h}$ represents a member independently selected from the group consisting of H, C$_{1-8}$ alkyl, C$_{1-8}$ haloalkyl, C$_{3-6}$ cycloalkyl, C$_{2-8}$ alkenyl and C$_{2-8}$ alkynyl, —COR$^a$, —CO$_2$R$^a$, —CONR$^a$R$^b$, —NR$^a$COR$^b$, —SO$_2$R$^a$, —X$^1$COR$^a$, —X$^1$CO$_2$R$^a$, —X$^1$CONR$^a$R$^b$, —X$^1$NR$^a$COR$^b$, —X$^1$SO$_2$R$^a$, —X$^1$SO$_2$NR$^a$R$^b$, —X$^1$NR$^a$R$^b$, —X$^1$OR$^a$, wherein X$^1$ is a member selected from the group consisting of C$_{1-4}$ alkylene, C$_{2-4}$ alkenylene and C$_{2-4}$ alkynylene and each R$^a$ and R$^b$ is independently selected from the group consisting of hydrogen, C$_{1-8}$ alkyl, C$_{1-8}$ haloalkyl, C$_{3-6}$ cycloalkyl and aryl-C$_{1-4}$alkyl, or optionally R$^a$ and R$^b$ when attached to the same nitrogen atom can be combined with the nitrogen atom to form a five or six-membered ring having from 0 to 2 additional heteroatoms as ring members, and wherein the aliphatic portions of each of the R$^1$ substituents is optionally substituted with from one to three members selected from the group consisting of —OH, —OR$^m$, —OC(O)NHR$^m$, —OC(O)N(R$^m$)$_2$, —SH$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each R$^m$ is independently an unsubstituted C$_{1-6}$ alkyl. The remaining groups have the meanings provided above with reference to formula I in their most complete interpretation. Preferably, Ar$^1$ is phenyl, optionally substituted with from one to five R$^2$ substitutents; and HAr is pyrazolyl, substituted with from 1 to 3 R$^3$ substituents. Still more preferably, L$^1$ is —CH$_2$—. Further preferred are those compounds in which Ar$^1$ is phenyl substituted with from one to three independently selected R$^2$ substituents and HAr is pyrazolyl substituted with one to three, more preferably three R$^3$ substituents. In still further preferred embodiments, Ar$^1$ is a substituted phenyl selected from those provided in FIGS. 1A through 1G. Even further preferred are those compounds in which HAr is selected from the substituted pyrazoles provided in FIGS. 2A through 2Z, 2AA through 2CC and 3. Still more preferably, no more than two of R$^{1a}$ through R$^{1h}$ are other than H.

In yet another group of embodiments, compounds are provided having formula III:

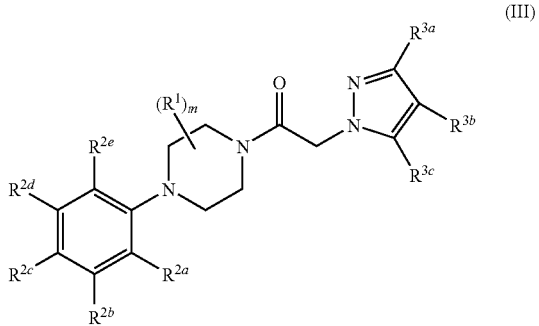

(III)

or a pharmaceutically acceptable salt or N-oxide thereof, wherein the subscript m is an integer of from 0 to 2; each $R^1$ is selected from the group consisting of —$CO_2H$, $C_{1-4}$ alkyl and $C_{1-4}$ haloalkyl, wherein the aliphatic portions are optionally substituted with —OH, —$OR'''$, —OC(O)NHR''', —OC(O)N($R'''$)$_2$, —SH, —$SR'''$, —S(O)$R'''$, —S(O)$_2R'''$, —$SO_2NH_2$, —S(O)$_2$NHR''', —S(O)$_2$N($R'''$)$_2$, —NHS(O)$_2$R''', —NR'''S(O)$_2R'''$, —C(O)$NH_2$, —C(O)NHR''', —C(O)N($R'''$)$_2$, —C(O)$R'''$, —NR'''C(O)$R'''$, —NHC(O)$NH_2$, —NR'''C(O)$NH_2$, —NR'''C(O)NHR''', —NHC(O)NHR''', —NR'''C(O)N($R'''$)$_2$, —NHC(O)N($R'''$)$_2$, —$CO_2H$, —$CO_2R'''$, —NHCO$_2R'''$, —NR'''$CO_2R'''$, —CN, —$NO_2$, —$NH_2$, —NHR''', —N($R'''$)$_2$, —NR'''S(O)$NH_2$ and —NR'''S(O)$_2$NHR''', wherein each $R'''$ is independently an unsubstituted $C_{1-6}$ alkyl. In certain preferred embodiments, $R^1$, when present is selected from methyl, ethyl, isopropyl, —$CH_2OH$, —$CH_2OCH_3$, —$CH_2OCH_2CH_3$, —$CH_2OCH(CH_3)_2$, —CH($CH_3$)OH and —CH($CH_3$)OCH$_3$, or more preferably, methyl, —$CH_2OH$ and —$CH_2OCH_3$. $R^{2a}$, $R^{2b}$, $R^{2c}$, $R^{2d}$ and $R^{2e}$ are each members independently selected from hydrogen, halogen, —$OR^c$, —OC(O)$R^c$, —$NR^cR^d$, —$SR^c$, —$R^e$, —CN, —$NO_2$, —$CO_2R^c$, —$CONR^cR^d$, —C(O)$R^c$, —OC(O)$NR^cR^d$, —$NR^dC(O)R^c$, —$NR^dC(O)_2R^e$, —$NR^c$—C(O)$NR^cR^d$, —NH—C($NH_2$)=NH, —$NR^eC(NH_2)$=NH, —NH—C($NH_2$)=$NR^e$, —NH—C(NHR$^e$)=NH, —S(O)$R^e$, —S(O)$_2R^e$, —$NR^cS(O)_2R^e$, —S(O)$_2NR^cR^d$, —$N_3$, —C(NOR$^c$)$R^d$, —C($NR^c$W)=NW, —N(W)C($R^c$)=NW, —$NR^cC(S)NR^cR^d$, —$X^2C(NOR^c)R^d$, —$X^2C(NR^cW)$=NW, —$X^2N(W)C(R^c)$=NW, —$X^2NR^cC(S)NR^cR^d$, —$X^2OR^c$, —O—$X^2OR^c$, —$X^2OC(O)R^c$, —$X^2NR^cR^d$, —O—$X^2NR^cR^d$, —$X^2SR^c$, —$X^2CN$, —$X^2NO_2$, —$X^2CO_2R^c$, —O—$X^2CO_2R^c$, —$X^2CONR^cR^d$, —O—$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—C($NH_2$)=NH, —$X^2NR^eC(NH_2)$=NH, —$X^2NH$—C($NH_2$)=$NR^e$, —$X^2NH$—C(NHR$^e$)=NH, —$X^2S(O)R^e$, —$X^2S(O)_2R^e$, —$X^2NR^cS(O)_2R^e$, —$X^2S(O)_2NR^cR^d$, —$X^2N_3$, —$NR^d$—$X^2OR^c$, —$NR^d$—$X^2NR^cR^d$, —$NR^d$—$X^2CO_2R^c$, and —$NR^d$—$X^2CONR^cR^d$, wherein each W is selected from $R^c$, —CN, —$CO_2R^e$ and —$NO_2$, and wherein each $X^2$ is a member selected from the group consisting of $C_{1-4}$ alkylene, $C_{2-4}$ alkenylene and $C_{2-4}$ alkynylene and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or optionally $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{1-8}$haloalkyl, $C_{3-6}$ cycloalkyl, $C_{2-8}$ alkenyl, $C_{2-8}$alkynyl, aryl, heteroaryl, aryl-$C_{1-4}$ alkyl, and aryloxy-$C_{1-4}$ alkyl, and each of $R^c$, $R^d$ and $R^e$ is optionally further substituted with from one to three members selected from the group consisting of —OH, —$OR''$, —OC(O)NHR'', —OC(O)N($R''$)$_2$, —SH, —$SR''$, —S(O)$R''$, —S(O)$_2R''$, —$SO_2NH_2$, —S(O)$_2$NHR'', —S(O)$_2$N($R''$)$_2$, —NHS(O)$_2R''$, —NR''S(O)$_2R''$, —C(O)$NH_2$, —C(O)NHR'', —C(O)N($R''$)$_2$, —C(O)$R''$, —NHC(O)$R''$, —NR''C(O)$R''$, —NHC(O)$NH_2$, —NR''C(O)$NH_2$, —$NR^RC(O)NHR''$, —NHC(O)NHR'', —NR''C(O)N($R''$)$_2$, —NHC(O)N($R''$)$_2$, —$CO_2H$, —$CO_2R''$, —NHCO$_2R''$, —NR''$CO_2R''$, —CN, —$NO_2$, —$NH_2$, —NHR'', —N($R''$)$_2$, —NR''S(O)$NH_2$ and —NR''S(O)$_2$NHR'', wherein each $R''$ is independently an unsubstituted $C_{1-6}$ alkyl, such that at least one of $R^{2a}$, $R^{2b}$, $R^{2c}$, $R^{2d}$ and $R^{2e}$ is other than H; $R^{3a}$, $R^{3b}$ and $R^{3c}$ are each members independently selected from hydrogen, halogen, —$OR^f$, —OC(O)$R^f$, —$NR^fR^g$, —$SR^f$, —$R^h$, —CN, —$NO_2$, —$CO_2R^f$, —$CONR^fR^g$, —C(O)$R^f$, —OC(O)$NR^fR^g$, —$NR^gC(O)R^f$, —$NR^gC(O)_2R^h$, —$NR^f$—C(O)$NR^fR^g$, —NH—C($NH_2$)=NH, —$NR^hC(NH_2)$=NH, —NH—C($NH_2$)=$NR^h$, —NH—C(NHR$^h$)=NH, —S(O)$R^h$, —S(O)$_2R^h$, —$NR^fS(O)_2R^h$, —S(O)$_2NR^fR^g$, —$NR^fS(O)_2NR^fR^g$, —$N_3$, —C(NOR$^f$)$R^g$, —C($NR^f$W$^a$)=NW$^a$, —N(W$^a$)C(R)=NW$^a$, —$X^3C(NOR^f)R^g$, —$X^3C(NR^fW^a)$=NW$^a$, —$X^3N(W^a)C(R^f)$=NW$^a$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^f$—C(O)$NR^fR^g$, —$X^3NH$—C($NH_2$)=NH, —$X^3NR^hC(NH_2)$=NH, —$X^3NH$—C($NH_2$)=$NR^h$, —$X^3NH$—C(NHR$^h$)=NH, —$X^3S(O)R^h$, —$X^3S(O)_2R^h$, —$X^3NR^fS(O)_2R^h$, —$X^3S(O)_2NR^fR^g$, —Y, —$X^3Y$, —$X^3N_3$, —O—$X^3OR^f$, —O—$X^3NR^fR^g$, —O—$X^3CO_2R^f$, —O—$X^3CONR^fR^g$, —$NR^g$—$X^3OR^f$, —$NR^g$—$X^3NR^fR^g$, —$NR^g$—$X^3CO_2R^f$, and —$NR^g$—$X^3CONR^fR^g$, wherein Y is a five or six-membered aryl, heteroaryl or heterocyclic ring, optionally substituted with from one to three substitutents selected from the group consisting of halogen, —$OR^f$, —$NR^fR^g$, —$R^h$, —SR; —CN, —$NO_2$, —$CO_2R^f$, —$CONR^fR^g$, —C(O)$R^f$, —$NR^gC(O)R^f$, —S(O)$R^h$, —S(O)$_2R^h$, —$NR^fS(O)_2R^h$, —S(O)$_2NR^fR^g$, —C(NOR$^f$)$R^g$, —C($NR^fW^a$)=NW$^a$, —N(W$^a$)C($R^f$)=NW$^a$, —$X^3C(NOR^f)R^g$, —$X^3C(NR^fW^a)$=NW$^a$, —$X^3N(W^a)C(R^f)$=NW$^a$, —$X^3OR^f$, —$X^3NR^fR^g$, —$X^3NR^fS(O)_2R^h$ and —$X^3S(O)_2NR^fR^g$, wherein each W$^a$ is selected from $R^f$, —CN, —$CO_2R^h$ and —$NO_2$, and wherein each $X^3$ is independently selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $R^f$, $R^g$ and $R^h$ is optionally further substituted with from one to three members selected from the group consisting of —OH, —$OR^o$, —OC(O)NHR$^o$, —OC(O)N($R^o$)$_2$, —SH, —$SR^o$, —S(O)$R^o$, —S(O)$_2R^o$, —$SO_2NH_2$, —S(O)$_2$NHR$^o$, —S(O)$_2$N($R^o$)$_2$, —NHS(O)$_2R^o$, —NR$^o$S(O)$_2R^o$, —C(O)$NH_2$, —C(O)NHR$^o$, —C(O)N($R^o$)$_2$, —C(O)$R^o$, —NHC(O)$R^o$, —NR$^o$C(O)$R^o$, —NHC(O)$NH_2$, —NR$^o$C(O)$NH_2$, —NR$^o$C(O)NHR$^o$, —NHC(O)NHR$^o$, —NR$^o$C(O)N($R^o$)$_2$, —NHC(O)N($R^o$)$_2$, —$CO_2H$, —$CO_2R^o$, —NHCO$_2R^o$, —NR$^o$CO$_2R^o$, —CN, —$NO_2$, —$NH_2$, —NHR$^o$, —N($R^o$)$_2$, —NR$^o$S(O)$NH_2$ and —NR$^o$S(O)$_2$NHR$^o$, wherein each $R^o$ is independently an unsubstituted $C_{1-6}$ alkyl, such that at least one of $R^{3a}$, $R^{3b}$ and $R^{3c}$ is other than H. Optionally, two of $R^{3a}$, $R^{3b}$ and $R^{3c}$, when attached to adjacent carbon atoms are combined to form a five or six-membered ring having 0-3 heteroatoms as ring members and which is further substituted with from 0-3 substituents provided for the aliphatic portions of $R^f$ above. Additionally, two of $R^{2a}$, $R^{2b}$, $R^{2c}$, $R^{2d}$ and $R^{2e}$, when attached to adjacent carbon atoms are optionally combined to form a five or six-membered ring having 0-3 heteroatoms as ring members and which is further substituted with from 0-3 substituents provided for the aliphatic portions of $R^c$ above.

Within the group of formula III above, certain groups of embodiments are particularly preferred. In one group of particularly preferred embodiments, the subscript m is 0 or 1 and at least one of $R^{2a}$ or $R^{2e}$ is hydrogen. More preferably, at least one of $R^{3a}$, $R^{3b}$ and $R^{3c}$ is selected from halogen, $C_{1-4}$ alkyl and $C_{1-4}$haloalkyl, wherein the aliphatic portions are optionally substituted as set forth above. Still more preferably, $R^{2d}$ is hydrogen and at least two of $R^{3a}$, $R^{3b}$ and $R^{3c}$ are selected from halogen, $C_{1-4}$ alkyl and $C_{1-4}$ haloalkyl, wherein the aliphatic portions are optionally substituted as set forth above, with the remaining member being other than hydrogen. In related, and preferred embodiments, m is 0 or 1 and at least one of $R^{2a}$ or $R^{2e}$ is hydrogen, $R^{2d}$ is hydrogen, $R^{2c}$ is selected from F, Cl, Br, CN, $NO_2$, $CO_2CH_3$, $C(O)CH_3$ and $S(O)_2CH_3$, and at least two of $R^{3a}$, $R^{3b}$ and $R^{3c}$ are selected from halogen, $C_{1-4}$ alkyl and $C_{1-4}$ haloalkyl, wherein the aliphatic portions are optionally substituted as set forth above, with the remaining member being other than hydrogen. In another group of particularly preferred embodiments, the subscript m is 0 or 1; and $R^{2a}$ and $R^{2e}$ are both hydrogen. More preferably, at least one of $R^{3a}$, $R^{3b}$ and $R^{3c}$ is selected from halogen, $C_{1-4}$ alkyl and $C_{1-4}$ haloalkyl, wherein the aliphatic portions are optionally substituted as set forth above. Still more preferably, at least one of $R^{3a}$, $R^{3b}$ and $R^{3c}$ is selected from halogen, $C_{1-4}$ alkyl and $C_{1-4}$ haloalkyl, wherein the aliphatic portions are optionally substituted as set forth above, and the remaining members of $R^{3a}$, $R^{3b}$ and $R^{3c}$ are other than hydrogen. In yet another group of particularly preferred embodiments, the subscript m is 0 or 1; and $R^{2b}$ and $R^{2e}$ are both hydrogen. More preferably, at least one of $R^{3a}$, $R^{3b}$ and $R^{3c}$ is selected from halogen, $C_{1-4}$ alkyl and $C_{1-4}$ haloalkyl, wherein the aliphatic portions are optionally substituted as set forth above. Still more preferably, at least one of $R^{3a}$, $R^{3b}$ and $R^{3c}$ is selected from halogen, $C_{1-4}$ alkyl and $C_{1-4}$ haloalkyl, wherein the aliphatic portions are optionally substituted as set forth above, and the remaining members of $R^{3a}$, $R^{3b}$ and $R^{3c}$ are other than hydrogen.

In other groups of preferred embodiments of formula III, at least one of $R^{3a}$, $R^{3b}$ and $R^{3c}$ is selected from —Y and —$X^3$—Y. Related embodiments are those in which m is 0 or 1 and at least one of $R^{2a}$ and $R^{2e}$ is hydrogen. In still other embodiments, $R^{3b}$ is hydrogen, halogen or cyano. Further preferred are those compounds in which $R^{3b}$ is halogen or cyano, and $R^1$, when present, is selected from the group consisting of —$CO_2H$ and $C_{1-4}$ alkyl optionally substituted with —OH, —$OR^m$, —$S(O)_2R^m$, —$CO_2H$ and —$CO_2R^m$. In yet other embodiments, m is 0 or 1; at least one of $R^{2a}$ and $R^{2e}$ is hydrogen; and at least one of $R^{3a}$, $R^{3b}$ and $R^{3c}$ is selected from halogen, $C_{1-4}$ alkyl and $C_{1-4}$ haloalkyl, wherein the aliphatic portions are optionally substituted as set forth above. More preferably, $R^{2d}$ is hydrogen and at least two of $R^{3a}$, $R^{3b}$ and $R^{3c}$ are selected from halogen, $C_{1-4}$ alkyl and $C_{1-4}$ haloalkyl, wherein the aliphatic portions are optionally substituted as set forth above. Still further preferred are those compounds in which $R^{2c}$ is selected from F, Cl, Br, CN, $NO_2$, $CO_2CH_3$, $C(O)CH_3$ and $S(O)_2CH_3$, and each of $R^{3a}$, $R^{3b}$ and $R^{3e}$ is other than hydrogen.

In another group of preferred embodiments of formula III, m is 0 or 1 and each of $R^{2a}$ and $R^{2e}$ are hydrogen. In still other embodiments, $R^{3b}$ is hydrogen, halogen or cyano. Further preferred are those compounds in which $R^{3b}$ is halogen or cyano, and $R^1$, when present, is selected from the group consisting of $C_{1-4}$ alkyl, optionally substituted with —OH, —$OR^m$, —$S(O)_2R^m$, —$CO_2H$ and —$CO_2R^m$. In yet other embodiments, m is 0 or 1; each of $R^{2a}$ and $R^{2e}$ are hydrogen; and at least one of $R^{3a}$, $R^{3b}$ and $R^{3c}$ is selected from halogen, $C_{1-4}$ alkyl and $C_{1-4}$haloalkyl, wherein the aliphatic portions are optionally substituted as set forth above. More preferably, each of $R^{3a}$, $R^{3b}$ and $R^{3c}$ is other than hydrogen. Still further preferred are those compounds in which $R^{2c}$ is selected from F, Cl, Br, CN, $NO_2$, $CO_2CH_3$, $C(O)CH_3$ and $S(O)_2CH_3$. In related embodiments, m is 0 or 1 and $R^{2b}$ and $R^{2e}$ are each hydrogen.

In other preferred groups of formula III, the compounds have a formula selected from

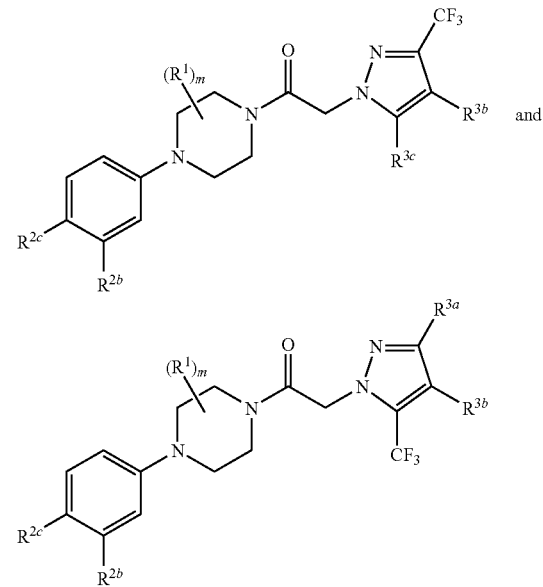

wherein each of the substituents has the meaning provided above with respect to formula III. In one group of embodiments, $R^{3c}$ and $R^{3a}$ are each independently selected from the group consisting of $C_{1-6}$ alkyl, $C_{1-6}$ haloalkyl and $C_{3-6}$ cycloalkyl; and $R^{3b}$ is hydrogen, halogen or cyano, more preferably halogen. In another group of embodiments, $R^{3c}$ and $R^{3a}$ are each independently selected from the group consisting of halogen, —$NR^fR^g$, —$SR^f$, —$CO_2R^f$, —Y and —$R^h$, wherein $R^h$ is $C_{1-6}$ alkyl, $C_{1-6}$ haloalkyl and $C_{3-6}$ cycloalkyl, wherein the aliphatic portions optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R)_2$, —$NR^oS(O)NH_2$ and —$NR^oS(O)_2NHR^o$. In still other embodiments, m is 0. For embodiments in which m is 1 or 2, $R^1$ is preferably —$CO_2H$ or $C_{1-4}$ alkyl, optionally substituted with —OH, —$S(O)_2R^m$, —$CO_2H$ and —$CO_2R^m$. In certain preferred embodiments, $R^1$, when present is selected from methyl, ethyl, isopropyl, —$CH_2OH$, —$CH_2OCH_3$, —$CH_2OCH_2CH_3$, —$CH_2OCH(CH_3)_2$, —$CH(CH_3)OH$ and —$CH(CH_3)OCH_3$, or more preferably, methyl, —$CH_2OH$ and —$CH_2OCH_3$.

In other preferred groups of formula III, the compounds have a formula selected from

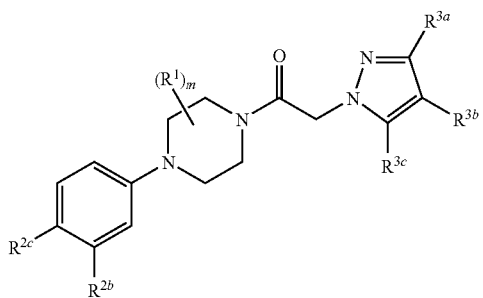

wherein each of the substituents has the meaning provided above with respect to formula III. In one group of embodiments, $R^{3c}$ and $R^{3a}$ are each independently selected from the group consisting of halogen, cyano, —$NO_2$, —$CO_2R^f$, —$CONR^fR^g$, —$C(O)R^f$, —$NR^fR^g$, —$SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl and $C_{3-6}$ cycloalkyl, where the alkyl and cycloalkyl substituents can be optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$; and $R^{3b}$ is hydrogen, halogen or cyano. Preferred groups for $R^{3a}$ are halogen, cyano, $C_{1-6}$ alkyl, $C_{1-6}$ haloalkyl, $C_{3-6}$ cycloalkyl, —$C(O)R^f$, —$NR^fR^g$, —$SR^f$, —$S(O)_2R^h$, —$X^3Y$ or Y wherein the aliphatic portions are optionally substituted as set forth above; while preferred groups for $R^{3c}$ are halogen, cyano, —$C(O)R^f$, —$S(O)_2R^h$, $C_{1-6}$ alkyl, $C_{1-6}$ haloalkyl or $C_{3-6}$ cycloalkyl, where the alkyl and cycloalkyl substituents can be optionally substituted as noted above. In another group of embodiments, $R^{3c}$ and $R^{3a}$ are each independently selected from the group consisting of $C_{1-6}$ alkyl, optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o_2,)$—$NHC(O)N(R^o_2$, —$CO_2H$, —$CO_2R^o$, —$NHCO_2R^o$, —$NR^oCO_2R^o$, —CN, —$NO_2$, —$NH_2$, —$NHR^o$, —$N(R)_2$, —$NR^oS(O)NH_2$ and —$NR^oS(O)_2NHR^o$. In some embodiments, $R^{2c}$ is other than hydrogen, and is preferably selected from halogen, cyano and nitro; and $R^{2b}$ is selected from —$SR^c$, —O—$X^2$—$OR^c$, —$X^2$—$OR^c$, —$R^c$, —$OR^c$, —$NR^cR^d$, —$NR^dC(O)R^c$ and —$NR^cSO_2R^d$. In still other embodiments, m is 0. For embodiments in which m is 1 or 2, $R^1$ is preferably —$CO_2H$ or $C_{1-4}$ alkyl, optionally substituted with —OH, —$OR^m$, —$N(R^m)_2$, —$S(O)_2R^m$, —$CO_2H$ and —$CO_2R^m$.

Other preferred compounds of formula III are represented by the formula:

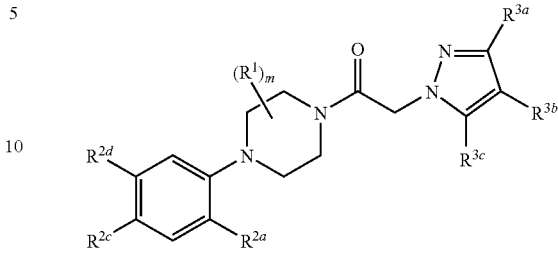

wherein $R^{2a}$ is other than hydrogen; $R^{2c}$ is halogen, cyano or nitro; $R^{2d}$ is —$SR^c$, —O—$X^2$—$OR^c$, —$X^2$—$OR^c$, —$R^c$, —$OR^c$, —$NR^cR^d$, —$NR^dC(O)R^c$ and —$NR^cSO_2R^d$; $R^{3a}$ is selected from the group consisting of $C_{1-6}$ alkyl, $C_{1-6}$ haloalkyl and $C_{3-6}$ cycloalkyl, optionally substituted with a member selected from the group consisting of —OH, —$OR^c$, —$OC(O)NHR^c$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$; $R^{3b}$ is hydrogen, F, Cl, Br or cyano; and $R^{3c}$ is selected from the group consisting of $NH_2$, $CF_3$, $SCH_3$ and Y. Further preferred are those compounds in which each $R^1$, when present, is selected from the group consisting of —$CO_2H$ and $C_{1-4}$ alkyl, optionally substituted with a member selected from the group consisting of —OH, —$S(O)_2R^m$, —$CO_2H$ and —$CO_2R^m$.

Related embodiments are those compounds having the formula:

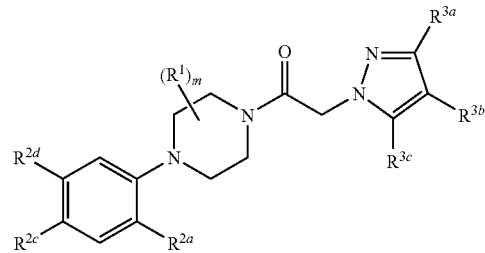

wherein $R^{2a}$ is other than hydrogen; $R^{2c}$ is halogen, cyano or nitro; $R^{2d}$ is —$SR^c$, —O—$X^2$—$OR^c$, —$X^2$—$OR^c$, —$R^c$, —$OR^c$, —$NR^cR^d$, —$NR^dC(O)R^c$ and —$NR^cSO_2R^d$; $R^{3a}$ is selected from the group consisting of —$NR^fR^g$, —$SR^f$, —$SO_2R^h$, —$R^h$, —$C(O)R^f$, —Y and —$X^3Y$, more preferably —$NH_2$, —$CF_3$, —$SCH_3$ and Y; $R^{3b}$ is hydrogen, F, Cl, Br or cyano; and $R^{3c}$ is selected from the group consisting of $C_{1-6}$ alkyl, $C_{1-6}$ haloalkyl and $C_{3-6}$ cycloalkyl, optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —NR$^o$CO$_2$R$^o$, —CN, —NO$_2$, —NH$_2$, —NHR$^o$, —N(R)$_2$, —NR$^o$S(O)NH$_2$ and —NR$^o$S(O)$_2$NHR$^o$. Further preferred are those compounds in which each R$^1$, when present, is selected from the group consisting of —CO$_2$H and C$_{1-4}$ alkyl, optionally substituted with a member selected from the group consisting of —OH, —OR$^m$, —S(O)$_2$R$^m$, —CO$_2$H and —CO$_2$R$^m$. In other preferred embodiments, R$^{3b}$ is hydrogen. In still other related embodiments, two adjacent R$^{3a}$, R$^{3b}$ or R$^{3c}$ groups are combined to form a five or six-membered fused ring, preferably a carbocyclic ring or a heterocyclic ring having from 1-2 heteroatoms as ring members.

Still other preferred groups of formula III above, are:

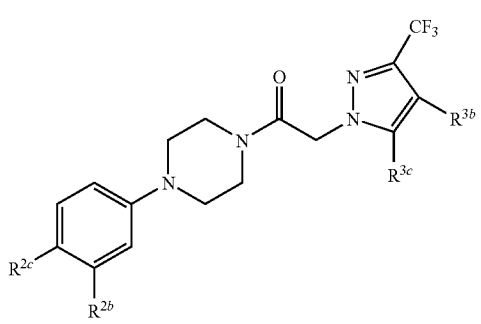

IIIa


IIIb

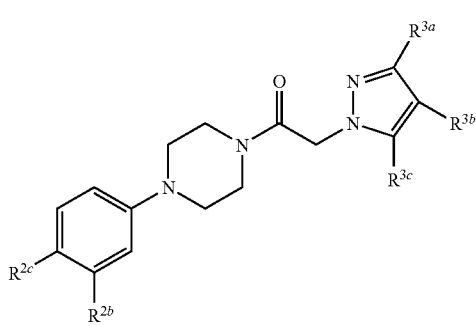

IIIc

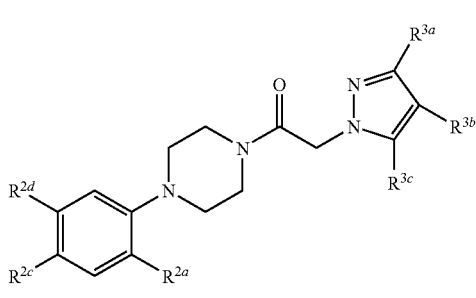

IIId

Turning first to the compounds of formula IIIa, R$^{3b}$ is preferably hydrogen, halogen, nitro or cyano, more preferably halogen and most preferably fluoro, chloro or bromo; R$^{3c}$ is preferably C$_{1-6}$ alkyl, C$_{1-6}$ haloalkyl or C$_{3-6}$ cycloalkyl; R$^{2c}$ is halogen and R$^{2b}$ is —SR$^c$, —O—X$^2$—OR$^c$, —NR$^c$R$^d$, —NR$^c$S(O)$_2$R$^e$ and —NR$^d$C(O)R$^c$; wherein R$^c$ and R$^d$ are selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl, and R$^e$ is selected from the group consisting of C$_{1-8}$ alkyl, C$_{1-8}$ haloalkyl, C$_{3-6}$ cycloalkyl, C$_{2-8}$ alkenyl and C$_{2-8}$ alkynyl, and each of R$^c$, R$^d$ and R$^e$ is optionally further substituted as described above, or in some embodiments with from one to three members selected from the group consisting of OH, O(C$_{1-8}$ alkyl), SH, S(C$_{1-8}$ alkyl), CN, NO$_2$, NH$_2$, NH(C$_{1-8}$ alkyl) and N(C$_{1-8}$ alkyl)$_2$.

For the compounds of formula IIIb, R$^{3b}$ is preferably hydrogen, halogen, nitro or cyano, more preferably halogen and most preferably fluoro, chloro or bromo; R$^{3a}$ is preferably C$_{1-6}$ alkyl, C$_{1-6}$ haloalkyl or C$_{3-6}$ cycloalkyl; R$^{2c}$ is preferably halogen and R$^{2b}$ is preferably —SR$^c$, —O—X$^2$—OR$^c$, —X$^2$—OR$^c$, —R$^e$, —OR$^c$, —NR$^c$R$^d$, —NR$^c$S(O)$_2$R$^e$ and —NR$^d$C(O)R$^c$; wherein R$^c$ and R$^d$ are selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl, and R$^e$ is selected from the group consisting of C$_{1-8}$ alkyl, C$_{1-8}$ haloalkyl, C$_{3-6}$ cycloalkyl, C$_{2-8}$ alkenyl and C$_{2-8}$ alkynyl, and each of R$^c$, R$^d$ and R$^e$ is optionally further substituted as described above, or in some embodiments, with from one to three members selected from the group consisting of OH, O(C$_{1-8}$ alkyl), SH, S(C$_{1-8}$ alkyl), CN, NO$_2$, NH$_2$, NH(C$_{1-8}$ alkyl) and N(C$_{1-8}$ alkyl)$_2$.

In one group of embodiments for the compounds of formula IIIc, each of R$^{3a}$ and R$^{3c}$ is selected from halogen, cyano, —NO$_2$, —CO$_2$R$^f$, —CONR$^f$R$^g$, —C(O)R$^f$, —NR$^f$R$^g$, —SR$^f$, —S(O)R$^h$, —S(O)$_2$R$^h$, —C(O)Y, —SO$_2$Y, —X$^3$Y, Y, C$_{1-6}$ alkyl, C$_{1-6}$ haloalkyl or C$_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$. More preferably, R$^{3a}$ is selected from halogen, cyano, C$_{1-6}$ alkyl, C$_{1-6}$ haloalkyl, C$_{3-6}$ cycloalkyl, —C(O)R$^f$, —NR$^f$R$^g$, —SR$^f$, —S(O)$_2$R$^h$, —X$^3$Y and Y; still more preferably R$^{3a}$ is halogen, cyano, C$_{1-6}$ alkyl, C$_{1-6}$ haloalkyl, C$_{3-6}$ cycloalkyl, —C(O)R$^f$ or —SO$_2$R$^h$ wherein the aliphatic portions are optionally substituted as set forth above. R$^{3b}$ is hydrogen, F, Cl, Br or cyano. R$^{3c}$ is preferably halogen, cyano, —C(O)R$^f$, —SO$_2$R$^h$, C$_{1-6}$ alkyl, C$_{1-6}$ haloalkyl or C$_{3-6}$ cycloalkyl wherein the aliphatic portions are substituted as set forth above. R$^{2c}$ is halogen, cyano or nitro; and R$^{2b}$ is selected from hydrogen, halogen, —OR$^c$, —OC(O)R$^c$, —NR$^c$R$^d$, —SR$^c$, —CO$_2$R$^c$, —CONR$^c$R$^d$, —C(O)R$^c$, —S(O)R$^e$, —S(O)$_2$R$^e$, —NR$^c$S(O)$_2$R$^e$, —NR$^d$C(O)R$^c$, —X$^2$OR$^c$, —X$^2$OC(O)R$^c$, —X$^2$NR$^c$R$^d$, —X$^2$SR$^c$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$S(O)R$^e$, —X$^2$S(O)$_2$R$^e$, —X$^2$NR$^c$S(O)$_2$R$^e$, —O—X$^2$—OR$^c$, —X$^2$S(O)$_2$NR$^c$R$^d$ and —X$^2$N$_3$, wherein X$^2$ is C$_{1-4}$ alkylene, and each R$^c$ and R$^d$ is independently selected from hydrogen, C$_{1-8}$ alkyl, C$_{1-8}$ haloalkyl, C$_{3-6}$ cycloalkyl, C$_{2-8}$ alkenyl and C$_{2-8}$ alkynyl, and each R$^e$ is independently selected from the group consisting of C$_{1-8}$ alkyl, C$_{1-8}$ haloalkyl, C$_{3-6}$ cycloalkyl, C$_{2-8}$ alkenyl and C$_{2-8}$ alkynyl, and each of R$^c$, R$^d$ and R$^e$ is optionally further substituted as described above for formula III, or with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$. In some preferred embodiments, $R^{2c}$ is halogen, cyano or nitro; $R^{2b}$ is —$SR^c$, —O—$X^2$—$OR^c$, —$X^2$—$OR^c$, —$R^e$, —$OR^c$, —$NR^cR^d$, —$NR^cS(O)_2R^e$ and —$NR^dC(O)R^c$; wherein $R^c$ and $R^d$ are selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and $R^e$ is selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$; $R^{3a}$ is $C_{1-6}$ alkyl, $C_{1-6}$ haloalkyl, $C_{3-6}$ cycloalkyl, —C(O)$R^f$, —$NR^fR^g$, —S(O)$_2R^h$, —$X^3Y$ or Y; $R^{3b}$ is hydrogen, F, Cl, Br or cyano; and $R^{3c}$ is halogen, cyano, —C(O)$R^f$, —$SO_2R^h$, $C_{1-6}$ alkyl, $C_{1-6}$ haloalkyl or $C_{3-6}$ cycloalkyl wherein the aliphatic portions are substituted as set forth above.

In related, and preferred embodiments, compounds of formula IIIc are provided wherein $R^{3c}$ is selected from halogen, cyano, $C_{1-6}$ alkyl, $C_{1-6}$ haloalkyl, $C_{3-6}$ cycloalkyl, —C(O)$R^f$, —$NR^fR^g$, —$SR^f$, —S(O)$_2R^h$, —$X^3Y$ and Y; still more preferably $R^{3c}$ is halogen, cyano, $C_{1-6}$ alkyl, $C_{1-6}$ haloalkyl, $C_{3-6}$ cycloalkyl, —C(O)$R^f$ or —$SO_2R^h$ wherein the aliphatic portions are optionally substituted as set forth above. $R^{3b}$ is hydrogen, F, Cl, Br or cyano; $R^{3a}$ is preferably halogen, cyano, —C(O)$R^f$, —$SO_2R^h$, $C_{1-6}$ alkyl, $C_{1-6}$ haloalkyl or $C_{3-6}$ cycloalkyl wherein the aliphatic portions are substituted as set forth above. $R^{2c}$ is halogen, cyano or nitro, preferably halogen; and $R^{2b}$ is selected from hydrogen, halogen, —$OR^c$, —OC(O)$R^c$, —$NR^cR^d$, —$SR^c$, —$R^e$, —$CO_2R^c$, —$CONR^cR^d$, —C(O)$R^c$, —S(O)$R^e$, —S(O)$_2R^e$, —$NR^cS(O)_2R^e$, —$NR^dC(O)R^c$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —O—$X^2$—$OR^c$, —$X^2S(O)_2NR^cR^d$ and —$X^2N_3$, wherein $X^2$ is $C_{1-4}$ alkylene, and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted as described above for formula III, or with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$. In some preferred embodiments, $R^{2c}$ is halogen, cyano or nitro; $R^{2b}$ is —$SR^c$, —O—$X^2$—$OR^c$, —$X^2$—$OR^c$, —$R^e$, —$OR^c$, —$NR^cR^d$, —$NR^cS(O)_2R^e$ or —$NR^dC(O)R^c$; $R^{3a}$ is selected from the group consisting of $C_{1-6}$ alkyl and $C_{3-6}$ cycloalkyl; $R^{3c}$ is selected from the group consisting of $NH_2$, $CF_3$, $SCH_3$ and Y; and $R^{3b}$ is chloro or bromo.

For selected compounds of formula IIId, $R^{3a}$ and $R^{3c}$ are each independently selected from halogen, cyano, —$NO_2$, —$CO_2R^f$, —$CONR^fR^g$, —C(O)$R^f$, —$NR^fR^g$, —$SR^f$, —S(O)$R^h$, —S(O)$_2R^h$, —C(O)Y, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —OC(O)$NHR^o$, —OC(O)N($R^o$)$_2$, —SH, —$SR^o$, —S(O)$R^o$, —S(O)$_2R^o$, —$SO_2NH_2$, —S(O)$_2NHR^o$, —S(O)$_2N(R^o)_2$, —NHS(O)$_2R^o$, —$NR^oS(O)_2R^o$, —C(O)$NH_2$, —C(O)$NHR^o$, —C(O)N($R^o$)$_2$, —C(O)$R^o$, —NHC(O)$R^o$, —$NR^oC(O)R^o$, —NHC(O)$NH_2$, —$NR^oC(O)NH_2$, —$NR^oC(O)NHR^o$, —NHC(O)NHR$^o$, —$NR^oC(O)N(R^o)_2$, —NHC(O)N($R^o$)$_2$, —$CO_2H$, —$CO_2R^o$, —$NHCO_2R^o$, —$NR^oCO_2R^o$, —CN, —$NO_2$, —$NH_2$, —$NHR^o$, —N($R^o$)$_2$, —$NR^oS(O)NH_2$ and —$NR^oS(O)_2NHR^o$. More preferably, $R^{3a}$ is selected from halogen, cyano, $C_{1-6}$ alkyl, $C_{1-6}$ haloalkyl, $C_{3-6}$ cycloalkyl, —C(O)$R^fR^g$, —$SR^f$, —S(O)$_2R^h$, —$X^3Y$ and Y, and still more preferably selected from $NH_2$, $CF_3$, $SCH_3$, $SO_2CH_3$, CN, $C(CH_3)_2OH$ and Y. $R^{3b}$ is hydrogen, F, Cl, Br or cyano; $R^{3c}$ is preferably $C_{1-6}$ alkyl, $C_{1-6}$ haloalkyl or $C_{3-6}$ cycloalkyl, optionally substituted as for formula III; $R^{2a}$ is preferably other than hydrogen, and is selected from halogen, —$OR^c$, —OC(O)$R^c$, —$NR^cR^d$, —$SR^c$, —$CO_2R^c$, —$CONR^cR^d$, —C(O)$R^c$, —S(O)$R^e$, —S(O)$_2R^e$, —$C(NOR^c)R^d$, —C($NR^cW$)=NW, —N(W)C($R^c$)=NW, —$X^2C(NOR^c)R^d$, —$X^2C(NR^cW)$=NW, —$X^2N(W)C(R^c)$=NW, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ and —$X^2N_3$; $R^{2c}$ is hydrogen, halogen, cyano or nitro, preferably halogen; and $R^{2d}$ is selected from hydrogen, halogen, —$OR^c$, —OC(O)$R^c$, —$NR^cR^d$, —$SR^c$, —$R^c$, —$CO_2R^c$, —$CONR^cR^d$, —C(O)$R^c$, —S(O)$R^e$, —S(O)$_2R^e$, —$NR^cS(O)_2R^e$, —$NR^dC(O)R^c$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —O—$X^2$—$OR^c$, —$X^2S(O)_2NR^cR^d$ and —$X^2N_3$, wherein $X^2$ is $C_{1-4}$ alkylene, and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted as described above for formula III, or with from one to three members selected from the group consisting of OH, O($C_{1-8}$ alkyl), SH, S($C_{1-8}$alkyl), CN, $NO_2$, $NH_2$, NH($C_{1-8}$ alkyl) and N($C_{1-8}$ alkyl)$_2$; and no more than one of $R^{2a}$ and $R^{2d}$ is hydrogen. Preferably, each of $R^{2a}$ and $R^{2d}$ is other than hydrogen. In the most preferred embodiments, $R^{2a}$ is other than hydrogen; $R^{2c}$ is halogen, cyano or nitro; $R^{2d}$ is —$SR^c$, —O—$X^2$—$OR^c$, —$X^2$—$OR^c$, —$R^e$, —$OR^c$, —$NR^cR^d$, —$NR^cS(O)_2R^e$ or —$NR^dC(O)R^c$; $R^{3c}$ is selected from the group consisting of $C_{1-6}$ alkyl and $C_{3-6}$ cycloalkyl; $R^{3b}$ is hydrogen, F, Cl, Br or cyano; and $R^{3a}$ is selected from the group consisting of —$NR^fR^g$, —$SO_2R^h$, —$R^h$, —C(O)$R^f$, —$X^3Y$, $SCH_3$ and Y, wherein Y is an unsubstituted or substituted 5- or 6-membered heteroaryl group or heterocyclic group such as pyridyl, pyrimidinyl, thienyl, furyl, oxadiazolyl, oxazolyl, thiazolyl, pyrazolyl, triazolyl, tetrazolyl, imidazolyl, morpholinyl, pyrrolidinyl, piperidinyl and the like.

In related and preferred embodiments, compounds of formula IIId are provided wherein $R^{3a}$ and $R^{3c}$ are each independently selected from halogen, cyano, —$NO_2$, —$CO_2R^f$, —$CONR^fR^g$, —C(O)$R^f$, —$NR^fR^g$, —$SR^f$, —S(O)$R^h$, —S(O)$_2R^h$, —C(O)Y, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —OC(O)$NHR^o$, —OC(O)N($R^o$)$_2$, —SH, —$SR^o$, —S(O)$R^o$, —S(O)$_2R^o$, —$SO_2NH_2$, —S(O)$_2NHR^o$, —S(O)$_2N(R^o)_2$, —NHS(O)$_2R^o$, —$NR^oS(O)_2R^o$, —C(O)$NH_2$, —C(O)$NHR^o$, —C(O)N($R^o$)$_2$, —C(O)$R^o$, —NHC(O)$R^o$, —$NR^oC(O)R^o$, —NHC(O)$NH_2$, —$NR^oC(O)NH_2$, —$NR^oC(O)NHR^o$, —NHC(O)$NHR^o$, —$NR^oC(O)N(R^o)_2$, —NHC(O)N($R^o$)$_2$, —$CO_2H$, —$CO_2R^o$, —$NHCO_2R^o$, —$NR^oCO_2R^o$, —CN, —$NO_2$, —$NH_2$, —$NHR^o$, —N($R^o$)$_2$, —$NR^oS(O)NH_2$ and —$NR^oS(O)_2NHR^o$. More preferably, $R^{3c}$ is selected from halogen, cyano, $C_{1-6}$ alkyl, $C_{1-6}$ haloalkyl, $C_{3-6}$ cycloalkyl, —C(O)R$^f$, —NR$^f$R$^g$, —SR$^f$, —S(O)$_2$R$^h$, —X$^3$Y and Y, and still more preferably selected from NH$_2$, CF$_3$, SCH$_3$, SO$_2$CH$_3$, CN, C(CH$_3$)$_2$OH and Y. R$^{3b}$ is hydrogen, F, Cl, Br or cyano; and R$^{3a}$ is preferably $C_{1-6}$ alkyl, $C_{1-6}$ haloalkyl or $C_{3-6}$ cycloalkyl. R$^{2a}$ is hydrogen, halogen, —OR$^c$, —OC(O)R$^c$, —NR$^c$R$^d$, —SR$^c$, —R$^e$, —CO$_2$R$^c$, —CONR$^c$R$^d$, —C(O)R$^c$, —S(O)R$^e$, —S(O)$_2$R$^e$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$OR$^c$, —X$^2$OC(O)R$^c$, —X$^2$NR$^c$R$^d$, —X$^2$SR$^c$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$S(O)R$^e$, —X$^2$S(O)$_2$R$^e$, —X$^2$NR$^c$S(O)$_2$R$^e$, —X$^2$S(O)$_2$NR$^c$R$^d$ and —X$^2$N$_3$; R$^{2c}$ is hydrogen, halogen, cyano or nitro; and R$^{2d}$ is selected from hydrogen, halogen, —OR$^c$, —OC(O)R$^c$, —NR$^c$R$^d$, —SR$^c$, —CO$_2$R$^c$, —CONR$^c$R$^d$, —C(O)R$^c$, —S(O)R$^e$, —S(O)$_2$R$^e$, —NR$^c$S(O)$_2$R$^e$, —NR$^d$C(O)R$^c$, —X$^2$OR$^c$, —X$^2$OC(O)R$^c$, —X$^2$NR$^c$R$^d$, —X$^2$SR$^c$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$S(O)R$^e$, —X$^2$S(O)$_2$R$^e$, —X$^2$NR$^c$S(O)$_2$R$^e$, —O—X$^2$—OR$^c$, —X$^2$S(O)$_2$NR$^c$R$^d$ and —X$^2$N$_3$, wherein X$^2$ is $C_{1-4}$ alkylene, and each R$^c$ and R$^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each R$^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of R$^c$, R$^d$ and R$^e$ is optionally further substituted as described above for formula III, or with from one to three members selected from the group consisting of OH, O($C_{1-8}$ alkyl), SH, S($C_{1-8}$ alkyl), CN, NO$_2$, NH$_2$, NH($C_{1-8}$ alkyl) and N($C_{1-8}$ alkyl)$_2$; and no more than one of R$^{2a}$ and R$^{2d}$ is hydrogen. Preferably, each of R$^{2a}$ and R$^{2d}$ is other than hydrogen. In some preferred embodiments, R$^{2a}$ is other than hydrogen; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, —NR$^c$S(O)$_2$R$^e$ or —NR$^d$C(O)R$^c$; R$^{3c}$ is selected from the group consisting of NH$_2$, CF$_3$, SCH$_3$, C(CH$_3$)$_2$OH and Y; R$^{3b}$ is hydrogen, F, Cl, Br or cyano; and R$^{3a}$ is selected from the group consisting of $C_{1-6}$ alkyl and $C_{3-6}$ cycloalkyl, optionally substituted as described above.

Returning to formula III above, a particularly preferred group of compounds are those in which m is 0 or 1; R$^1$, when present, is $C_{1-2}$ alkyl, optionally substituted with a member selected from the group consisting of —OH, —OR$^m$, —N(R$^m$)$_2$, —S(O)$_2$R$^m$, —CO$_2$H and —CO$_2$R$^m$; R$^{2a}$ is selected from H, —CH$_3$, halogen, —C(O)CH$_3$, —CO$_2$CH$_3$, —CH$_2$OH, —CH$_2$OCH$_3$, —CH$_2$NH$_2$, —CH(CH$_3$)OH, —CH$_2$NHCH$_3$, —CH$_2$N(CH$_3$)$_2$, —CH$_2$SO$_2$CH$_3$, —CH(CH$_3$)NH$_2$, —C(=NOH)H, —C(=NOH)CH$_3$, —C(=NOCH$_3$)H and —C(=NOCH$_3$)CH$_3$; R$^{2b}$ is H; R$^{2c}$ is selected from H, F, Cl and Br; R$^{2d}$ is selected from OCH$_3$, OCH$_2$CH$_3$, NHCH$_3$, CH$_2$OCH$_3$ and CH$_3$; R$^{2e}$ is H, such that at least one of R$^{2a}$ and R$^{2c}$ is other than H; R$^{3b}$ is hydrogen, F, Cl, Br or cyano; one of R$^{3a}$ and R$^{3c}$ is cyclopropyl, CH$_3$, CF$_3$ or methyl optionally substituted with NH$_2$, NHCH$_3$, N(CH$_3$)$_2$, OH, OCH$_3$, SO$_2$CH$_3$ or NHSO$_2$CH$_3$, and the other of R$^{3a}$ and R$^{3c}$ is selected from the group consisting of CF$_3$, Br, methyl, ethyl, isopropyl, —CO$_2$CH$_3$, —CO$_2$Et, —SO$_2$CH$_3$, —C(O)CH$_3$, —CH$_2$OH, —CH(CH$_3$)OH, —SCH$_3$, —C(CH$_3$)$_2$OH, —NHCH$_3$, —N(CH$_3$)$_2$, —NH$_2$, substituted phenyl and substituted or unsubstituted pyridyl, pyrimidinyl, thienyl, furyl, oxadiazolyl, oxazolyl, thiazolyl, pyrazolyl, triazolyl, tetrazolyl, imidazolyl, morpholinyl, pyrrolidinyl, piperazinyl and piperidinyl.

Another particularly preferred group of embodiments of formula III are those in which m is 0 or 1, preferably 0; R$^1$, when present, is —CO$_2$R$^a$, —X$^1$—SO$_2$R$^a$, or $C_{1-6}$ alkyl, optionally substituted with a member selected from the group consisting of —OH, —OR$^m$, —OC(O)NHR$^m$, —OC(O)N(R$^m$)$_2$, —SH, —SR$^m$, —S(O)R$^m$, —S(O)$_2$R$^m$, —SO$_2$NH$_2$, —S(O)$_2$NHR$^m$, —S(O)$_2$N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —NR$^m$C(O)NHR$^m$, —NHC(O)NHR$^m$, —NR$^m$C(O)N(R$^m$)$_2$, —NHC(O)N(R$^m$)$_2$, —CO$_2$H, —CO$_2$R$^m$, —NHCO$_2$R$^m$, —NR$^m$CO$_2$R$^m$, —CN, —NO$_2$, —NH$_2$, —NHR$^m$, —N(R$^m$)$_2$, —NR$^m$S(O)NH$_2$ and —NR$^m$S(O)$_2$NHR$^m$, wherein each R$^m$ is independently an unsubstituted $C_{1-6}$ alkyl; R$^{2a}$, R$^{2b}$ and R$^{2e}$ are each hydrogen; R$^{2c}$ is halogen or cyano; R$^{2d}$ is selected from —SR$^c$, —O—X$^2$—OR$^c$, —X$^2$—OR$^c$, —R$^e$, —OR$^c$, —NR$^c$R$^d$, —NR$^c$S(O)$_2$R$^e$ and —NR$^d$C(O)R$^c$; R$^{3b}$ is hydrogen, F, Cl, Br or cyano; and R$^{3a}$ and R$^{3c}$ are each independently selected from halogen, cyano, —NO$_2$, —CO$_2$R$^f$, —CONR$^f$R$^g$, —C(O)R$^f$, —NR$^f$R$^g$, —SR$^f$, —S(O)R$^h$, —S(O)$_2$R$^h$, —C(O)Y, —SO$_2$Y, —X$^3$Y, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$. Further preferred within this group of embodiments are those compounds in which (a) at least one of R$^{3a}$ and R$^{3c}$ is $C_{1-6}$ alkyl, optionally further substituted with from one to three members selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; (b) at least one of R$^{3a}$ and R$^{3c}$ is —NR$^f$R$^g$; (c) at least one of R$^{3a}$ and R$^{3c}$ is Y, wherein when Y is phenyl, the phenyl group is substituted; (d) at least one of R$^{3a}$ and R$^{3c}$ is Y, wherein Y is an unsubstituted or substituted 5- or 6-membered heteroaryl group or heterocyclic group such as pyridyl, pyrimidinyl, thienyl, furyl, oxadiazolyl, oxazolyl, thiazolyl, pyrazolyl, triazolyl, tetrazolyl, imidazolyl, morpholinyl, pyrrolidinyl, piperidinyl and the like; or (e) at least one of R$^{3a}$ and R$^{3c}$ is —SO$_2$R$^h$ or —C(O)R$^f$. Any substituents not particularly set forth are meant to have their most complete meaning with reference to formula III. Additionally, all compounds are meant to include their pharmaceutically acceptable salts, as well as any N-oxides thereof.

Yet another particularly preferred group of embodiments of formula III are those in which m is 0 or 1; R$^1$, when present, is —CO$_2$R$^a$, —X$^1$—SO$_2$R$^a$, or $C_{1-6}$ alkyl, optionally substituted with a member selected from the group consisting of —OH, —OR$^m$, —OC(O)NHR$^m$, —OC(O)N(R$^m$)$_2$, —SH, —S(O)R$^m$, —S(O)$_2$R$^m$, —SO$_2$NH$_2$, —S(O)$_2$NHR$^m$, —S(O)$_2$ N(R$^m$)$_2$, —NHS(O)$_2$R$^m$, —NR$^m$S(O)$_2$R$^m$, —C(O)NH$_2$, —C(O)NHR$^m$, —C(O)N(R$^m$)$_2$, —C(O)R$^m$, —NHC(O)R$^m$, —NR$^m$C(O)R$^m$, —NHC(O)NH$_2$, —NR$^m$C(O)NH$_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl; $R^{2a}$ is hydrogen, halogen, —$OR^c$, —$OC(O)R^c$, —$NR^cR^d$, —$SR^c$, —$R^e$, —$CO_2R^c$, —$CONR^cR^d$, —$C(O)R^c$, —$S(O)R^e$, —$S(O)_2R^e$, —$C(NOR^c)R^d$, —$C(NR^cW)=NW$, —$N(W)C(R^c)=NW$, —$X^2C(NOR^c)R^d$, —$X^2C(NR^cW)=NW$, —$X^2N(W)C(R^c)=NW$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —$X^2S(O)_2NR^cR^d$ or —$X^2N_3$; $R^{2b}$ is hydrogen; $R^{2c}$ is halogen or cyano; $R^{2d}$ is selected from —$SR^c$, —O—$X^2$—$OR^c$, —$X^2$—$OR^c$, —$OR^c$, —$NR^cR^d$, —$NR^cS(O)_2R^e$ and —$NR^dC(O)R^c$, or optionally is combined with $R^{2e}$ to form a five or six-membered ring fused to the phenyl ring to which each is attached. $R^{3b}$ is hydrogen, F, Cl, Br or cyano; and $R^{3a}$ and $R^{3c}$ are each independently selected from halogen, —$NR^fR^g$, —$SR^f$, —$CO_2R^f$, —$C(O)R^f$, —$SO_2R^h$, —$X^3Y$, —Y and —$R^h$, wherein $R^h$ is $C_{1-6}$ alkyl, $C_{1-6}$ haloalkyl and $C_{3-6}$ cycloalkyl, wherein the aliphatic portions are optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$. Further preferred within this group of embodiments are those compounds in which (a) at least one of $R^{3a}$ and $R^{3b}$ is $C_{1-6}$ alkyl, optionally further substituted with from one to three members selected from the group consisting of —OH, —$OR^o$, —$OC(O)NHR^o$, —$OC(O)N(R)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$; (b) at least one of $R^{3a}$ and $R^{3c}$ is —$NR^fR^g$; (c) at least one of $R^{3a}$ and $R^{3c}$ is Y, wherein when Y is phenyl, the phenyl group is substituted; (d) at least one of $R^{3a}$ and $R^{3c}$ is Y, wherein Y is an unsubstituted or substituted 5- or 6-membered heteroaryl group or heterocyclic group such as pyridyl, pyrimidinyl, thienyl, furyl, oxadiazolyl, oxazolyl, thiazolyl, pyrazolyl, triazolyl, tetrazolyl, imidazolyl, morpholinyl, pyrrolidinyl, piperidinyl and the like; or (e) at least one of $R^{3a}$ and $R^{3c}$ is —$SO_2R^h$ or —$C(O)R^f$.

In still another group of embodiments of formula III, two adjacent members of $R^{3a}$, $R^{3b}$ and $R^{3c}$ are joined together to form a five or six-membered ring fused to the pyrazole moiety to which each is attached. The remaining member of ($R^{3a}$ or $R^{3c}$) is selected from —$NR^fR^g$, —$SR^f$, —$CO_2R^f$, —$C(O)R^f$, —$SO_2R^h$, —$X^3Y$, —Y and —$R^h$, wherein $R^h$ is $C_{1-6}$ alkyl, $C_{1-6}$ haloalkyl and $C_{3-6}$ cycloalkyl, wherein the aliphatic portions are optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R)_2$, —$NHS(O)_2R^o$, —$NR^oS(O)_2R^o$, —$C(O)NH_2$, —$C(O)$ $NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$.

Another particularly preferred group of embodiments of formula III are those in which m is 0 or 1, preferably 0; $R^1$, when present, is —$CO_2R^a$, —$X^1$—$SO_2R^a$, or $C_{1-6}$ alkyl, optionally substituted with a member selected from the group consisting of —OH, —$OR^m$, —$OC(O)NHR^m$, —$OC(O)N(R^m)_2$, —SH, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl; $R^{2b}$ is selected from hydrogen, halogen, —$OR^c$, —$OC(O)R^c$, —$NR^cR^d$, —$SR^c$, —$R^e$, —$CO_2R^c$, —$CONR^cR^d$, —$C(O)R^c$, —$S(O)R^e$, —$S(O)_2R^e$, —$NR^cS(O)_2R^e$, —$NR^dC(O)R^c$, —$X^2OR^c$, —$X^2OC(O)R^c$, —$X^2NR^cR^d$, —$X^2SR^c$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2S(O)R^e$, —$X^2S(O)_2R^e$, —$X^2NR^cS(O)_2R^e$, —O—$X^2$—$OR^c$, —$X^2S(O)_2NR^cR^d$ and —$X^2N_3$, wherein $X^2$ is $C_{1-4}$ alkylene, and each $R^c$ and $R^d$ is independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl, and each $R^e$ is independently selected from the group consisting of $C_{1-8}$ alkyl, $C_{1-8}$ haloalkyl, $C_{3-6}$ cycloalkyl, $C_{2-8}$ alkenyl and $C_{2-8}$ alkynyl, and each of $R^c$, $R^d$ and $R^e$ is optionally further substituted as described above for formula III, or with from one to three members selected from the group consisting of OH, O($C_{1-8}$ alkyl), SH, S($C_{1-8}$ alkyl), CN, $NO_2$, $NH_2$, NH($C_{1-8}$ alkyl) and N($C_{1-8}$ alkyl)$_2$. More preferably $R^{2b}$ is hydrogen and $R^{2e}$ is hydrogen; $R^{2a}$ is hydrogen, halogen, —CN, —$C(O)R^c$, —$C(NOR^c)R^d$, —$C(NR^cW)=NW$, —$N(W)C(R^c)=NW$, —$X^2C(NOR^c)R^d$, —$X^2C(NR^cW)=NW$, —$X^2N(W)C(R^c)=NW$, —$X^2NR^cR^d$, or —$R^e$; $R^{2d}$ is selected from —$SR^c$, —O—$X^2$—$OR^c$, —$X^2$—$OR^c$, —$R^e$, —$OR^o$, —$NR^cR^d$, —$NR^cS(O)_2R^e$ and —$NR^dC(O)R^c$; $R^{3b}$ is hydrogen, F, Cl, Br or cyano; and $R^{3a}$ and $R^{3c}$ are each independently selected from halogen, cyano, —$NO_2$, —$CO_2R^f$, —$CONR^fR^g$, —$C(O)R^f$, —$NR^fR^g$, —$SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R)_2$, —$NR^oS(O)NH_2$ and —$NR^oS(O)_2NHR^o$. Further preferred within this group of embodiments are those compounds in which (a) at least one of $R^{3a}$ and $R^{3b}$ is $C_{1-6}$ alkyl, optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)$ $NH_2$, —$C(O)NHR^o$, —$C(O)N(R^o)_2$, —$C(O)R^o$, —$NHC(O)$ R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R)$_2$, —NR$^o$S(O)NH$_2$ and —NR$^o$S(O)$_2$NHR$^o$; (b) at least one of R$^{3a}$ and R$^{3b}$ is —NR$^f$R$^g$; (c) at least one of R$^{3a}$ and R$^{3c}$ is Y, wherein when Y is phenyl, the phenyl group is substituted; (d) at least one of R$^{3a}$ and R$^{3b}$ is Y, wherein Y is an unsubstituted or substituted 5- or 6-membered heteroaryl group or heterocyclic group such as pyridyl, pyrimidinyl, thienyl, furyl, oxadiazolyl, oxazolyl, thiazolyl, pyrazolyl, triazolyl, tetrazolyl, imidazolyl, morpholinyl, pyrrolidinyl, piperidinyl and the like; or (e) at least one of R$^{3a}$ and R$^{3c}$ is —SO$_2$R$^h$ or —C(O)R$^f$.

Still other preferred groups of formula III above, are formulae IIIe through IIIvvv, wherein the substituents are as defined for formula III, with preferred embodiments provided below. Formulae IIIe through IIIvvv are provided in FIG. 5A through 5J. Turning first to the compounds of formula IIIe, IIIg, IIIi, IIIk, IIIm, IIIo, IIIq, IIIs, IIIu, IIIw, IIIy, IIIaa, IIIcc, IIIee, IIIgg, IIIii, IIIkk, IIImm, IIIoo, IIIqq, IIIss, IIIuu, IIIww, IIIyy, IIIaaa, IIIccc, IIIeee, IIIggg, IIIiii, IIIkkk, IIImmm, IIIooo, IIIqqq, IIIsss, and IIIuuu, R$^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^e$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; R$^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; R$^{3c}$ is preferably halogen, cyano, —NO$_2$, —CO$_2$R$^f$, —CONR$^f$R$^g$, —C(O)R$^f$, NR$^f$R$^g$, SR$^f$, —S(O)R$^h$, —S(O)$_2$R$^h$, —C(O)Y, —SO$_2$Y, —X$^3$Y, Y, C$_{1-6}$ alkyl, C$_{1-6}$ haloalkyl or C$_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —C(NOR$^f$)R$^g$, —C(NR$^f$W$^a$)=NW$^a$, —N(W$^a$)C(R$^f$)=NW$^a$, —X$^3$OR$^f$, —X$^3$NR$^f$R$^g$, —X$^3$NR$^f$S(O)$_2$R$^h$ and —X$^3$S(O)$_2$NR$^f$R$^g$; R$^5$ is attached to a ring nitrogen and is preferably hydrogen, —R$^h$, —S(O)$_2$R$^h$, —X$^3$OR$^f$, —X$^3$NR$^f$R$^g$, —X$^3$NR$^f$S(O)$_2$R$^h$ and —X$^3$S(O)$_2$NR$^f$R$^g$; m is preferably 0-2; n is preferably 0-3. Further preferred are those compounds in which each R$^1$, when present, is selected from the group consisting of C$_{1-4}$ alkyl, optionally substituted with a member selected from the group consisting of —OH, —OR$^m$, —S(O)$_2$R$^m$, —CO$_2$H and —CO$_2$R$^m$; when n is 1 or more, at least one R$^4$ substituent is attached to a ring carbon atom adjacent to a ring heteroatom. Even more preferably, R$^{2a}$ is hydrogen, halogen, —CN, —C(O)R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, or —R$^e$; R$^{2c}$ is halogen or cyano; R$^5$ is hydrogen, C$_{1-4}$ alkyl, or C$_{3-6}$ cycloalkyl. Still more preferably, m is 0 or 1, n is 0 or 1, and R$^1$ when present is —CH$_3$. In the most preferred embodiments, R$^{2d}$ is —SR$^c$, —R$^e$, or —OR$^c$; R$^{3b}$ is hydrogen, halogen, cyano, or —NO$_2$; R$^{3c}$ is C$_{1-6}$ alkyl, C$_{1-6}$ haloalkyl or C$_{3-6}$ cycloalkyl which are optionally substituted as set forth above; and R$^4$ when present is —CH$_3$, —CF$_3$ or —CN.

For compounds of formula IIIf, IIIh, IIIj, IIIl, IIIn, IIIp, IIIr, IIIt, IIIy, IIIx, IIIz, IIIbb, IIIdd, IIIff, IIIhh, IIIjj, IIIll, IIInn, IIIpp, IIIrr, IIItt, IIIvv, IIIxx, IIIzz, IIIbbb, IIIddd, IIIfff, IIIhhh, IIIjjj, IIIlll, IIInnn, IIIppp, IIIrrr, IIIttt, and IIIvvv, R$^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^e$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; R$^{3a}$ is preferably halogen, cyano, —NO$_2$, —CO$_2$R$^f$, —CONR$^f$R$^g$, —C(O)R$^f$, NR$^f$R$^g$, SR$^f$, —S(O)R$^h$, —S(O)$_2$R$^h$, —C(O)Y, —SO$_2$Y, —X$^3$Y, Y, C$_{1-6}$ alkyl, C$_{1-6}$ haloalkyl or C$_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; R$^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —C(NOR$^f$)R$^g$, —C(NR$^f$W$^a$)=NW$^a$, —N(W$^a$)C(R$^f$)=NW$^a$, —X$^3$OR$^f$, —X$^3$NR$^f$R$^g$, —X$^3$NR$^f$S(O)$_2$R$^h$ and —X$^3$S(O)$_2$NR$^f$R$^g$; R$^5$ is attached to a ring nitrogen and is preferably hydrogen, —R$^h$, —S(O)$_2$R$^h$, —X$^3$OR$^f$, —X$^3$NR$^f$R$^g$, —X$^3$NR$^f$S(O)$_2$R$^h$ and —X$^3$S(O)$_2$NR$^f$R$^g$; m is preferably 0-2; n is preferably 0-3. Further preferred are those compounds in which each R$^1$, when present, is selected from the group consisting of C$_{1-4}$ alkyl, optionally substituted with a member selected from the group consisting of —OH, —OR$^m$, —S(O)$_2$R$^m$, —CO$_2$H and —CO$_2$R$^m$; when n is 1 or more, at least one R$^4$ substituent is attached to a ring carbon atom adjacent to a ring heteroatom. Even more preferably, R$^{2a}$ is hydrogen, halogen, —CN, —C(O)R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, or —R$^e$; R$^{2c}$ is halogen or cyano; R$^5$ is hydrogen, C$_{1-4}$ alkyl, or C$_{3-6}$ cycloalkyl. Still more preferably, m is 0 or 1, n is 0 or 1, and R$^1$ when present is —CH$_3$. In the most preferred embodiments, R$^{2d}$ is —SR$^c$, —R$^e$, or —OR$^c$; R$^{3a}$ is halogen, cyano, C$_{1-6}$ alkyl, C$_{1-6}$ haloalkyl, C$_{3-6}$ cycloalkyl, —C(O)R$^f$ or —SO$_2$R$^h$ wherein the aliphatic portions are optionally substituted as set forth above; R$^{3b}$ is hydrogen, halogen, cyano, or —NO$_2$; R$^4$ when present is —CH$_3$, —CF$_3$, —CN, —C(O)R$^f$ or —SO$_2$R$^h$.

N-Linked Heteroaryls

Figure 5A:
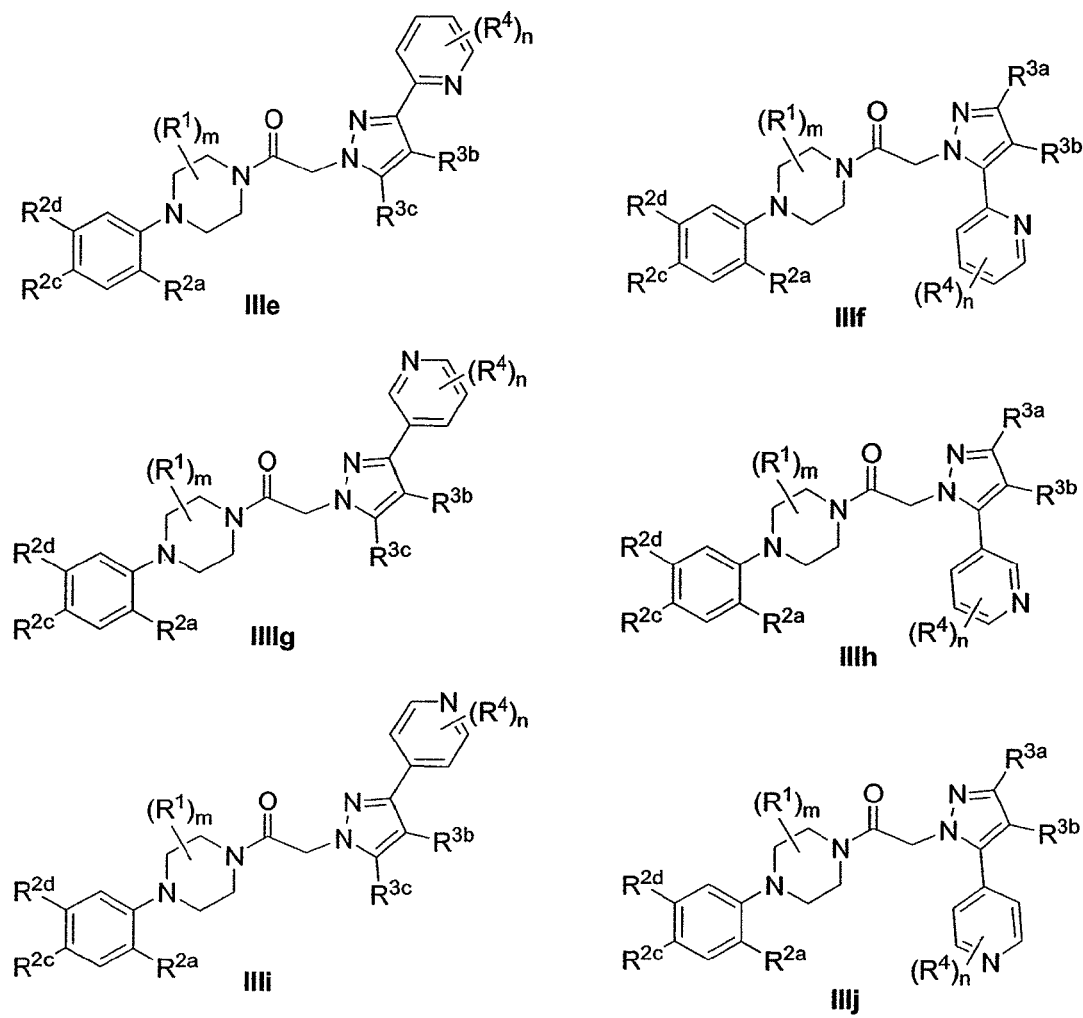
FIGS. 5A-5L provide generic formulae of preferred embodiments of the invention.
Figure 5B:
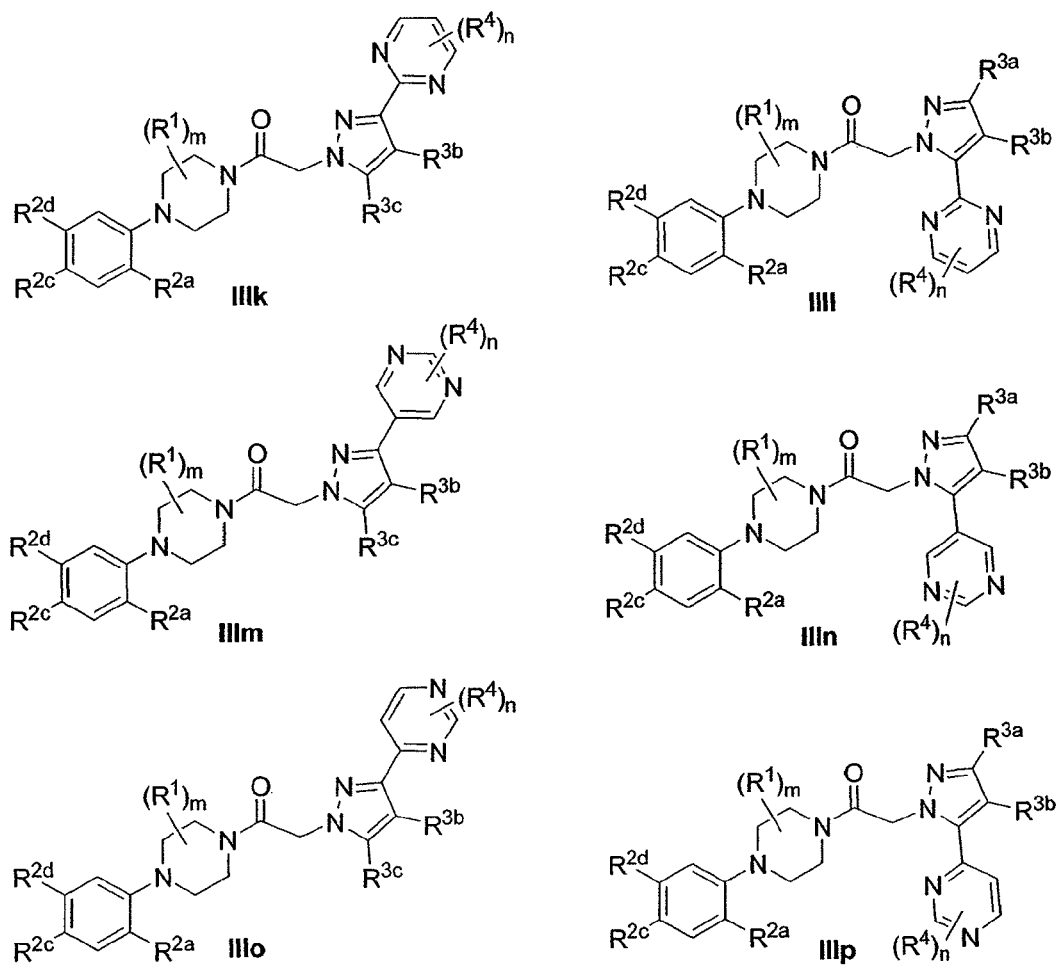
Figure 5C:
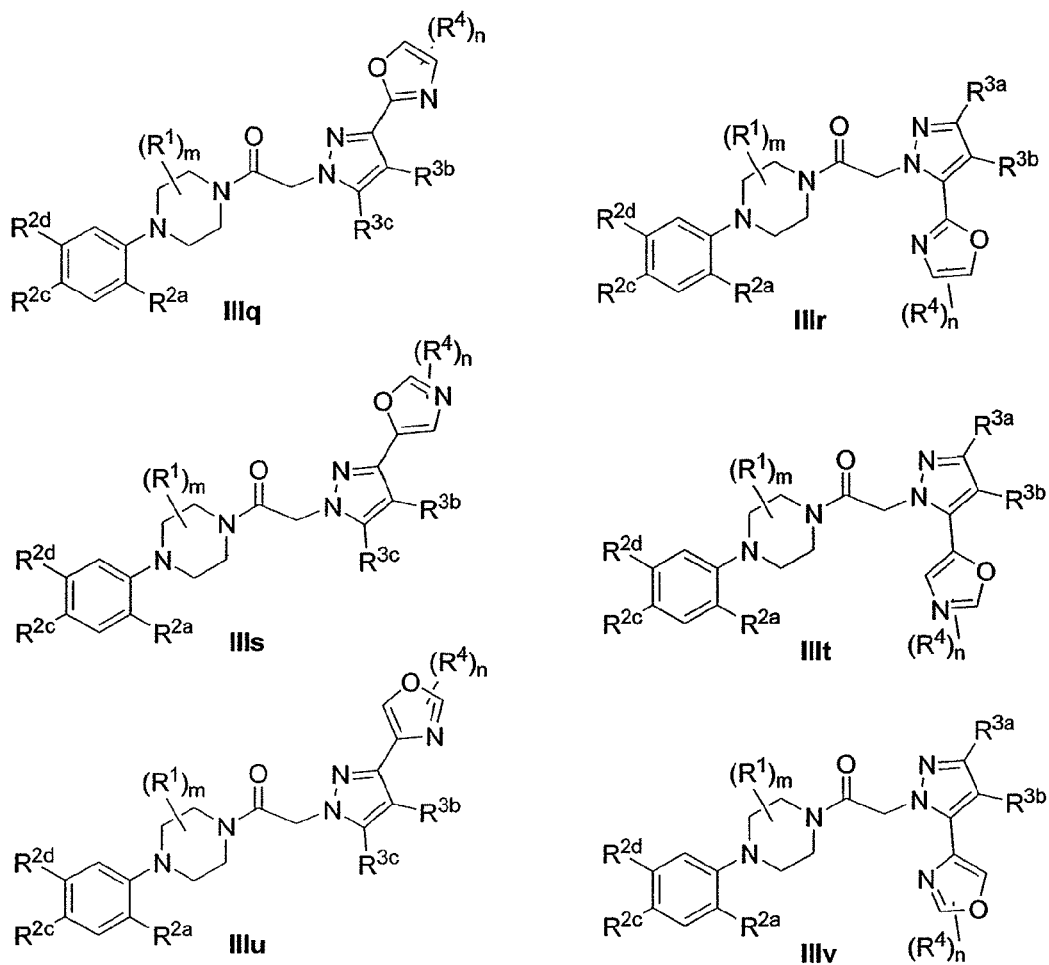
Figure 5D:
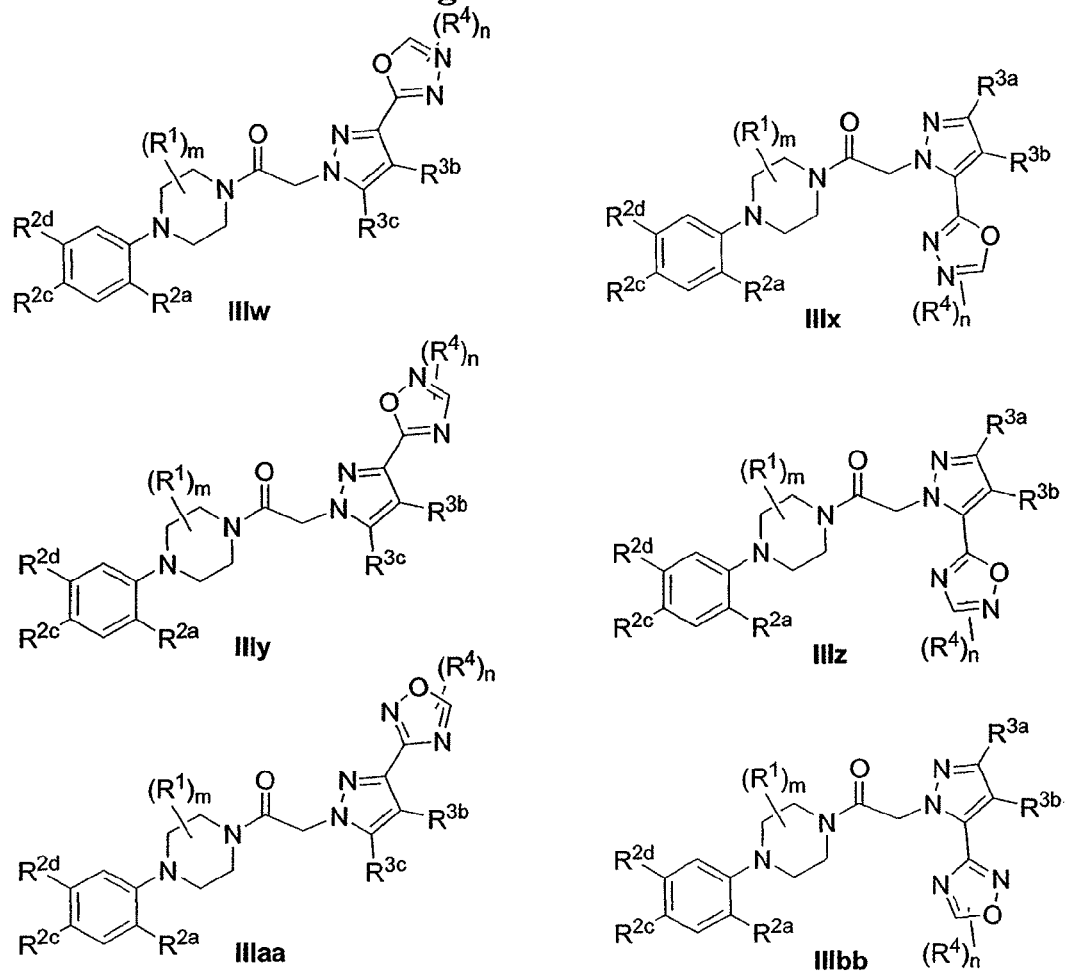
Figure 5E:
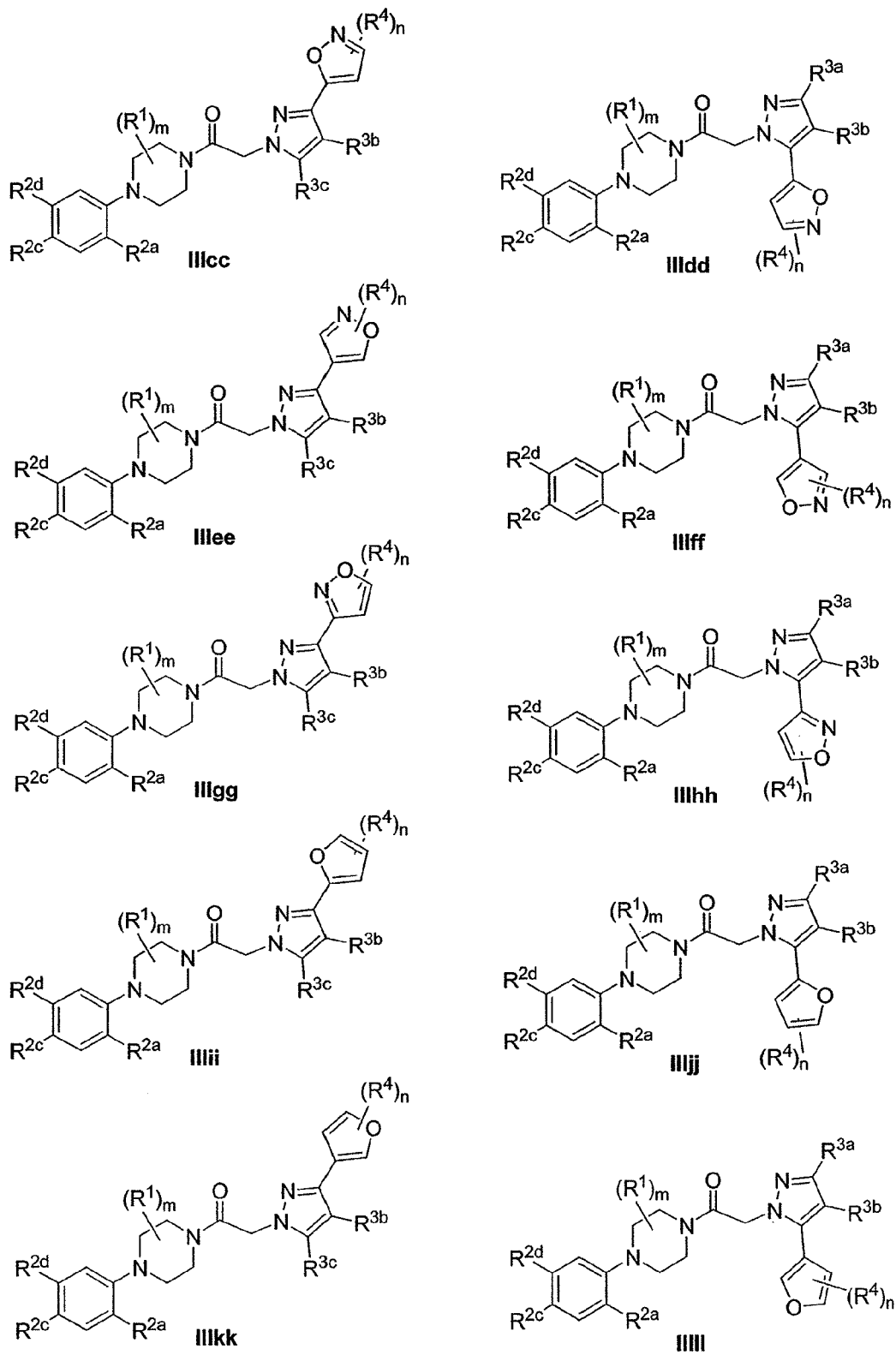
Figure 5F:
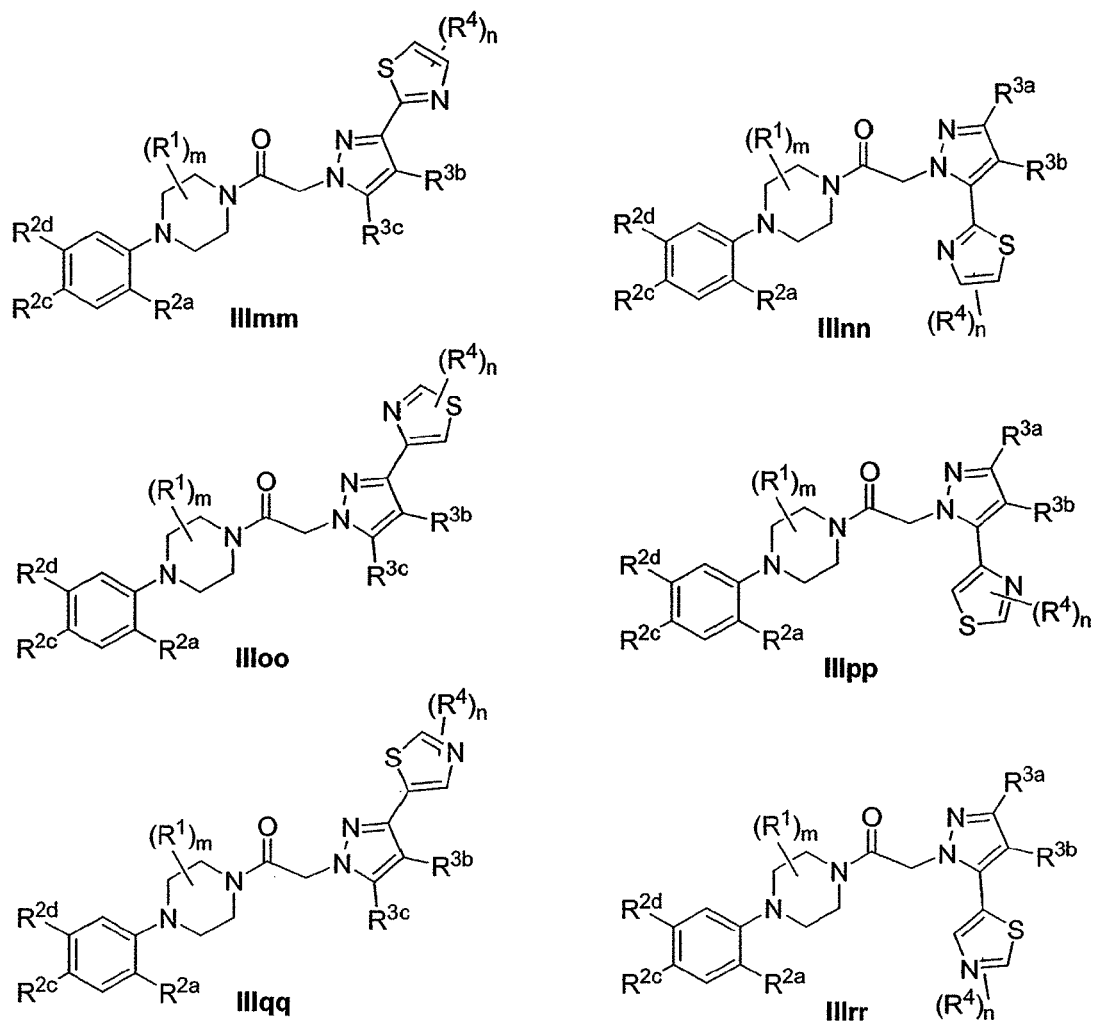
Figure 5G:
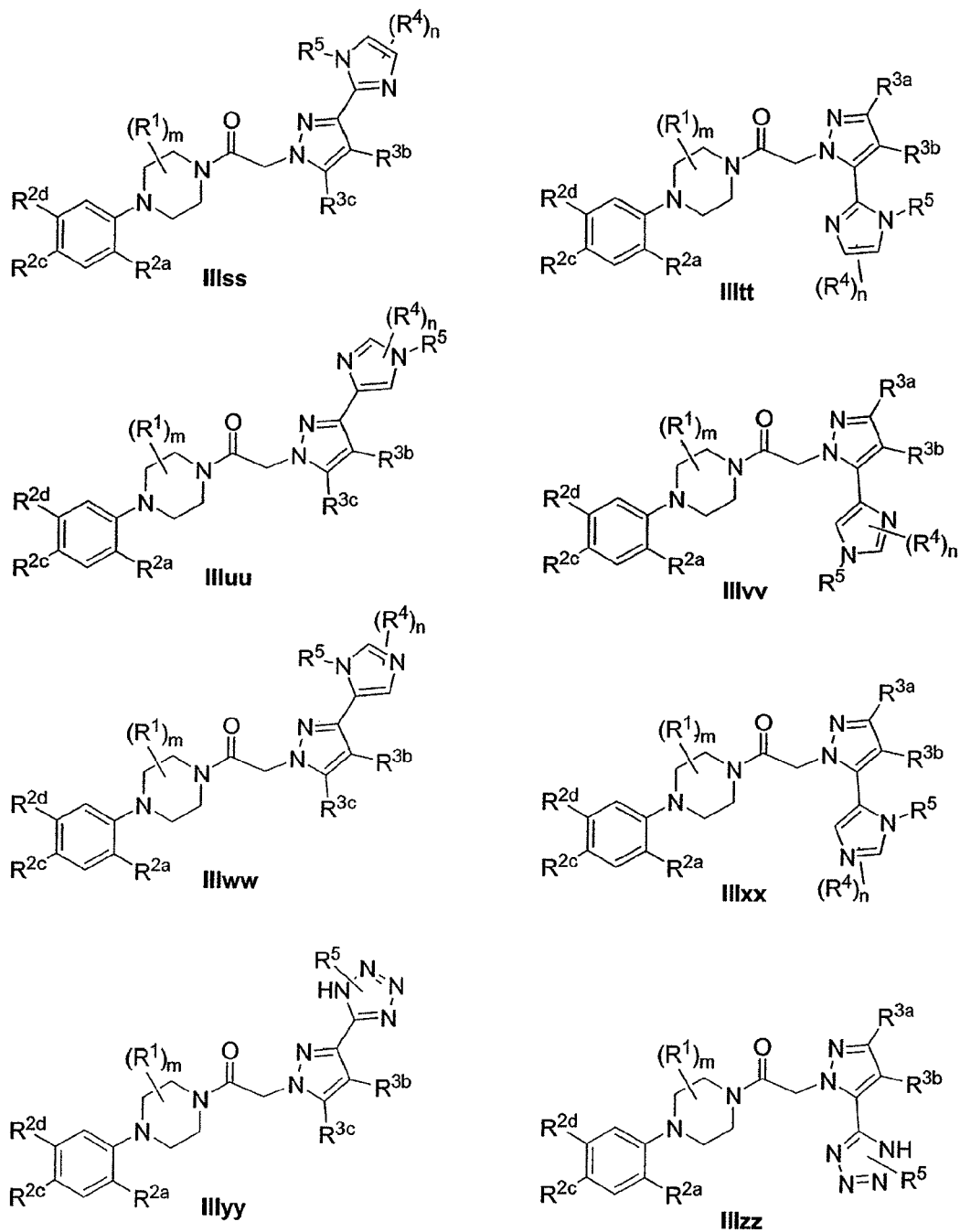
Figure 5H:
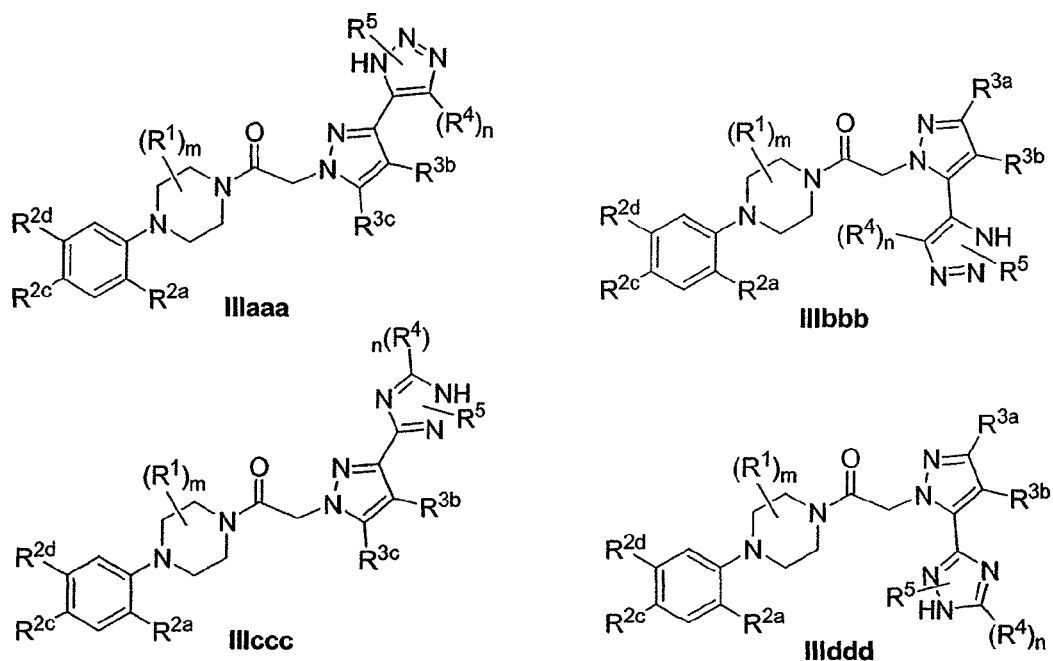
Figure 5I:
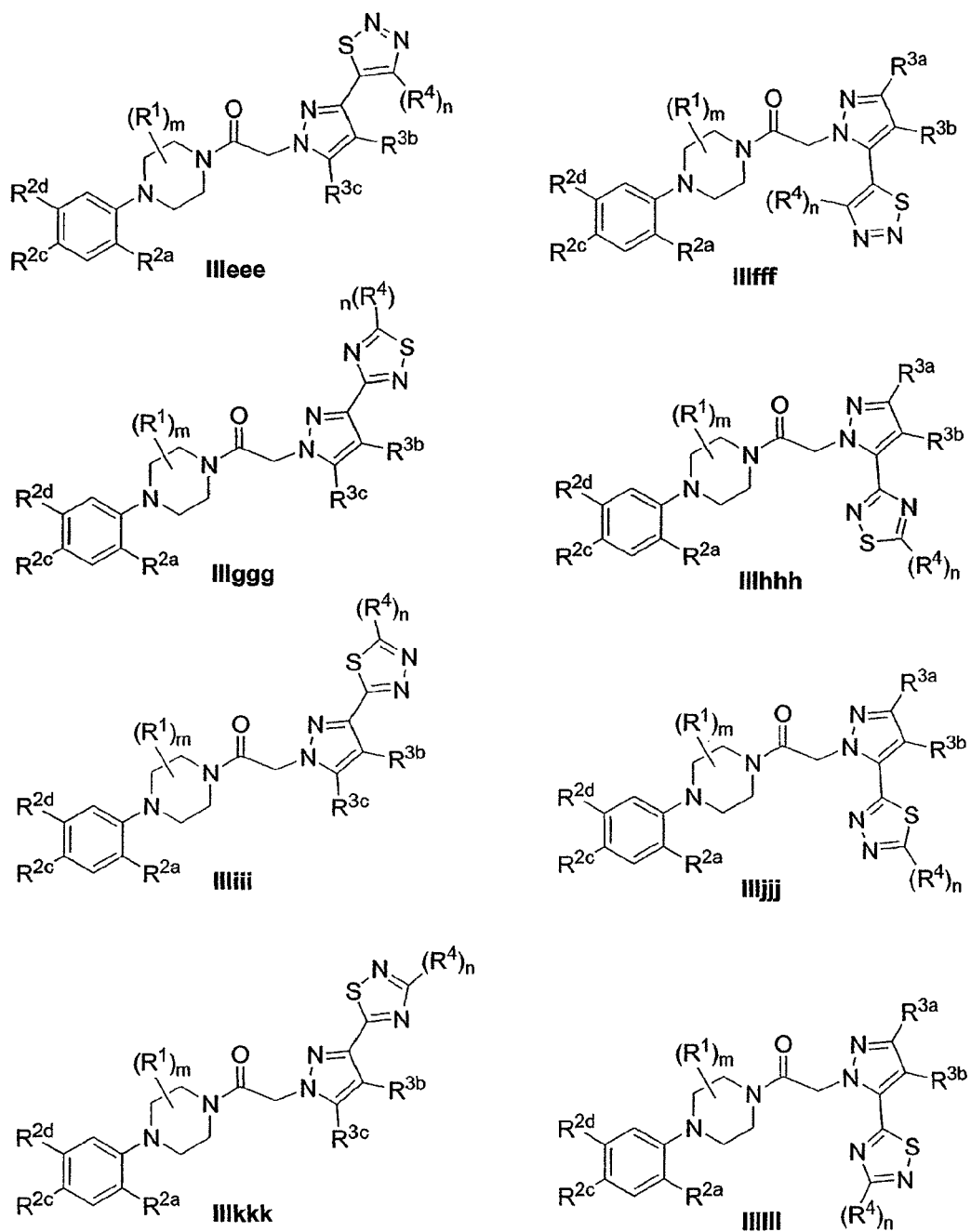
Figure 5J:
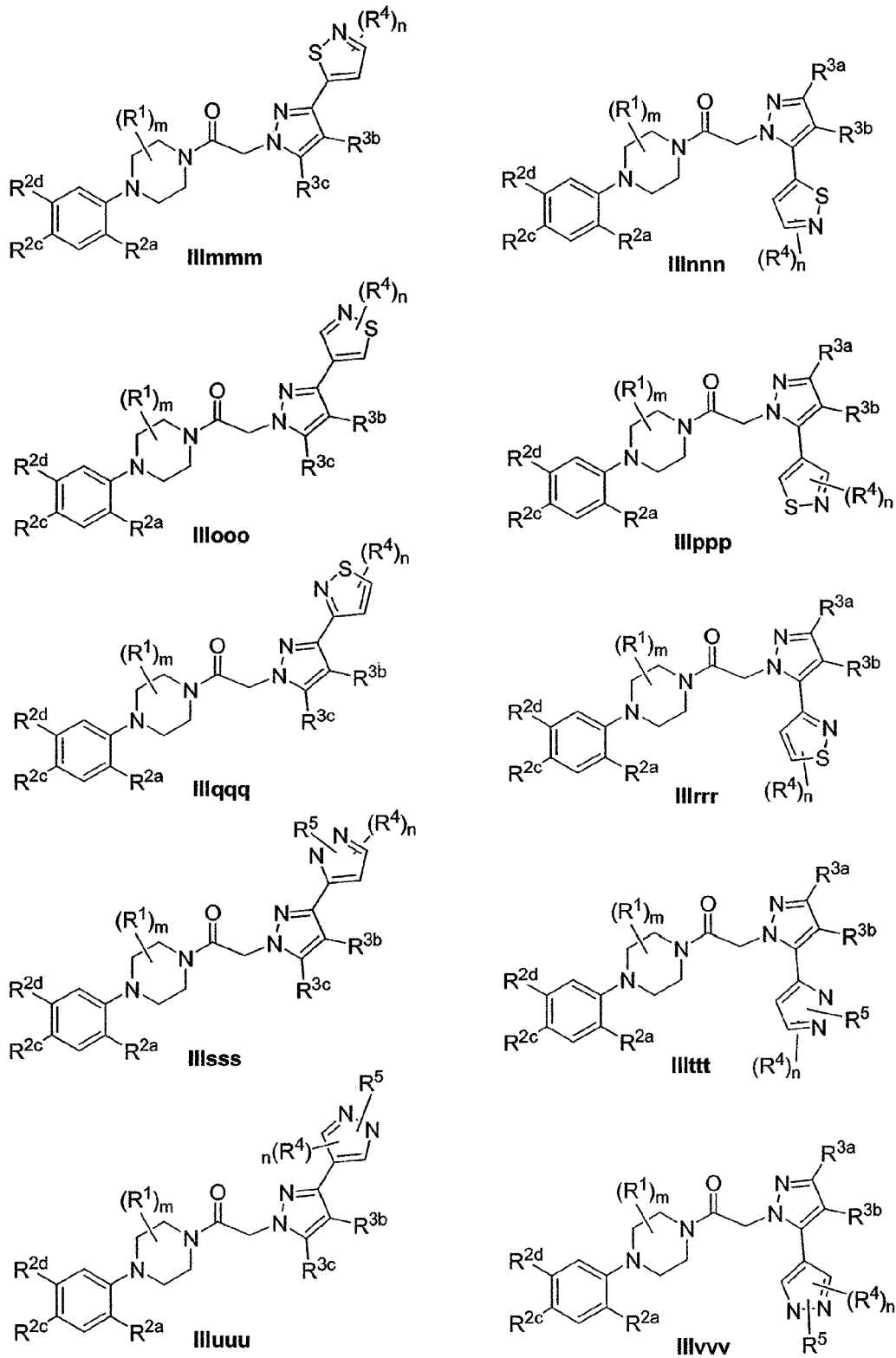
Figure 5K:
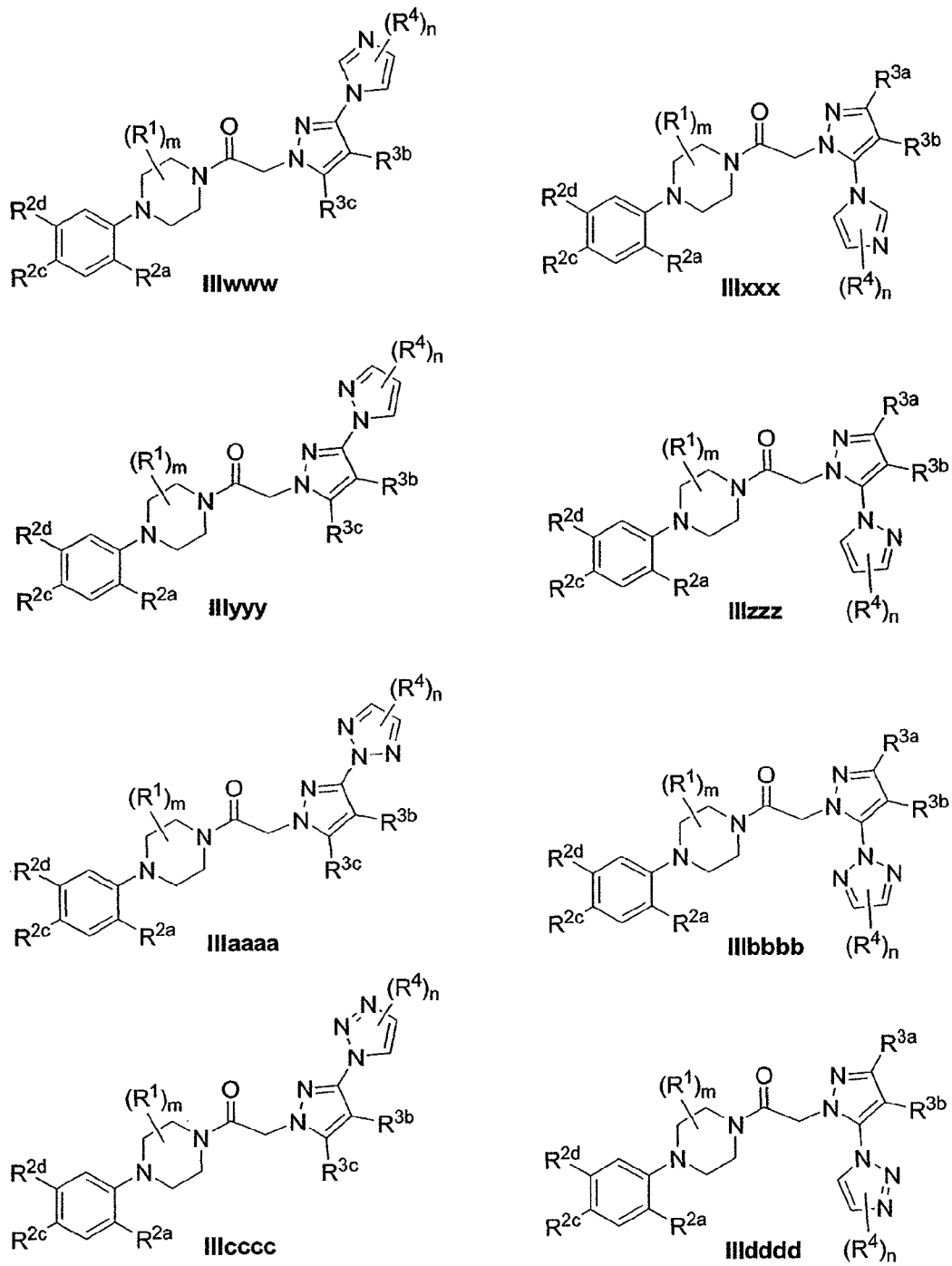

In other preferred groups of formula III, the compounds have a formula selected from formulae IIIwww through IIIdddd, FIG. 5K, wherein the substituents have the meanings provided with respect to formula III above. Turning first to the compounds of formula IIIwww, IIIyyy, IIIaaaa and IIIcccc, R$^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^e$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; R$^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; R$^{3c}$ is preferably halogen, cyano, —NO$_2$, —CO$_2$R$^f$, —CONR$^f$R$^g$, —C(O)R$^f$, —NR$^f$R$^g$, —SR$^f$, —S(O)R$^h$, —S(O)$_2$R$^h$, —C(O)Y, —SO$_2$Y, —X$^3$Y, Y, C$_{1-6}$ alkyl, C$_{1-6}$ haloalkyl or C$_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$NR$^f$R$^g$, and two adjacent R$^4$ groups can form a five or six-membered saturated or unsaturated ring having from 0 to 2 additional heteroatoms as ring members; m is preferably 0-2; n is preferably 0-3. Further preferred are those compounds in which each R$^1$, when present, is selected from the group consisting of C$_{1-4}$ alkyl, optionally substituted with a member selected from the group consisting of —OH, —OR$^m$, —S(O)$_2$R$^m$, —CO$_2$H and —CO$_2$R$^m$; when n is 1 or more, at least one R$^4$ substituent is attached to a ring carbon atom adjacent to a ring heteroatom. Even more preferably, R$^{2a}$ is hydrogen, halogen, —CN, —C(O)R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, or —R$^e$; R$^{2c}$ is halogen or cyano. Still more preferably, m is 0 or 1, n is 0 or 1, and R$^1$ when present is —CH$_3$. In the most preferred embodiments, R$^{2d}$ is —SR$^c$, —R$^e$, or —OR$^c$; R$^{3b}$ is hydrogen, halogen, cyano, or —NO$_2$; R$^{3c}$ is halogen, cyano, —C(O)R$^f$, —SO$_2$R$^h$, C$_{1-6}$ alkyl, C$_{1-6}$ haloalkyl or C$_{3-6}$ cycloalkyl wherein the aliphatic portions are substituted as set forth above; and R$^4$ when present is —CH$_3$, —CF$_3$ or —CN.

For compounds of formula IIIxxx, IIIzzz, IIIbbbb, IIIdddd, R$^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^e$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; R$^{2c}$ is halogen, cyano or nitro; R$^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; R$^{3a}$ is preferably halogen, cyano, —NO$_2$, —CO$_2$R$^f$, —CONR$^f$R$^g$, —C(O)R$^f$, —NR$^f$R$^g$, —SR$^f$, —S(O)R$^h$, —S(O)$_2$R$^h$, —C(O)Y, —SO$_2$Y, —X$^3$Y, Y, C$_{1-6}$ alkyl, C$_{1-6}$ haloalkyl or C$_{3-6}$ cycloalkyl, where the alkyl and cycloalkyl substituents can be optionally substituted with a member selected from the group consisting of —OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; R$^{3b}$ is preferably hydrogen, halogen, cyano, —NO$_2$, —CO$_2$R$^f$, —CONR$^f$R$^g$, —C(O)R$^f$, —S(O) R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; R$^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O) R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$ NR$^f$R$^g$, and two adjacent R$^4$ groups can form a five or six-membered saturated or unsaturated ring having from 0 to 2 additional heteroatoms as ring members; m is preferably 0-2; n is preferably 0-3. Further preferred are those compounds in which each R$^1$, when present, is selected from the group consisting of C$_{1-4}$ alkyl, optionally substituted with a member selected from the group consisting of —OH, —OR$^m$, —S(O)$_2$ R$^m$, —CO$_2$H and —CO$_2$R$^m$; when n is 1 or more, at least one R$^4$ substituent is attached to a ring carbon atom adjacent to a ring heteroatom. Even more preferably, R$^{2a}$ is hydrogen, halogen, —CN, —C(O)R$^c$, —C(NOR$^c$)R$^d$, —C(NR$^c$W)= NW, —N(W)C(R$^c$)=NW, —X$^2$C(NOR$^c$)R$^d$, —X$^2$C $(NR^cW)$=NW, —$X^2N(W)C(R^c)$=NW, —$X^2NR^cR^d$, or —$R^e$; $R^{2c}$ is halogen or cyano. Still more preferably, m is 0 or 1, n is 0 or 1, and $R^1$ when present is —$CH_3$. In the most preferred embodiments, $R^{2d}$ is —$SR^c$, —$R^e$, or —$OR^c$; $R^{3a}$ is halogen, cyano, —$C(O)R^f$, —$S(O)_2R^h$, $C_{1-6}$ alkyl, $C_{1-6}$ haloalkyl or $C_{3-6}$ cycloalkyl, where the alkyl and cycloalkyl substituents can be optionally substituted as noted above; $R^{3b}$ is hydrogen, halogen, cyano or —$NO_2$; $R^4$ when present is —$CH_3$, —$CF_3$ or —CN.

Figure 5L:
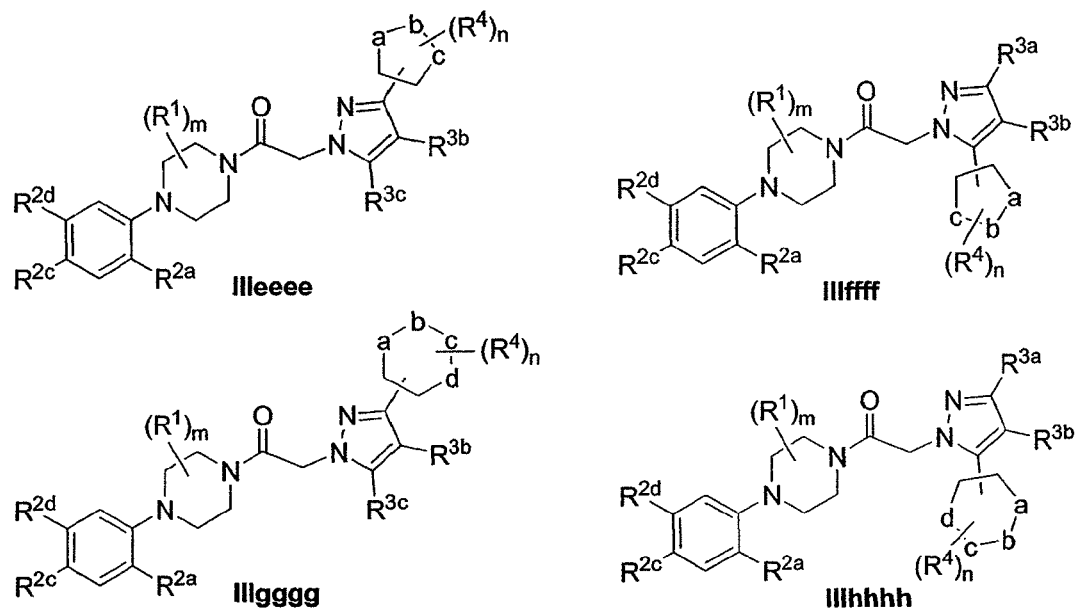

5-Membered C- and N-Linked Heterocycles:

In other preferred groups of formula III, the compounds have a formula selected from formulae IIIeeee and IIIffff, FIG. 5L, wherein the substituents have the meanings provided with respect to formula III above. Turning first to the compounds of formula IIIeeee, $R^{2a}$ is preferably hydrogen, halogen, cyano, —$NO_2$, —$CO_2R^c$, —$CONR^cR^d$, —$C(O)R^e$, —$S(O)R^e$, —$S(O)_2R^e$, —$R^c$, —$C(NOR^c)R^d$, —$C(NR^cW)$=NW, —$N(W)C(R^c)$=NW, —$X^2C(NOR^c)R^d$, —$X^2C(NR^cW)$=NW, —$X^2N(W)C(R^c)$=NW, —$X^2NR^cR^d$, —$X^2SR^c$, —$X^2CN$, —$X^2NO_2$, —$X^2CO_2R^c$, —$X^2CONR^cR^d$, —$X^2C(O)R^e$, —$X^2OC(O)NR^cR^d$, —$X^2NR^dC(O)R^c$, —$X^2NR^dC(O)_2R^e$, —$X^2NR^cC(O)NR^c R^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$, or —$X^2N_3$; $R^{2c}$ is halogen, cyano or nitro; $R^{2d}$ is —$SR^c$, —O—$X^2$—$OR^c$, —$X^2$—$OR^c$, —$R^e$, —$OR^c$, —$NR^cR^d$, or —$NR^cSO_2R^d$; $R^{3b}$ is preferably hydrogen, halogen, cyano, —$NO_2$, —$CO_2R^f$, —$CONR^fR^g$, —$C(O)R^f$, —$S(O)R^h$, —$S(O)_2R^h$, —$R^h$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —$X^3N_3$, Y, or —$X^3Y$; $R^{3c}$ is preferably halogen, cyano, —$NO_2$, —$CO_2R^f$, —$CONR^fR^g$, —$C(O)R$, —$NR^fR^g$, —$SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$; $R^4$ is preferably halogen, —$OR^f$, —$NR^fR^g$, —$R^h$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$X^3OR^f$, —$X^3NR^fR^g$, —$X^3NR^fS(O)_2R^h$ and —$X^3S(O)_2NR^fR^g$, and two adjacent $R^4$ groups can form a five or six-membered saturated or unsaturated ring having from 0 to 2 additional heteroatoms as ring members; m is preferably 0-2; n is preferably 0-3; a, b, and c can be N, $NR^5$, S, SO, $SO_2$, O, or $C(R^4)_o$, where o can be 0-2; $R^5$ is preferably hydrogen, —$R^h$, —$S(O)_2R^h$, —$X^3OR^f$, —$X^3NR^fR^g$, —$X^3NR^fS(O)_2R^h$ and —$X^3S(O)_2NR^fR^g$, —$CO_2R^f$, —$CONR^fR^g$, or —$C(O)R^f$. Further preferred are those compounds in which each $R^1$, when present, is selected from the group consisting of $C_{1-4}$ alkyl, optionally substituted with a member selected from the group consisting of —OH, —$OR^m$, —$S(O)_2R^m$, —$CO_2H$ and —$CO_2R^m$; when a and c are other than $C(R^4)_o$, b must be $C(R^4)_o$ or $SO_2$; when a and b are other than $C(R^4)^o$, then c must be $C(R^4)_o$ or $SO_2$. Even more preferably, $R^{2a}$ is hydrogen, halogen, —CN, —$C(O)R^c$, —$C(NOR^c)R^d$, —$C(NR^cW)$=NW, —$N(W)C(W)$=NW, —$X^2C(NOR^c)R^d$, —$X^2C(NR^cW)$=NW, —$X^2N(W)C(R^c)$=NW, —$X^2NR^cR^d$, or —$R^e$; $R^{2c}$ is halogen or cyano. Still more preferably, m is 0 or 1, n is 0 or 1, and $R^1$ when present is —$CH_3$. In the most preferred embodiments, $R^{2d}$ is —$SR^c$, —$R^e$, or —$OR^c$; $R^{3b}$ is hydrogen, halogen, cyano or —$NO_2$; $R^{3c}$ is halogen, cyano, —$C(O)R^f$, —$SO_2R^h$, $C_{1-6}$ alkyl, $C_{1-6}$ haloalkyl or $C_{3-6}$ cycloalkyl wherein the aliphatic portions are substituted as set forth above.

For compounds of Formula IIIffff, $R^{2a}$ is preferably hydrogen, halogen, cyano, —$NO_2$, —$CO_2R^c$, —$CONR^cR^d$, —$C(O)R^e$, —$S(O)R^e$, —$S(O)_2R^e$, —$R^c$, —$C(NOR^c)R^d$, —$C(NR^cW)$=NW, —$N(W)C(R^c)$=NW, —$X^2C(NOR^c)R^d$, —$X^2C(NR^cW)$=NW, —$X^2N(W)C(R^c)$=NW, —$X^2NR^cR^d$, —$X^2SR^c$, —$X^2CN$, —$X^2NO_2$, —$X^2CO_2R^c$, —$X^2CONR^cR^d$, —$X^2C(O)R^e$, —$X^2OC(O)NR^cR^d$, —$X^2NR^dC(O)R^c$, —$X^2NR^dC(O)_2R^e$, —$X^2NR^cC(O)NR^c R^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$, or —$X^2N_3$; $R^{2c}$ is halogen, cyano or nitro; $R^{2d}$ is —$SR^c$, —O—$X^2$, —$OR^c$, —$R^e$, —$OR^c$, —$NR^cR^d$, or —$NR^cSO_2R^d$; $R^{3a}$ is preferably halogen, cyano, —$NO_2$, —$CO_2R^f$, —$CONR^fR^g$, —$C(O)R$, —$NR^fR^g$, —$SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$; $R^{3b}$ is preferably hydrogen, halogen, cyano, —$NO_2$, —$CO_2R^f$, —$CONR^fR^g$, —$C(O)R^f$, —$S(O)R^h$, —$S(O)_2R^h$, —$R^h$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —$X^3N_3$, Y, or —$X^3Y$; $R^4$ is preferably halogen, —$OR^f$, —$NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$X^3OR^f$, —$X^3NR^fR^g$, —$X^3NR^fS(O)_2R^h$ and —$X^3S(O)_2NR^fR^g$, and two adjacent $R^4$ groups can form a five or six-membered saturated or unsaturated ring having from 0 to 2 additional heteroatoms as ring members; m is preferably 0-2; n is preferably 0-3; a, b, and c can be N, $NR^5$, S, SO, $SO_2$, O, or $C(R^4)_o$, where o can be 0-2; $R^5$ is preferably hydrogen, —$R^h$, —$S(O)_2R^h$, —$X^3OR^f$, —$X^3NR^fRg$, —$X^3NR^fS(O)_2R^h$, —$X^3S(O)_2NR^fR^g$, —$CO_2R^f$, —$CONR^fR^g$, or —$C(O)R^f$. Further preferred are those compounds in which each $R^1$, when present, is selected from the group consisting of $C_{1-4}$ alkyl, optionally substituted with a member selected from the group consisting of —OH, —$OR^m$, —$S(O)_2R^m$, —$CO_2H$ and —$CO_2R^m$; when a and c are other than $C(R^4)_o$, b must be $C(R^4)_o$ or $SO_2$; when a and b are other than $C(R^4)_o$, then c must be $C(R^4)_o$ or $SO_2$. Even more preferably, $R^{2a}$ is hydrogen, halogen, —CN, —$C(O)R^c$, —$C(NOR^c)R^d$, —$C(NR^cW)$= NW, —$N(W)C(R^c)$=NW, —$X^2C(NOR^c)$ R'", —$X^2C(NR^cW)$=NW, —$X^2N(W)C(R^c)$=NW, —$X^2NR^cR^d$, or —$R^e$; $R^{2c}$ is halogen or cyano. Still more preferably, m is 0 or 1, n is 0 or 1, and $R^1$ when present is —$CH_3$. In the most preferred embodiments, $R^{2d}$ is —$SR^c$, —$R^e$, or —$OR^e$; $R^{3a}$ is halogen, cyano, —$C(O)R^f$, —$S(O)_2R^h$, $C_{1-6}$ alkyl, $C_{1-6}$ haloalkyl or $C_{3-6}$ cycloalkyl, where the alkyl and cycloalkyl substituents can be optionally substituted as noted above; and $R^{3b}$ is hydrogen, halogen, cyano or —$NO_2$.

6-Membered C- and N-Linked Heterocycles:

In other preferred groups of formula III, the compounds have a formula selected from formulae IIIgggg and IIIhhh, FIG. 5L, wherein the substituents have the meanings provided with respect to formula III above. Turning first to the compounds of formula IIIgggg, $R^{2a}$ is preferably hydrogen, halogen, cyano, —$NO_2$, —$CO_2R^c$, —$CONR^cR^d$, —$C(O)R^c$, —$S(O)R^e$, —$S(O)_2R^e$, —$R^c$, —$C(NOR^c)R^d$, —$C(NR^cW)$=NW, —$N(W)C(R^c)$=NW, —$X^2C(NOR^c)R^d$, —$X^2C(NR^cW)$=NW, —$X^2N(W)C(R^c)$=NW, —$X^2NR^cR^d$, —$X^2SR^c$, —$X^2CN$, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$, or —$X^2N_3$; $R^{2c}$ is halogen, cyano or nitro; $R^{2d}$ is —$SR^c$, —O—$X^2$—$OR^c$, —$X^2$—$OR^c$, —$R^e$, —$OR^c$, —$NR^cR^d$, or —$NR^cSO_2R^d$; $R^{3b}$ is preferably hydrogen, halogen, cyano, —$NO_2$, —$CO_2R^f$, —$CONR^fR^g$, —$C(O)R^f$, —$S(O)R^h$, —$S(O)_2R^h$, —$R^h$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^h$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^3S(O)_2R^h$, —$X^3NR^fS(O)_2R^h$, —$X^3S(O)_2NR^fR^g$, —$X^3N_3$, Y, or —$X^3Y$; $R^{3c}$ is preferably halogen, cyano, —$NO_2$, —$CO_2R^f$, —$CONR^fR^g$, —$C(O)R^f$, $NR^fR^g$, $SR^f$, —$S(O)R^h$, —$S(O)_2R^h$, —$C(O)Y$, —$SO_2Y$, —$X^3Y$, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of —OH, —$OR^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R$^o$)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; $R^4$ is preferably halogen, O, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$, —X$^3$S(O)$_2$NR$^f$R$^g$, and two adjacent $R^4$ groups can form a five or six-membered saturated or unsaturated ring having from 0 to 2 additional heteroatoms as ring members; m is preferably 0-2; n is preferably 0-3; a, b, c, and d can be N, NR$^5$, S, SO, SO$_2$, O, or C(R$^4$)$_o$, where o can be 0-2; $R^5$ is preferably hydrogen, —R$^h$, —S(O)$_2$R$^h$, —X$^3$OR$^f$, —X$^3$NR$^f$R$^g$, —X$^3$NR$^f$S(O)$_2$R$^h$ and —X$^3$S(O)$_2$NR$^f$R$^g$, —CO$_2$R$^f$, —CONR$^f$R$^g$, or —C(O)R$^f$. Further preferred are those compounds in which each $R^1$, when present, is selected from the group consisting of $C_{1-4}$ alkyl, optionally substituted with a member selected from the group consisting of —OH, —OR$^m$, —S(O)$_2$R$^m$, —CO$_2$H and —CO$_2$R$^m$; when b and d are other than C(R$^4$)$_o$, c must be C(R$^4$)$_o$ or SO$_2$; when b and c are other than C(R$^4$)$_o$, then d must be C(R$^4$)$_o$ or SO$_2$; when a and d are other than C(R$^4$)$_o$, then at least one of a and b must be C(R$^4$)$_o$ or SO$_2$. Even more preferably, $R^{2a}$ is hydrogen, halogen, —CN, —C(O)R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, or —R$^e$; $R^{2c}$ is halogen or cyano. Still more preferably, m is 0 or 1, n is 0 or 1, and $R^1$ when present is —CH$_3$. In the most preferred embodiments, $R^{2d}$ is —SR$^c$, —R$^e$, or —OR$^c$; $R^{3b}$ is hydrogen, halogen, cyano, or —NO$_2$; $R^{3c}$ is halogen, cyano, —C(O)R$^f$, —SO$_2$R$^h$, $C_{1-6}$ alkyl, $C_{1-6}$ haloalkyl or $C_{3-6}$ cycloalkyl wherein the aliphatic portions are substituted as set forth above.

For compounds of Formula IIIhhh, $R^{2a}$ is preferably hydrogen, halogen, cyano, —NO$_2$, —CO$_2$R$^c$, —CONR$^c$R$^d$, —C(O)R$^c$, —S(O)R$^e$, —S(O)$_2$R$^e$, —R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, or —X$^2$N$_3$; $R^{2c}$ is halogen, cyano or nitro; $R^{2d}$ is —SR$^c$, —O—X$^2$—OR$^c$, —X$^2$—OR$^c$, —R$^e$, —OR$^c$, —NR$^c$R$^d$, or —NR$^c$SO$_2$R$^d$; $R^{3a}$ is preferably halogen, cyano, —NO$_2$, —CO$_2$R$^f$, —CONR$^f$R$^g$, —C(O)R$^f$, NR$^f$R$^g$, SR$^f$, —S(O)R$^h$, —S(O)$_2$R$^h$, —C(O)Y, —SO$_2$Y, —X$^3$Y, Y, $C_{1-6}$ alkyl, $C_{1-6}$ haloalkyl or $C_{3-6}$ cycloalkyl, where the alkyl and cycloalkyl substituents can be optionally substituted with a member selected from the group consisting of—OH, —OR$^o$, —OC(O)NHR$^o$, —OC(O)N(R$^o$)$_2$, —SH, —SR$^o$, —S(O)R$^o$, —S(O)$_2$R$^o$, —SO$_2$NH$_2$, —S(O)$_2$NHR$^o$, —S(O)$_2$N(R$^o$)$_2$, —NHS(O)$_2$R$^o$, —NR$^o$S(O)$_2$R$^o$, —C(O)NH$_2$, —C(O)NHR$^o$, —C(O)N(R)$_2$, —C(O)R$^o$, —NHC(O)R$^o$, —NR$^o$C(O)R$^o$, —NHC(O)NH$_2$, —NR$^o$C(O)NH$_2$, —NR$^o$C(O)NHR$^o$, —NHC(O)NHR$^o$, —NR$^o$C(O)N(R$^o$)$_2$, —NHC(O)N(R$^o$)$_2$, —CO$_2$H, —CO$_2$R$^o$, —NHCO$_2$R$^o$, —NR$^o$CO$_2$R$^o$, —CN, —NO$_2$, —NH$_2$, —NHR$^o$, —N(R$^o$)$_2$, —NR$^o$S(O)NH$_2$ and —NR$^o$S(O)$_2$NHR$^o$; $R^{3b}$ is preferably hydrogen, halogen, cyano, —NO$_2$, —CO$_2$R$^f$, —CONR$^f$R$^g$, —C(O)R$^f$, —S(O)R$^h$, —S(O)$_2$R$^h$, —R$^h$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —X$^3$N$_3$, Y, or —X$^3$Y; $R^4$ is preferably halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$ NR$^f$R$^g$, and two adjacent $R^4$ groups can form a five or six-membered saturated or unsaturated ring having from 0 to 2 additional heteroatoms as ring members; m is preferably 0-2; n is preferably 0-3; a, b, c, and d can be N, NR$^5$, S, SO, SO$_2$, O, or C(R$^4$)$_o$, where o can be 0-2; $R^5$ is preferably hydrogen, —R$^h$, —S(O)$_2$R$^h$, —X$^3$OR$^f$, —X$^3$NR$^f$R$^g$, —X$^3$NR$^f$S(O)$_2$R$^h$, —X$^3$S(O)$_2$NR$^f$R$^g$, —CO$_2$R$^f$, —CONR$^f$R$^g$, or —C(O)R$^f$. Further preferred are those compounds in which each $R^1$, when present, is selected from the group consisting of $C_{1-4}$ alkyl, optionally substituted with a member selected from the group consisting of —OH, —OR$^m$, —S(O)$_2$R$^m$, —CO$_2$H and —CO$_2$R$^m$; when b and d are other than C(R$^4$)$_o$, c must be C(R$^4$)$_o$ or SO$_2$; when b and c are other than C(R$^4$)$_o$, then d must be C(R$^4$)$_o$ or SO$_2$; when a and d are other than C(R$^4$)$_o$, then at least one of b and c must be C(R$^4$)$_o$ or SO$_2$. Even more preferably, R$^{2a}$ is hydrogen, halogen, —CN, —C(O)R$^c$, —C(NOR$^c$)R$^d$, —C(NR$^c$W)=NW, —N(W)C(R$^c$)=NW, —X$^2$C(NOR$^c$)R$^d$, —X$^2$C(NR$^c$W)=NW, —X$^2$N(W)C(R$^c$)=NW, —X$^2$NR$^c$R$^d$, or —R$^e$; R$^{2c}$ is halogen or cyano. Still more preferably, m is 0 or 1, n is 0 or 1, and R$^1$ when present is —CH$_3$. In the most preferred embodiments, R$^{2d}$ is —SR$^c$, —R$^e$, or —OR$^c$; R$^{3a}$ is halogen, cyano, C$_{1-6}$ alkyl, C$_{1-6}$ haloalkyl, C$_{3-6}$ cycloalkyl, —C(O)R$^f$ or —SO$_2$R$^h$ wherein the aliphatic portions are optionally substituted as set forth above; R$^{3b}$ is hydrogen, halogen, cyano, or —NO$_2$.

For each of the groups of embodiments of formula III (e.g., IIIa through IIIhhhh) additional preferred embodiments of the invention are those in which two adjacent R$^{3a}$, R$^{3b}$ or R$^{3c}$ substituents are combined to form a fused five or six-membered ring, having from 0-3 additional heteroatoms as ring members. Further preferred are those embodiments in which the ring is a fused six-membered ring, preferably a fused benzene, pyridine or piperidine ring.

Any substituents not particularly set forth above for the various embodiments of formula III (e.g., IIIa through IIIhhhh) are meant to have their most complete meaning with reference to formula III. Additionally, all compounds are meant to include their pharmaceutically acceptable salts, as well as any N-oxides thereof.

In yet another group of preferred embodiments, the compounds are selected from formulae IVa-IVe:

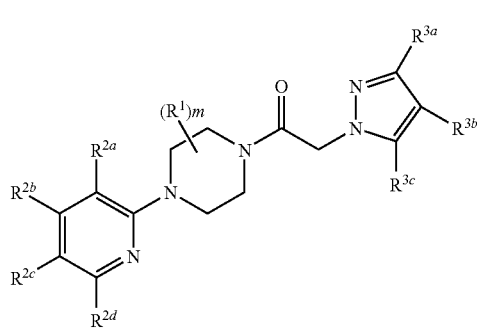

IVa

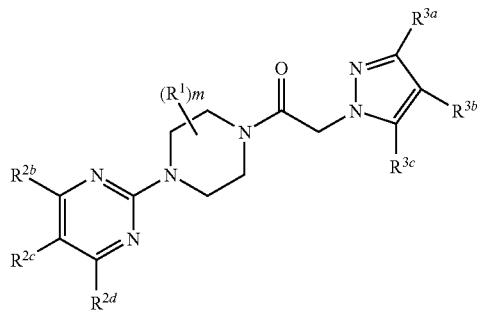

IVb

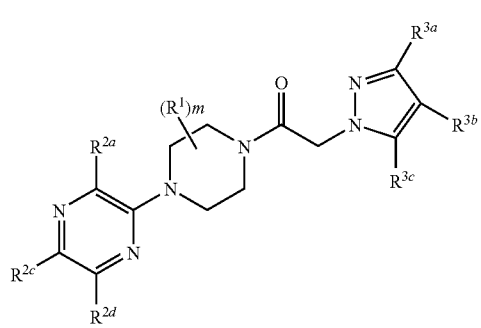

IVc

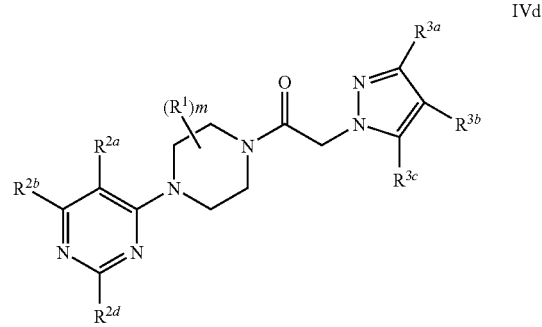

IVd

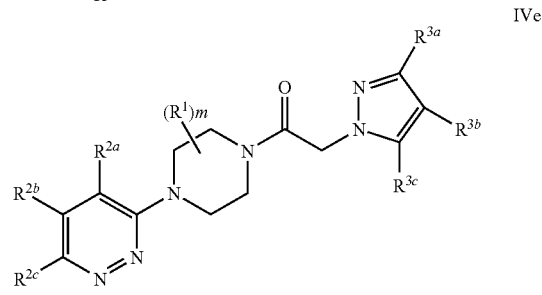

IVe wherein R$^1$ and the subscript m have the meaning provided above for formula III, and each of R$^{2a}$, R$^{2b}$, R$^{2c}$ and R$^{2d}$ are substituents independently selected from hydrogen, halogen, —OR$^c$, —OC(O)R$^c$, —NR$^c$R$^d$, —SR$^c$, —CN, —NO$_2$, —CO$_2$R$^c$, —CONR$^c$R$^d$, —C(O)R$^c$, —OC(O)NR$^c$R$^d$, —NR$^d$C(O)R$^c$, —NR$^d$C(O)$_2$R$^e$, —NR$^c$—C(O)NR$^c$R$^d$, —NH—C(NH$_2$)=NH, —NR$^e$C(NH$_2$)=NH, —NH—C(NH$_2$)=NR$^e$, —NH—C(NHR$^e$)=NH, —S(O)R$^e$, —S(O)$_2$R$^e$, —S(O)$_2$NR$^c$R$^d$, —NR$^c$S(O)$_2$R$^e$, —NR$^c$S(O)$_2$NR$^c$R$^d$, —N$_3$, —X$^2$OR$^c$, —X$^2$OC(O)R$^c$, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$S(O)$_2$NR$^c$R$^d$, —X$^2$NR$^c$S(O)$_2$R$^e$, —X$^1$N$_3$, aryl and heteroaryl, wherein X$^2$, R$^c$, R$^d$ and R$^e$ have the meanings provided above with respect to the compounds of formula I. Similarly, each of R$^{3a}$, R$^{3b}$ and R$^{3c}$ represents a substituent independently selected from hydrogen, halogen, phenyl, thienyl, furanyl, pyridyl, pyrimidinyl, pyrazinyl, pyridizinyl, pyrazolyl, imidazolyl, thiazolyl, oxazolyl, isoxazolyl, isothiazolyl, triazolyl, tetrazolyl, oxadiazolyl, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)=NH, —NR$^h$C(NH$_2$)=NH, —NH—C(NH$_2$)=NR$^h$, —NH—C(NHR$^h$)=NH, —S(O)R$^h$, —S(O)$_2$R$^h$, —S(O)$_2$ NR$^f$R$^g$, —NR$^f$S(O)$_2$R$^h$, —NR$^f$S(O)$_2$NR$^f$R$^g$, —N$_3$, —X$^3$OR$^1$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$S(O)$_2$NR$^f$R$^g$, —X$^3$NR$^f$S(O)$_2$R$^h$ and —X$^3$N$_3$ wherein X$^3$, R$^f$, R$^g$ and R$^h$ have the meaning provided above with respect to the compounds of formula I, and wherein no more than two of R$^{3a}$, R$^{3b}$ and R$^{3c}$ are hydrogen, preferably, no more than one of R$^{3a}$, R$^{3b}$ and R$^{3c}$ is hydrogen, and still more preferably, each of R$^{3a}$, R$^{3b}$ and R$^{3c}$ is other than hydrogen.

Turning first to the compounds of formula IVa, in one group of particularly preferred embodiments, at least one of $R^{3a}$, $R^{3b}$ and $R^{3c}$ is selected from halogen and $C_{1-4}$ haloalkyl. Still more preferably, at least one of $R^{2b}$ and $R^{2d}$ is hydrogen and at least two of $R^{3a}$, $R^{3b}$ and $R^{3c}$ are selected from halogen and $C_{1-4}$ haloalkyl. In related, and preferred embodiments, $R^{2c}$ is selected from F, Cl, Br, CN, $NO_2$, $CO_2CH_3$, $C(O)CH_3$ and $S(O)_2CH_3$, and at least two of $R^{3a}$, $R^{3b}$ and $R^{3c}$ are selected from halogen and $C_{1-4}$ haloalkyl with the remaining member being other than hydrogen.

Similarly, certain compounds of formula IVb are preferred. Particularly preferred are those compounds of formula IVb in which at least one of $R^{3a}$, $R^{3b}$ and $R^{3c}$ is selected from halogen and $C_{1-4}$ haloalkyl. Still more preferably, at least one of $R^{2b}$ and $R^{2d}$ is hydrogen and at least two of $R^{3a}$, $R^{3b}$ and $R^{3c}$ are selected from halogen and $C_{1-4}$ haloalkyl. In related, and preferred embodiments, $R^{2c}$ is selected from F, Cl, Br, CN, $NO_2$, $CO_2CH_3$, $C(O)CH_3$ and $S(O)_2CH_3$, and at least two of $R^{3a}$, $R^{3b}$ and $R^{3c}$ are selected from halogen and $C_{1-4}$ haloalkyl with the remaining member being other than hydrogen.

Turning next to the compounds of formula IVc, preferred embodiments are those in which at least one of $R^{2a}$, $R^{2c}$ and $R^{3d}$, preferably $R^{2c}$ is selected from F, Cl, Br, CN, $NO_2$, $CO_2CH_3$, $C(O)CH_3$ and $S(O)_2CH_3$; and at least two of $R^{3a}$, $R^{3b}$ and $R^{3c}$ are selected from halogen and $C_{1-4}$ haloalkyl with the remaining member being other than hydrogen. In other preferred embodiments, one of $R^{2c}$ and $R^{2d}$ is selected from F, Cl, Br, CN, $NO_2$, $CO_2CH_3$, $C(O)CH_3$ and $S(O)_2CH_3$, and the other is an aryl or heteroaryl group, for example, phenyl, thienyl, furanyl, oxazolyl, isoxazolyl, thiazolyl and isothiazolyl, and at least two of $R^{3a}$, $R^{3b}$ and $R^{3c}$ are selected from halogen and $C_{1-4}$ haloalkyl with the remaining member being other than hydrogen.

For the compounds of formula IVd, preferred embodiments are those in which at least one of $R^{2a}$, $R^{2b}$ and $R^{2d}$ is selected from F, Cl, Br, CN, $NO_2$, $CO_2CH_3$, $C(O)CH_3$ and $S(O)_2CH_3$, and at least two of $R^{3a}$, $R^{3b}$ and $R^{3c}$ are selected from halogen and $C_{1-4}$haloalkyl with the remaining member being other than hydrogen. In other preferred embodiments, one of $R^{2b}$ and $R^{2d}$ is selected from F, Cl, Br, CN, $NO_2$, $CO_2CH_3$, $C(O)CH_3$ and $S(O)_2CH_3$, and the other is an aryl or heteroaryl group, for example, phenyl, thienyl, furanyl, oxazolyl, isoxazolyl, thiazolyl and isothiazolyl, and at least two of $R^{3a}$, $R^{3b}$ and $R^{3c}$ are selected from halogen and $C_{1-4}$ haloalkyl with the remaining member being other than hydrogen.

For the compounds of formula IVe, preferred embodiments are those in which at least one of $R^{2a}$, $R^{2b}$ and $R^{2c}$ is selected from F, Cl, Br, CN, $NO_2$, $CO_2CH_3$, $C(O)CH_3$ and $S(O)_2CH_3$, and at least two of $R^{3a}$, $R^{3b}$ and $R^{3c}$ are selected from halogen and $C_{1-4}$ haloalkyl with the remaining member being other than hydrogen. In other preferred embodiments, one of $R^{2b}$ and $R^{2c}$ is selected from F, Cl, Br, CN, $NO_2$, $CO_2CH_3$, $C(O)CH_3$ and $S(O)_2CH_3$, and the other is an aryl or heteroaryl group, for example, phenyl, thienyl, furanyl, oxazolyl, isoxazolyl, thiazolyl and isothiazolyl, and at least two of $R^{3a}$, $R^{3b}$ and $R^{3c}$ are selected from halogen and $C_{1-4}$ haloalkyl with the remaining member being other than hydrogen.

In yet another group of preferred embodiments, the compounds are selected from formulae IVf-IVi:

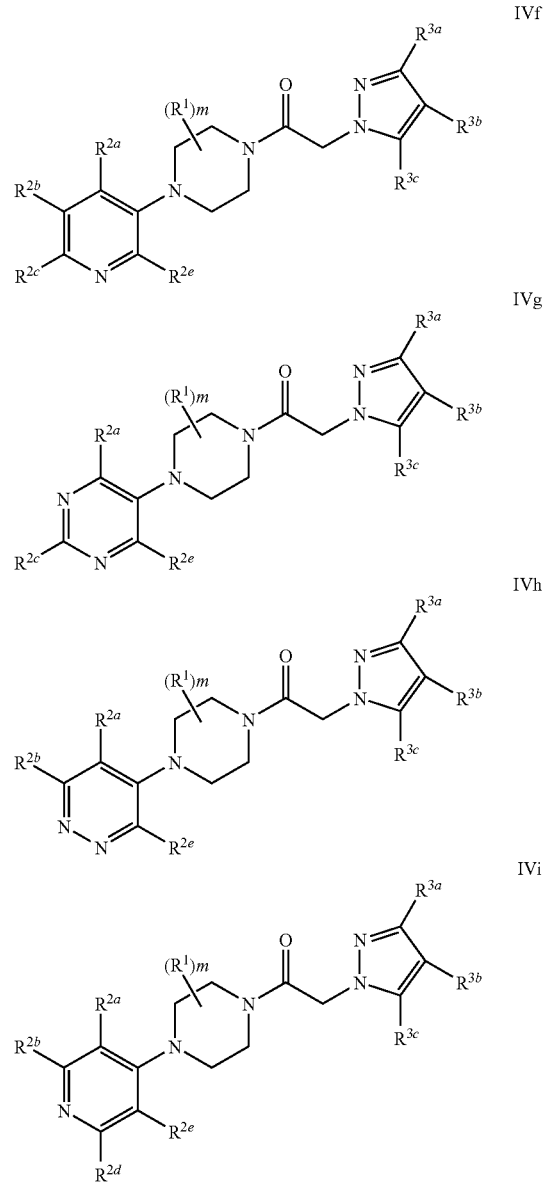

wherein $R^1$ and the subscript m have the meaning provided above for formula III, and each of $R^{2a}$, $R^{2b}$, $R^{2c}$, $R^{2d}$, $R^{3a}$, $R^{3b}$ and $R^{3c}$ have the meaning provided above for formulae IVa-IVe. Additionally, $R^{2e}$ represents a substituent selected from the groups provided for $R^{2a}$ in formulae IVa-IVe above.

In still other embodiments, compounds are provided having formulae Va and Vb:

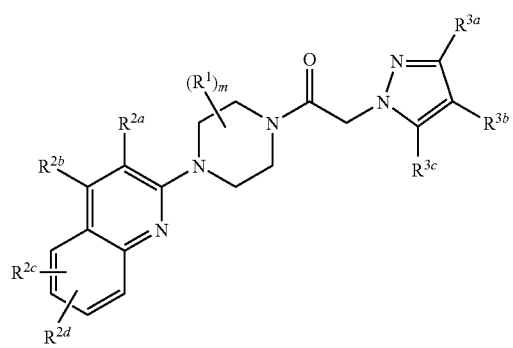

-continued

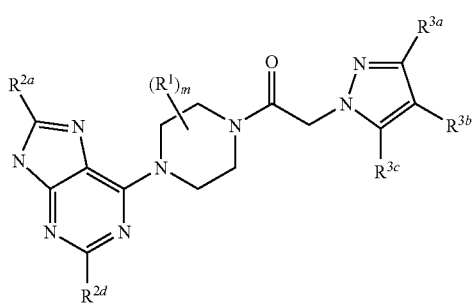

wherein each of $R^1$, the subscript m, $R^{2a}$, $R^{2b}$, $R^{2c}$, $R^{2d}$, $R^{3a}$, $R^{3b}$ and $R^{3c}$ have the meaning provided above for formulae IVa-IVe.

Preparation of Compounds

As provided in the examples below, the compounds of the present invention can be prepared by one of skill in the art in a component assembly manner. A number of compounds are prepared beginning with preparation of a suitably substituted pyrazole (or other HAr component). Schemes Ia-Ik illustrate a variety of methods for the preparation of substituted pyrazoles. In each of these schemes, non-interfering substituents are provided as —R, —$R^w$, —$R^y$ and $R^z$.

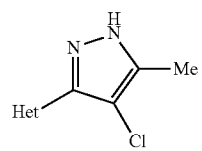

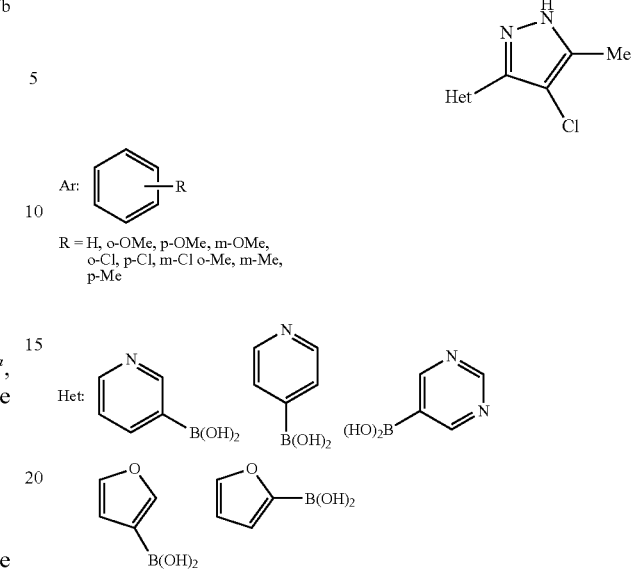

Scheme 1a

Arylpyrazoles via Suzuki Coupling:

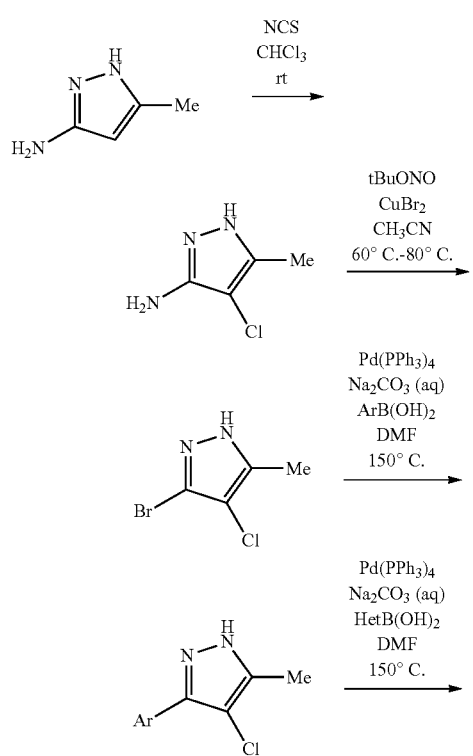

Scheme 1b

Arylpyrazoles via Stille Coupling:

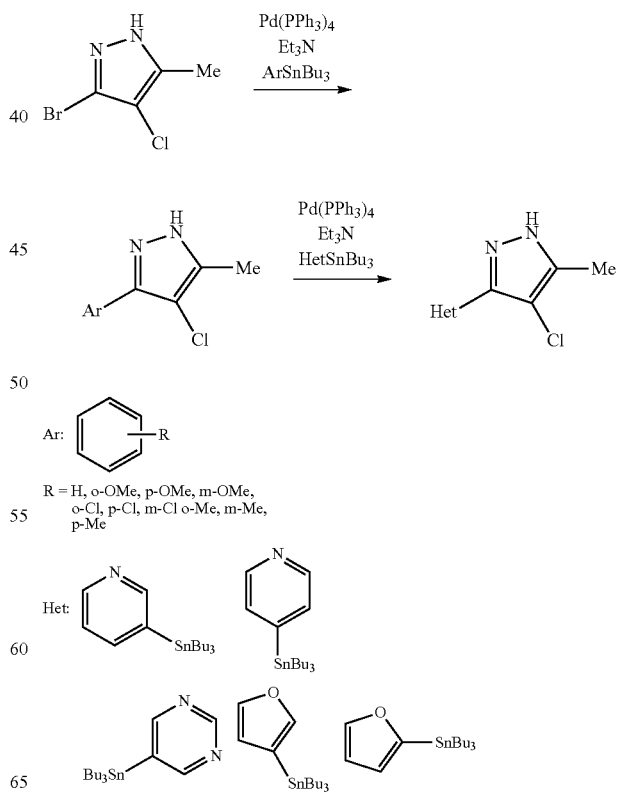

Scheme 1c
Arylpyrazoles via Negishi Cross-Coupling reactions:
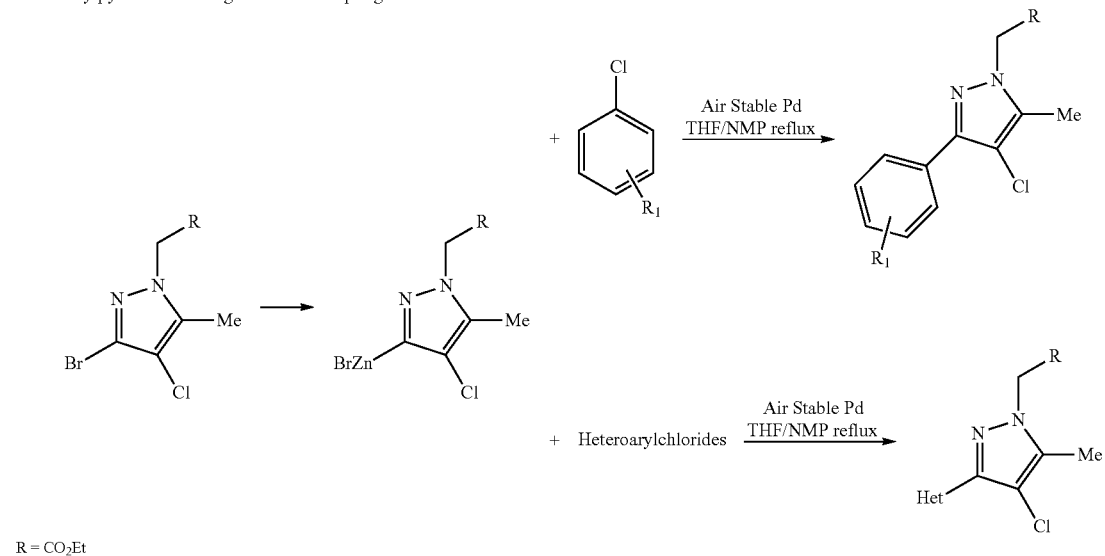
R = CO₂Et
Scheme 1d
Arylpyrazoles via Kumada-Tamao-Corriu Cross-Coupling reactions:
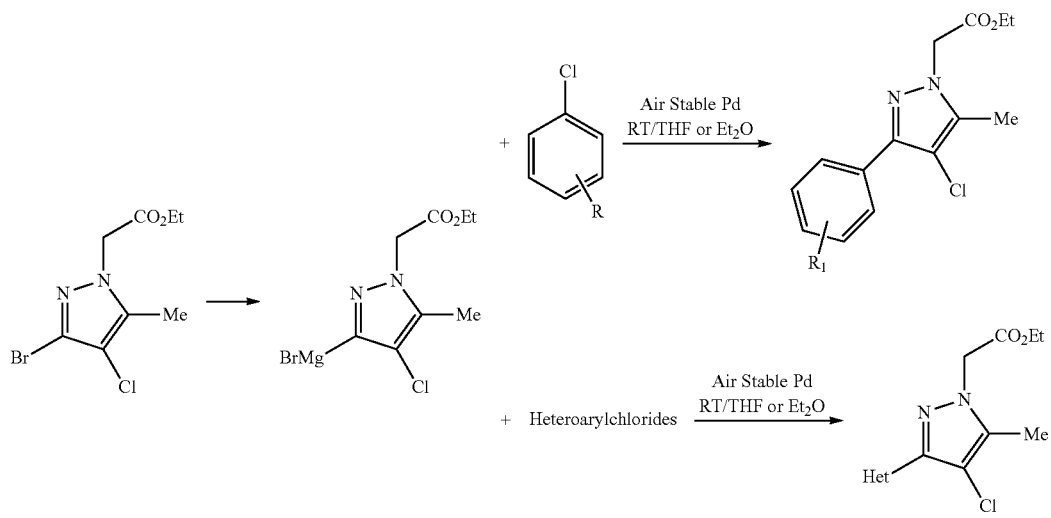

Scheme 1e

Substituted pyrazoles via Buchwald Chemistry:

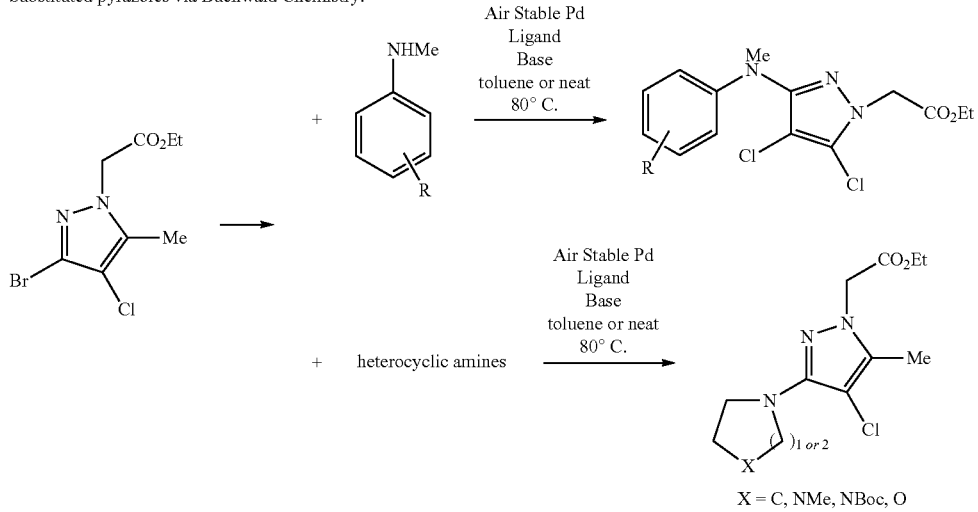

Scheme 1f

Arylpyrazoles by condensation of 1,3-diketones with hydrazines:

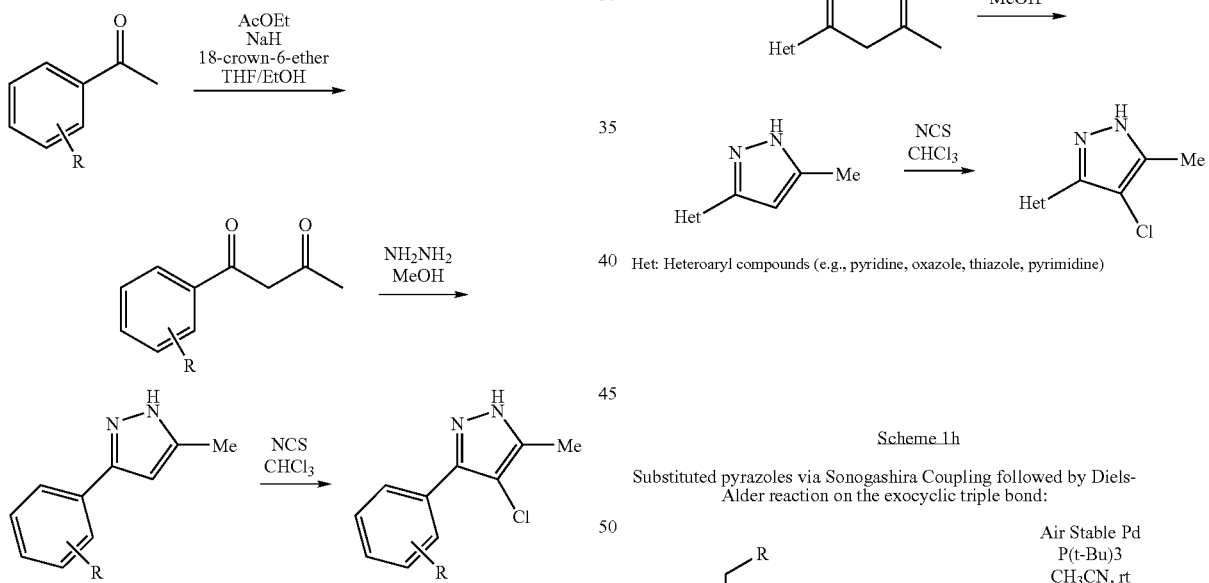

Scheme 1g

Heteroarylpyrazoles by condensation of 1,3-diketones with hydrazines:

-continued

Het: Heteroaryl compounds (e.g., pyridine, oxazole, thiazole, pyrimidine)

Scheme 1h

Substituted pyrazoles via Sonogashira Coupling followed by Diels-Alder reaction on the exocyclic triple bond:

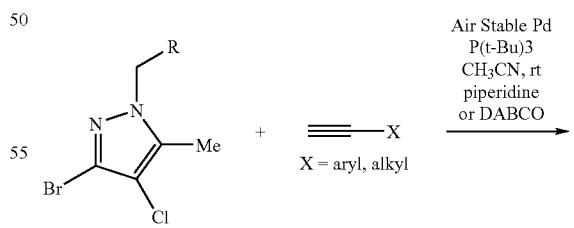

Scheme 1i

Substituted pyrazoles via Heck coupling followed by Diels-Alder reaction on the exocyclic double bond:

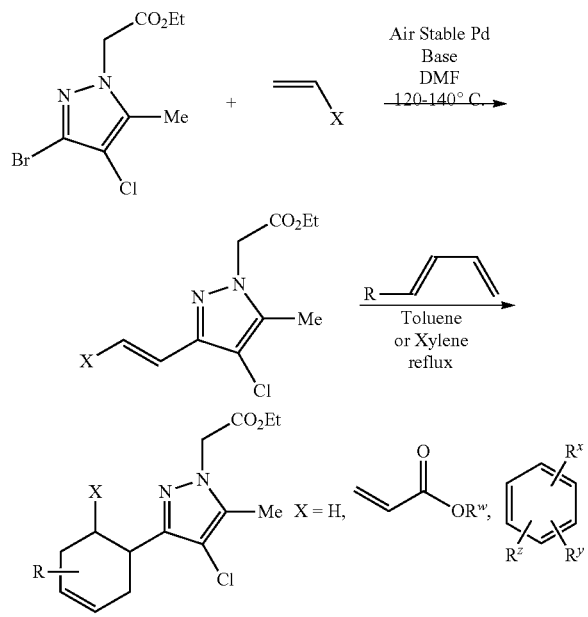

Scheme 1j

Substituted arylpyrazoles via Ullmann coupling:

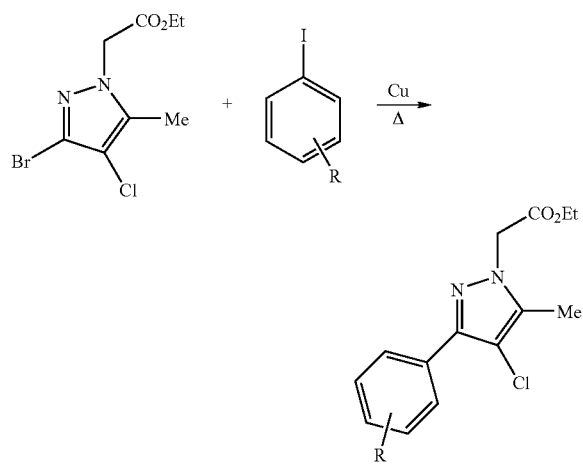

Scheme 1k

Substituted aminopyrazoles via curtius rearrangement and amination:

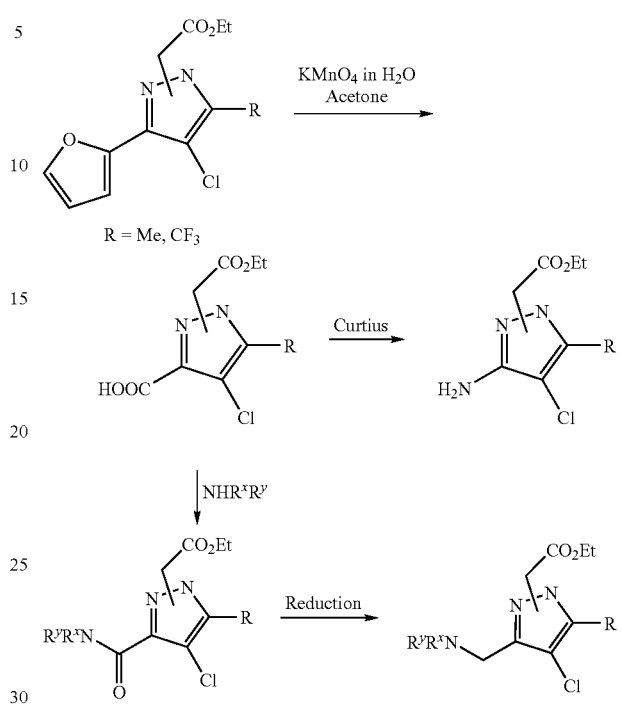

R = Me, CF$_3$

IV. Pharmaceutical Compositions

In addition to the compounds provided above, compositions for modulating CCR1 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

V. Methods of Treating Diseases Modulated by CCR1

In yet another aspect, the present invention provides methods of treating CCR1-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, neutrophils, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 may be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalgia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection and graft-v-host disease), and (11) other diseases in which undesired inflammatory responses or immune disorders are to be inhibited, such as cardiovascular disease including atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout and (12) immune mediated food allergies such as Celiac disease.

In another group of embodiments, diseases or conditions can be treated with modulators of CCR1 function. Examples of diseases to be treated with modulators of CCR1 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCeptO); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafinlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, rniroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. EXAMPLES

The following examples are offered to illustrate, but not to limit the claimed invention.

Reagents and solvents used below can be obtained from commercial sources such as Aldrich Chemical Co. (Milwaukee, Wis., USA). ¹H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M–H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP 1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

Figure 4A:
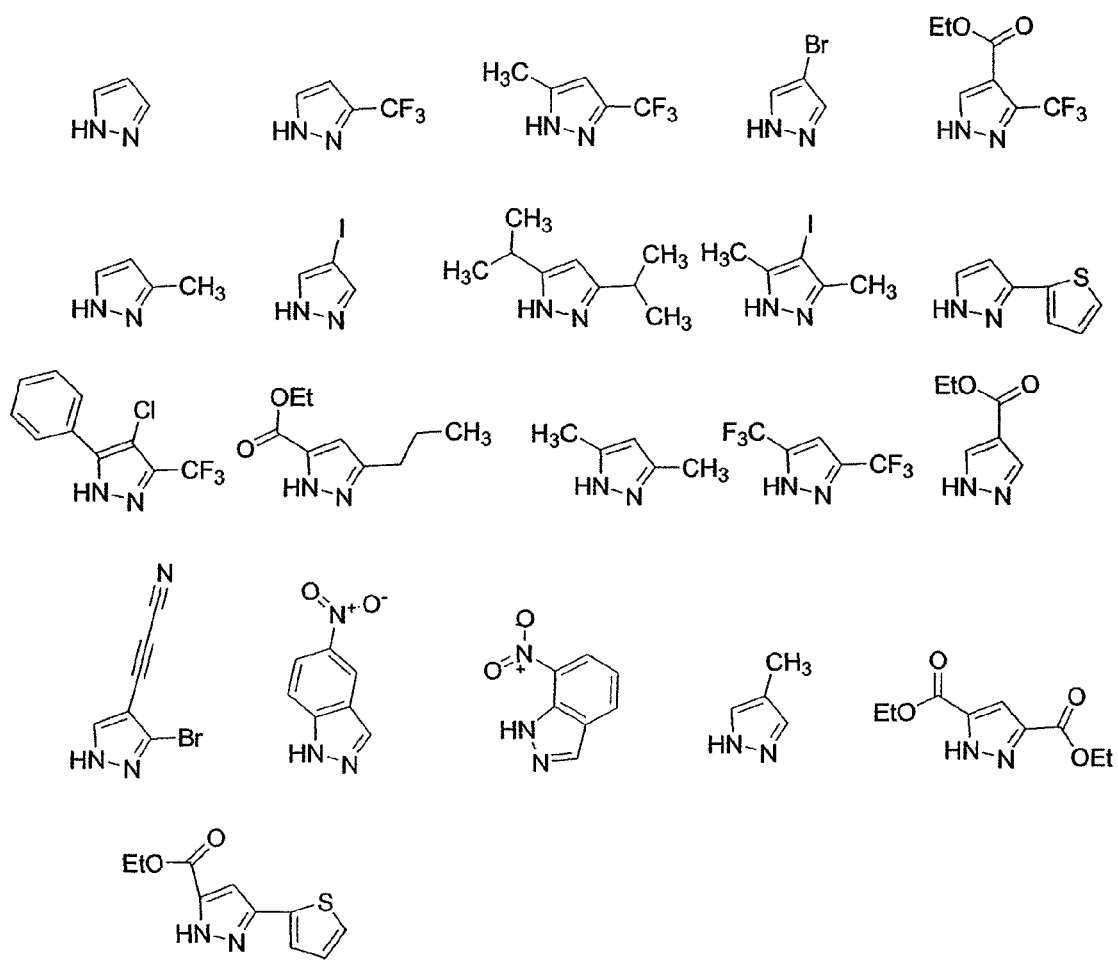
FIGS. 4A-4C provide structures of selected commercially available starting materials.
Figure 4B:
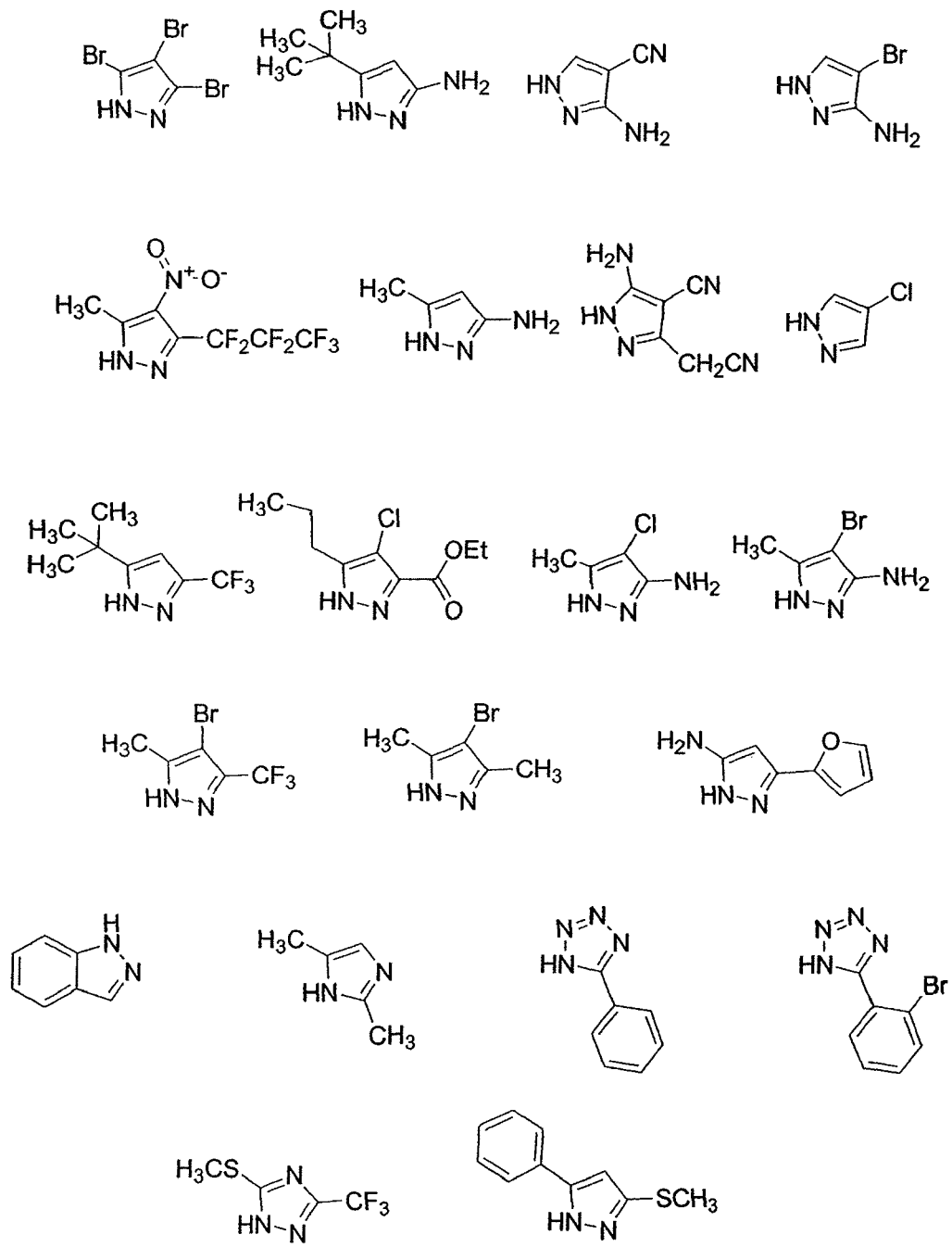
Figure 4C:
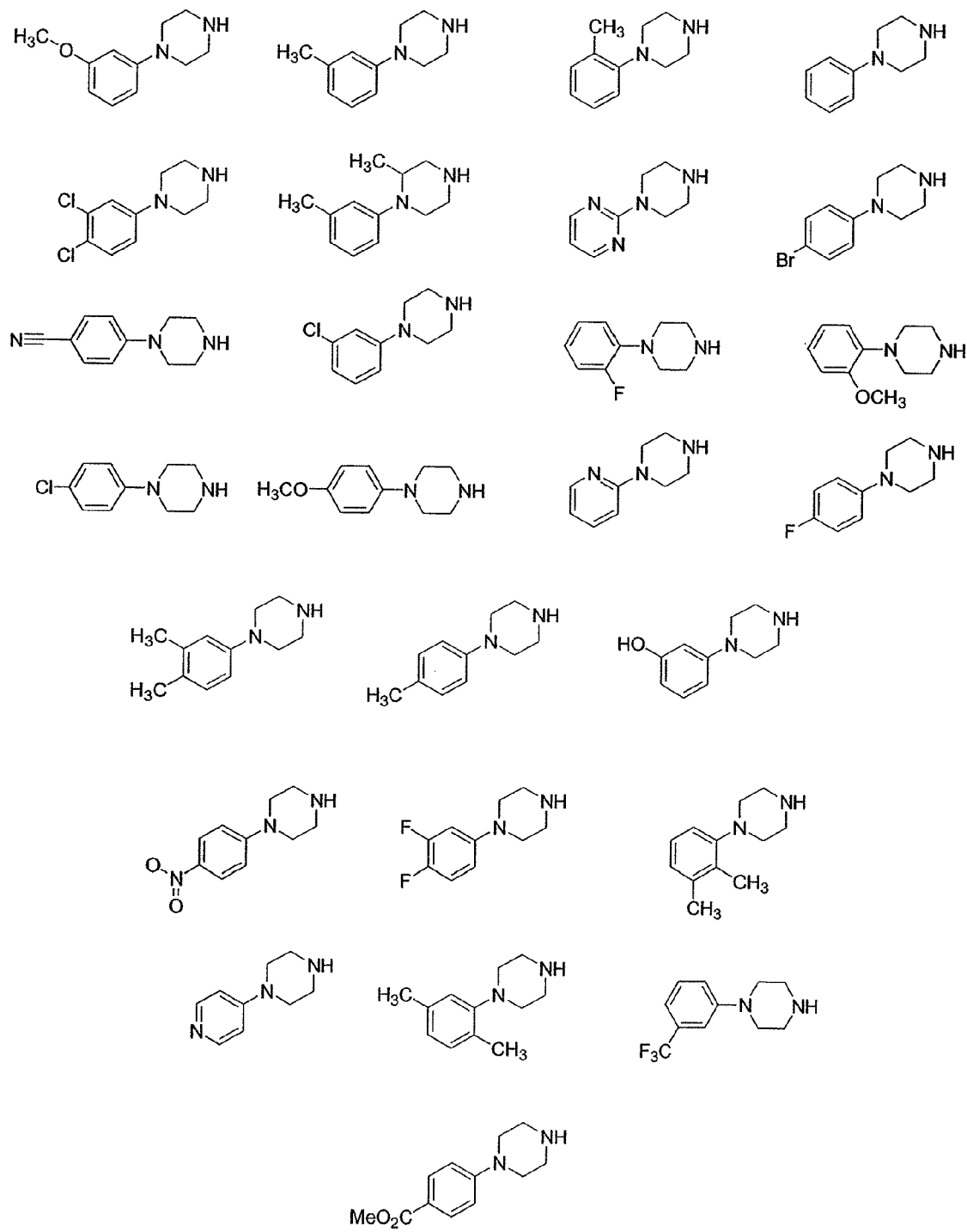

Compounds within the scope of this invention can be synthesized as described below, using a variety of reactions known to the skilled artisan. A sample of useful routes to both the arylpiperazine subunits and to the heteroaromatic subunit are provided below. In the descriptions of the syntheses that follow, some of the arylpiperazine and pyrazole precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals. Some examples of these commercially available compounds are shown in the FIGS. 4A-4C. Also, standard chemistries have been employed to link the arylpiperazine and heteroaromatic subunits (whether commercially obtained or prepared by the methods below) using a suitably optimized linker, such as the acetyl unit described in the body of this invention.

One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

Regioisomerism is a common property in organic chemistry, and is especially common with regards to certain structural types provided herein. Those skilled in the art will recognize, with respect to the compounds described herein, that the coupling reactions with the heteroaromatic ring systems can lead to either one of or a mixture of detectable regioisomers.

The detailed description of the experimental procedures used to synthesize key compounds in this text lead to molecules that are described by the physical data identifying them as well as by the structural depictions associated with them.

Two regioisomers can sometimes exist for certain compounds of the invention. For example, compounds such as those of formula III can be prepared wherein the pyrazole moiety is linked to the remainder of the molecule via either of the nitrogen atoms in the pyrazole ring. In these cases, both regioisomeric types have demonstrated biological properties and are meant to be within the scope of all the appended claims, whether explicitly drawn or not.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

The piperazine ring can be formally attached to the terminal aryl unit in a number of ways: by aromatic nuclephilic displacement reactions, metal catalyzed coupling reactions (arylation reactions of secondary amines), ring expansion, rearrangement and cyclization reactions and the like. Also, different protection/deprotection strategies can be utilized. Hence, either all or only part of the final molecular architecture can be present during the key aryl coupling step. Examples for a variety of such aryl coupling strategies are listed below.

Protocol A: Metal catalysed arylation reactions of secondary amines

Synthesis of (5-Chloro-2-piperazin-1-yl-phenyl)phenyl-methanone

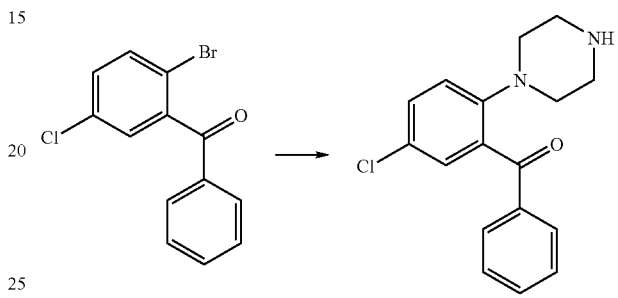

Piperazine (3.6 g, 42.5 mmol), Pd(II)acetate (0.007 g, 0.043 mmol), sodium t-butoxide (0.22 g, 2.4 mmol) and BINAP (0.042 g, 0.068 mmol) were stirred at room temperature in 10 mL dry toluene for 15 min. (2-Bromo-5-chlorophenyl)-phenyl-methanone (0.5 g, 1.7 mmol) in 10 mL dry toluene was then added into the reaction mixture. The reaction mixture was refluxed at 110° C. for 20 hrs, filtered through a celite bed, washed with toluene, concentrated, taken in ethyl acetate and extracted with 1.5 (N) HCl solution three times. The combined aqueous layers were washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate and concentrated. Purification by flash chromatography (eluted with $CHCl_3$-MeOH) afforded the title compound as product.

Synthesis of 1-(4-Trifluoromethoxy-phenyl)-piperazine

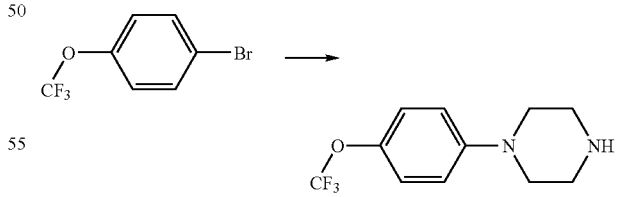

Piperazine (0.588 g, 6.84 mmol), Pd(II)acetate (0.027 g, 0.123 mmol), sodium t-butoxide (0.837 g, 10.06 mmol) and BINAP (0.154 g, 0.286 mmol) were stirred at room temperature in 10 mL dry toluene for 15 min. 4-trifluoromethoxy bromo benzene (1.5 g, 6.22 mmol) in 10 mL dry toluene was added into the reaction mixture. Then the reaction mixture was refluxed at 110° C. for 20 hrs. The reaction mixture was filtered through a celite bed, washed with toluene, concentrated, ethyl acetate added and then extracted with 1.5 (N)

aqueous HCl solution three times. The combined aqueous layers were washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate and concentrated to afford the product.

Synthesis of 1-(4-Methanesulfonyl-phenyl)-piperazine

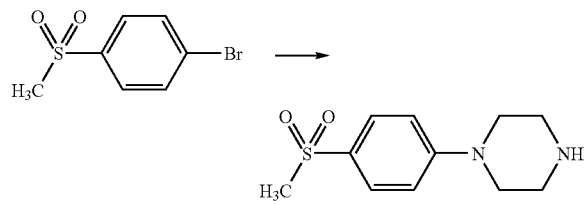

Piperazine (0.98 g, 11.5 mmol), Pd(II)acetate (0.017 g), sodium t-butoxide (0.37 g, 4.2 mmol) and BINAP (0.049 g) were stirred at room temperature in 10 mL dry toluene for 15 min. 1-Bromo-4-methanesulfonyl-benzene (0.9 g, 3.8 mmol) in 10 mL dry toluene was added into the reaction mixture. Then the reaction mixture was refluxed at 110° C. for 20 hrs. The reaction mixture was filtered through a celite bed and washed with toluene. The toluene was concentrated and the reaction mixture was taken in ethyl acetate and extracted with 1.5 (N) HCl solution three times. The combined aqueous layers were washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate, concentrated and chromatographed (9/1-CHCl$_3$/MeOH) to afford the product.

Synthesis of 1-(4-Chloro-3-methoxy-phenyl)-piperazine

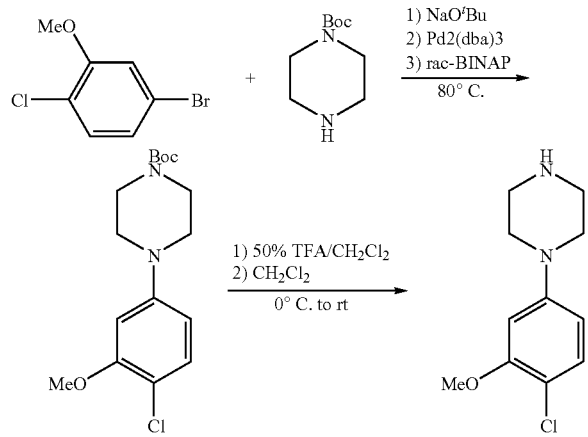

An oven dried glass vial was charged with 5-Bromo-2-chloroanisole (1.0 mmol), N-Bocpiperazine (1.2 mmol), NaOtBu (1.4 mmol), tris(dibenzylideneacetone)-dipalladium (0) {Pd$_2$dba$_3$} (0.0025 mmol, 0.5 mol %) and BINAP (0.0075 mmol), and the vial was then flushed with nitrogen and capped tightly. The mixture was heated to 80° C. overnight and then cooled to room temperature, taken up in ether, filtered and concentrated. The crude product was purified by flash column chromatography on silica gel with ethyl acetate to yield 4-(4-Chloro-3-methoxy-phenyl)-piperazine-1-carboxylic acid tert-butyl ester.

This product (ca. 1 mmol) was dissolved in a methylene chloride (10 mL) and the reaction mixture was cooled to 0° C. To the reaction mixture was added TFA:CH$_2$Cl$_2$ (2:1)(50% overall) slowly and the reaction was allowed to warm to room temperature. When TLC (1:1 Ethyl acetate:hexane) suggested total consumption of starting material, solvent was removed and the oil residue was taken in ethyl acetate (2×25 mL) and washed with saturated aqueous NaHCO$_3$. The organic layer was dried by MgSO$_4$ and solvent was removed to yield the title compound as a yellow oil, which solidified on standing. $^1$H NMR (400 MHz, CDCl$_3$) δ 7.18-7.22 (d, 1H), 6.44-6.48 (d, 1H), 6.36-6.42 (dd, 1H), 4.8 (s, 2H), 6.62-3.8 (m, 4H), 3.46-3.6 (m, 4H). $^{13}$C NMR (400 MHz, CDCl$_3$) δ 164, 158.2, 156.4, 148, 119.2, 117, 52.8, 52.2, 48.5, 46.2, 42, 40.4.

Similar approaches, using a key Buchwald coupling, were taken for the preparation of related phenylpiperazines, some examples of which are listed below.

Synthesis of 1-(4-Chloro-3-isopropoxy-phenyl)-piperazine

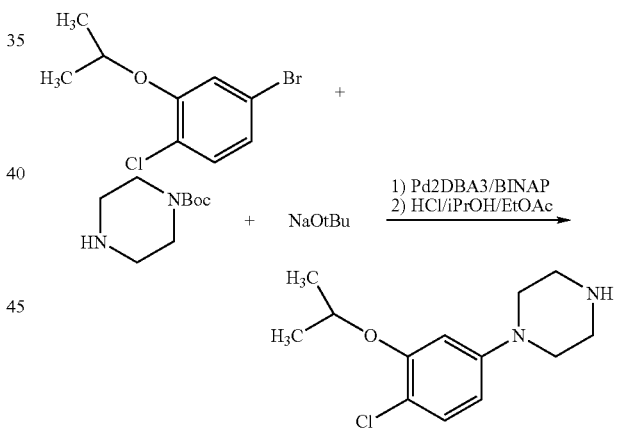

1-Bromo-3-isopropoxy-4-chlorobenzene (preparation described elsewhere) was combined with 1.11 g (6 mmol) of 1-Bocpiperazine, 672 mg (7.0 mmol) of sodium tert-butoxide, 93 mg (0.15 mmol) of rac-2,2'-Bis(diphenylphosphine)-1,1'-binaphthyl, and 45 mg (0.05 mmol) Tris(dibenzylideneacetone)dipalladium (0) in a flask under an N2 atmosphere, and the mixture was heated at 85° C. for 3.5 hours. The resulting residue was partitioned between a 1/1 mixture of ether and ethyl acetate and water, and the phases were separated. The ether/ethyl acetate phase was diluted with one volume of hexanes, washed twice with 0.5M pH=7 phosphate buffer, and once each with 1M NaOH and brine. The final organic phase was dried over Na$_2$SO$_4$, filtered, and concentrated in vacuo to an oil. The oil was dissolved in ethyl acetate, 10 mL each of 2M HCl in ether and methanol were added, and the product was isolated by filtration after crystallization. $^1$H NMR (D₂O, 400 MHz) δ 7.23 (d, 1H), 6.69 (s, 1H), 6.59 (d, 1H), 4.53 (m, 1H), 3.28 (m, 8H), 1.20 (d, 6H) ppm.

Synthesis of 1-(4-Chloro-3-ethoxy-phenyl)-piperazine

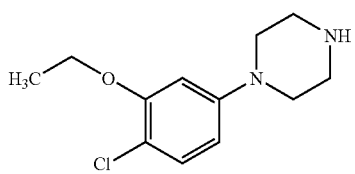

Title compound was obtained following the same procedure as that used to obtain 1-(4-Chloro-3-isopropoxy-phenyl)-piperazine hydrochloride, with the single modification of adding ethanol in place of isopropanol during the ether-forming reaction. ¹H NMR (D₂O, 400 MHz) 7.22 (d, 1H), 6.64 (s, 1H), 6.54 (d, 1H), 4.03 (q, 2H), 3.29 (m, 8H), 1.25 (t, 3H) ppm.

Synthesis of 4-Piperazin-1-yl-benzoic acid methyl ester

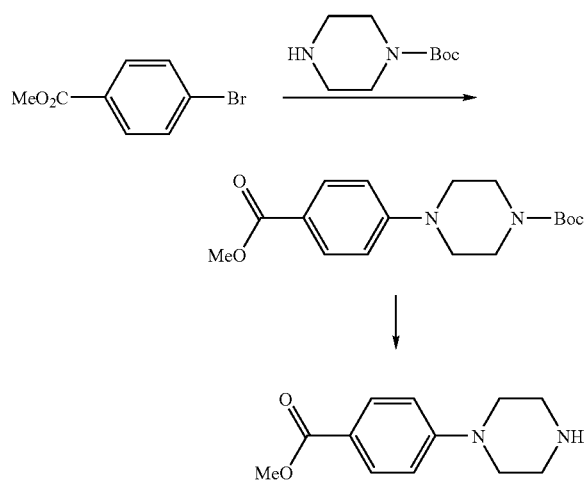

BINAP (230 mg, 0.37 mmol), Pd(II)acetate (417 mg, 0.186 mmol), tBuONa (1.25 g, 13 mmol), N-boc piperazine (1.9 g, 10.2 mmol) and THF (40 mL) were mixed together and stirred at room temperature for 30 min under a nitrogen atmosphere. 4-bromomethyl benzoate (2 g, 9.3 mmol) in THF (10 mL) was added to the mixture drop wise and heated at 70° C. for 14 h. Excess THF was then evaporated and extracted with ethyl acetate. The crude product was obtained on concentration of the ethyl acetate layer after washing with brine and drying. Flash chromatography on silica gel done eluting with 8% ethyl acetate in petroleum ether yielded pure N-BOC protected product. This intermediate (650 mg, 2.01 mmol) was dissolved in methanol (20 mL) and then HCl saturated ether (7 mL) was added. The mixture was stirred at room temperature for 14 hours and concentrated. The concentrate was washed with petroleum ether to obtain white solid compound, 4-Piperazin-1-yl-benzoic acid methyl ester.

Synthesis of 1-(2,4-Dichloro-phenyl)-piperazine

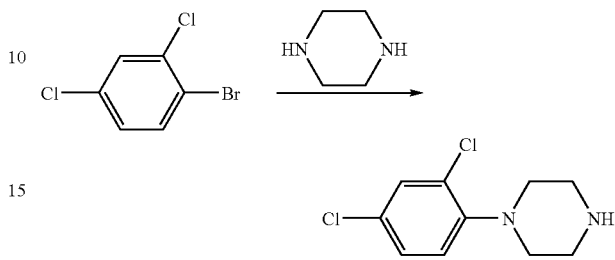

BINAP (219 mg), Pd(II)acetate (397 mg, 0.176 mmol), tBuONa (1.19 g, 12.3 mmol), piperazine (837 mg, 9.73 mmol) and THF (40 mL) were mixed together and stirred at room temperature for 30 min under nitrogen atmosphere. 2,4-dichlorobromobenzene (2 g, 8.84 mmol) in THF (10 mL) was added to the mixture drop wise and heated at 70° C. for 14 h. Excess THF was then evaporated and extracted with ethyl acetate. The crude product was obtained on concentration of the ethyl acetate layer after washing with brine and drying. Flash chromatography on silica gel eluting with 2% MeOH in CHCl₃ gave 1-(2,4-Dichloro-phenyl)-piperazine.

Synthesis of 1-(4-Chloro-phenyl)-3-(R)-methyl-piperazine

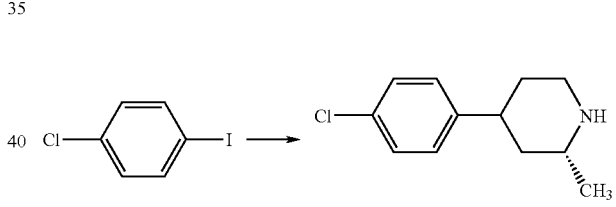

A single neck round bottom flask was charged with 1-chloro-4-iodo benzene (1.0 g, 0.0041 mol) and R(−)-2-methylpiperazine (0.5 g, 0.005 mol), potassium t-butoxide (0.705 g, 0.0062 mol), tris(benzylideneacetone)dipalladium (O) (0.095 g, 0.0002 mol) and 1,3 bis(2,6-diisopropylphenyl) imidazole-2-ylidene) (0.073 g, 0.0001 mol). The flask was evacuated and filled with nitrogen. Dry dioxane (20 mL) was added and stirred at 70° C. overnight. The reaction mixture was diluted with dichloromethane and filtered. Crude compound was purified by column chromatography. The compound was dissolved in ether and purged with HCl gas to yield 1-(4-Chloro-phenyl)-3-methyl-piperazine.

Synthesis of 1-(4-Chloro-2-Fluorophenyl)-piperazine

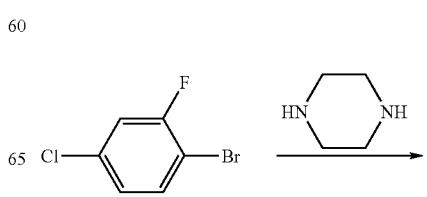

-continued

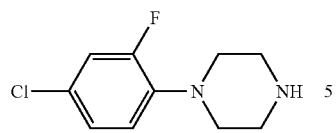

Piperazine (1.5 g, 17.8 mmol), Pd(II)acetate (0.032 g, 0.143 mmol), sodium t-butoxide (0.688 g, 10.06 mmol) and BINAP (0.18 g, 0.286 mmol) were stirred at room temperature in 10 mL dry toluene for 15 min. 1-bromo-4-chloro-2-fluorobenzene (1.5 g, 7.15 mmol) in 10 mL dry toluene was added into the reaction mixture. Then the reaction mixture was refluxed at 110° C. for 20 hrs. The reaction mixture was filtered through a celite bed and washed with toluene, then concentrated and the reaction mixture was taken into ethyl acetate and extracted with 1.5 (N) HCl solution three times. The combined aqueous layer was washed with diethyl ether. The aqueous layer was neutralized with 10% aqueous sodium hydroxide solution and then extracted with ethyl acetate three times. The combined ethyl acetate layers were washed with water and saturated brine solution, dried over anhydrous sodium sulfate, and concentrated to afford the product as a white solid.

Synthesis of 1-(3-methoxy-phenyl)-3-(S)-methyl-piperazine

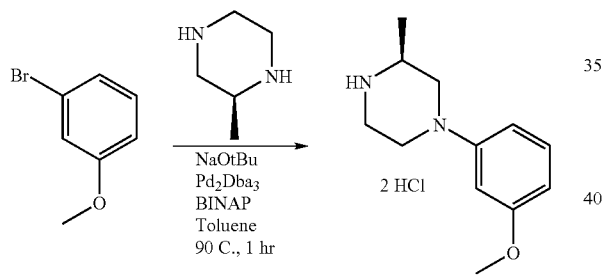

Combined 467 mg (2.5 mmol, 1.0 eq) of 3-bromoanisole, 300 mg (2.99 mmol, 1.2 eq) S-(+)-2-methylpiperazine, 336 mg NaOtBu (3.5 mmol, 1.4 eq), 50 mg BINAP (0.08 mmol, 0.03 eq), 27 mg Pd2Dba3 (0.03 mmol, 0.01 eq), and 500 uL toluene in a 4 mL vial. The mixture was briefly agitated then placed in a 90 C oil bath. LC/MS showed complete conversion in one hour. An excess of 2M HCl/Et2O was added to the reaction mixture, and the solid collected by vacuum filtration and dried down to get 700 mg of the dihydrochloride.

Synthesis of 1-(3-trifluoromethoxy-phenyl)-piperazine

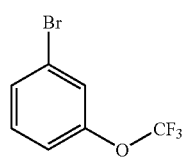

-continued

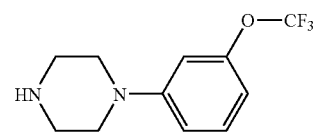

Following protocol A, 1-Bromo-3-(trifluoromethoxy)-benzene (1.0 g, 0.0042 mol), piperazine (5.4 g, 0.0632 mol), potassium tert-butoxide (0.72 g, 0.0076 mol), palladium acetate (0.94 g, 0.0002 mol) and Diisopropylimidazolium chloride (0.08 g, 0.0002 mol) in 5 mL of dry dioxane were heated at 100° C. for 24 hours under argon. The reaction mixture was cooled to ambient temperature, quenched with water, and extracted with ethyl acetate. The ethyl acetate phase was washed once each with water and brine, and was concentrated. The residue was purified by column chromatography to give the title compound.

1-(4-Chloro-3-methoxyphenyl)-3-(S)-methyl-piperazine

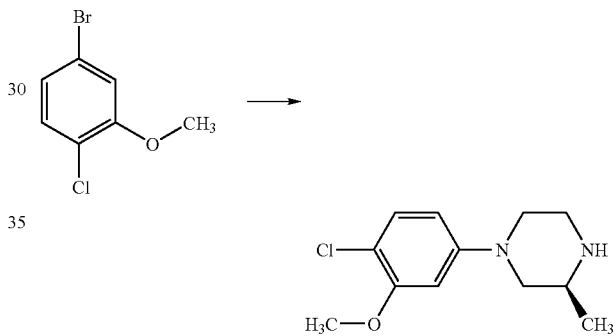

Following protocol A, 5-Bomo-2-chloroaniline (0.5 g, 0.0023 mol), (S)-(+)-2-methyl piperazine (0.35 g, 0.0035 mol), palladium acetate (0.026 g, 0.0001 mol), BINAP (0.14 g, 0.00023 mol) and sodium tert-butoxide (0.35 g, 0.0037 mol) in 5 mL of dry toluene were heated at 110° C. under argon atmosphere for 18 h. The reaction mixture was quenched with water and extracted with ethyl acetate. The extract was washed with water, brine, and concentrated in vacuo. The product was purified by column chromatography to give an oil.

1-(4-Chloro-3-methoxyphenyl)-3-(R)-methyl-piperazine

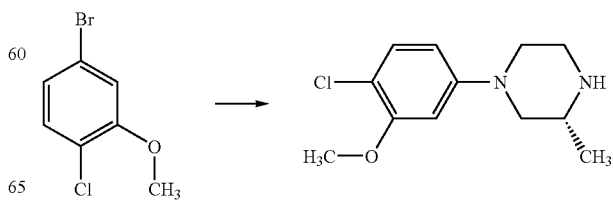

The title compound was prepared following protocol A, using (R)-(+)-2-methyl piperazine as the starting material. The product was isolated as a low-melting solid.

1-(4-Fluoro-2-methoxy-phenyl)-piperazine

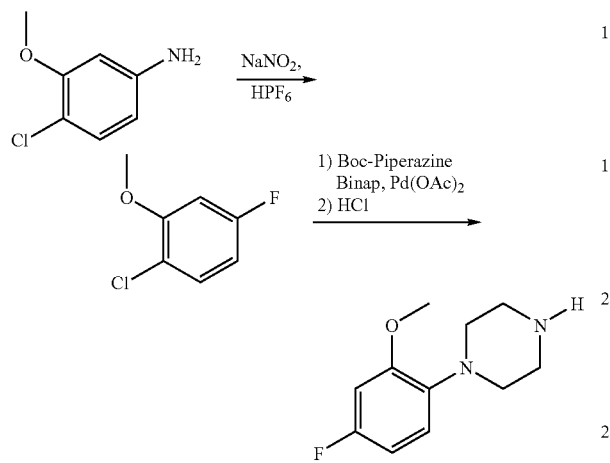

4-Chloro-3-methoxy-aniline (25 g, 158 mmol) was dissolved in conc. HCl (160 mL) at 80° C., and the solution was cooled to −10° C. An aqueous solution of NaNO$_2$ (12.04 g, 174.6 mmol) was added drop wise with stirring. After an additional 20 minutes, HPF$_6$ (80 mL) was added with stirring, keeping the temperature at or below 0° C. After an additional 30 minutes, the solid was filtered and washed with cold water and an ether-methanol mixture (4:1), and dried overnight in vacuo. The solid was added in portions to mineral oil at 170° C. with stirring. After complete addition the mixture was cooled to ambient temperature, and 175 mL of 10% Na$_2$CO$_3$ was added slowly to it. The mixture was steam distilled, and the distillate was extracted with dichloromethane. The dichloromethane phase was washed with brine, dried with Na$_2$SO$_4$, filtered, and concentrated to give 2-Chloro-5-fluoroanisole.

Following protocol A, Mono Boc-piperazine (7.64 g, 41.12 mmol), Pd (II) acetate (153 mg, 0.65 mmol), sodium tert. butoxide (4.61 g, 47 mmol) and BINAP (0.853 g, 1.37 mmol) were mixed together and stirred at rt in 100 mL dry toluene for 15 min under nitrogen atmosphere. 2-chloro-5-fluoroanisole (5.5 g, 34.2 mmol) in dry toluene (10 mL) was then added, and the mixture was refluxed for 20 hours. After cooling, the reaction mixture was filtered through a celite bed, followed by extensive washing with toluene. The toluene was concentrated, and the residue was extracted with ethyl acetate. The ethyl acetate was decanted, and was concentrated to obtain crude material that was taken directly to the next step.

The crude compound from the previous step was dissolved in 20 mL of dichloromethane, and 2M HCl in dry ether (20 mL) was added to it. The reaction mixture was stirred overnight, and the solvent was evaporated. The residue was dissolved in water, and was washed once with ethyl acetate. The aqueous layer was basified with 10% sodium hydroxide solution to pH 12, and was extracted with ethyl acetate three times. The combined ethyl acetate layers were washed with water and saturated brine solution, dried over anhydrous sodium sulfate, filtered, and concentrated to afford 1-(4-Fluoro-2-methoxy-phenyl)-piperazine as a white solid.

Synthesis of 1-[4-Chloro-3-(2-ethoxy-ethoxy)-phenyl]-piperazine

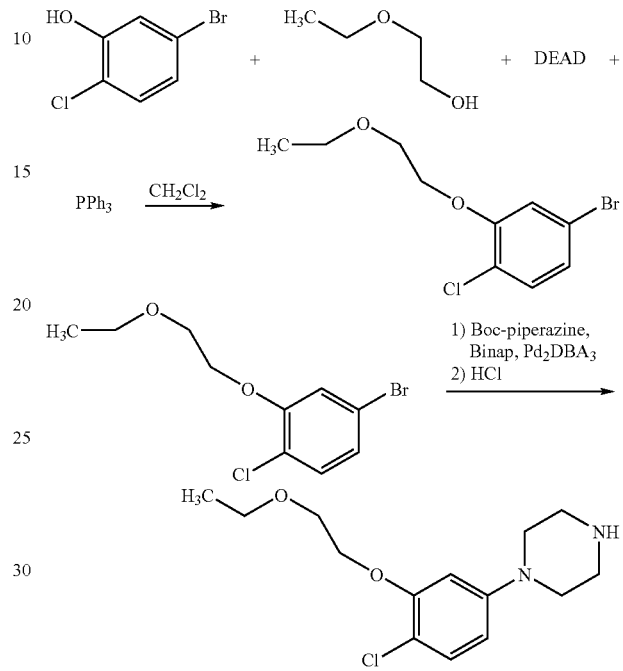

Following protocol F1 (below), to 1.11 g (4.24 mmol) of triphenylphosphine in 25 mL of CH$_2$Cl$_2$ at 0° C. was added 0.67 mL (4.24 mmol) of diethylazodicarboxylate. After 10 minutes, 0.80 g (3.86 mmol) of 5-Bromo-2-chlorophenol was added, followed rapidly by 0.38 g (4.24 mmol) of 2-Ethoxy-ethanol. The reaction was complete within three hours, and was partitioned between ether and water. The phases were separated, and the ether phase was diluted with hexanes and washed twice with 10% aqueous methanol and once with brine. The ether/hexanes phase was dried over Na$_2$SO$_4$, filtered, and concentrated in vacuo to yield (5-Bromo-2-chloro-ethoxy-ethoxy-benzene as a clear oil.

418 mg (1.5 mmol) of (5-Bromo-2-chloro-ethoxy-ethoxy-benzene, 335 mg (1.8 mmol) of 1-Boc-piperazine, 202 mg (2.1 mmol) sodium tert-butoxide, 30 mg (0.045 mmol) of rac-binap, and 14 mg (0.015 mmol) of Pd$_2$DBA$_3$ were slurried in 0.5 mL of dry toluene, and the mixture was heated at 90° C. for 12 hours. The reaction was partitioned between water and ethyl acetate, and the phases were separated. The ethyl acetate phase was washed with brine, dried over Na$_2$SO$_4$, filtered, and concentrated to an oil. The oil via chromatography to give 1-[4-Chloro-3-(2-ethoxy-ethoxy)-phenyl]-piperazine.

Further Examples of Arylpiperazines Synthesized by Metal Catalysed Arylation Methods (Protocol A)

Many other arylpiperazine derivatives were prepared in addition to the specific experimental examples listed above using similar Palladium mediated coupling methodologies. Examples are listed below.

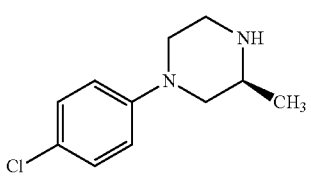
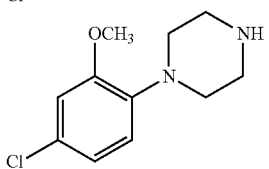
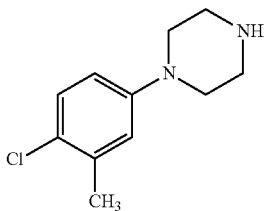
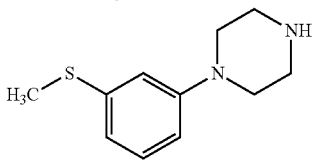
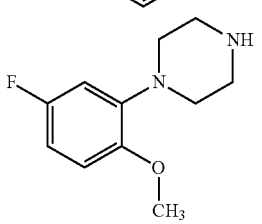
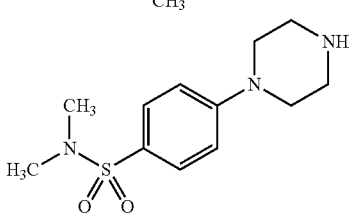
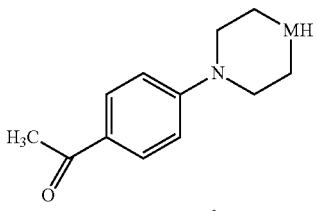
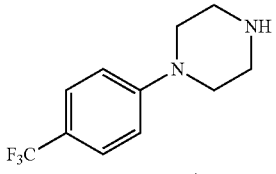
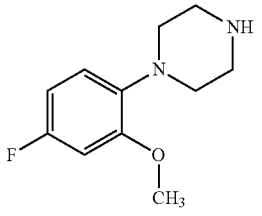

Protocol B: Piperazine Ring Formation Via Cyclization Reactions

Synthesis of 1-(3,4-Difluorophenyl)piperazine

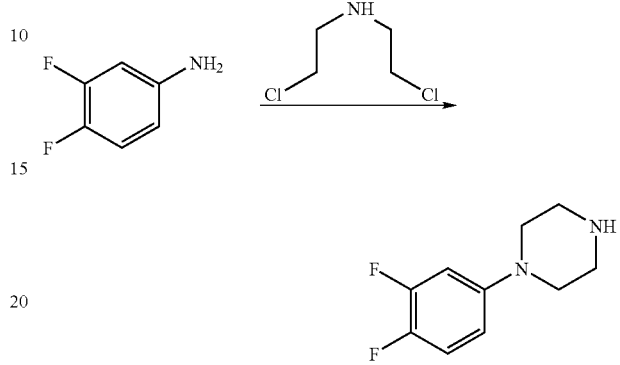

3,4-Difluoro-aniline (1 g, 7.7 mmol) was dissolved in dry n-butanol (10 mL) and dry sodium carbonate (3.2 g, 30 mmol) was added to it and the reaction mixture stirred, for 1 hour under nitrogen. Bis(2-chloroethyl) amine hydrochloride (1.38 g, 7.7 mmol) in nBuOH (10 mL) were then added to the mixture via a syringe. The reaction was then heated at 120° C. for 48 h. The nBuOH was evaporated in vacuo and the residue was extracted with ethyl acetate. Drying of the organic layer with $Na_2SO_4$ followed by concentration afforded the crude product. Purification using flash column chromatography (chloroform/methanol) afforded 1-(3,4-Difluorophenyl)-piperazine as an off white solid.

Synthesis of 1-(4-bromo-phenyl)-piperazine

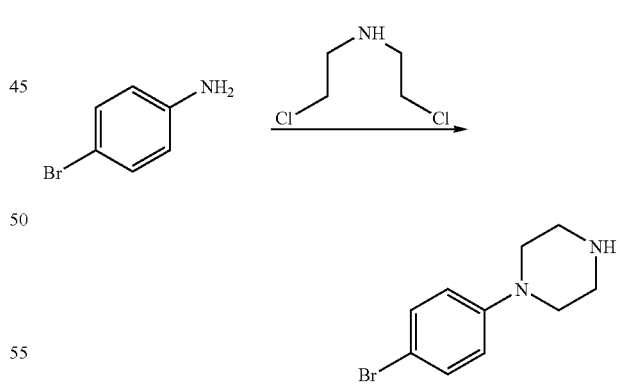

4-Bromo-aniline (2 g, 1.162 mmol) was taken in dry nBuOH (25 mL) and dry potassium carbonate (4.8 g, 34.8 mmol) was added to it and stirred at rt for 1 h under nitrogen. Bis-(2-chloroethyl) amine hydrochloride 2 (2.49 g, 13.9 mmol) in nBuOH (10 mL) was then added to the mixture through a syringe. The reaction mass was then heated at 100° C. for 12 h. nBuOH was evaporated in vacuo and the residue was extracted with ethyl acetate. Drying of the organic layer with $Na_2SO_4$ followed by concentration afforded the crude product that on purification silica gel column (chloroform/methanol) afforded the title compound.

Protocol C: Piperazine Ring Formation Via a Ring Opening/Ring Cyclization Strategy Synthesis of 3-[2-(5-Methoxy-2-methyl-phenylamino)-ethyl]-oxazolidin-2-one

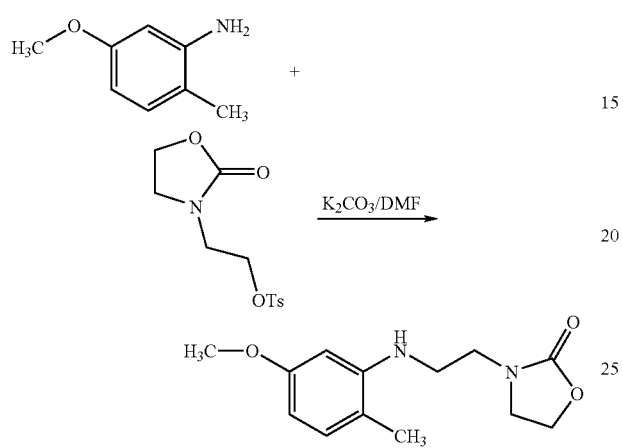

To a flask was added 2.95 g (10.3 mmol) of Toluene-4-sulfonic acid, 2-(2-oxo-oxazolidin-3-yl)-ethyl ester, 1.56 g (11.4 mmol) of 2-methyl-5-methoxyaniline, 2.58 g (18.7 mmol) of potassium carbonate, and 22 mL of anhydrous dimethylformamide, and the mixture was heated at 100° C. for seven hours. The reaction was allowed to cool to room temperature, and was partitioned between ethyl acetate and water. The phases were separated, and the ethyl acetate phase was washed with brine, dried over $Na_2SO_4$, filtered, and concentrated to an oil. The oil was purified by chromatography (120 mL silica, 60 ethyl acetate/40 hexanes) to give the corresponding product as a clear oil that solidified upon drying: $^1$H NMR (DMSO-d6, 400 MHz) 6.81 (d, 1H), 6.11 (s, 1H), 6.04 (d, 1H), 4.92 (t, 1H), 4.21 (t, 2H), 3.65 (s, 3H), 3.59 (m, 2H), 3.31 (m, 2H), 3.23 (m, 2H), 1.95 (s, 3H) ppm.

Synthesis of 1-(5-Methoxy-2-methyl-phenyl)-piperazine

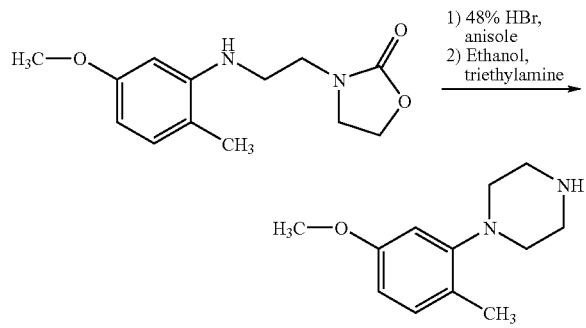

To 505 mg (2.0 mmol) of 3-[2-(5-Methoxy-2-methyl-phenylamino)-ethyl]-oxazolidin-2-one in a flask was added 2 mL of 48% HBr in acetic acid, 1 mL of acetic acid, and 1 mL of anisole, and the mixture was heated at 90° C. for six hours. The solution was allowed to cool to room temperature, and 5 mL of $CH_2Cl_2$ was added. The product crystallized and was isolated by filtration. The solids were dissolved in 55 mL of ethanol, 201 mg (2 mmol) of triethylamine were added, and the solution was heated at reflux for 3 hours. The solution was then concentrated in vacuo to give a residue that was partitioned between ether and water. The phases were separated, and the aqueous phase as basified with 1M NaOH. The aqueous phase was then extracted twice with ethyl acetate. The combined ethyl acetate phases were washed once with brine, dried over $Na_2SO_4$, filtered, and acidified with 2M HCl in ether. The product was isolated via filtration.

Addition of various piperazines to aryl halides and heteroaryl halides via aryl-halogen displacement methodologies A direct halogen displacement strategy, with thermal assistance if necessary, can be complimentary to the metal mediated approaches, discussed above, for the construction of the ring systems provided herein.

Synthesis of 4-Piperazin-1-yl-benzoic acid ethyl ester

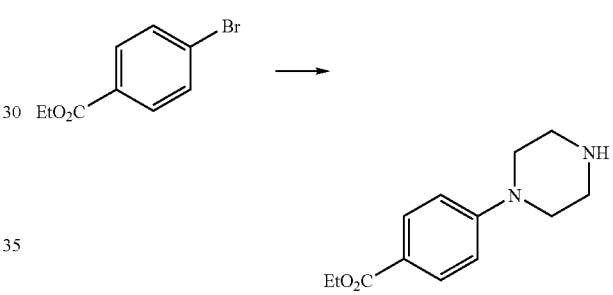

To 4-bromobenzoic acid (25 g) and ethanol (1000 mL) was added conc. sulfuric acid (20 g) drop wise. The reaction mixture was heated at 85° C. overnight. The reaction was cooled and ethanol was removed by distillation and the reaction mixture quenched with water and extracted with ethyl acetate. The extract was washed with 10% sodium bicarbonate, water, brine and then concentrated to yield the crude ester. 4-bromoethyl benzoate (10.0 g, 0.0437 mol) was taken into 250 mL of dry DMF, piperazine (37 g, 0.437 mol) was added, followed by 30 g (0.2185 mol) of dry potassium carbonate, 1.0 g of TBAI and 1.5 g of potassium iodide. The reaction mixture was heated at 135° C. for over night. The reaction mixture was quenched with water and extracted with ethyl acetate. The extracts were washed with water, then brine and then concentrated to yield 4-Piperazin-1-yl-benzoic acid ethyl ester as an off-white solid.

Synthesis of 1-(4-Methoxy-pyridin-2-yl)-piperazine

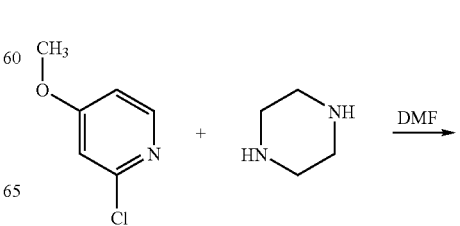

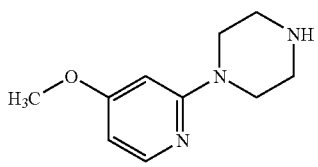

To 756 mg (5.29 mmol) of 2-Chloro-4-methoxypyridine and 2.27 g (26 mmol) of piperazine in a pressure flask was added 2.7 mL dimethylformamide, and the mixture was heated at 115° C. for 5 hours. The solution was allowed to cool before opening the flask, and the resulting slurry was partitioned between ethyl acetate and water. The phases were separated, and the aqueous phase was back-extracted once with ethyl acetate. The combined ethyl acetate phases were washed once with brine, dried over $Na_2SO_4$, filtered, and the filtrate was acidified with 2M HCl in ether. The product crystallized over night, and the solids were isolated by filtration to yield product as a white solid: $^1$H NMR ($D_2O$, 400 MHz) 7.72 (d, 1H), 6.61 (d, 1H), 6.48 (s, 1H), 3.88 (s, 3H), 3.79 (m, 4H), 3.36 (m, 4H) ppm.

Synthesis of 1-(3-Methoxy-pyridin-2-yl)-piperazine

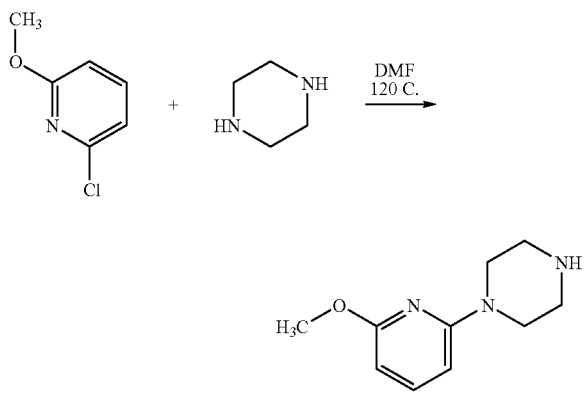

To 966 mg (6.7 mmol) of 2-Chloro-6-methoxypyridine and 2.90 g (34 mmol) of piperazine in a pressure flask was added 3.3 mL dimethylformamide, and the mixture was heated at 115° C. for 5 hours. The solution was allowed to cool before opening the flask, and the resulting slurry was partitioned between ethyl acetate and water. The phases were separated, and the aqueous phase was back-extracted once with ethyl acetate. The combined ethyl acetate phases were washed once with brine, dried over $Na_2SO_4$, filtered, and the filtrate was acidified with 2M HCl in ether. The product crystallized overnight, and was isolated by filtration to give a white solid: $^1$H NMR ($D_2O$, 400 MHz) 7.73 (t, 1H), 6.52 (d, 1H), 6.31 (d, 1H), 3.81 (s, 3H), 3.68 (m, 4H), 3.26 (m, 4H) ppm.

Protocol D: Synthesis and Addition of Elaborated Piperazines to Aryl and Heteroaryl Halides Via Aryl-Halogen Displacement Methodologies

Synthesis of 2-(4-Chloro-5-methyl-3-trifluoromethyl-pyrazol-1-yl)-1-piperazin-1-yl-ethanone

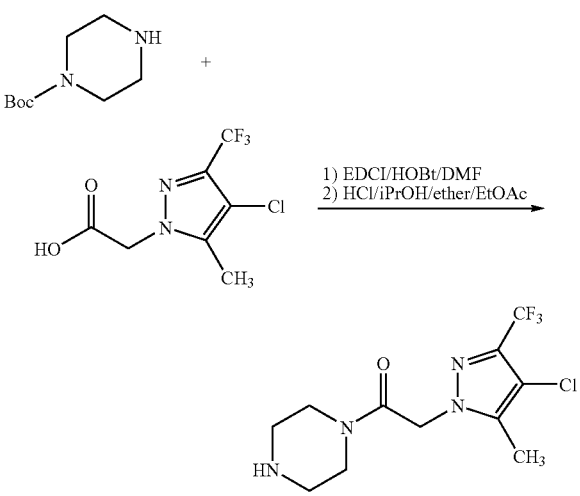

To a solution of 1.69 g (9.1 mmol) Boc-piperazine, 2.0 g (8.3 mmol) of (4-Chloro-5-methyl-3-trifluoromethyl-pyrazol-1-yl)-acetic acid, and 1.12 g (8.3 mmol) of 1-Hydroxybenzotriazole in 20 mL of dimethylformamide at 0° C. was added 1.73 g (9.1 mmol) of 1-(3-Dimethylaminopropyl)-3-ethylcarbodiimide hydrochloride. The reaction was allowed to stir and warm to room temperature over night, then was partitioned between ether and water. The phases were separated, and the ether phase was washed once each with 1M HCl, water, 1M NaOH, and brine. The ether phase was then dried over $Na_2SO_4$, filtered, and concentrated to a residue.

This crude residue was dissolved in 20 mL ether and 8 mL ethyl acetate, and 20 mL of 5M HCl in isopropanol was added. After 1 hour the mixture was placed in the freezer over night. The product was isolated by filtration to give a white solid. $^1$H NMR (DMSO-d6, 400 MHz) 9.21 (br s, 2H), 5.38 (s, 2H), 3.69 (m, 4H), 3.32 (m, 4H), 2.20 (s, 3H) ppm.

Alternative Synthesis of 2-(4-Chloro-5-methyl-3-trifluoromethyl-pyrazol-1-yl)-1-piperazin-1-yl-ethanone

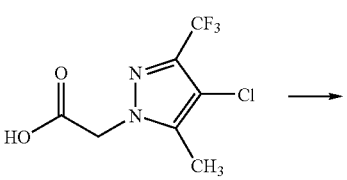

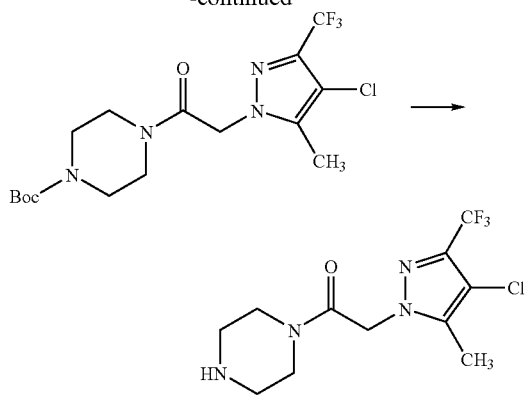

(4-Chloro-5-methyl-3-trifluoromethyl-pyrazol-1-yl)-acetic acid (1.5 g, 6.18 mmol) was taken in dry DCM (20 mL) and cooled to 0° C. To this cold mixture was added N-boc piperazine (1.15 g, 6.18 mmol) followed by addition of T3P (8 g, 12.4 mmol, 50% solution in EtOAc). The reaction was left overnight at rt. The mixture was diluted with $CH_2Cl_2$, washed with NaHCO3 soln, brine, dried ($Na_2SO_4$) and concentrated to afford the crude product that was washed thoroughly with ether-pet ether to afford 4-[2-(4-Chloro-5 methyl-3-trifluoromethyl-pyrazol-1-yl)-acetyl]-piperazine-1-carboxylic acid tert-butyl ester (1.2 g, 2.9 mmol). This was dissolved in methanol (25 mL) cooled to 0° C. and HCl saturated ether (3 mL) was added to it. The mixture was stirred at room temperature for 4 h and concentrated. Crystallization from MeOH/Petroleum ether yielded product.

Synthesis of 1-[4-(5-Bromo-pyrimiclin-2-yl)-piperazin-1-yl]-2-(4-chloro-5-methyl-3-trifluoromethyl-pyrazol-1-yl)-ethanone (Protocol D)

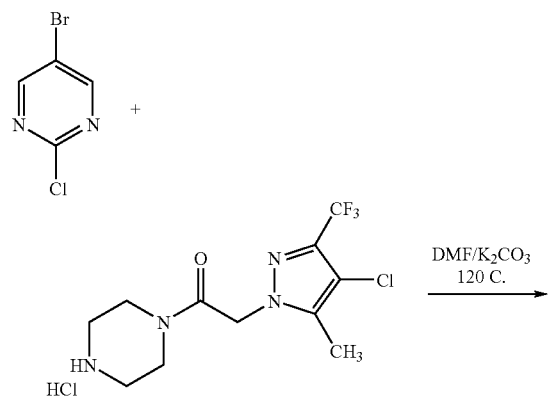

To 86 mg (0.25 mmol) of 2-(4-Chloro-5-methyl-3-trifluoromethyl-pyrazol-1-yl)-1-piperazin-1-yl-ethanone hydrochloride, 76 mg (0.6 mmol) potassium carbonate, and 48 mg (0.3 mmol) of 5-Bromo-2-chloropyrimidine in a vial was added 0.7 mL anhydrous dimethylformamide, and the mixture was heated at 120° C. for 12 hours. The reaction was allowed to cool to room temperature, and was partitioned between ethyl acetate and water. The phases were separated, and the aqueous phase was back-extracted once with ethyl acetate. The combined ethyl acetate phases were washed once each with water, 0.5M pH=7 phosphate buffer, water, 1M NaOH, and brine. The ethyl acetate phase was dried over $Na_2SO_4$, filtered, and acidified with 2M HCl in ether to precipitate the product as a powder: $^1$H NMR (DMSO-d6, 400 MHz) 8.48 (s, 2H), 5.37 (s, 2H), 3.81 (m, 2H), 3.72 (m, 2H), 3.57 (m, 4H), 2.18 (s, 3H) ppm; MS (ES) M+H expected=467.0, found 466.9.

Additional Compounds of the Invention Prepared by the Aryl-Halogen Displacement Method Synthesis of 2-(4-Chloro-5-methyl-3-trifluoromethyl-pyrazol-1-yl)-1-[4-(7H-purin-6-yl)piperazin1-yl]-ethanone:

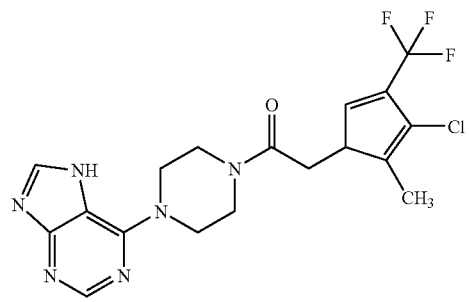

Title compound was prepared following protocol D, wherein 6-Chloropurine was used as the heteroaryl halide component: $^1$H NMR (DMSO-d6, 400 MHz) 8.23 (s, 1H), 8.14 (s, 1H), 5.39 (s, 2H), 4.32 (br, 2H), 4.22 (br, 2H), 3.60 (m, 4H), 2.19 (s, 3H) ppm; MS (ES) expect M+H=429.1, found 429.0.

Synthesis of 2-(4-Chloro-5-methyl-3-trifluoromethyl-pyrazol-1-yl)-1-(4-quinolin-2-yl-piperazin-1-yl)ethanone

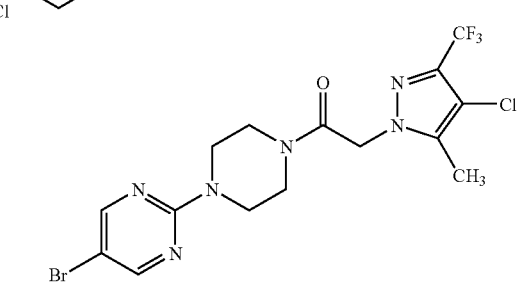

Title Compound was prepared following protocol D, wherein 2-Chloroquinoline was used as the heteroaryl halide component: $^1$H NMR (DMSO-d6, 400 MHz) 8.44 (d, 1H), 8.29 (br, 1H), 7.91 (d, 1H), 7.77 (t, 1H), 7.57 (d, 1H), 7.48 (t, 1H), 5.44 (s, 2H), 4.14 (br, 2H), 4.01 (br, 2H), 3.78 (br, 2H), 3.70 (br, 2H), 2.20 (s, 3H) ppm; MS (ES) expect M+H=438.1, found 438.0.

Synthesis of 2-(4-Chloro-5-methyl-3-trifluoromethyl-pyrazol-1-yl)-1-[4-(5-chloro-pyridin-2-yl)-piperazin-1-yl]-ethanone

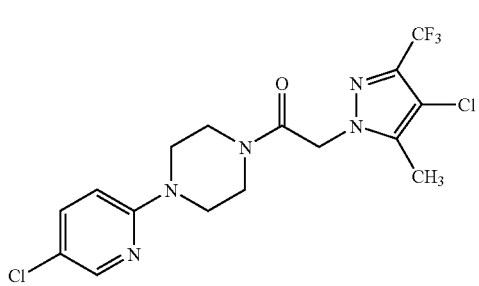

Title compound was prepared following protocol D, wherein 2,5-Dichloropyridine was used as the heteroaryl halide component: MS (ES) expect M+H=422.1, found=422.0; HPLC retention time=4.75 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-(2,3,5,6-tetrahydro-[1,2']bipyrazinyl-4-yl)-ethanone

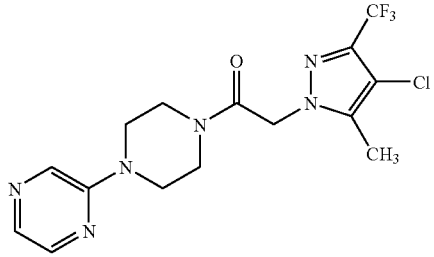

Title compound was prepared following protocol D, wherein 2-Chloropyrazine was used as the heteroaryl halide component: $^1$H NMR (DMSO-d6, 400 MHz) 8.34 (s, 1H), 8.09 (d, 1H), 7.85 (d, 1H), 5.38 (s, 2H), 3.68 (m, 2H), 3.58 (m, 4H), 3.44 (m, 2H), 2.19 (s, 3H) ppm; MS (ES) expect M+H=389.1, found 389.0.

Synthesis of 2-(4-Chloro-5-methyl-3-trifluoromethyl-pyrazol-1-yl)-1-[4-(6-methyl-pyridazin-3-yl)-piperazin-1-yl]-ethanone:

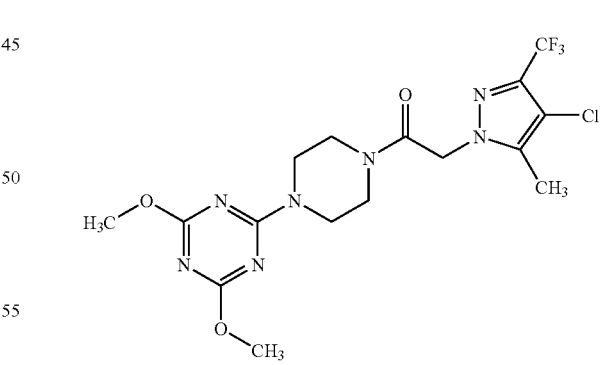

Title compound was prepared following protocol D, wherein 3-Chloro-6-methylpyridazine was used as the heteroaryl halide component:MS (ES) expect M+H=403.1, found=403.0; HPLC retention time=1.68 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-[4-(4,6-dimethoxy-[1,3,5]triazin-2-yl)-piperazin-1-yl]-ethanone Title compound was prepared following protocol D, wherein 2-Chloro-4,6-dimethoxytriazine was used as the heteroaryl halide component: MS (ES) expect M+H=450.1, found=450.0; HPLC retention time=4.24 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-[4-(2-methylsulfanyl-pyrimidin-4-yl)-piperazin-1-yl]-ethanone

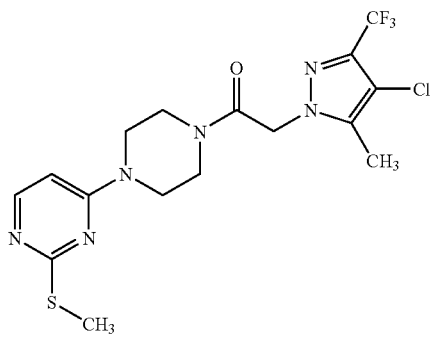

Title compound was prepared following protocol D, wherein 4-Chloro-2-methylthiopyrimidine was used as the heteroaryl halide component: $^1$H NMR (DMSO-d6, 400 MHz) 8.16 (d, 1H), 6.87 (d, 1H), 5.41 (s, 2H), 3.90 (br m, 4H), 3.62 (m, 4H), 2.57 (s, 3H), 2.19 (s, 3H) ppm; MS (ES) expect M+Na=435.1, found 435.0.

Synthesis of 2-(4-Chloro-5-methyl-3-trifluoromethyl-pyrazol-1-yl)-1-[4-(4,6-dimethoxy-pyrimidin-2-yl)-piperazin-1-yl]-ethanone

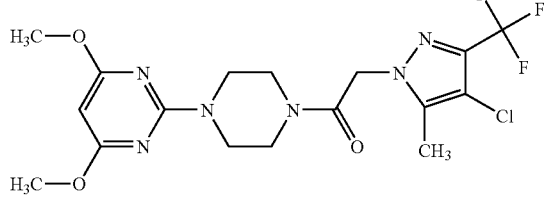

Title compound was prepared following protocol D, wherein 2-Chloro-4,6-dimethoxypyrimidine was used as the heteroaryl halide component: MS (ES) expect M+H=449.1, found=449.0; HPLC retention time=4.92 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(6-Chloro-5-methyl-pyridazin-3-yl)-piperazin-1-yl]-2-(4-chloro-5-methyl-3-trifluoromethyl-pyrazol-1-yl)-ethanone

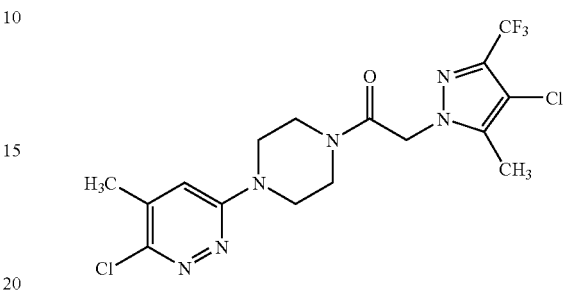

Title compound was prepared following protocol D, wherein 3,6-Dichloro-4-methylpyridazine was used as the heteroaryl halide component: MS (ES) expect M+H=437.1, found=437.0; HPLC retention time=4.17 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-methyl-3-trifluoromethyl-pyrazol-1-yl)-1-[4-(5-methoxy-1-H-benzoimidazol-2-yl)-piperazin-1-yl]-ethanone Title compound was prepared following protocol D, wherein 2-Chloro-5-methoxybenzimidazole was used as the heteroaryl halide component: MS (ES) expect M+H=457.1, found=457.0; HPLC retention time=2.85 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Further Functionalization of Arylpiperazine Ring System After its Formal Construction Key compounds of the current invention have, in addition to other selected substituents, a halogen atom at the 2- or 4-position. Approaches to install this are described in the following section.

Functionalization of the aryl ring within the arylpiperazine ring system can, in general, take place either before or after introduction of the piperazine ring, as illustrated in the examples below.

Protocol E: Selected Examples of Halogenation of Aromatic Systems After Attachment of the Piperazine Ring System Synthesis of 1-(4-Bromo-3-methoxy-phenyl)-piperazine hydrochloride

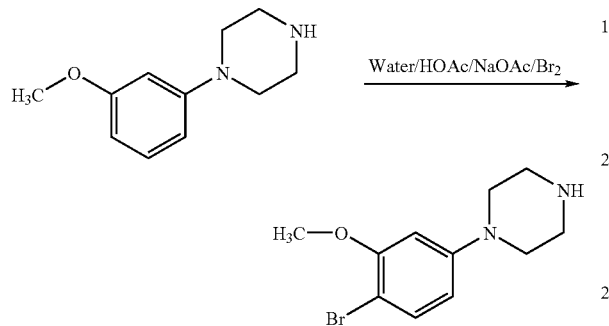

To a solution of 2.33 g (8.8 mmol) of 1-(3-Methoxyphenyl)piperazine dihydrochloride and 756 mg (9.7 mmol) sodium acetate in 70 mL of acetic acid and 15 mL of water at 0° C. was added 1.55 g (9.7 mmol) bromine. After 1 hour, the reaction was concentrated to an oil in vacuo, and the oil was partitioned between ethyl acetate and 1M NaOH. The phases were separated, and the ethyl acetate phase was washed once each with water and brine, dried over $Na_2SO_4$, filtered, and the filtrate was concentrated to an oil in vacuo. The oil was dissolved in a minimum volume of methanol, and the solution was acidified with 2M HCl in ether. The product was isolated by filtration. $^1$H NMR ($D_2O$, 400 MHz) 7.36 (d, 1H), 6.73 (s, 1H), 6.50 (d, 1H), 3.75 (s, 3H), 3.32 (m, 8H) ppm.

Synthesis of 1-(4-Bromo-3-methyl-phenyl)-piperazine hydrochloride

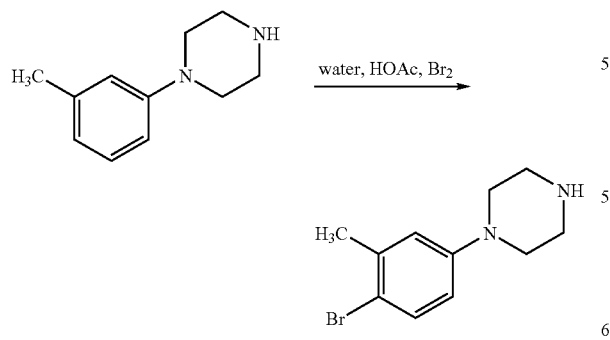

To a solution of 966 mg (4.0 mmol) of 1-(3-Methylphenyl)piperazine dihydrochloride in 9 mL of acetic acid and 1 mL of water at 0° C. was added 640 mg (4.0 mmol) of bromine. After 1 hour, the reaction was concentrated to an oil in vacuo, and the oil was partitioned between ethyl acetate and 1M NaOH. The phases were separated, and the ethyl acetate phase was washed once each with water and brine, dried over $Na_2SO_4$, filtered, and the filtrate was concentrated to an oil in vacuo. The oil was dissolved in a minimum volume of methanol, and the solution was acidified with 2M HCl in ether. The product was isolated by filtration. $^1$H NMR ($D_2O$, 400 MHz) 7.37 (d, 1H), 6.85 (s, 1H), 6.76 (d, 1H), 3.37 (m, 8H), 2.17 (s, 3H) ppm.

Synthesis of 1-(2-Chloro-5-methoxy-phenyl)-piperazine hydrochloride

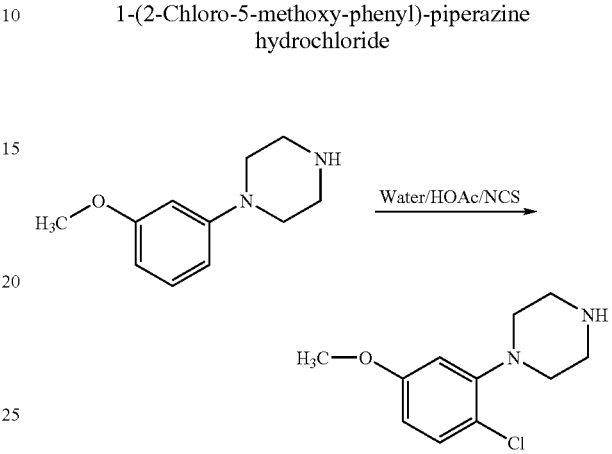

To a solution of 5.3 g (20 mmol) of 1-(3-Methoxyphenyl)piperazine dihydrochloride in 120 mL of acetic acid and 30 mL of water at 0° C. was added 3.3 g (20 mmol) of N-chlorosuccinimide. After 5 hours, the reaction was concentrated to an oil in vacuo, and the oil was partitioned between ethyl acetate and 1M NaOH. The phases were separated, and the ethyl acetate phase was washed once each with water and brine, dried over $Na_2SO_4$, filtered, and the filtrate was concentrated to an oil in vacuo. The oil was dissolved in a minimum volume of methanol, and the solution was acidified with 2M HCl in ether. The product was isolated by filtration. $^1$H NMR ($D_2O$, 400 MHz) 7.28 (d, 1H), 6.66 (m, 3H), 3.70 (s, 3H), 3.32 (m, 4H), 3.20 (m, 4H) ppm.

Synthesis of 1-(2,4-Dichloro-5-methoxy-phenyl)-piperazine hydrochloride

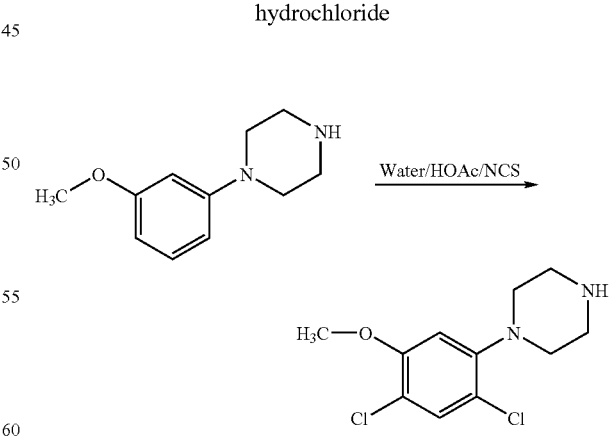

To a solution of 530 mg (2.0 mmol) of 1-(3-Methoxyphenyl)piperazine dihydrochloride in 7 mL of acetic acid and 4 mL of water at 0° C. was added 700 mg (4.4 mmol) of N-chlorosuccinimide. The reaction was taken out of the ice/water bath after 2 hours, and allowed to stir overnight. After 12 hours, the reaction was concentrated to an oil in vacuo, and the oil was partitioned between ether and water. The phases were separated, the aqueous was basified with 1M NaOH, and was extracted with ethyl acetate. The ethyl acetate phase was washed once each with water and brine, dried over Na₂SO₄, filtered, and the filtrate was concentrated to an oil in vacuo. The oil was dissolved in a minimum volume of methanol, the solution was acidified with 5M HCl in isopropanol and was diluted with ethyl acetate to effect crystallization. The product was isolated by filtration. $^1$H NMR (D$_2$O, 400 MHz) 7.38 (s, 1H), 6.72 (s, 1H), 3.78 (s, 3H), 3.32 (m, 4H), 3.19 (m, 4H) ppm.

Synthesis of
1-(4-Chloro-5-Methoxy-2-methyl-phenyl)-piperazine

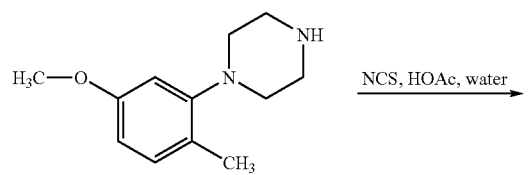

Following protocol E, to 90 mg (0.32 mmol) of 1-(5-Methoxy-2-methyl-phenyl)-piperazine hydrochloride in 1.3 mL of acetic acid and 1 mL of water at 0° C. was added 58 mg (0.36 mmol) of N-chlorosuccinimide. The reaction was allowed to warm to ambient temperature over two hours, and after 14 hours it was concnentrated to a dark residue in vacuo. The residue was partitioned between ether and water, and the phases were separated. The aqueous phase was basified to pH >10 with 1M NaOH, and was extracted twice with ethyl acetate. The combined ethyl acetate phases were washed once with brine, dried over Na₂SO₄, filtered, and concentrated to an oil. The oil was dissolved in methanol, acidified with 2 M HCl in ether, and diluted with ether to give the product as a solid.

Synthesis of 1-(4-Bromo-3-Methoxy-phenyl)-3-(S)-methyl-piperazine

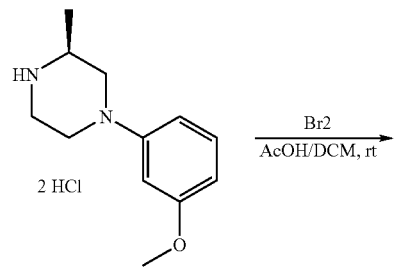

To 500 mg of S-(+)-3-methyl-N1-(4-chloro-3-methoxy) phenylpiperazine (1.79 mmol, 1.0 eq) in 5 mL of 1:1 AcOH/DCM was added 91 uL Br2 (1.79 mmol, 1.0 eq) to the stirring slurry. LC/MS shows mixture of polyhalogenated species. Crude mixture purified by preparative HPLC to get the titled intermediate.

Synthesis of 1-(2,4-Dichloro-5-Methoxy-phenyl)-3-(S)-methyl-piperazine

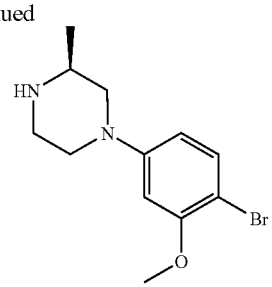

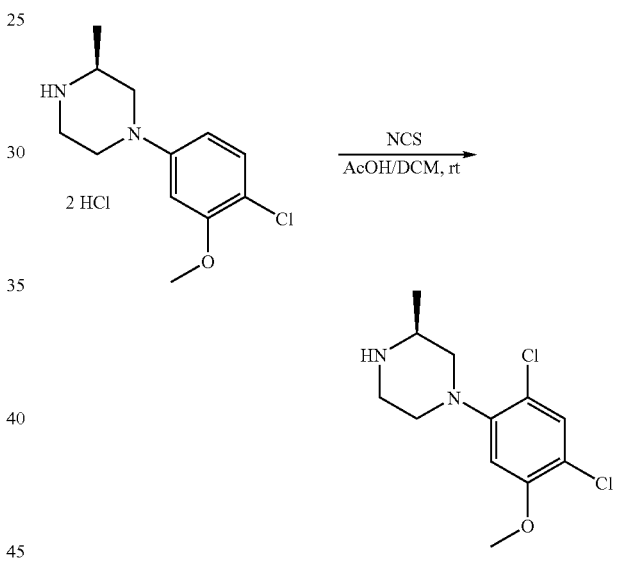

To 500 mg of S-(+)-3-methyl-N1-(4-chloro-3-methoxy) phenylpiperazine (1.44 mmol, 1.0 eq) in 2 mL of 1:1 AcOH/DCM was added 85 mg NCS (0.64 mmol, 0.44 eq) to the stirring slurry. LC/MS shows mixture of polyhalogenated species. Crude mixture purified by preparative HPLC to get the desired intermediate.

Protocol F1: Selected Examples of Demethylation/Etherification of Aromatic Precursors for Attachment of the Piperazine Ring System to Access Key Arylpiperazine Moieties Synthesis of 3-Bromo-6-chlorophenol

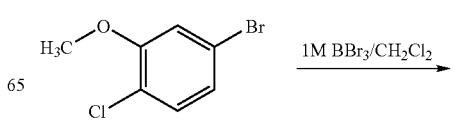

-continued

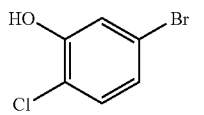

To 50 mL of a 1M solution of boron tribromide in CH$_2$Cl$_2$ at 0° C. was added 5.71 g (25.8 mmol) of 5-Bromo-2-chloroanisole. After 2 hours, the reaction was allowed to warm to room temperature. After 5 hours, the solution was cooled to 0° C., and quenched with methanol. The resulting solution was partitioned between water and ethyl acetate, and the phases were separated. The aqueous phase was back-extracted once with ethyl acetate. The combined ethyl acetate phases were diluted with one volume of ether, and were extracted twice with 1M NaOH. The combined basic aqueous phases were acidified with 12M HCl, and were extracted once with ethyl acetate. The final ethyl acetate phase was washed once with brine, dried over MgSO4, filtered, and concentrated to give the phenol as a tan solid. $^1$H NMR (DMSO-d6, 400 MHz) 10.66 (s, 1H), 7.27 (d, 1H), 7.08 (s, 1H), 6.95 (d, 1H) ppm.

Synthesis of 1-Bromo-3-isopropoxy-4-chlorobenzene

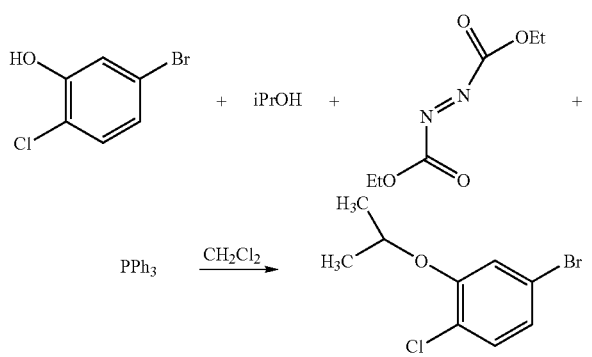

To 1.70g (6.5 mmol) of triphenylphosphine in 25 mL of CH$_2$Cl$_2$ at 0° C. was added 1.14 g (6.5 mmol) of diethylazodicarboxylate. After 10 minutes, 390 mg (6.5 mmol) of isopropanol was added, followed rapidly by 1.03 g (5.0 mmol) of 3-Bromo-6-chlorophenol. The reaction was complete within three hours, and was partitioned between ether and water. The phases were separated, and the ether phase was diluted with hexanes and washed twice with 10% aqueous methanol and once with brine. The ether/hexanes phase was dried over Na$_2$SO$_4$, filtered, and concentrated in vacuo to yield product as a clear oil.

Protocol F2: Additional Examples of Analogous Ring Systems Constructed Using Similar Demethylation/Etherification Strategies

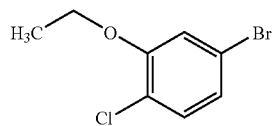

Synthesis of 2-chloro-5-bromo-O-(4-methylbenzenesulfonyl)benzyl alcohol

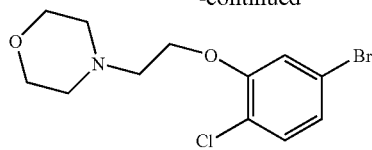

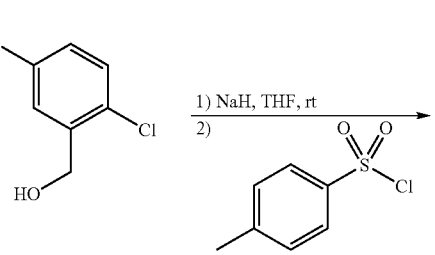

To 1.0 g of 2-chloro-5-bromobenzyl alcohol (4.5 mmol, 1.0 eq) in 5 mL dry THF, was added 200 mg 60% NaH/mineral oil dispersion (5.0 mmol, 1.1 eq), and the resulting slurry was stirred under nitrogen for 0.5 hours. 900 mg portion of 4-methylbenzenesulfonyl chloride (4.8 mmol, 1.05 eq) was added, and the mixture allowed to stir overnight for 12 hours. The reaction was poured into 25 mL aqueous K$_2$CO$_3$, and this was extracted with 2×10 mL of 20% Hexane/EtOAc. The aqueous phase was discarded, and the combined organic phases were dried under vacuum to obtain a white crystalline solid.

Preparation of (2-Chloro-5-piperazin-1-yl-benzyl)-methyl-carbamic acid benzyl ester

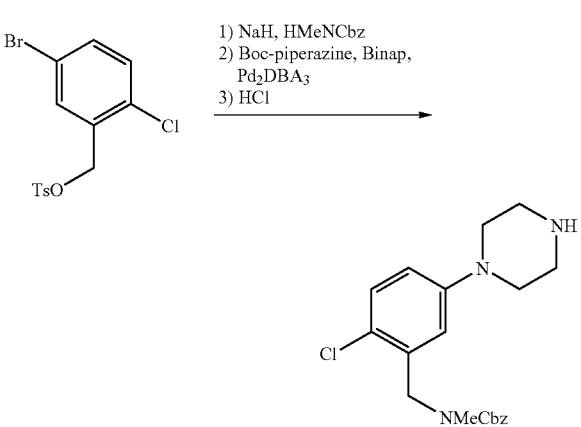

To 200 mg of 2-chloro-5-bromo-O-(4-methylbenzene-sulfonyl)benzyl alcohol (0.53 mmol, 1.0 eq) in 500 uL dry THF was added 230 mg of 60% NaH dispersion in mineral oil (0.58 mmol, 1.1 eq), followed by 1.5 eq of the N-Cbz-methylamine. The mixture was heated at 60° C. overnight, and the crude products were purified by preperative HPLC to give (5-Bromo-2-chloro-benzyp-methyl-carbamic acid benzyl ester.

500 mg of (5-Bromo-2-chloro-benzyl)-methyl-carbamic acid benzyl ester (1.36 mmol), 303 mg (1.63 mmol) of N-Boc-piperazine, 182 mg (1.90 mmol) of NaOtBu, 27 mg (0.04 mmol) of BINAP, and 12 mg (0.01 mmol) of Pd$_2$Dba$_3$ in 0.5 mL of toluene were heated at 90° C. overnight. The crude material was purified by prep HPLC to give 4-{3-[(Benzyloxycarbonyl-methyl-amino)-methyl]-4-chloro-phenyl}-piperazine-1-carboxylic acid tert-butyl ester.

220 mg of 4-{3-[(Benzyloxycarbonyl-methyl-amino)-methyl]-4-chloro-phenyl}-piperazine-1-carboxylic acid tert-butyl ester was dissolved in 2 mL of a 1:2 TFA:dichloromethane solution. After 0.5 hour, the solvent and TFA are removed under vacuum to give (2-Chloro-5-piperazin-1-yl-benzyl)-methyl-carbamic acid benzyl ester as an oil.

Other Substituted Arylpiperazines Prepared Using this Procedure

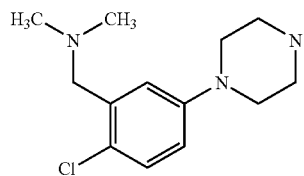

(2-Chloro-5-piperazin-1-yl-phenyl)-carbamic acid tert-butyl ester

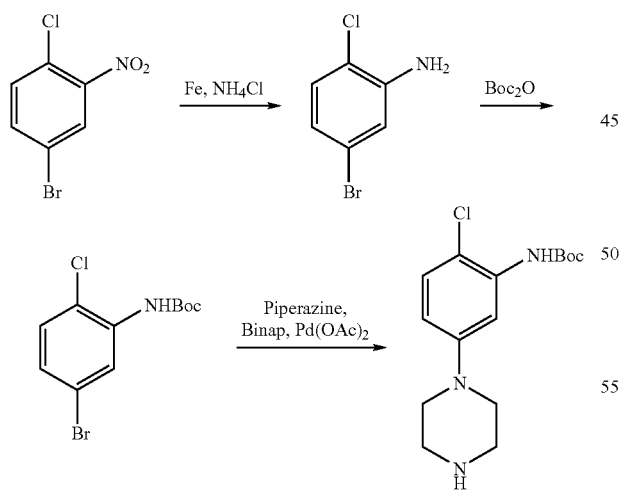

To 25 g (0.106 mol) of 4-bromo-1-chloro-2-Nitrobenzene in 400 mL of methanol was added 30 g (0.528 mol) of iron powder. The mixture was heated to 50° C., and 45 g (0.8456 mol) of ammonium chloride in 200 mL of water was slowly added. The reaction was heated to 70° C. over night, cooled to ambient temperature, and filtered through paper. The filtrate was concentrated in vacuo, the residue was dissolved in water, and this was extracted with ethyl acetate. The ethyl acetate phase was washed once each with water and brine, dried with Na$_2$SO$_4$, filtered, and concentrated to give 5-Bromo-2-chloroaniline.

To 10 g (0.048 mol) of 5-bromo-2-chloroaniline in 300 mL of dry dichloromethane was added 15 g (0.1452 mol) of triethylamine. The reaction was cooled to 0° C., and 13 g (0.0581 mol) of Boc-anhydride was added. The reaction was warmed to ambient temperature, and 6 g (0.048 mol) of DMAP was added. After 14 hours the solvent was removed in vacuo, and the residue was purified by chromatography to give tert-butyl-5-bromo-2-chlorophenyl carbamate as a pale orange solid.

Following protocol A, 5 g (0.02 mol) of tert-butyl-5-bromo-2-chlorophenyl carbamate, 14 g (0.1628 mol) of piperazine, 8.6 g (0.025 mol) of cesium carbonate, 0.1 g (0.0025 mol) of palladium acetate, and 0.1 g (0.002 mol) of BINAP in 5 mL of dry toluene were heated at 110° C. for 12 hours. After cooling to ambient temperature, the reaction was quenched with water, and the mixture was extracted with ethyl acetate. The ethyl acetate phase was washed with brine, dried with Na$_2$SO$_4$, filtered, and concentrated. The residue was purified by 60-120 silica gel using 0.5% of methanol in chloroform, to give (2-Chloro-5-piperazin-1-yl-phenyl)-carbamic acid tert-butyl ester as a low melting solid.

1-(4-Chloro-3-methoxymethyl-phenyl)-piperazine

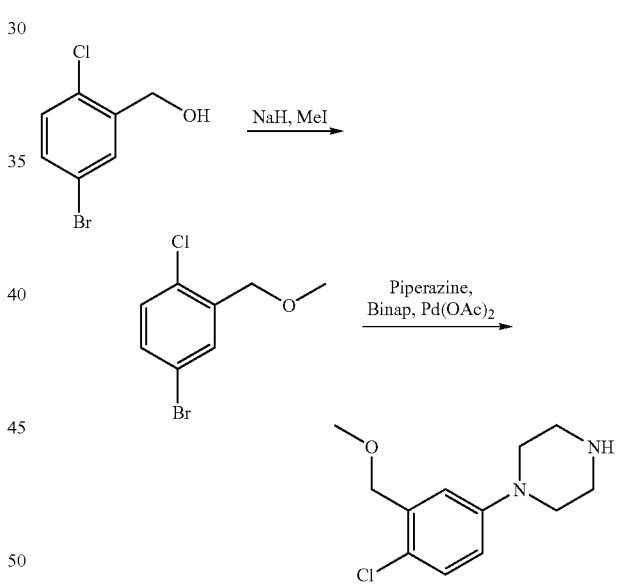

1 g (0.0045 mol) of 5-bromo-2-chlorobenzyl alcohol in dry THF was added to 0.4 g (0.00032 mol) of sodium hydride in dry THF at 0° C., and the mixture was stirred at 0° C. for 1 hour. 1.28 g (0.009 mol) of methyl iodide was added, and the reaction was allowed to warm to ambient temperature. After stirring for 12 hours, the reaction was quenched with water, and was extracted with ethyl acetate. The ethyl acetate phase was washed once each with water and brine, dried with Na$_2$SO$_4$, filtered, and concentrated to give 4-Bromo-1-chloro-2-methoxymethyl-benzene.

Following protocol A, 0.98 g (0.0041 mol) of 4-bromo-1-chloro-2-methoxymethyl-benzene, 0.35 g (0.0041 mol) of piperazine, 0.0466 g (0.0002 mol) of palladium acetate, 0.25 g (0.00041 mol) of BINAP, and 0.63 g (0.0066 mol, 1.6 eq) of sodium tert-butoxide in 10 mL of dry toluene were heated at 110° C. under argon atmosphere for 24 hours. The reaction mixture was quenched with water and extracted with ethyl acetate. The extract was washed once each with water and brine, dried with Na$_2$SO$_4$, filtered, and concentrated. The residue was purified by chromatography to give 1-(4-Chloro-3-methoxymethyl-phenyl)-piperazine as a low melting solid.

1-(4-chloro-3-methoxy-phenyl)-2-(R)-methyl-piperazine

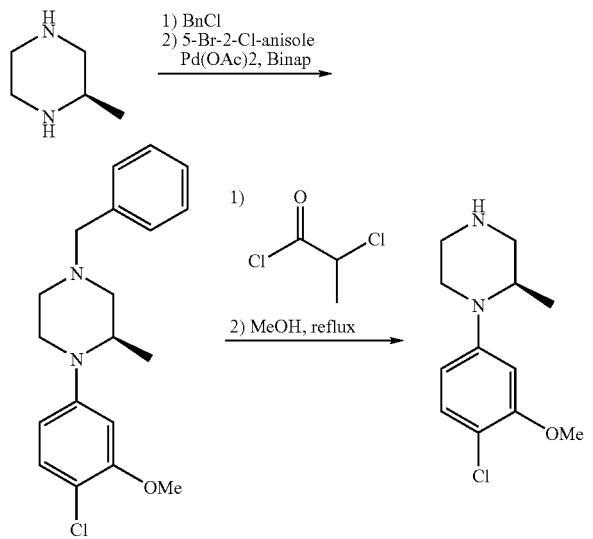

2 g (0.02 mol) of R-(−)-2-methylpiperazine, 2.5 g (0.0197 mol) of benzylchloride, and 5 g (0.0599 mol) of sodium bicarbonate in 25 mL of ethanol were heated to 85° C. for 12 hours. After cooling, the reaction was filtered through paper, and the ethanol was removed under vacuum. The residue was purified by chromatography to give 1-Benzyl-3-(R)-methyl-piperazine as a yellow liquid.

1.2 g (0.0054 mol) of 5-bromo-2-chloroanisole, 1 g (0.0054 mol) of 1-Benzyl-3-(R)-methyl-piperazine, 0.06 g (0.00027 mol) of palladium acetate, 0.34 g (0.00054 mol) of BINAP, and 0.83 g (0.0086 mol) of sodium tert-butoxide in dry toluene (5 mL) were heated at 110° C. for 48 hours. After cooling, the reaction mixture was quenched with water and extracted with ethyl acetate. The ethyl acetate phase was washed with water, brine, dried with Na$_2$SO$_4$, filtered, and concentrated. The residue was purified by chromatography to give 4-Benzyl-1-(4-chloro-3-methoxy-phenyl)-2-(R)-methyl-piperazine as a yellow semi solid.

0.3 g (0.00091 mol, 1 eq) of 4-Benzyl-1-(4-chloro-3-methoxy-phenyl)-2-(R)-methyl-piperazine in 20 mL of dry 1,2-Dichloroethane was cooled to 0° C., 0.16 g (0.0011 mol) of 1-chloroethylchloroformate was added drop wise, and the resulting mixture was stirred at 0° C. for 15 min. The mixture was then heated at 70° C. for 1 hr, followed by removal of the 1,2-Dichloroethane under vacuum. The residue was dissolved in 30 mL of methanol, and heated at 65° C. for 1 hr. The methanol was removed under vacuum, the residue was dissolved in 10 mL of water, and this was washed with ether twice. The aqueous phase was basified to pH>9 using solid sodium bicarbonate, and was extracted with dichloromethane. The dichloromethane phase was washed with brine, dried with Na$_2$SO$_4$, filtered, and concentrated to give 1-(4-chloro-3-methoxy-phenyl)-2-(R)-methyl-piperazine as a low melting solid.

1-(4-chloro-3-methoxy-phenyl)-2-(S)-methyl-piperazine

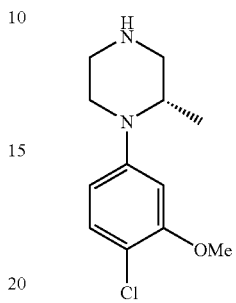

This compound was prepared following the same procedure as that used to synthesize 1-(4-chloro-3-methoxy-phenyl)-2-(R)-methyl-piperazine, using 2-(S)-(+)-Methyl-piperazine as the starting material, to give the title compound as a pale yellow semi solid.

Synthesis of 2-(R)-Benzyloxymethyl-1-(4-chloro-3-methoxy-phenyl)-piperazine

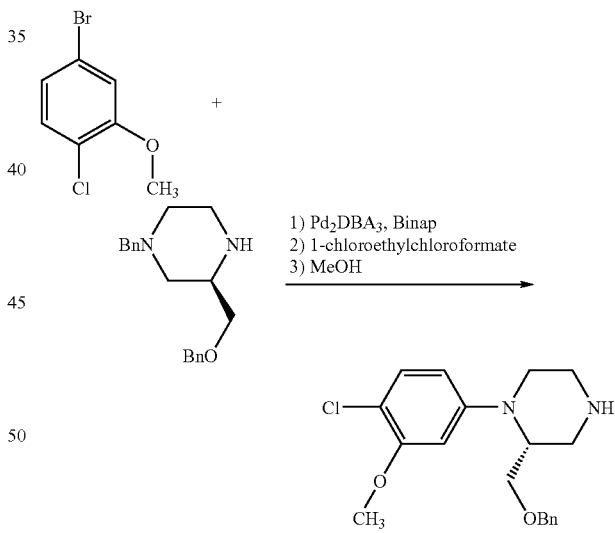

Following protocol A, 818 mg (3.70 mmol) of 5-Bromo-2-chloroanisole, 1.15 g (3.88 mmol) of 1-Benzyl-3-(R)-benzyloxymethyl-piperazine, 0.50 g (5.18 mmol) of sodium tert-butoxide, 33 mg (0.037 mmol) of tris-dibenzylideneacetone-dipalladium(0), and 66 mg (0.11 mmol) of rac-Binap in 2 mL of dry toluene were heated at 85° C. for 6 hours. The mixture was cooled to ambient temperature, and was partitioned between ethyl acetate and water. The phases were separated, and the ethyl acetate phase was washed with brine, dried over Na$_2$SO$_4$, filtered, and concentrated. The residue was chromatographed to give 4-Benzyl-2-(R)-benzyloxymethyl-1-(4-chloro-3-methoxy-phenyl)-piperazine.

1.05 g (2.40 mmol) of 4-Benzyl-2-(R)-benzyloxymethyl-1-(4-chloro-3-methoxy-phenyl)-piperazine in 50 mL of dichloromethane was cooled to 0° C., and 406 mg (2.88 mmol) of 1-Chloroethyl chloroformate was added. The mixture was allowed to warm to ambient temperature after 30 minutes, then was heated at 75° C. in a sealed vessel for 3 hours. The solution was then concentrated in vacuo, the residue was dissolved in 30 mL of methanol, and the solution was heated at 60° C. for 2 hours. The solution was concentrated in vacuo, and the residue was partitioned between ethyl acetate and 1M NaOH. The phases were separated, and the ethyl acetate phase was washed with brine, dried over $Na_2SO_4$, filtered, and concentrated to give 2-(R)-Benzyloxymethyl-1-(4-chloro-3-methoxy-phenyl)-piperazine.

Synthesis of [4-(4-Chloro-3-methoxy-phenyl)-piperazin-2-(S)-yl]-methanol

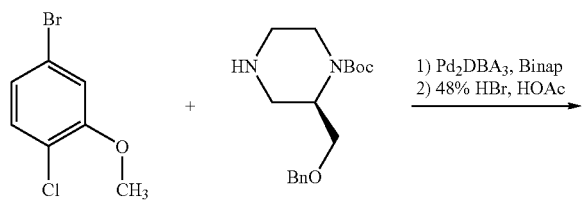

Following protocol A, 1.41 g (6.34 mmol) of 5-Bromo-2-chloroanisole, 2.04 g (6.66 mmol) of $N^1$-Boc-2-(R)-Benzyloxymethyl-piperazine, 0.85 g (8.86 mmol) of sodium tert-butoxide, 28 mg (0.032 mmol) of tris-dibenzylideneacetone-dipalladium(0), and 58 mg (0.095 mmol) of rac-Binap in 3 mL of dry toluene were heated at 90° C. for 6 hours. The mixture was cooled to ambient temperature, and was partitioned between ethyl acetate and water. The phases were separated, and the ethyl acetate phase was washed with brine, dried over $Na_2SO_4$, filtered, and concentrated. The residue was chromatographed to give a white foam.

The purified material from above was heated in 25 mL of 48% HBr in acetic acid at 75° C. for 1 hour. The reaction was allowed to cool to room temperature, and was partitioned between ether and water. The phases were separated, the aqueous phase was basified to pH>10 with solid K2CO3, and was extracted twice with ethyl acetate. The combined ethyl acetate phases were washed with brine, dried over $Na_2SO_4$, filtered, and was concentrated to give [4-(4-Chloro-3-methoxy-phenyl)-piperazin-2-(S)-yl]-methanol as a tan solid.

Synthesis of 1-(4-Chloro-2-fluoro-5-methoxy-phenyl)-piperazine

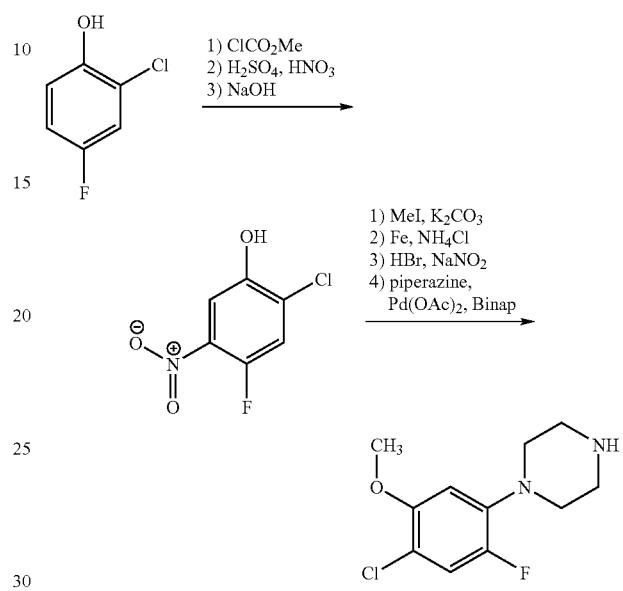

5.0 g (34.1 mmol) of 2-chloro-4-fluorophenol in 75 mL of 10% sodium hydroxide was cooled to 0° C., and 4.0 g (42.6 mmol) of methylchloroformate was added. After 45 minutes, the solids were isolated by filtration to give 2-chloro-4-fluoro-phenyl-methyl carbonate.

To 6.0 g (29.3 mmol) of 2-chloro-4-fluoro-phenyl-methyl carbonate in 3 mL of concentrated sulfuric acid at 0° C. was added 6 mL of nitrating mixture. After 45 minutes, the reaction was quenched with ice-water, and the solids were isolated by filtration to give 2-chloro-4-fluoro-5-nitrophenyl methyl carbonate.

To 7.0 g (28.0 mmol) of 2-chloro-4-fluoro-5-nitrophenyl methyl carbonate in 100 mL of methanol at 0° C. was added 75 mL of 0.5M NaOH. After 1 hour, the methanol was removed in vacuo, the solution was acidified with 1.5M HCl, and was extracted with ethyl acetate. The ethyl acetate phase was washed with water and brine, and concentrated to give 2-chloro-4-fluoro-5-nitrophenol.

To 5.6 g (29.2 mmol) of 2-chloro-4-fluoro-5-nitrophenol in 250 mL of dry acetone were added 21 g (146 mmol) of methyl iodide and 20 g (146 mmol) of potassium carbonate, and the mixture was heated at 55° C. for three hours. The acetone was removed in vacuo, and the residue was partitioned between ethyl acetate and water. The phases were separated, and the ethyl acetate phase was washed with brine, and concentrated to give 2-chloro-4-fluoro-5-nitro-anisole.

To 4.5 g (22.2 mmol) of 2-chloro-4-fluoro-5-nitro-anisole in 75 mL of methanol was added 6 g (11 mmol) of iron powder, the mixture was heated to 50° C., and 10 g (175 mmol) of ammonium chloride in 150 mL of water was added. The reaction was warmed further to 70° C., and was stirred for 12 hours. The mixture was cooled to ambient temperature, filtered through celite, and the filtrate was concentrated in vacuo. The residue was partitioned between ethyl acetate and water, and the phases were separated. The ethyl acetate phase was washed with brine, and was concentrated to give 4-Chloro-2-fluoro-5-methoxy-aniline.

3.0 g (17.1 mmol) of 4-Chloro-2-fluoro-5-methoxy-aniline in 23 mL of hydrobromic acid and 23 mL of water, and the solution was cooled to 0° C. To this was added 1.5 g (21.4 mmol) of sodium nitrite in 2 mL of water. 9 g (36 mmol) of copper bromide was added in 30 mL of 50% hydrobromic acid. After the addition, the mixture was heated to 55° C. for one hour. The mixture was cooled, and was extracted with ethyl acetate. The ethyl acetate phase was washed once each with water and brine, and was concentrated to give 5-Bromo-2-chloro-4-fluoroanisole.

1.0 g (4.2 mmol) of 5-Bromo-2-chloro-4-fluoroanisole, 47 mg (0.21 mmol) of palladium acetate, 180 mg (0.29 mmol) of binap, 0.65 g (6.7 mmol) of sodium tert-butoxide, and 3.6 g (42 mmol) of piperazine in 3 mL of dry toluene were heated at 110° C. for 24 hours. The reaction was partitioned between ethyl acetate and water, and the phases were separated. The ethyl acetate phase was washed once each with water and brine, and was concentrated. The residue was purified by chromatography to give 1-(4-Chloro-2-fluoro-5-methoxy-phenyl)-piperazine.

Synthesis of 1-(4-Chloro-3-methoxy-phenyl)-3-methoxymethyl-piperazine

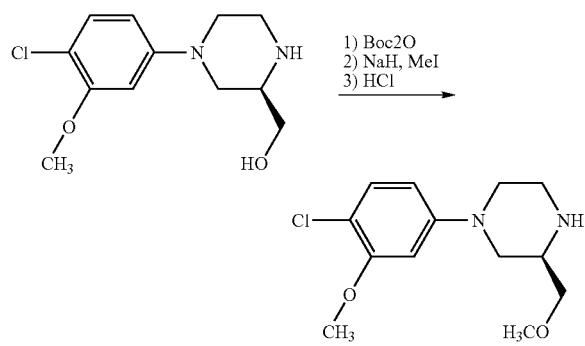

To 1.26 g (4.90 mmol) of [4-(4-Chloro-3-methoxy-phenyl)-piperazin-2-(S)-yl]-methanol and 779 mg (6.37 mmol) of 2,4,6-collidine in 15 mL of dry N,N-dimethylformamide at 0° C. was added 1.18 g (5.40 mmol) of Di-tert-butyldicarbonate. The reaction was allowed to warm to ambient temperature after two hours, and was stirred for 14 additional hours. The reaction was partitioned between water and ethyl acetate, and the phases were separated. The ethyl acetate phase was washed once each with 1M NaHSO4, water, brine, dried over Na₂SO₄, filtered, and concentrated to give 4-(4-Chloro-3-methoxy-phenyl)-2-(R)-hydroxymethyl-piperazine-1-carboxylic acid tert-butyl ester as an oil that solidified on standing.

To 122 mg (0.34 mmol) of 4-(4-Chloro-3-methoxy-phenyl)-2-(R)-hydroxymethyl-piperazine-1-carboxylic acid tert-butyl ester and 57 mg (0.41 mmol) of methyl iodide in dry N,N-dimethylformamide at 0° C. was added 20 mg (0.48 mmol) of 60% sodium hydride in oil. The reaction was allowed to warm to ambient temperature in ten minutes, and the reaction was quenched with water after one hour. The mixture was extracted with ethyl acetate, and the phases were separated. The ethyl acetate phase was washed with brine, dried over Na₂SO₄, filtered, and concentrated to give 4-(4-Chloro-3-methoxy-phenyl)-2-methoxymethyl-piperazine-1-carboxylic acid tert-butyl ester as an oil.

The oil from above was dissolved in 1 mL of ethyl acetate and 1 mL of 5M HCl in isopropanol. After 10 hours, the solution was concentrated, and the residue was partitioned between 1M NaOH and ethyl acetate. The phases were separated, and the ethyl acetate phase was washed with brine, dried over Na₂SO₄, filtered, and concentrated to give 1-(4-Chloro-3-methoxy-phenyl)-3-methoxymethyl-piperazine.

Synthesis of 4-(4-Chloro-3-methoxy-phenyl)-piperazine-2-carboxylic acid (−)-menthol ester

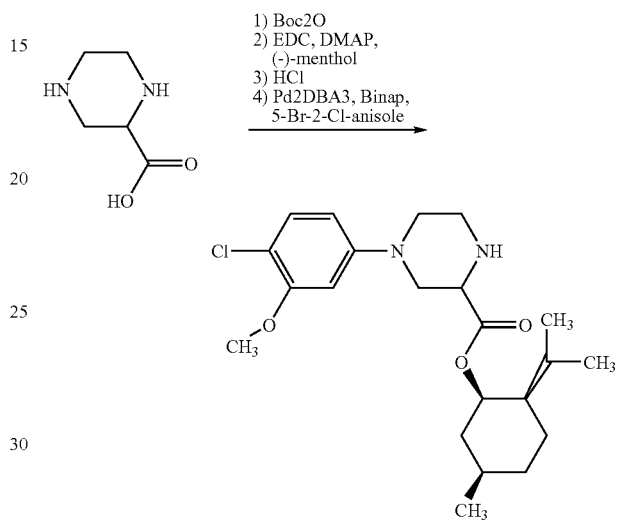

8.75 g (43.4 mmol) of 2-piperazine carboxylic acid and 16.4 g (195 mmol) of sodium hydrogencarbonate were dissolved in 140 mL of water, 140 mL of acetonitrile was added, and the mixture was cooled to 0° C. To this was added 20.9 g (95.4 mmol) of Di-tert-butyldicarbonate, and the mixture was allowed to warm to ambient temperature after 2 hours. After stirring for twelve hours, the mixture was concentrated in vacuo to remove the acetonitrile, and the mixture was washed with ether. The aqueous solution was acidified with 1M NaHSO4, and was extracted with ethyl acetate. The ethyl acetate phase was washed with brine, dried over Na₂SO₄, filtered, and concentrated to give Piperazine-1,2,4-tricarboxylic acid 1,4-di-tert-butyl ester.

A solution of 13 g (39 mmol) of piperazine-1,2,4-tricarboxylic acid 1,4-di-tert-butyl ester, 13.4 g (86 mmol) of (−)-menthol, and 940 mg (7.8 mmol) of 4-N,N-Dimethylaminopyridine in 200 mL of dichloromethane was cooled to 0° C., and 8.90 g (47 mmol) of 1-[3-(Dimethylamino)propyl]-3-ethylcarbodiimide hydrochloride was added. The solution was allowed to warm to ambient temperature after two hours, and was stirred for an additional 12 hours. The reaction was concentrated in vacuo, and the residue was partitioned between ether and water, and the phases were separated. The organic phase was washed once each with 1M NaHSO4 and brine, dried over Na₂SO₄, filtered, and concentrated to give a semi-solid.

The semi-solid from above was dissolved in 300 mL of ethyl acetate, 100 mL of dichloromethane, and 100 mL of 5M HCl in isopropanol. After 20 hours, the solids were isolated by filtration to give piperazine-2-carboxylic acid 2-(−)-menthol ester dihydrochloride.

1.36 g (4.0 mmol) of piperazine-2-carboxylic acid 2-(−)-menthol ester dihydrochloride, 803 mg (3.63 mmol) of 5-Bromo-2-chloroanisole, 1.09 g (11.4 mmol) of sodium tert-butoxide, 62 mg (0.10 mmol) of rac-Binap, and 30 mg (0.034 mmol) of Tris-dibenzylideneacetone dipalladium (0) were slurried in 5 mL of toluene, and the mixture was heated at 80° C. for 12 hours. The reaction was partitioned between ethyl acetate and water, and the phases were separated. The ethyl acetate phase was washed once each with water, brine, dried over Na₂SO₄, filtered, and concentrated. The residue was chromatographed to give 4-(4-Chloro-3-methoxy-phenyl)-piperazine-2-carboxylic acid (–)-menthol ester.

Synthesis of 1-(4-Chloro-3-methoxy-phenyl)-3-(S)-(2-methanesulfonyl-ethyl)-piperazine

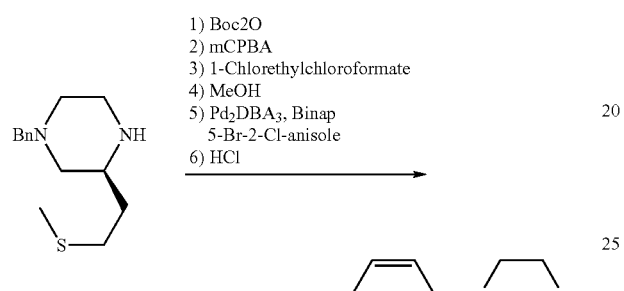

1.00 g (3.99 mmol) of 1-Benzyl-3-(S)-(2-methylsulfanyl-ethyl)-piperazine, and 81 mg (0.8 mmol) of triethylamine in 5 mL of dichloromethane were cooled to 0° C., and 1.05 g (4.79 mmol) of Di-tert-butyldicarbonate was added. After stirring for two hours, the solution was allowed to warm to ambient temperature, and was stirred for an additional 12 hours. The reaction was partitioned between ether and water, and the phases were separated. The organic phase was washed with brine, dried over Na₂SO₄, filtered, and concentrated to give 1-Benzyl-3-(S)-(2-methylsulfanyl-ethyl)-4-tert-butoxycarbonylpiperazine as an oil.

608 mg (1.74 mmol) of 1-Benzyl-3-(S)-(2-methylsulfanyl-ethyl)-4-tert-butoxycarbonylpiperazine was dissolved in 8 mL of dichloromethane, and the solution was cooled to 0° C. To this was added 899 mg (5.21 mmol) of meta-Chloroperbenzoic acid, and the mixture was allowed to warm to ambient temperature over one hour. The reaction was partitioned between ethyl acetate and water, and the phases were separated. The organic phase was washed with 1M NaOH, brine, dried over Na₂SO₄, filtered, and concentrated to give 1-Benzyl-3-(S)-(2-methylsulfonyl-ethyl)-4-tert-butoxycarbonylpiperazine as an oil.

180 mg (0.47 mmol) of 1-Benzyl-3-(S)-(2-methylsulfonyl-ethyl)-4-tert-butoxycarbonylpiperazine in 2.5 mL of methanol was purged with nitrogen, 20 mg of 20% Pd(OH)2 on carbon was added, and the mixture was stirred under a hydrogen atmosphere for 30 hours. The mixture was flushed with nitrogen, filtered through celite, and concentrated to give 3-(S)-(2-methylsulfonyl-ethyl)-4-tert-butoxycarbonylpiperazine as an oil.

96 mg (0.33 mmol) of 3-(S)-(2-methylsulfonyl-ethyl)-4-tert-butoxycarbonylpiperazine, 73 mg (0.33 mmol) of 5-Bromo-2-chloroanisole, 6 mg (0.01 mmol) of rac-Binap, 3 mg (0.003 mmol) of Tris-benzylidineacetone dipalladium (0), and 44 mg (0.46 mmol) of sodium tert-butoxide were slurried in 0.6 mL of toluene, and the mixture was heated at 85° C. for 8 hours. The reaction was partitioned between ethyl acetate and water, and the phases were separated. The ethyl acetate phase was washed once each with water, brine, dried over Na₂SO₄, filtered, and concentrated. The residue was chromatographed to give 4-(4-Chloro-3-methoxy-phenyl)-2-(S)-(2-methanesulfonyl-ethyl)-piperazine-1-carboxylic acid tert-butyl ester.

30 mg (0.07 mmol) of 4-(4-Chloro-3-methoxy-phenyl)-2-(S)-(2-methanesulfonyl-ethyl)-piperazine-1-carboxylic acid tert-butyl ester was dissolved in 1 mL of ethyl acetate, and 0.5 mL of 5M HCl in isopropanol was added. After 20 hours, the solids were isolated by filtration to give 1-(4-Chloro-3-methoxy-phenyl)-3-(S)-(2-methanesulfonyl-ethyl)-piperazine as the hydrochloride salt.

Synthesis of 1-(4-Chloro-3-methylsulfanyl-phenyl)-piperazine

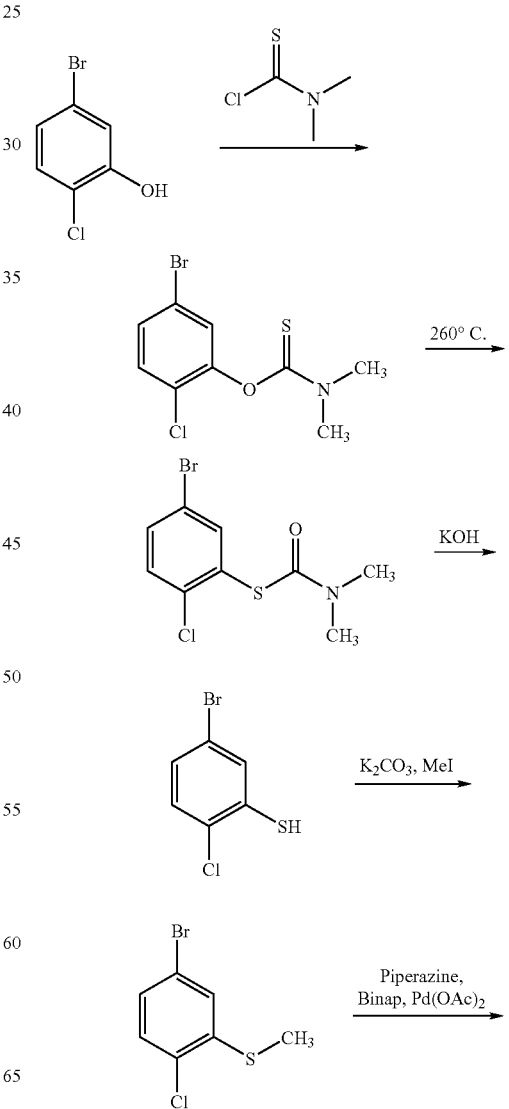

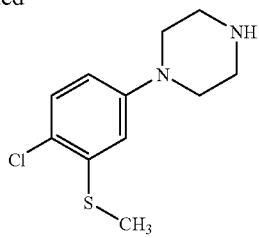

To 5-Bromo-2-chlorophenol (1.7 g, 0.0087 mol) in 9 mL of water was added potassium carbonate (0.5 g, 0.0087 mol), and the mixture was stirred for 15 min, then cooled to 10° C. N,N-dimethylthiocarbamylchloride (1.4 g, 0.0117 mol) in 3 mL of THF was added, the reaction was allowed to warm to ambient temperature, and was stirred for 2 hours. The mixture was extracted with ethyl acetate, washed once each with water and brine, and concentrated to give O-(5-bromo-2-chlorophenyl) dimethylthiocarbamate as a yellow solid.

O-(5-bromo-2-chlorophenyl) dimethylthiocarbamate (1.8 g, 0.0061 mol) in 60 mL of diphenyl ether was heated to 260° C. over sand bath for 15 hours. The reaction was allowed to cool to ambient temperature, and was directly loaded onto a bed of silica. The column was eluted with petroleum ether to give S-(5-bromo-2-chlorophenyl)dimethylthiocarbamate as a solid.

To S-(5-bromo-2-chlorophenyl)dimethylthiocarbamate (0.5 g, 0.0022 mol) in 10 mL of ethylene glycol was added potassium hydroxide (0.19 g, 0.0033 mol) dissolved in 3 mL of water. The reaction was heated to 150° C. for 4 hours. The reaction was cooled to ambient temperature, was quenched with water, and was extracted with ethyl acetate. The ethyl acetate phase was washed once each with water and brine, and was concentrated to give 5-Bromo-2-chlorobenzenethiol as an off-white solid.

5-Bromo-2-chlorobenzenethiol (0.34 g, 0.0015 mol), methyl iodide (1.1 g, 0.5 mL, 0.0075 mol), and dry potassium carbonate (0.64 g, 0.0045 mol) in 15 mL of dry acetone were heated to 50° C. for 9 hours. The solvent was removed in vacuo, and the residue was dissolved in ethyl acetate, washed once each with water and brine, and concentrated to give 5-Bromo-2-chlorothioanisole as a yellow liquid.

5-Bromo-2-chlorothioanisole (0.3 g, 0.0012 mol), piperazine (1.0 g, 0.012 mol), palladium acetate (0.015 g, 0.00006 mol), BINAP (0.075 g, 0.00012 mol), and sodium tert-butoxide (0.17 g, 0.0018 mol) in 5 mL of dry toluene were heated to 110° C. under an argon atmosphere for 18 hours. The reaction mixture was cooled to ambient temperature, quenched with water, and extracted with ethyl acetate. The ethyl acetate phase was washed once each with water and brine, and was concentrated to a residue. The residue was purified by column chromatography, using 2% methanol in chloroform, to give the 1-(4-Chloro-3-methylsulfanyl-phenyl)-piperazine as a low melting solid.

5-Chloro-4-methoxy-2-piperazin-1-yl-phenylamine

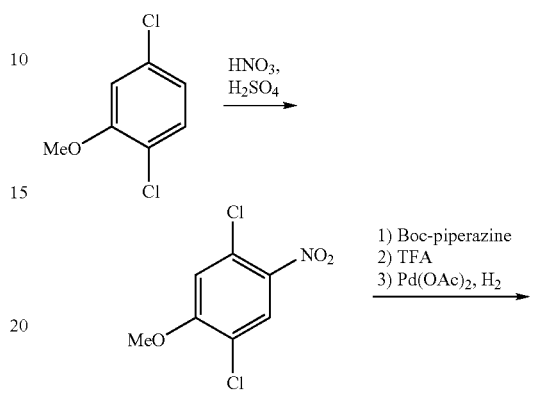

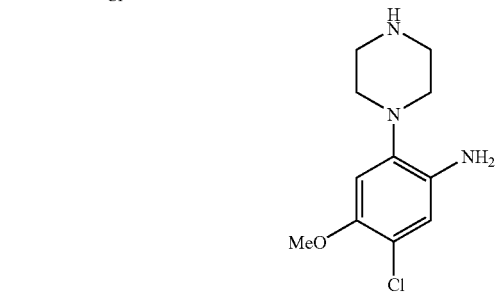

17.5 g (0.09943 mol) of 2,5-dichloroanisole was dissolved in 4 mL of conc. sulfuric acid, the solution was cooled to 0° C., and 18 mL of nitrating mixture (prepared by adding 9 mL of conc. sulfuric acid to 9 mL of nitric acid at 0° C.) was added. The reaction was allowed to warm to ambient temperature, and was stirred for 2 hours. The solids were isolated by filtration, and were washed with pet ether to give 2,5-Dichloro-4-nitroanisole.

5 g (0.0225 mol) of 2,5-Dichloro-4-nitroanisole, 8.3 g (0.0450 mol) of mono-boc piperazine, 7.7 g (0.056 mol) of dry potassium carbonate, and 0.2 g of TBAI in 100 mL of dry DMSO was heated at 120° C. for 10 hours. After cooling, the reaction mixture was quenched with water, and extracted with ethyl acetate. The ethyl acetate phase was washed with water and brine, and concentrated. The residue was purified by chromatography to give 4-(4-Chloro-5-methoxy-2-nitrophenyl)-piperazine-1-carboxylic acid tert-butyl ester.

5.3 g (0.0142 mol) of 4-(4-Chloro-5-methoxy-2-nitrophenyl)-piperazine-1-carboxylic acid tert-butyl ester and 5.4 mL (0.07 mol) of trifluoroacetic acid in 100 mL of dichloromethane were stirred over night. The reaction mixture was basified using 1M NaOH, and was extracted with dichloromethane. The dichloromethane phase was washed with water and brine, dried over $Na_2SO_4$ and concentrated to give 4-(4-Chloro-5-methoxy-2-nitro-phenyl)-piperazine.

To 3.5 g (0.012 mol) of 4-(4-Chloro-5-methoxy-2-nitrophenyl)-piperazine in 25 mL of methanol was added 0.4 g of 10% palladium acetate, and the mixture was stirred under 1 Atm. hydrogen for 15 minutes. The reaction mixture was filtered through Celite, and concentrated. The residue was purified by column chromatography to give 5-Chloro-4-methoxy-2-piperazin-1-yl-phenylamine.

Synthesis of 1-(4-oxazol-5-yl-phenyl)-piperazine

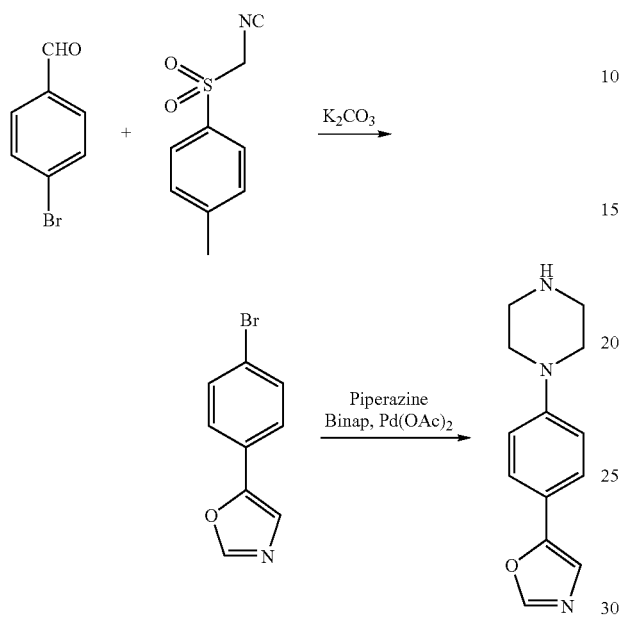

To 4-Bromobenzaldehyde (1.0 g, 0.0054 mol) in 20 mL of dry methanol was added the TOSMIC reagent (1.2 g, 0.0059 mol), followed by dry potassium carbonate (0.8 g, 0.0058 mol). The reaction mixture was heated to 65° C. for 2 hours. The reaction mixture was dissolved in ethyl acetate, washed once each with water and brine, and concentrated. The residue was purified by column chromatography, using 10% ethyl acetate in pet ether, to give 4-Bromo-oxazol-5-yl-benzene.

4-Bromo-oxazol-5-yl-benzene (0.5 g, 0.0023 mol), piperazine (1.9 g, 0.022 mol), palladium acetate (0.026 g, 0.00011 mol), BINAP (0.14 g, 0.00023 mol) and sodium tert-butoxide (0.35 g, 0.0037 mol) in 5 mL of dry toluene were heated to 110° C. under an argon atmosphere for 18 hours. The reaction mixture was cooled to ambient temperature, quenched with water, and was extracted with ethyl acetate. The ethyl acetate phase was washed once each with water and brine, and concentrated. The residue was purified by column chromatography, using 2% of methanol in chloroform, to give 1-(4-oxazol-5-yl-phenyl)-piperazine as a yellow solid.

Protocol G1: General Procedure for the Synthesis of Elaborated Aryl Bromides from Anilines Synthesis of 4-Chloro-2-fluoro-1-bromobenzene

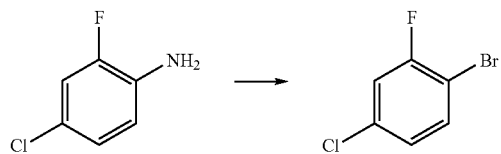

Sodium nitrite (2.35 g, 34.13 mmol) solution (40 mL) was added dropwise to 4-Chloro-2-fluoro aniline (4.5 g, 31 mmol) in 170 mL HBr at −10° C. bath temperature, then the mixture was stirred for 30 min at −10° C. bath temperature. In parallel, copper sulfate (10.22 g, 24.29 mmol) and sodium bromide (3.79 g, 36.8 mmol) were mixed and the reaction mixture was heated at 60° C. for 30 min. Then sodium sulfite (2.66 g, 21.2 mmol) was added into this copper sulfate reaction mixture and heated for 95° C. for 30 min. The reaction mixture was cooled to room temperature and solid formed was washed with water to afford white solid cuprous bromide. The diazonium salt was portion wise added into the freshly prepared cuprous bromide in 40 mL HBr at −10° C. bath temperature and the reaction mixture was then warmed to room temperature. The reaction mixture was heated at 55° C. for 20 min, cooled and then extracted with ethyl acetate three times. The combined organic layer was washed with water and saturated brine solution, dried over sodium sulfate and concentrated. The crude material was purified by column chromatography (5:95 ethyl acetate: pet ether) to afford solid product.

Synthesis of (2-Bromo-5-chloro-phenyl)-phenyl-methanone

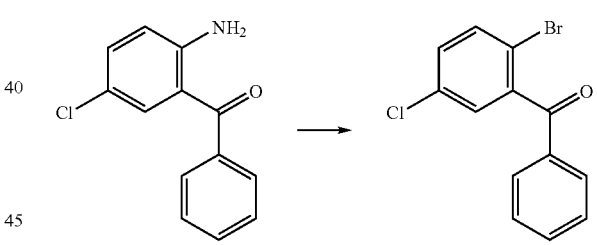

Sodium nitrite (2.5 g, 36.28 mmol) solution (40 mL) was dropwise added to the aniline (7 g, 30.2 mmol) in 100 mL HBr at −10° C. bath temperature, then the mixture was stirred for 30 min at −10° C. bath temperature to make diazonium salt.

Copper sulfate (10.22 g, 24.29 mmol) and sodium bromide (3.79 g, 36.8 mmol) was heated at 60° C. for 30 min. Then sodium sulfite (2.66 g, 21.2 mmol) was added into copper sulfate reaction mixture and heated for 95° C. for 30 min. Then the reaction mixture was cooled to rt and solid formed was washed with water to afford white solid cuprous bromide.

Diazonium salt was portion wise added into the freshly prepared cuprous bromide in 40 mL HBr at −10° C. bath temperature and the reaction mixture warmed to room temperature. Then the reaction mixture was heated at 55° C. for 20 min, cooled to room temperature and extracted with ethyl acetate three times. The combined organic layer was washed with water and saturated brine solution, dried over sodium sulfate and concentrated. The product was purified by crystallization from DCM/Pet ether.

Protocol G2: Additional Examples of Analogous Ring Systems Constructed Using Similar Sandmeyer Type Strategies

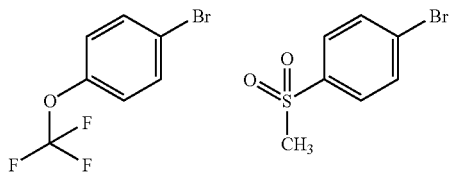

These preceding aryl bromides and similar substrates were used in a variety of chemistries, already described, to access arylpiperazines such as those listed below.

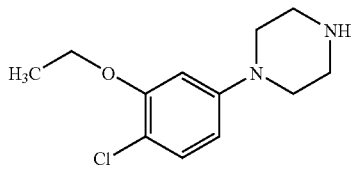

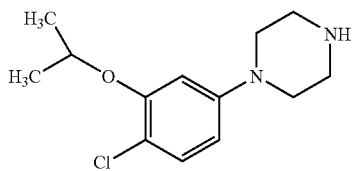

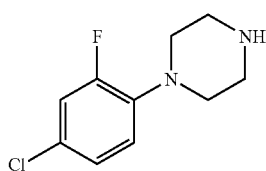

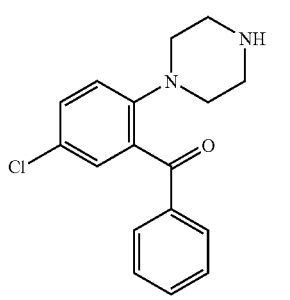

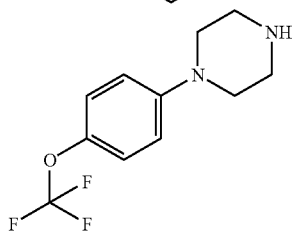

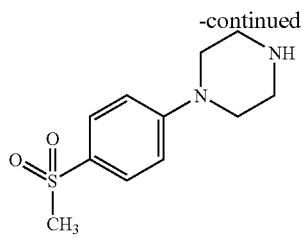

Synthesis of Heteroaromatic Ring Systems: Core Ring Structure Formation

The types of chemistries which can be applied to synthesize the key heteroaryl ring structures are listed below. They are separated into examples of ring formation and ring functionalization reactions.

Protocol H: Pyrazole Synthesis Via Addition of Hydrazines to Cal-Acetylenic Ketones Synthesis of 5-Butyl-3-trifluoromethyl-1H-pyrazole

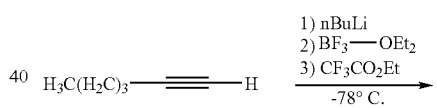

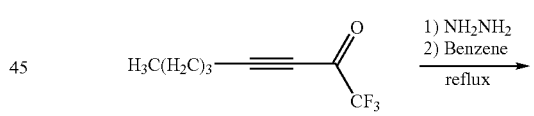

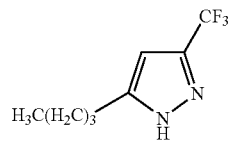

To a solution of 1-Hexyne (3.37 mL, 29.4 mmol) in THF (30 mL) was added n-BuLi (2.78 M, 10.2 mL, 29.4 mmol). The solution was stirred at −78° C. for 30 minutes then CF$_3$CO$_2$Et (3.5 mL, 29.35 mL) and BF$_3$-OEt$_2$ were added successively. The reaction was further stirred at −78° C. for 2 h and was quenched with satd. NH$_4$Cl. It was then warmed up to the room temperature. The THF was removed, the residue taken into ether, washed with saturated brine solution, dried over Na$_2$SO$_4$ and reduced. The crude product was then dissolved in benzene (25 mL) and hydrazine (29.4 mmol) was added. The reaction mixture was refluxed overnight, then cooled, the solvent evaporated, and the residue taken into CH$_2$Cl$_2$ (30 mL), washed with brine, dried over Na$_2$SO$_4$ and concentrated to give the title compound as colorless oil.

Synthesis of 5-isopropyl-3-trifluoromethyl-1H-pyrazol

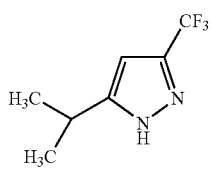

Following protocol H, 3-methylbutyne was treated with n-BuLi, CF$_3$CO$_2$Et and BF$_3$—OEt$_2$ in THF. Reaction with hydrazine in benzene under similar reaction conditions yielded title compound.

Synthesis of 5-propyl-3-trifluoromethyl-1H-pyrazole

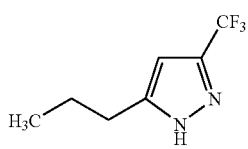

Following protocol H, 1-pentyne was treated with n-BuLi, CF$_3$CO$_2$Et and BF$_3$—OEt$_2$ in THF. Reaction with hydrazine in benzene under similar reaction conditions yielded title compound.

Synthesis of 5-(3-Fluorophenyl)-3-trifluoromethyl-1H-pyrazole

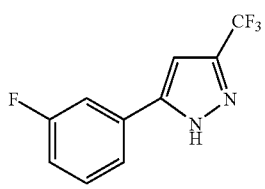

Following protocol H, 1-Ethynyl-3-fluoro-benzene was treated with n-BuLi, CF$_3$CO$_2$Et and BF$_3$—OEt$_2$ in THF. Reaction with hydrazine in benzene under similar reaction conditions yielded title compound.

Other Pyrazoles Synthesized Via this Method:

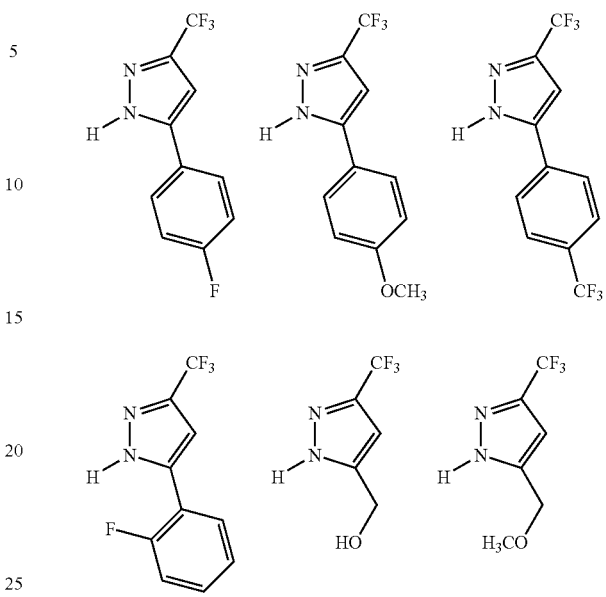

Protocol I: General Procedure for the Synthesis of Pyrazoles Via Condensation of Hydrazines with β-Diketones Synthesis of 5-ethyl-3-trifluoromethyl-1H-pyrazole

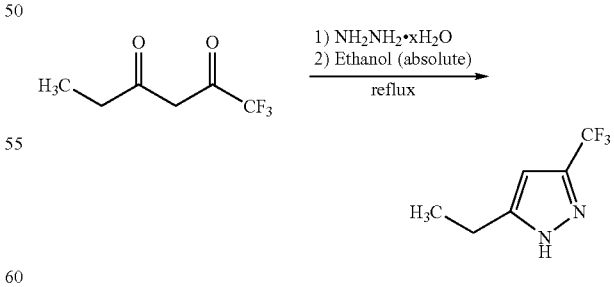

To a solution of 1,1,1-Trifluoro-hexane-2,4-dione (1 g, 5.95 mmol) in absolute ethanol (10 mL) was added NH$_2$NH$_2$.xH$_2$O drop-wise at 0° C. The reaction mixture warmed to the room temperature during 1 hour and refluxed overnight. Ethanol was then evaporated, residue dissolved in ethyl acetate (20 mL), washed consecutively with saturated brine solution and water, dried with Na$_2$SO$_4$ and concentrated to give the title compound as colorless oil.

Synthesis of
4-Chloro-3-methyl-5-thiophen-2-yl-pyrazole

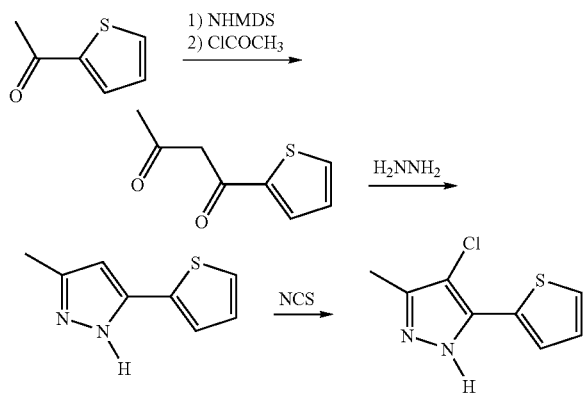

To a solution of 2-acetyl-thiophene (5 g, 0.04 mol) in 200 mL of THF at −78° C. was added 24.5 mL of a solution of NaHMDS (0.05 mol) in hexane. After the addition was complete, the reaction was kept at this temperature for 1 h. Acetyl chloride (3.4 g, 0.04 mol) was then added dropwise, and the reaction mixture was then allowed to warm to ambient temperature, and stirring was continued for 2 hours. The reaction was quenched with saturated NH$_4$Cl solution, and the THF was removed in vacuo. The aqueous mixture was extracted with ethyl acetate, and the phases were separated. The ethyl acetate layer was washed once each with water and brine, dried with Na$_2$SO$_4$, filtered, and concentrated. The residue was purified by column chromatography to give the diketone.

The diketone (1.6 g, 9.5 mmol) was dissolved in ethanol (60 mL) and cooled to 0° C. To this solution was added hydrazine hydrate (0.6 g, 11.4 mmol) dropwise with stirring. After the addition was complete, the mixture was refluxed overnight. The ethanol was evaporated in vacuo, and the residue was dissolved in ethyl acetate. The solution was washed once each with water and brine, and dried over Na$_2$SO$_4$, filtered, and concentrated to give 3-Methyl-5-thiophen-2-yl-pyrazole.

3-Methyl-5-thiophen-2-yl-pyrazole (1.4 g, 8.5 mmol) was dissolved in 50 mL of chloroform, and N-Chlorosuccinimide (1.6 g, 11.9 mmol) was added. The mixture was stirred overnight at ambient temperature. The solution was washed with brine, dried over Na$_2$SO$_4$, filtered, and concentrated in vacuo. The residue was purified by chromatography to give 4-Chloro-3-methyl-5-thiophen-2-yl-pyrazole.

Protocol J: Pyrazole Synthesis Via condensation of Hydrazines with β-Cyanoketones Synthesis of 5-Phenyl-1-pyrazol-3-amine

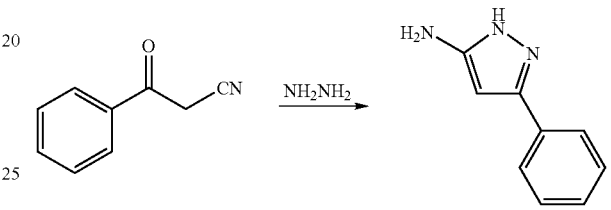

2.0 g (0.0138 mol, 1 eq) of benzoylacetonitrile in 40 mL of absolute ethanol was added 2.0 g (0.0399 mol, 3 eq) of anhydrous hydrazine and the reaction mixture stirred at 85° C. for 2 h. Ethanol was removed at 50° C. under vacuum. 5-Phenyl-1-pyrazol-3-amine, obtained as a yellow solid, was washed with pet ether (100 mL) and dried under vacuum.

Synthesis of Functionalized Heteroaryl Ring Systems

Chlorination or Bromination of Pyrazoles

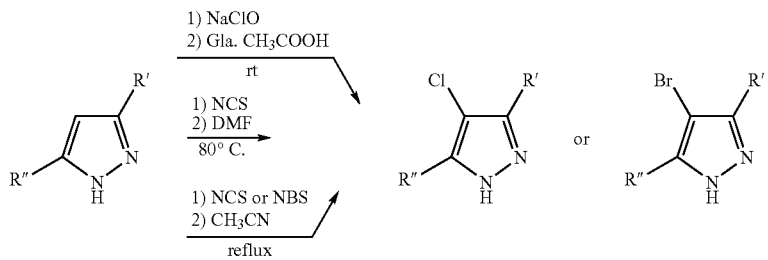

Protocol K: Chlorination of Pyrazoles with NaOCl in Glacial Acetic Acid

Synthesis of 4-Chloro-1H-pyrazole

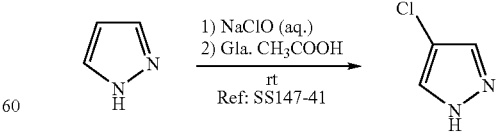

To a solution of pyrazole (0.5 g, 7.34 mmol) in glacial acetic acid (4 mL) was added NaOCl (0.55 g, 7.34 mmol). The reaction mixture was left at room temperature for 18 h, then neutralized with saturated Na$_2$CO$_3$ solution, extracted with CH$_2$Cl$_2$ (2×25 mL), the combined organic layers evaporated, then diluted with NaOH, and further extracted with CH$_2$Cl$_2$ Synthesis of 4-Chloro-3-trifluoromethyl-1H-pyrazole

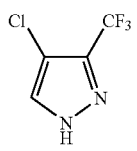

Following protocol K, 3-trifluoromethylpyrazole was treated with glacial acetic acid and NaOCl, yielding title compound.

Synthesis of 4-Chloro-3-methyl-1H-pyrazole

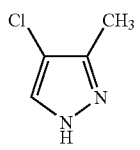

Following protocol K, 3-methylpyrazole was treated with glacial acetic acid and NaOCl, yielding title compound.

Synthesis of 4-Chloro-5-propyl-1H-pyrazole-3-carboxylic acid ethyl ester.

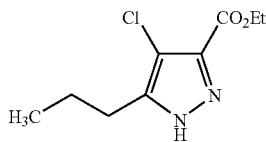

Following protocol K, 5-propyl-1H-pyrazole-3-carboxylic acid ethyl ester was treated with glacial acetic acid and NaOCl under similar reaction conditions, yielding the title compound.

Protocol L: Chlorination or Bromination of Pyrazoles with N-Chlorosuccinimide (NCS) or N-Bromosuccinimide (NBS)

Synthesis of 4-Chloro-3-methyl-5-trifluoromethyl-1H-pyrazole

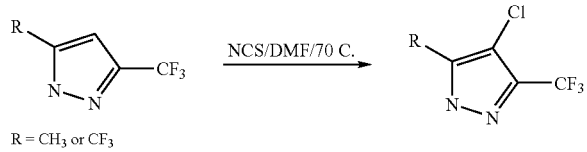

R = CH₃ or CF₃

3-methyl-5-trifluoromethylpyrazole or 3,5-bistrifluoromethylpyrazole was taken into dry DMF (20 mL) and N-chloro succinimide (1.78 g) was added in portions. The mixture was then heated at 70° C. for 22 h, cooled to room temperature, and then water (100 mL) was added and the mixture extracted with ethyl acetate (4×25 mL). The organic layer was washed with water and brine and dried with Na₂SO₄. Evaporation of the solvent afforded the title compounds.

Other Halogenated Pyrazoles Prepared Using Protocol L

Synthesis of 4-Chloro-5-(4-fluoro-phenyl)-3-trifluoromethyl-1H-pyrazole

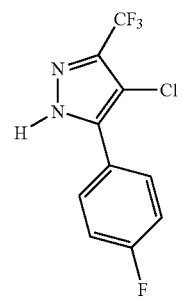

Following protocol L, 5-(4-Fluorophenyl)-3-trifluoromethyl-1-H-pyrazole was treated with NCS in acetonitrile to yield the title compound.

Synthesis of 4-Chloro-5-(4-methoxy-phenyl)-3-trifluoromethyl-1-H-pyrazole

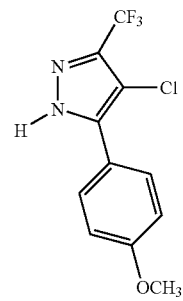

Following protocol L, 5-(4-methoxyphenyl)-3-trifluoromethyl-1-H-pyrazole was treated with NCS in acetonitrile to yield the title compound.

Synthesis of 4-Chloro-5-(4-trifluoromethyl-phenyl)-3-trifluoromethyl-1H-pyrazole

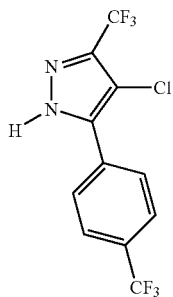

Following protocol L, 5-(4-trifluoromethyl-phenyl)-3-trifluoromethyl-1-H-pyrazole was treated with NCS in acetonitrile to yield the title compound.

Synthesis of 4-Chloro-5-(2-fluoro-phenyl)-3-trifluoromethyl-1H-pyrazole

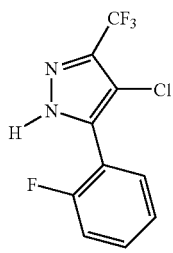

Following protocol L, 5-(2-fluoro-phenyl)-3-trifluoromethyl-1-H-pyrazole was treated with NCS in acetonitrile to yield the title compound.

Synthesis of (4-Chloro-5-trifluoromethyl-2H-pyrazol-3-yl)-methanol

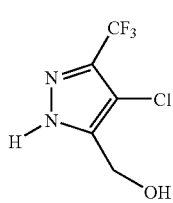

Following protocol L, (5-trifluoromethyl-2H-pyrazol-3-yl)-methanol was treated with NCS in acetonitrile to yield the title compound.

Synthesis of 4-Chloro-5-methoxymethyl-3-trifluoromethyl-1H-pyrazole

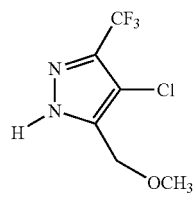

Following protocol L, 5-methoxymethyl-3-trifluoromethyl-1H-pyrazole was treated with NCS in acetonitrile to yield the title compound.

Synthesis of 4-Chloro-5-cyclopropyl-3-trifluoromethyl-1H-pyrazole

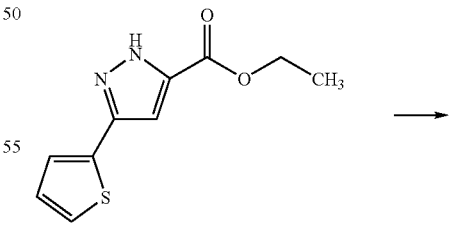

Following protocol L, 5-cyclopropyl-3-trifluoromethyl-1H-pyrazole was treated with NCS in acetonitrile to yield the title compound.

Syntheses of 4-Chloro-5-thiophen-2-yl-2H-pyrazole-3-carboxylic acid ethyl ester

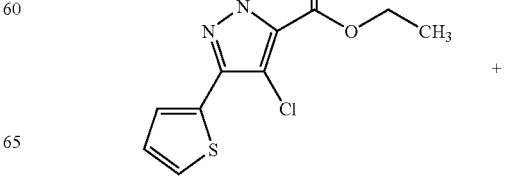

-continued

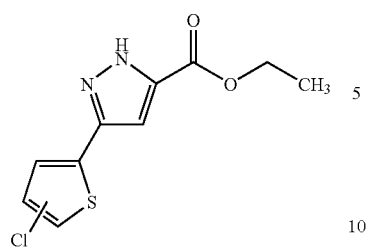

Pyrazole (1 eq) in DMF (0.14M Solution) was treated with NCS (1.5 eq.) in portions, and when all the NCS was dissolved in the reaction mixture, it was then heated at 70° C. overnight. The reaction mixture was then cooled to rt and quenched with water, extracted with ethyl acetate and dried in $MgSO_4$. Two products were isolated, including the title compound Synthesis of 4-Chloro-3,5-diisopropyl-pyrazole

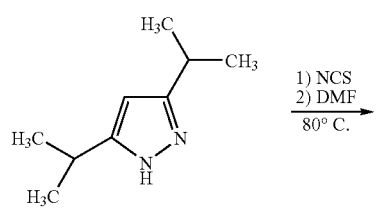

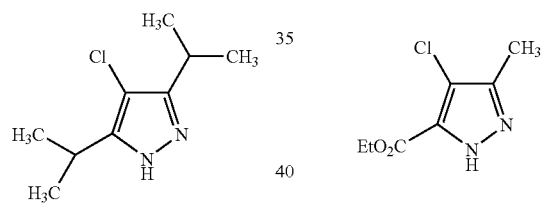

Following protocol L, a the solution of 3,5-diisopropyl-pyrazole (0.5 g, 3.57 mmol) in DMF (10 mL) was added NCS (0.72 g, 5.3 mmol) in portions under vigorous stirring. The reaction mixture was then heated at 80° C. for 14 h and then the reaction was quenched with water. It was then extracted with ethyl acetate (2×30 mL). The combined organics were washed with brine. The organic extracts were combined and dried with $Na_2SO_4$ and finally evaporated to give the title compound as colorless oil.

Synthesis of 4-Chloro-3-thiophen-2-yl-1H-pyrazole

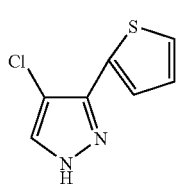

Following protocol L, 3-thiophen-2-yl-1H-pyrazole was treated with NCS in DMF., to yield title compound.

Synthesis of 5-tert-Butyl-4-chloro-3-trifluoromethyl-1H-pyrazole

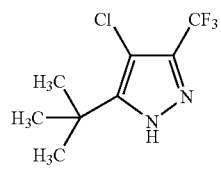

Following protocol L, 5-tert-butyl-3-trifluoromethyl-1H-pyrazole was treated with NCS in DMF to yield title compound.

Synthesis of 4-Chloro-3-methyl-1H-pyrazole-5-carboxylic acid ethyl ester

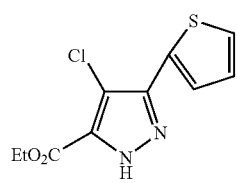

Following protocol L, 3-methyl-2H-pyrazole-5-carboxylic acid ethyl ester was treated with NCS in DMF to yield the title compound.

Synthesis of 4-Chloro-3-thiophen-2-yl-1H-pyrazole-5-carboxylic acid ethyl ester

Following protocol L, 3-Thiophen-2-yl-1H-pyrazole-5-carboxylic acid ethyl ester was treated with NCS in DMF to yield the title compound.

Synthesis of 4-Chloro-5-(5-chloro-thiophen-2-yl)-2H-pyrazole-3-carboxylic acid ethyl ester

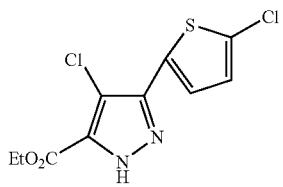

Following protocol L, 3-Thiophen-2-yl-1H-pyrazole-5-carboxylic acid ethyl ester was treated with NCS in DMF under to yield the title compound.

Synthesis of 4-Chloro-3-(4-fluoro-phenyl)-5-methyl-sulfanyl-1H-pyrazole

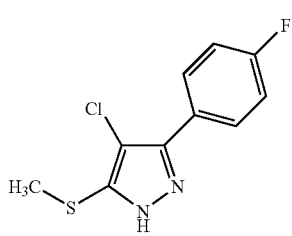

Following protocol L, 3-(4-fluoro-phenyl)-5-methylsulfanyl-1H-pyrazole was treated with NCS in to yield the title compound.

Synthesis of 5-Butyl-4-chloro-3-trifluoromethyl-1H-pyrazole

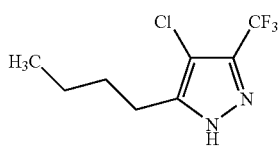

Following protocol L, 5-butyl-3-trifluoromethyl-1H-pyrazole was treated with NCS in DMF to yield the title compound.

Synthesis of 4-Chloro-5-phenyl-1-pyrazol-3-amine

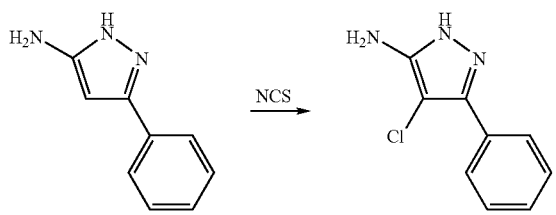

Following protocol L, to 0.5 g (0.0031 mol, 1 eq) of 5-phenyl-1-pyrazol-3-amine in 25 mL of dry acetonitrile was added 0.4 g (0.0031 mol, 1 eq) of N-chlorosuccinimide portion wise and the reaction mixture stirred at room temperature for 30 min. The reaction mixture was quenched with water and extracted with ethyl acetate. The organic layer was washed with water, brine and concentrated. The product was purified by 60-120 silica gel column (1% of methanol in chloroform).

Synthesis of 4-Bromo-5-phenyl-1-pyrazol-3-amine

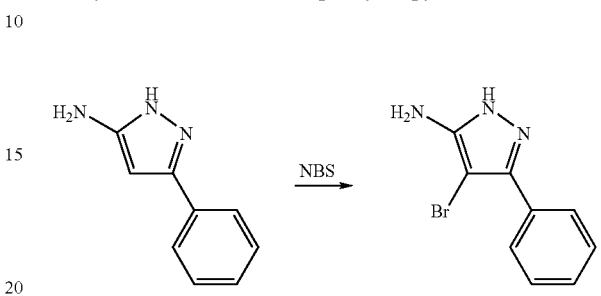

Following protocol L, to 0.5 g (0.0031 mol, 1 eq) of 5-phenyl-1-pyrazol-3-amine in 25 mL of dry acetonitrile was added 0.55 g (0.0031 mol, 1 eq) of N-bromosuccinimide portion wise and the reaction mixture stirred at room temperature for 30 min. The reaction mixture was quenched with water and extracted with ethyl acetate. The organic layer was washed with water, brine and concentrated. The product was purified by 60-120 silica gel column (1% of methanol in chloroform).

Synthesis of 4-Chloro-5-isopropyl-3-trifluoromethylpyrazole

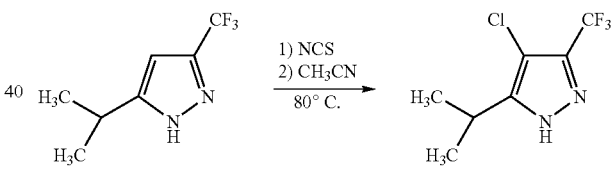

Following protocol L, to the solution of 3-trifluoromethyl-5-isopropyl-pyrazole (0.22 g, 1.23 mmol) in CH$_3$CN (10 mL) was added NCS (0.19 g, 1.43 mmol) in portions with vigorous stirring. The reaction mixture was then heated under reflux for 14 h, cooled and the reaction quenched with saturated NaHCO$_3$, extracted with methylene chloride (2×30 mL) and the combined organic extracts was washed with brine, dried with Na$_2$SO$_4$ and evaporated to give the title compound as a white solid.

Synthesis of 4-chloro-5-Ethyl-3-trifluoromethyl-1H-pyrazole

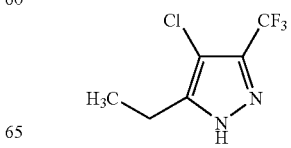

Following protocol L, 5-ethyl-3-trifluoromethyl-1H-pyrazole was treated with NCS in CH₃CN to yield title compound

Synthesis of 4-chloro-5-propyl-3-trifluoromethyl-1H-pyrazole

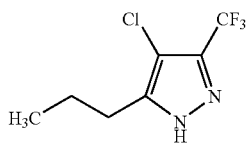

Following protocol L, 5-propyl-3-trifluoromethyl-1H-pyrazole was treated with NCS in CH₃CN to yield the title compound.

Synthesis of 4-chloro-5-(3-fluorophenyl)-3-trifluoromethyl-1H-pyrazole

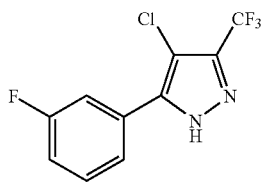

Following protocol L, 5-(3-fluorophenyl)-3-trifluoromethyl-1H-pyrazole was treated with NCS in CH₃CN to yield the title compound.

Synthesis of 4-chloro-3,5-bistrifluoromethyl-1H-pyrazole

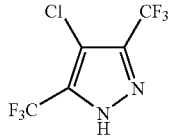

Following protocol L, 3,5-bistrifluoromethyl-1H-pyrazole was treated with NCS in CH₃CN to yield the title compound.

Synthesis of N-(4-Chloro-5-methyl-1H-pyrazol-3-yl)-2,2,2-trifluoro-acetamide

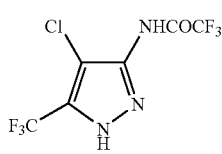

Following protocol L, 2,2,2-Trifluoro-N-(5-methyl-1H-pyrazol-3-yl)-acetamide was treated with NCS in CH₃CN to yield the title compound.

Protocol M: General Procedure for Reduction of Nitropyrazoles

Synthesis of 3-Heptafluoropropyl-5-methyl-1H-pyrazol-4-ylamine

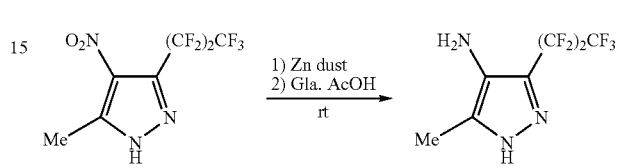

To a suspension of zinc dust (1.5 g) in glacial acetic acid (10 mL) was added drop-wise, a solution of 3-Heptafluoropropyl-5-methyl-4-nitro-1H-pyrazole (0.295 g, 1.0 mmol) in glacial acetic acid (5 mL). The reaction mixture was then allowed to stir at room temperature for 14 h. The zinc salts were then removed by filtration and the residue washed with ethyl acetate. The combined organic extract was concentrated in vaccum, re-dissolved in CHCl₃, washed with NaHCO₃, water and brine. Finally the organic layer was dried with Na₂SO4 and solvent evaporated to give the title compound as white solid.

Synthesis of Bromo-Pyrazoles for Aryl-Aryl Cross Coupling Reactions and for Metal Mediated Aminations

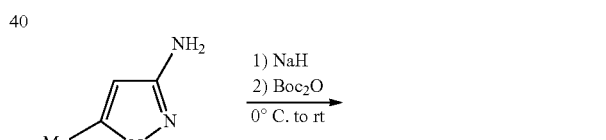

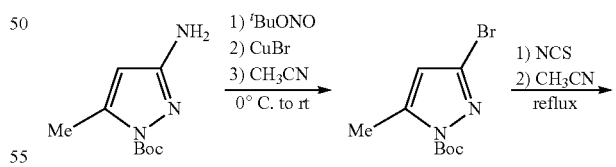

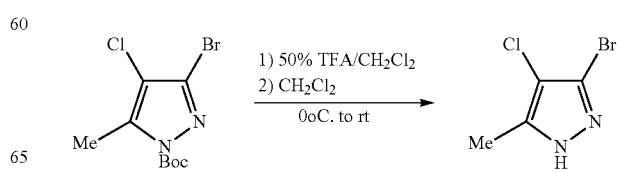

General Procedure for Trifluoroacetylation of Aminopyrazoles:

Synthesis of 2,2,2-Trifluoro-N-(5-methyl-1H-pyrazol-3-yl)-acetamide

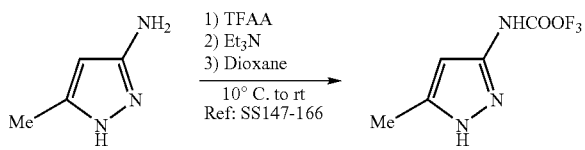

To a solution of 3-amino-5-methylpyrazole (0.97 g, 10 mmol) and Et$_3$N (1.39 mL, 10 mmol) in dioxane (25 mL) was added Trifluoroacetic anhydride (TFAA) (1.39 mL, 10 mmol) drop-wise at 10° C. The reaction mixture was stirred at that temperature for 1 h then slowly warmed to room temperature through next 1 h. Once the reaction is over dioxane was evaporated, residue resolved in water (20 mL), washed with methylene chloride (30 mL). Organic layer was then dried with Na$_2$SO$_4$ and concentrated to give the title compound as white solid.

Protocol N: Functionalization of Alkyl Substituted Heteroaryl Ring Systems: Aminomethylation Synthesis of (5-Bromomethyl-4-chloro-3-methyl-pyrazol-1-yl)-acetic acid ethyl ester

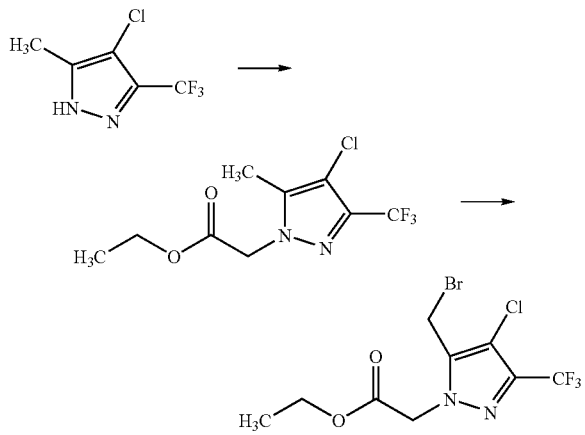

Reagents and Conditions: i) BrCH$_2$CO$_2$Et/K$_2$CO$_3$/CH$_3$CN; ii) NBS/AIBN/CCl$_4$ 4-Chloro-3-methyl-5-trifluoromethyl-1H-pyrazole, (10 g, 54 mmol) was dissolved in acetonitrile (100 mL) and potassium carbonate (30 g, 0.215 mol) added. After stirring at room temperature for 1 hour, ethyl bromoacetate (11 g, 65 mmol) was added. After 14 h at 70° C., the mixture was filtered and the filtrate was concentrated to obtain the crude product, which was re-crystallized from petroleum ether.

This intermediate ester (5 g, 0.019 mol) was taken in CCl$_4$ (100 mL) and AIBN (0.053 g, 0.33 mmol) was added to it under nitrogen. The mixture was irradiated with a regular light bulb. The mixture was brought to reflux and then NBS (3.42 g, 0.019 mol), in four portions in 15 min intervals, was added to the mixture. After complete addition the mixture was left refluxing under the influence of light for 3 h. The reaction mixture was then filtered and the filtrate was washed with water and brine. Drying the organic layer (Na$_2$SO$_4$) followed by evaporation of the solvent afforded (5-Bromomethyl-4-chloro-3-trifluoromethyl-pyrazol-1-yl)-acetic acid ethyl ester.

Protocol O: Synthesis of (5-Azidomethyl-4-chloro-3-trifluoromethyl-pyrazol-1-yl)-acetic acid

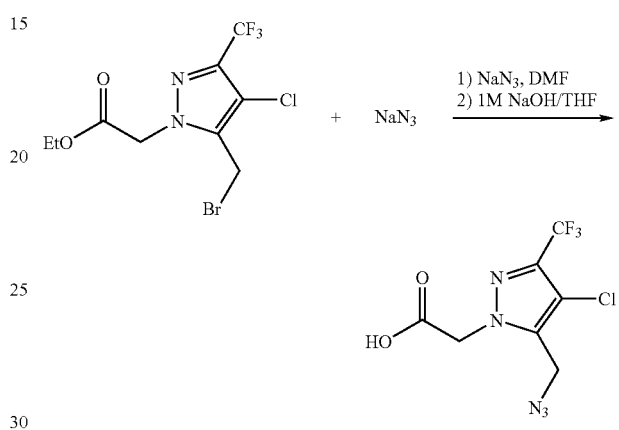

To 4.6 g (13.2 mmol) of (5-Bromomethyl-4-chloro-3-trifluoromethyl-pyrazol-1-yl)-acetic acid ethyl ester dissolved in 40 mL of anhydrous dimethylformamide was added 1.03 g (15.8 mmol) of sodium azide. After stirring for 12 hours, the solution was partitioned between ethyl acetate and water. The phases were separated, the aqueous phase was back-extracted with ethyl acetate and the combined ethyl acetate phases were washed with water and brine, dried over Na$_2$SO$_4$, filtered, and concentrated in vacuo to yield an orange oil.

The oil was dissolved in 25 mL of tetrahydrofuran, 25 mL of 1M NaOH was added, and the mixture was stirred vigorously for three hours. The tetrahydrofuran was then removed in vacuo, and the aqueous solution was washed once with ether. The aqueous phase was then acidified with 1M HCl, and extracted twice with ethyl acetate. The combined ethyl acetate phases were washed with brine, dried over Na$_2$SO$_4$, filtered, and concentrated to yield the title compounds as an orange solid.

Coupling of Pyrazolyl Systems with Carboxylic Acid Equivalents

The following synthesis is an example of this type of chemistry: additional examples (procedure N) have been described above.

Synthesis of 4-Chloro-3-methyl-5-trifluoromethylpyrazol-1-yl)-acetic acid

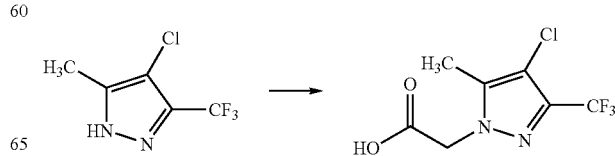

Reagents and conditions: BrCH$_2$CO$_2$Et/K$_2$CO$_3$/ CH$_3$CN, then LiOH/THF

4-Chloro-3-methyl-5-trifluoromethylpyrazole (10 g, 0.0539 mol) was taken up in acetonitrile (100 mL) and K$_2$CO$_3$ (30 g, 0.213 mol) was added to it. The mixture was stirred at rt for 1 h and ethyl bromoacetate (11 g, 0.065 mol) was added slowly to it. The mixture was then stirred for 12 h at 70° C. The mixture was filtered and the filtrate was concentrated to get a crude mixture. This crude product was re-crystallized from pet ether to obtain the corresponding ester The ester (14.8 g, 0.0565 mol) was dissolved in THF (100 mL) and a solution of LiOH (6.9 g) in water (50 mL) was added to it. The mixture was stirred for 10 h at room temperature. Excess THF was evaporated under reduced pressure and the aqueous layer was washed with ethyl acetate to remove any unhydrolysed material. The aqueous layer was then acidified with 1.5N HCl and extracted with ethyl acetate. The ethyl acetate layer was dried and concentrated to obtain the crude acid. On re-crystallization from ether/petroleum ether, the product was obtained as white crystals.

Protocol P: Couplings of Arylpiperazines with Pyrazolyl-Acetic Acid Derivatives—Compounds Prepared by HATU Mediated Coupling Synthesis of 2-(5-Azidomethyl-4-chloro-3-triflurom-ethyl-pyrazol-1-yl)-1-[4-(4-chlorophenyl)-piperazin-1-yl]-ethanone

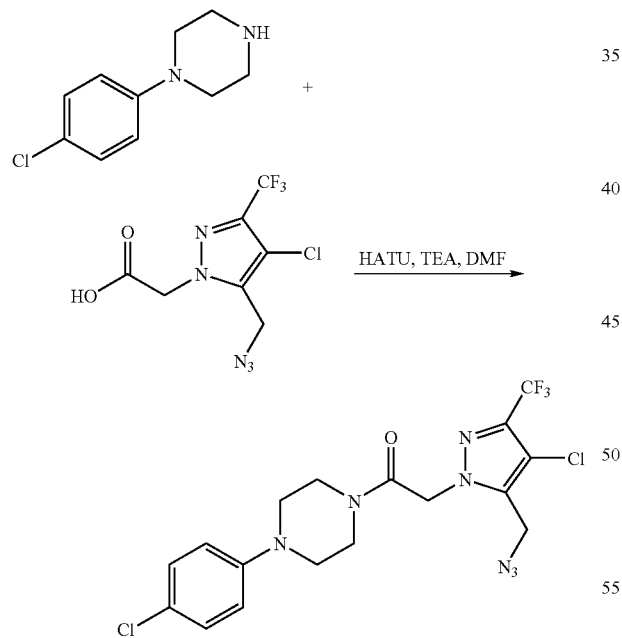

To 2.71 g (13.7 mmol) of 1-(4-Chlorophenyl)piperazine and 3.58 g (12.5 mmol) of (5-Azidomethyl-4-chloro-3-trifluoromethyl-pyrazol-1-yl)-acetic acid in 40 mL of anhydrous dimethylformamide was added 4.36 mL (31.2 mmol) of triethylamine. The solution was cooled to 0° C., and 5.21 g (13.7 mmol) of O-(7-Azabenzotriazol-1-yl)-N,N,N',N'-tetramethyluronium hexafluorophosphate (HATU) was added. After 2 hours the reaction was diluted with two volumes of water, and the solvent was decanted away from the resulting oil. The oil was crystallized by dissolving in methanol and adding water in small portions. The product was isolated as a white solid by filtration: $^1$H NMR (DMSO-d6, 400 MHz) 7.23 (d, 2H), 6.97 (d, 2H), 5.48 (s, 2H), 4.62 (s, 2H), 3.60 (m, 4H), 3.24 (m, 2H), 3.12 (m, 2H) ppm; MS (ES) M+H expected=462.1, found=462.0.

Synthesis of 2-(4-Chloro-5-methyl-3-trifluorom-ethyl-pyrazol-1-yl)-1-[4-(2,5-dimethyl-phenyl)-piperazin-1-yl]-ethanone

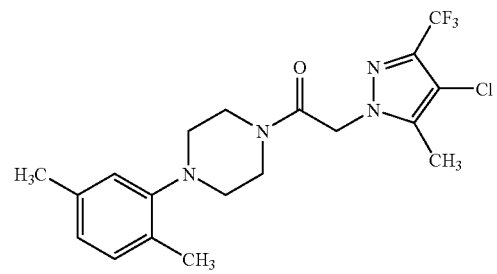

To 38 mg (0.20 mmol) of 1-(2,5-Dimethylphenyl)piperazine and 53 mg (0.22 mmol) of (4-Chloro-5-methyl-3-trifluoromethyl-pyrazol-1-yl)-acetic acid in 1.6 mL of anhydrous dimethylformamide was added 62 mg (0.6 mmol) of triethylamine, followed by 84 mg (0.22 mmol) of O-(7-Azabenzotriazol-1-yl)-N,N,N',N'-tetramethyluronium hexafluorophosphate (HATU). After 6 hours, the reaction was partitioned between ethyl acetate and water, and the phases were separated. The aqueous phase was back-extracted once with ethyl acetate, and the combined ethyl acetate phases were washed once each with 0.5M pH=7 phosphate buffer, water, 1M NaOH, water, brine. The ethyl acetate phase was then dried over Na$_2$SO$_4$, filtered, and concentrated to a residue in vacuo. The residue was dissolved in a minimum volume of 5M HCl in isopropanol, and was precipitated by diluting the solution with ethyl acetate. The product was isolated by filtration to give a white solid: NMR (DMSO-d6, 400 MHz) 7.07 (d 1H), 6.90 (s, 1H), 6.82 (d, 1H), 5.39 (s, 2H), 3.66 (m, 4H), 2.98 (m, 2H), 2.89 (m, 2H), 2.26 (s, 3H), 2.24 (s, 3H), 2.20 (s, 3H) ppm; MS (ES) M+H expected=415.1, found 415.1.

Examples of Additional Compounds Prepared by HATU Mediated Coupling

Synthesis of 2-(4-Chloro-5-methyl-3-trifluorom-ethyl-pyrazol-1-yl)-1-[4-(3-methoxy-phenyl)-piperazin-1-yl]-ethanone

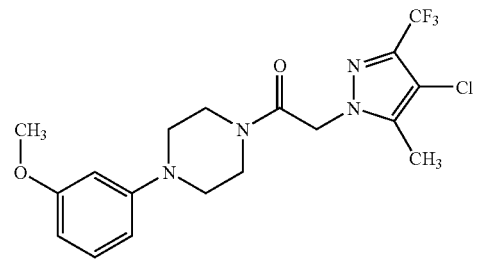

Title compound was prepared following protocol P, wherein 1-(3-methoxyphenyl)piperazine and (4-Chloro-5-methyl-3-trifluoromethyl-pyrazol-1-yl)-acetic acid were used as the coupling components, to give the product as a white solid: $^1$H NMR (DMSO-d6, 400 MHz) 7.15 (t, 1H), 6.65 (d, 1H), 6.60 (s, 1H), 6.47 (d, 1H), 5.38 (s, 2H), 3.72 (s, 3H), 3.65 (m, 4H), 3.28 (m, 2H), 3.19 (m, 2H), 2.18 (s, 3H) ppm; MS (ES) M+H expect=417.1, found=417.1.

Synthesis of 2-(4-Chloro-5-methyl-3-trifluoromethyl-pyrazol-1-yl)-1-[4-(4-chloro-phenyl)-2-(R)-methyl-pinerazin-1-yl]-ethanone

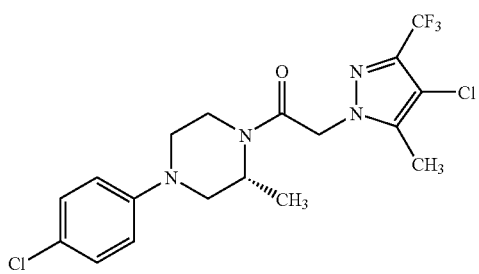

Title compound was prepared following the HATU mediated coupling protocol P, wherein 1-(4-Chlorophenyl)-3-(R)-methylpiperazine and (4-Chloro-5-methyl-3-trifluoromethyl-pyrazol-1-yl)-acetic acid were used as the coupling components, to give the product as a white solid: $^1$H NMR (CDCl$_3$, 300 MHz) 7.25 (d 2H), 6.83 (d, 2H), 4.91 (m, 3H), 4.28 (m, 1H), 3.80-3.10 (m, 4H), 2.86 (m, 1H), 2.71 (m, 1H), 2.29 (s, 3H), 1.40 (m, 3H) ppm; MS (ES) expect M+H=435.1, found 435.0.

Synthesis of 2-(4-Chloro-5-methyl-3-trifluoromethyl-pyrazol-1-yl)-1-(4-o-tolyl-piperazin-1-yl)-ethanone

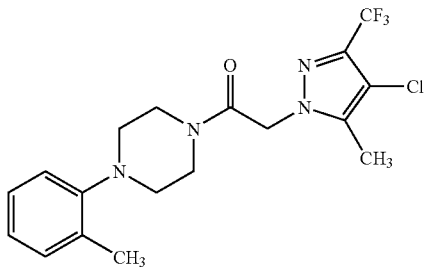

Title compound was prepared following the HATU mediated coupling protocol P, wherein 1-(2-Methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.14 (m, 2H), 6.98 (m, 2H), 5.37 (s, 2H), 3.60 (m, 4H), 2.89 (m, 2H), 2.81 (m, 2H), 2.27 (s, 3H), 2.20 (s, 3H) ppm; MS (ES) M+H expect=401.1, found=401.1.

Synthesis of 2-(4-Chloro-5-methyl-3-trifluoromethyl-pyrazol-1-yl)-1-[4-(4-chloro-phenyl)-2-(S)-methyl-piperazin-1-yl]-ethanone

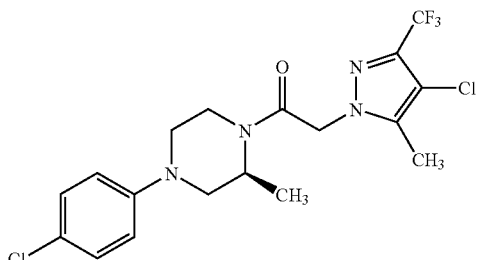

Title compound was prepared following the HATU mediated coupling protocol P, wherein 1-(4Chlorophenyl)-3-(S)-methylpiperazine and (4-Chloro-5-methyl-3-trifluoromethyl-pyrazol-1-yl)-acetic acid were used as the coupling components, to give the product as a solid: $^1$H NMR (CDCl$_3$, 300 MHz) 7.25 (d 2H), 6.83 (d, 2H), 4.91 (m, 3H), 4.28 (m, 1H), 3.80-3.10 (m, 4H), 2.86 (m, 1H), 2.71 (m, 1H), 2.29 (s, 3H), 1.40 (m, 3H) ppm; MS (ES) M+H expected=435.1, found=435.0.

Synthesis of 2-(4-Chloro-3-trifluoromethyl-5-methyl-pyrazol-1-yl)-1-[4-(5-fluoro-2-methoxy-phenyl)-piperazin-1-yl]-ethanone

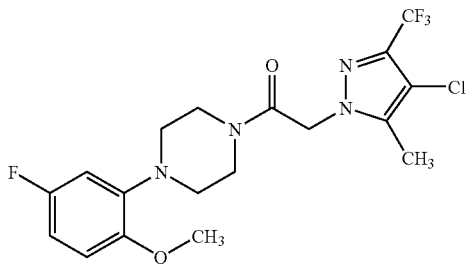

Title compound was prepared following the HATU mediated coupling protocol P, wherein 1-(2-Methoxy-5-fluorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 6.93 (m, 1H), 6.77 (m, 3H), 5.36 (s, 2H), 3.77

(s, 3H), 3.59 (m, 4H), 3.07 (m, 2H), 2.98 (m, 2H), 2.19 (s, 3H) ppm; MS (ES) M+H expect 435.1, found 435.0.

Synthesis of 2-{4-chloro-3-methyl-5-trifluoromethyl-pyrazol-1-yl}-1-[4-(3-Methylsulfanyl-phenyl)-piperazin-1-yl]-ethanone

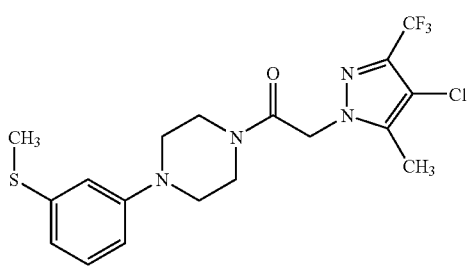

Title compound was prepared following the HATU mediated coupling protocol P, wherein 1-(3-Methylthiophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.21 (t, 1H), 6.98 (s, 1H), 6.91 (d, 1H), 6.81 (d, 1H), 5.39 (s, 2H), 3.68 (m, 4H), 3.34 (m, 2H), 3.24 (m, 2H), 2.44 (s, 3H), 2.19 (s, 3H) ppm; MS (ES) M+H expect 433.1, found 433.0.

Synthesis of 1-[4-(4-Bromo-phenyl)-piperazin-1-yl]-2-(4-chloro-5-methyl-3-trifluoromethyl-pyrazol-1yl)-ethanone

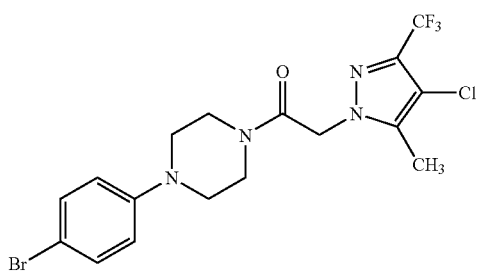

Title compound was prepared following the HATU mediated coupling protocol P, wherein 1-(4-Bromophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.36

(d, 2H), 6.92 (d, 2H), 5.37 (s, 2H), 3.60 (m, 4H), 3.24 (m, 2H), 3.14 (m, 2H), 2.18 (s, 3H) ppm; MS (ES) M+H expect=465.0, found=465.0.

Synthesis of 2-(4-Chloro-3-trifluoromethyl-5-methyl-pyrazol-1-yl)-1-[4-(2,3-dimethyl-phenyl)piperazin-1-yl]-ethanone

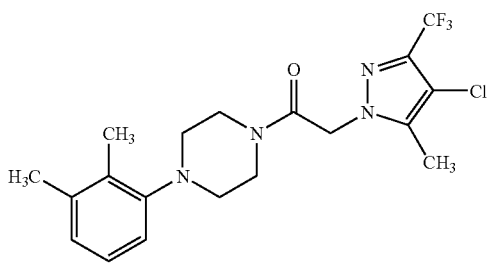

Title compound was prepared following the HATU mediated coupling protocol P, wherein 1-(2,3-Dimethylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.04 (t, 1H), 6.99 (m, 2H), 5.38 (s, 2H), 3.64 (m, 4H), 2.89 (m, 2H), 2.81 (m, 2H), 2.21 (m, 9H) ppm; MS (ES) M+H expect 415.1, found 415.1.

Synthesis of 2-(4-Chloro-3-trifluoromethyl-5-methyl-pyrazol-1-yl)-1-[4-(2-chloro-5-methoxy-phenyl)-piperazin-1-yl]-ethanone

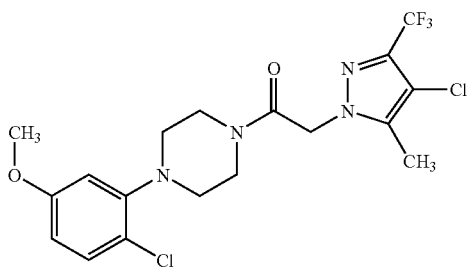

Title compound was prepared following the HATU mediated coupling protocol P, wherein 1-(2-Chloro-5-methoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.31 (d, 1H), 6.65 (m, 2H), 5.37 (s, 2H), 3.73 (s, 3H), 3.62 (m, 4H), 3.02 (m, 2H), 2.96 (m, 2H), 2.19 (s, 3H) ppm; MS (ES) M+H expect=451.1, found=451.0.

4H), 3.01 (m, 2H), 2.94 (m, 2H), 2.19 (s, 3H) ppm; MS (ES) M+H expect 455.0, found=454.9.

Synthesis of 1-[4-(4-Bromo-3-methoxy-phenyl)-piperazin-1-yl]-2-(4-chloro-5-methyl-3-trifluoromethyl-pyrazol-1-yl)-ethanone

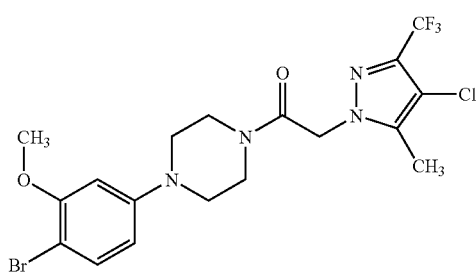

Title compound was prepared following the HATU mediated coupling protocol P, wherein 1-(4-Bromo-3-methoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.34 (d, 1H), 6.71 (s,1H), 6.52 (d, 1H), 5.39 (s, 2H), 3.82 (s, 3H), 3.62 (m, 4H), 3.30 (m, 2H), 3.20 (m, 2H), 2.19 (s, 3H) ppm; MS (ES) M+H expected=495.0, found=495.0.

Synthesis of 2-(4-Chloro-5-methyl-3-trifluoromethyl-pyrazol-1-yl)-1-[4-(4-methoxy-pyridin-2-yl)-piperazin-1-yl]-ethanone

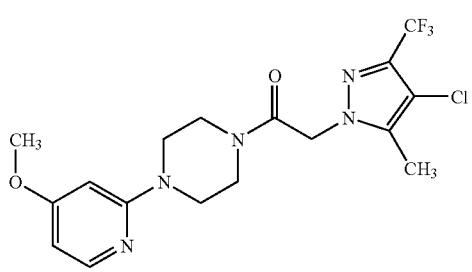

Title compound was prepared following the HATU mediated coupling protocol P, wherein 1-(4-Methoxy-pyridin-2-yl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.92 (d, 1H), 6.67 (s 1H), 6.63 (d, 1H), 5.42 (s, 2H), 3.96 (s, 3H), 3.88 (m, 2H), 3.73 (m, 4H), 3.62 (m, 2H), 2.19 (s, 3H) ppm; MS (ES) M+H expected=418.1, found=418.0.

Synthesis of 2-(4-Chloro-5-methyl-3-trifluoromethyl-pyrazol-1-yl)-1-[4-(2,4-dichloro-phenyl)-piperazin-1-yl]-ethanone

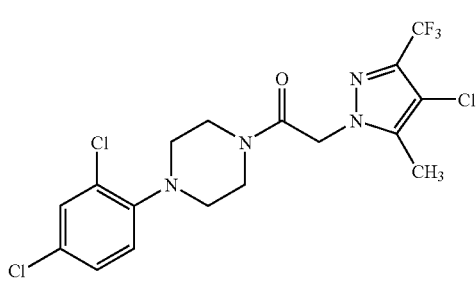

Title compound was prepared following the HATU mediated coupling protocol P, wherein 1-(2,4-Dichlorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.56 (s, 1H), 7.36 (d, 1H), 7.15 (d, 1H), 5.37 (s, 2H), 3.61 (m, Synthesis of 2-(4-Chloro-5-methyl-3-trifluoromethyl-pyrazol-1-yl)-1-[4-(3,4-dimethyl-phenyl)-piperazin1-yl]-ethanone

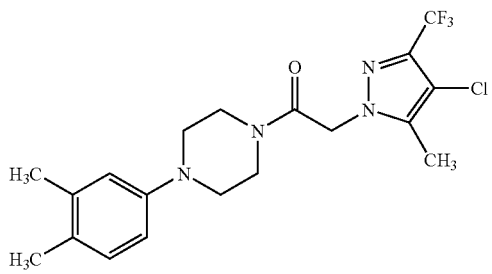

Title compound was prepared following the HATU mediated coupling protocol P, wherein 1-(3,4-Dimethylphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.03 (d, 1H), 6.94 (br s, 1H), 6.84 (br s, 1H), 5.38 (s, 2H), 3.68 (m, 4H), 3.25 (m, 2H), 3.15 (m, 2H), 2.18 (s, 6H), 2.14 (s, 3H) ppm; MS (ES) M+H expected=415.1, found=415.1.

Synthesis of 2-(4-Chloro-3-trifluoromethyl-5-methyl-pyrazol-1-yl)-1-[4-(4-trifluoromethoxy-phenyl)-piperazin-1-yl]-ethanone

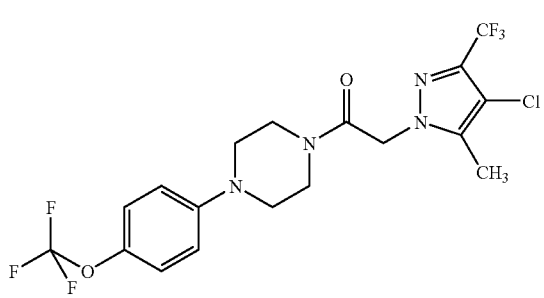

Title compound was prepared following the HATU mediated coupling protocol P, wherein 1-(4-Trifluoromethoxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.20 (d, 2H), 7.04 (d, 2H), 5.38 (s, 2H), 3.60 (m, 4H), 3.27 (m, 2H), 3.17 (m, 2H), 2.18 (s, 3H) ppm; MS (ES) M+H expected=471.1, found=471.0.

Synthesis of 2-(4-Chloro-3-trifluoromethyl-5-methyl-pyrazol-1-yl)-1-[4-(2,4-dichloro-5-methoxy-phenyl)-piperazin-1-yl]-ethanone

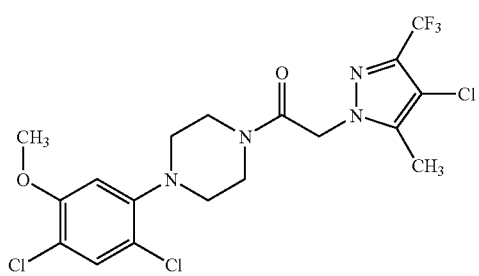

Title compound was prepared following the HATU mediated coupling protocol P, wherein 1-(2,4-Dichloro-5-methoxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.50 (s, 1H), 6.84 (s, 1H), 5.37 (s, 2H), 3.85 (s, 3H), 3.62 (m, 4H), 3.07 (m, 2H), 3.00 (m, 2H), 2.19 (s, 3H) ppm; MS (ES) M+H expected=485.1, found=485.0.

Synthesis of 2-(4-Chloro-5-methyl-3-trifluoromethyl-pyrazol-1-yl)-1-[4-(4-nitro-phenyl)-piperazin-1-yl]-ethanone

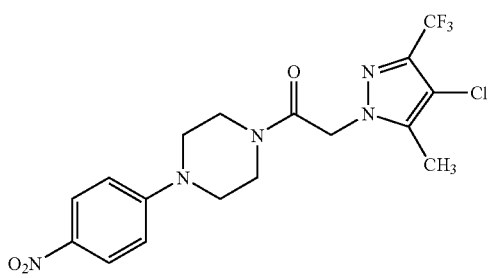

Title compound was prepared following the HATU mediated coupling protocol P, wherein 1-(4-Nitrophenyl)-piperazine and (4-Chloro-5-methyl-3-trifluoromethyl-pyrazol-1-yl)-acetic acid were used as the coupling components, to give the product as a yellow solid: $^1$H NMR (DMSO-d6, 400 MHz) 8.05 (d, 2H), 7.01 (d, 2H), 5.38 (s, 2H), 3.62 (m, 6H), 3.52 (m, 2H), 2.19 (s, 3H) ppm; MS (ES) expect M+H=432.1, found=432.0.

Synthesis of 2-(4-Chloro-5-methyl-3-trifluoromethyl-pyrazol-1-yl)-1-[4-(4-chloro-2-methoxy-phenyl)-piperazin-1-yl]-ethanone

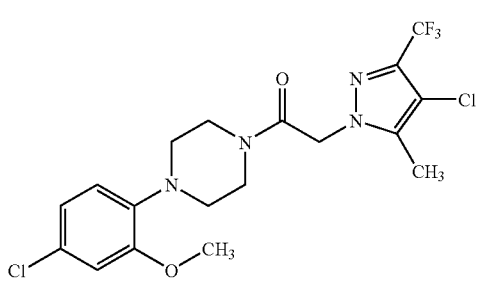

Title compound was prepared following the HATU mediated coupling protocol P, wherein 1-(4-Chloro-2-methoxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.02 (s, 1H), 6.93 (m, 2H), 5.36 (s, 2H), 3.82 (s, 3H), 3.60 (m, 4H), 3.03 (m, 2H), 2.95 (m, 2H), 2.19 (s, 3H) ppm; MS (ES) M+H expected=451.1, found=451.0.

Synthesis of 1-[4-(4-Bromo-3-methyl-phenyl)-piperazin-1-yl]-2-(4-chloro-5-methyl-3-trifluoromethyl-pyrazol-1-yl)-ethanone

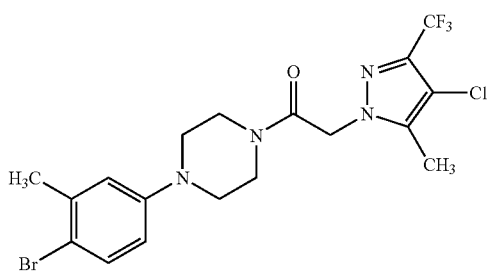

Title compound was prepared following the HATU mediated coupling protocol P, wherein 1-(4-Bromo-3-methylphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.38 (d, 1H), 7.01 (s,1H), 6.78 (d, 1H), 5.38 (s, 2H), 3.60 (m, 4H), 3.26 (m, 2H), 3.16 (m, 2H), 2.28 (s, 3H), 2.19 (s, 3H) ppm; MS (ES) M+H expected=479.0, found=478.9.

Synthesis of 1-[4-(4-Acetyl-phenyl)-piperazin-1-yl]-2-(4-chloro-5-methyl-3-trifluoromethyl-pyrazol-1-yl)-ethanone

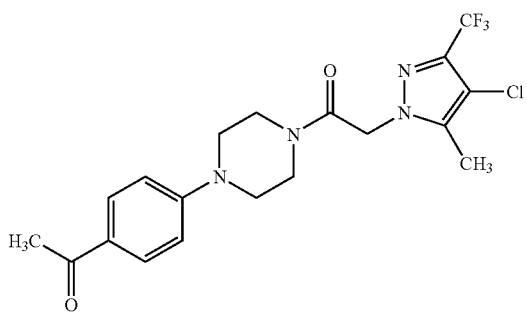

Title compound was prepared following the HATU mediated coupling protocol P, wherein 1-(4-Acetyl-phenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.80 (d, 1H), 6.98 (d,2H), 5.38 (s, 2H), 3.61 (m, 4H), 3.48 (m, 2H), 3.39 (m, 2H), 2.46 (s, 3H), 2.19 (s, 3H) ppm; MS (ES) M+H expected=429.1, found=429.0.

Synthesis of 2-(4-Chloro-5-methyl-3-trifluoromethyl-pyrazol-1-yl)-1-[4-(3,4-dichloro-phenyl)-piperazin-1-yl]-ethanone

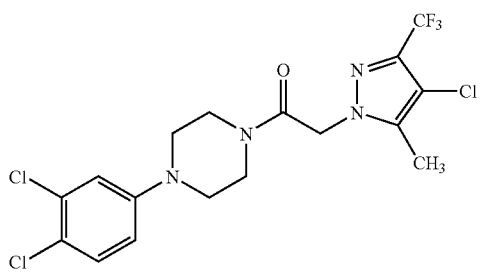

Title compound was prepared following the HATU mediated coupling protocol P, wherein 1-(3,4-Dichlorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.40 (d, 1H), 7.16 (s, 1H), 6.95 (d, 1H), 5.37 (s, 2H), 3.59 (m, 4H), 3.31 (m, 2H), 3.21 (m, 2H), 2.18 (s, 3H) ppm; MS (ES) M+H expected=455.0, found=455.0.

Synthesis of 2-(4-Chloro-5-methyl-3-trifluoromethyl-pyrazol-1-yl)-1-[4-(3-chloro-phenyl)-piperazin-1yl]-ethanone

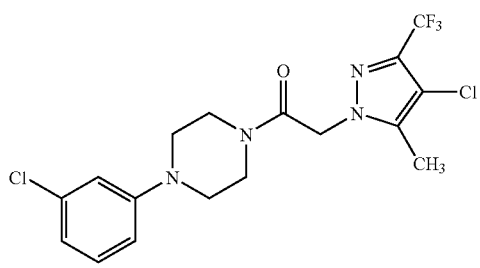

Title compound was prepared following the HATU mediated coupling protocol P, wherein 1-(3-Chlorophenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.23 (t, 1H), 7.19 (s, 1H), 6.90 (d, 1H), 6.79 (d, 1H), 5.37 (s, 2H), 3.58 (m, 4H), 3.29 (m, 2H), 3.19 (m, 2H), 2.18 (s, 3H) ppm; MS (ES) M+H expected=421.1, found=421.0.

2H), 3.82 (s, 3H), 3.63 (m, 4H), 3.30 (m, 2H), 3.19 (m, 2H), 2.19 (s, 3H) ppm; MS (ES) M+H expected=451.1, found 451.0.

Synthesis of 2-(4-Chloro-5-methyl-3-trifluoromethyl-pyrazol-1-yl)-1-(4-m-tolyl-piperazin-1-yl)-ethanone

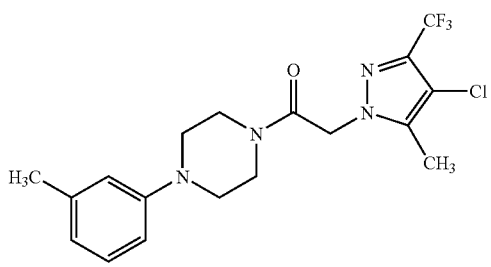

Title compound was prepared following the HATU mediated coupling protocol P, wherein 1-(3-Methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.17 (t, 1H), 6.97 (br, 2H), 6.77 (d, 1H), 5.39 (s, 2H), 3.68 (m, 4H), 3.31 (m, 2H), 3.22 (m, 2H), 2.27 (s, 3H), 2.19 (s, 3H) ppm; MS (ES) M+H expected=401.1, found=401.1.

Synthesis of 4-{4-[2-(4-Chloro-5-methyl-3-trifluoromethyl-pyrazol-1-yl)-acetyl]-piperazin-1-yl}-benzoic acid methyl ester

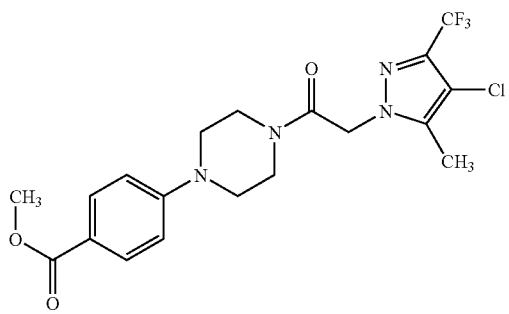

Title compound was prepared following the HATU mediated coupling protocol P, wherein 4-Piperazin-1-yl-benzoic acid methyl ester and (4-Chloro-5-methyl-3-trifluoromethyl-pyrazol-1-yl)-acetic acid were used as the coupling components, to give the product as a solid: $^1$H NMR (DMSO-d6, 400 MHz) 7.78 (d, 2H), 6.98 (d, 2H), 5.38 (s, 2H), 3.71 (s, 3H), 3.60 (m, 4H), 3.46 (m, 2H), 3.37 (m, 2H), 2.19 (s, 3H) ppm; MS (ES) expect M+H=445.1, found 445.0.

Synthesis of 1-[4-(4-Chloro-3-methoxy-phenyl)-piperazin-1-yl]-2-(4-chloro-5-methyl-3-trifluoromethyl-pyrazol-1-yl)-ethanone

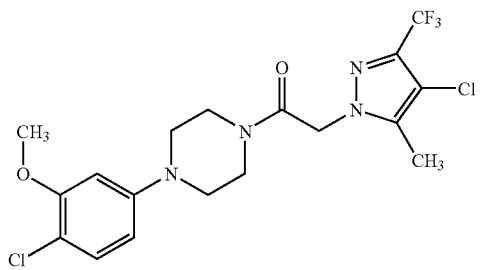

Title compound was prepared following the HATU mediated coupling protocol P, wherein 1-(4-Chloro-3-methoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.21 (d, 1H), 6.74 (s,1H), 6.56 (d, 1H), 5.39 (s, Synthesis of 2-(4-Chloro-3,5-dimethyl-pyrazol-1-yl)-1-(4-pyridin-4-yl-piperazin-1-yl)-ethanone

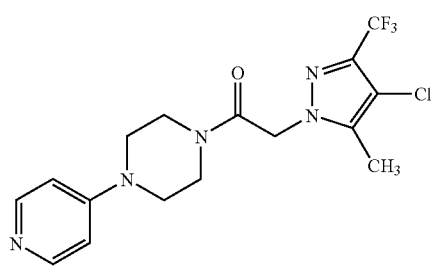

Title compound was prepared following the HATU mediated coupling protocol P, wherein 1-(4-pyridyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 8.28 (d, 2H), 7.18 (d,2H), 5.41 (s, 2H), 3.83 (m, 2H), 3.72 (m, 4H), 3.63 (m, 2H), 2.18 (s, 3H) ppm; MS (ES) M+H expected=388.1, found=388.0.

Synthesis of 2-(4-Chloro-5-methyl-3-trifluoromethyl-pyrazol-1-yl)-1-[4-(5-methoxy-2-methyl-phenyl)-piperazin-1-yl]-ethanone

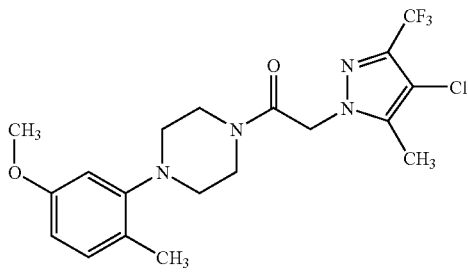

Title compound was prepared following the HATU mediated coupling protocol P, wherein 1-(3-Methoxy-5-methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.06 (d, 1H), 6.56 (m,2H), 5.38 (s, 2H), 3.69 (s, 3H), 3.62 (m, 4H), 2.92 (m, 2H), 2.84 (m, 2H), 2.20 (s, 3H) ppm; MS (ES) M+H expected=431.1, found=431.1.

Synthesis of 2-(4-Chloro-3-trifluoromethyl-5-methyl-pyrazol-1-yl)-1-(4-phenyl-piperazin-1-yl)-ethanone

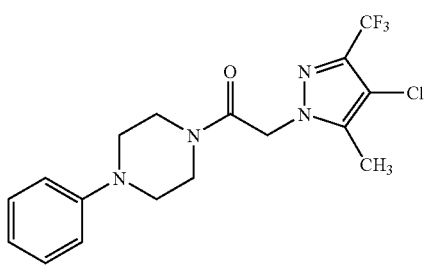

Title compound was prepared following the HATU mediated coupling protocol P, wherein 1-Phenylpiperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.32 (m 4H), 7.02 (m, 1H), 5.40 (s, 2H), 3.74 (m, 4H), 3.39 (m, 2H), 3.29 (m, 2H), 2.19 (s, 3H) ppm; MS (ES) expect M+H=387.1, found 387.1.

Synthesis of 1-[4-(4-Chloro-3-ethoxy-phenyl)-piperazin-1-yl]-2-(4-chloro-5-methyl-3-trifluoromethyl-pyrazol-1-yl)-ethanone

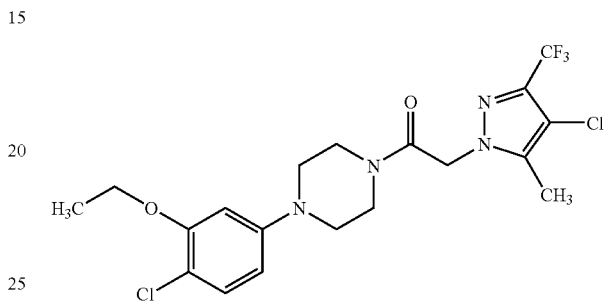

Title compound was prepared following the HATU mediated coupling protocol P, wherein 1-(4-Chloro-3-ethoxyphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.20 (d, 1H), 6.66 (s,1H), 6.48 (d, 1H), 5.38 (s, 2H), 4.08 (q, 2H), 3.61 (m, 4H), 3.25 (m, 2H), 3.16 (m, 2H), 2.18 (s, 3H), 1.33 (t, 3H) ppm; MS (ES) M+H expected=465.1, found 465.0.

Synthesis of 2-(4-Chloro-5-methyl-3-trifluoromethyl-pyrazol-1-yl)-1-(4-pyridin-2-yl-piperazin-1-yl)-ethanone

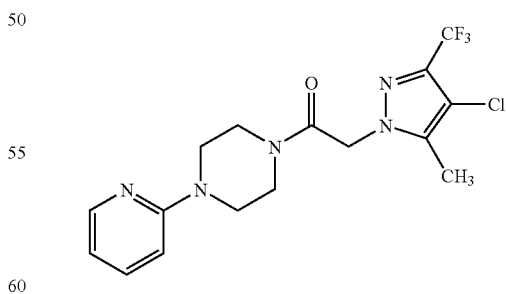

Title compound was prepared following the HATU mediated coupling protocol P, wherein 1-(2,Pyridyppiperazine and (4-Chloro-5-methyl-3-trifluoromethyl-pyrazol-1-yl)-acetic acid were used as the coupling components, to give the product as a solid: $^1$H NMR (DMSO-d6, 400 MHz) 8.11 (d, 1H), 7.53 (t, 1H), 6.85 (d,1H), 6.65 (t, 1H), 5.37 (s, 2H), 3.59-3.50 (m, 8H), 2.18 (s, 3H) ppm; MS (ES) M+H expected=388.1, found=388.0.

Synthesis of 2-(4-Chloro-5-methyl-3-trifluoromethyl-pyrazol-1-yl)-1-(4-p-tolyl-piperazin-1-yl)-ethanone

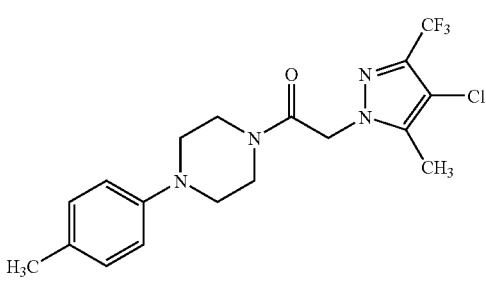

Title compound was prepared following the HATU mediated coupling protocol P, wherein 1-(4-Methylphenyl)piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.20 (m, 4H), 5.40 (s, 2H), 3.79 (m, 4H), 3.37 (m, 2H), 3.28 (m, 2H), 2.49 (s, 3H), 2.19 (s, 3H) ppm; MS (ES) M+H expected=401.1, found 401.0.

Synthesis of 1-[(4-Methanesulfonyl-phenyl)-piperazine-1-yl]-2-(4-chloro-5-methyl-3-trifluoromethyl-pyrazol-1-yl)-ethanone

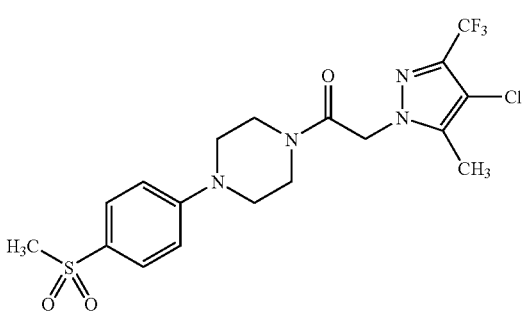

Title compound was prepared following the HATU mediated coupling protocol P, wherein 1-(4-Methanesulfonyl-phenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.69 (d, 2H), 7.08 (d,2H), 5.38 (s, 2H), 3.59 (m, 4H), 3.49 (m, 2H), 3.38 (m, 2H), 3.09 (s, 3H), 2.19 (s, 3H) ppm; MS (ES) M+H expected=465.1, found=465.0.

Synthesis of 2-(4-Chloro-5-methyl-3-trifluoromethyl-pyrazol-1-yl)-1-[4-(4-chloro-phenyl)-piperazin-1-yl]-ethanone

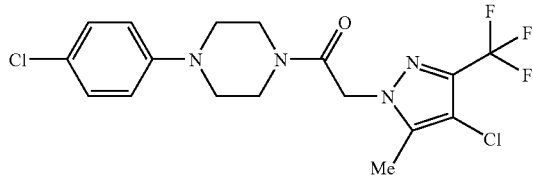

Title compound was prepared following the HATU mediated coupling protocol P, wherein 1-(4-Chlorophenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 7.22 (d, 2H), 6.83 (d, 2H), 4.99 (s, 2H), 3.77 (m, 2H), 3.72 (m, 2H), 3.19 (m, 2H), 3.16 (m, 2H), 2.28 (s, 3H) ppm; MS (ES) M+Na expected=443.0, found 443.0.

Synthesis of 2-(4-Chloro-5-methyl-3-trifluoromethyl-pyrazol-1-yl)-1-[4-(4-methoxy-phenyl)-piperazin-1-yl]-ethanone

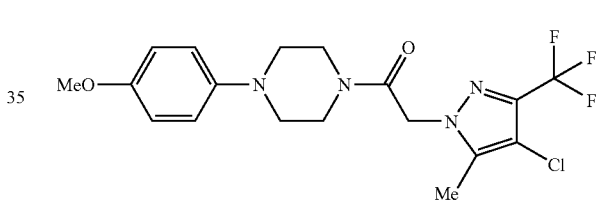

Title compound was prepared following the HATU mediated coupling protocol P, wherein 1-(4-Methoxyphenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) 6.88 (m, 4H), 5.00 (s, 2H), 3.78 (m, 3H), 3.76 (m, 2H), 3.70 (m, 2H), 3.08 (m, 4H), 2.30 (s, 3H) ppm; MS (ES) M+Na expected=439.0, found 439.0.

Synthesis of 4-{4-[2-(4-Chloro-5-methyl-3-trifluoromethyl-pyrazol-1-yl)-acetyl]-piperazin-1-yl}-benzonitrile

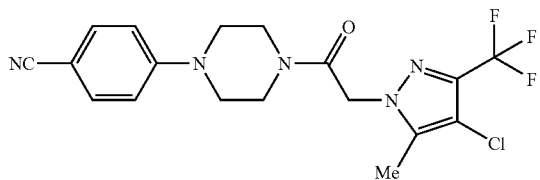

Title compound was prepared following the HATU mediated coupling protocol P, wherein 1-(4-Cyanophenyl)-piperazine and (4-Chloro-5-methyl-3-trifluoromethyl-pyrazol-1-yl)-acetic acid were used as the coupling components, to give the product as a solid: ¹H NMR (CDCl₃, 400 MHz) 7.44 (d, 2H), 6.77 (d, 2H), 4.90 (s, 2H), 3.67 (m, 4H), 3.29 (m, 4H), 2.22 (s, 3H) ppm; MS (ES) M+Na expected=434.0, found 434.0.

Synthesis of 2-(4-Chloro-5-methyl-3-trifluoromethyl-pyrazol-1-yl)-1-[4-(2-fluoro-phenyl)-piperazin-1-yl]-ethanone

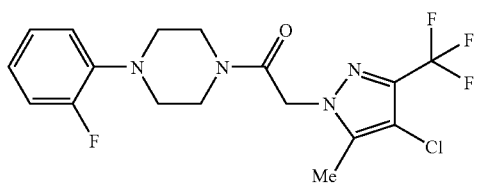

Title compound was prepared following the HATU mediated coupling protocol P, wherein 1-(2-Fluorophenyl)-piperazine and (4-Chloro-5-methyl-3-trifluoromethyl-pyrazol-1-yl)-acetic acid were used as the coupling components, to give the product as a solid: ¹H NMR (CDCl₃, 400 MHz) 7.02 (m, 4H), 5.00 (s, 2H), 3.80 (m, 2H), 3.70 (m, 2H), 3.53 (m, 2H), 3.25 (m, 2H), 2.30 (s, 3H) ppm; MS (ES) M+Na expected=427.0, found 427.0.

Synthesis of 2-(4-Chloro-5-methyl-3-trifluoromethyl-pyrazol-1-yl)-1-[4-(2-methoxy-phenyl)-piperazin-1-yl]-ethanone

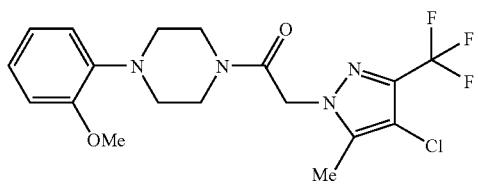

Title compound was prepared following the HATU mediated coupling protocol P, wherein 1-(2-Methoxyphenyl)-piperazine and (4-Chloro-5-methyl-3-trifluoromethyl-pyrazol-1-yl)-acetic acid were used as the coupling components, to give the product as a solid: ¹H NMR (CDCl₃, 400 MHz) 6.62 (m, 1H), 6.48 (m, 3H), 5.01 (s, 2H), 3.73 (s, 3H), 3.61 (m, 4H), 3.43 (m, 2H), 2.31 (s, 3H) ppm; MS (ES) M+H expected=439.0, found 439.1.

Synthesis of 2-(4-Chloro-5-methyl-3-trifluoromethyl-pyrazol-1-yl)-1-[4-(3-trifluoromethyl-phenyl)-piperazin-1-yl]-ethanone

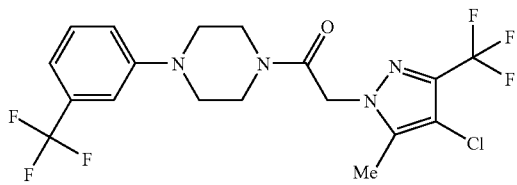

Title compound was prepared following the HATU mediated coupling protocol P, wherein 1(3-Trifluoromethylphenyl)-piperazine and (4-Chloro-5-methyl-3-trifluoromethyl-pyrazol-1-yl)-acetic acid were used as the coupling components, to give the product as a solid: ¹H NMR (CDCl₃, 400 MHz) 7.38 (m, 1H), 7.11 (m, 3H), 5.00 (s, 2H), 3.79 (m, 2H), 3.73 (m, 2H), 3.27 (m, 2H), 3.23 (m, 2H), 2.30 (s, 3H) ppm; MS (ES) M+H expected=455.0, found 455.0.

Synthesis of 2-(4-Chloro-5-methyl-3-trifluoromethyl-pyrazol-1-yl)-1-(4-pyrimidin-2-yl-piperazin-1-yl)-ethanone

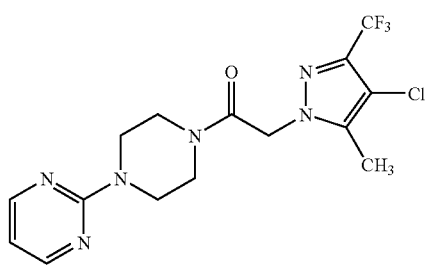

Title compound was prepared following the HATU mediated coupling protocol P, wherein 1-(2-Pyrimidinyl)-piperazine and (4-Chloro-5-methyl-3-trifluoromethyl-pyrazol-1-yl)-acetic acid were used as the coupling components, to give the product as a solid: MS (ES) M+H expected=389.1, found=389.0; HPLC retention time=3.99 minutes (Agilent Zorbax SB-C18, 2.1×50 mm, 5μ, 35° C.) using a 4.5 minute gradient of 20% to 95% B (A=0.1% formic acid/5% acetonitrile/94.9% water, B=0.08% formic acid/99.9% acetonitrile).

Synthesis of 1-[4-(4-Chloro-3-isopropoxy-phenyl)-piperazin-1-yl]-2-(4-chloro-5-methyl-3-trifluoromethyl-pyrazol-1-yl)-ethanone

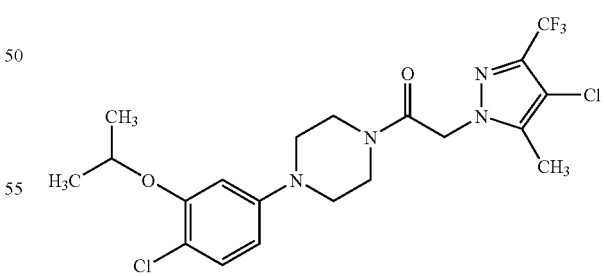

Title compound was prepared following the HATU mediated coupling protocol P, wherein 1-(4-Chloro-3-isopropoxyphenyl)-piperazine and (4-Chloro-5-methyl-3-trifluoromethyl-pyrazol-1-yl)-acetic acid were used as the coupling components, to give the product as a solid: ¹H NMR (DMSO-d6, 400 MHz) 7.21 (d, 1H), 6.71 (s,1H), 6.53 (d, 1H), 5.38 (s, 2H), 4.66 (m, 1H), 3.58 (m, 4H), 3.25 (m, 2H), 3.15 (m, 2H), 2.18 (s, 3H), 1.26 (d, 6H) ppm; MS (ES) M+H expected=479.1, found=479.0.

Synthesis of 2-(4-Chloro-5-methyl-3-trifluoromethyl-pyrazol-1-yl)-1-[4-(3,4-difluoro-phenyl)piperazin-1-yl]-ethanone

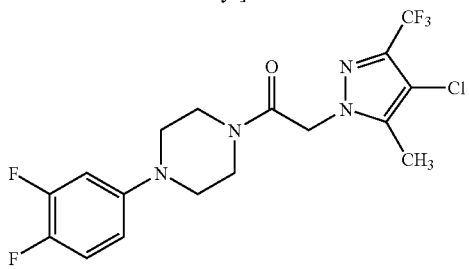

Title compound was prepared following the HATU mediated coupling protocol P, wherein 1-(3,4-Difluorophenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz, not F-decoupled) 7.25 (q, 1H), 7.04 (m,1H), 6.74 (d, 1H), 5.37 (s, 2H), 3.57 (m, 4H), 3.24 (m, 2H), 3.12 (m, 2H), 2.18 (s, 3H) ppm; MS (ES) M+H expected=423.1, found 423.0.

Synthesis of 2-(4-Chloro-5-methyl-3-trifluoromethyl-pyrazol-1-yl)-1-[4-(6-methoxy-pyridin-2-yl)-piperazin-1-yl]-ethanone

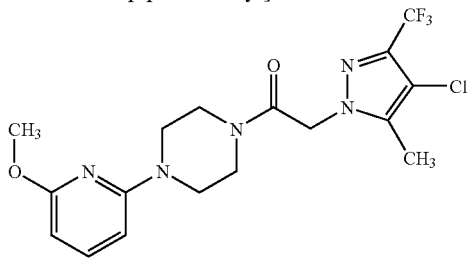

Title compound was prepared following the HATU mediated coupling protocol P, wherein 1-(6-Methoxy-pyridin-2-yl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.45 (t, 1H), 6.34 (d,1H), 6.05 (d, 1H), 5.37 (s, 2H), 3.77 (s, 3H), 3.50 (m, 6H), 3.34 (m, 2H), 2.18 (s, 3H) ppm; MS (ES) M+H expected=418.1, found=418.0.

Synthesis of 4-{4-[2-(4-Chloro-5-methyl-3-trifluoromethyl-pyrazol-1-yl)-acetyl]-piperazin-1-yl}-N,N-dimethyl-benzenesulfonamide

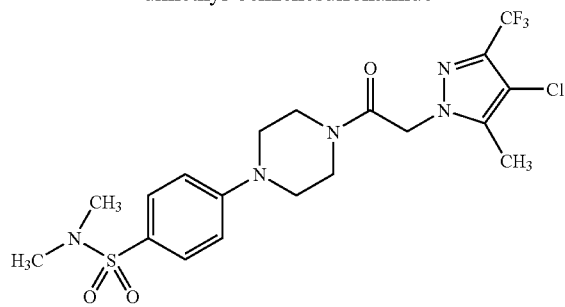

Title compound was prepared following the HATU mediated coupling protocol P, wherein N,N-Dimethyl-4-piperazin-1-yl-benzenesulfonamide and (4-Chloro-5-methyl-3-trifluoromethyl-pyrazol-1-yl)-acetic acid were used as the coupling components, to give the product as a solid: $^1$H NMR (DMSO-d6, 400 MHz) 7.54 (d, 2H), 7.08 (d, 2H), 5.38 (s, 2H), 3.62 (m, 4H), 3.48 (m, 2H), 3.37 (m, 2H), 2.19 (s, 3H) ppm; MS (ES) M+H expected=494.1, found=494.0.

Synthesis of 1-[4-(4-Chloro-3-methyl-phenyl)-piperazin-1-yl]-2-(4-chloro-5-methyl-3-trifluoromethyl-pyrazol-1-yl)-ethanone

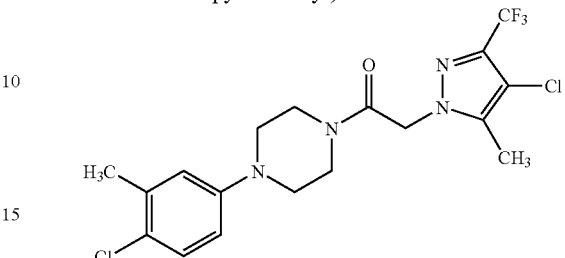

Title compound was prepared following the HATU mediated coupling protocol P, wherein 1-(4-Chloro-3-methylphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.25 (d, 1H), 7.05 (s,1H), 6.90 (d, 1H), 5.38 (s, 2H), 3.64 (m, 4H), 3.27 (m, 2H), 3.17 (m, 2H), 2.26 (s, 3H), 2.19 (s, 3H) ppm; MS (ES) M+H expected=435.1, found=435.0.

Synthesis of 2-(4-Chloro-5-methyl-3-trifluoromethyl-pyrazol-1-yl)-1-[4-(3-hydroxy-phenyl)-piperazin-1-yl]-ethanone

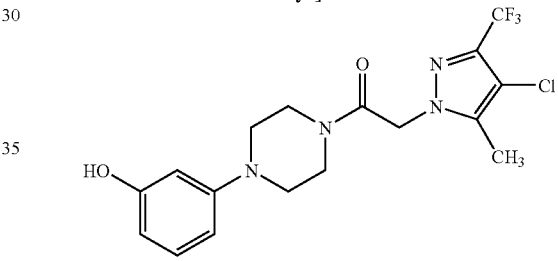

Title compound was prepared following the HATU mediated coupling protocol P, wherein 1-(3-Hydroxyphenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.10 (t, 1H), 6.66 (m,2H), 6.45 (d, 1H), 5.39 (s, 2H), 3.74 (m, 4H), 3.33 (br, 2H), 3.24 (br, 2H), 2.19 (s, 3H) ppm; MS (ES) M+H expected=403.1, found 403.0.

Synthesis of 2-(4-Chloro-5-methyl-3-trifluoromethyl-pyrazol-1-yl)-1-[4-(4-trifluoromethyl-phenyl)-piperazin-1-yl]-ethanone

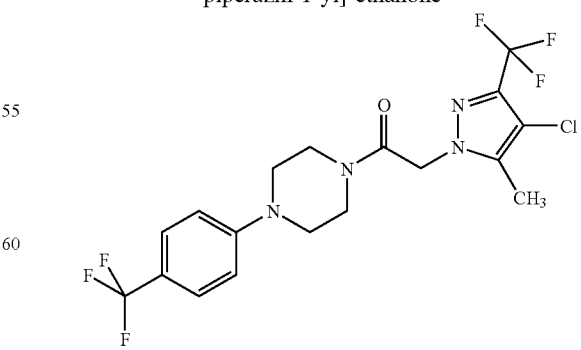

Title compound was prepared following the HATU mediated coupling protocol P, wherein 1-(4-Trifluromethylphenyl)-piperazine and (4-Chloro-5-methyl-3-trifluoromethyl-pyrazol-1-yl)-acetic acid were used as the coupling components, to give the product as a solid: ¹H NMR (DMSO-d6, 400 MHz) 7.50 (d, 2H), 7.07 (d,2H), 5.38 (s, 2H), 3.60 (m, 4H), 3.41 (m, 2H), 3.31 (m, 2H), 2.19 (s, 3H) ppm; MS (ES) M+H expected=455.1, found=455.0.

Synthesis of 2-(4-Chloro-5-methyl-3-trifluoromethyl-pyrazol-1-yl)-1-(3-methyl-4-tolyl-piperazin-1-yl)-ethanone

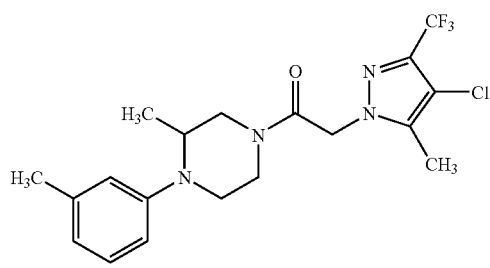

Title compound was prepared following the HATU mediated coupling protocol P, wherein 1-(3-Methylphenyl)-2-methyl-piperazine and (4-Chloro-5-methyl-3-trifluoromethyl-pyrazol-1-yl)-acetic acid were used as the coupling components, to give the product as a solid: ¹H NMR (DMSO-d6, 400 MHz) 7.68 (br, 1H), 7.17 (br, 1H), 6.71 (br, 2H), 5.41 (m, 2H), 4.08 (m, 4H), 3.70 (m, 2H), 3.50 (br m, 2H), 2.30 (s, 3H), 2.18 (s, 3H), 1.01 (m, 3H) ppm; MS (ES) M+H expected=415.1, found=415.1.

Synthesis of 1-[4-(4-Chloro-3-methoxy-phenyl)-2-(S)-methyl-piperazin-1-yl]-2-(4-chloro-5-methyl-3-trifluoromethyl-pyrazol-1-yl)-ethanone

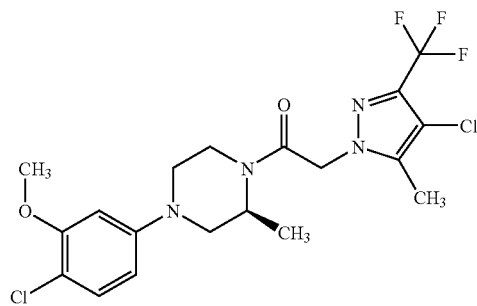

Title compound was prepared following the HATU mediated coupling protocol P, wherein 1-(4-Chloro-3-methoxyphenyl)-3-(S)-methyl-piperazine and (4-Chloro-5-methyl-3-trifluoromethyl-pyrazol-1-yl)-acetic acid were used as the coupling components, to give the product as a solid: ¹H NMR (DMSO-d6, 400 MHz, 95° C.) δ 7.16 (d, 1H), 6.62 (s, 1H), 6.48 (d, 1H), 5.26 (br, 2H), 3.65 (m, 1H), 3.53 (m, 1H), 3.01 (m, 4H), 2.84 (m, 1H), 2.21 (s, 3H), 1.29 (d, 3H) ppm; MS (ES) M+H expect=465.1, found=465.0.

Synthesis of 1-[4-(4-Chloro-3-methylsulfanyl-phenyl)-piperazin-1-yl]-2-(4-chloro-5-methyl-3-trifluoromethyl-pyrazol-1-yl)-ethanone

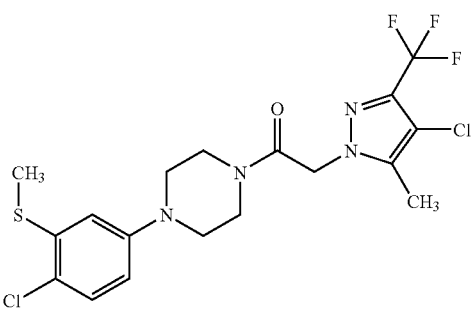

Title compound was prepared following the HATU mediated coupling protocol P, wherein 1-(4-Chloro-3-methylsulfanyl-phenyl)-piperazine and (4-Chloro-5-methyl-3-trifluoromethyl-pyrazol-1-yl)-acetic acid were used as the coupling components, to give the product as a solid: ¹H NMR (DMSO-d6, 400 MHz) δ 7.27 (m, 1H), 6.81 (m, 2H), 5.40 (s, 2H), 3.64 (m, 4H), 3.31 (m, 2H), 3.21 (m, 2H), 2.50 (s, 3H), 2.92 (s, 3H) ppm; MS (ES) M+H expect=467.0, found=467.0.

Synthesis of 1-[4-(3-trifluoromethoxy-phenyl)-piperazin-1-yl]-2-(4-chloro-5-methyl-3-trifluoromethyl-pyrazol-1-yl)-ethanone

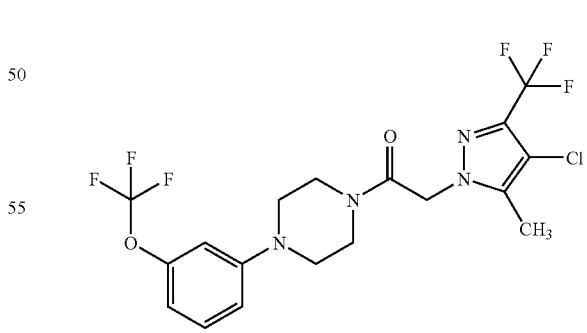

Title compound was prepared following the HATU mediated coupling protocol P, wherein 1-(3-Trifluoromethoxyphenyl)piperazine and (4-Chloro-5-methyl-3-trifluoromethyl-pyrazol-1-yl)-acetic acid were used as the coupling components, to give the product as a solid: ¹H NMR (DMSO-d6, 400 MHz) δ 7.33 (t, 1H), 6.99 (m, 1H), 6.90 (s, 1H), 6.76

(m, 1H), 5.39 (s, 2H), 3.62 (m, 4H), 3.33 (m, 2H), 3.23 (m, 2H), 2.19 (s, 3H) ppm; MS (ES) M+H expect=471.0, found=471.0.

Synthesis of 2-(4-Chloro-5-methyl-3-trifluoromethyl-pyrazol-1-yl)-1-[4-(4-oxazol-5-yl-phenyl)-piperazin-1-yl]-ethanone

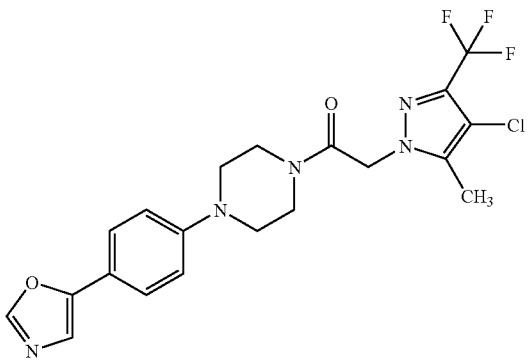

Title compound was prepared following the HATU mediated coupling protocol P, wherein 1-(4-oxazol-5-yl-phenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 8.34 (s, 1H), 7.59 (d, 2H), 7.48 (s, 1H), 7.07 (d, 2H), 5.40 (s, 2H), 3.63 (m, 4H), 3.35 (m, 2H), 3.25 (m, 2H), 2.20 (s, 3H) ppm; MS (ES) M+H expect=454.0, found=454.0.

Synthesis of 2-(5-Azidomethyl-4-chloro-3-trifluoromethyl-pyrazol-1-yl)-1-[4-(4-chloro-3-methoxyphenyl)-piperazin-1-yl]-ethanone

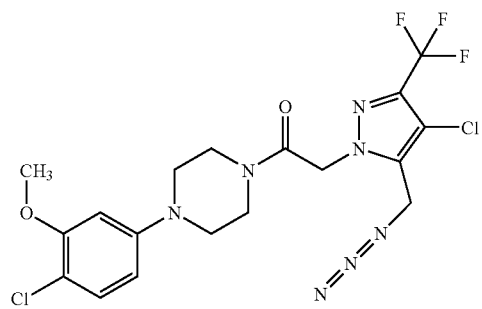

Title compound was prepared following the HATU mediated coupling protocol P, wherein 1-[4-(4-chloro-3-methoxyphenyl)-piperazine and (5-Azidomethyl-4-Chloro-3-trifluoromethyl-pyrazol-1-yl)-acetic acid were used as the coupling components, to give the product as a solid: $^1$H NMR (DMSO-d6, 400 MHz) δ 7.21 (d, 1H), 6.71 (d, 1H), 6.53 (dd, 1H), 5.50 (s, 2H), 4.64 (s, 2H), 3.80 (s, 3H), 3.62 (m, 4H), 3.29 (m, 2H), 3.18 (m, 2H) ppm; MS (ES) M+H expect=492.0, found=492.0.

Synthesis of 1-[4-(3-Chloro-4-methoxy-naphthalen-1-yl)-piperazin-1-yl]-2-(4-chloro-5-methyl-3-trifluoromethyl-pyrazol-1-yl)-ethanone

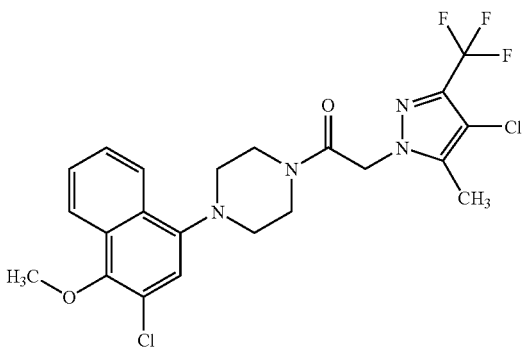

Title compound was prepared following the HATU mediated coupling protocol P, wherein 1-[4-(3-Chloro-4-methoxy-naphthalen-1-yl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 8.22 (m, 1H), 8.07 (m, 1H), 7.64 (m,

Synthesis of 1-[4-(5-Bromo-6-methoxy-pyridin-2-yl)-piperazin-1-yl]-2-(4-chloro-5-methyl-3-trifluoromethyl-pyrazol-1-yl)-ethanone

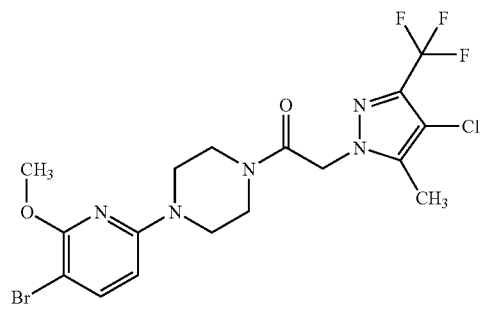

Title compound was prepared following the HATU mediated coupling protocol P, wherein 1-(5-Bromo-6-methoxy-pyridin-2-yl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) 7.69 (d, 1H), 6.37 (d, 1H), 5.39 (s, 2H), 3.87 (s, 3H), 3.62 (m, 4H), 3.55 (m, 4H), 2.20 (s, 3H) pm; MS (ES) M+H expect=496.0, found=496.0.

Synthesis of 1-[4-(4-Chloro-5-methoxy-2-methyl-phenyl)-piperazin-1-yl]-2-(4-chloro-5-methyl-3-trifluoromethyl-pyrazol-1-yl)-ethanone

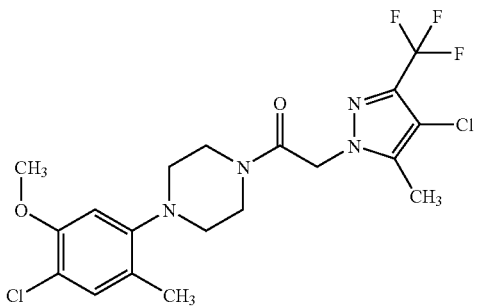

Title compound was prepared following the HATU mediated coupling protocol P, wherein 1-(4-Chloro-5-methoxy-2-methyl-phenyl)-piperazine and (4-Chloro-5-methyl-3-trifluoromethyl-pyrazol-1-yl)-acetic acid were used as the coupling components, to give the product as a solid: MS (ES) M+H expect=465.0, found=465.0; HPLC retention time=5.27 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

(s, 3H), 3.62 (m, 4H), 3.29 (m, 2H), 3.21 (m, 2H), 2.19 (s, 3H) ppm; MS (ES) M+H expect=452.0, found=452.0.

Synthesis of 1-[4-(3-tert-Butoxycarbonylamino-4-chloro-phenyl)-piperazin-1-yl]-2-(4-chloro-5-methyl-3-trifluoromethyl-pyrazol-1-yl)-ethanone

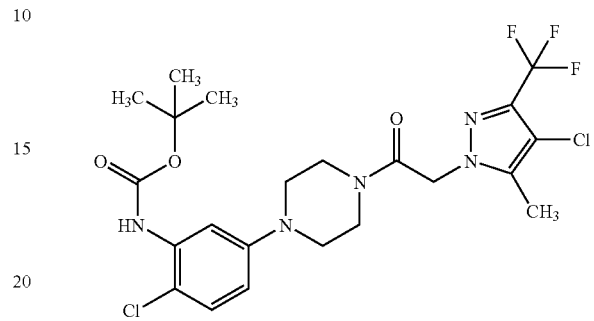

Title compound was prepared following the HATU mediated coupling protocol P, wherein 1-(3-tert-Butoxycarbonylamino-4-chloro-phenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 8.43 (s, 1H), 7.25 (s, 1H), 7.21 (m, 1H), 6.78 (m, 1H), 5.39 (s, 1H), 3.62 (m, 4H), 3.22 (m, 2H), 3.13 (m, 2H), 2.19 (s, 3H), 1.45 (s, 9H) ppm; MS (ES) M+H expect=536.0, found=536.0.

Synthesis of 1-[4-(5-Chloro-4-methoxy-pyridin-2-yl)-piperazin-1-yl]-2-(4-chloro-5-methyl-3-trifluoromethyl-pyrazol-1-yl)-ethanone

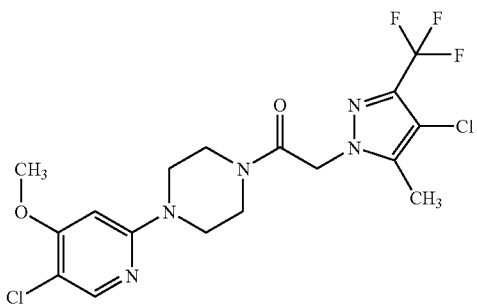

Title compound was prepared following the HATU mediated coupling protocol P, wherein 1-(5-Chloro-4-methoxy-pyridin-2-yl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 8.13 (m, 1H), 6.92 (m, 1H), 5.38 (s, 2H), 3.91

Synthesis of 1-{4-[4-Chloro-3-(2-ethoxy-ethoxy)-phenyl]-piperazin-1-yl}-2-(4-chloro-5-methyl-3-trifluoromethyl-pyrazol-1-yl)-ethanone

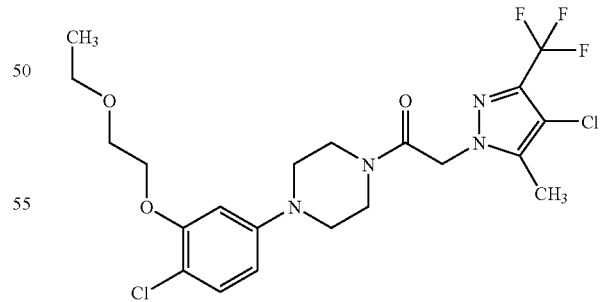

Title compound was prepared following the HATU mediated coupling protocol P, wherein 1-[4-Chloro-3-(2-ethoxy-ethoxy)-phenyl]-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) δ 7.22 (d, 1H), 6.57 (s, 1H), 6.45 (d, 1H), 4.99 (s, 2H), 4.17 (t, 2H), 3.84 (t, 2H) 3.77 (t, 2H), 3.71 (t, 2H), 3.64 (q, 2H), 3.16 (m, 4H), 2.30 (s, 3H), 1.25 (t, 3H) ppm; MS (ES) M+H expect=449.0, found=449.0.

Synthesis of 1-[4-(2-Amino-4-chloro-5-methoxy-phenyl)-piperazin-1-yl]-2-(4-chloro-5-methyl-3-trifluoromethyl-pyrazol-1-yl)-ethanone

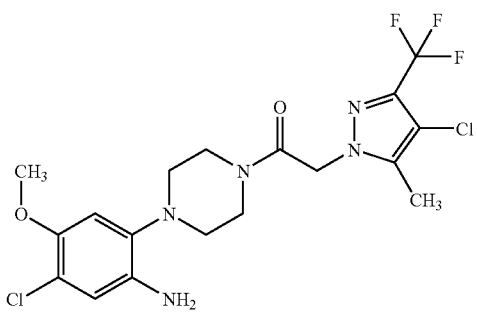

Title compound was prepared following the HATU mediated coupling protocol P, wherein 1-(2-Amino-4-chloro-5-methoxy-phenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) δ 6.79 (s, 1H), 6.59 (s, 1H), 5.00 (s, 5 2H), 3.82 (s, 3H), 3.70 (m, 4H), 2.92 (m, 4H), 2.31 (s, 3H) ppm; MS (ES) M+H expect=449.0, found=449.0.

Synthesis of 1-[4-(4-Chloro-2-fluoro-5-methoxy-phenyl)-piperazin-1-yl]-2-(4-chloro-5-methyl-3-trifluoromethyl-pyrazol-1-yl)-ethanone

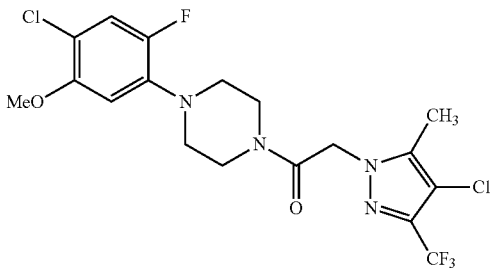

Title compound was prepared following the HATU mediated coupling protocol P, wherein 1-(4-chloro-2-fluoro-5-methoxy-phenyl)-piperazine and (4-Chloro-5-methyl-3-trifluoromethyl-pyrazol-1-yl)-acetic acid were used as the coupling components, to give the product as a solid: $^1$H NMR (400 MHz, CDCl$_3$) δ 7.11 (d, 1H), 6.50 (d, 1H), 5.02 (s, 2H), 3.87 (s, 3H), 3.83-3.74 (m, 4H), 3.14-3.08 (m, 4H), 2.31 (s, 3H) MS (ES) (M+H) expected=469.1, found=469.0

Synthesis of 1-[4-(4-Bromo-3-methoxy-phenyl)-2-(S)-methyl-piperazin-1-yl]-2-(4-bromo-5-methyl-3-trifluoromethyl-pyrazol-1-yl)-ethanone

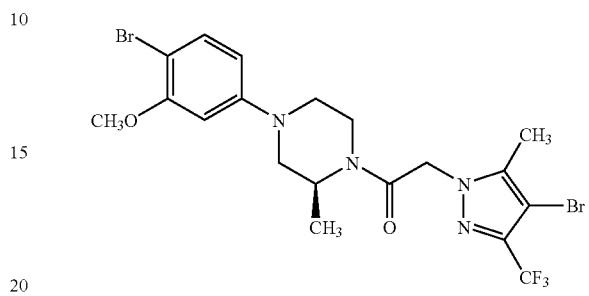

Title compound was prepared following the HATU mediated coupling protocol P, wherein 1-(4-Bromo-3-methoxy-phenyl)-3-(S)-methyl-piperazine and (4-Bromo-5-methyl-3-trifluoromethyl-pyrazol-1-yl)-acetic acid were used as the coupling components, to give the product as a solid: $^1$H NMR (400 MHz, CDCl$_3$) δ 7.37 (d, 1H), 6.42 (s, 1H), 6.37 (d, 1H), 5.00 (s, 2H), 3.89 (s, 3H), 3.60-2.90 (m, 7H), 2.32 (s, 3H), 1.41 (d, 3H); HPLC retention time=7.25 minutes (Agilent Zorbax SB-C18, 2.1×50 mm, 5μ, 35° C.) using a 2.0 starting isocratic period, followed by a 5.0 minute gradient of 20% to 95% B with a 1.1 minute wash at 95% B (A=0.1% formic acid/5% acetonitrile/94.9% water, B=0.08% formic acid/99.9% acetonitrile), and a final 2.5 minute isocratic period at 95% B.

Synthesis of 1-[4-(2,4-Dichloro-5-methoxy-phenyl)-piperazin-1-yl]-2-(4-bromo-5-methyl-3-trifluoromethyl-pyrazol-1-yl)-ethanone

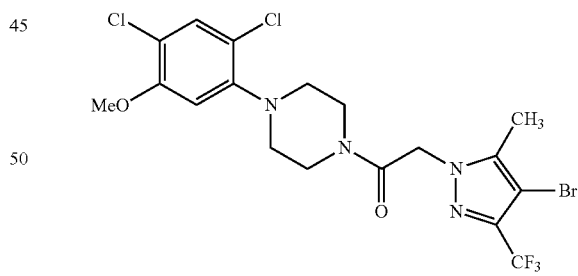

Title compound was prepared following the HATU mediated coupling protocol P, wherein 1-(2,4-dichloro-5-methoxy-phenyl)-piperazine and (4-Bromo-5-methyl-3-trifluoromethyl-pyrazol-1-yl)-acetic acid were used as the coupling components, to give the product as a solid: $^1$H NMR (400 MHz, CDCl$_3$) δ 7.38 (s, 1H), 6.55 (s, 1H), 5.02 (s, 2H), 3.89 (s, 3H), 3.82-3.73 (m, 4H), 3.08-3.02 (m, 4H), 2.33 (s, 3H); HPLC retention time=7.72 minutes (Agilent Zorbax SB-C18, 2.1×50 mm, 5μ, 35° C.) using a 2.0 starting isocratic period, followed by a 5.0 minute gradient of 20% to 95% B with a 1.1 minute wash at 95% B (A=0.1% formic acid/5% acetonitrile/

94.9% water, B=0.08% formic acid/99.9% acetonitrile), and a final 2.5 minute isocratic period at 95% B.

Synthesis of 1-[4-(2,4-Dichloro-5-methoxy-phenyl)-2-(S)-methyl-piperazin-1-yl]-2-(4-bromo-5-methyl-3-trifluoromethyl-pyrazol-1-yl)-ethanone

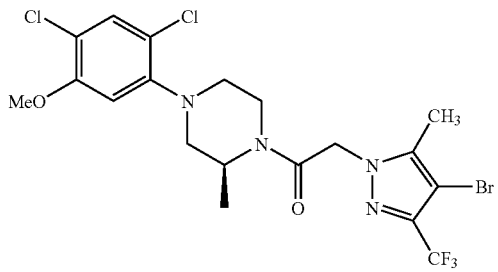

Title compound was prepared following the HATU mediated coupling protocol P, wherein 1-(2,4-dichloro-5-methoxy-phenyl)-3-(S)-methyl-piperazine and (4-Bromo-5-methyl-3-trifluoromethyl-pyrazol-1-yl)-acetic acid were used as the coupling components, to give the product as a solid: $^1$H NMR (400 MHz, CDCl$_3$) δ 7.40 (s, 1H), 6.55 (s, 1H), 4.99 (d, 2H), 3.90 (s, 3H), 3.54-2.73 (m, 7H), 2.32 (s, 3H), 1.52 (d, 3H); HPLC retention time=7.92 minutes (Agilent Zorbax SB-C18, 2.1×50 mm, 5µ, 35° C.) using a 2.0 starting isocratic period, followed by a 5.0 minute gradient of 20% to 95% B with a 1.1 minute wash at 95% B (A=0.1% formic acid/5% acetonitrile/94.9% water, B=0.08% formic acid/99.9% acetonitrile), and a final 2.5 minute isocratic period at 95% B.

Synthesis of 1-[4-(4-Chloro-3-ethyl-phenyl)-piperazin-1-yl]-2-(4-chloro-5-methyl-3-trifluoromethyl-pyrazol-1-yl)-ethanone

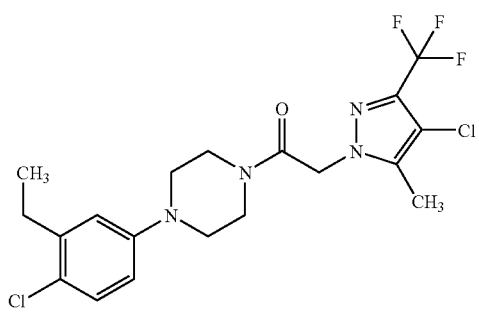

Title compound was prepared following the HATU mediated coupling protocol P, wherein 1-(4-Chloro-3-ethyl-phenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 7.26 (m, 1H), 7.03 (, 1H), 6.90 (m, 1H), 5.40 (d, 2H), 3.64 (m, 4H), 3.29 (m, 2H), 3.20 (m, 2H), 2.64 (q, 2H), 2.20 (s, 3H), 1.16 (t, 3H) ppm; MS (ES) M+H expect=449.0, found=449.0.

Synthesis of 2-(4-Chloro-5-methyl-3-trifluoromethyl-pyrazol-1-yl)-1-[4-(4-fluoro-2-methoxy-phenyl)-pinerazin-1-yl]-ethanone

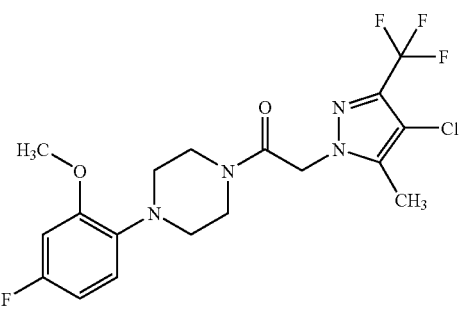

Title compound was prepared following the HATU mediated coupling protocol P, wherein 1-(4-Fluoro-3-methoxy-phenyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 7.01 (m, 1H), 6.93 (m, 1H), 6.73 (m, 1H), 5.38 (s, 2H), 3.83 (s, 3H), 3.63 (m, 4H), 3.06 (m, 2H), 2.97 (m, 2H), 2.19 (s, 3H) ppm; MS (ES) M+H expect=435.0, found=435.0.

Synthesis of 1-[4-(4-Chloro-3-methoxy-phenyl)-2-(R)-methyl-piperazin-1-yl]-2-(4-chloro-5-methyl-3-trifluoromethyl-pyrazol-1-yl)-ethanone Title compound was prepared following the HATU mediated coupling protocol P, wherein 1-(4-Chloro-3-methoxy-phenyl)-2-(R)-methyl-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 7.21 (m, 1H), 6.65 (m, 1H), 6.52 (m, 1H), 5.53 (m, 1H), 5.27 (m, 1H), 4.22 (m, 1H), 3.85 (s, 3H), 3.80-3.49 (m, 4H), 3.10-2.83 (m, 2H), 2.19 (s, 3H), 1.38-1.10 (m, 3H) ppm (mixture of rotamers); MS (ES) M+H expect=465.0, found=465.0.

Synthesis of 1-[4-(4-Chloro-3-methoxy-phenyl)-2-(S)-(2-methanesulfonyl-ethyl)-piperazin-1-yl]-2-(4-chloro-5-methyl-3-trifluoromethyl-pyrazol-1-yl)-ethanone

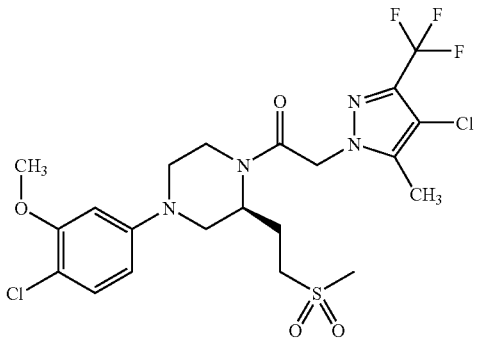

Title compound was prepared following the HATU mediated coupling protocol P, wherein 1-(4-Chloro-3-methoxyphenyl)-3-(S)-(2-methanesulfonyl-ethyl)-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 7.20 (m, 1H), 6.67 (m, 1H), 6.52 (m, 1H), 5.49 (m, 1H), 5.37 (m, 1H), 4.75 (m, 1H), 4.21 (par.obsc.m, 1H), 3.83 (s, 3H), 3.81-3.65 (m, 4H), 3.41 (m, 1H), 3.06 (m, 1H), 2.95 (s, 3H), 2.81 (m, 1H), 2.26 (m, 1H), 2.19 (s, 3H), 2.05 (m, 1H) ppm (rotamers); MS (ES) M+H expect=557.0, found=557.0.

Synthesis of 1-[4-(4-Chloro-3-methoxy-phenyl)-2-(R)-hydroxymethyl-piperazin-1-yl]-2-(4-chloro-5-methyl-3-trifluoromethyl-pyrazol-1-yl)-ethanone

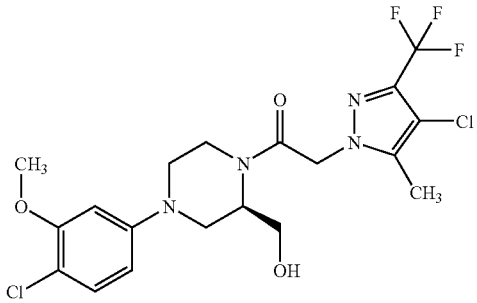

Title compound was prepared following the HATU mediated coupling protocol P, wherein 1-(4-Chloro-3-methoxyphenyl)-2-(R)-hydroxymethyl-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 7.21 (d, 1H), 6.66 (m, 1H), 6.52 (m, 1H), 5.50 (m, 1H), 5.32 (m, 1H), 5.24 (t, 1H), 4.22 (m, 1H), 4.06 (m, 1H), 3.84 (s, 3H), 3.83-3.63 (m, 4H), 3.04-2.62 (m, 3H), 2.17 (s, 3H) ppm (rotamers); MS (ES) M+H expect=481.0, found=481.0.

Synthesis of 1-[4-(4-Chloro-3-dimethylaminomethyl-phenyl)-piperazin-1-yl]-2-(4-chloro-5-methyl-3-trifluoromethyl-pyrazol-4-yl)-ethanone

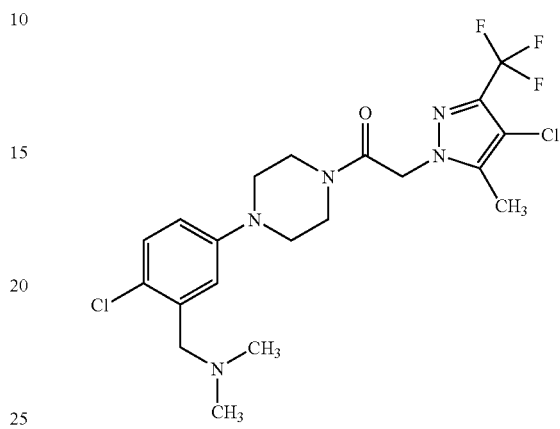

Title compound was prepared following the HATU mediated coupling protocol P, wherein (2-Chloro-5-piperazin-1-yl-benzyl)-dimethyl-amine and (4-Chloro-5-methyl-3-trifluoromethyl-pyrazol-1-yl)-acetic acid were used as the coupling components, to give the product as a solid: $^1$H NMR (CDCl$_3$, 400 MHz) δ 7.32 (d, 1H), 7.25 (s, 1H), 6.88 (dd, 1H), 5.01 (s, 3H), 4.88 (s, 2H), 4.35 (s, 2H), 3.75 (t, 2H), 3.65 (t, 2H), 3.25 (t, 2H), 3.20 (t, 2H), 2.86 (s, 6H) ppm; MS (ES) M+H expect=481.0, found=481.0.

Synthesis of (2-Chloro-5-{4-[2-(4-chloro-5-methyl-3-trifluoromethyl-pyrazol-1-yl)-acetyl]-piperazin-1-yl}-benzyl)-methyl-carbamic acid benzyl ester

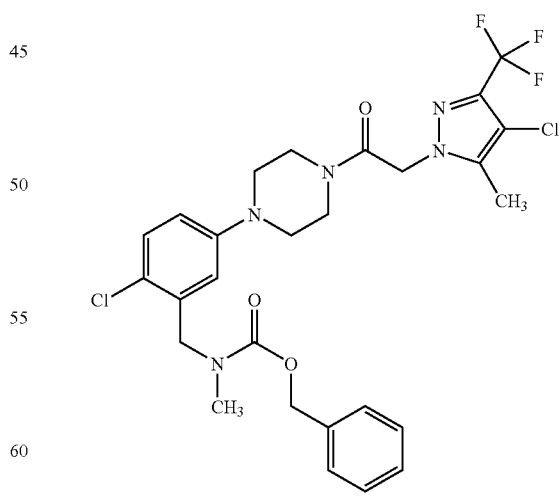

Title compound was prepared following the HATU mediated coupling protocol P, wherein (2-Chloro-5-piperazin-1-yl-benzyl)-methyl-carbamic acid benzyl ester and (4-Chloro-5-methyl-3-trifluoromethyl-pyrazol-1-yl)-acetic acid were used as the coupling components, to give the product as a solid: MS (ES) M+H expect=481.0, found=481.0.

Synthesis of 2-(4-Chloro-5-methyl-3-trifluoromethyl-pyrazol-1-yl)-1-{4-[4-chloro-3-(2-morpholin-4-yl-ethoxy)-phenyl]-piperazin-1-yl}-ethanone

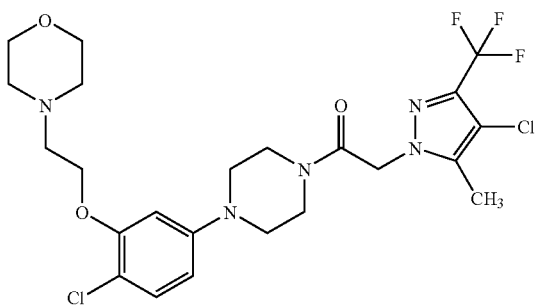

Title compound was prepared following the HATU mediated coupling protocol P, wherein 1-[4-chloro-3-(2-morpholin-4-yl-ethoxy)-phenyl]-piperazine and (4-Chloro-5-methyl-3-trifluoromethyl-pyrazol-1-yl)-acetic acid were used as the coupling components, to give the product as a solid: $^1$H NMR (DMSO-d6, 400 MHz) δ 7.27 (d, 1H), 6.79 (m, 1H), 6.60 (m, 1H), 5.41 (s, 2H), 4.48 (m, 2H), 4.01 (m, 2H), 3.75 (m, 2H), 3.62 (m, 8H), 3.30 (par obsc m, 6H), 3.20 (m, 2H), 2.20 (s, 3H) ppm; MS (ES) M+H expect=550.0, found=551.1.

Synthesis of 1-[4-(4-Chloro-3-methoxy-phenyl)-3-(S)-methyl-piperazin-1-yl]-2-(4-chloro-5-methyl-3-trifluoromethyl-pyrazol-1-yl)-ethanone

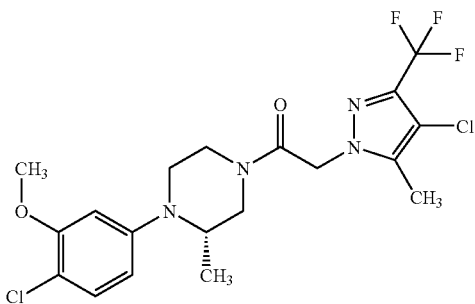

Title compound was prepared following the HATU mediated coupling protocol P, wherein 1-(4-Chloro-3-methoxyphenyl)-3-(S)-methyl-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) δ 7.25 (s, 1H), 6.55 (d, 1H), 6.47 (d, 1H), 5.07-4.91 (m, 2H), 3.88 (s, 3H), 3.76-3.13 (m, 5H), 2.30 (s, 3H), 1.01 (q, 3H) ppm (mixture of rotomers); MS (ES) M+H expect=465.0, found=465.0.

Synthesis of 1-[4-(4-Chloro-3-methoxy-phenyl)-3-(R)-methyl-piperazin-1-yl]-2-(4-chloro-5-methyl-3-trifluoromethyl-pyrazol-1-yl)-ethanone

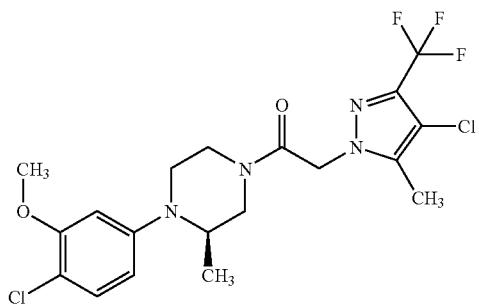

Title compound was prepared following the HATU mediated coupling protocol P, wherein 1-(4-Chloro-3-methoxyphenyl)-3-(R)-methyl-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) δ 7.25 (s, 1H), 6.55 (d, 1H), 6.47 (d, 1H),

Synthesis of 1-[4-(4-Chloro-3-methoxymethyl-phenyl)-piperazin-1-yl]-2-(4-chloro-5-methyl-3-trifluoromethyl-pyrazol-1-yl)-ethanone

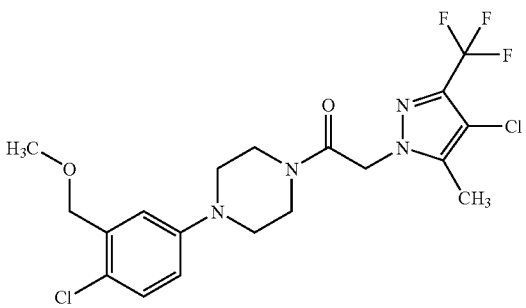

Title compound was prepared following the HATU mediated coupling protocol P, wherein 1-(4-Chloro-3-methoxymethyl-phenyl)-piperazine and (4-Chloro-5-methyl-3-trifluoromethyl-pyrazol-1-yl)-acetic acid were used as the coupling components, to give the product as a solid: $^1$H NMR (CDCl$_3$, 400 MHz) δ 7.25 (s, 1H), 7.05 (d, 1H), 6.78 (dd, 1H), 4.99 (s, 2H), 4.52 (s, 2H), 3.75 (dt, 4H), 3.48 (s, 3H), 3.21 (dt, 4H), 2.30 (s, 3H) ppm; MS (ES) M+H expect=465.1, found=465.0.

Synthesis of 2-(5-Aminomethyl-4-chloro-3-trifluoromethyl-pyrazol-1-yl)-1-[4-(2,4-dichloro-5-methoxy-phenyl)-piperazin-1-yl]-ethanone

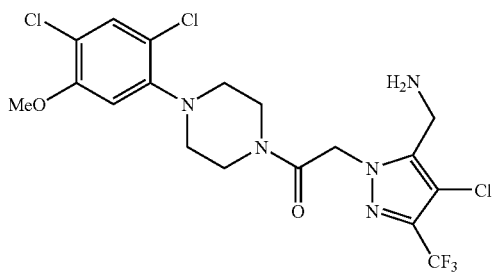

Title compound was prepared following the HATU mediated coupling protocol P, wherein 1-(2,4-dichloro-5-methoxy-phenyl)-piperazine and (5-Azidomethyl-4-chloro-3-trifluoromethyl-pyrazol-1-yl)-acetic acid were used as the coupling components. Following completion of the coupling reaction, a 10-fold excess of Tin (II) chloride was added directly to the reaction, and stirring was continued for an additional 4 hours. The reaction was purified by reverse-phase HPLC to give the product: $^1$H NMR (400 MHz, CDCl$_3$) δ 7.38 (s, 1H), 6.73 (d, 2H), 6.56 (s, 1H), 5.32 (d, 2H), 4.41 (d, 2H) 3.89 (s, 3H), 3.80-3.73 (m, 4H), 3.37-3.02 (m, 4H); HPLC retention time=5.83 minutes (Agilent Zorbax SB-C18, 2.1×50 mm, 5μ, 35° C.) using a 2.0 starting isocratic period, followed by a 5.0 minute gradient of 20% to 95% B with a 1.1 minute wash at 95% B (A=0.1% formic acid/5% acetonitrile/94.9% water, B=0.08% formic acid/99.9% acetonitrile), and a final 2.5 min isocratic period at 95% B.

Synthesis of 2-(5-Aminomethyl-4-chloro-3-trifluoromethyl-pyrazol-1-yl)-1-[4-(4-Bromo-3-methoxy-phenyl)-piperazin-1-yl]-ethanone

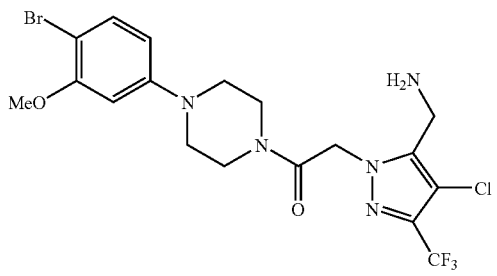

Title compound was prepared following the HATU mediated coupling protocol P, wherein 1-(4-Bromo-3-methoxy-phenyl)-piperazine and (5-Azidomethyl-4-chloro-3-trifluoromethyl-pyrazol-1-yl)-acetic acid were used as the coupling components. Following completion of the coupling reaction, a 10-fold excess of Tin (II) chloride was added directly to the reaction, and stirring was continued for an additional 4 hours. The reaction was purified by reverse-phase HPLC to give the product; $^1$H NMR (400 MHz, CDCl$_3$) δ 7.53 (d, 1H), 6.82 (s, 1H), 6.68 (d, 1H), 5.35 (s, 2H), 4.41 (s, 2H), 3.93 (s, 4H), 3.90 (s, 3H), 3.52-3.39 (m, 4H); HPLC retention time=5.44 minutes (Agilent Zorbax SB-C18, 2.1×50 mm, 5μ, 35° C.) using a 2.0 starting isocratic period, followed by a 5.0 minute gradient of 20% to 95% B with a 1.1 minute wash at 95% B (A=0.1% formic acid/5% acetonitrile/94.9% water, B=0.08% formic acid/99.9% acetonitrile), and a final 2.5 min isocratic period at 95% B.

Synthesis of 2-(5-Aminomethyl-4-chloro-3-trifluoromethyl-pyrazol-1-yl)-1-[4-(4-Chloro-2-fluoro-5-methoxy-phenyl)-piperazin-1-yl]-ethanone

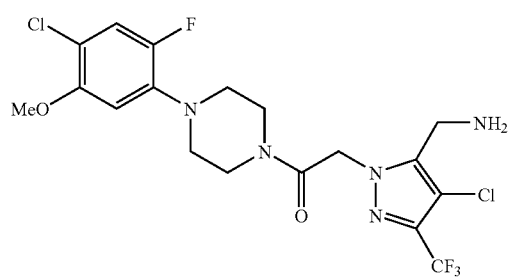

Title compound was prepared following the HATU mediated coupling protocol P, wherein 1-(4-Chloro-2-fluoro-5-methoxy-phenyl)-piperazine and (5-Azidomethyl-4-chloro-3-trifluoromethyl-pyrazol-1-yl)-acetic acid were used as the coupling components. Following completion of the coupling reaction, a 10-fold excess of Tin (II) chloride was added directly to the reaction, and stirring was continued for an additional 4 hours. The reaction was purified by reverse-phase HPLC to give the product: $^1$H NMR (400 MHz, CDCl$_3$) δ 7.10 (d, 1H), 6.48 (d, 1H), 5.33 (s, 2H), 4.39 (s, 2H), 3.85 (s, 3H), 3.78 (m, 4H), 3.05 (m, 4H) MS (ES) (M+H) expected=484.1, found=484.0

Synthesis of 2-(5-Aminomethyl-4-chloro-3-trifluoromethyl-pyrazol-1-yl)-1-[4-(4-Chloro-3-methoxy-phenyl)-2-(S)-methyl-piperazin-1-yl]-ethanone

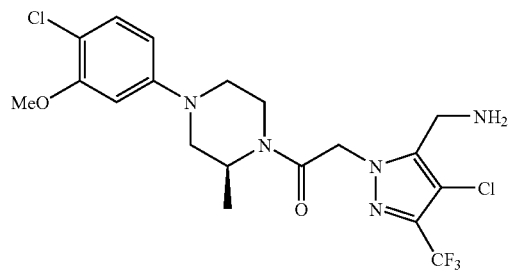

Title compound was prepared following the HATU mediated coupling protocol P, wherein 1-(4-Chloro-3-methoxy-phenyl)-3-(S)-methyl-piperazine and (5-Azidomethyl-4-chloro-3-trifluoromethyl-pyrazol-1-yl)-acetic acid were used as the coupling components. Following completion of the coupling reaction, a 10-fold excess of Tin (II) chloride was added directly to the reaction, and stirring was continued for an additional 4 hours. The reaction was purified by reverse-phase HPLC to give the product: $^1$H NMR (400 MHz, CDCl$_3$) δ 7.22 (d, 1H), 6.46 (s, 1H), 6.42 (s, 1H), 5.27 (m, 2H), 4.35

(s, 2H), 3.81 (s, 3H), 3.76-3.42 (m, 4H), 3.35-2.96 (m, 4H), 1.45 (d, 3H) MS (ES) (M+H) expected=480.1, found=480.1

Synthesis of 2-(5-Aminomethyl-4-chloro-3-trifluoromethyl-pyrazol-1-yl)-1-[4-(4-Bromo-3-methoxyphenyl)-2-(S)-methyl-piperazin-1-yl]-ethanone

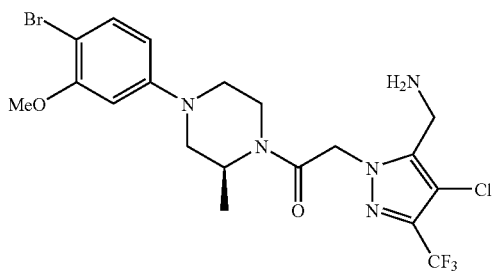

Title compound was prepared following the HATU mediated coupling protocol P, wherein 1-(4-Bromo-3-methoxyphenyl)-3-(S)-methyl-piperazine and (5-Azidomethyl-4-chloro-3-trifluoromethyl-pyrazol-1-yl)-acetic acid were used as the coupling components. Following completion of the coupling reaction, a 10-fold excess of Tin (II) chloride was added directly to the reaction, and stirring was continued for an additional 4 hours. The reaction was purified by reverse-phase HPLC to give the product: $^1$H NMR (400 MHz, CDCl$_3$) δ 7.51 (d, 1H), 6.98 (s, 1H), 6.59 (d, 1H), 5.35 (m, 2H), 4.45 (s, 2H), 3.90 (s, 3H), 3.83-3.60 (m, 5H), 3.32-3.19 (m, 4H), 1.45 (d, 3H); HPLC retention time=5.72 minutes (Agilent Zorbax SB-C18, 2.1×50 mm, 5µ, 35° C.) using a 2.0 starting isocratic period, followed by a 5.0 minute gradient of 20% to 95% B with a 1.1 minute wash at 95% B (A=0.1% formic acid/5% acetonitrile/94.9% water, B=0.08% formic acid/99.9% acetonitrile), and a final 2.5 min isocratic period at 95% B.

Protocol Q: Synthesis of 2-(5-Aminomethyl-4-chloro-3-trifluromethyl-pyrazol-1-yl)-1-[4(4-chlorophenyl)-piperazin-1-yl]-ethanone

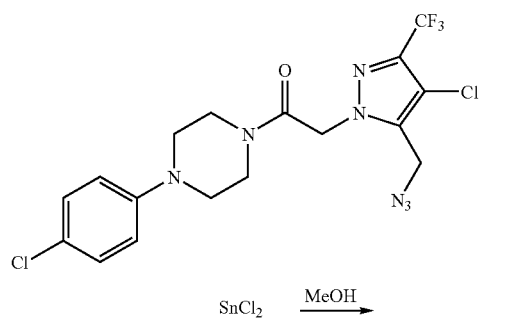

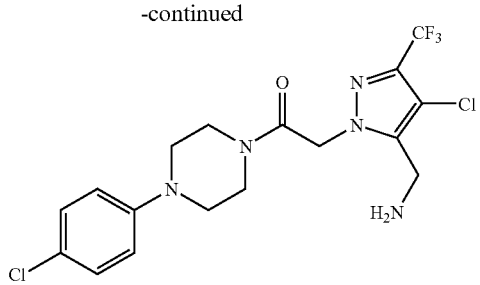

2.85 g (6.2 mmol) of 2-(5-Azidomethyl-4-chloro-3-trifluromethyl-pyrazol-1-yl)-1-[4-(4-chlorophenyl)-piperazin-1-yl]-ethanone was dissolved in 80 mL methanol, and 3.61 g (16.0 mmol) of SnCl$_2$ hydrate was added. After two hours, the reaction was concentrated in vacuo to remove the methanol. The residue was partitioned between 0.5M NaOH and ethyl acetate, and the phases were separated. The aqueous phase was back-extracted once with ethyl acetate. The combined ethyl acetate phases were extracted twice with 1M HCl. The acidic aqueous phase was basified with 1M NaOH, and was extracted once with ethyl acetate. The final ethyl acetate phase was washed once with brine, dried over Na$_2$SO$_4$, filtered, and concentrated to an oil. The oil was dissolved in methanol, acidified with 2M HCl in ether, and the product was isolated by filtration after precipitation: $^1$H NMR (DMSO-d6, 400 MHz) 8.58 (s, 3H), 7.27 (d, 2H), 7.03 (d, 2H), 5.71 (s, 2H), 4.10 (d, 2H), 3.64 (m, 4H), 3.32 (m, 2H), 3.19 (m, 2H) ppm; MS (ES) M+H expected=436.1, found=436.0.

Synthesis of 2-(5-N,N-Dimethylaminomethyl-4-chloro-3-trifluromethyl-pyrazol-1-yl)-1-[4-(4-chlorophenyl)-piperazin-1-yl]-ethanone

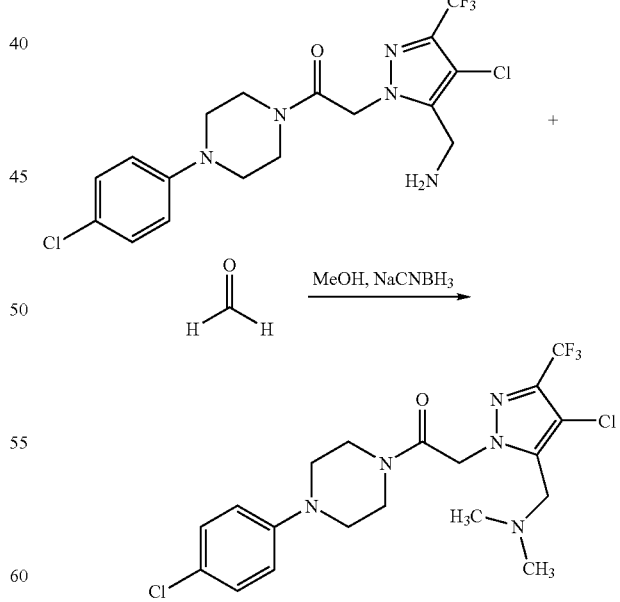

To a solution of 50 mg (0.1 mmol) of 2-(5-Aminomethyl-4-chloro-3-trifluromethyl-pyrazol-1-yl)-1-[4-(4-chlorophenyl)-piperazin-1-yl]-ethanone hydrochloride and 13 mg (0.20 mmol) sodium cyanoborohydride in 0.7 mL methanol was added 0.025 mL (0.3 mmol) of 37% aqueous formaldehyde. After stirring for four hours, the reaction was quenched with 0.1 mL 12M HCl. One hour later, the solution was concentrated in vacuo. The residue was partitioned between water and ether, and the phases were separated. The ether phase was back-extracted once with water. The combined aqueous phases were basified with 1M NaOH, and was extracted once with ethyl acetate. The ethyl acetate phase was washed once with brine, dried over $Na_2SO_4$, filtered, and concentrated to an oil. The oil was dissolved in methanol, acidified with 2M HCl in ether, and the product was isolated as a white solid by filtatration: $^1$H NMR (DMSO-d6, 400 MHz) 11.07 (br, 1H), 7.26 (d, 2H), 7.02 (d, 2H), 5.76 (s, 2H), 4.43 (s, 2H), 3.62 (m, 4H), 3.31 (m, 2H), 3.18 (m, 2H), 2.81 (s, 6H) ppm; MS (ES) M+H expected=464.1, found=464.0.

Synthesis of 2-(5-Aminomethyl-4-chloro-3-trifluoromethyl-pyrazol-1-yl)-1-[4-(4-chloro-3-methoxy-phenyl)-piperazin-1-yl]-ethanone

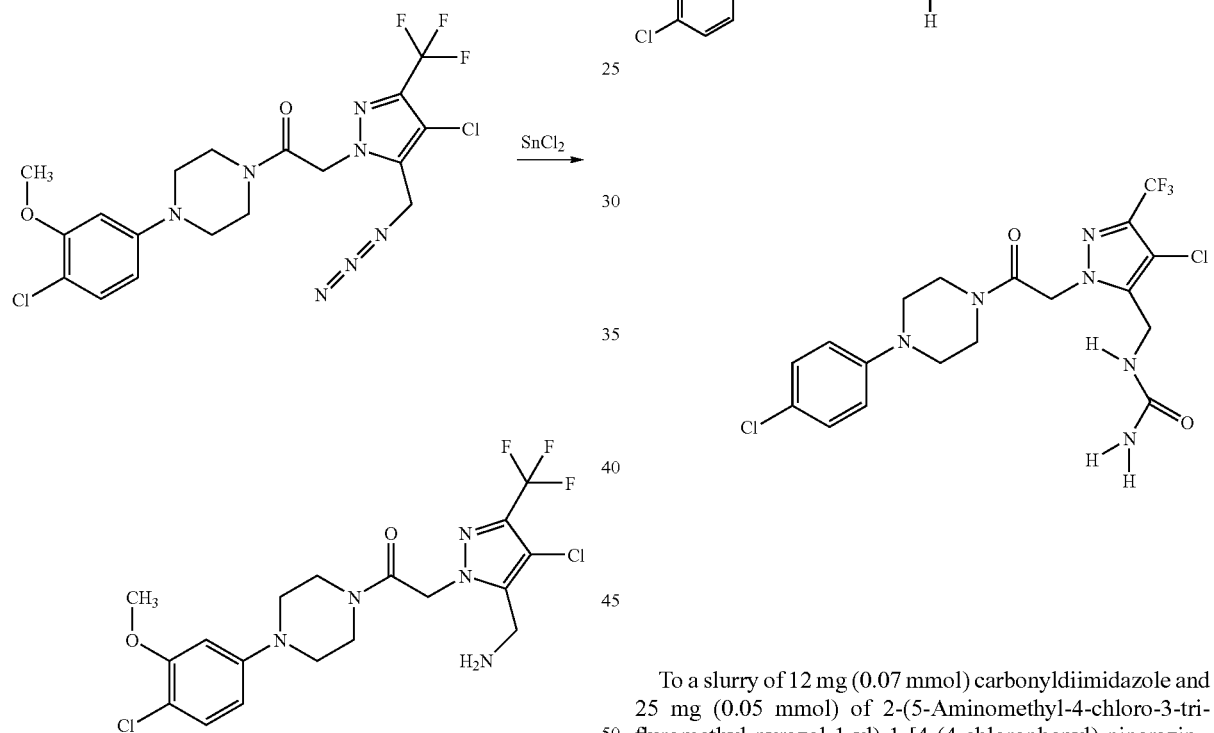

Following protocol Q, 224 mg (0.46 mmol) of 2-(5-Azidomethyl-4-chloro-3-trifluoromethyl-pyrazol-1-yl)-1-[4-(4-chloro-3-methoxy-phenyl)-piperazin-1-yl]-ethanone was dissolved in 5 mL of methanol, and 256 mg (1.14 mmol) of Tin (II) chloride was added. After 4 hours, the solution was concentrated in vacuo to an oil. The oil was partitioned between ether and water, and the phases were separated. The aqueous phase was basified to pH>9 with 1 M NaOH, and was extracted twice with ethyl acetate. The combined ethyl acetate phases were washed twice with water, once with brine, dried over $Na_2SO_4$, filtered, and concentrated to an oil. The oil was dissolved in methanol, acidified with 2 M HCl in ether, and diluted with ether to give the product as a solid: $^1$H NMR (DMSO-d6, 400 MHz) δ 8.50 (br, 3H), 7.23 (m, 1H), 6.74 (m, 1H), 6.56 (m, 1H), 5.70 (s, 2H), 4.13 (m, 2H), 3.84 (s, 3H), 3.64 (m, 4H), 3.35 (m, 2H), 3.23 (m, 2H) ppm; MS (ES) M+H expect=466.0, found=466.0.

Protocol R: Urea Derivatization of Aminomethyl Functionality on Pyrazole Ring System Synthesis of 1-(4-Chloro-2-{2-[4-(4-chloro-phenyl)-piperazin-1-yl]-2-oxo-ethyl}-5-trifluoromethyl-2H-pyrazol-3-ylmethyl)-urea

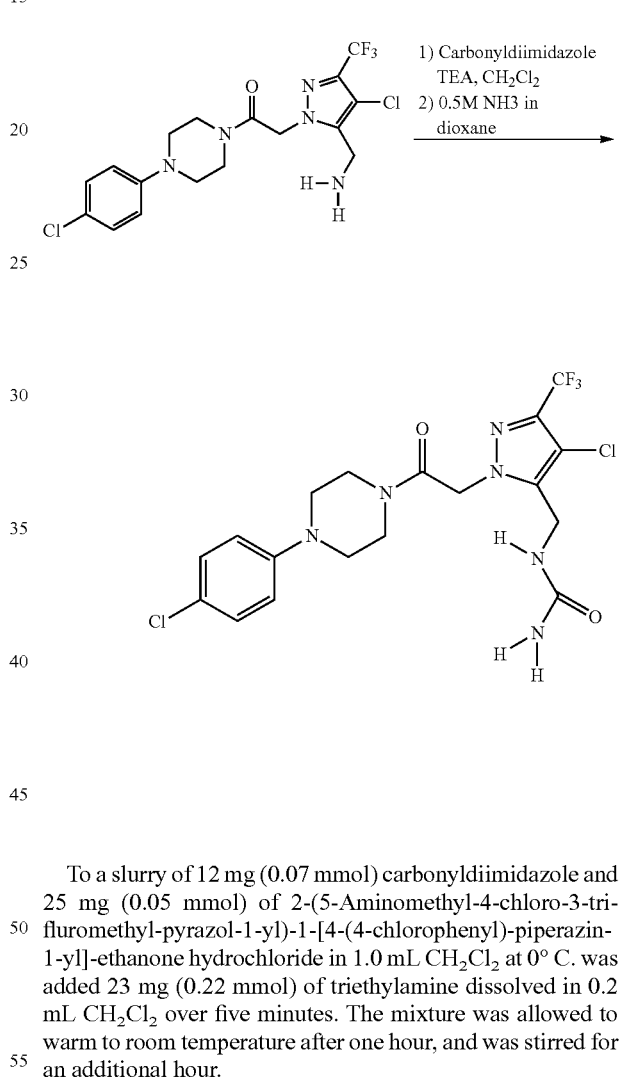

To a slurry of 12 mg (0.07 mmol) carbonyldiimidazole and 25 mg (0.05 mmol) of 2-(5-Aminomethyl-4-chloro-3-tri-flurometyl-pyrazol-1-yl)-1-[4-(4-chlorophenyl)-piperazin-1-yl]-ethanone hydrochloride in 1.0 mL $CH_2Cl_2$ at 0° C. was added 23 mg (0.22 mmol) of triethylamine dissolved in 0.2 mL $CH_2Cl_2$ over five minutes. The mixture was allowed to warm to room temperature after one hour, and was stirred for an additional hour.

1.0 mL (0.5 mmol) of 0.5M ammonia in dioxane was added, and the resulting solution was stirred for 12 hours. The solution was concentrated in vacuo, and the resulting residue was partitioned between ethyl acetate and water. The phases were separated, and the aqueous phase was back-extracted once with ethyl acetate. The combined ethyl acetate phases were washed once each with water, 1M NaOH, brine, dried over $Na_2SO_4$, filtered, and concentrated to a residue. The residue was triturated with ethyl acetate, and the product was isolated as a white solid by filtration: $^1$H NMR (DMSO-d6, 400 MHz) 7.23 (d, 2H), 6.96 (d, 2H), 6.48 (t, 1H), 5.62 (s, 2H), 5.48 (s, 2H), 4.16 (d, 2H), 3.57 (m, 4H), 3.25 (m, 2H), 3.14 (m, 2H) ppm; MS (ES) M+H expected=479.1, found=479.0.

Synthesis of 3-(4-Chloro-2-{2-[4-(4-chloro-phenyl)-piperazin-1-yl]-2-oxo-ethyl}-5-trifluoromethyl-2H-pyrazol-3-ylmethyl)-1,1-dimethyl-urea

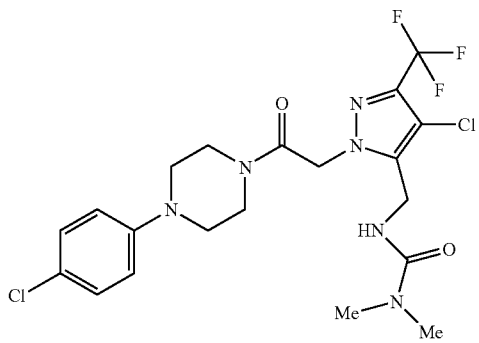

Title compound was prepared following protocol R, using 2M dimethylamine in tetrahydrofuran as the amine component in the second step, to give the desired product as a solid: $^1$H NMR (DMSO-d6, 400 MHz) δ 7.23 (d, 2H), 6.96 (d, 2H), 6.81 (t, 1H), 5.43 (s, 2H), 4.21 (d, 2H), 3.56 (m, 4H), 3.22 (m, 2H), 3.13 (m, 2H), 2.73 (s, 3H) ppm; MS (ES) M+H expected=507.1, found=507.1.

Synthesis of 1-(4-Chloro-2-{2-[4-(4-chloro-phenyl)-piperazin-1-yl]-2-oxo-ethyl}-5-trifluoromethyl-2H-pyrazol-3-ylmethyl)-3-methyl-urea

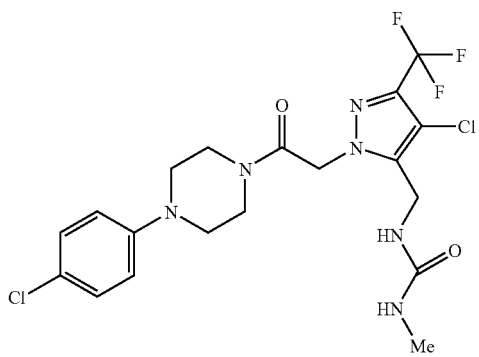

Title compound was prepared following the protocol R, using 2M methylamine in tetrahydrofuran as the amine component in the second step, to give the desired product as a solid: $^1$H NMR (DMSO-d6, 400 MHz) 7.23 (d, 2H), 6.96 (d, 2H), 6.45 (t, 1H), 5.86 (m, 1H), 5.48 (s, 2H), 4.18 (d, 2H), 3.58 (m, 4H), 3.31 (s, 3H), 3.25 (m, 2H), 3.13 (m, 2H) ppm; MS (ES) M+H expected=493.1, found=493.0.

Synthesis of 3-(4-Chloro-2-{2-[4-(4-chloro-phenyl)-piperazin-1-yl]-2-oxo-ethyl}-5-trifluoromethyl-2H-pyrazol-3-ylmethyl)-1-methoxy-1-methyl-urea

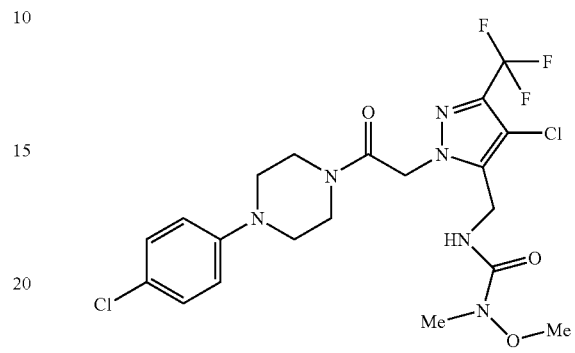

Title compound was prepared following protocol R, using 1M N,O-dimethylhydroxylamine in tetrahydrofuran as the amine component in the second step, to give the desired product as a solid: $^1$H NMR (DMSO-d6, 400 MHz) 7.63 (t, 1H), 7.23 (d, 2H), 6.96 (d, 2H), 5.42 (s, 2H), 4.25 (d, 2H), 3.57 (m, 4H), 3.52 (s, 3H), 3.25 (m, 2H), 3.13 (m, 2H), 2.89 (s, 3H) ppm; MS (ES) M+H expected=523.1, found 523.0.

Synthesis of 1-(4-Chloro-2-{2-[4-(4-chloro-phenyl)-piperazin-1-yl]-2-oxo-ethyl}-5-trifluoromethyl-2H-pyrazol-3-ylmethyl)-3-ethyl-urea

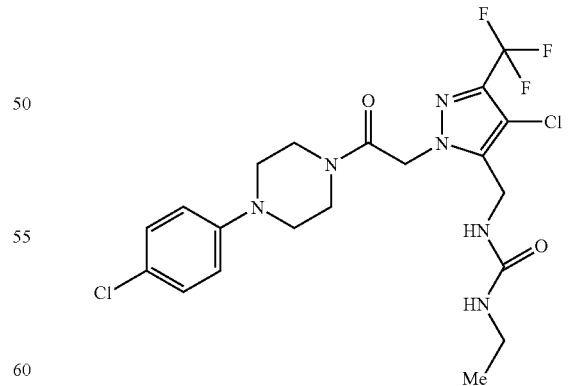

Title compound was prepared following protocol R, using 2M ethylamine in tetrahydrofuran as the amine component in the second step, to give the desired product as a solid: $^1$H NMR (DMSO-d6, 400 MHz) 7.26 (d, 2H), 7.03 (d, 2H), 6.95 (br, 1H), 6.47 (br, 1H), 5.49 (s, 2H), 4.17 (s, 1H), 3.61 (m, 4H), 3.28 (m, 2H), 3.17 (m, 2H), 2.95 (q, 2H), 0.93 (t, 3H) ppm; MS (ES) M+H expected=507.1, found=507.0

Protocol S: Preparation of Chloroacetyl Arylpiperazines

Synthesis of 2-Chloro-1-[4-(4-fluoro-phenyl)-piperazin-1-yl]-ethanone

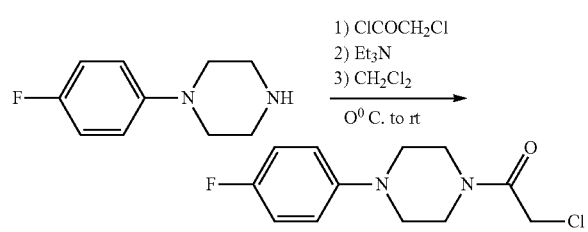

1-(4-Fluorophenyl) piperazine (2.8 mmol) was dissolved in 10 mL of $CH_2Cl_2$. Triethylamine (5.5 mmol) was added to it and the reaction was cooled to 0° C. Chloroacetylchloride (4.2 mmol) was added to it slowly, and the reaction was warmed to room temperature overnight. After completion, the reaction was quenched with brine solution and reaction mixture was extracted with methylene chloride. The combined organic phases were washed with brine and water and dried over magnesium sulfate. The solvent was evaporated and the compound purified by column chromatography (hexane/ethyl acetate=1.5/1) to afford the title compound as a white solid. $^1$H NMR (400 MHz, $CDCl_3$) δ 6.9-7.2 (m, 2H), 6.82-6.92 (m, 2H), 4.1 (s, 2H), 6.62-3.8 (m, 4H), 3.46-3.6 (m, 4H). $^{13}$C NMR (400 MHz, $CDCl_3$) δ 164, 158, 156.2, 148.5, 118.2, 116.8, 52.6, 52.2, 48, 46, 42.1, 40.6.

Synthesis of 2-Chloro-1-[4-(4-chloro-phenyl)-piperazin-1-yl]-ethanone

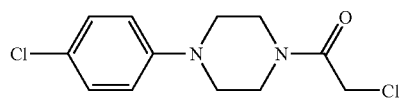

Protocol S was followed using 1-(4-chloro-phenyl) piperazine, $Et_3N$, chloroacetyl chloride and methylene chloride. Column chromatography using a solvent mixture (hexane/ethyl acetate=1.5/1) afforded the title compound as a white solid.

Synthesis of 2-Chloro-1-[4-(4-chloro-3-methoxyphenyl)-piperazin-1-yl]-ethanone

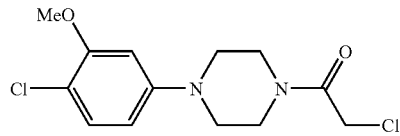

Protocol S was followed using 1-(4-chloro-3-methoxyphenyl) piperazine, $Et_3N$, chloroacetyl chloride and methylene chloride. Column chromatography using a solvent mixture (hexane/ethyl acetate=1.5/1) afforded the title compounds as a white solid Synthesis of 2-Chloro-1-[4-(4-bromo-3-methoxyphenyl)-piperazin-1-yl]-ethanone

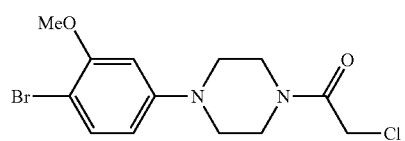

Protocol S was followed using 1-(4-bromo-3-methoxyphenyl) piperazine, $Et_3N$, chloroacetyl chloride and methylene chloride. Column chromatography using a solvent mixture (hexane/ethyl acetate=1.5/1) afforded the title compounds as a white solid.

Synthesis of 2-Chloro-1-[4-(4-chloro-phenyl)-2-methyl-(R)-piperazin-1-yl]-ethanone

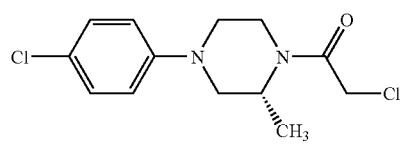

Protocol S was followed using 1-(4-Chloro-phenyl)-3-(R)-methyl-piperazine, $Et_3N$, chloroacetyl chloride and methylene chloride. Column chromatography afforded the title compound.

Synthesis of 2-Chloro-1-[4-(4-chloro-phenyl)-2-methyl-(S)-piperazin-1-yl]-ethanone

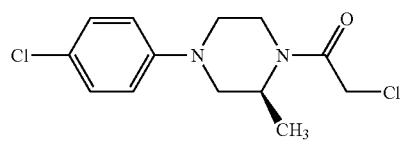

Protocol S was followed using 1-(4-Chloro-phenyl)-3-(S)-methyl-piperazine, Et₃N, chloroacetyl chloride and methylene chloride. Column chromatography afforded the title compound.

Protocol T: K₂CO₃ Mediated Coupling Reaction of Chloroacetyl Arylpiperazines with Pyrazoles Synthesis of 1-[4-(4-Fluoro-phenyl)-piperazin-1-yl]-2-pyrazol-1-yl-ethanone

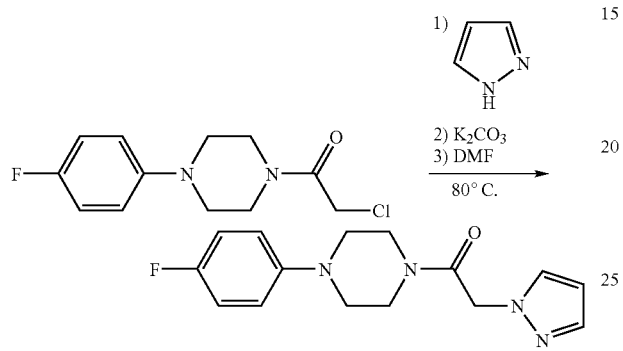

Pyrazole (112.33 mg, 1.65 mmol) was dissolved in DMF (10 mL). K₂CO₃ (228.05 mg, 1.65 mmol) and 2-Chloro-1-[4-(4-fluoro-phenyl)-piperazin-1-yl]-ethanone (300 mg, 1.67 mmol) were added to it. The reaction was heated to 80° C. for 14 h. After completion, the reaction was cooled to room temperature, quenched with brine and then extracted with ethyl acetate. The organic layer was further washed with water (2×25 mL) and brine (2×25 mL) and dried over magnesium sulfate. The solvent was removed by rotary evaporation to give the crude product which was purified by column chromatography on silica gel using a solvent mixture (hexane/ethyl acetate=1/1) to afford the title compound as white solid. ¹H NMR (400 MHz, CDCl₃) δ 7.2-7.58 (d, 2H), 6.94-7.2 (t, 2H), 6.84-6.9 (dd, 2H), 6.32-6.36 (t, 1H), 5.6 (s, 2H), 3.76-3.82 (m, 2H), 3.68-3.74 (m, 2H), 3.04-3.1 (m, 2H), 3.0-3.04 (m, 2H). ¹³C NMR (400 MHz, CDCl₃) δ 165, 158, 146.5, 140, 130, 118.4, 118.2, 116, 115.8, 107, 54, 51, 50.8 45.8, 42.8.

Synthesis of 2-(4-Chloro-5-phenyl-3-trifluoromethyl-pyrazol-1-yl)-1-[4-(4-fluoro-phenyl)-piperazin-1-yl]-ethanone and 2-(4-Chloro-3-phenyl-5-trifluoromethyl-pyrazol-1-yl)-1-[4-(4-fluoro-phenyl)-piperazin-1-yl]-ethanone

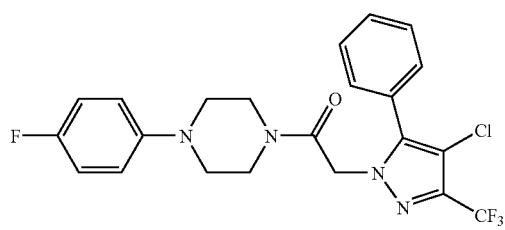

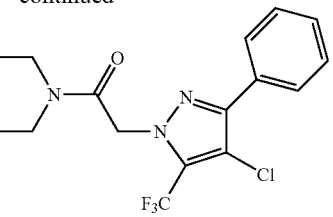

Protocol T was followed using 4-Chloro-5-phenyl-3-trifluoromethyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1.5/1) afforded a mixture of the title compounds, both as white solids

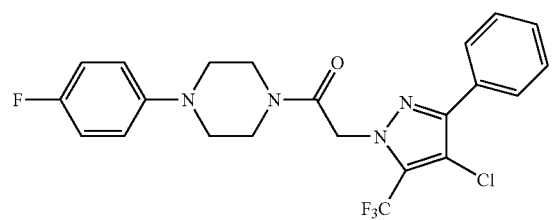

¹H NMR (400 MHz, CDCl₃) δ 7.44-7.54 (m, 5H), 6.94-7.2 (t, 2H), 6.84-6.9 (dd, 2H), 4.94 (s, 1H), 3.72-3.8 (m, 2H), 3.5-3.6 (m, 2H), 3.0-3.1 (m, 4H). ¹³C NMR (400 MHz, CDCl₃) δ 163.8, 158, 146.5, 130, 128.6, 128.2, 118.2, 114.5, 52, 50, 44.5, 42.

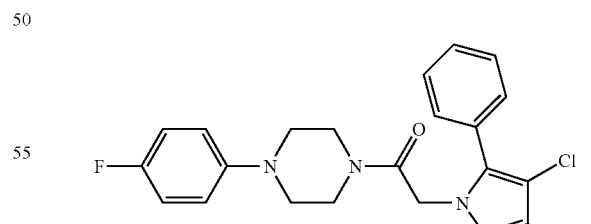

¹H NMR (400 MHz, CDCl₃) δ 7.82-7.88 (m, 2H), 7.38-7.48 (m, 3H), 6.96-7.04 (m, 2H), 6.86-6.94 (m, 2H), 5.2 (s, 1H), 3.76-3.86 (m, 2H), 3.62-3.68 (m, 2H), 3.06-3.22 (m,

4H). $^{13}$C NMR (400 MHz, CDCl$_3$) δ 164, 130, 128.4, 126, 118, 116.4, 52, 50, 43.8, 41.6.

Synthesis of 2-{2-[4-(4-Fluoro-phenyl)-piperazin-1-yl]-2-oxo-ethyl}-5-thiophen-2-yl-2H-pyrazole-3-carboxylic acid ethyl ester

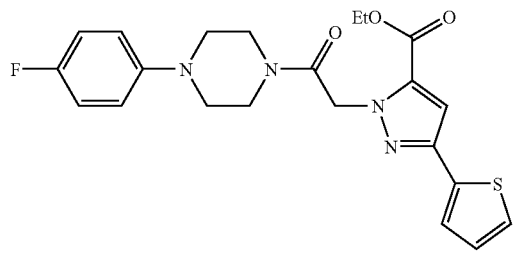

Protocol T was followed using 5-Thiophen-2-yl-2H-pyrazole-3-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=1.5/1) afforded the title compound. $^1$H NMR (400 MHz, CDCl$_3$) δ 7.32-7.36 (m, 1H), 7.22-7.26 (m, 1H), 7.08 (s, 1H), 7.02-7.08 (dd, 1H), 6.96-7.2 (m, 2H), 6.86-6.92 (m, 2H), 4.3-4.4 (q, 2H), 3.52-3.58 (m, 4H), 3.05-3.25 (m, 4H), 1.3-1.42 (m, 3H). 13C NMR (400 MHz, CDCl3) δ 164, 130, 126.8, 126.4, 120, 118.2, 115.4, 62.3, 54, 50.5, 42, 44.5, 14.6.

Synthesis of 2-(3-Amino-4-bromo-5-phenyl-pyrazol-1-yl)-1-[4-(4-fluoro-phenyl)-piperazin-1-yl]-ethanone

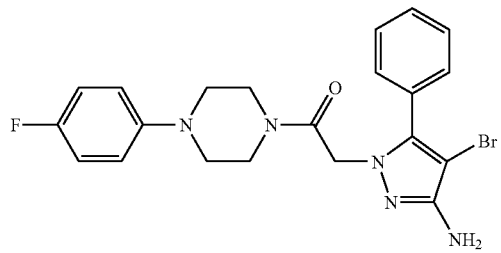

Protocol T was followed using 4-Bromo-5-phenyl-1H-pyrazol-3-ylamine, K$_2$CO$_3$, 2-Chloro-1-[4-(4-fluoro-phenyl)-piperazin-1-yl]-ethanone and DMF. Column chromatography using a solvent mixture (hexane/ethyl acetate=3/7) afforded the title compound as yellow solid. $^1$H NMR (400 MHz, CDCl$_3$) δ 7.74-7.78 (m, 2H), 7.24-7.36 (m, 3H), 6.86-6.92 (m, 2H), 6.74-6.78 (m, 2H), 4.9 (s, 2H), 4.22 (s, 2H), 3.64-3.74 (m, 4H), 2.86-3.04 (m, 4H). $^{13}$C NMR (400 MHz, CDCl$_3$) δ 164, 146.2, 144.8, 128, 126.8, 118, 114.8, 60, 50.2, 50, 48.8, 46, 42, 20.

Synthesis of 2-(3-Amino-4-bromo-5-phenyl-pyrazol-1-yl)-1-[4-(4-chloro-phenyl)-piperazin-1-yl]-ethanone

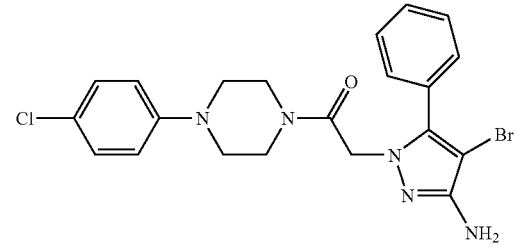

Protocol T was followed using 4-Bromo-5-phenyl-1H-pyrazol-3-ylamine, K$_2$CO$_3$, 2-Chloro-1-[4-(4-chloro-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$) δ 7.7-7.8 (m, 2H), 7.24-7.3 (m, 3H), 6.8-6.92 (m, 2H), 6.74-6.78 (m, 2H), 4.9 (s, 2H), 4.2 (s, 2H), 3.6-3.7 (m, 4H), 2.86-3.04 (m, 4H). $^{13}$C NMR (400 MHz, CDCl$_3$) δ 164, 146, 145, 128, 127, 118, 114.8, 60.2, 50.4, 50, 48.8, 46, 42, 22.

Synthesis of 1-[4-(4-Fluoro-phenyl)-piperazin-1-yl]-2-(3-heptafluoropropyl-5-methyl-4-nitro-pyrazol-1-yl)-ethanone

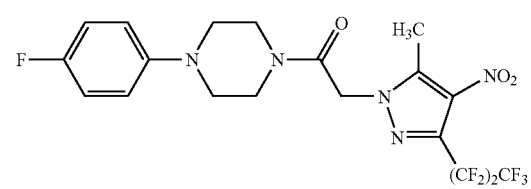

Protocol T was followed using 3-Heptafluoropropyl-5-methyl-4-nitro-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=3/7) afforded the title compound as oil. $^1$H NMR (400 MHz, CDCl$_3$) δ 6.9-7.0 (m, 2H), 6.8-6.9 (m, 2H), 5.06-5.14 (d, 2H), 3.6-3.8 (m, 4H), 3.06-3.18 (m, 4H), 2.56-2.66 (d, 3H). $^{13}$C NMR (400 MHz, CDCl$_3$) δ 160, 146.2, 144, 119.2, 118, 52.2, 50.8, 50.4, 46, 42.2, 12.

Synthesis of 1-[4-(4-Chloro-phenyl)-piperazin-1-yl]-2-(4-chloro-5-phenyl-3-trifluoromethyl-pyrazol-1-yl)-ethanone

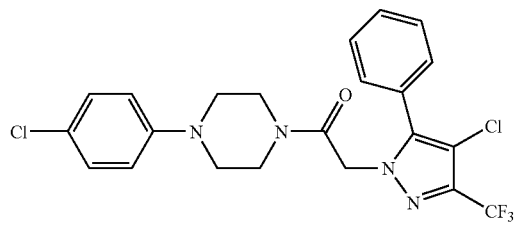

Protocol T was followed using 4-Chloro-5-phenyl-3-trifluoromethyl-1H-pyrazole, K$_2$CO$_3$, 2-Chloro-1-[4-(4-chlorophenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$) δ 7.82-7.84 (m, 2H), 7.4-7.48 (m, 3H), 6.9-7.04 (m, 2H), 6.88-6.94 (m, 2H), 5.22 (s, 1H), 3.76-3.88(m, 2H), 3.6-3.68 (m, 2H), 3.1-3.22 (m, 4H). $^{13}$C NMR (400 MHz, CDCl$_3$) δ 164.2, 130.4, 128, 126, 118.2, 116.4, 52.2, 50, 44, 41.8.

Synthesis of 1-[4-(4-Fluoro-phenyl)-piperazin-1-yl]-2-(4-bromo-5-methyl-3-trifluoromethyl-pyrazol-1-yl)-ethanone

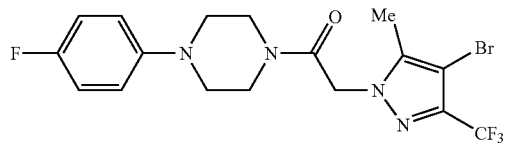

Protocol T was followed using 4-Bromo-5-methyl-3-trifluoromethyl-1H-pyrazole, K$_2$CO$_3$, 2-Chloro-1-[4-(4-fluorophenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$) δ 6.96-7 (m, 2H), 6.84-6.9 (m, 2H), 5 (s, 2H), 3.6-3.8 (m, 4H), 3.02-3.16 (m, 4H), 2.3 (s, 3H). $^{13}$C NMR (400 MHz, CDCl$_3$) δ 162.6, 146.5, 142, 118.5, 116, 52.2, 50.4, 46, 42.2, 15.

Synthesis of 1-[4-(4-Chloro-phenyl)-piperazin-1-yl]-2-(4-bromo-5-methyl-3-trifluoromethyl-pyrazol-1-yl)-ethanone

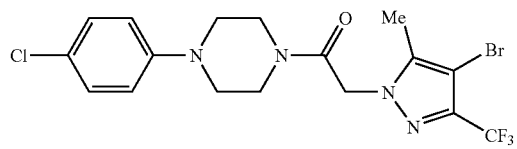

Protocol T was followed using 4-Bromo-5-methyl-3-trifluoromethyl-1H-pyrazole, K$_2$CO$_3$, 2-Chloro-1-[4-(4-chlorophenyl)-piperazin-1-yl]-ethanone and DMF. Column chromatography using a solvent mixture (hexane/ethyl acetate=2/3) afforded the title compound as white solid. $^1$H NMR (400 MHz, CDCl$_3$) δ 6.96-7.1 (m, 2H), 6.84-6.89 (m, 2H), 5.2(s, 2H), 3.6.2-3.8 (m, 4H), 3.0-3.16 (m, 4H), 2.32 (s, 3H). $^{13}$C NMR (400 MHz, CDCl$_3$) δ 162, 146.4, 142.2, 118.5, 116.2, 52, 50.4, 46.2, 42.2, 15.2.

Synthesis of 1-[4-(4-Chloro-phenyl)-piperazin-1-yl]-2-(3-heptafluoropropyl-5-methyl-4-nitro-pyrazol-1-yl)-ethanone

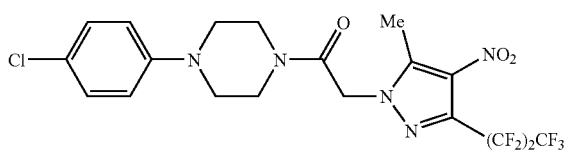

Protocol T was followed using 3-Heptafluoropropyl-5-methyl-4-nitro-1H-pyrazole, K$_2$CO$_3$, 2-Chloro-1-[4-(4-chlorophenyl)-piperazin-1-yl]-ethanone and DMF. Column chromatography using a solvent mixture (hexane/ethyl acetate=1/4, R$_f$=0.81) afforded the title compound as colorless oil. $^1$H NMR (400 MHz, CDCl$_3$) δ 6.92-7.02 (m, 2H), 6.82-6.9 (m, 2H), 5.04-5.14 (m, 2H), 3.64-3.82 (m, 4H), 3.06-3.18 (m, 4H), 2.6-2.66 (d, 3H). $^{13}$C NMR (400 MHz, CDCl$_3$) δ 160.4, 146, 144.2, 119.2, 118.2, 52, 50.8, 50.6, 46, 42, 12.2.

Synthesis of 1-[4-(4-Chloro-3-methoxyphenyl)-piperazin-1-yl]-2-(4-chloro-5-phenyl-3-trifluoromethyl-pyrazol-1-yl)-ethanone

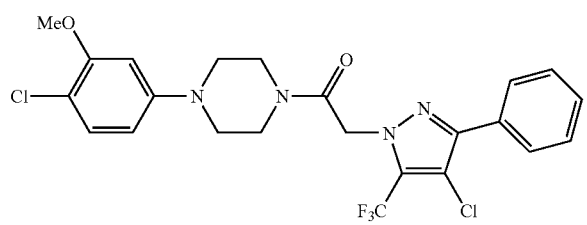

Protocol T was followed using 4-Chloro-5-phenyl-3-trifluoromethyl-1H-pyrazole, K$_2$CO$_3$, 2-Chloro-1-[4-(4-chloro-3-methoxy-phenyl)-piperazin-1-yl]-ethanone and DMF. Column chromatography using a solvent mixture (hexane/ethyl acetate=2/3) afforded the title compound as a white solid. $^1$H NMR (400 MHz, CDCl$_3$) δ 7.4-7.52 (m, 5H), 7.18-7.22 (d, 1H), 6.44-6.48 (d, 1H), 6.36-6.42 (dd, 1H), 4.72 (s, 2H), 3.86

(s, 3H), 3.5-3.78 (m, 4H), 3.1 (s, 4H). $^{13}$C NMR (400 MHz, CDCl$_3$) 164, 156.2, 150.4, 130.5, 130, 128.5, 110, 102.2, 56, 52, 50, 44.8, 42.

3.2 (m, 4H), 2.3 (s, 3H). $^{13}$C NMR (400 MHz, CDCl$_3$) δ 162, 146.6, 142.2, 118.8, 116, 52.2, 50.4, 46.2, 42.2, 15.2.

Synthesis of 1-[4-(4-Bromo-3-methoxyphenyl)-piperazin-1-yl]-2-(4-chloro-3-phenyl-5-trifluoromethyl-pyrazol-1-yl)-ethanone Synthesis of 2-(3-Amino-4-bromo-5-phenyl-pyrazol-1-yl)-1-[4-(4-chloro-3-methoxyphenyl)-piperazin-1-yl]-ethanone

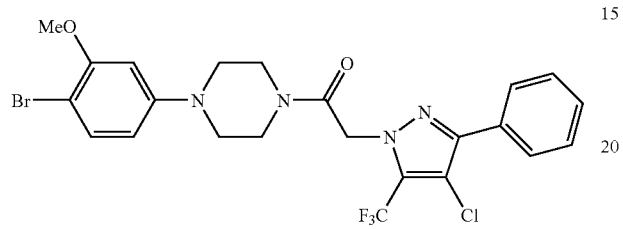
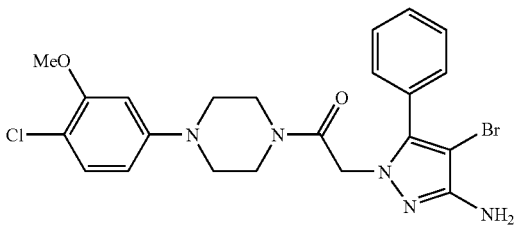

Protocol T was followed using 4-Chloro-5-phenyl-3-trifluoromethyl-1H-pyrazole, K$_2$CO$_3$, 2-Chloro-1-[4-(4-bromo-3-methoxy-phenyl)-piperazin-1-yl]-ethanone and DMF. Column chromatography using a solvent mixture (hexane/ethyl acetate=2/3) afforded the title compound as a white solid. $^1$H NMR (400 MHz, CDCl$_3$) δ 7.42-7.52 (m, 4H), 7.36-7.38 (d, 1H), 6.42-6.46 (d, 1H), 6.34-6.38 (dd, 1H), 4.72 (s, 2H), 3.88 (s, 3H), 3.74-3.78 (m, 2H), 3.54-3.58 (m, 2H), 3.12-3.18 (m, 4H). $^{13}$C NMR (400 MHz, CDCl$_3$) δ 164, 156.2, 152, 132.6, 130.2, 130, 128.8, 110, 102.2, 56, 52, 50, 44.8, 42.

Protocol T was followed using 4-Bromo-5-phenyl-1H-pyrazol-3-ylamine, K$_2$CO$_3$, 2-Chloro-1-[4-(4-chloro-3-methoxy-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$) δ 7.78-7.84 (d, 2H), 7.32-7.42 (m, 3H), 7.18-7.22 (d, 1H), 6.44-6.48 (d, 1H), 6.36-6.42 (dd, 1H), 4.94 (s, 2H), 4.28 (s, 2H), 3.88 (s, 3H), 3.76-3.86 (m, 4H), 3.12-3.18 (m, 4H). $^{13}$C NMR (400 MHz, CDCl$_3$) δ 164.6, 154.8, 150.2, 144.6, 130, 128.2, 128, 126.4, 109.2, 102, 56, 51, 50, 49.6, 45.6, 42.

Synthesis of 1-[4-(4-Chloro-3-methoxy-piperazin-1-yl]-2-(4-bromo-5-methyl-3-trifluoromethyl-pyrazol-1-yl)-ethanone Synthesis of 2-(3-Amino-4-chloro-5-methyl-pyrazol-1-yl)-1-[4-(4-chloro-3-methoxyphenyl)-piperazin-1-yl]-ethanone

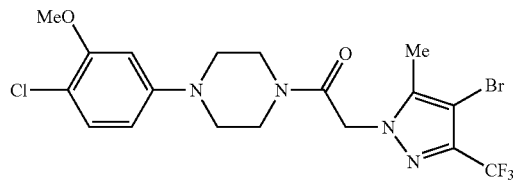
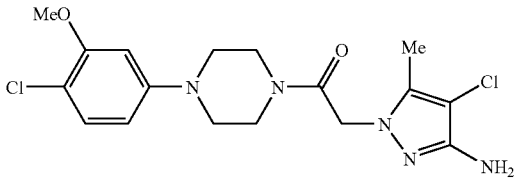

Protocol T was followed using 4-Bromo-5-methyl-3-trifluoromethyl-1H-pyrazole, K$_2$CO$_3$, 2-Chloro-1-[4-(4-chloro-3-methoxy-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$) δ 7.18-7.22 (d, 1H), 6.44-6.48 (d, 1H), 6.36-6.42 (dd, 1H), 5.0 (s, 2H), 3.6.2-3.8 (m, 4H), 3.1-

Protocol T was followed using 4-Chloro-5-methyl-1H-pyrazol-3-ylamine, K$_2$CO$_3$, 2-Chloro-1-[4-(4-chloro-3-methoxy-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$) δ 7.18-7.22 (d, 1H), 6.36-6.42 (dd, 1H), 5.0 (s, 2H), 4.24 (s, 2H), 2.4 (s, 3H), 3.76-3.86 (m, 4H), 3.12-3.18 (m, 4H). $^{13}$C NMR (400 MHz, CDCl$_3$) δ 164.6, 154.8, 144.6, 130.2, 130, 128.8, 109.2, 102, 56, 51, 49.6, 45.6, 42.

Synthesis of 1-[4-(4-Bromo-3-methoxy-piperazin-1-yl]-2-(4-bromo-5-methyl-3-trifluoromethyl-pyrazol-1-yl)-ethanone

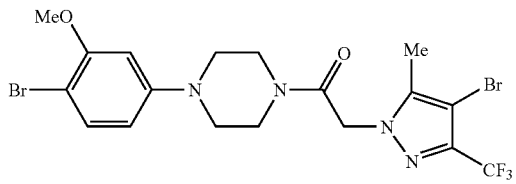

Protocol T was followed using 4-Bromo-5-methyl-3-trifluoromethyl-1H-pyrazole, K$_2$CO$_3$, 2-Chloro-1-[4-(4-bromo-3-methoxy-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$) δ 7.38-7.4 (d, 1H), 6.44-6.46 (d, 1H), 6.26-6.4 (dd, 2H), 5.0 (s, 2H), 3.88 (s, 3H), 3.68-3.8 (m, 4H), 3.14-3.22 (m, 4H), 2.3 (s, 3H). $^{13}$C NMR (400 MHz, CDCl$_3$) δ 164.4, 158, 152.2, 144, 134, 110, 102.2, 56.6, 54.2, 50, 48.8, 46, 42.2, 12.

NMR (400 MHz, CDCl$_3$) δ 164.4, 158, 152.2, 144, 134, 132, 126, 124, 123.8, 118, 116, 115.8, 102.2, 54, 51.2, 50.8, 45.8, 42.2.

Synthesis of 2-(4-Chloro-3-trifluoromethyl-pyrazol-1-yl)-1-[4-(4-fluoro-phenyl)-piperazin-1-yl]-ethanone

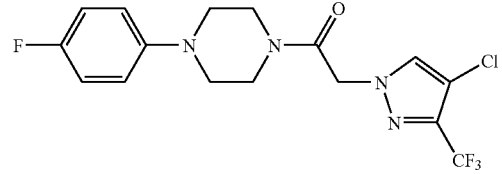

Protocol T was followed using 4-Chloro-3-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as colorless oil. $^1$H NMR (400 MHz, CDCl$_3$) δ 7.64-7.68 (d, 1H), 6.98-7.4 (m, 2H), 6.86-6.92 (m, 2H), 6.98-7.2 (m, 1H), 5.4 (s, 2H), 3.78-3.84 (m, 2H), 3.68-3.92 (m, 2H), 3-3.1 (m, 4H). $^{13}$C NMR (400 MHz, CDCl$_3$) δ 164.4, 158, 152.2, 144, 132, 118.2, 116, 54, 50.2, 50.0, 46.0, 42.2.

Synthesis of 1-[4-(4-Fluoro-phenyl)-piperazin-1-yl]-2-(3-thiophen-2-yl-pyrazol-1-yl)-ethanone

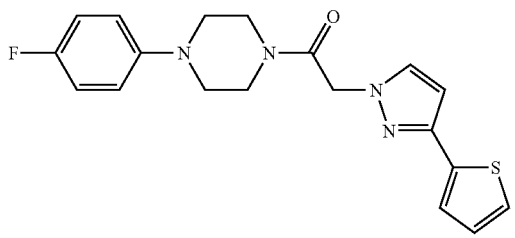

Protocol T was followed using 3-(2-thienyl)pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 7.48-7.52 (d, 1H), 7.24-7.28 (dd, 1H), 7.14-7.2 (dd, 1H), 6.98-7.2 (m, 1H), 6.88-6.96 (m, 2H), 6.78-6.84 (m, 2H), 6.46-6.52 (d, 1H), 5.0 (s, 2H), 3.62-3.8 (m, 4H), 2.94-3.1 (m, 4H). $^{13}$C Synthesis of 1-[4-(4-Fluoro-phenyl)-piperazin-1-yl]-2-(3,4,5-tribromo-pyrazol-4-yl)-ethanone

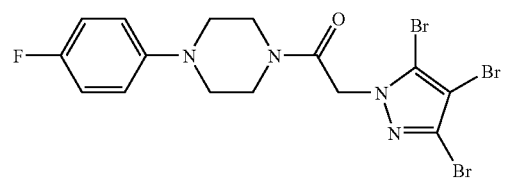

Protocol T was followed using 3,4,5-Tribromo-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as white solid. $^1$H NMR (400 MHz, CDCl$_3$) δ 6.96-7.2 (m, 2H), 6.84-6.9 (m, 2H), 5.4 (s, 2H), 3.74-3.8 (m, 2H), 3.6-3.68 (m, 2H), 3.04-3.14 (m, 4H). $^{13}$C NMR (400

MHz, CDCl₃) δ 164.4, 158, 156, 144.2, 128, 118.4, 118.2, 116, 100, 52.8, 50.2, 50.0, 46.0, 42.2.

Synthesis of 2-(3-tert-Butyl-4-chloro-5-trifluoromethyl-pyrazol-1-yl)-1-[4-(4-fluoro-phenyl)-piperazin-1-yl]-ethanone

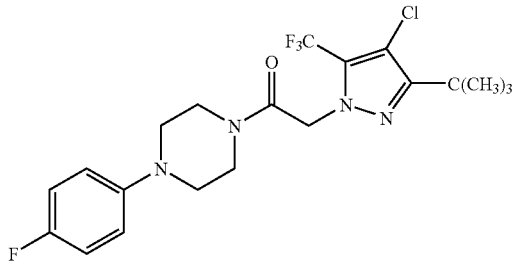

Protocol T was followed using 5-tert-Butyl-4-chloro-3-trifluoromethyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as white solid. ¹H NMR (400 MHz, CDCl₃) δ 6.94-7.22 (m, 2H), 6.84-6.92 (m, 2H), 5.3 (s, 2H), 3.68-3.8 (m, 2H), 3.6-3.68 (m, 2H), 3.04-3.2 (m, 4H), 1.4 (s, 9H). ¹³C NMR (400 MHz, CDCl₃) δ 164.8, 119, 118.4, 118.2, 116.2, 116, 54, 51, 50.8, 45.4, 42.2, 30, 29, 27.

Synthesis of 2-[3-(4-Fluoro-phenyl)-5-methylsulfanyl-pyrazol-1-yl]-1-[4-(4-fluoro-phenyl)-piperazin-1-yl]-ethanone MeS structure Protocol T was followed using 3-(4-Fluoro-phenyl)-5-methylsulfanyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=2/3) afforded the title compound as white solid. ¹H NMR (400 MHz, CDCl₃) δ 7.7-7.76 (m, 2H), 6.96-7.1 (m, 4H), 6.88-6.92 (m, 2H), 6.64 (s, 1H), 5.3 (s, 2H), 3.7-3.84 (m, 4H), 3.04-3.2 (m, 4H), 2.5 (s, 3H). ¹³C NMR (400 MHz, CDCl₃) δ 164.8, 152, 140, 127.4, 119, 118.4, 118.2, 116.2, 116, 108, 52.8, 52, 51.8, 45.4, 42.2, 20.

Synthesis of 2-[4-Chloro-5-(4-Fluoro-phenyl)-3-methylsulfanyl-pyrazol-1-yl]-1-[4-(4-fluoro-phenyl)-piperazin-1-yl]-ethanone

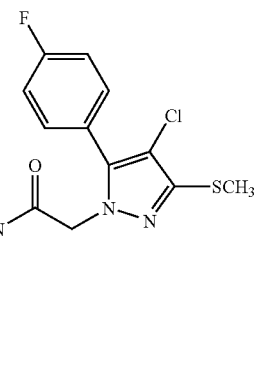

Protocol T was followed using 4-Chloro-3-(4-Fluoro-phenyl)-5-methylsulfanyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=2/3) afforded the title compound as white solid. ¹H NMR (400 MHz, CDCl₃) δ 7.82-7.88 (m, 2H), 7.06-7.12 (m, 2H), 6.96-7.1 (m, 2H), 6.88-6.92 (m, 2H), 5.2 (s, 2H), 3.68-3.84 (m, 4H), 3.06-3.18 (m, 4H), 2.4 (s, 3H). ¹³C NMR (400 MHz, CDCl₃) δ 164.8, 158, 147, 135, 127.4, 127, 119, 112.4, 112.2, 110, 108.8, 52.8, 52, 51.8, 45.4, 42.2, 18.6.

Synthesis of 2-[4-Chloro-3-(4-Fluoro-phenyl)-5-methylsulfanyl-pyrazol-1-yl]-1-[4-(4-fluoro-phenyl)-piperazin-1-yl]-ethanone

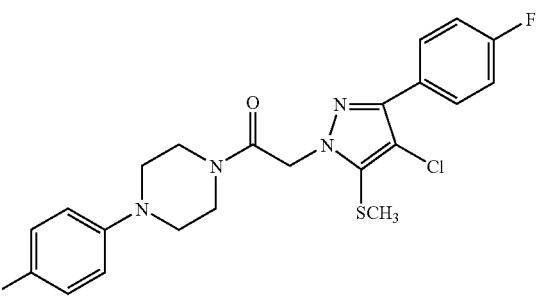

Protocol T was followed using 4-Chloro-3-(4-Fluoro-phenyl)-5-methylsulfanyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=2/3) afforded the title compound as white solid. ¹H NMR (400 MHz, CDCl₃) δ 7.46-7.5 (m, 2H), 7.12-7.18 (m, 2H), 6.96-7.1 (m, 2H), 6.88-6.92 (m, 2H), 4.86 (s, 2H), 3.72-3.78 (m, 2H), 3.56-3.62 (m, 2H), 3.06-3.18 (m, 4H), 2.54 (s, 3H).

Synthesis of 2-{2-[4-(4-Fluoro-phenyl)-piperazin-1-yl]-2-oxo-ethyl}-4-Chloro-3-thiophen-2-yl-2H-pyrazole-5-carboxylic acid ethyl ester

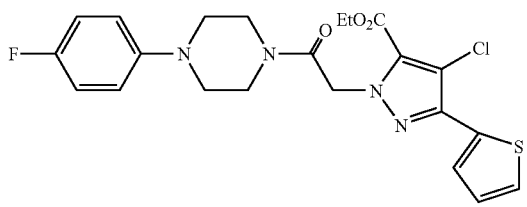

Protocol T was followed using 4-Chloro-3-Thiophen-2-yl-2H-pyrazole-5-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=1.5/1: R$_f$=0.62) afforded the title compound. $^1$H NMR (400 MHz, CDCl$_3$) δ 7.06-7.36 (m, 1H), 6.96-7.2 (m, 3H), 6.84-6.92 (m, 3H), 54.46 (s, 21-1), 4.3-4.4 (q, 2H), 3.6-3.82 (m, 4H), 3.05-3.25 (m, 4H), 1.3-1.42 (m, 3H).

Synthesis of 2-(4-Amino-3-heptafluoropropyl-5-methyl-pyrazol-1-yl)-1-[4-(4-fluoro-phenyl)-piperazin-1-yl]-ethanone

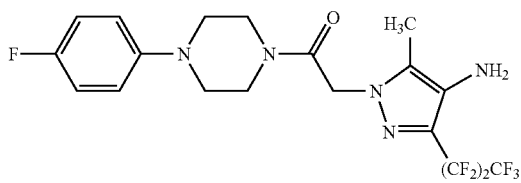

Protocol T was followed using 4-Amino-3-heptafluoropropyl-5-methyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$) δ 6.92-7.02 (m, 4H), 5.14 (s, 2H), 3.64-3.82 (m, 4H), 3.6 (s, 2H), 3.1-3.22 (m, 4H), 2.16 (s, 3H). $^{13}$C NMR (400 MHz, CD$_6$CO) δ 160.4, 158, 146, 144.2, 119.8, 118.2, 52, 50.8, 50.6, 46, 42, 12.2.

Synthesis of 2-(5-Butyl-3-trifluoromethyl-pyrazol-1-yl)-1-[4-(4-chloro-phenyl)-piperazin-1-yl]-ethanone

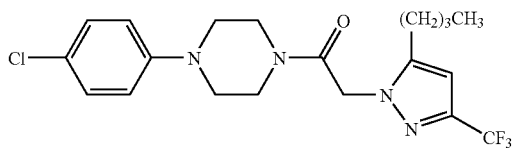

Protocol T was followed using 5-n-Butyl-3-trifluoromethyl-1H-pyrazole, K$_2$CO$_3$, 2-Chloro-1-[4-(4-fluoro-phenyl)-piperazin-1-yl]-ethanone and DMF. Column chroma-tography using a solvent mixture (hexane/ethyl acetate=1/4) afforded the title compound as colorless oil. $^1$H NMR (400 MHz, CDCl$_3$) δ 7.18-7.24 (m, 2H), 6.78-6.84 (m, 2H), 6.32 (s, 1H), 5.0 (s, 2H), 3.66-3.78 (m, 4H), 3.08-3.18 (m, 4H), 2.58-2.64 (t, 2H), 1.6-1.7 (m, 2H), 1.38-1.48 (m, 2H), 0.6-1.0 (t, 3H). $^{13}$C NMR (400 MHz, CDCl$_3$) δ 160.4, 150, 148, 142, 130, 126, 119.8, 103.2, 52, 50.8, 50.6, 46, 42, 30, 26, 22, 14.

Synthesis of 2-(4-Chloro-5-butyl-3-trifluoromethyl-pyrazol-1-yl)-1-[4-(4-chloro-phenyl)-piperazin-1-yl]-ethanone

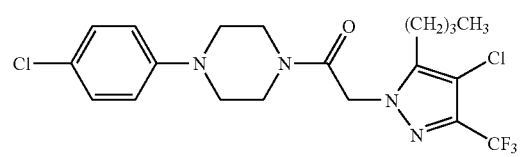

Protocol T was followed using 4-Chloro-5-n-butyl-3-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$) δ 7.18-7.24 (m, 2H), 6.78-6.84 (m, 2H), 5.0 (s, 2H), 3.66-3.78 (m, 4H), 3.08-3.2 (m, 411), 2.58-2.64 (t, 2H), 1.5-1.56 (m, 2H), 1.38-1.48 (m, 2H), 0.6-1.0 (t, 3H). $^{13}$C NMR (400 MHz, CDCl$_3$) δ 160.4, 148, 142, 130, 128, 119.8, 52, 50.8, 50.6, 46, 42, 30.4, 26, 23, 14.

Synthesis of 2-(3-Amino-4-bromo-5-phenyl-pyrazol-1-yl)-1-[4-(4-bromo-3-methoxyphenyl)-piperazin-1-yl]-ethanone

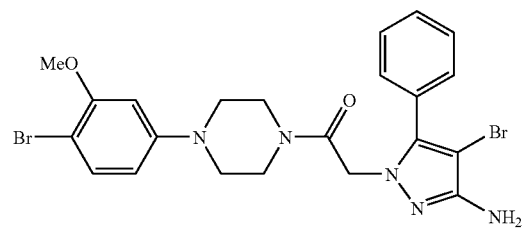

Protocol T was followed using 4-Bromo-5-phenyl-1H-pyrazol-3-ylamine, K$_2$CO$_3$, 2-Chloro-1-[4-(4-bromo-3-methoxy-phenyl)-piperazin-1]-ethanone and DMF. Column chromatography using a solvent mixture (hexane/ethyl acetate=1/1.5) afforded the title compound as white solid. $^1$H NMR (400 MHz, CDCl$_3$) δ 7.78-7.84 (d, 2H), 7.32-7.42 (m, 3H), 7.18-7.22 (d, 1H), 6.44-6.52 (d, 1H), 6.36-6.42 (dd, 111), 4.94 (s, 2H), 4.28 (s, 2H), 3.84 (s, 3H), 3.76-3.82 (m, 4H), 3.12-3.18 (m, 4H). $^{13}$C NMR (400 MHz, CDCl$_3$) δ

164.6, 154.8, 150.2, 144.6, 130, 128.8, 128.6, 126.4, 109.2, 102, 56, 51, 50, 49.6, 45.6, 42.

Synthesis of 2-(4-Bromopyrazol)-1-[4-(4-fluoro-phenyl)-piperazin-1-yl]-ethanone

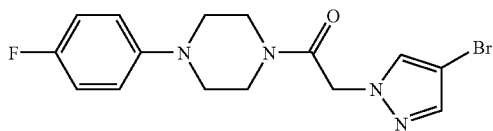

Protocol T was followed using 4-Bromo-1H-pyrazol, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 7.52-7.58 (d, 1H), 7.48-7.52 (d, 1H), 6.95-7.0 (m, 2H), 6.82-6.92 (dd, 2H), 5.00 (s, 2H), 3.72-3.80 (t, 2H), 3.64-3.72 (t, 2H), 3.02-3.12 (m, 4H). $^{13}$C NMR (400 MHz, CDCl$_3$) δ 164.6, 158.2, 156.2, 146.6, 141.6, 140.2, 130.5, 129.6, 118.2, 118.0, 115.2, 116.4, 94.2, 53.8, 50.8, 50.2, 45.4, 42.

Synthesis of 2-(4-Iodopyrazol)-1-[4-(4-fluoro-phenyl)-piperazin-1-yl]-ethanone

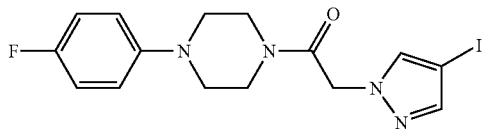

Protocol T was followed using 4-Iodo-1H-pyrazol, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 7.58-7.62 (d, 1H), 7.52 (s, 1H), 6.95-7.1 (m, 2H), 6.84-6.92 (dd, 2H), 5.00 (s, 2H), 3.72-3.80 (t, 2H), 3.64-3.72 (t, 2H), 3.02-3.12 (m, 4H). $^{13}$C NMR (400 MHz, CDCl$_3$) δ 164.6, 158.2, 156.2, 146.8, 140.8, 140.2, 130.5, 129.6, 118.2, 118.0, 115.4, 116.8, 96.0, 53.4, 51.2, 50.2, 45.2, 42.

Synthesis of 2-(3,5-Diisopropyl-pyrazol-1-yl)-1-[4-(4-fluoro-phenyl)-piperazin-1-yl]-ethanone

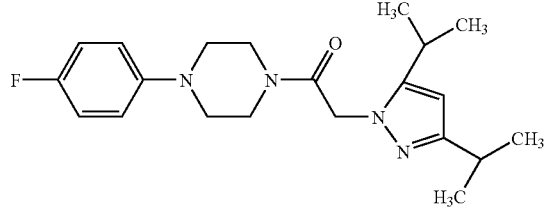

Protocol T was followed using 3,5-Diisopropyl-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as white solid. $^1$H NMR (400 MHz, CDCl$_3$) δ 6.92-7.0 (m, 2H), 6.80-6.88 (dd, 2H), 5.88 (s, 1H), 4.92 (s, 2H), 3.70-3.80 (t, 4H), 2.90-3.10 (m, 4H), 1.40-1.60 (m, 12H). $^{13}$C NMR (400 MHz, CDCl$_3$) δ 160.6, 158.2, 150.2, 119.2, 118.0, 100.0, 50.8, 50.5, 50.2, 45.2, 42, 28.2, 26.0, 22.4.

Synthesis of 1-{2-[4-(4-Fluoro-phenyl)-piperazin-1-yl]-2-oxo-ethyl}-3-trifluoromethyl-1H-pyrazole-4-carboxylic acid ethyl ester

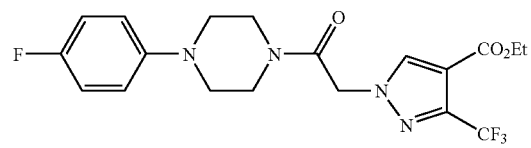

Protocol T was followed using 3-Trifluoromethyl-1H-pyrazole-4-carboxylic acid ethyl ester, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as colorless oil. $^1$H NMR (400 MHz, CDCl$_3$) δ 8.15 (s, 1H), 6.98-7.04 (m, 2H), 6.86-6.92 (m, 2H), 5.1 (s, 2H), 4.28-4.38 (q, 2H), 3.78-3.84 (m, 2H), 3.62-3.74 (m, 2H), 3.04-3.2 (m, 4H), 1.3-1.4 (t, 3H). $^{13}$C NMR (400 MHz, CDCl$_3$) δ 163.4, 160.5, 159.2, 156.2, 147, 137.2, 119, 118.8, 116, 115.8, 61, 54, 50.8, 50.0, 45.0, 42.2, 14.2.

Synthesis of 1-[4-(4-Fluoro-phenyl)-piperazin-1-yl]-2-(4-iodo-3,5-dimethyl-pyrazol-1-yl)-ethanone

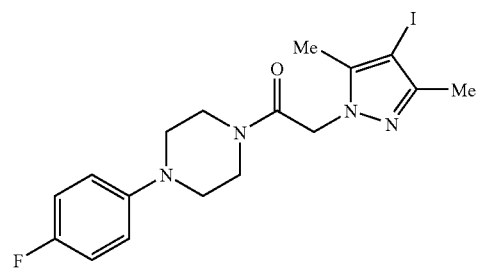

Protocol T was followed using 4-Iodo-3,5-dimethyl-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 6.95-7.1 (m, 2H), 6.84-6.92 (dd, 2H), 5.00 (s, 2H), 3.62-3.82 (m, 4H), 3.02-3.12 (m, 4H), 2.22-2.32 (d, 6H). $^{13}$C NMR (400

MHz, CDCl$_3$) δ 165, 158.2, 156.2, 150.2, 146.8, 141.8, 118.8, 115.4, 115.2, 52.8, 51.6, 50.2, 45.2, 42, 14.8, 12.6.

Synthesis of 2-(3-Chloro-indazol-1-yl)-1-[4-(4-fluoro-phenyl)-piperazin-1-yl]-ethanone

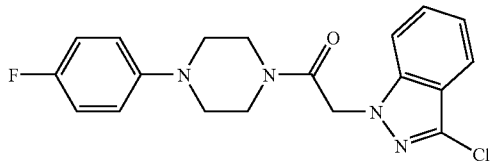

Protocol T was followed using 3-Chloro-1H-indazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as a white solid. $^1$H NMR (400 MHz, CDCl$_3$) δ 7.64-7.70 (m, 1H), 7.38-7.48 (m, 2H), 7.18-7.26 (m, 2H), 6.94-7.0 (m, 2H), 6.82-6.88 (dd, 2H), 5.2 (s, 2H), 3.72-3.82 (m, 4H), 3.02-3.08 (m, 4H). $^{13}$C NMR (400 MHz, CDCl$_3$) δ 165, 158.2, 142.8, 134.8, 128.8, 128.4, 122, 121.6, 118.8, 118.6, 115.4, 115.2, 110.6, 110.0, 51.8, 50.6, 50.2, 45.2, 42.

Synthesis of 2-{2-[4-(4-Fluoro-phenyl)-piperazin-1-yl]-2-oxo-ethyl}-3-propyl-2H-pyrazole-5-carboxylic acid ethyl ester

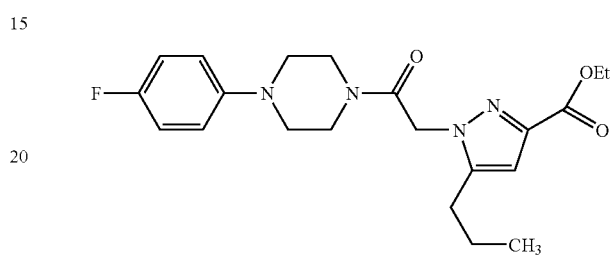

Protocol T was followed using 5-Propyl-2H-pyrazole-3-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as white solid. NMR (400 MHz, CDCl$_3$) δ 6.94-7.0 (m, 2H), 6.82-6.90 (dd, 2H), 6.2 (s, 1H), 5.06 (s, 2H), 4.34-4.40 (q, 2H), 3.62-3.8 (m, 4H), 3.02-3.12 (m, 4H), 2.54-2.60 (t, 2H), 1.64-1.78 (m, 2H), 1.34-1.38 (t, 3H), 0.98-1.4 (t, 3H). $^{13}$C NMR (400 MHz, CDCl$_3$) δ 165, 160, 156.4, 152.2, 146.6, 132.8, 118.4, 118.2, 115.8, 115.4, 113.2, 61, 53, 50.6, 50.2, 45.2, 42, 28, 21.8, 14.2, 14.

Synthesis of 2-{2-[4-(4-Fluoro-phenyl)-piperazin-1-yl]-2-oxo-ethyl}-5-propyl-2H-pyrazole-3-carboxylic acid ethyl ester

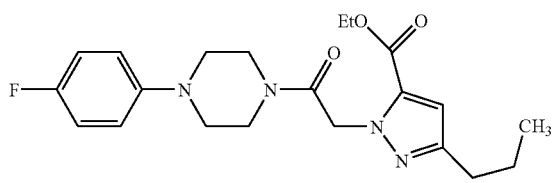

Protocol T was followed using 5-Propyl-2H-pyrazole-3-carboxylic acid ethyl ester, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 6.94-7.0 (m, 2H), 6.82-6.90 (dd, 2H), 6.7 (s, 1H), 5.5 (s, 2H), 4.26-4.32 (q, 2H), 3.62-3.82 (m, 4H), 3.04-3.18 (m, 4H), 2.58-2.64 (t, 2H), 1.64-1.74 (m, 2H), 1.34-1.38 (t, 3H), 0.96-1.0 (t, 3H). $^{13}$C NMR (400 MHz, CDCl$_3$) δ 165, 160, 156.2, 152.4, 146.8, 132.8, 118.2, 118.1, 115.8, 115.4, 110.2, 61, 53, 50.6, 50.2, 45, 42, 30, 22.8, 14.2, 14.

Synthesis of 2-(3,5-Bis-trifluoromethyl-pyrazol-1-yl)-1-[4-(4-fluoro-phenyl)-piperazin-1-yl]-ethanone

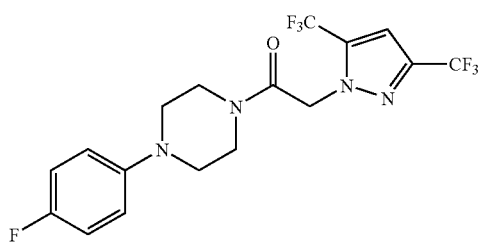

Protocol T was followed using 3,5-Bis-trifluoromethyl-1H-pyrazole, K$_2$CO$_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 6.94-7.0 (m, 2H), 6.92 (s, 1H), 6.82-7.90 (dd, 2H), 5.2 (s, 2H), 3.72-3.8 (t, 2H), 3.58-3.66 (t, 2H), 3.12-3.18 (t, 2H), 3.02-3.12 (t, 2H). $^{13}$C NMR (400 MHz, CDCl$_3$) δ 162.2, 158.2, 156.4, 146.5, 118.4, 116.2, 115.8, 113.2, 60.4, 53.2, 50.6, 50.2, 45.2, 42.2, 21.2, 14.2.

Synthesis of 1-{2-[4-(4-Fluoro-phenyl)-piperazin-1-yl]-2-oxo-ethyl}-1H-pyrazole-3,5-dicarboxylic acid diethyl ester

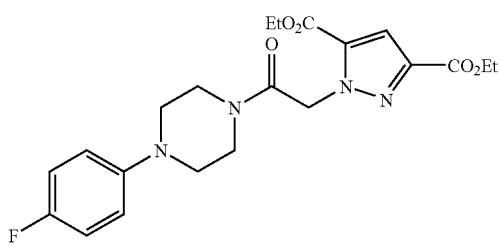

Protocol T was followed using 1H-Pyrazole-3,5-dicarboxylic acid diethyl ester, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃) δ 7.38 (s, 1H), 6.94-7.0 (m, 2H), 6.82-7.90 (dd, 2H), 5.54 (s, 2H), 4.36-4.42 (q, 2H), 4.26-4.32 (q, 2H), 3.60-3.80 (m, 4H), 3.02-3.20 (m, 4H), 1.22-1.42 (m, 6H). ¹³C NMR (400 MHz, CDCl₃) δ 164.2, 162.2, 158.2, 157.4, 156.2, 148.5, 144.4, 134.2, 118.4, 116.2, 115.8, 114.2, 62, 61.8, 54.2, 50.6, 50.2, 45.2, 42.2, 14.6, 14.2.

Synthesis of 2-(3-Amino-4-t-butyl-pyrazol-1-yl)-1-[4-(4-fluorophenyl)-piperazin-1-yl]-ethanone

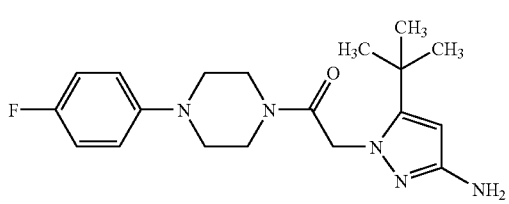

Protocol T was followed using 5-tert-Butyl-1H-pyrazol-3-ylamine, K₂CO₃, 2-Chloro-1-[4-(4-fluoro-phenyl)-piperazin-1-yl]-ethanone and DMF. Column chromatography using a solvent mixture (hexane/ethyl acetate=3/7: R_f=0.49) afforded the title compound as colorless oil. ¹H NMR (400 MHz, CDCl₃) δ 6.92-7.98 (t, 2H), 6.82-6.88 (dd, 2H), 4.84 (s, 2H), 3.95 (s, 2H), 3.70-3.90 (m, 4H), 2.95-3.10 (m, 4H), 1.25 (s, 9H).

Synthesis of 2-{2-[4-(4-Fluoro-phenyl)-piperazin-1-yl]-2-oxo-ethyl}-4-chloro-5-propyl-2H-pyrazole-3-carboxylic acid ethyl ester

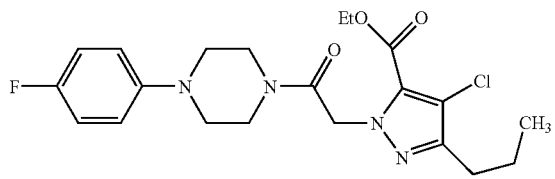

Protocol T was followed using 4-Chloro-5-Propyl-2H-pyrazole-3-carboxylic acid ethyl ester, K₂CO₃, 2-Chloro-1-[4-(4-fluoro-phenyl)-piperazin-1-yl]-ethanone and DMF. Column chromatography using a solvent mixture (hexane/ethyl acetate=3/7) afforded the title compound as a white solid. ¹H NMR (400 MHz, CDCl₃) δ 6.94-7.0 (m, 2H), 6.82-6.90 (dd, 2H), 5.0 (s, 2H), 4.36-4.40 (q, 2H), 3.62-3.82 (m, 4H), 3.04-3.18 (m, 4H), 2.58-2.66 (t, 2H), 1.64-1.76 (m, 2H), 1.34-1.38 (t, 3H), 0.94-1.0 (t, 3H). ¹³C NMR (400 MHz, CDCl₃) δ 165, 160.2, 156.2, 152.4, 147, 133, 118.4, 118.2, 115.8, 115.4, 112.2, 61, 53, 50.6, 50.2, 45, 42, 30, 22.8, 14.4, 14.2.

Synthesis of 2-(3-tert-Butyl-5-trifluoromethyl-pyrazol-1-yl)-1-[4-(4-fluoro-phenyl)-piperazin-1-yl]-ethanone Protocol T was followed using 5-tert-Butyl-3-trifluoromethyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a colorless oil. ¹H NMR (400 MHz, CDCl₃) δ 6.92-7.08 (t, 2H), 6.82-6.88 (dd, 2H), 6.52 (s, 1H), 5.08 (s, 2H), 3.70-3.80 (m, 2H), 3.58-3.68 (m, 2H), 3.05-3.15 (m, 4H), 1.3 (s, 9H). ¹³C NMR (400 MHz, CDCl₃)

δ 164, 161.2, 158.2, 156.4, 147.2, 118.4, 118.2, 115.8, 115.4, 108.2, 54, 50.6, 50.2, 45, 44, 30.

Synthesis of 2-(5-Amino-3-furan-2-yl-pyrazol-1-yl)-1-[4-(4-fluoro-phenyl)-piperazin-1-yl]-ethanone

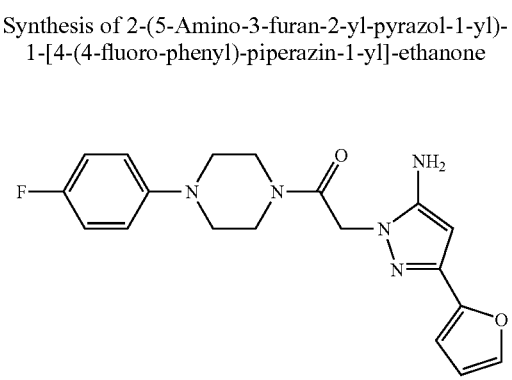

Protocol T was followed using 3-Furan-2-yl-2H-pyrazol-5-ylamine, $K_2CO_3$, 2-Chloro-1-[4-(4-fluoro-phenyl)-piperazin-1-yl]-ethanone and DMF. Column chromatography using 100% ethyl acetate afforded the title compound as a white solid. $^1$H NMR (400 MHz, $CD_6CO$) δ 7.48-7.52 (m, 1H), 6.98-7.06 (m, 2H), 6.52-6.56 (m, 2H), 6.44-6.48 (m, 2H), 5.74 (s, 1H), 4.98 (s, 2H), 3.68-3.88 (m, 4H), 3.12-3.24 (m, 4H). MS (ES) M+H) expected=369.4, found 370.1.

Synthesis of 1-[4-(4-Fluoro-phenyl)-piperazin-1-yl]-2-(4-bromo-3,5-dimethyl-pyrazol-1-yl)-ethanone

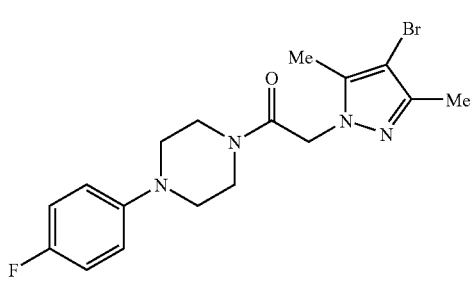

Protocol T was followed using 4-Bromo-3, 5-dimethyl-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, $CDCl_3$) δ 6.95-7.1 (m, 2H), 6.84-6.92 (dd, 2H), 4.90 (s, 2H), 3.62-3.82 (m, 4H), 3.02-3.12 (m, 4H), 2.24-2.34 (d, 6H). $^{13}$C NMR (400 MHz, $CDCl_3$) δ 165, 158.4, 156.6, 150.6, 146.8, 141.4, 119, 115.6, 115.2, 52.6, 51.6, 50.4, 45.2, 42.2, 14.8, 12.6.

Synthesis of 2-[4-Chloro-3-(5-chloro-thiophen-2-yl)-pyrazol-1-yl]-1-[4-(4-fluoro-phenyl)-piperazin-1-yl]-ethanone

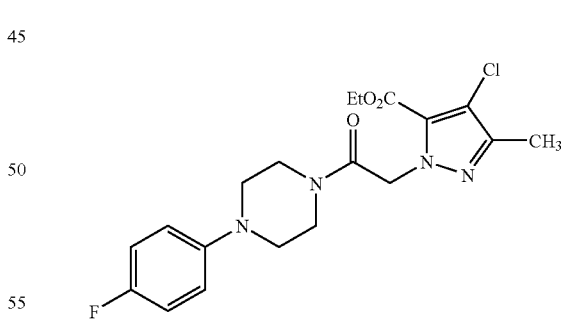

Protocol T was followed using 4-Chloro-3-(5-chloro-thiophen-2-yl)-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as yellow solid. $^1$H NMR (400 MHz, $CDCl_3$) δ 7.58 (s, 1H), 7.38-7.42 (d, 1H), 6.94-7.1 (m, 2H), 6.84-6.88 (dd, 2H), 4.96 (s, 2H), 3.62-3.81 (m, 4H), 3.02-3.14 (m, 4H). $^{13}$C NMR (400 MHz, $CDCl_3$) δ 165, 158.8, 156.8, 142.4, 131, 126.8, 124.8, 119, 116, 115.6, 54, 52, 51.6, 46, 42.6.

Synthesis of 4-Chloro-2-{2-[4-(4-fluoro-phenyl)-piperazin-4-yl]-2-oxo-ethyl}-5-methyl-2H-pyrazole-3-carboxylic acid ethyl ester Protocol T was followed using 4-Chloro-5-methyl-2H-pyrazole-3-carboxylic acid ethyl ester, $K_2CO_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as a white solid. $^1$H NMR (400 MHz, $CDCl_3$) δ 6.94-7.1 (m, 2H), 6.84-6.88 (dd, 2H), 5.04 (s, 2H), 4.38-4.44 (q, 2H), 3.62-3.80 (m, 4H), 3.02-3.14 (m, 4H), 2.3 (s, 3H), 1.36-1.42 (t, 3H). $^{13}$C NMR (400 MHz, $CDCl_3$) δ 182, 165, 119, 116.2, 116, 61.4, 52.3, 51, 50.8, 45.8, 42.6, 14.4, 10.

Synthesis of 4-Chloro-5-(5-chloro-thiophen-2-yl)-2-{2-[4-(4-fluoro-phenyl)-piperazin-1-yl]-2-oxo-ethyl}-2H-pyrazole-3-carboxylic acid ethyl ester

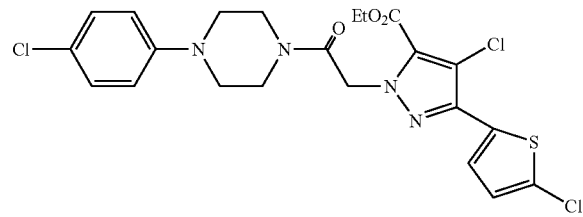

Protocol T was followed using 4-Chloro-5-(5-chloro-thiophen-2-yl)-2H-pyrazole-3-carboxylic acid ethyl ester, $K_2CO_3$, 2-Chloro-1-[4-(4-fluoro-phenyl)-piperazin-1-yl]-ethanone and DMF. Column chromatography using a solvent mixture (hexane/ethyl acetate=2/3) afforded the title compound as a yellow solid. $^1$H NMR (400 MHz, CDCl$_3$) δ 7.46-7.48 (m, 1H), 6.94-7.1 (m, 2H), 6.84-6.92 (m, 3H), 5.4 (s, 2H), 4.34-4.4 (q, 2H), 3.62-3.81 (m, 4H), 3.04-3.24 (m, 4H), 1.36-1.44 (m, 3H). MS (ES) M+H expected=511.41, found 511.

Synthesis of 2-(3-Amino-4-chloro-5-methyl-pyrazol-1-yl)-1-[4-(4-chlorophenyl)-piperazin-1-yl]-ethanone

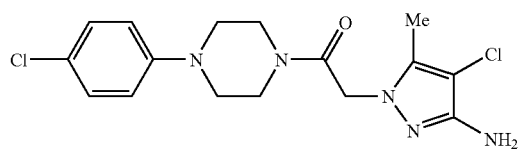

Protocol T was followed using 4-Chloro-5-methyl-1H-pyrazol-3-ylamine, $K_2CO_3$, 2-Chloro-1-[4-(4-chloro-phenyl)-piperazin-1-yl]-ethanone and DMF. Column chromatography using a solvent mixture (hexane/ethyl acetate=1/4) afforded the title compound as a colorless oil. $^1$H NMR (400 MHz, CDCl$_3$) δ 7.18-7.22 (d, 1H), 6.78-6.84 (d, 2H), 4.8 (s, 2H), 4.4 (s, 2H), 3.72-3.82 (m, 4H), 3.08-3.18 (m, 4H), 2.14 (s, 3H).

Synthesis of 1-[4-(4-Bromo-3-methoxyphenyl)-piperazin-1-yl]-2-(4-chloro-5-phenyl-3-trifluoromethyl-pyrazol-1-yl)-ethanone

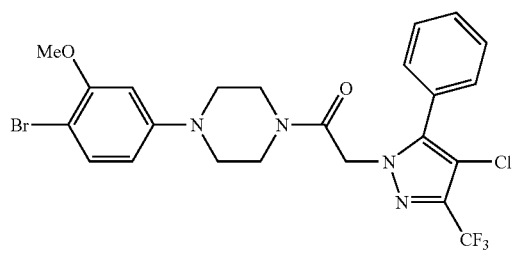

Protocol T was followed using 4-Chloro-5-phenyl-3-trifluoromethyl-1H-pyrazole, $K_2CO_3$, 2-Chloro-1-[4-(4-bromo-3-methoxy-phenyl)-piperazin-1-yl]-ethanone and DMF. Column chromatography using a solvent mixture (hexane/ethyl acetate=2/3: R$_f$=0.58) afforded the title compound as a white solid. $^1$H NMR (400 MHz, CDCl$_3$) δ 7.81-7.86 (m, 1H), 7.36-7.44 (m, 4H), 6.42-6.48 (d, 1H), 6.34-6.38 (dd, 2H), 5.2 (s, 2H), 3.88 (s, 3H), 3.62-3.82 (m, 4H), 3.12-3.22 (m, 4H).

Synthesis of 1-[4-(4-Fluorophenyl)-piperazin-1-yl]-2-(3-trifluoromethyl-pyrazol)-ethanone

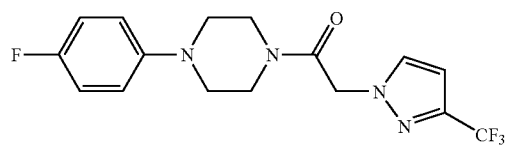

Protocol T was followed using 3-trifluoromethyl-1H-pyrazole, $K_2CO_3$, 2-Chloro-1-[4-(4-fluoro-phenyl)-piperazin-1-yl]ethanone and DMF. Column chromatography using a solvent mixture (hexane/ethyl acetate=1/1) afforded the title compound as a white solid. $^1$H NMR (400 MHz, CDCl$_3$) δ 7.54-7.60 (m, 1H), 6.94-7.0 (m, 2H), 6.80-6.88 (m, 2H), 6.52-6.58 (d, 1H), 5.2 (s, 2H), 3.72-3.80 (t, 2H), 3.62-3.72 (t, 2H), 3.02-3.12 (m, 4H). MS (ES) M+H expected 356.33, found 357.1.

Synthesis of 1-[4-(4-Fluorophenyl)-piperazin-1-yl]-2-(3-methyl-pyrazol)-ethanone

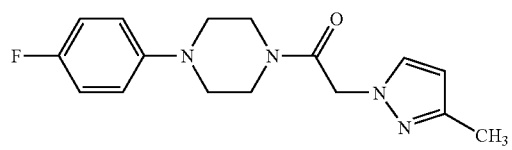

Protocol T was followed using 3-methyl-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 7.38-7.41 (m, 1H), 6.94-7.0 (m, 2H), 6.80-6.88 (m, 2H), 6.08-6.10 (d, 1H), 4.95 (s, 2H), 3.74-3.82 (t, 2H), 3.62-3.72 (t, 2H), 3.0-3.1 (m, 4H), 2.28 (s, 3H). MS (ES) M+H expected 302.05, found 303.1.

Synthesis of 1-{2-[4-(4-Fluoro-phenyl)-piperazin-1-yl]-2-oxo-ethyl}-1H-pyrazole-4-carboxylic acid ethyl ester

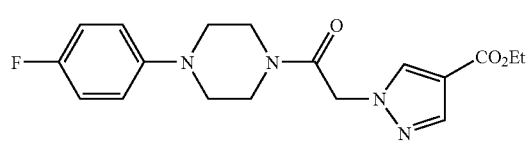

Protocol T was followed using 1H-Pyrazole-4-carboxylic acid ethyl ester, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 8.2 (s, 1H), 7.92 (s, 1H), 6.94-7.0 (m, 2H), 6.82-6.88 (m, 2H), 5.0 (s, 2H), 4.1-4.2 (q, 2H), 3.74-3.82 (t, 2H), 3.62-3.72 (t, 2H), 3.0-3.12 (m, 4H), 1.28-1.42 (t, 3H). MS (ES) M+H expected 360.39, found 361.1.

Synthesis of 1-[4-(4-Fluorophenyl)-piperazin-1-yl]-2-(4-methyl-pyrazol)-ethanone

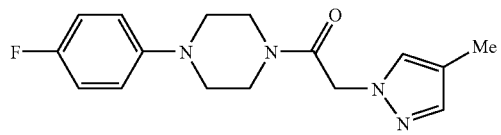

Protocol T was followed using 4-methyl-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1) afforded the title compound as a white solid. ¹H NMR (400 MHz, CDCl₃) δ 7.26-7.32 (m, 1H), 6.94-7.0 (m, 2H), 6.80-6.88 (m, 2H), 5.0 (s, 2H), 3.62-3.82 (m, 4H), 3.0-3.1 (m, 4H), 2.1 (s, 3H). MS (ES) M+H expected 302.35, found 303.1.

Synthesis of 1-[4-(4-Fluorophenyl)-piperazin-1-yl]-2-(3-amino-4-bromopyrazole)-ethanone

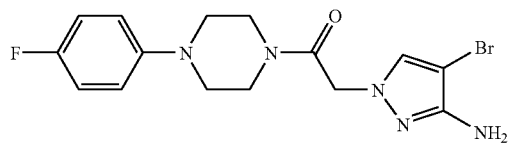

Protocol T was followed using 4-bromo-3-aminopyrazole, K₂CO₃, 2-Chloro-1-[4-(4-fluoro-phenyl)-piperazin-1-yl]-ethanone and DMF. Column chromatography using a solvent mixture (hexane/ethyl acetate=3/7) afforded the title compound as a white solid. ¹H NMR (400 MHz, CDCl₃) δ 7.23 (s, 1H), 6.94-7.0 (m, 2H), 6.80-6.88 (m, 2H), 4.9 (s, 2H), 4.2 (s, 2H), 3.72-3.82 (m, 4H), 3.0-3.14 (m, 4H). MS (ES) M+H expected 382.24, found 382.

Synthesis of 1-[4-(4-Fluorophenyl)-piperazin-1-yl]-2-(3-amino-4-cyanopyrazole)-ethanone

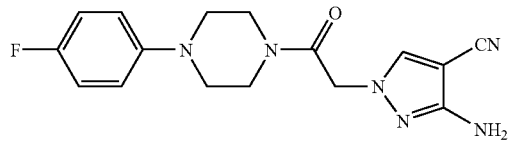

Protocol T was followed using 3-amino-4-cyano-pyrazole, K₂CO₃, 2-Chloro-1-[4-(4-fluoro-phenyl)-piperazin-1-yl]-ethanone and DMF. Column chromatography using a solvent mixture (hexane/ethyl acetate=3/7) afforded the title compound as a solid. ¹H NMR (400 MHz, CDCl₃) δ 7.48 (s, 1H), 6.96-7.2 (m, 2H), 6.86-6.92 (m, 2H), 4.96 (s, 2H), 4.88 (s, 2H), 3.78-3.86 (m, 4H), 3.08-3.16 (m, 4H). MS (ES) M+H expected 328.25, found 329.1

Synthesis of 3-Amino-5-cyanomethyl-1-{2-[4-(4-fluoro-phenyl)-piperazin-1-yl]-2-oxo-ethyl}-1H-pyrazole-4-carbonitrile

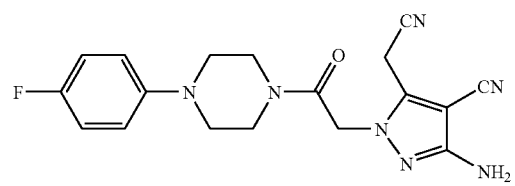

Protocol T was followed using 5-amino-3-cyanomethyl-1H-pyrazole-4-carbonitrile, K₂CO₃, 2-Chloro-1-[4-(4-fluoro-phenyl)-piperazin-1-yl]-ethanone and DMF. Column chromatography using a solvent mixture (hexane/ethyl acetate=3/2) afforded the title compound as white solid. ¹H NMR (400 MHz, CDCl₃) δ 6.96-7.2 (m, 2H), 6.86-6.92 (m, 2H), 5.2 (s, 2H), 4.86 (s, 2H), 3.78-3.86 (m, 4H), 3.7 (s, 2H), 3.08-3.16 (m, 4H). MS (ES) M+H expected 367.39, found 368.1.

Synthesis of 1-[4-(4-Fluorophenyl)-piperazin-1-yl]-2-(4-chloro-pyrazol)-ethanone

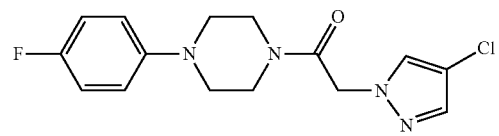

Protocol T was followed using 4-chloro-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=3/2) afforded the title compound as a white solid. ¹H NMR (400 MHz, CDCl₃) δ 7.54-7.56 (d, 2H), 7.46 (s, 1H), 6.94-7.2 (m, 2H), 6.84-6.88 (m, 2H), 4.98 (s, 2H), 3.62-3.82 (m, 4H), 3.0-3.1 (m, 4H). MS (ES) M+H expected 322.77, found 323.1

Synthesis of 2-(3-Amino-5-methyl-pyrazol-1-yl)-1-[4-(4-fluorophenyl)-piperazin-1-yl]-ethanone

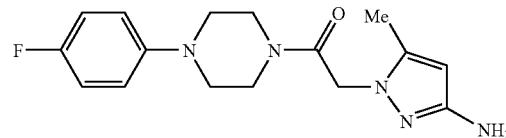

Protocol T was followed using 5-methyl-1H-pyrazol-3-ylamine, K₂CO₃, 2-Chloro-1-[4-(4-fluoro-phenyl)-piperazin-1-yl]-ethanone and DMF. Column chromatography using a solvent mixture (hexane/ethyl acetate=1/4) afforded the title compound as a colorless oil. ¹H NMR (400 MHz, CDCl₃) δ 7.12-7.18 (m, 3H), 7.0-7.08 (t, 2H), 4.8 (s, 2H), 5.1

(s, 2H), 3.78-3.88 (m, 4H), 3.18-3.38 (m, 4H), 2.28 (s, 3H). MS (ES) M+H expected 317.37, found 318.1

Synthesis of 3-Amino-1-{2-[4-(4-fluoro-phenyl)-piperazin-1-yl]-2-oxo-ethyl}-5-methyl-1H-pyrazole-4-carboxylic acid ethyl ester

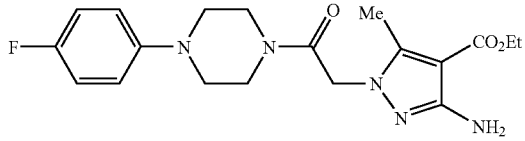

Protocol T was followed using 3-Amino-5-methyl-1H-pyrazole-4-carboxylic acid ethyl ester, $K_2CO_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as a colorless oil. $^1$H NMR (400 MHz, CDCl$_3$) δ 6.94-7.1 (m, 2H), 6.84-6.88 (m, 2H), 5.52 (s, 2H), 4.78 (s, 2H), 4.24-4.32 (q, 2H), 3.74-3.82 (m, 4H), 3.0-3.1 (m, 4H), 2.3 (s, 3H), 1.31-1.38 (t, 3H). MS (ES) M+H expected 389.43, found 390.1.

Synthesis of 2-(3-Amino-4-chloro-5-methyl-pyrazol-1-yl)-1-[4-(4-fluorophenyl)-piperazin-1-yl]-ethanone

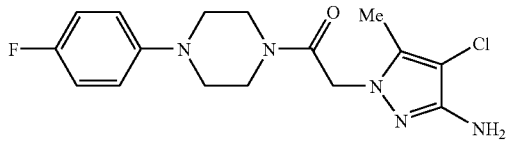

Protocol T was followed using 4-Chloro-5-methyl-1H-pyrazol-3-ylamine, $K_2CO_3$, 2-Chloro-1-[4-(4-fluoro-phenyl)-piperazin-1-yl]-ethanone and DMF. Column chromatography using a solvent mixture (hexane/ethyl acetate=1/4) afforded the title compound as colorless oil. $^1$H NMR (400 MHz, CDCl$_3$) δ 7.02-7.08 (m, 2H), 6.94-7.0 (t, 2H), 4.85 (s, 2H), 4.2 (s, 2H), 3.80-3.88 (m, 4H), 3.14-3.34 (m, 4H), 2.34 (s, 3H), MS (ES) M+H expected 317.37, found 318.1. MS (ES) M+H expected 351.81, found 352.1.

Synthesis of 2-(3-Amino-4-bromo-5-methyl-pyrazol-1-yl)-1-[4-(4-fluorophenyl)-piperazin-1-yl]-ethanone

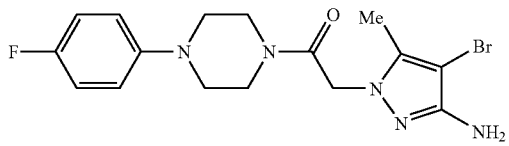

Protocol T was followed using 4-Bromo-5-methyl-1H-pyrazol-3-ylamine, $K_2CO_3$, 2-Chloro-1-[4-(4-fluoro-phenyl)-piperazin-1-yl]-ethanone and DMF. Column chromatography ethyl acetate afforded the title compound as a colorless oil. $^1$H NMR (400 MHz, CDCl$_3$) δ 6.94-7.02 (m, 2H), 6.82-6.88 (t, 2H), 4.84 (s, 2H), 4.1 (s, 2H), 3.72-3.78 (m, 4H), 3.04-3.08 (m, 4H), 2.16 (s, 3H). MS (ES) M+H expected 317.37, found 318.1. MS (ES) M+H expected 396.27, found 396.

Synthesis of 2-(5-tert-Butyl-3-trifluoromethyl-pyrazol-1-yl)-1-[4-(4-fluoro-phenyl)-piperazin-1-yl]-ethanone

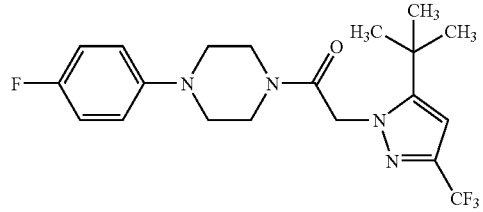

Protocol T was followed using 5-tert-Butyl-3-trifluoromethyl-1H-pyrazole, $K_2CO_3$, 2-Chloro-1-[4-(4-fluoro-phenyl)-piperazin-1-yl]-ethanone and DMF. Column chromatography using a solvent mixture (hexane/ethyl acetate=1/1) afforded the title compound as a colorless oil. $^1$H NMR (400 MHz, CDCl$_3$) δ 6.94-7.08 (t, 2H), 6.82-6.88 (dd, 2H), 6.32 (s, 1H), 5.14 (s, 2H), 3.62-3.80 (m, 4H), 3.05-3.18 (m, 4H), 1.35 (s, 9H). MS (ES) M+H expected 412.43, found 413.1

Synthesis of 2-{2-[4-(4-Fluoro-phenyl)-piperazin-1-yl]-2-oxo-ethyl}-5-methyl-2H-pyrazole-3-carboxylic acid ethyl ester

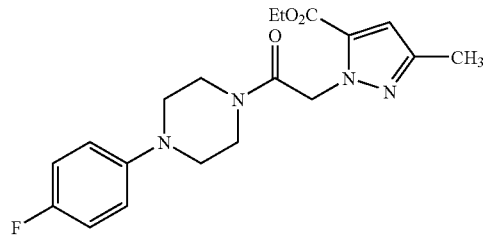

Protocol T was followed using 5-methyl-2H-pyrazole-3-carboxylic acid ethyl ester, $K_2CO_3$, 2-Chloro-1-[4-(4-fluorophenyl)-piperazin-1-yl]-ethanone and DMF. Column chromatography using a solvent mixture (hexane/ethyl acetate=1/1) afforded the title compound as a white solid. $^1$H NMR (400 MHz, CDCl$_3$) δ 6.94-7.0 (m, 2H), 6.84-6.88 (dd, 2H), 6.58 (s, 1H), 5.04 (s, 2H), 4.3-4.38 (q, 2H), 3.62-3.80 (m, 4H), 3.02-3.14 (m, 4H), 2.3 (s, 3H), 1.32-1.38 (t, 3H). $^{13}$C NMR (400

MHz, CDCl₃) δ 180, 165, 119, 116.2, 116, 109, 61.8, 52, 51.5, 50.8, 45.8, 42.6, 14.4, 10.2.

Synthesis of 2-(3,5-Diisopropyl-4-chloro-pyrazol-1-yl)-1-[4-(4-fluoro-phenyl)-piperazin-1-yl]-ethanone

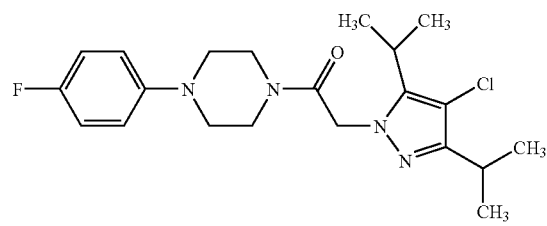

Protocol T was followed using 3,5-Diisopropyl-4-chloro-1H-pyrazole, K₂CO₃, 2-Chloro-1-[4-(4-fluoro-phenyl)-piperazin-1-yl]-ethanone and DMF. Column chromatography using a solvent mixture (hexane/ethyl acetate=1/1, R$_f$=0.76) afforded the title compound as white solid. MS (ES) M+H expected=406.9, found 407.1.

Synthesis of 2-{2-[4-(4-Chloro-phenyl)-piperazin-1-yl]-2-oxo-ethyl}-5-thiophen-2-yl-2H-pyrazole-3-carboxylic acid ethyl ester

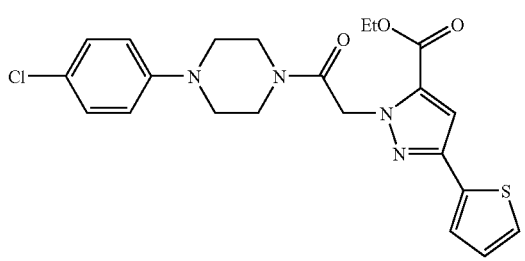

Protocol T was followed using 5-Thiophen-2-yl-2H-pyrazole-3-carboxylic acid ethyl ester, K₂CO₃, 2-Chloro-1-[4-(4-Chloro-phenyl)-piperazin-1-yl]-ethanone and DMF. Column chromatography using a solvent mixture (hexane/ethyl acetate=1.5/1) afforded the title compound. ¹H NMR (400 MHz, CDCl₃) δ 7.34-7.38 (m, 1H), 7.24-7.26 (m, 1H), 7.12 (s, 1H), 7.04-7.08 (dd, 1H), 6.96-7.2 (m, 2H), 6.88-6.94 (m, 2H), 4.32-4.42 (q, 2H), 3.52-3.58 (m, 4H), 3.05-3.35 (m, 4H), 1.32-1.42 (m, 3H). 13C NMR (400 MHz, CDCl3) δ 164.2, 128, 126.8, 126.6, 120.2, 118.4, 115.2, 62.5, 54.2, 50.5, 42.6, 44, 14.6.

Synthesis of 2-(4-Amino-3-heptafluoropropyl-5-methyl-pyrazol-1-yl)-1-[4-(4-chloro-phenyl)-piperazin-1-yl]-ethanone

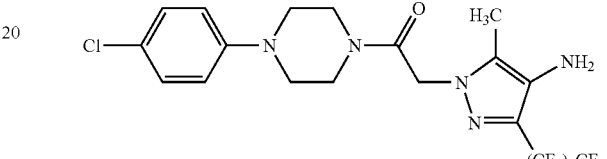

Protocol T was followed using 4-Amino-3-heptafluoropropyl-5-methyl-1H-pyrazole, K₂CO₃, 2-Chloro-1-[4-(4-chloro-phenyl)-piperazin-1-yl]-ethanone and DMF. Column chromatography using a solvent mixture (hexane/ethyl acetate=1/4, R$_f$=0.42) afforded the title compound as colorless oil. ¹H NMR (400 MHz, CDCl₃) δ 6.88-6.94 (d, 2H), 7.22-7.26 (d, 2H), 4.98 (s, 2H), 3.64-3.82 (m, 4H), 3.1-3.22 (m, 4H), 2.98 (s, 2H), 2.18 (s, 3H). MS (ES) M+H expected=501.82, found 502.1.

Synthesis of 1-[4-(4-Chloro-3-methoxy-phenyl)-piperazin-1-yl]-2-(4-chloro-5-ethyl-3-trifluoromethyl-pyrazol-1-yl)-ethanone

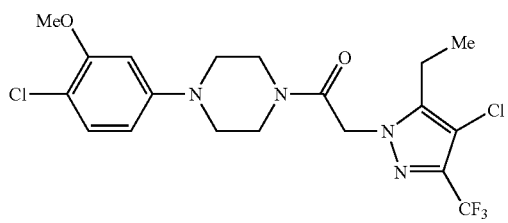

Protocol T was followed using 4-Chloro-5-ethyl-3-trifluoromethyl-1-H-pyrazol, K₂CO₃, 1-[4-(4-Chloro-3-methoxyphenyl)-piperazin-1-yl]-ethanone and DMF. Column chromatography using a solvent mixture (hexane/ethyl acetate=2/3, R$_f$=0.53) afforded the title compound as white solid. ¹H NMR (400 MHz, CDCl₃) δ 7.18-7.22 (d, 2H), 6.38-6.48 (m, 2H), 4.98 (s, 2H), 3.86 (s, 3H), 3.66-3.76 (m, 4H), 3.1-3.2 (m, 4H), 2.66-2.74 (q, 2H), 1.18-1.28 (m, 3H). MS (ES) M+H) expected=464.82, found 465.

NMR (400 MHz, CDCl3) δ 163.8, 154.8, 150.5, 130, 109.8, 102, 56.4, 52.8, 50, 49.8, 45.2, 42.6, 26.8, 20.

Synthesis of 2-(4-Chloro-5-isopropyl-3-trifluoromethyl-pyrazol-1-yl)-1-[4-(4-chloro-3-methoxy-phenyl)-piperazin-1-yl]-ethanone

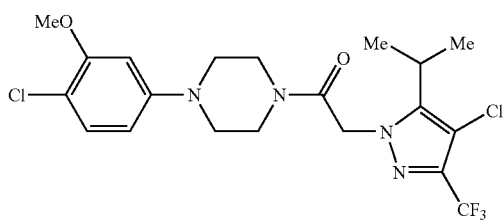

Protocol T was followed using 4-Chloro-5-isopropyl-3-trifluoromethyl-1-H-pyrazol, K₂CO₃, 1-[4-(4-Chloro-3-methoxyphenyl)-piperazine-1-yl]-ethanone and DMF. Column chromatography using a solvent mixture (hexane/ethyl acetate=5.5/4.5, $R_f$=0.52) afforded the title compound as white solid. ¹H NMR (400 MHz, CDCl₃) δ 7.19-7.22 (d, 2H), 6.42-6.48 (m, 2H), 5.18 (s, 2H), 3.88 (s, 3H), 3.56-3.78 (m, 4H), 3.22-3.44 (m, 4H), 3.04-3.14 (m, 1H), 1.44-1.48 (d, 6H). 13C NMR (400 MHz, CDCl3) δ 164.2, 154.8, 151, 130, 109.8, 102, 56.2, 54, 50.5, 50, 45.2, 42.6, 26.2, 22.1.

Synthesis of 2-(4-Chloro-3-n-propyl-5-trifluoromethyl-pyrazol-1-yl)-1-[4-(4-chloro-3-methoxy-phenyl)-piperazin-1-yl]-ethanone

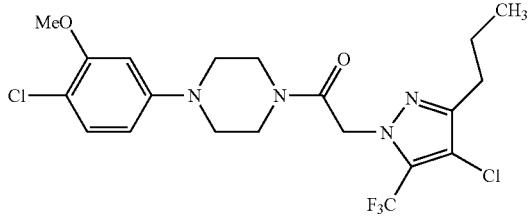

Protocol T was followed using 4-Chloro-3-n-propyl-5-trifluoromethyl-1-H-pyrazol, K₂CO₃, 1-[4-(4-Chloro-3-methoxyphenyl)-piperazine-1-yl]-ethanone and DMF. Column chromatography using a solvent mixture (hexane/ethyl acetate=3/7, $R_f$=0.78) afforded the title compound as white solid. ¹H NMR (400 MHz, CDCl₃) δ 7.22-7.24 (d, 2H), 6.42-6.48 (m, 2H), 5.7 (s, 2H), 3.8 (s, 3H), 3.72-3.78 (m, 4H), 3.22-3.42 (m, 4H), 2.66-2.72 (t, 2H), 1.58-1.68 (m, 2H), 0.98-1.02 (t, 3H). 13C NMR (400 MHz, CDC3) δ 8 164, 154.8, 150.5, 130, 109.8, 102.2, 56.4, 52.8, 50, 49.8, 45.2, 42.6, 26, 21.8, 14.

Synthesis of 2-(4-Chloro-3-isopropyl-5-trifluoromethyl-pyrazol-1-yl)-1-[4-(4-chloro-3-methoxy-phenyl)piperazin-1-yl]-ethanone

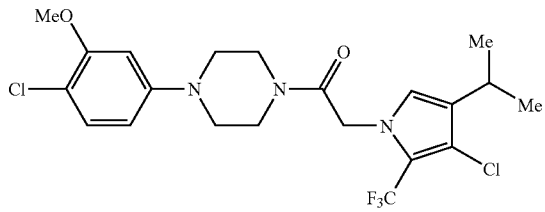

Protocol T was followed using 4-Chloro-3-isopropyl-5-trifluoromethyl-1-H-pyrazol, K₂CO₃, 1-[4-(4-Chloro-3-methoxyphenyl)-piperazine-1-yl]hethanone and DMF. Column chromatography using a solvent mixture (hexane/ethyl acetate=2/3, $R_f$=0.45) afforded the title compound as white solid. ¹H NMR (400 MHz, CDCl₃) δ 7.19-7.22 (d, 2H), 6.38-6.48 (m, 2H), 5 (s, 2H), 3.86 (s, 3H), 3.62-3.78 (m, 4H), 3.08-3.18 (m, 4H), 2.98-3.04 (m, 1H), 1.35-1.41 (d, 6H). 13C

Synthesis of 1-[4-(4-Chloro-3-methoxyphenyl)-piperazin-1-yl]-2-(4-bromo-3-phenyl-5-trifluoromethyl-pyrazol-1-yl)-ethanone

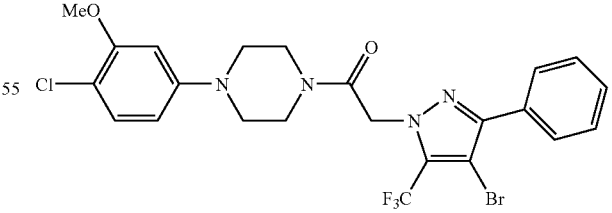

Protocol T was followed using 4-Bromo-3-phenyl-5-trifluoromethyl-1H-pyrazole, K₂CO₃, 2-Chloro-1-[4-(4-chloro-3-methoxy-phenyl)-piperazin-1-yl]-ethanone and DMF. Column chromatography using a solvent mixture (hexane/ethyl acetate=1/1, $R_f$=0.51) afforded the title compound as a white solid. ¹H NMR (400 MHz, CDCl₃) δ 7.42-7.52 (m, 5H), 7.18-7.22 (d, 1H), 6.38-6.42 (dd, 1H), 6.46-6.48 (d, 1H), 4.94 (s, 2H), 3.88 (s, 3H), 3.5-3.78 (m, 4H), 3.18 (s, 4H).

1H), 7.18-7.28 (m, 4H), 6.38-6.48 (m, 2H), 4.94 (s, 2H), 3.84 (s, 3H), 3.52-3.78 (m, 4H), 3.12 (s, 4H).

Synthesis of 1-[4-(4-Chloro-3-methoxyphenyl)-piperazin-1-yl]-2-(4-chloro-5-phenyl-3-trifluoromethyl-pyrazol-1-yl)-ethanone

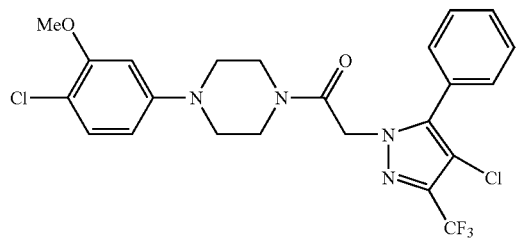

Protocol T was followed using 4-Chloro-5-phenyl-3-trifluoromethyl-1H-pyrazole, K$_2$CO$_3$, 2-Chloro-1-[4-(4-chloro-3-methoxy-phenyl)-piperazin-1-yl]-ethanone and DMF. Column chromatography using a solvent mixture (hexane/ethyl acetate=2/3, R$_f$=0.92) afforded the title compound as a white solid. $^1$H NMR (400 MHz, CDCl$_3$) δ 7.78-7.84 (m, 2H), 7.36-7.52 (m, 4H), 6.38-6.48 (m, 2H), 5.2 (s, 2H), 3.88 (s, 3H), 3.62-3.78 (m, 4H), 3.18-3.26 (s, 4H). $^{13}$C NMR (400 MHz, CDCl$_3$) 164.4, 156, 150.4, 130.4, 130, 128.6, 110.2, 102.4, 56.4, 52, 50.4, 44.6, 42.

Synthesis of 1-[4-(4-Chloro-3-methoxyphenyl)-piperazin-1-yl]-2-(4-chloro-5-[3-Fluoro-phenyl]-3-trifluoromethyl-pyrazol-1-yl)-ethanone

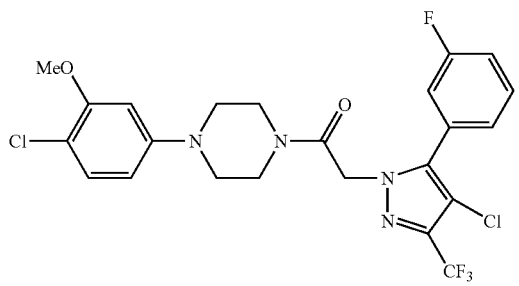

Protocol T was followed using 4-Chloro-5-[3-Fluorophenyl]-3-trifluoromethyl-1H-pyrazole, K$_2$CO$_3$, 2-Chloro-1-[4-(4-chloro-3-methoxy-phenyl-piperazin-1-yl]-ethanone and DMF. Column chromatography using a solvent mixture (hexane/ethyl acetate=2/3, R$_f$=0.59) afforded the title compound as a white solid. $^1$H NMR (400 MHz, CDCl$_3$) δ 7.64-7.68 (d, 1H), 7.56-7.62 (d, 1H), 7.36-7.42 (m, 1H), 7.22-7.24 (m, 2H), 7.08-7.12 (m, 1H), 6.42-6.52 (m, 2H), 5.2 (s, 2H), 3.9 (s, 3H), 3.62-3.82 (m, 4H), 3.12-3.22 (m, 4H).

Synthesis of 1-[4-(4-Chloro-3-methoxyphenyl)-piperazin-1-yl]-2-(4-chloro-3-[3-Fluoro-phenyl]-5-trifluoromethyl-pyrazol-1-yl)-ethanone

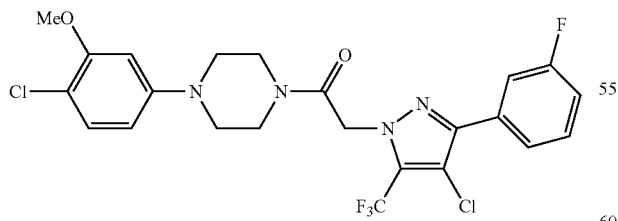

Protocol T was followed using 4-Chloro-3-[3-Fluorophenyl]-5-trifluoromethyl-1H-pyrazole, K$_2$CO$_3$, 2-Chloro-1-[4-(4-chloro-3-methoxy-phenyl)-piperazin-1-yl]-ethanone and DMF. Column chromatography using a solvent mixture (hexane/ethyl acetate=2/3, R$_f$=0.51) afforded the title compound as a white solid. $^1$H NMR (400 MHz, CDCl$_3$) δ 7.44-7.52 (m,

1-[4-(4-Chloro-3-methoxyphenyl)-piperazin-1-yl]-2-(4-chloro-3,5-ditrifluoromethyl-pyrazol-1-yl)-ethanone

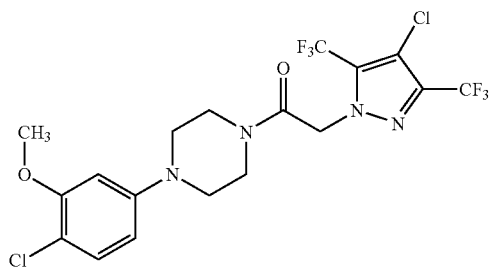

The general protocol T was followed using 4-Chloro-3,5-ditrifluoromethyl-pyrazole, K$_2$CO$_3$, 2-Chloro-1-[4-(4-chloro-3-methoxy-phenyl)-piperazin-1-yl]-ethanone, and DMF. Column chromatography using a solvent mixture (hexane/ethyl acetate=1/1) afforded the title compound as white solid. $^1$H NMR (400 MHz, CDCl$_3$) δ 7.22-7.24 (m, 2H), 6.42-6.52 (m, 2H), 5.2 (s, 2H), 3.88 (s, 3H), 3.58-3.82 (m, 4H), 3.14-3.24 (m, 4H). MS (ES) (M+H) expected=505.24, found 506.

6.36-6.42 (dd, 1H), 4.94 (s, 2H), 4.28 (s, 2H), 3.88 (s, 3H), 3.76-3.86 (m, 4H), 3.12-3.18 (m, 4H). MS (ES) (M+H) expected=460.36, found 460.

1-[4-(4-Chloro-3-methoxyphenyl)-piperazin-1-yl]-2-(3-methyl-4,5-dibromopyrazol-1-yl)-ethanone

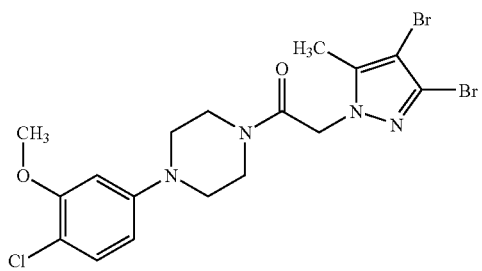

The general protocol T was followed using 3-Methyl-4,5-dibromo-pyrazole, $K_2CO_3$, 2-Chloro-1-[4-(4-chloro-3-methoxy-phenyl)-piperazin-1-yl]ethanone and DMF. Column chromatography using a solvent mixture (hexane/ethyl acetate=1/1) afforded the title compound as white solid. $^1$H NMR (400 MHz, CDCl$_3$) δ 7.22-7.23 (m, 1H), 6.42-6.50 (m, 2H), 4.95 (s, 2H), 3.90 (s, 3H), 3.68-3.78 (m, 4H), 3.14-3.24 (m, 4H). MS (ES) (M+H) expected=506.6, found 506.9.

1-[4-(4-Chloro-3-methoxyphenyl)-piperazin-1-yl]-2-(4-chloro-3,5-dimethyl-pyrazol-1-yl)-ethanone

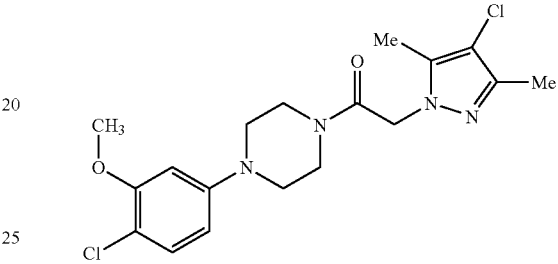

The general protocol T was followed using 4-Chloro-3,5-dimethyl-pyrazole, $K_2CO_3$, 2-Chloro-1-[4-(4-chloro-3-methoxy-phenyl)-piperazin-1-yl]-ethanone, and DMF. Column chromatography using a solvent mixture (hexane/ethyl acetate=1/1, $R_f$=0.28) afforded the title compound as white solid. $^1$H NMR (400 MHz, CDCl$_3$) δ 7.19-7.22 (m, 2H), 6.39-6.49 (m, 2H), 4.86 (s, 2H), 3.84 (s, 3H), 3.64-3.78 (m, 4H), 3.1-3.18 (m, 4H), 2.12-2.42 (d, 6H). MS (ES) (M+H) expected=397.3, found 397.

2-(3-Amino-4-chloro-5-phenyl-pyrazol-1-yl)-1-[4-(4-chloro-3-methoxyphenyl)-piperazin-1-yl]-ethanone

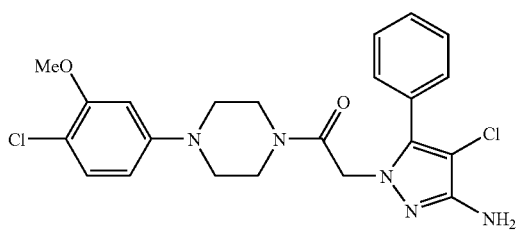

The general protocol T was followed using 4-Chloro-5-phenyl-1H-pyrazol-3-ylamine, $K_2CO_3$, 2-Chloro-1-[4-(4-chloro-3-methoxy-phenyl)-piperazin-1-yl]-ethanone, and DMF. Column chromatography using a solvent mixture (hexane/ethyl acetate=1/4, $R_f$=0.68) afforded the title compound as white solid. $^1$H NMR (400 MHz, CDCl$_3$) δ 7.79-7.81 (d, 2H), 7.32-7.42 (m, 3H), 7.18-7.22 (d, 1H), 6.44-6.48 (d, 1H), 1-[4-(4-Chloro-3-methoxy-phenyl)-2-methyl-piperazin-1-yl]-2-(4-chloro-3-phenyl-5-trifluoromethyl-pyrazol-1-yl)-ethanone

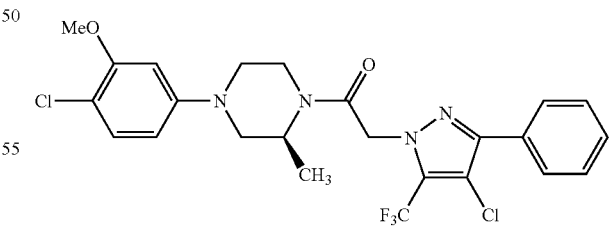

The general protocol T was followed using 4-Chloro-5-phenyl-3-trifluoromethyl-1H-pyrazole, $K_2CO_3$, 2-Chloro-1-[4-(4-chloro-3-methoxy-phenyl)-2-(S)-methyl-piperazin-1-yl]-ethanone and DMF. Column chromatography using a solvent mixture (hexane/ethyl acetate=2/3, $R_f$=0.6) afforded the title compound as white solid. $^1$H NMR (400 MHz, CDCl$_3$) δ 7.4-7.52 (m, 5H), 7.19-7.22 (d, 1H), 6.38-6.48 (d, 2H), 4.78-5.22 (m, 3H), 4.4-4.42 (m, 2H), 4.0 (s, 1H), 3.88 (s, 3H), 3.42-3.58 (m, 2H), 3.32-3.38 (d, 1H), 3.15 (s, 1H), 2.72-2.96 (m, 3H) 1.28-1.38 (m, 4H). MS (ES) (M+H) expected=527.4, found 527.

1-[4-(4-Chloro-3-methoxyphenyl)-piperazin-1-yl]-2-(3-methyl-4-chloro-5-bromo pyrazol-1-yl)-ethanone

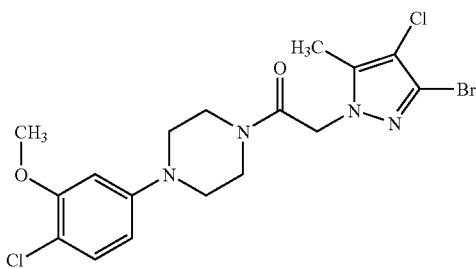

The general protocol T was followed using 3-Methyl-4-chloro-5-bromo-pyrazole, K₂CO₃, 2-Chloro-1-[4-(4-chloro-3-methoxy-phenyl)-piperazin-1-yl]-ethanone and DMF. Column chromatography using a solvent mixture (hexane/ethyl acetate=1/1) afforded the title compound as white solid. ¹H NMR (400 MHz, CDCl₃) δ 7.22-7.23 (m, 1H), 6.42-6.50 (m, 2H), 4.92 (s, 2H), 3.90 (s, 3H), 3.70-3.80 (m, 4H), 3.12-3.22 (m, 4H). MS (ES) (M+H) expected=462.17, found 462.9.

1-[4-(4-Chloro-3-methoxy-phenyl)-2-(S)-methyl-piperazin-1-yl]-2-(3-methyl-4-chloro-5-bromopyrazol-1-yl)-ethanone

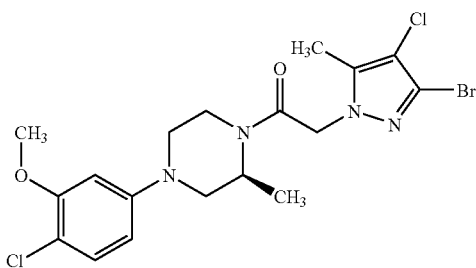

The general protocol T was followed using 3-Methyl-4-chloro-5-bromo-pyrazole, K₂CO₃, 2-Chloro-1-[4-(4-chloro-3-methoxy-phenyl)-2-(S)-methyl-piperazin-1-yl]-ethanone, and DMF. Column chromatography using a solvent mixture (hexane/ethyl acetate=1/1) afforded the title compound as white solid. ¹H NMR (400 MHz, CDCl₃) δ 7.18-7.22 (m, 1H), 6.38-6.46 (m, 2H), 4.78-5.22 (m, 3H), 4.38-4.42 (m, 1H), 4.2 (s, 1H), 3.85 (s, 3H), 3.8 (s, 1H), 3.42-3.58 (m, 2H), 3.32-3.38 (d, 1H), 3.15 (s, 1H), 2.72-2.96 (m, 3H) 1.26-1.38 (m, 4H). MS (ES) (M+H) expected=476.19, found 476.9.

1-[4-(4-Chloro-3-methoxyphenyl)-piperazin-1-yl]-2-(4-chloro-5-[2-fluoro-phenyl]-3-trifluoromethyl-pyrazol-1-yl)-ethanone

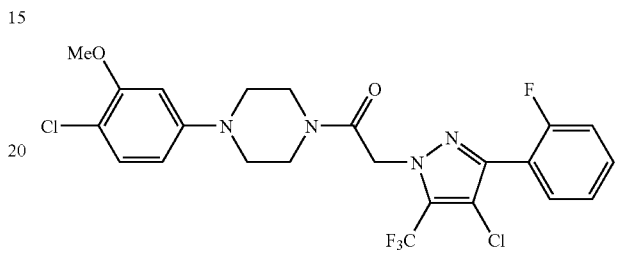

The general protocol T was followed using 4-Chloro-5-[2-fluorophenyl]-3-trifluoromethyl-1H-pyrazole, K₂CO₃, 2-Chloro-1-[4-(4-chloro-3-methoxy-phenyl)-piperazin-1-yl]-ethanone and DMF. Column chromatography using a solvent mixture (hexane/ethyl acetate=2/3, R_f=0.6) afforded the title compound as white solid. ¹H NMR (400 MHz, CDCl₃) δ 7.44-7.56 (m, 2H), 7.26-7.32 (t, 1H), 7.18-7.26 (m, 2H), 6.44-6.46 (d, 1H), 6.36-6.42 (dd, 1H), 4.95 (s, 2H), 3.86 (s, 3H), 3.5-3.68 (m, 4H), 3.02-3.14 (s, 4H). MS (ES) (M+H) expected=531.3, found 531.

1-[4-(4-Chloro-3-methoxy-phenyl)-piperazin-1-yl]-2-(4-chloro-5-methyl-3-phenyl-pyrazol-1-yl)-ethanone

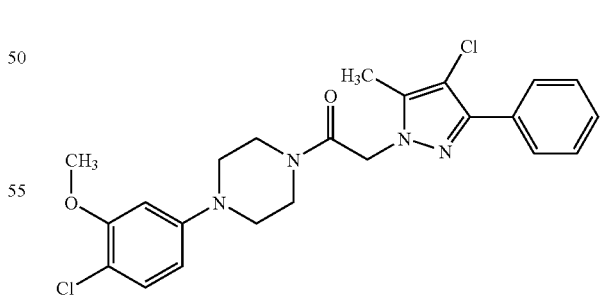

The general protocol T was followed using 4-Chloro-5-methyl-3-phenyl-pyrazole, K₂CO₃, 2-Chloro-1-[4-(4-chloro-3-methoxy-phenyl)-piperazin-1-yl]-ethanone and DMF. Column chromatography using a solvent mixture (hexane/ethyl acetate=1/3, R_f=0.7) afforded the title compound as white solid. ¹H NMR (400 MHz, CDCl₃) δ 7.82-7.88 (m, 2H), 7.38-7.42 (t, 2H), 7.32-7.36 (m, 1H), 7.18-7.22 (d, 1H), 6.38-

6.48 (m, 2H), 4.99 (s, 2H), 3.88 (s, 3H), 3.72 (m, 4H), 3.08-3.18 (m, 4H), 2.34 (s, 3H). MS (ES) (M+H) expected=459.38, found 459.

7.24 (m, 1H), 6.44-6.52 (m, 2H), 5.22 (s, 2H), 3.85 (s, 3H), 3.62-3.82 (m, 4H), 3.16-3.24 (m, 4H). MS (ES) (M+H) expected=581.35, found 581.

1-[4-(4-Chloro-3-methoxyphenyl)-piperazin-1-yl]-2-(4-chloro-3-[2-fluoro-phenyl]-5-trifluoromethyl-pyrazol-1-yl)-ethanone 1-[4-(4-Chloro-3-methoxyphenyl)-piperazin-1-yl]-2-(4-chloro-5-[4-trifluoromethyl-phenyl]-3-trifluoromethyl-pyrazol-1-yl)-ethanone

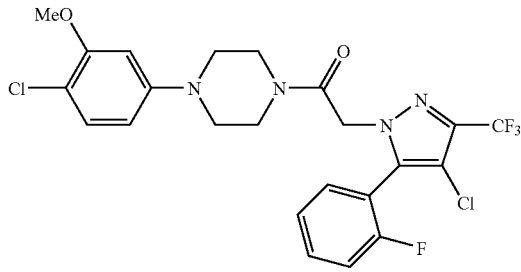

The general protocol T was followed using 4-Chloro-5-[2-fluorophenyl]-3-trifluoromethyl-1H-pyrazole, K₂CO₃, 2-Chloro-1-[4-(4-chloro-3-methoxy-phenyl)-piperazin-1-yl]-ethanone, and DMF. Column chromatography using a solvent mixture (hexane/ethyl acetate=2/3, $R_f$=0.6) afforded the title compound as white solid. ¹H NMR (400 MHz, CDCl₃) δ 7.52-7.58 (m, 1H), 7.38-7.46 (m, 1H), 7.14-7.26 (m, 3H), 6.44-6.51 (m, 2H), 5.22 (s, 2H), 3.84 (s, 3H), 3.62-3.82 (m, 4H), 3.12-3.24 (m, 4H). MS (ES) (M+H) expected=531.0, found 531.

The general protocol T was followed using 4-Chloro-3-[4-trifluoromethylphenyl]-5-trifluoromethyl-1H-pyrazole, K₂CO₃, 2-Chloro-1-[4-(4-chloro-3-methoxy-phenyl)-piperazin-1-yl]-ethanone, and DMF. Column chromatography using a solvent mixture (hexane/ethyl acetate=1/3, $R_f$=0.85) afforded the title compound as white solid. ¹H NMR (400 MHz, CDCl₃) δ 7.78-7.8 (d, 1H), 7.62-7.66 (d, 1H), 7.20-7.22 (m, 1H), 6.40-6.48 (m, 2H), 4.92 (s, 2H), 3.88 (s, 3H), 3.60-3.78 (m, 4H), 3.16-3.20 (m, 4H). MS (ES) (M+H) expected=581.35, found 581.

1-[4-(4-Chloro-3-methoxyphenyl)-piperazin-1-yl]-2-(4-chloro-3-[4-trifluoromethyl-phenyl]-5-trifluoromethyl-pyrazol-1-yl)-ethanone 1-[4-(4-Chloro-3-methoxyphenyl)-piperazin-1-yl]-2-(4-chloro-3-[4-methoxyphenyl]-5-trifluoromethyl-pyrazol-1-yl)-ethanone

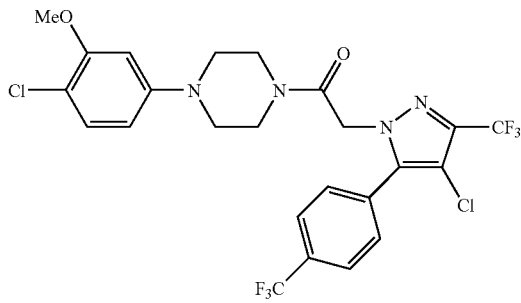

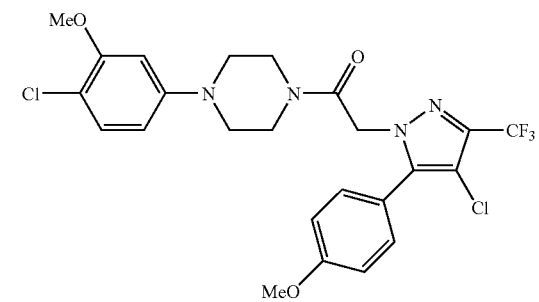

The general protocol T was followed using 4-Chloro-5-[4-trifluoromethylphenyl]-3-trifluoromethyl-1H-pyrazole, K₂CO₃, 2-Chloro-1-[4-(4-chloro-3-methoxy-phenyl)-piperazin-1-yl]-ethanone, and DMF. Column chromatography using a solvent mixture (hexane/ethyl acetate=1/3, $R_f$=0.91) afforded the title compound as colorless oil. ¹H NMR (400 MHz, CDCl₃) δ 7.99-8.12 (d, 1H), 7.66-7.71 (d, 1H), 7.22-

The general protocol T was followed using 4-Chloro-5-[4-methoxyphenyl]-3-trifluoromethyl-1H-pyrazole, K₂CO₃, 2-Chloro-1-[4-(4-chloro-3-methoxy-phenyl)-piperazin-1-yl]-ethanone, and DMF. Column chromatography using a solvent mixture (hexane/ethyl acetate=3/7, $R_f$=0.45) afforded the title compound as colorless oil. ¹H NMR (400 MHz, CDCl₃) δ 7.76-7.78 (d, 1H), 7.22-7.24 (d, 1H), 6.94-6.96 (d, 1H), 6.42-6.52 (m, 2H), 4.98 (s, 2H), 3.88 (s, 3H), 3.82 (s, 3H), 3.62-3.82 (m, 4H), 3.16-3.24 (m, 4H). MS (ES) (M+H) expected=543.38, found 543.

CDCl$_3$) δ 164.8, 158, 152, 147, 135, 131, 130, 119, 115.4, 115, 110, 104, 56.5, 52.8, 50.8, 50, 45.4, 42.2, 18.6.

1-[4-(4-Chloro-3-methoxyphenyl)-piperazin-1-yl]-2-(4-chloro-5-[4-methoxyphenyl]-3-trifluoromethyl-pyrazol-1-yl)-ethanone

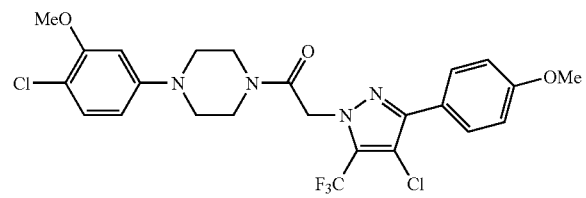

The general protocol T was followed using 4-Chloro-5-[4-methoxyphenyl]-3-trifluoromethyl-1H-pyrazole, K$_2$CO$_3$, 2-Chloro-1-[4-(4-chloro-3-methoxy-phenyl)-piperazin-1-yl]-ethanone, and DMF. Column chromatography using a solvent mixture (hexane/ethyl acetate=3/7, R$_f$=0.36) afforded the title compound as colorless oil. $^1$H NMR (400 MHz, CDCl$_3$) δ 7.36-7.39 (d, 1H), 7.20-7.22 (d, 1H), 6.88-7.22 (d, 2H), 6.38-6.48 (m, 2H), 4.92 (s, 2H), 3.88 (s, 3H), 3.84 (s, 3H), 3.56-3.78 (m, 4H), 3.14-3.18 (m, 4H). MS (ES) (M+H) expected=543.38, found 542.9.

1-[4-(4-Chloro-3-methoxyphenyl)-piperazin-1-yl]-2-(4-chloro-5-[4-fluorophenyl]-3-trifluoromethyl-pyrazol-1-yl)-ethanone

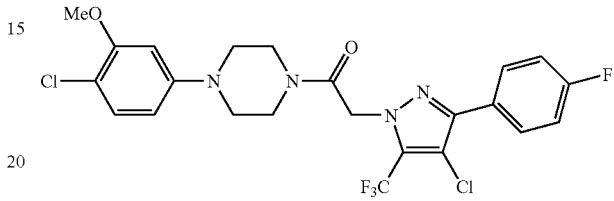

The general protocol T was followed using 4-Chloro-3-[4-fluorophenyl]-5-trifluoromethyl-1H-pyrazole, K$_2$CO$_3$, 2-Chloro-1-[4-(4-chloro-3-methoxy-phenyl)-piperazin-1-yl]-ethanone, and DMF. Column chromatography using a solvent mixture (hexane/ethyl acetate=3.5/6.5, R$_f$=0.83) afforded the title compound as white solid. $^1$H NMR (400 MHz, CDCl$_3$) δ 7.44-7.49 (m, 2H), 7.14-7.22 (m, 3H), 6.38-6.48 (m, 2H), 4.9 (s, 2H), 3.89 (s, 3H), 3.54-3.78 (m, 4H), 3.14 (s, 4H). $^{13}$C NMR (400 MHz, CDCl$_3$) δ 164.8, 162, 155, 152, 143, 132, 131, 122, 115.4, 115, 110, 100, 56.2, 52.2, 50.8, 50, 45.4, 42.2.

2-[4-Chloro-5-(4-fluoro-phenyl)-3-methylsulfanyl-pyrazol-1-yl]-1-[4-(4-chloro-3-methoxy-phenyl)-piperazin-1-yl]-ethanone

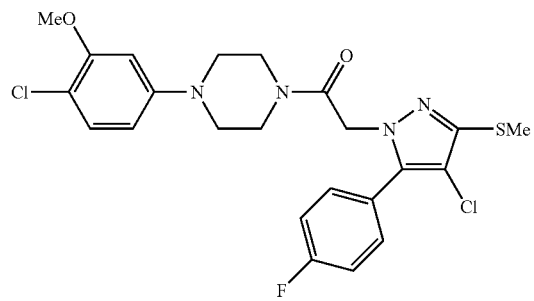

The general protocol T was followed using 4-Chloro-5-(4-fluoro-phenyl)-3-methylsulfanyl-pyrazol-1-yl, K$_2$CO$_3$, 2-Chloro-1-[4-(4-chloro-3-methoxy-phenyl)-piperazin-1-yl]-ethanone, and DMF. Column chromatography using a solvent mixture (hexane/ethyl acetate=1/4, R$_f$=0.77) afforded the title compound as colorless oil. $^1$H NMR (400 MHz, CDCl$_3$) δ 7.82-7.88 (m, 2H), 7.21-7.25 (m, 1H), 7.04-7.14 (t, 2H), 6.42-6.51 (m, 2H), 5.4 (s, 2H), 3.9 (s, 3H), 3.7-3.8 (m, 4H), 3.25-3.52 (m, 4H), 2.4 (s, 3H). $^{13}$C NMR (400 MHz,

2-[4-Chloro-3-(5-chloro-thiophen-2-yl)-5-methyl-pyrazol-1-yl]-1-[4-(4-chloro-3-methoxy-phenyl)-piperazin-1-yl]-ethanone

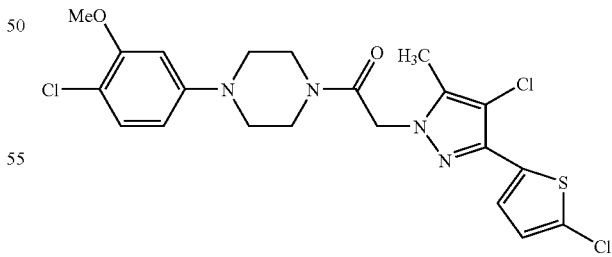

The general protocol T was followed using 4-Chloro-3-(5-chloro-thiophen-2-yl)-5-methyl-pyrazol-1-yl, K$_2$CO$_3$, 2-Chloro-1-[4-(4-chloro-3-methoxy-phenyl)-piperazin-1-yl]-ethanone, and DMF. Column chromatography using a solvent mixture (hexane/ethyl acetate=1/4, R$_f$=0.8) afforded the title compound. $^1$H NMR (400 MHz, CDCl$_3$) δ 7.39-7.41 (d, 1H), 7.21-7.24 (m, 1H), 6.86-6.88 (d, 1H), 6.42-648 (dd, 1H), 6.48-6.51 (m, 1H) 4.95 (s, 2H), 3.88 (s, 3H), 3.72-3.82 (m, 4H), 3.11-3.21 (m, 4H), 2.3 (s, 3H).

2-[4-Chloro-3-(2-thiophene)-5-methyl-pyrazol-1-yl]-1-[4-(4-chloro-3-methoxy phenyl)-piperazin-1-yl]-ethanone

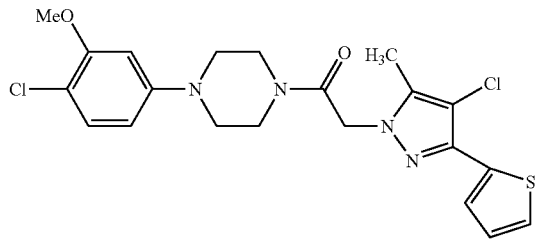

The general protocol T was followed using 4-Chloro-3-(5-chloro-thiophen-2-yl)-5-methyl-pyrazol-1-yl, $K_2CO_3$, 2-Chloro-1-[4-(4-chloro-3-methoxy-phenyl)-piperazin-1-yl]-ethanone, and DMF. Column chromatography using a solvent mixture (hexane/ethyl acetate=1/4, $R_f$=0.8) afforded the title compound. $^1$H NMR (400 MHz, $CDCl_3$) δ 7.62-7.66 (m, 1H), 7.24-7.26 (m, 1H), 7.18-7.22 (d, 1H), 7.45-7.8 (m, 1H), 6.39-6.48 (m, 2H), 4.95 (s, 2H), 3.86 (s, 3H), 3.70-3.78 (m, 4H), 3.09-3.18 (m, 4H), 2.3 (s, 3H).

2-(4-Chloro-5-hydroxymethyl-3-trifluoromethyl-pyrazol-1-yl)-1-[4-(4-chloro-3-methoxy-phenyl)-piperazin-1-yl]-ethanone

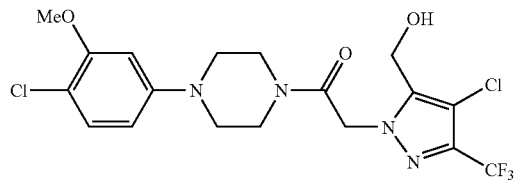

The general protocol T was followed using 4-Chloro-5-hydroxymethyl-3-trifluoromethyl-pyrazol-1-yl, $K_2CO_3$, 2-Chloro-1-[4-(4-chloro-3-methoxy-phenyl)-piperazin-1-yl]-ethanone, and DMF. Column chromatography using a solvent mixture (hexane/ethyl acetate=1/8, $R_f$=0.5) afforded the title compound. $^1$H NMR (400 MHz, $CDCl_3$) δ 7.21-7.28 (m, 1H), 6.41-6.51 (m, 2H), 5.18 (s, 2H), 4.66 (s, 2H), 3.86 (s, 3H), 3.70-3.78 (m, 4H), 3.11-3.24 (m, 4H).

2-(4-Chloro-5-methoxymethyl-3-trifluoromethyl-pyrazol-1-yl)-1-[4-(4-chloro-3-methoxy-phenyl)-piperazin-1-yl]-ethanone

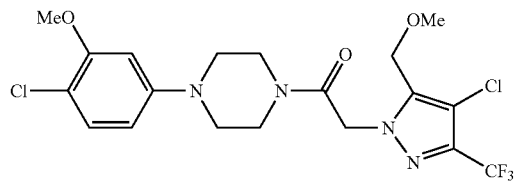

The general protocol T was followed using 4-Chloro-5-methoxymethyl-3-trifluoromethyl-pyrazol-1-yl, $K_2CO_3$, 2-Chloro-1-[4-(4-chloro-3-methoxy-phenyl)-piperazin-1-yl]-ethanone, and DMF. Column chromatography using a solvent mixture (hexane/ethyl acetate=1/4, $R_f$=0.65) afforded the title compound. $^1$H NMR (400 MHz, $CDCl_3$) δ 7.15-7.18 (d, 1H), 6.65-6.68 (d, 1H), 6.51-6.58 (dd, 1H), 5.32 (s, 2H), 4.58 (s, 3H), 4.52 (s, 2H), 3.86 (s, 3H), 3.70-3.75 (m, 4H), 3.18-3.28 (m, 4H). MS (ES) (M+H) expected=481.31, found 481.2.

4-Chloro-1-{2-[4-(4-chloro-3-methoxy-phenyl)-piperazin-1-yl]-2-oxo-ethyl}-5-methyl-1H-pyrazole-3-carboxylic acid ethyl ester

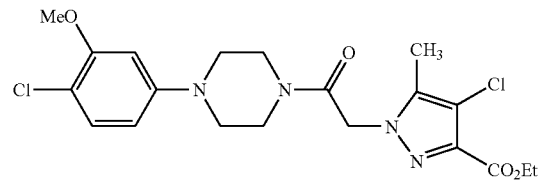

The general protocol T was followed using 4-Chloro-5-methyl-1H-pyrazole-3-carboxylic acid ethyl ester, $K_2CO_3$, 2-Chloro-1-[4-(4-chloro-3-methoxy-phenyl)-piperazin-1-yl]-ethanone, and DMF. Column chromatography using a solvent mixture (hexane/ethyl acetate=1/4, $R_f$=0.81) afforded the title compound. $^1$H NMR (400 MHz, $CDCl_3$) δ 7.18-7.21 (d, 1H), 6.66-6.68 (d, 1H), 6.52-6.55 (dd, 1H), 5.42 (s, 2H), 4.30-4.36 (q, 2H), 3.85 (s, 3H), 3.70-3.77 (m, 4H), 3.18-3.28 (m, 4H), 2.22 (s, 3H), 1.32-1.38 (t, 3H). MS (ES) (M+H) expected=455.34, found 455.2.

4-Chloro-1-{2-[4-(4-chloro-3-methoxy-phenyl)-piperazin-1-yl]-2-oxo-ethyl}-3-methyl-1H-pyrazole-5-carboxylic acid ethyl ester

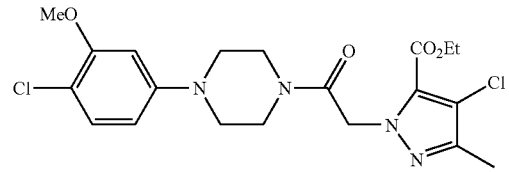

The general protocol T was followed using 4-Chloro-3-methyl-1H-pyrazole-5-carboxylic acid ethyl ester, $K_2CO_3$, 2-Chloro-1-[4-(4-chloro-3-methoxy-phenyl)-piperazin-1-yl]-ethanone, and DMF. Column chromatography using a solvent mixture (hexane/ethyl acetate=1/4, $R_f$=0.75) afforded the title compound. $^1$H NMR (400 MHz, $CDCl_3$) δ 7.19-7.22 (d, 1H), 6.64-6.66 (d, 1H), 6.54-6.58 (dd, 1H), 5.44 (s, 2H), 4.30-4.35 (q, 2H), 3.85 (s, 3H), 3.70-3.77 (m, 4H), 3.20-3.28

(m, 4H), 2.24 (s, 3H), 1.34-1.38 (t, 3H). MS (ES) (M+H) expected=455.34, found 455.2.

2-(4-Chloro-5-cyclopropyl-3-trifluoromethyl-pyrazol-1-yl)-1-[4-(4-chloro-3-methoxy-phenyl)-piperazin-1-yl]-ethanone

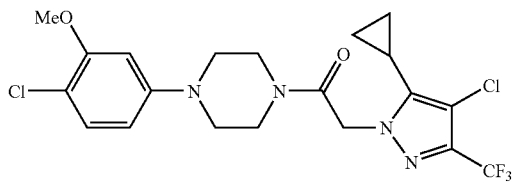

The general protocol T was followed using 4-Chloro-5-cyclopropyl-3-trifluoromethyl-pyrazol-1-yl, K$_2$CO$_3$, 2-Chloro-1-[4-(4-chloro-3-methoxy-phenyl)-piperazin-1-yl]-ethanone, and DMF. Column chromatography using a solvent mixture (hexane/ethyl acetate=1/5, R$_f$=0.88) afforded the title compound. $^1$H NMR (400 MHz, CDCl$_3$) δ 7.20-7.24 (d, 1H), 6.48-6.50 (d, 1H), 6.42-6.46 (dd, 1H), 5.03 (s, 2H), 3.85 (s, 3H), 3.58-3.78 (m, 4H), 3.14-3.24 (m, 4H), 1.86-1.94 (m, 1H), 0.51-0.59 (m, 4H). MS (ES) (M+H) expected=477.32, found 477.2.

4-Chloro-1-{2-[4-(4-chloro-3-methoxy-phenyl)-2-methylpiperazin-1-yl]-2-oxo-ethyl}-5-methyl-1H-pyrazole-3-carboxylic acid ethyl ester

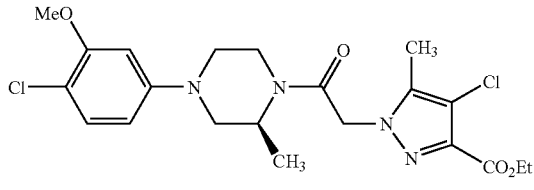

The general Protocol T was followed using 4-Chloro-5-methyl-1H-pyrazole-3-carboxylic acid ethyl ester, K$_2$CO$_3$, 2-Chloro-1-[4-(4-chloro-3-methoxy-phenyl)-2-(S)-methyl-piperazin-1-yl]ethanone, and DMF. Column chromatography using a solvent mixture (hexane/ethyl acetate=1/4, R$_f$=0.81) afforded the title compound: HPLC retention time=4.51 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-(4-Chloro-3-(3-Methoxyphenyl)-5-trifluoromethyl-pyrazol-1-yl)-1-[4-(4-chloro-3-methoxy-phenyl)-2-methyl-piperazin-4-yl]-ethanone

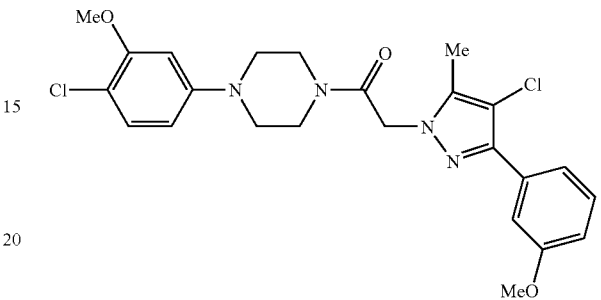

The general protocol T was followed using 4-Chloro-3-(3-Methoxyphenyl)-5-trifluoromethyl-pyrazol-1-yl, K$_2$CO$_3$, 2-Chloro-1-[4-(4-chloro-3 -methoxy-phenyl)-piperazin-1-yl]-ethanone, and DMF. Column chromatography using a solvent mixture (hexane/ethyl acetate=1/5, R$_f$=0.82) afforded the title compound. $^1$H NMR (400 MHz, CDCl$_3$) δ 7.42-7.48 (m, 2H), 7.28-7.34 (m, 1H), 7.19-7.22 (d, 1H), 6.86-6.91 (dd, 1H), 6.39-6.47 (m, 2H), 4.99 (s, 2H), 3.88 (s, 3H), 3.84 (s, 3H), 3.72-3.8 (m, 4H), 3.12-3.18 (m, 4H), 2.3 (3H). MS (ES) (M+H) expected=491.34, found 491.2. $^{13}$C NMR (400 MHz, CDCl$_3$) δ 164.8, 160, 156, 152, 145, 140, 132, 131, 120, 115.4, 115, 110, 108, 100, 56.2, 52.2, 50.8, 50, 45.4, 42.2, 20.

4-Chloro-1-{2-[4-(4-chloro-3-methoxy-phenyl)-2-methylpiperazin-1-yl]-2-oxo-ethyl}-3-methyl-1H-pyrazole-5-carboxylic acid ethyl ester

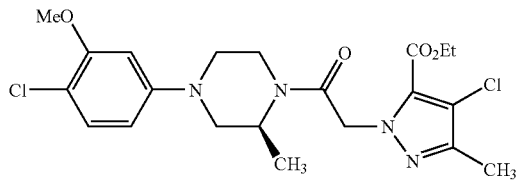

The general protocol T was followed using 4-Chloro-3-methyl-1H-pyrazole-5-carboxylic acid ethyl ester, K$_2$CO$_3$, 2-Chloro-1-[4-(4-chloro-3-methoxy-phenyl)-2-(S)-methyl-piperazin-1-yl]-ethanone, and DMF. Column chromatography using a solvent mixture (hexane/ethyl acetate=1/4, 0.75) afforded the title compound: HPLC retention time=4.74 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-(4-Chloro-3-cyclopropyl-5-trifluoromethyl-pyrazol-1-yl)-1-[4-(4-chloro-3-methoxy-phenyl)-piperazin-1-yl]-ethanone

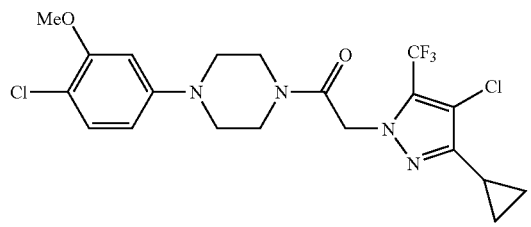

The general protocol T was followed using 4-Chloro-3-cyclopropyl-5-trifluoromethyl-pyrazol-1-yl, K$_2$CO$_3$, 2-Chloro-1-[4-(4-chloro-3-methoxy-phenyl)-piperazin-1-yl]-ethanone, and DMF. Column chromatography using a solvent mixture (hexane/ethyl acetate=1/5, R$_f$=0.83) afforded the title compound. $^1$H NMR (400 MHz, CDCl$_3$) δ 7.20-7.24 (d, 1H), 6.46-6.49 (d, 1H), 6.42-6.46 (dd, 1H), 5.1 (s, 2H), 3.88 (s, 3H), 3.65-3.78 (m, 4H), 3.14-3.24 (m, 4H), 1.65-1.72 (m, 1H), 1.01-1.12 (m 2H), 0.51-0.59 (m, 2H). MS (ES) (M+H) expected=477.32, found 477.22.

2-(4-Chloro-5-cyclopropyl-3-trifluoromethyl-pyrazol-1-yl)-1-[4-(4-chloro-3-methoxy-phenyl)-2-methyl-piperazin-1-yl]-ethanone

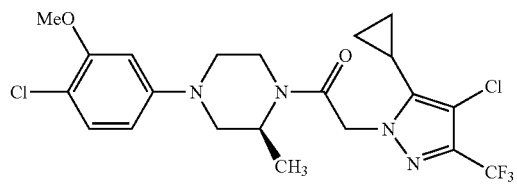

The general protocol T was followed using 4-Chloro-5-cyclopropyl-3-trifluoromethyl-pyrazol-1-yl, K$_2$CO$_3$, 2-Chloro-1-[4-(4-chloro-3-methoxy-phenyl)-2-(S)-methyl-piperazin-1-yl]-ethanone and DMF. Column chromatography using a solvent mixture (hexane/ethyl acetate=1/5, R$_f$=0.68) afforded the title compound. $^1$H NMR (400 MHz, CDCl$_3$) δ 7.19-7.22 (d, 1H), 6.41-6.49 (m, 2H), 4.94-5.26 (m, 2H), 4.8 (s, 1H), 4.41-4.44 (d, 1H), 4.0 (s, 1H), 3.91 (s, 3H), 3.52-3.58 (d, 2H), 3.36-3.42 (m, 1H), 3.2 (s, 1H), 2.8 (s, 1H), 1.84-1.94 (m, 1H), 1.3-1.5 (m, 3H), 0.51-0.59 (m, 4H). MS (ES) (M+H) expected=491.34, found 491.2.

2-(4-Chloro-3-cyclopropyl-5-trifluoromethyl-pyrazol-1-yl)-1-[4-(4-chloro-3-methoxy-phenyl)-2-methyl-piperazin-1-yl]-ethanone

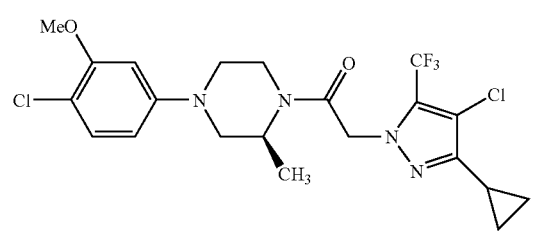

The general protocol T was followed using 4-Chloro-3-cyclopropyl-5-trifluoromethyl-pyrazol-1-yl, K$_2$CO$_3$, 2-Chloro-1-[4-(4-chloro-3-methoxy-phenyl)-2-(S)-methyl-piperazin-1-yl]-ethanone and DMF. Column chromatography using a solvent mixture (hexane/ethyl acetate=1/5, R$_f$=0.62) afforded the title compound. $^1$H NMR (400 MHz, CDCl$_3$) δ 7.19-7.22 (d, 1H), 6.39-6.48 (m, 2H), 5.01-5.21 (m, 2H), 4.75 (s, 1H), 4.38-4.42 (d, 1H), 4.18 (s, 1H), 3.92 (s, 3H), 3.53-3.59 (d, 2H), 3.42-3.48 (m, 1H), 3.25 (s, 1H), 2.8 (s, 1H), 1.84-1.94 (m, 1H), 1.3-1.5 (m, 3H), 0.98-1.41 (d, 2H), 0.51-0.59 (m, 2H). MS (ES) (M+H) expected=491.34, found 491.2.

Protocol U: For the K$_2$CO$_3$ Mediated Coupling Reaction of Chloroacetyl Substituted Arylpiperazines with Novel Heteraryl Ring Systems

Synthesis of 1-[4-(4-Fluoro-phenyl)-piperazin-1-yl]-2-[5-nitro-indazol-1-yl]-ethanone

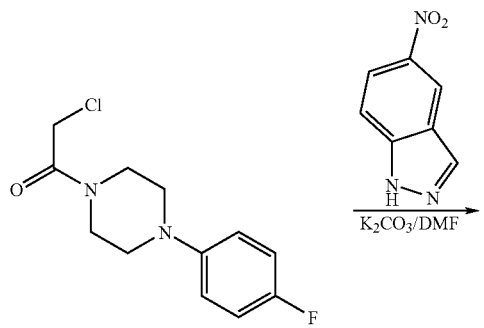

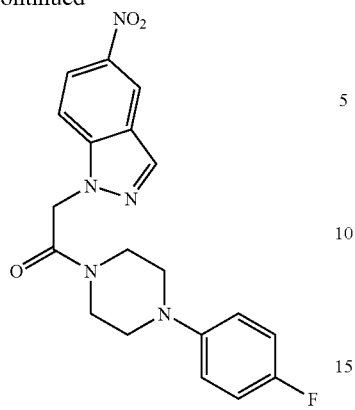

2-Chloro-1-[4-(4-fluoro-phenyl)-piperazin-1-yl]-ethanone (0.834 g, 3.3 mmol) was taken in dry DMF (15 mL) and dry potassium carbonate (1.6 g, 11.6 mmol) was added to it and the reaction mixture stirred at room temperature for 1 h under nitrogen. 5-Nitro-1H-indazole (0.5 g, 2.9 mmol) in DMF (2 mL) was then added to the mixture through a syringe. The reaction was heated at 70° C. for 14 h, cooled and then quenched with water and extracted with ethyl acetate. Drying of the organic layer with Na$_2$SO$_4$ followed by concentration afforded material that on purification on neutral alumina column (pet ether/ethyl acetate) gave title compound as a pale yellow solid.

Synthesis of 1-[4-(4-Fluoro-phenyl)-piperazin-1-yl]-2-[7-nitro-indazol-1-yl]-ethanone

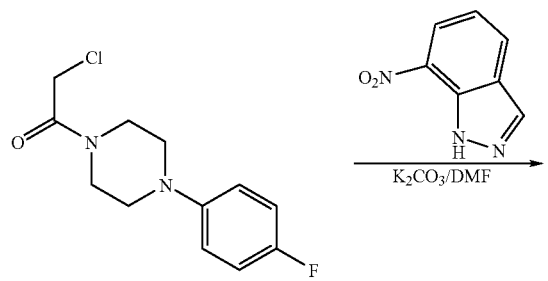

2-Chloro-1-[4-(4-fluoro-phenyl)-piperazin-1-yl]-ethanone (0.834 g, 3.3 mmol) was taken in dry pMF (15 mL) and dry potassium carbonate (1.6 g, 11.6 mmol) was added to it and the reaction mixture stirred at room temperature for 1 h under nitrogen. 7-Nitro-1H-indazole (0.5 g, 2.9 mmol) in DMF (2 mL) was then added to the mixture through a syringe. The reaction was then heated at 70° C. for 14 h, cooled and then quenched with water and extracted with ethyl acetate. Drying of the organic layer with Na$_2$SO$_4$ followed by concentration afforded material that was purified on neutral alumina column (pet ether/ethyl acetate). The resulting solid was recrystallized from DCM/pet ether to obtain pure product as a pale yellow solid.

Synthesis of 2-Benzoimidazol-1-yl-1-[4-(4-chloro-phenyl)-piperazin-1-yl]-ethanone

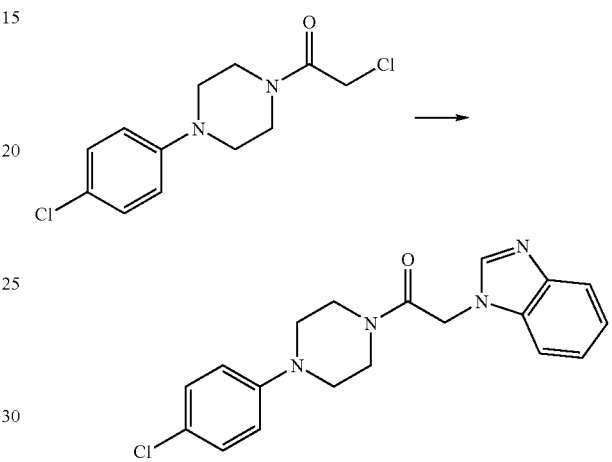

Benzimidazole (0.785 g, 0.7 mmol) was taken in dry DMF (15 mL) and dry potassium carbonate (340 mg) and KI (20 mg) was added to it and the reaction mixture stirred at room temperature for 1 h under nitrogen. 2-Chloro-1-[4-(4-chloro-phenyl)-piperazin-1-yl]-ethanone (200 mg, 1.1 mmol) in DMF (5 mL) was then added to the mixture through a syringe. The reaction was then heated at 140° C. for 14 h, cooled and then quenched with water and extracted with ethyl acetate. Drying of the organic layer with Na$_2$SO$_4$ followed by concentration gave material that on purification by flash chromatography (CHCl$_3$/MeOH) afforded pure product: $^1$H NMR (300 MHz, CDCl$_3$) δ 8.10-7.65 (m, 4H), 7.26 (d, 2H), 6.83 (d, 2H), 4.99 (s, 2H), 3.79-3.66 (m, 4H), 3.14 (br, 4H).

Synthesis of 1-[4-(4-Chloro-phenyl)-piperazin-1-yl]-2-(2,4-dimethyl-imidazol-1-yl)-ethanone

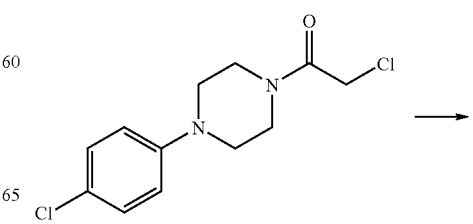

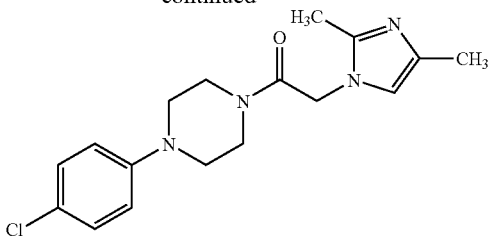

2,4-dimethylimidazole (0.633 g, 0.7 mmol) was taken up in dry DMF (15 mL) and dry potassium carbonate (340 mg) and KI (20 mg) was added and the reaction mixture was stirred at room temperature for 1 h under nitrogen. 2-Chloro-1-[4-(4-chloro-phenyl)-piperazin-1-yl]-ethanone (200 mg, 1.1 mmol) in DMF (5 mL) was then added to the mixture through a syringe. The reaction was then heated at 140° C. for 14 h, cooled and quenched with water and extracted with ethyl acetate. Drying of the organic layer with $Na_2SO_4$ followed by concentration gave material that was purified on a silica gel column ($CHCl_3$/MeOH) δ $^1H$ NMR (300 MHz, $CDCl_3$) δ 7.25 (d, 2H), 6.80 (d, 2H), 6.53 (s, 1H), 4.62 (s, 2H), 3.78 (br, 2H), 3.59 (br, 2H), 3.21 (br, 4H), 2.31 (s, 3H), 2.17 (s, 1H).

Synthesis of 2-(5-Amino-3-methylsulfanyl-[1,2,4]triazol-1-yl)-1-[4-(4-chloro-phenyl)-piperazin-1-yl]-ethanone

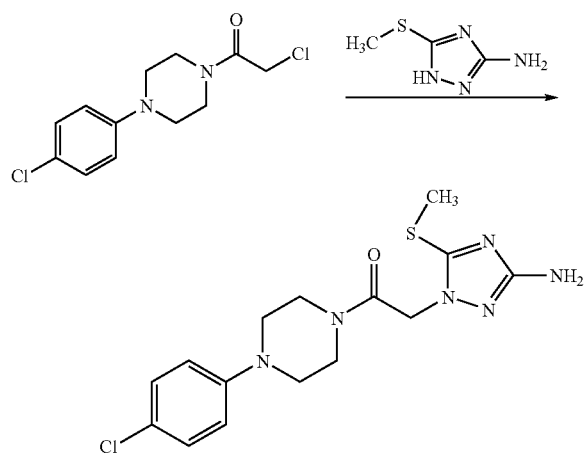

5-Methylsulfanyl-2H-[1,2,4]triazol-3-ylamine (0.216 g, 1.7 mmol) was taken in dry DMF (15 mL) and dry potassium carbonate (800 mg) and KI (20 mg) was added to it and the reaction mixture stirred at room temperature for 1 h under nitrogen. 2-Chloro-1-[4-(4-chloro-phenyl)-piperazin-1-yl]-hethanone (500 mg, 1.8 mmol) in DMF (5 mL) was then added to the mixture through a syringe. The reaction was then heated at 140° C. for 14 h, cooled and then quenched with water and extracted with ethyl acetate. Drying of the organic layer with $Na_2SO_4$ followed by concentration afforded crude product that was purified by column chromatography ($CHCl_3$/MeOH) δ $^1H$ NMR (300 MHz, DMSO-d6) δ 7.24 (d, 2H), 6.98 (d, 2H), 6.24 (s, 2H), 4.84 (s, 2H), 3.57 (m, 4H), 3.21 (m, 2H), 3.13 (m, 2H), 2.27 (s, 3H).

Synthesis of 2-[5-(2-Bromo-phenyl)-tetrazol-1-yl]-1-[4-(4-chloro-phenyl)-piperazin-1-yl]-ethanone

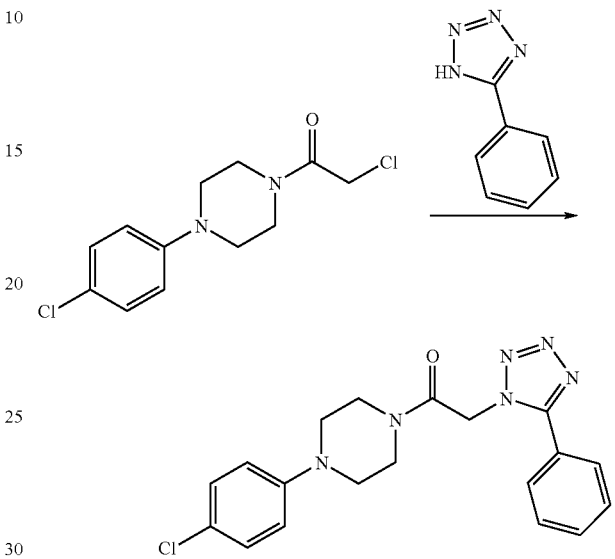

5-phenyl-1H-tetrazole (0.1216 g, 0.832 mmol) was taken in dry DMF (15 mL) and dry potassium carbonate (400 mg) and KI (20 mg) was added to it and the reaction mixture stirred at room temperature for 1 h under nitrogen. 2-Chloro-1-[4-(4-chloro-phenyl)-piperazin-1-yl]-ethanone (250 mg, 0.92 mmol) in DMF (5 mL) was then added to the mixture through a syringe. The reaction was then heated at 140° C. for 14 h, cooled and quenched with water and extracted with ethyl acetate. Drying of the organic layer with $Na_2SO_4$ followed by concentration afforded material that was further purified by flash column chromatography (ethyl acetate/pet ether): $^1H$ NMR (300 MHz, $CDCl_3$) δ 8.17 (br, 2H), 7.49 (br, 3H), 7.24 (br, 2H), 6.85 (br, 2H), 5.60 (s, 2H), 3.82 (m, 2H), 3.71 (m, 2H), 3.19 (m, 4H).

Synthesis of 2-[5-(2-Bromo-phenyl)-tetrazol-1-yl]-1-[4-(4-chloro-phenyl)-piperazin-1-yl]-ethanone

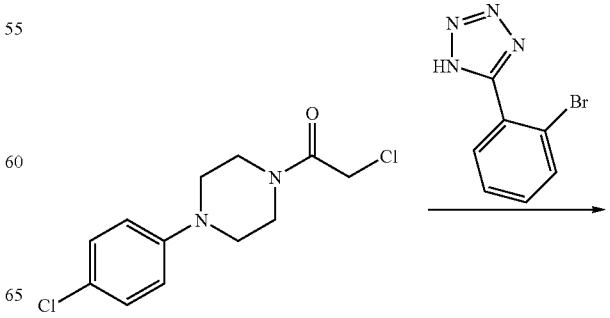

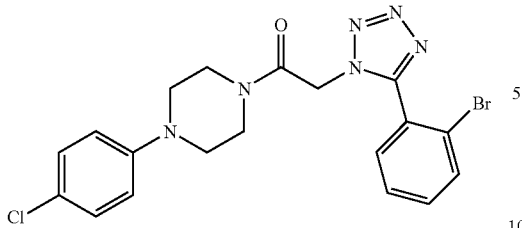

5-(2-Bromo-phenyl)-1H-tetrazole (0.374 g, 1.66 mmol) was taken in dry DMF (15 mL) and dry potassium carbonate (800 mg) and KI (20 mg) was added to it and stirred at rt for 1 h under nitrogen. 2-Chloro-1-[4-(4-chloro-phenyl)-piperazin-1-yl]-ethanone (500 mg, 1.8 mmol) in DMF (5 mL) was then added to the mixture through a syringe. The reaction was then heated at 140° C. for 14 h, cooled and quenched with water and extracted with ethyl acetate. Drying of the organic layer with Na$_2$SO$_4$ followed by concentration afforded material that was further purified by flash column chromatography (ethyl acetate/pet ether): $^1$NMR (300 MHz, CDCl$_3$) δ 7.90 (d, 1H), 7.74 (d, 1H), 7.45 (t, 1H), 7.35 (t, 1H), 7.25 (d, 2H), 6.87 (d, 2H), 5.65 (s, 2H), 3.84 (m, 2H), 3.73 (m, 2H), 3.20 (m, 4H).

Synthesis of 2-(5-methyl-3-trifluoromethyl-1,2,4-triazol-1-yl)-1-[4-(4-chloro-3-methoxy-phenyl)-piperazin-1-yl]-ethanone

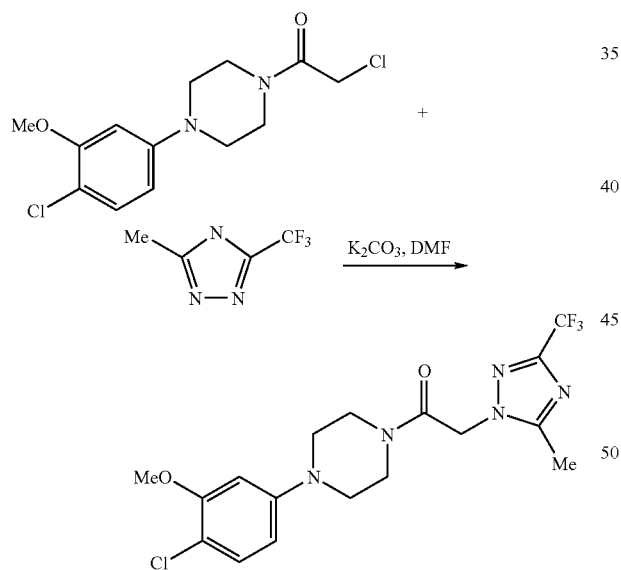

0.04 g (0.00026 mol) of 5-Methyl-3-trifluoromethyl-1,2,4-triazole, 0.078 g (0.00026 mol) of 1-(chloroacetyl)-4-(4-chloro-3-methoxyphenyl)-piperazine, and 0.04 g (0.0004 mol) of potassium carbonate in 3 mL dry DMF were heated at 80° C. for 14 hours. The reaction mixture was quenched with water, and was extracted with ethyl acetate. The ethyl acetate phase was washed once each with water and brine, dried with Na$_2$SO$_4$, filtered, and concentrated to give 2-(5-methyl-3-trifluoromethyl-1,2,4-triazol-1-yl)-1-[4-(4-chloro-3-methoxy-phenyl)piperazin-1-yl]-ethanone: $^1$H NMR (CDCl$_3$, 300 MHz) δ 7.22 (m, 1H), 6.48 (s, 1H), 6.443 (m, 1H), 5.07 (s, 2H), 3.87 (s, 3H), 3.71 (m, 4H), 3.18 (m, 4H), 2.50 (s, 3H) ppm; MS (ES) M+H expect=418.0, found=418.2.

Protocol V: Preparation of Compounds Via Acid or Base-Mediated De-Protections

Synthesis of 1-[4-(4-Chloro-3-methoxy-phenyl)-3-(R)-hydroxymethyl-piperazin-1-yl]-2-(4-chloro-5-methyl-3-trifluoromethyl-pyrazol-1-yl)-ethanone and Acetic acid 1-(4-chloro-3-methoxy-phenyl)-4-[2-(4-chloro-5-methyl-3-trifluoromethyl-pyrazol-1-yl)-acetyl]-piperazin-2-(R)-ylmethyl ester

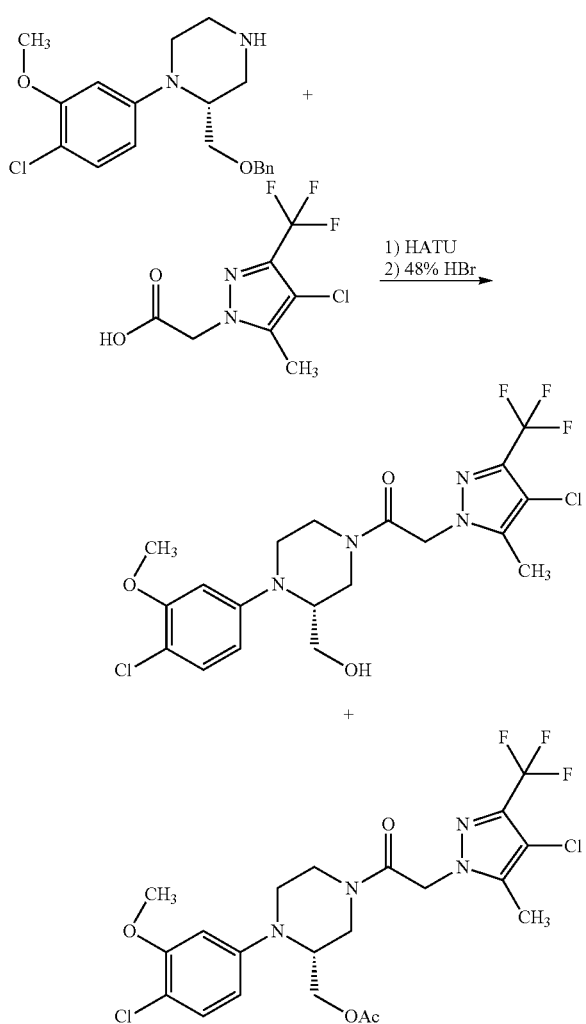

To 620 mg (1.79 mmol) of 2-(R)-Benzyloxymethyl-1-(4-chloro-3-methoxy-phenyl)-piperazine, 500 mg (2.05 mmol) of (4-Chloro-5-methyl-3-trifluoromethyl-pyrazol-1-yl)-acetic acid, and 280 mg (2.05 mmol) of 1-Hydroxybenzotriazole in 6 mL of N,N-Dimethylformamide at 0° C. was added 430 mg (2.24 mmol) of 1-[3-(Dimethylamino)propyl]-3-ethyl-carbodiimide hydrochloride. After two hours, the reaction was allowed to warm to ambient temperature, and was stirred for an additional 12 hours. The solution was partitioned between water and ethyl acetate, and the phases were separated. The ethyl acetate phase was washed once each with 1M NaHSO4, water, 1M NaOH, water, and brine, dried over Na$_2$SO$_4$, filtered, and concentrated to an oil.

The oil from above was heated in 6 mL of 48% HBr in acetic acid, with an additional 5 mL of acetic acid, at 70° C. for one hour, followed by cooling to ambient temperature. The mixture was partitioned between ethyl acetate and water, and the phases were separated. The ethyl acetate phase was washed once each with 1M NaOH and brine, dried over $Na_2SO_4$, filtered, and concentrated. The residue was chromatographed to give 1-[4-(4-Chloro-3-methoxy-phenyl)-3-(R)-hydroxymethyl-piperazin-1-yl]-2-(4-chloro-5-methyl-3-trifluoromethyl-pyrazol-1-yl)-ethanone as a white foam: $^1$H NMR (DMSO-d6, 400 MHz) δ 7.18 (m, 1H), 6.59 (m, 1H), 6.51 (m, 1H), 5.43 (m, 1H), 5.24 (m, 1H), 5.14 (m, 1H). 4.34-3.90 (m, 2H), 3.18 (s, 3H), 3.17 (par.obsc.m, 1H), 3.49-3.30 (m, 4H), 3.27-3.07 (m, 3H), 2.18 (m, 3H) ppm (rotomers); MS (ES) M+H expect=481.0, found=481.0.

In addition, Acetic acid 1-(4-chloro-3-methoxy-phenyl)-4-[2-(4-chloro-5-methyl-3-trifluoromethyl-pyrazol-1-yl)-acetyl]-piperazin-2-ylmethyl ester was also isolated as a colorless glass: $^1$H NMR (DMSO-d6, 400 MHz) δ 7.19 (m, 1H), 6.68 (s, 1H), 6.46 (m, 1H), 5.50 (m, 1H), 5.37(m, 1H), 4.28-3.87 (m, 5H), 3.82 (s, 3H), 3.59-3.10 (m, 4H), 2.18 (s, 3H), 1.84 (m, 3H) ppm (rotomers); MS (ES) M+H expect=523.0, found=523.0.

Synthesis of 1-[4-(4-Chloro-3-methylaminomethyl-phenyl)-piperazin-1-yl]-2-(4-chloro-5-methyl-3-trifluoromethyl-pyrazol-1-yl)-ethanone

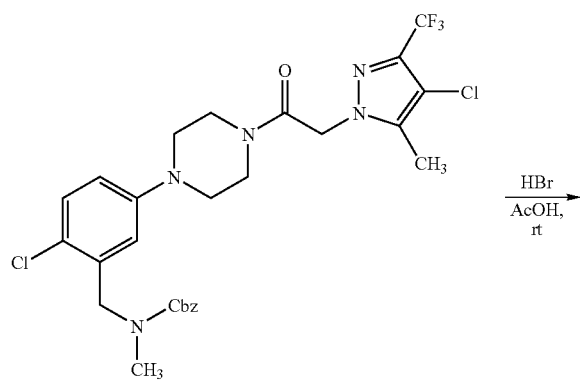

90 mg (0.15 mmol) of (2-Chloro-5-{4-[2-(4-chloro-5-methyl-3-trifluoromethyl-pyrazol-1-yl)-acetyl]piperazin-1-yl}-benzyl)-methyl-carbamic acid benzyl ester was treated with an excess of HBr/AcOH at room temperature for several hours, then purified by prep HPLC to give 1-[4-(4-Chloro-3-methylaminomethyl-phenyl)-piperazin-1-yl]-2-(4-chloro-5-methyl-3-trifluoromethyl-pyrazol-1-yl)-ethanone: $^1$H NMR (CDCl$_3$, 400 MHz) δ 7.30 (d, 1H), 7.10 (s, 1H), 6.87 (d, 1H), 5.08 (s, 2H), 4.24 (s, 2H), 3.71 (d, 4H), 3.21 (d, 4H), 2.71 (s, 3H), 2.28 (s, 3H) ppm MS (ES) M+H expect=464.1, found=464.0.

Synthesis of 1-[4-(3-Amino-4-chloro-phenyl)-piperazin-1-yl]-2-(4-chloro-5-methyl-3-trifluoromethyl-pyrazol-1-yl)-ethanone

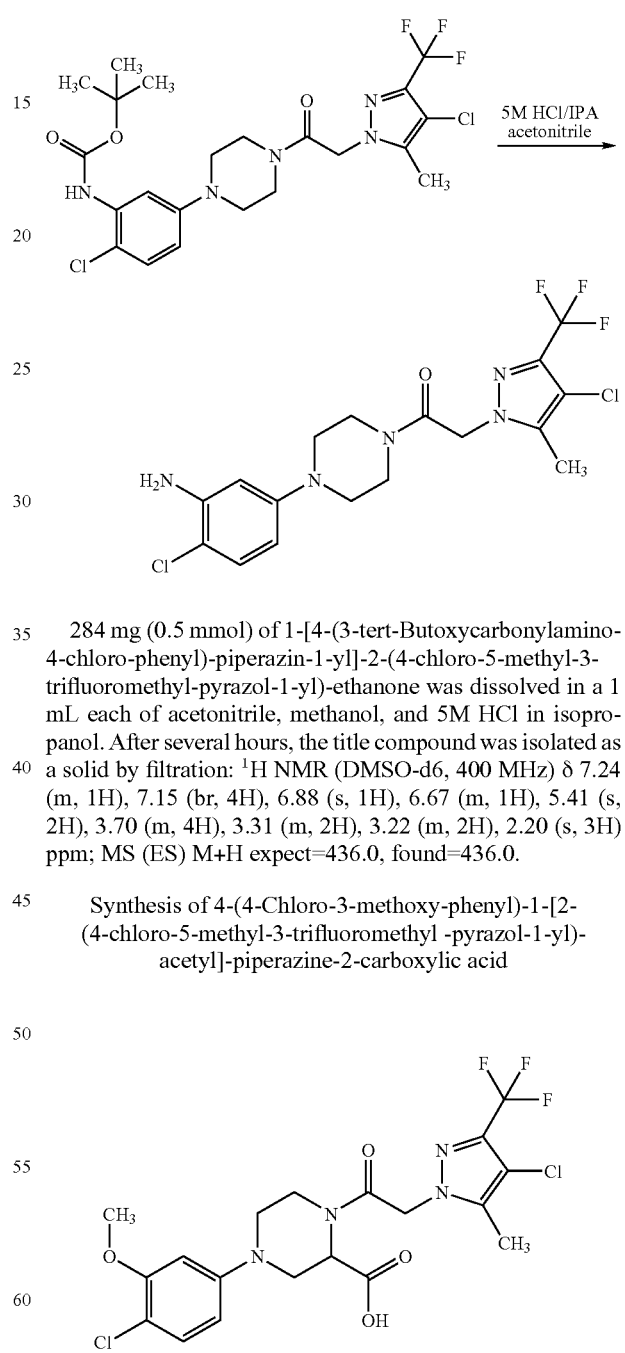

284 mg (0.5 mmol) of 1-[4-(3-tert-Butoxycarbonylamino-4-chloro-phenyl)-piperazin-1-yl]-2-(4-chloro-5-methyl-3-trifluoromethyl-pyrazol-1-yl)-ethanone was dissolved in a 1 mL each of acetonitrile, methanol, and 5M HCl in isopropanol. After several hours, the title compound was isolated as a solid by filtration: $^1$H NMR (DMSO-d6, 400 MHz) δ 7.24 (m, 1H), 7.15 (br, 4H), 6.88 (s, 1H), 6.67 (m, 1H), 5.41 (s, 2H), 3.70 (m, 4H), 3.31 (m, 2H), 3.22 (m, 2H), 2.20 (s, 3H) ppm; MS (ES) M+H expect=436.0, found=436.0.

Synthesis of 4-(4-Chloro-3-methoxy-phenyl)-1-[2-(4-chloro-5-methyl-3-trifluoromethyl -pyrazol-1-yl)-acetyl]-piperazine-2-carboxylic acid

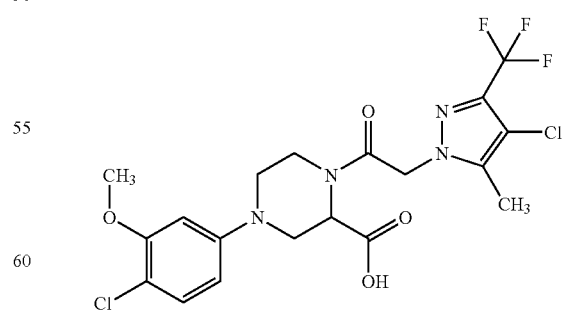

Title compound was prepared following the HATU mediated coupling protocol P, wherein 4-(4Chloro-3-methoxy-phenyl)-piperazine-2-carboxylic acid (−)-menthol ester and (4-Chloro-5-methyl-3-trifluoromethyl-pyrazol-1-yl)-acetic acid were used as the coupling components, to give the product as a solid. The product was further treated with a ten-fold excess of LiOH in 1/1 THF/water for 24 hours, and the reaction was purified by reverse phase HPLC to give the product as an oil: $^1$H NMR (400 MHz, CDCl$_3$) δ 7.27 (s, 1H), 6.79 (d, 1H), 6.59 (d, 1H), 5.22 (m, 2H), 3.91 (s, 3H), 3.05-2.99 (m, 3H), 3.32-3.19 (m, 4H), 2.29 (m, 3H), 2.06 (m, 1H) MS (ES) (M+H) expected=495.1, found=495.1

Protocol W: Preparation of Compounds Via Borohydride-Mediated Reductive Alkylation Synthesis of 1-[4-(4-Chloro-3-methylamino-phenyl)-piperazin-1-yl]-2-(4-chloro-5-methyl-3-trifluoromethyl-pyrazol-1-yl)-ethanone

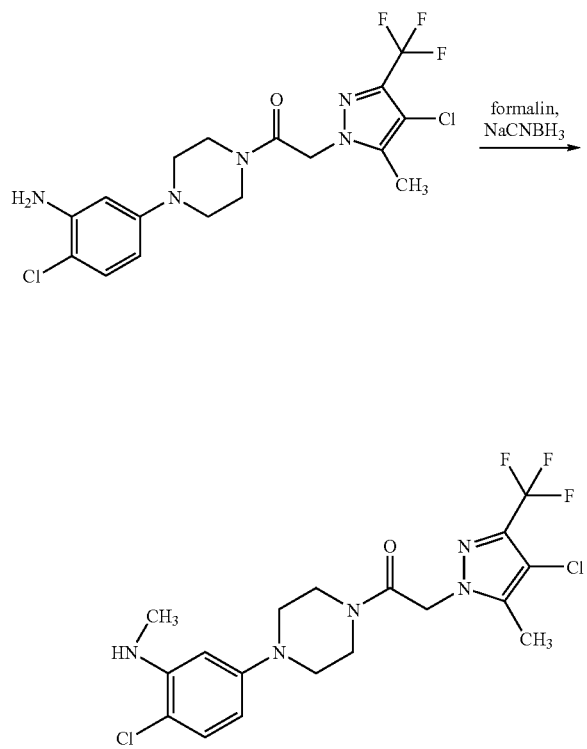

35° C.) using a 4.5 minute gradient of 20% to 95% B with a 1.1 minute wash at 95% B (A=0.1% formic acid/5% acetonitrile /94.9% water, B=0.08% formic acid/99.9% acetonitrile).

Synthesis of 2-(4-Chloro-3-dimethylamino-5-methyl-pyrazol-1-yl)-1-[4-(4-chloro-3-methoxy-phenyl)-piperazin-1-yl]-ethanone

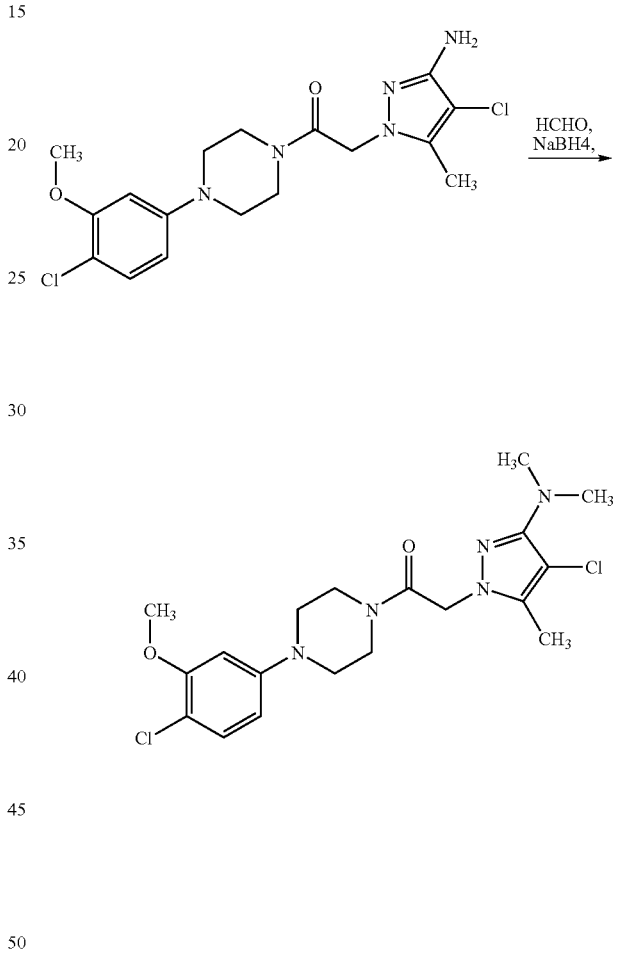

To 60 mg (0.13 mmol) of 1-[4-(3-Amino-4-chloro-phenyl)-piperazin-1-yl]-2-(4-chloro-5-methyl-3-trifluoromethyl-pyrazol-1-yl)-ethanone in 1 mL methanol was added 13 mg (0.19 mmol) of sodium cyanoborohydride and 14 microliters (0.16 mmol) of a 12.3M solution of formaldehyde in water. After 3 hours, the reaction was quenched by adding 50 microliters concentrated HCl. After 30 minutes, the solution was partitioned between ether and water, and the phases were separated. The aqueous phase was basified with 1M NaOH, and was extracted twice with ethyl actate. The combined ethyl acetate phases were washed once with brine, dried over Na$_2$SO$_4$, filtered, and concentrated to an oil. The oil was dissolved in methanol, acidified with 2 M HCl in ether, and diluted with ether to give the product as a solid: MS (ES) M+H expect=450.0, found=450.0; HPLC retention time=4.89 minutes (Agilent Zorbax SB-C18, 2.1×50 mm, 5µ, 120 mg (0.30 mmol) of 2-(4-Chloro-3-amino-5-methyl-pyrazol-1-yl)-1-[4-(4-chloro-3-methoxy-phenyl)-piperazin-1-yl]-ethanone was dissolved in 5 mL of tetrahydrofuran, and 0.10 mL of 0.1M H$_2$SO$_4$ was added. To this, 0.75 mL (9 mmol) of 37% formaldehyde in water was added, followed by 113 mg (3 mmol) of sodium borohydride. After 4 hours, the solution was quenched with 50 microliters of concentrated HCl. The mixture was then partitioned between 1/1 ether/hexanes and water, and the phases were separated. The aqueous phase was basified to pH>10 with 1 M NaOH, and was extracted twice with ethyl acetate. The combined ethyl acetate phases were washed twice with water, once with brine, dried over Na$_2$SO$_4$, filtered, and concentrated to an oil. The oil was purified by chromatography to give the product as a solid: $^1$H NMR (CDCl$_3$, 300 MHz) δ 7.20 (d, 1H), 6.48 (s, 1H), 6.42 (d, 1H), 4.84 (s, 2H), 3.86 (s, 3H), 3.74 (m, 2H), 3.63 (m, 2H), 3.17 (m, 4H), 2.79 (s, 6H), 2.16 (s, 3H) ppm; MS (ES) M+H expect=426.0, found=426.0.

Synthesis of 1-[4-(4-Chloro-3-dimethylamino-phenyl)-piperazin-1-yl]-2-(4-chloro-5-methyl-3-trifluoromethyl-pyrazol-1-yl)-ethanone

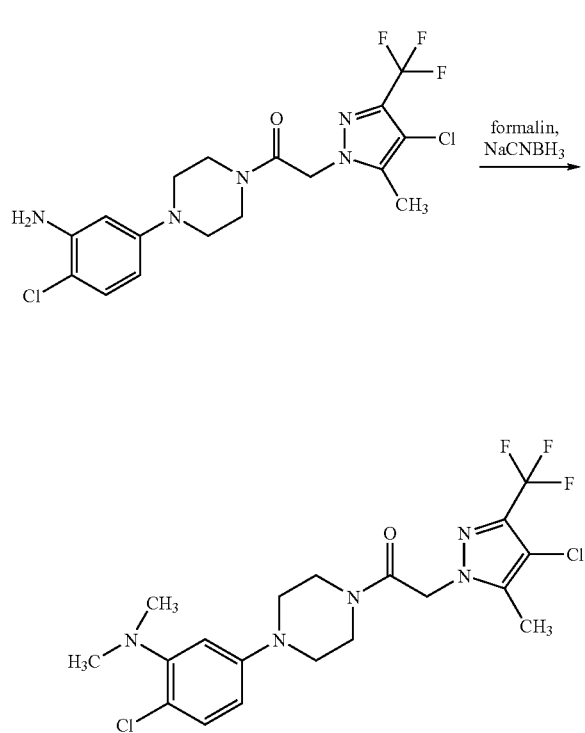

To 80 mg (0.17 mmol) of 1-[4-(3-Amino-4-chloro-phenyl)-piperazin-1-yl]-2-(4-chloro-5-methyl-3-trifluoromethyl-pyrazol-1-yl)-ethanone in 1 mL methanol was added 30 mg (0.39 mmol) of sodium cyanoborohydride and 32 microliters (0.39 mmol) of a 12.3M solution of formaldehyde in water. After 3 hours, the reaction was quenched by adding 50 microliters concentrated HCl. After 30 minutes, the solution was partitioned between ether and water, and the phases were separated. The aqueous phase was basified with 1M NaOH, and was extracted twice with ethyl actate. The combined ethyl acetate phases were washed once with brine, dried over Na₂SO₄, filtered, and concentrated to an oil. The oil was dissolved in methanol, acidified with 2 M HCl in ether, and diluted with ether to give the product as a solid: NMR (DMSO-d6, 400 MHz) δ 7.35 (m, 1H), 7.14 (s, 1H), 6.89 (m, 1H), 5.41 (s, 2H), 3.68 (m, 4H), 3.35 (m, 2H), 3.25 (m, 2H), 2.91 (br s, 6H), 2.20 (s, 3H) ppm; MS (ES) M+H expect=464.0, found=464.0.

Protocol X: Preparation of Compounds Via Acylation or Sulfonylation

Synthesis of N-(2-Chloro-5-{4-[2-(4-chloro-5-methyl-3-trifluoromethyl-pyrazol-1-yl)-acetyl]-piperazin-1-yl}-phenyl)-methanesulfonamide

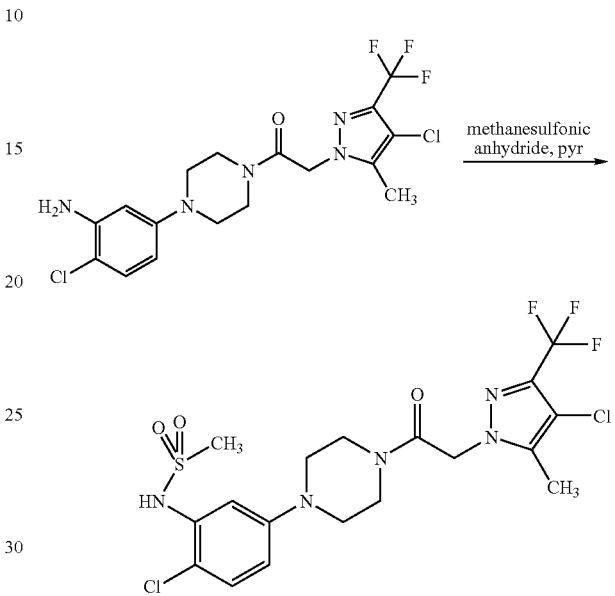

To 50 mg (0.1 mmol) of 1-[4-(4-Chloro-3-dimethylamino-phenyl)-piperazin-1-yl]-2-(4-chloro-5-methyl-3-trifluoromethyl-pyrazol-1-yl)-ethanone in 1.5 mL dichloromethane were added 39 mg (0.5 mmol) of pyridine and 21 mg (0.12 mmol) of methansulfonic anhydride. After 20 hours, the solution was partitioned between ethyl acetate and water, and the phases were separated. The ethyl acetate phase was washed once with brine, dried over Na₂SO₄, filtered, and concentrated to an oil. The oil was triturated with ether to give the title product as a solid: ¹H NMR (DMSO-d6, 400 MHz) δ 9.33 (s, 1H), 7.34 (m, 1H), 6.97 (m, 1H), 6.90 (m, 1H), 5.39 (s, 2H), 3.63 (m, 4H), 3.26 (m, 2H), 3.17 (m, 2H), 3.03 (s, 3H), 2.20 (s, 3H) ppm; MS (ES) M+H expect=514.0, found=514.0.

Synthesis of N-(2-Chloro-5-{4-[2-(4-chloro-5-methyl-3-trifluoromethyl-pyrazol-1-yl)-acetyl]-piperazin-1-yl}-phenyl)-acetamide

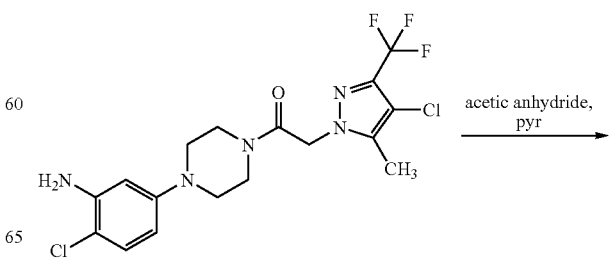

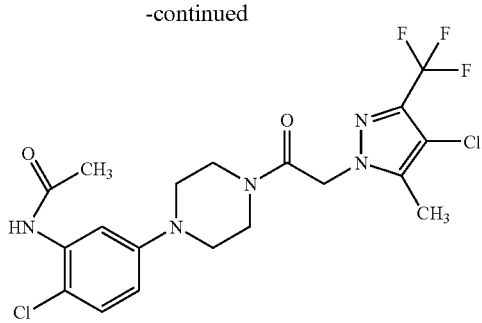

To 50 mg (0.1 mmol) of 1-[4-(4-Chloro-3-dimethylamino-phenyl)-piperazin-1-yl]-2-(4-chloro-5-methyl-3-trifluoromethyl-pyrazol-1-yl)-ethanone in 1.5 mL dichloromethane were added 39 mg (0.5 mmol) of pyridine and 11 mg (0.12 mmol) of acetic anhydride. After 20 hours, the solution was partitioned between ethyl acetate and water, and the phases were separated. The ethyl acetate phase was washed once with brine, dried over $Na_2SO_4$, filtered, and concentrated to an oil. The oil was triturated with ether to give the title product as a solid: $^1$H NMR (DMSO-d6, 400 MHz) δ 9.38 (s, 1H), 7.33 (s, 1H), 7.29 (m, 1H), 6.81 (m, 1H), 5.39 (s, 2H), 3.61 (m, 4H), 3.22 (m, 2H), 3.13 (m, 2H), 2.19 (s, 3H), 2.07 (s, 3H) ppm; MS (ES) M+H expect=478.0, found=478.0.

Synthesis of N-(2-Chloro-5-{4-[2-(4-chloro-5-methyl-3-trifluoromethyl-pyrazol-1-yl)-acetyl]-piperazin-1-yl}-phenyl)-formamide

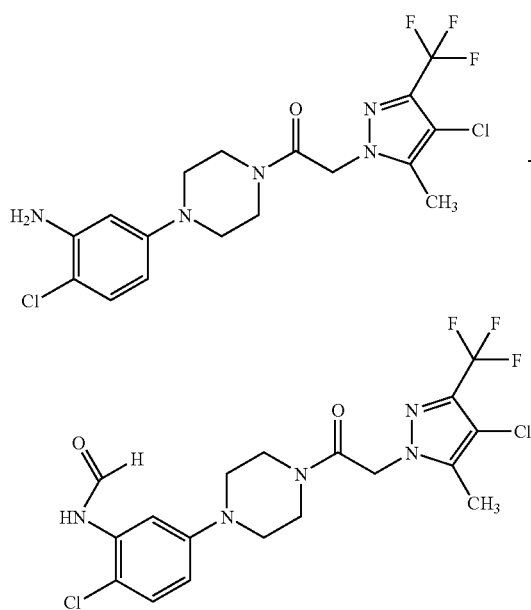

To 50 mg (0.1 mmol) of 1-[4-(4-Chloro-3-dimethylamino-phenyl)-piperazin-1-yl]-2-(4-chloro-5-methyl-3-trifluoromethyl-pyrazol-1-yl)-ethanone in 1.5 mL N,N-Dimethylformamide were added 22 mg (0.2 mmol) of triethylamine and 30 microliters (0.25 mmol) of Formic acid cyanomethyl ester, and the mixture was heated at 90° C. for 18 hours. The solution was partitioned between ethyl acetate and water, and the phases were separated. The ethyl acetate phase was washed once with brine, dried over $Na_2SO_4$, filtered, and concentrated to an oil. The oil was triturated with ether to give the title product as a solid: $^1$H NMR (DMSO-d6, 400 MHz) δ 9.76 (s, 1H), 8.34 (s, 1H), 7.79 (m, 1H), 7.32 (m, 1H), 6.79 (m, 1H), 5.40 (s, 2H), 3.61 (m, 4H), 3.23 (m, 2H), 3.14 (m, 2H), 2.20 (s, 3H) ppm; MS (ES) M+H expect=464.0, found=464.0.

Protocol Y: Preparation of Compounds Via Alkylation

Synthesis of 1-[4-(4-Chloro-3-methoxy-phenyl)-3-(R)-methoxymethyl-piperazin-1-yl]-2-(4-chloro-5-methyl-3-trifluoromethyl-pyrazol-1-yl)-ethanone

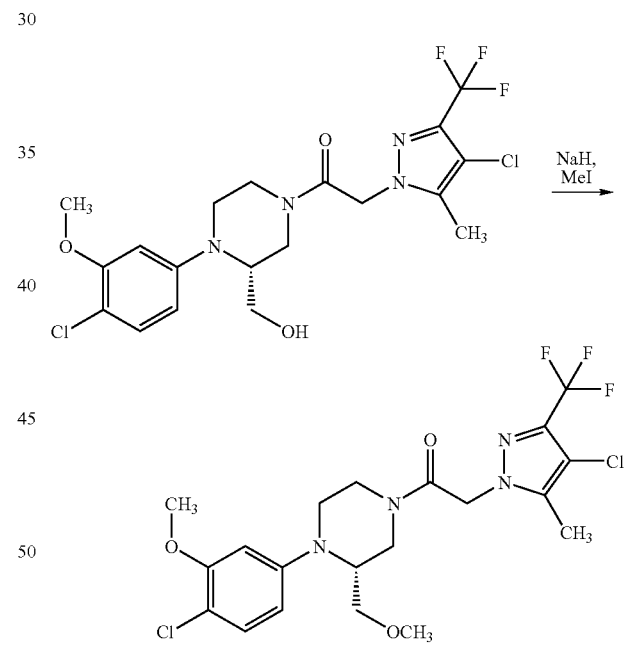

To 53 mg (0.11 mmol) of 1-[4-(4-Chloro-3-methoxy-phenyl)-3-(R)-hydroxymethyl-piperazin-1-yl]-2-(4-chloro-5-methyl-3-trifluoromethyl-pyrazol-1-yl)-ethanone and 19 mg (0.13 mmol) of methyliodide in 0.7 mL of N,N-dimethylformamide was added 9 mg (0.22 mmol) of 60% sodium hydride in oil. After 1 hour, the reaction was quenched with water, and was extracted with ethyl acetate. The ethyl acetate phase was washed with brine, dried over $Na_2SO_4$, filtered, and concentrated to give the title product as a foam: MS (ES) M+H expect=495.0, found=495.0; HPLC retention time=5.08 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-2-(R)-methoxymethyl-piperazin-1-yl]-2-(4-chloro-5-methyl-3-trifluoromethyl-pyrazol-1-yl)-ethanone

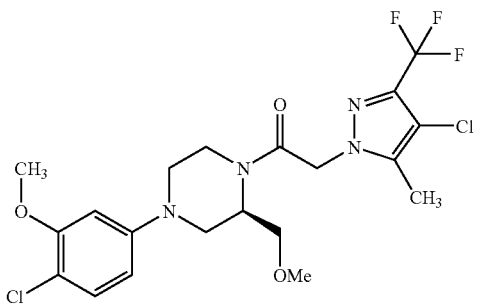

Title compound was prepared following the HATU mediated coupling protocol P, wherein 1-(4-Chloro-3-methoxy-phenyl)-3-(R)-methoxymethyl-piperazine and (4-Chloro-5-methyl-3-trifluoromethyl-pyrazol-1-yl)-acetic acid were used as the coupling components, to give the product as a solid: ¹H NMR (DMSO-d6, 400 MHz) δ 7.20 (m, 1H), 6.63 (m, 1H), 6.49 (m, 1H), 5.50 (m, 1H), 5.25 (m, 1H), 4.21 (m, 1H), 3.82 (s, 3H), 3.81-3.40 (m, 5H), 3.25 (s, 3H), 3.08-2.82 (m, 2H), 2.63 (m, 1H), 2.16 (m, 3H) ppm (rotamers); MS (ES) M+H expect=495.0, found=495.0.

Protocol Z: Preparation of Compounds Via Peroxyacid-Mediated N-Oxidation

Synthesis of 1-[4-(4-Chloro-3-methoxy-phenyl)-4-oxy-piperazin-1-yl]-2-(4-chloro-5-methyl-3-trifluoromethyl-pyrazol-1-yl)-ethanone

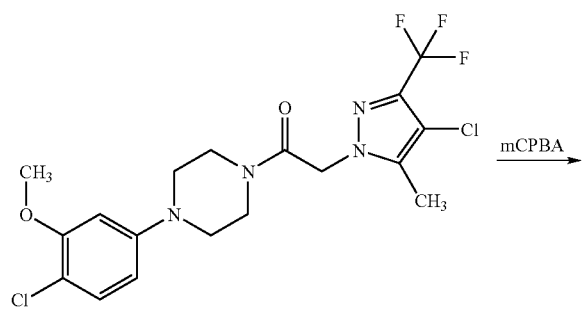

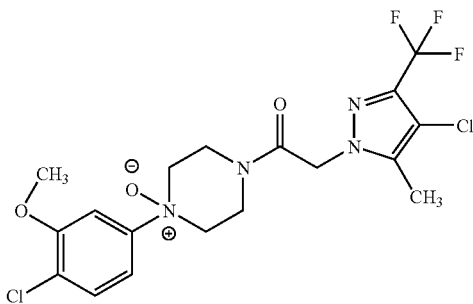

To 103 mg (0.23 mmol) of 1-[4-(4-Chloro-3-methoxy-phenyl)-piperazin-1-yl]-2-(4-chloro-5-methyl-3-trifluoromethyl-pyrazol-1-yl)-ethanone in 3 mL dichloromethane at 0° C. was added 60 mg (0.34 mmol) of meta-Chloroperoxybenzoic acid. After 30 minutes, the reaction was partitioned between 1/1 ether/ethyl acetate and water, and the phases were separated. The organic phase was washed once each with 1M NaOH, water, brine, dried over Na₂SO₄, filtered, and the product precipitated as a solid: ¹H NMR (DMSO-d6, 400 MHz) δ 8.09 (s, 1H), 7.70 (m, 1H), 7.52 (m, 1H), 5.40 (m, 2H), 4.28 (m, 1H), 4.10 (m, 2H), 3.98 (m, 1H), 3.90 (s, 3H), 3.85 (par.obs.m, 1H), 3.66 (m, 1H), 2.90 (m, 2H), 2.20 (s, 3H) ppm; MS (ES) M+H expect=467.0, found=467.0.

Protocol AA: Synthesis of Tri-Substituted Pyrazoles Via Suzuki Coupling

4-Chloro-3-methyl-5-phenyl-pyrazole

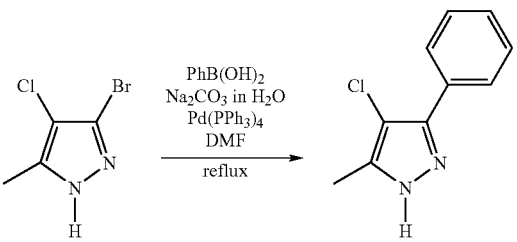

4-Chloro-3-methyl-5-bromopyrazole (1.27 mmole) was taken into dry DMF (20 mL) and Pd(PPH₃)₄ (0.44 mmole) was added, followed by addition of Na₂CO₃ (344.1 mg in 1 mL of water) and phenylboronic (1.41 mmole) acid. The mixture was then refluxed at 150° C. for 22 h, cooled to room temperature, and then inorganic salts were removed by filtration. 20 mL of dichloromethane was added to it and was washed with water to remove any DMF. The organic layer was then dried in Na₂SO₄ and removed to get the crude product which was then chromatographed to obtain the pure compound.

Other Pyrazoles Prepared Via Protocol AA

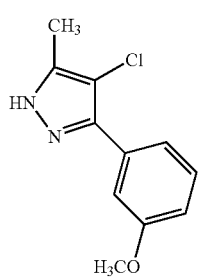

Protocol BB: Triazole Via Cyclocondensation of Acylhydrazine and Thioamide

5-Methyl-3-trifluoromethyl-1,2,4-triazole

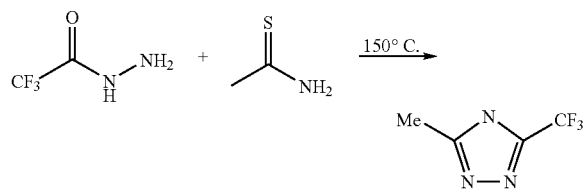

2.3 g (0.03125 mol) of thioacetamide and 4 g (0.03125 mol) of trifluoroaceticacid hydrazide were heated at 150° C. for 2 days. The white solid obtained were washed with ether, and dried under vacuum to give 5-Methyl-3-trifluoromethyl-1,2,4-triazole.

Preparation of Compounds with Modified Linker Regions

α-Substituted Acetyl Linkers

Synthesis of 2-(4-Chloro-5-methyl-3-trifluoromethyl-pyrazol-1-yl)-1-[4-(4-fluoro-phenyl)-piperazin-1-yl]-propan-1-one

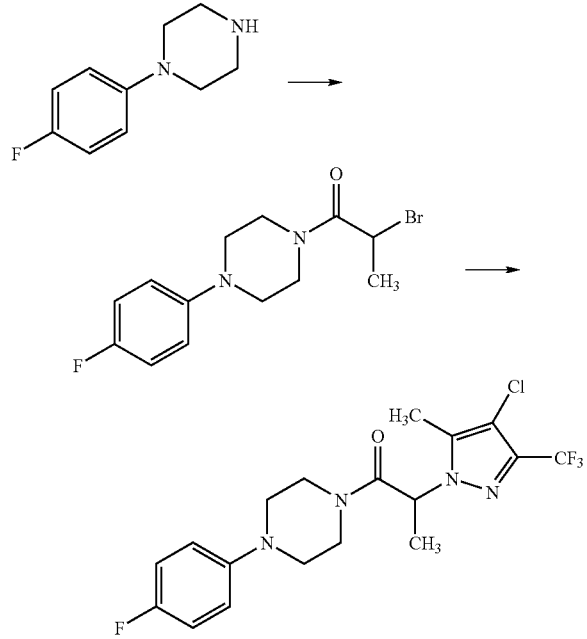

1-(4-Fluorophenyl)-piperazine (1 g, 5.5 mmol) dissolved in dry CH$_2$Cl$_2$ (20 mL) was cooled to 0° C. and triethylamine (1.66 g, 16.5 mmol) was added to it. 2-bromopropionyl chloride (1.14 g, 6.6 mol) was added slowly and the reaction mixture stirred for another 1 h at the same temperature. The mixture was washed with sodium bicarbonate and brine and dried (Na$_2$SO$_4$). Evaporation of the solvent afforded the intermediate alkyl bromide (0.68 g, 3.7 mmol) which was taken into dry DMF (20 mL). Potassium carbonate (2.1 g) was added. After stirring for 1 h at room temperature under nitrogen, 3-Methyl-4-chloro-5-trifluoromethyl-(1H)-pyrazole (1.3 g, 4.1 mmol) in DMF (5 mL) was then added to the mixture through a syringe. The reaction was then heated at 70° C. for 14 h, cooled and quenched with water and extracted with ethyl acetate. Drying of the organic layer over Na$_2$SO$_4$ followed by concentration afforded material that was purified on a neutral alumina column (chloroform/methanol).

Synthesis of 2-(4-Chloro-5-methyl-3-trifluoromethyl-pyrazol-1-yl)-1-[4-(4-chloro-phenyl)-piperazin-1-yl]-2-phenyl-ethanone

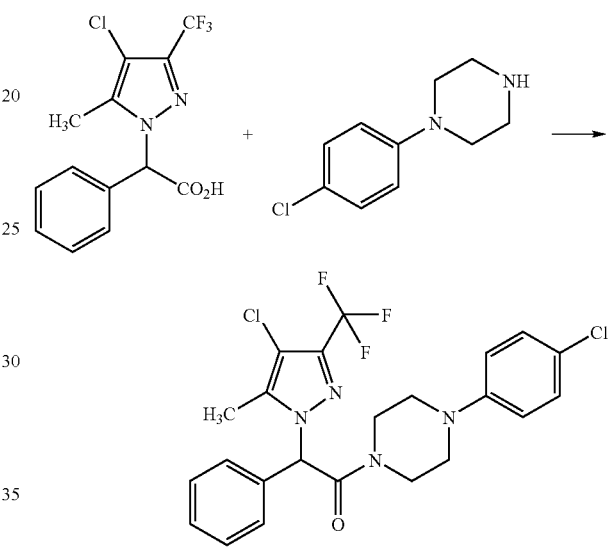

To 4-Chloro-5-methyl-3-(trifluoromethyl)-1H-pyrazol-1-yl]phenylacetic acid (0.1 g, 0.00036 mol) and 1-(4-chlorophenyl) piperazine (0.060 g, 0.00031 mol) in 20 mL of dry CH$_2$Cl$_2$ was added 0.2 mL of triethylamine and the reaction mixture stirred at room temperature for 30 min. TBTU (0.1 g, 0.00031 mol) was then added and the reaction mixture was stirred at room temperature for 17 h. The reaction mixture was diluted with 60 mL of CH$_2$Cl$_2$ and washed with saturated aqueous NaHCO$_3$ (2×50 mL), brine and then dried over sodium sulfate. The crude product obtained after concentration was purified by column chromatography to give the product as an off white solid: $^1$H NMR (CDCl$_3$, 300 MHz) 7.40-6.61 (m, 10H), 3.99 (m, 1H), 3.80 (m, 1H), 3.50-2.81 (m, 6H), 1.90 (s, 3H) ppm; MS (ES) M+H expected=497.1, found 497.2.

Synthesis of 2-(4-Chloro-5-methyl-3-trifluoromethyl-pyrazol-1-yl)-1-[4-(4-chloro-phenyl)-piperazin-1-yl]-2-(3-methoxy-phenyl)-ethanone

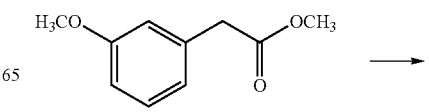

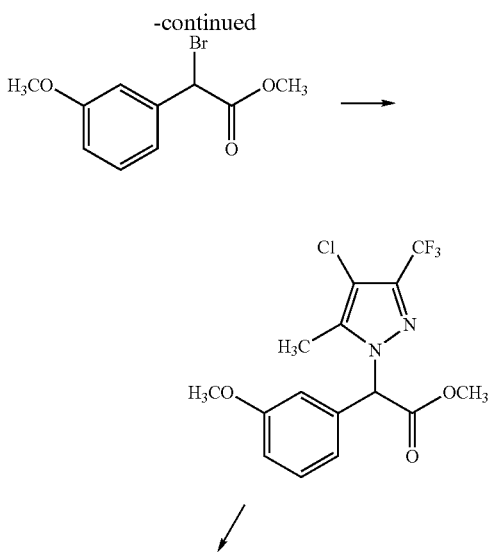

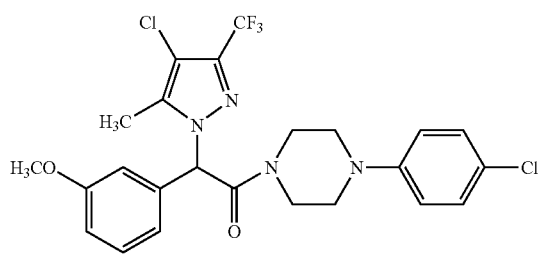

AIBN (10 mg) was added to a solution of (3-Methoxyphenyl)-acetic acid methyl ester (2 g, 11 mmol) in CCl4 (30 mL). The solution was then heated to reflux and NBS (2.3 g, 13 mmol) was added in portions. After complete addition the reaction mixture was refluxed for 4 h. After cooling, solid residue was filtered off and the filtrate concentrated to yield product Bromo-(3-methoxy-phenyl)-acetic acid methyl ester, that was washed repeatedly with pet ether.

4-Chloro-3-methyl-5-trifluoromethyl-1H-pyrazole (610 mg, 3.3 mmol) was taken into dry $CH_3CN$ (15 mL), dry potassium carbonate (1.15 g) was added to this and the resulting mixture stirred at room temperature for 1 h under nitrogen. Bromo-(3-methoxy-phenyl)-acetic acid methyl ester (900 mg, 2.8 mmol) in CH3CN (5 mL) was then added to the mixture through a syringe. The reaction was then heated at reflux for 10 h, cooled and then filtered through a celite filter bed. The filtrate was concentrated to obtain (4-Chloro-5-methyl-3-trifluoromethyl-pyrazol-1-yl)-(3-methoxy-phenyl)-acetic acid ethyl ester that was purified by column chromatography on silica (pet ether/ethyl acetate)

(4-Chloro-5-methyl-3-trifluoromethyl-pyrazol-1-yl)-(3-methoxy-phenyl)-acetic acid methyl ester was then dissolved in THF (20 mL) and LiOH (0.39 g) in water (5 mL) were added. The mixture was stirred at room temperature for 4 h. After this period the THF was completely evaporated from the reaction mixture under vacuum. The remaining aqueous layer was extracted with ethyl acetate (3×5 mL) and the organic layer was discarded. The aqueous layer was cooled in ice and neutralized by using concentrated HCl. This neutral aqueous layer was extracted with ethyl acetate (3×10 mL), the organic layer dried over $Na_2SO_4$, concentrated and purified by flash chromatography ($CHCl_3$/MeOH) to yield (4-Chloro-5-methyl-3-trifluoromethyl-pyrazol-1-yl)-(3-methoxy-phenyl)-acetic acid This compound (90 mg, 0.275 mmol) was taken into dry $CH_2Cl_2$ (10 mL) and cooled to 0° C. To this cold mixture was first added 4-chlorophenyl-piperazine (0.059 g, 0.31 mmol) followed by the addition of T3P (0.35 g, 0.55 mmol, 50% solution in EtOAc). The reaction was left overnight at room temperature. The mixture was diluted with $CH_2Cl_2$, and then washed sequentially with saturated NaHCO3 solution, brine, dried over $Na_2SO_4$, and concentrated to afford the crude product. Purification by column chromatograhpy on neutral alumina yielded 2-(4-Chloro-5-methyl-3-trifluoromethyl-pyrazol-1-yl)-1-[4-(4-chloro-phenyl)-piperazin-1-yl]-2-(3-methoxy-phenyl)-ethanone: $^1H$ NMR (300 MHz, CDCl$_3$) δ 7.37-7.21 (m, 3H), 6.96-6.79 (m, 4H), 6.60 (s, 1H), 5.31 (s, 1H), 3.99 (m, 1H), 3.80 (s, 3H), 3.79 (m, 1H), 3.46 (m, 2H), 3.24 (m, 1H), 3.13 (m, 2H), 2.91 (m, 1H), 1.95 (s, 3H).

Example 2

Protocols referred to within the following example are the protocols described within Example 2.

Protocol A: Metal Catalysed Arylation Reactions of Secondary Amines

Synthesis of 1-[4-(4-chloro-3-methoxy-phenyl)-[1,4]diazepane-1-carboxylic acid t-butyl ester

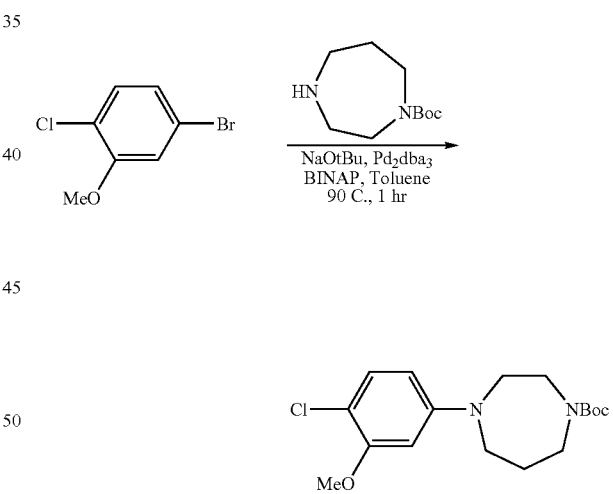

A mixture of 5-bromo-2-chloroanisole (1.10 g, 5 mmol, 1.0 equiv), N-Boc-homopiperazine (1.0 g, 1 equiv), NaOtBu (0.72 g, 1.5 eq), racemic-BINAP (58 m g, 0.015 equiv) and Pd2Dba3 (28 mg, 0.005 eq) in 3 mL of toluene was heated at 90° C. overnight. After cooling to room temperature, the residue was taken up in EtOAc and washed with water and brine. The organic layer was dried over $Na_2SO_4$, filtered, evaporated and subjected to flash column (1:4 EtOAc/hexane) to give 1-[4-(4-chloro-3-methoxy-phenyl)-[1,4]diazepane-1-carboxylic acid t-butyl ester. 1H NMR (400 MHz, CDCl3) δ 7.13 (d, 1H), 6.22 (d, 1H), 6.20 (dd, 1H), 3.86 (s, 3H), 3.45 (m, 6H), 3.32 (m, 2H), 3.20 (m, 2H), 1.95 (m, 2H), 1.20 (s, 9H). LCMS observed for (M+H-Boc)+: 241.

1-(4-chloro-3-propoxy-phenyl)-piperazine dihydrochloride

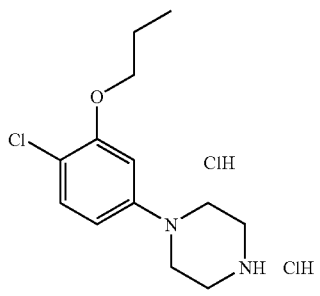

Following Protocol A, 4-bromo-1-chloro-2-propoxybenzene N-Boc-piperazine were coupled to give the Boc-protected intermediate.

The Boc-protected intermediate was treated with 4M HCl in p-dioxane to give the title compound.

1-(4-chloro-3-(2,2,2-trifluoro)ethoxy-phenyl)-piperazine dihydrochloride

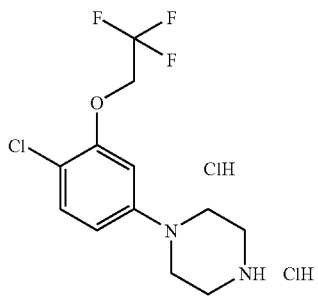

Following Protocol A, 4-bromo-1-chloro-2-(2,2,2-trifluoro)ethoxybenzene and N-Boc-piperazine were coupled to give the corresponding Boc-protected intermediate.

The Boc-protected intermediate was treated with 4M HCl in p-dioxane to give the title compound.

1-(4-chloro-3-(2-fluoro)ethoxy-phenyl)-piperazine dihydrochloride

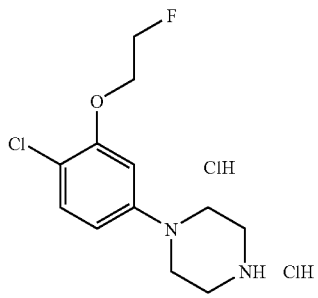

Following Protocol A, 4-bromo-1-chloro-2-(2-fluoro)ethoxybenzene N-Boc-piperazine were coupled to give the corresponding Boc-protected intermediate.

The Boc-protected intermediate was treated with 4M HCl in p-dioxane to give the title compound.

1-(4-Chloro-3-methoxy-phenyl)-3-trifluoromethyl-piperazine

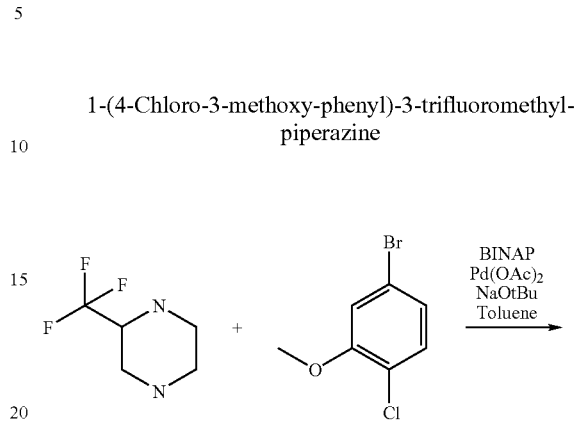

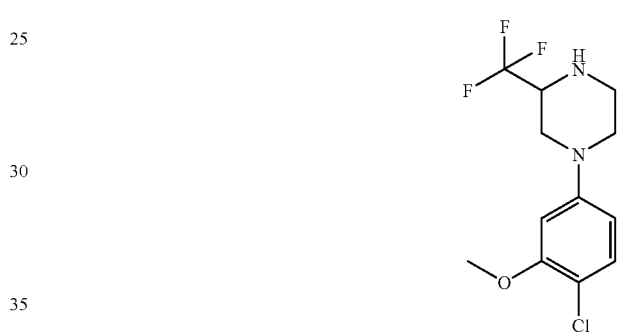

Following Protocol A, 2-trifluomethylpiperazine and 5-Bromo-2-chloro-anisole were coupled to give the title compound.

(S)-1-(3-Methoxy-phenyl)-3-methyl-piperazine

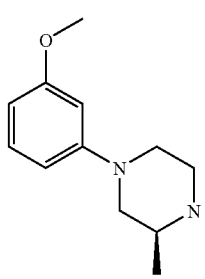

Took 467 mg 3-bromoanisole (2.5 mmol, 1.0 eq), 300 mg (S)-2-methylpiperazine (2.99 mmol, 1.2 eq), 27 mg Pd$_2$dba$_3$ (0.03 mmol, 0.01 eq), 50 mg BINAP (0.08 mmol, 0.03 eq), 336 mg NaOtBu (3.5 mmol, 1.4 eq), and 5 mL toluene in a 25 mL flask. The mixture was stirred in an 85° C. oil bath under N₂ overnight, then the solvents were removed under vacuum and the crude material treated with aqueous HCl to get the dihydrochloride.

1-(4-Chloro-3-methoxy-phenyl)-2,3-(cis)-dimethyl-piperazine

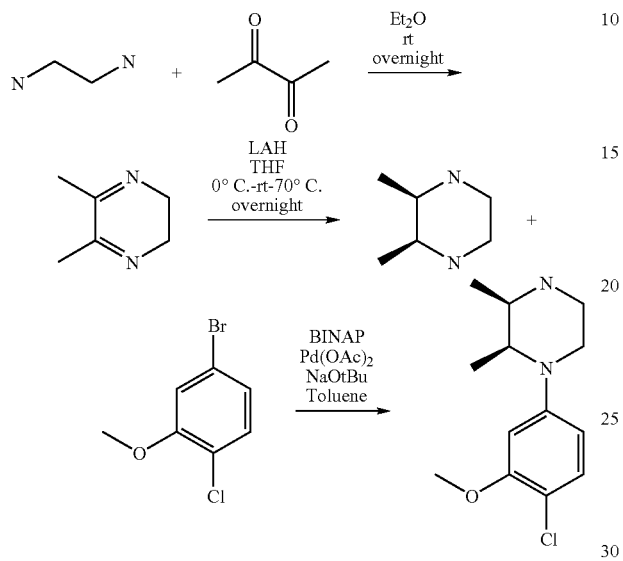

Step 1: 26 gm of ethylene diamine (0.43 mole) and 37.2 gm of 2,3-but-dione (0.433 mole) were dissolved in 1.2 l of dry diethyl ether, and the reaction mixture was stirred overnight. The solvent was removed, and the oily residue was distilled to obtain 22 gm (45%) of the intermediate diimine.

Step 2: To a solution of LAH (1.86 gm, 0.049 mole) in dry THF (10 ml) was added the intermediate diamine (5 gm, 0.047 mole) dissolved in THF (5 ml) at 0° C. The reaction mixture was then refluxed overnight at 70° C. The reaction was cooled to room temperature, was quenched with 5 mL 15% NaOH, and was filtered through celite. The filtrate was concentrated to obtain the intermediate cis-2,3-dimethylpiperazine.

Step 3: Following Protocol A, 2,3-dimethylpiperazine and 5-Bromo-2-chloro-anisole were coupled to give the title compound.

Synthesis of 1-(7-Chloro-benzofuran-4-yl)-piperazine

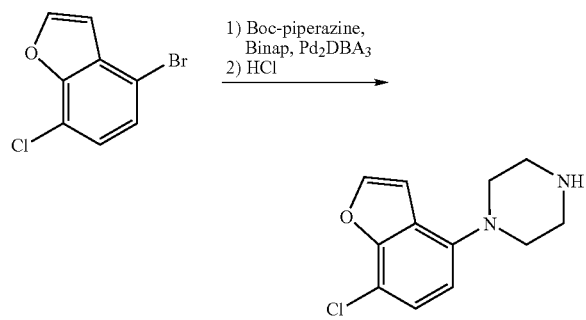

Step 1: Following Protocol A, mono-BOC-piperazine and 4-Bromo-7-chloro-benzofuran were coupled to give the Boc-protected intermediate.

Step 2: 0.139 g (0.41 mmol) of the Boc-protected intermediate from above was dissolved in dry ether, and 2 mL of 1M HCl in ether was added. After nine hours the solids were isolated by filtration, and washed with dry diethyl ether to give the title compound.

1-(4-Chloro-3-methoxy-phenyl)-cis-2,5-dimethyl-piperazine

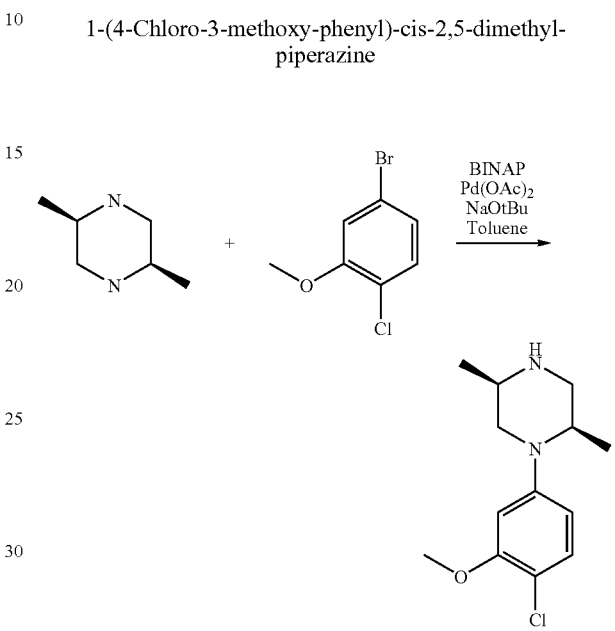

Following Protocol A, Cis-2,5-dimethylpiperazine and 5-Bromo-2-chloro-anisole were coupled to give the title compound.

Synthesis of 1-(4-Chloro-3-methoxy-phenyl)-trans-2,5-dimethyl-piperazine

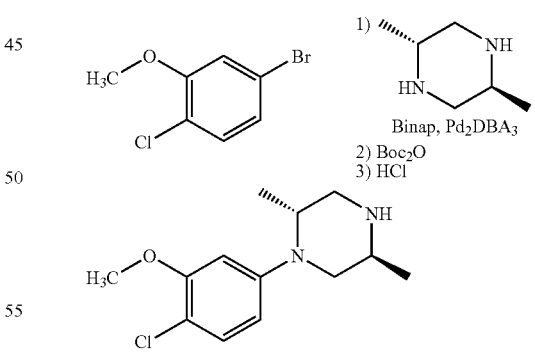

Step 1: Following Protocol A, trans-2,4-dimethyl piperazine and 5-Bromo-2-chloroanisole were coupled to give the crude title compound. Purification was not possible, so the mixture was taken on to Step 2:

Step 2: 0.159 g (0.624 mmols) of the impure title compound, 0.204 g (0.936 mmols) of BOC-anhydride, and 0.26 mL (1.87 mmols) of triethylamine were dissolved in dry dichloromethane (10 ml), and the solution was stirred for 4 hours. The solution was then washed twice with 10% citric acid, once with 10% NaHCO₃, dried over Na₂SO₄, and concentrated. The residue was purified by column chromatography.

Step 3: To 150mg (0.42 mmol) of the above BOC-intermediate in methanol was added 5 m HCl in ether under N₂ atmosphere, and the mixture was stirred for 7 hours. The solids formed were isolated by filtration to give the title compound as the HCl salt (0.110 g, 85%).

Protocol B: Piperazine Ring Formation Via Cyclization Reactions

Synthesis of 1-(4-Fluoro-3-methoxy-phenyl)-piperazine

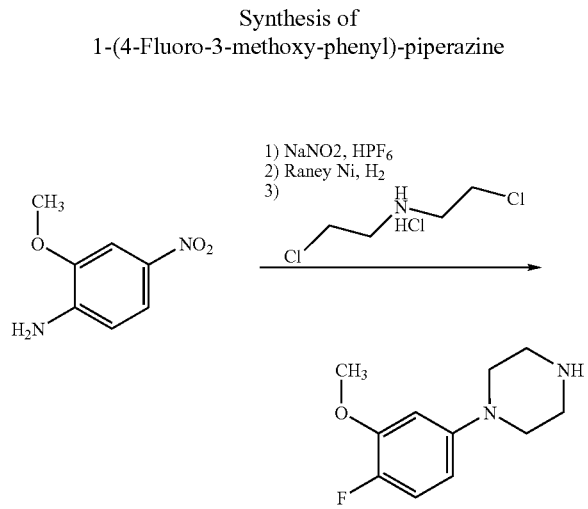

Step 1: Concentrated HCl (54.26 g, 1.486 mol) was added to 2-methoxy-4-nitroaniline (50 g, 0.29 mols) in a 3 Lt 3-necked round bottom flask. Reaction mixture was heated at 80° C. for half an hour. Then it was cooled to −10° C. An aqueous solution of sodium nitrate (24.62 g, 0.356 mol) was added to it. Hexafluorophosphoric acid (86.82 g, 0.594 mol) was then added while maintaining the temperature within −2 to 0° C. and was stirred for half an hour. Solid separates. The solid was filtered and washed with cold water followed by 50% methanol in ether. Then the solid was dried under high vacuum overnight at rt.

The solid was added to hot mineral oil (170° C.) and was stirred for half an hour at 170° C., then it was cooled to rt and satd. Sodium carbonate solution (300 mL) was added and steam-distilled to obtain 4-fluoro-3-methoxy nitro benzene (3.5 g, 6.8%).

Step 2: Raney nickel (0.6 g) was added to a solution of 4-fluoro-3-methoxy nitro benzene (3.5 g, 0.02046 mol) in dry methanol, and this was shaken for 12 hours in a par-shaker under 10 PSI of hydrogen. The Raney nickel was then filtered off, and the filtrate was concentrated to obtained the crude compound. This material was purified by column chromatography using pet-ether:Ethyl acetate (100:3) as eluent to give 4-fluoro-3-methoxy aniline as a reddish liquid (1.4 g, 48%).

Step 3: 4-fluoro-3-methoxy aniline (0.5 g, 0.00354 mol) dissolved in n-butyl alcohol (10 mL), and this was added to a stirring solution of Bis(2-chloro ethyl)amine hydrochloride (0.632 g, 0.00354 mol) in n-butyl alcohol at rt. The reaction mixture was then refluxed for 2 days, cooled to rt, and anhydrous sodium carbonate (1.12 g, 0.01062 mol) was added. The mixture was refluxed for an additional 2 days, after which the solvent was evaporated. The residue was dissolved in ethyl acetate, washed with water, brine solution, dried over Na₂SO₄, and concentrated. The crude residue was purified by column chromatography using chloroform:methanol as eluent (100:5) to give the title compound as off white solid (58 mg, 7%).

Protocol D: Synthesis and Addition of Elaborated Piperazines to Aryl and Heteroaryl Halides Via Aryl-Halogen Displacement Methodologies 2-Chloro-5-piperazin-1-yl-benzoic acid ethyl ester

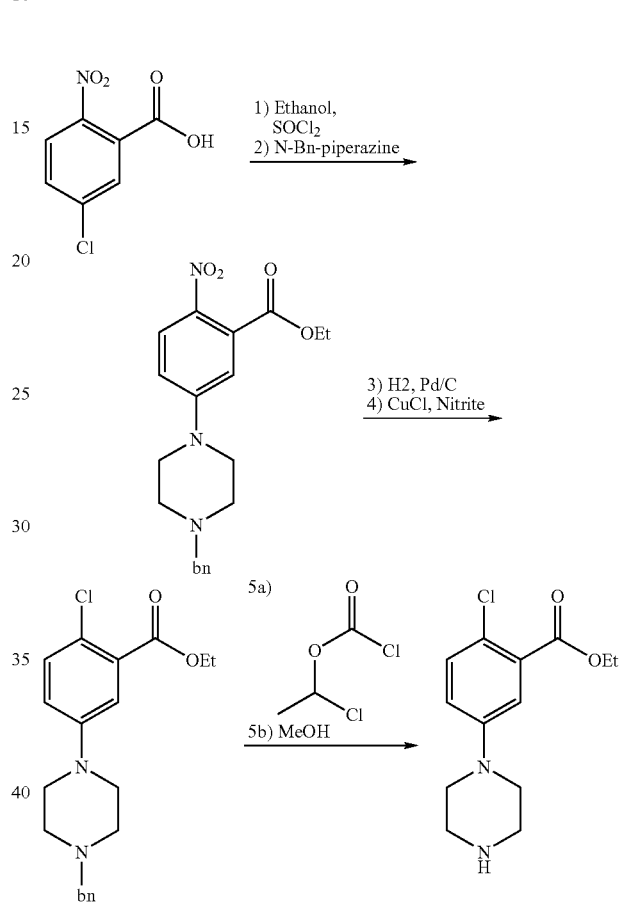

Step 1: To 5-Chloro-2-nitrobenzoic acid (15 g, 0.07 mol) in ethanol (200 ml) was added thionylchloride (27 ml, 0.37 mol) drop wise at 0° C. The reaction mixture was refluxed at 85° C. overnight. The reaction was cooled to ambient temperature, the methanol was removed under vacuum, and the residue was added to ice water. The resulting mixture was basified using solid NaHCO3, and was extracted with ethyl acetate. The ethyl acetate layer was washed with water, brine, dried over Na₂SO₄, and concentrated to give the corresponding ethyl ester.

Step 2: Ethyl 5-Chloro-2-nitrobenzoate (15 g, 0.0655 mol), benzylpiperazine (28.8 g, 0.16 mol), dry K₂CO₃ (9 g, 0.16 mol), tetrabutylammonium iodide (1.5 g) in dry DMSO (150 ml) was heated at 120° C. overnight. The mixture was cooled to ambient temperature, quenched with water, and extracted with ethyl acetate. The ethyl acetate layer was extracted with 1.5N HCl, and was discarded. The acid layer was washed with ether, basified with NaHCO₃, and extracted with fresh ethyl acetate. The ethyl acetate layer was washed with water and brine, dried over Na₂SO₄, and concentrated to give 2-Nitro-5-piperazin-1-yl-benzoic acid ethyl ester.

Step 3: To 2-Nitro-5-piperazin-1-yl-benzoic acid ethyl ester (22 g, 0.059 mol) in methanol (150 ml) was added Palladium on carbon (2.2 g, 10%) under nitrogen. The reaction mixture was stirred under $H_2$ for 2 hours. The mixture was filtered and concentrated to give the corresponding aniline.

Step 4: To cupric chloride (3.0 g, 0.017 mol) in acetonitrile (50 ml) was added t-butylnitrite (1.7 ml, 0.015 mol) slowly, and the mixture was heated to 60° C. for 15 minutes. The aniline from above (5.0 g, 0.015 mol) in acetonitile (10 ml) was added slowly, and the mixture was stirred 30 minutes at 60° C. The reaction was cooled to ambient temperature, quenched with water, and extracted with ethyl acetate. The ethyl acetate phase was washed with water and brine, dried over $Na_2SO_4$, and concentrated. The crude was purified by column chromatography to give 2-Chloro-5-piperazin-1-yl-benzoic acid ethyl ester.

Step 5: To 2-Chloro-5-piperazin-1-yl-benzoic acid ethyl ester (0.8 g, 0.0022 mol) in dry dichloroethane (20 ml) was added 1-chloroethyl chloroformate (0.3 ml, 0.0026 mol), and the mixture was heated at 85° C. for 3.0 hours. The solvent was removed under vacuum, the residue was dissolved in methanol (10 ml), and the solution was refluxed for 1 hour at 85° C. The solution was cooled to ambient temperature, the methanol was removed under vacuum, and the residue was dissolved in water. The solution was washed with ether and chloroform. The water layer was then basified with $NaHCO_3$, extracted with dichloromethane, dried over $Na_2SO_4$, and concentrated. The residue was purified by chromatography to give the title compound.

1-(2-Bromo-4-chloro-5-methoxy-phenyl)-piperazine

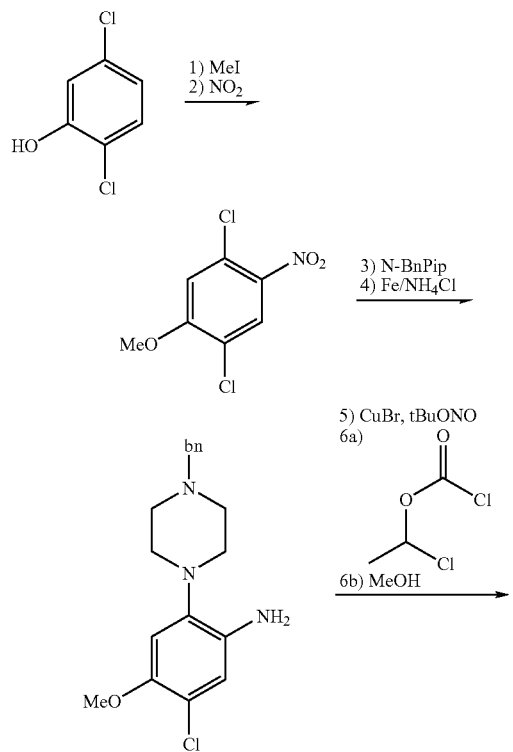

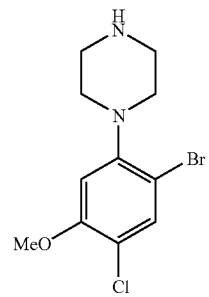

Step 1: 2,5-Dichlorophenol (25 g, 0.15 mol), methyliodide (108 g, 0.76 mol), and dry $K_2CO_3$ (105 g, 0.76 mol) were combined in dry acetone (250 ml), and the mixture was stirred at for 12 hours. The reaction mixture was concentrated. The residue was slurried in ethyl acetate, washed with water and brine, dried over $Na_2SO_4$, and concentrated to give 2,5-dichloroanisole.

Step 2: To 2,5-Dichloroanisole (17.5 g, 0.099 mol) in acetic acid (50 ml) was added a mixture of concentrated nitric acid (9 ml) and concentrated Sulfuric acid (13 ml) at 0° C. The reaction mixture was stirred for 2 hours. The solids were isolated by filtration, washed with water, and dried. The mixture was washed with pet ether to remove the ortho-isomer, and the remaining solids were clean 2,5-Dichloro-4-nitroanisole.

Step 3: 2,5-Dichloro-4-nitroanisole (6.0 g, 0.027 mol), benzylpiperazine (9.5 g, 0.05 mol), and dry $K_2CO_3$ (9.36 g, 0.067 mol) were combined in dry DMSO (150 ml). Tetrabutylammonium iodide (0.6 g) was added, and the mixture was heated at 120° C. for 12 hours. The reaction was cooled to ambient temperature, quenched with water, and extracted with ethyl acetate. The ethyl acetate phase was dried over $Na_2SO_4$, and concentrated to give the N-benzylpiperazine intermediate.

Step 4: To the intermediate from Step 3 (11 g, 0.033 mol) in dry methanol was added iron powder (7.38 g, 0.13 mol), followed by ammonium chloride (12.7 g, 0.23 mol) in water (100 ml) drop wise, and the mixture was heated at 75° C. for 14 hours. The reaction mixture was cooled to ambient temperature, filtered, and concentrated. The residue was dissolved in ethyl acetate, washed with water and brine, dried over $Na_2SO_4$, and concentrated to give 2-(4-Benzyl-piperazin-1-yl)-5-chloro-4-methoxy-phenylamine.

Step 5: Following Protocol G, 2-(4-Benzyl-piperazin-1-yl)-5-chloro-4-methoxy-phenylamine was treated with cupricbromide and tert-butylnitrite to give 1-Benzyl-4-(2-bromo-4-chloro-5-methoxy-phenyl)-piperazine.

Step 6: To 1-Benzyl-4-(2-bromo-4-chloro-5-methoxy-phenyl)-piperazine (1.0 g, 0.0025 mol) in dry 1,2-dichloroethane (20 ml) was added 1-chloroethyl chloroformate (0.3 ml, 0.0026 mol), and the reaction was heated at 85° C. for 3.0 hours. The solvent was removed under vacuum, methanol (10 ml) was added, and the solution was refluxed for 1 hour. The methanol was removed under vacuum, the residue was dissolved in water, and the aqueous layer was washed with ether. The water layer was basified with NaHCO3, and was extracted with dichloromethane. The dichlormethane phase was dried over Na$_2$SO$_4$, and was concentrated. The crude was purified by chromatography to give the title compound.

Protocol E: Selected Examples of Halogenation of Aromatic Systems after Attachment of the Piperazine Ring System 1-(2,4-Dichloro-5-methoxy-phenyl)-3-(S)-methyl-piperazine

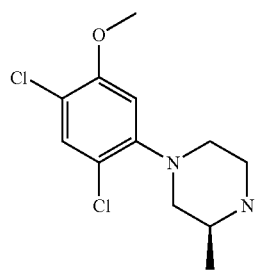

Took 500 mg 1-(3-Methoxy-phenyl)-3-(S)-methyl-piperazine (1.79 mmol, 1.00 eq) in 5 mL of 1:1 DCM:AcOH in a 25 mL flask. The mixture was cooled to 0° C. in an ice water bath, then 550 mg NCS (3.58 mmol, 2.00 eq) was added to the stirring solution at once. The ice bath was removed and the mixture allowed to stir at room temperature for approximately one hour. LC/MS revealed a mixture of chlorinated products which were isolated by preparative HPLC.

(S)-1-(4-Bromo-3-methoxy-phenyl)-3-methyl-piperazine

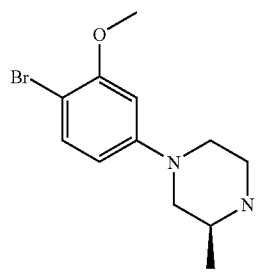

Took 500 mg (S)-1-(3-Methoxy-phenyl)-3-methyl-piperazine (1.79 mmol, 1.00 eq) in 5 mL of 1:1 DCM:AcOH in a 25 mL flask. The mixture was cooled to 0° C. in an ice water bath, then 91 uL of Br$_2$ (1.79 mmol, 1.00 eq) was added to the stirring solution at once. The ice bath was removed and the mixture allowed to stir at room temperature for approximately one hour. LC/MS revealed a mixture of brominated products which were isolated by preparative HPLC.

Protocol F: Selected Examples of Demethylation/Etherification of Aromatic Precursors for Attachment of the Piperazine Ring System to Access Key Arylpiperazine Moieties Synthesis of 4-Bromo-7-chloro-benzofuran

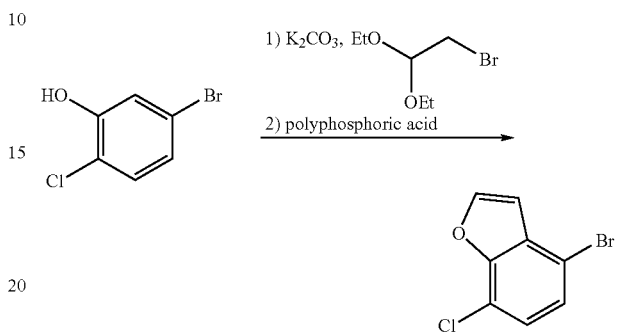

Step 1: 1.46 g (6.99 mmols) of 3-Bromo-6-chlorophenol, 1.93 g (13.98 mmols) of anhydrous K$_2$CO$_3$, and 2.07 g (10.48 mmols) of bromoacetaldehyde diethyl acetal were combined and heated at 140° C. for 3 hours. The reaction was then cooled to ambient temperature, partitioned between ethyl acetate and water, and the phases were separated. The ethyl acetate layer was washed once each with water and brine, dried over Na$_2$SO$_4$, and concentrated to give the crude acetal (2.3 g, 99%).

Step 2: 2.29 g of the crude acetal from above and 4 g of polyphosphoric acid were combined in 20 mL of toluene, and the mixture was heated at 90° C. for 3 hours. The reaction was then cooled to ambient temperature, partitioned between ethyl acetate and water, and the phases were separated. The ethyl acetate layer was washed once each with water, 10% NaHCO$_3$, and brine, dried over Na$_2$SO$_4$, and concentrated. The residue was purified by column chromatography to give the title compound (0.550 g, 31%).

4-bromo-1-chloro-2-(2,2,2-trifluoro)ethoxybenzene

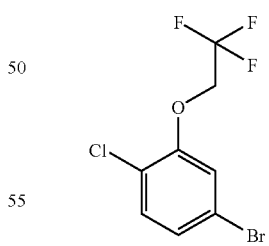

14.7 g of 5-bromo-2-chlorophenol (71 mmol, 1.0 eq), 18.6 g triphenylphosphine (71 mmol, 1.0 eq), and 200 mL dry THF were combined in a 500 mL round bottom flask fitted with an N$_2$ inlet. The mixture was cooled in an ice water bath, then 12.4 g diethylazodicarboxylate (71 mmol, 1.0 eq) was added. After one hour of stirring, 5.7 mL of 2,2,2-trifluoroethanol (78 mmol, 1.1 eq) was added, and the flask was removed from the ice bath and allowed to stir at room temperature overnight. The reaction was quenched with a small amount of water, and the solvents removed under vacuum. The residue was dissolved in 150 mL DCM, and diluted with hexane until it became cloudy. The solution was placed in freezer for several hours, the crystalline triphenylphosphine oxide by-product was discarded and the mother liquor was concentrated under vacuum and purified by column chromatography (EtOAc/Hexane).

4-bromo-1-chloro-2-(2-fluoro)ethoxybenzene

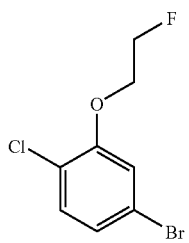

14.7 g 5-bromo-2-chlorophenol (71 mmol, 1.0 eq), 18.6 g triphenylphosphine (71 mmol, 1.0 eq), and 200 mL dry THF were combined in a 500 mL round bottom flask fitted with an N₂ inlet. The mixture was cooled in an ice water bath, then 12.4 g diethylazodicarboxylate (71 mmol, 1.0 eq) was added. After one hour of stirring, 4.6 mL of 2-fluoroethanol was added, and the flask was removed from the ice bath and allowed to stir at room temperature overnight. The reaction was quenched with a small amount of water, and the solvents removed under vacuum. The residue was dissolved in 150 mL DCM, and diluted with hexane until it became cloudy. The solution was placed in freezer for several hours, the crystalline triphenylphosphine oxide by-product was discarded and the mother liquor was concentrated under vacuum and purified by column chromatography (EtOAc/Hexane).

4-bromo-1-chloro-2-propoxybenzene

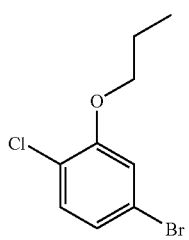

1.2 g of 5-bromo-2-chlorophenol (5.9 mmol, 1.0 eq), 1.6 g of K₂CO₃ (11.8 mmol, 2.0 eq), 1.0 g of iodopropane (5.9 mmol, 1.0 eq) and 16 mL acetone were combined in a 50 mL round bottom flask fitted with a reflux condenser and N₂ inlet. The mixture was refluxed overnight under N₂: LC/MS showed reaction was complete. Added 5 mL H2O to flask and the mixture extracted with 2×20 mL of 1:1 EtOAc/Hexane. The aqueous phase was discarded and the combined organics were dried under vacuum to get 1.8 g clean product.

Protocol H: Pyrazole Synthesis Via Addition of Hydrazines to α,β-Acetylenic Ketones Synthesis of 2(5-Methyl-1H-pyrazol-3-yl)-6-trifluoromethylpyridine

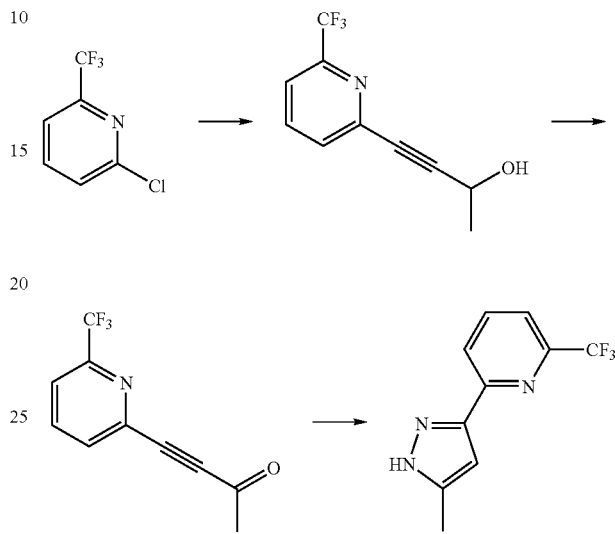

Step 1: To a solution of 2-chloro-6-trifluoromethylpyridine (91 mg), 2-butynol (0.043 mL), Pd₂(PPh₃)₂Cl₂ (17.5 mg) and CuI (4.8 mg) in DMF (1 mL) was added Et₃N mL). The reaction mixture was stirred at 25° C. for 12 h and residue was purified on preparative HPLC to afford the coupled alcohol.

Step 2: The alcohol was dissolved in CH₂Cl₂ (2 mL) and Dess-Martin periodinate (320 mg) was added. The reaction mixture was stirred at 25° C. for 2 h and evaporated in vacuo. The residue was purified by preparative HPLC to afford the ketone.

Step 3: The ketone was dissolved in EtOH (10 mL) and hydrazine was added. The reaction mixture was heated to reflux for 1 h, cooled to room temperature and evaporated in vacuo. The residue was purified by preparative HPLC to afford the title compound.

5-(5-Methyl-1H-pyrazol-3-yl)-pyridine-2-carbonitrile

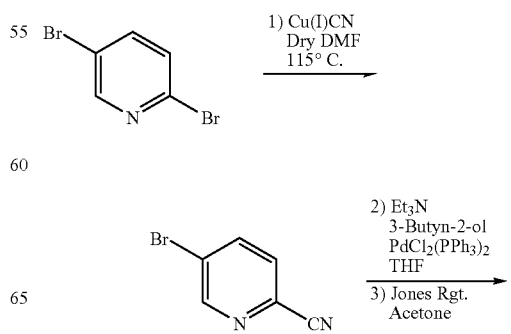

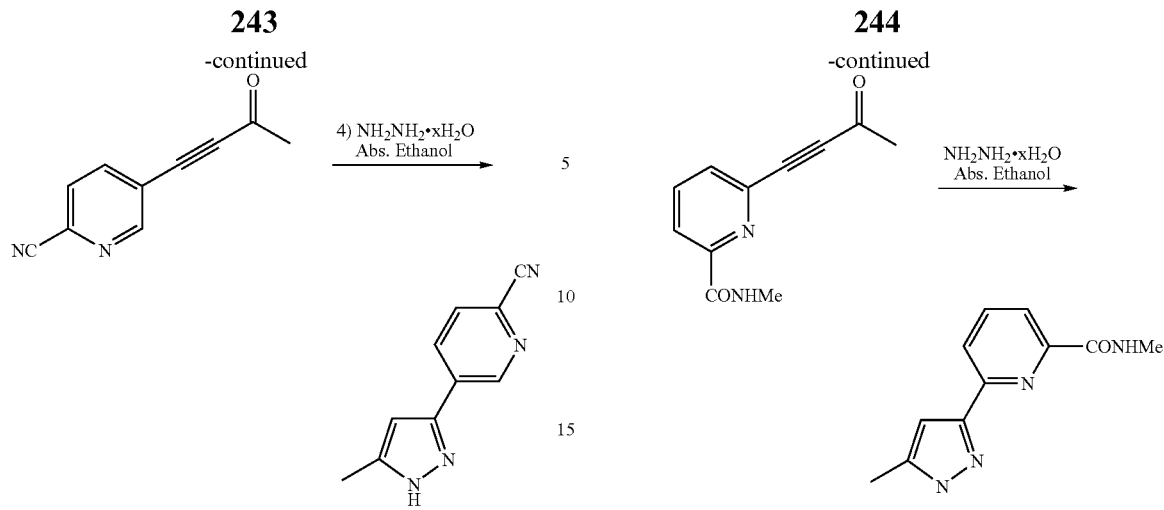

Step 1: To a solution of 2,5-Dibromopyridine (10 gm, 0.0422 mole) in DMF (100 ml) under $N_2$ was added Cu(I)CN (2.5 g, 3.4 mole). The reaction mixture was then heated to 115° C. overnight. The reaction mixture was then cooled to ambient temperature, poured into water, and extracted four times with EtOAc. The combined ethyl acetate phases were concentrated, and the residue was purified by chromatography to yield 5-bromo-2-cyanopyridine.

Steps 2 and 3: To 5-bromo-2-cyanopyridine (1.8 g, 9.84 mmole) in dry THF (50 ml) was added $Et_3N$ (2.75 ml, 19.7 mmole), 3-butyn-2-ol (1.03 gm, 14.75 mmole) and $PdCl_2(PPh_3)_2$ (200 mg), and the reaction mixture was refluxed at 80° C. overnight. The reaction mixture was cooled to ambient temperature, and the THF was removed in vacuo. The residue was slurried with water and extracted with chloroform. The chloroform layer was separated, washed once each with water, $NaHCO_3$, 1M citric acid, and brine. The chloroform layer was dried with $Na_2SO_4$ and concentrated. The crude residue was dissolved in acetone (25 ml), cooled to 0° C., and Jones reagent (4 ml) was added. After 12 hours the acetone was removed, and residue was washed with water and brine, dried over $Na_2SO_4$ and concentrated to give the corresponding alkynone.

Step 4: The alkynone intermediate (1.83 g, 10.75 mmole) was dissolved in dry THF (30 ml), hydrazine hydrate (0.582 g, 11.83 mmole) was added, and the solution was stirred for 3 hours. The reaction mixture was then concentrated and the residue was partitioned between water and $CHCl_3$. The chloroform layer was washed with water and brine, dried over $Na_2SO_4$, and concentrated. The residue was purified by chromatography to give the title compound.

6-(5-Methyl-1H-pyrazol-3-yl)-pyridine-2-carboxylic acid methylamide

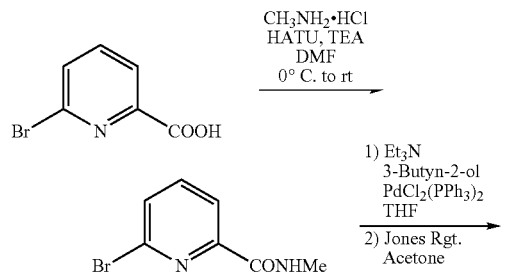

Step 1: Following Protocol X, 6-bromopicolinic acid was coupled with methylamine to give the corresponding amide.

Steps 2 and 3: Following the same two step procedure as in the previous example, the 6-Bromo-N-methylpicolinamide was converted to the corresponding conjugated ketone.

Step 4: Following the same procedure as in the previous example, the conjugated ketone was reacted with hydrazine to give the title compound.

6-(5-Methyl-1H-pyrazol-3-yl)-pyridine-2-carboxylic acid ethyl ester

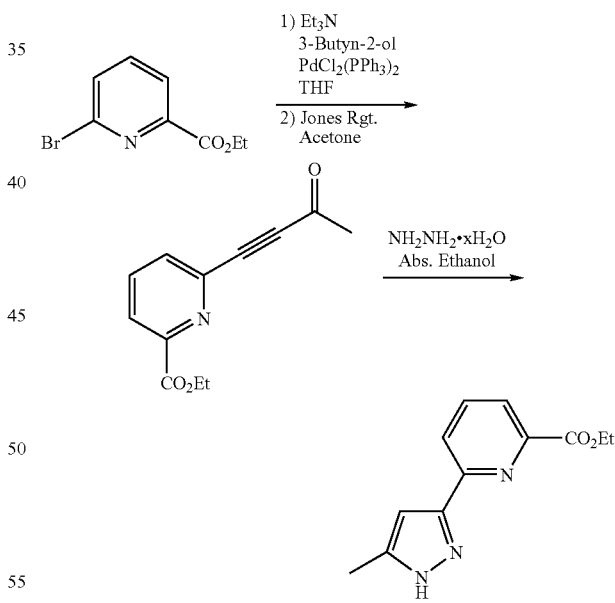

Steps 1 and 2: To Ethyl 6-Bromopicolinate (5.37 g, 0.23 mole) in dry THF (60 ml) was added $Et_3N$ (3 ml, 0.0215 mole), 3-butyn-2-ol (1.5 ml, 0.0214 mole), and $PdCl_2(PPh_3)_2$ (200 mg), and the reaction mixture was refluxed at 80° C. overnight. The reaction mixture was cooled to ambient temperature, the solvent was removed, and the residue was partitioned between water and chloroform. The chloroform layer was washed once each with water, $NaHCO_3$, 1M citric acid, and brine, dried over $Na_2SO_4$, and concentrated. The residue was dissolved in acetone (25 ml), cooled to 0° C., and Jones reagent (25 ml) was added. After stirring overnight, the acetone was removed in vacuo, and the residue was partitioned between water and $CHCl_3$. The chloroform layer was washed with water and brine, dried over $Na_2SO_4$, and concentrated to give the corresponding ketone.

Step 3: Following Protocol H, the intermediate ketone was treated with hydrazine to give the title compound.

2-Methyl-4-(5-methyl-1H-pyrazol-3-yl)-pyridine

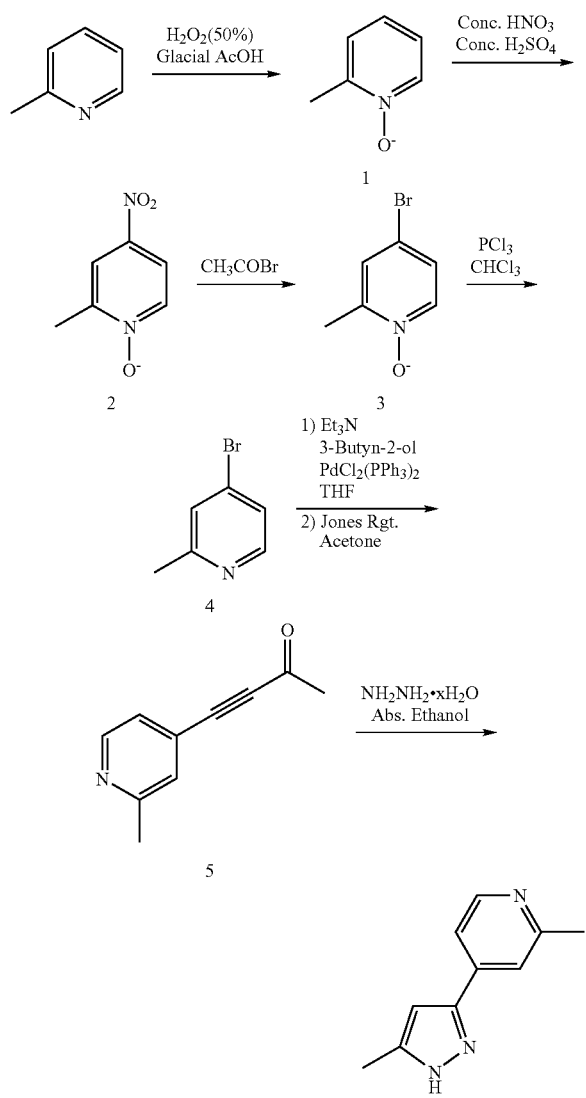

Step 1: 2-Methylpyridine (25 g, 0.268 mole) was dissolved in 150 mL glacial acetic acid and 20 mL of 50% $H_2O_2$ was added to it. The reaction mixture was heated to 85° C. overnight. When TLC indicates the total consumption of the starting material the reaction mixture was cooled to ambient temperature and was treated with Pd/C to destroy the excess $H_2O_2$. Then the Pd/C was filtered off and the excess AcOH was rotavaped off. It was then further treated with toluene and the excess toluene was removed azeotropically to generate 27 g of the N-oxide 1 in 95% yield.

Step 2: The N-oxide 1 (27 g, 0.247 mole) was dissolved in 62 mL of concentrated $H_2SO_4$ and cooled to 0° C. Then a mixture of 90 mL of $H_2SO_4$ and 115 mL $HNO_3$ was add slowly, and the resultant mixture was heated at 95° C. for 12 hours. The solution was cooled to ambient temperature, basified with aqueous $NH_3$ to pH 3, and was then extracted three times with $CHCl_3$. The combined $CHCl_3$ layers were washed once each with water and brine, dried over $Na_2SO_4$, and the concentrated to yield the product 2 as a yellow solid (37 g, 96%).

Step 3: 2-Methyl-4-Nitropyridine-N-oxide 2 (10 g, 0.0649 mole) was cooled and $CH_3COBr$ (30 ml) was then added to it drop-wise. After complete addition the reaction mixture was heated at 50° C. for 5 hours. The reaction mixture was cooled to ambient temperature, basified with 10% $NaHCO_3$, and extracted with $CHCl_3$. The chloroform phase was washed with water and brine, dried over $Na_2SO_4$, and concentrated. The residue was purified by chromatography to give 3.

Step 4: 3 (7 g, 0.0372 mole) was dissolved in $CHCl_3$ (45 ml), and the solution was cooled to 0° C. $PCl_3$ (14 ml) was then added via a dropping funnel, and the reaction mixture was allowed to for 12 hours. The reaction was then quenched with 10% $NaHCO_3$, and was extracted with $CHCl_3$. The $CHCl_3$ layer was washed with water and brine, dried over $Na_2SO_4$, and concentrated to obtain the pyridine 4 (5.9 g, 91%).

Steps 5 and 6: 4 (5.8 g, 0.0337 mole) was dissolved in dry THF (30 ml). e $t_3N$ (9.5 ml, 0.0674 mole), 3-butyn-2-ol (3.6 ml, 0.505 mole) and $PdCl_2(PPh_3)_2$ (400 mg) were and the reaction mixture was refluxed at 75° C. overnight. The reaction mixture was cooled to ambient temperature, and the THF was removed in vacuo. The residue was partitioned between water and chloroform, and the layers was separated. The chloroform layer was washed once each with water, $NaHCO_3$, 1M citric acid, and brine, dried with $Na_2SO_4$, and concentrated.

The residue from above was dissolved in acetone (25 ml), cooled to 0° C., and Jones reagent (10 ml) was added. After stirring for 12 hours, the acetone was removed in vacuo, and the residue was partitioned between water and $CHCl_3$. The chloroform layer was washed with water and brine, then dried with $Na_2SO_4$, and concentrated to give the product 5 in 20% yield.

Step Intermediate 5 (0.6 g, 0.0038 mole) was dissolved in ethanol (15 ml), hydrazine hydrate (3.5 ml) was added, and the solution was stirred for 12 hours. The reaction mixture was concentrated, and the residue was partitioned between water and $CHCl_3$. The chloroform layer was washed with water and brine, dried over $Na_2SO_4$, and then concentrated. The residue was purified by chromatography to give the title compound.

Protocol I: General Procedure for the Synthesis of Pyrazoles Via Condensation of Hydrazines with β-Diketones Synthesis of 3-(2-pyridyl)-5-methylpyrazole

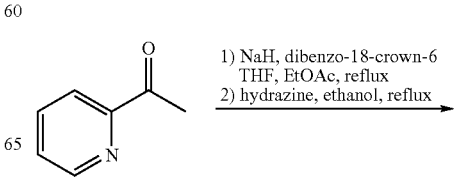

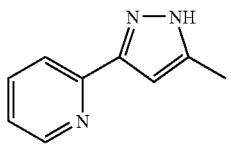

Step 1: NaH (9.6 g, 400 mmol) was added in one portion into a solution of dibenzo-18-crown-6 (1.24 g, 3.4 mmol) and 2-acetylpyridine (22.4 mL, 200 mmol) in THF (80 mL) stirring at room temperature. The mixture was allowed to stir at room temperature for 30 min and EtOAc (25 mL) was added. The mixture was then heated to reflux for 2 hr and allowed to cool to room temperature. More EtOAc (300 mL) was added and the reaction mixture was quenched by saturated aqueous NaHCO$_3$ solution (150 mL). The organic layer was separated and the aqueous layer was extracted with EtOAc (3×100 mL). The combined organic solvents was dried (Na$_2$SO$_4$), filtered and evaporated in vacuo. The crude mixture was used as it was.

Step 2: A solution of crude mixture from last step in denatured EtOH (500 mL) was stirring at room temperature and hydrazine hydrate (15 mL) was added. The solution was then heated to reflux for 1 hr, cooled to room temperature and evaporated in vacuo. The residue was dissolved in EtOAc (300 mL) and washed by saturated aqueous NaCl solution (3×50 mL). The organic layer was dried (Na$_2$SO$_4$), filtered and evaporated in vacuo. The crude mixture was used as it was.

Synthesis of 3-(3-pyridyl)-4-chloro-5-methylpyrazole

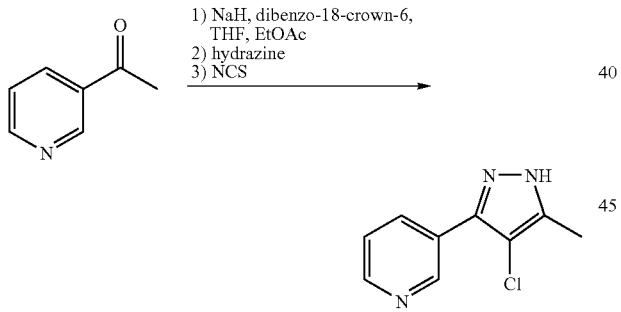

Following the same procedure as in the above example, 3-acetylpyridine first converted to the corresponding diketone, and this was then treated with hydrazine in methanol to give the pyrazole. This intermediate was treated with N-chlorosuccinimide to give the title compound.

Synthesis of 2-(5-trifluoromethyl-2H-pyrazol-3-yl)-pyridine

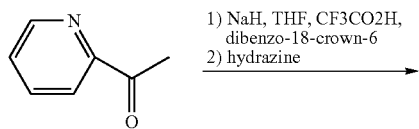

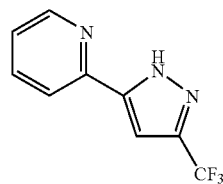

The above pyrazole was prepared by following the first two steps in the previous example, to give the title compound: LC MS (M+1)=214.1.

4-(4-Chloro-5-methyl-1H-pyrazol-3-yl)pyridine

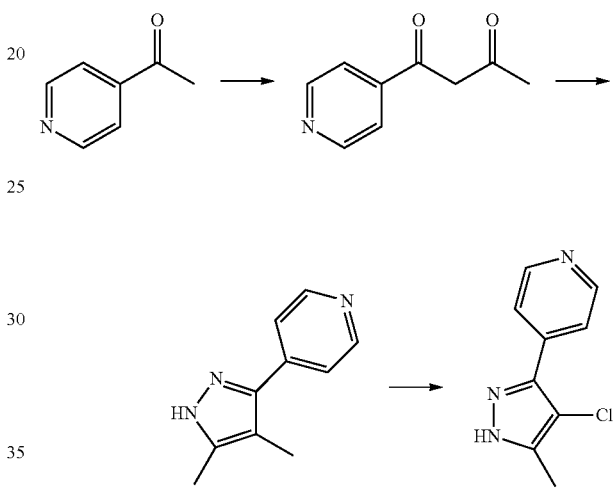

The title compound was obtained by following the same procedures used to prepare 3-(3-pyridyl)-4-chloro-5-methylpyrazole, starting from 4-acetylpyridine.

Synthesis of 2-Methyl-6-(5-methyl-1H-pyrazol-3-yl)-pyridine

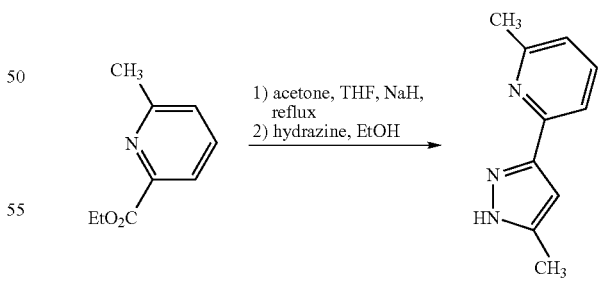

Step 1: 6-methyl picolinic ethyl ester (10 g, 0.061 mol) and acetone (8.91 ml, 0.12 mol) in THF were added to NaOMe (4.19 g, 0.091 mol) in dry THF(10 ml) under nitrogen at ambient temperature. The reaction mixture was refluxed overnight at 65° C. The reaction was then cooled to −10° C., diluted with water (150 ml) and THF was removed under vacuum. The pH was adjusted to 3.5 using acetic acid, and the mixture was extracted with chloroform. The chloroform layer was washed once each with water and brine, dried over Na$_2$SO$_4$ and concentrated to obtain the corresponding diketone.

Step 2: Following Protocol I, the diketone from Step 1 was treated with hydrazine to give the title compound.

Synthesis of Pyrimidine-4-carboxylic acid ethyl ester

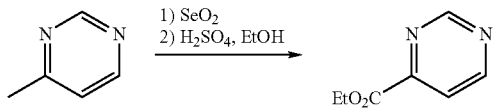

Step 1: To 4-Methyl pyrimidine (5 g, 0.05 mol) in pyridine (50 ml) was added selenium dioxide portion wise with stirring over 10 minutes. The reaction mixture was heated at 60° C. for 2 hours, it was then cooled to ambient temperature and stirred for 12 additional hours. The solution was concentrated and brown solid obtained was washed with water and dried under vacuum to give 8 gm of 4-pyrimidine carboxylic acid.

Step 2: To 4-Pyrimidine carboxylic acid (8 g, 0.06 mol) in absolute ethanol (150 ml) was added sulphuric acid (3.16 ml), and the mixture was refluxed for 12 hours. The reaction mixture was concentrated, partitioned between 10% sodium bicarbonate and ethyl acetate, and the phases were separated. The ethyl acetate layer was washed with water, brine, dried over sodium sulphate and concentrated to give 7.7 gm of the title compound.

Synthesis of 4-(5-Methyl-1H-pyrazol-3-yl)-pyrimidine

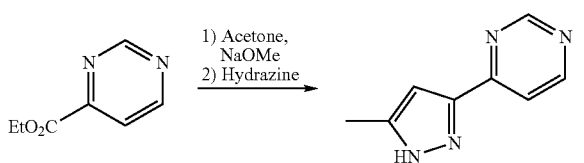

Step 1: To sodium methoxide (0.02 mol) in dry THF (15 ml) under nitrogen atmosphere was added dry acetone (0.07 mol), and the solution was stirred for 30 minutes. Pyrimidine-4-carboxylic acid ethyl ester (3.0 g, 0.02 mol) in dry THF (20 ml) was added drop wise. The reaction mixture was stirred for 30 minutes, followed by heating at reflux for 1 hour. The reaction mixture was cooled to room temperature, neutralised with acetic acid, and extracted with ethyl acetate. The ethyl acetate layer was washed once each with water and brine, dried over sodium sulphate, and concentrated to give the corresponding diketone.

Step 2: Following Protocol I, the diketone from Step 1 was treated with hyrdazine to give the title compound.

5-(5-Methyl-1H-pyrazol-3-yl)-pyridine-2-carboxylic acid ethyl ester

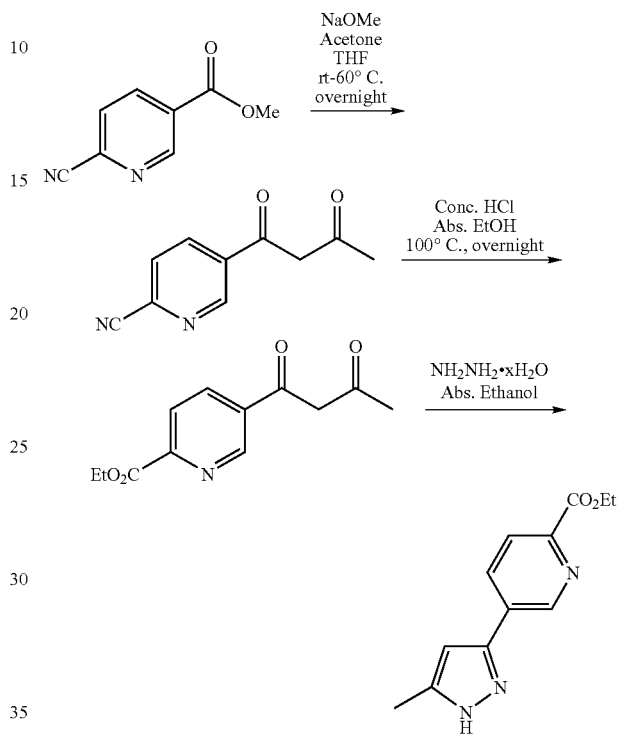

Step 1: Following the procedure used in the previous example, Methyl-2-cyano-nicotinate was reacted with acetone to give the corresponding diketone intermediate.

Step 2: To a solution of the diketone intermediate (1.85 gm) in 50 mL of ethanol was added 2.5 mL of concentrated HCl. The reaction mixture was heated at 100° C. for 12 hours. The solvent was rotavaped off, and 10% NaHCO$_3$ was added until the reaction pH was >8. The mixture was extracted with CHCl$_3$. The chloroform layer was then washed with water, dried over Na$_2$SO$_4$, and concentrated to give the corresponding ethyl ester.

Step 3: Following Protocol I, the intermediate from Step 2 was reacted with hydrazine to give the title compound.

Pyrimidine-2-carboxylic acid methyl ester

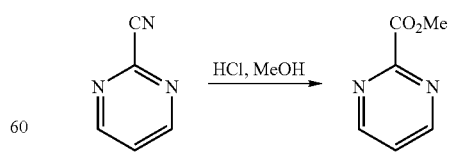

2-Cyanopyrimidine (3 g, 0.0285 mol) in dry methanol was sparged with HCl gas for 2 hours. The reaction vessel was stoppered and kept at 4° C. for 3 days. The reaction mixture was concentrated and the residue was basified using 10% sodium bicarbonate solution and extracted with dichloromethane. The dichloromethane layer was washed with water brine, dried over sodium sulphate, and concentrated to give the title compound.

Synthesis of 2-(5-Methyl-1H-pyrazol-3-yl)-pyrimidine

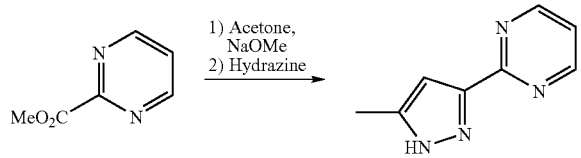

Step 1: Sodium methoxide (0.86 g, 0.0159 mol) in dry THF (20 ml) was added dry acetone (0.9 g, 0.015 mol) and stirred for about 30 minutes. Pyrimidine-2-carboxylic acid methyl ester (1.1 g, 0.007 mol) in dry THF (20 ml) was added drop wise. The reaction mixture was stirred for 30 minutes, followed by heating at reflux for 1 hour. The reaction mixture was cooled to room temperature, neutralised with acetic acid, and extracted with ethyl acetate. The ethyl acetate layer was washed once each with water and brine, dried over sodium sulphate, and concentrated to give the corresponding diketone.

Step 2: Following Protocol I, the diketone from Step 1 was treated with hydrazine hydrate to give the title compound.

1-Oxy-isonicotinic acid methyl ester

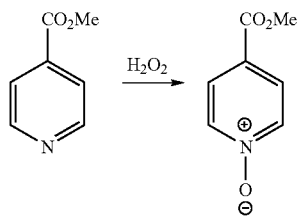

To methyl isonicotinate (44 g, 0.2913 mol) in acetic acid (135 ml) was added $H_2O_2$ (44 ml) drop wise, and the mixture was heated at 90° C. for 12 hours. The mixture was cooled to ambient temperature, Pd/C (0.5 g) was added slowly, and the mixture was stirred for 15 minutes. The reaction mixture was then filtered through Celite, and the filtrate was concentrated to give the title compound.

Synthesis of 4-(5-Methyl-1H-pyrazol-3-yl)-pyridine 1-oxide

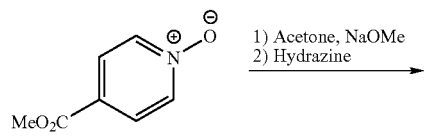

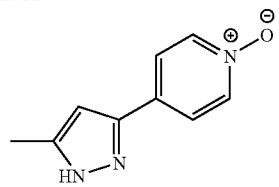

Step 1: To NaOMe (19.4 g, 0.3592 mol) in dry ether (300 ml) was added dry acetone (27.7 g, 0.4790 mol) and the reaction mixture was stirred for 20 minutes. 1-Oxy-isonicotinic acid methyl ester (40 g, 0.2395) in 300 mL of ether was added slowly, the mixture was warmed to reflux, and was stirred for one hour. The reaction mixture was cooled to ambient temperature, neutralised with acetic acid, and extracted with ethyl acetate. The ethyl acetate layer was washed once each with water and brine, dried over $Na_2SO_4$, and concentrated to give the corresponding diketone.

Step 2: Following Protocol I, the diketone from Step 1 was treated with hydrazine hydrate to give the title compound.

Synthesis of 4(5-Methyl-1H-pyrazol-3-yl)-pyridine-2-carbonitrile

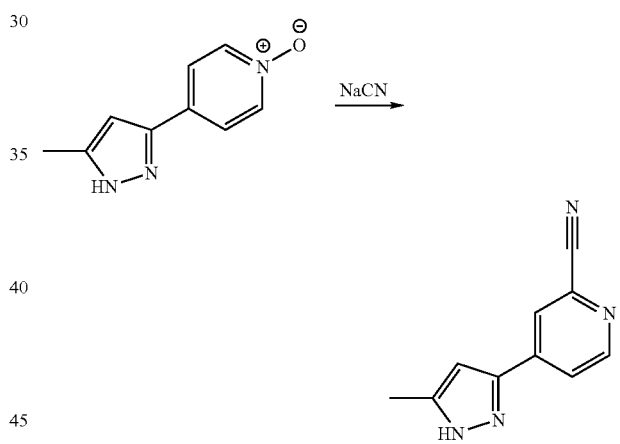

To 4-(5-Methyl-1H-pyrazol-3-yl)-pyridine 1-oxide (7.0 g, 0.024 mol) in water/1,4-dioxane mixture (140/175 ml) was added NaCN (3 g, 0.0614 mol). The reaction mixture was stirred for 14 hours, followed by extraction with ethyl acetate. The ethyl acetate layer was washed once each with water and brine, dried over $Na_2SO_4$, and concentrated. The crude residue was purified by column chromatography to give the title compound.

Synthesis of 2-Methyl-5-(5-methyl-2H-pyrazol-3-yl)-pyridine

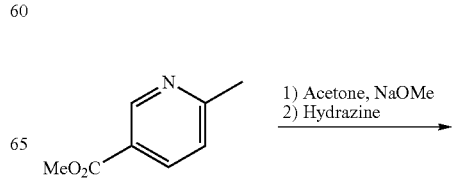

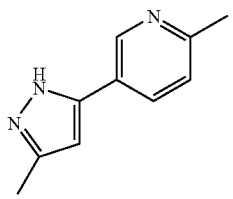

Step 1: Sodium methoxide (1.5 g, 0.027 mol) in dry THF (20 ml) was added dry acetone (3.2 g, 0.055 mol), and this was stirred for about 30 minutes. 6-Methyl-nicotinic acid methyl ester (2.3 g, 0.027 mol) in dry THF (20 ml) was added drop wise. The reaction mixture was stirred for 30 minutes, followed by heating at reflux for 1 hour. The reaction mixture was cooled to room temperature, neutralised with acetic acid, and extracted with ethyl acetate. The ethyl acetate layer was washed once each with water and brine, dried over sodium sulphate, and concentrated to give the corresponding diketone.

Step 2: Following Protocol I, the diketone from Step 1 was treated with hydrazine hydrate to give the title compound.

Synthesis of 4-(5-Methyl-2H-pyrazol-3-yl)-pyridine

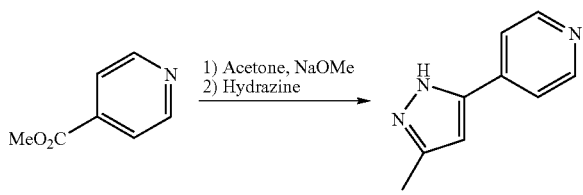

Step 1: To sodium methoxide (5.9 g, 0.1 mol) in dry THF (100 ml) under nitrogen atmosphere was added dry acetone (12.7 g, 0.2 mol), and stirred for 30 minutes. Methyl isonicotinate (15 g, 0.1 mol) in dry THF (100 ml) was added drop wise. The reaction mixture was stirred for 30 minutes, followed by heating at reflux for 1 hour. The reaction mixture was cooled to room temperature, neutralised with acetic acid, and extracted with ethyl acetate. The ethyl acetate layer was washed once each with water and brine, dried over sodium sulphate, and concentrated to give the corresponding diketone.

Step 2: Following Protocol I, the diketone from Step 1 was treated with hydrazine hydrate to give the title compound.

Synthesis of 2-Chloro-5-(5-methyl-1H-pyrazol-3-yl)-pyridine

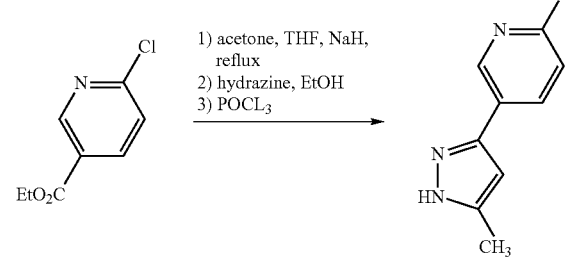

Step 1: 5 g (0.0269 mols) of 6-chloro nicotinic ethyl ester was dissolved in dry THF, and was added to 2.18 g (0.041 mols) of sodium methoxide in dry THF. To this was added 3.96 mL (0.054 mols) of acetone under $N_2$ atmosphere, and the mixture was refluxed at 65° C. for 12 hours. The reaction mixture was cooled to ambient temperature, and was quenched with water. The THF was removed in vacuo, the pH was adjusted to 3.5 using acetic acid, and the mixture was extracted with chloroform. The chloroform phase was washed once each with water and brine, dried over $Na_2SO_4$, and concentrated. The resulting residue was a mixture of 1-(6-chloropyridine-3-yl) butane-1.3-dione and 1-(6-ethoxy-pyridine-3-yl) butane-1.3-dione.

Step 2: Following Protocol I, the above mixture was treated with hydrazine hydrate to give the crude pyrazole.

Step 3: 1.7 g of the above crude pyrazole was dissolved in 20 mL of dry dioxane, 10 mL $POCl_3$ was added to it, and the mixture was heated at 80° C. for 12 hours. The reaction mixture was cooled to −20° C., 50 mL water was added to it, and the pH was adjusted to 9 using $NaHCO_3$ solution. The mixture was extracted with chloroform. The chloroform phase was washed three times with water, once with brine, dried over $Na_2SO_4$, and concentrated.

The residue was purified by column chromatography using pet ether/ethyl acetate as eluent, to give the title compound.

5-Furan-2-yl-3-trifluoromethyl-1H-pyrazole

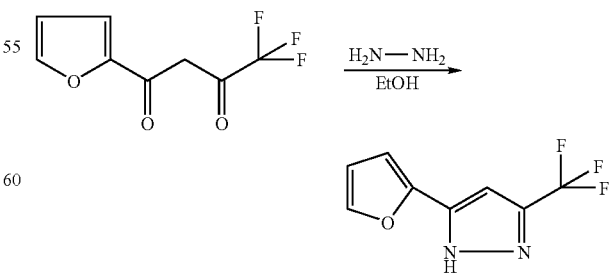

The above compound was synthesized following Protocol I using the commercially available diketone: $^1$H NMR (400

MHz, CDCl₃): δ 6.51 (dd, J=1.8 & 3.3 Hz, 1H), 6.67-6.68 (m, 1H), 6.71 (s, 1H), 7.48-7.49 (m, 1H).

Protocol L: Chlorination or Bromination of Pyrazoles with N-Chlorosuccinimide (NCS) or N-Bromosuccinimide (NBS)

4-Chloro-5-methyl-1H-pyrazole-3-carboxylic acid ethyl ester

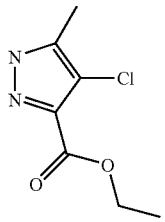

Following Protocol L, 5-methyl-1H-pyrazole-3-carboxylic acid ethyl was treated with NCS to give the title compound.

(4-Chloro-5-methyl-1H-pyrazol-3-yl)-methanol

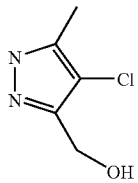

3.0 g of 4-Chloro-5-methyl-1H-pyrazole-3-carboxylic acid ethyl ester (15.9 mmol, 1.0 eq) was dissolved in 17 mL dry THF, and the solution was cooled in an ice water bath. 1.2 g of LiAlH₄ (31.8 mmol, 2.0 eq) was added in portions under N₂, taking care that the reaction did not become too vigorous. The grey slurry was refluxed for three hours. The mixture was cooled in an ice water bath and carefully quenched with 1M NaOH. The solvents were removed under vacuum, and the solids washed with hot MeOHH and discarded. The methanol solution was concentrated under vacuum and purified by preparative HPLC.

5-(4-Chloro-5-methyl-1H-pyrazol-3-yl)-pyridine-2-carbonitrile

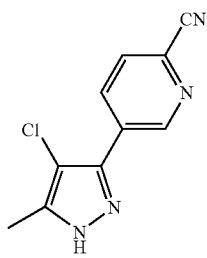

Following Protocol L, 545-Methyl-1H-pyrazol-3-yl)-pyridine-2-carbonitrile was treated with N-Chlorosuccinimide to give the target compound.

Synthesis of 2-(4-chloro-5-trifluoromethyl-2H-pyrazol-3-yl)-pyridine

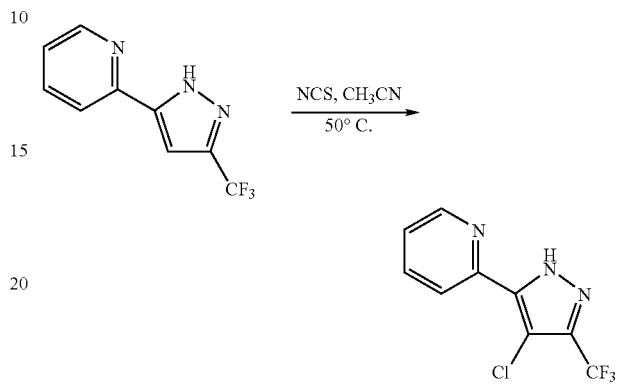

Following Protocol L, 2(5-trifluoromethyl-2H-pyrazol-3-yl)-pyridine was treated with N-chlorosuccinimide. The crude product was purified by recrystallisation from hexane and ethyl acetate (9:1): ¹H NMR (400 MHz, CDCl₃): δ 7.35-7.38 (m, 1H), 7.85-7.90 (m, 1H), 8.20 (d, J=8.1 Hz, 1H), 8.63 (d, J=4.0 Hz, 1H).

6-(4-Chloro-5-methyl-1H-pyrazol-3-yl)-pyridine-2-carboxylic acid methylamide

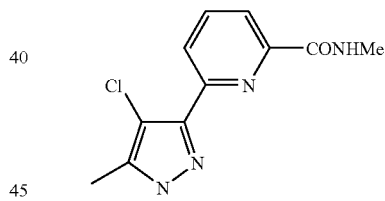

Following Protocol L, 6(5-Methyl-1H-pyrazol-3-yl)-pyridine-2-carboxylic acid methylamide was treated with N-Chlorosuccinimide to give the title compound.

4-(4-Chloro-5-methyl-1H-pyrazol-3yl)-pyridine-2-carbonitrile

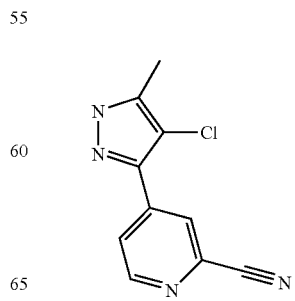

Following Protocol L, 4-(5-Methyl-1H-pyrazol-3-yl)-pyridine-2-carbonitrile was treated with NCS to give the title compound.

Following Protocol L, 3-(2-pyridyl)-5-methylpyrazole was treated with N-chlorosuccinimide to give the title compound as a pale yellow solid.

Synthesis of 2-(4-Chloro-5-methyl-1H-pyrazol-3-yl)-6-methyl-pyridine 2-(4-Chloro-5-methyl-1H-pyrazol-3-yl)-6-trifluoromethyl-pyridine

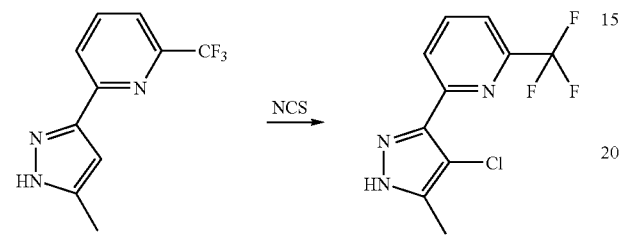

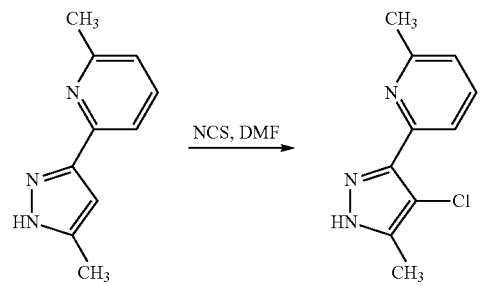

Following Protocol L, 2-(5-methyl-1H-pyrazol-3-yl)-6-trifluoromethyl-pyridine was treated with NCS to give the title compound.

Following Protocol L, 2-Methyl-6-(5-methyl-1H-pyrazol-3-yl)-pyridine was treated with N-chlorosuccinimide to give the title compound.

Synthesis of 2-(4-Bromo-5-methyl-1H-pyrazol-3-yl)-6-methyl-pyridine

3-Bromoindazole

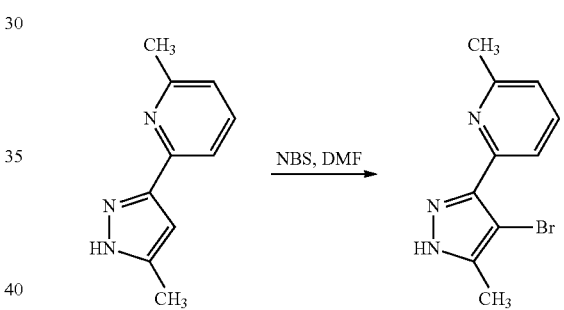

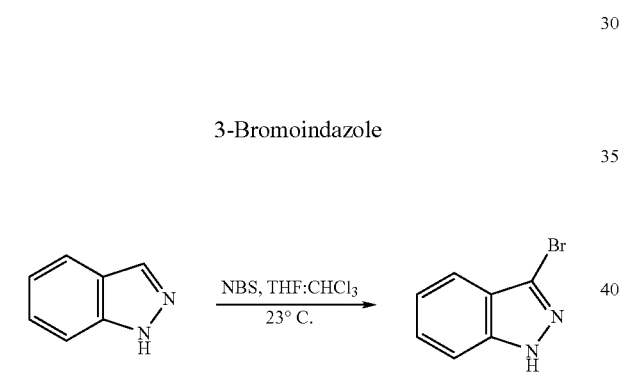

Following Protocol L, Indazole was converted to 3-Bromoindazole.

Following Protocol L, 2-Methyl-6-(5-methyl-1H-pyrazol-3-yl)-pyridine was treated with N-bromosuccinimide to give the title compound.

Synthesis of 3-methyl-4-iodo-5-(trifluoromethyl)pyrazole

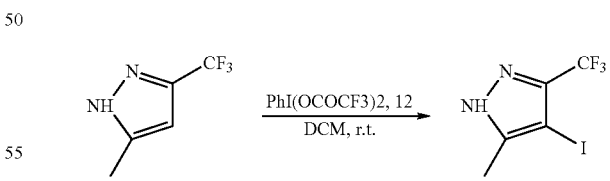

Synthesis of 3-(2-pyridyl)-4-chloro-5-methylpyrazole

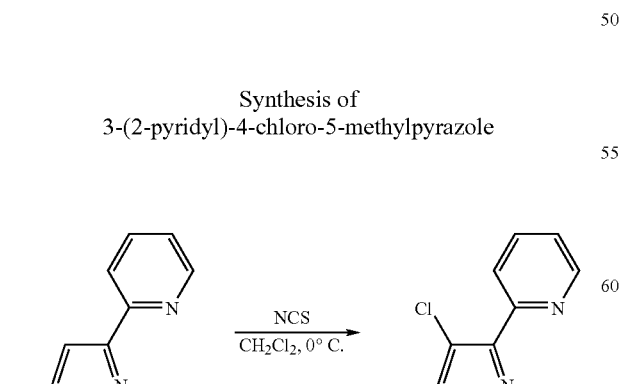

3-Methyl-5(trifluoromethyl)pyrazole (1.5 g, 10 mmol), [Bis(trifluoroacetoxy)iodo]benzene (4.8 g, 11 mmol) and Iodine(2.8 g, 11 mmol) were mixtured in 120 mL DCM and stirred at r.t. for 2 hrs. 0.5 L EtOAc was added into the mixture, washed it with 1M $Na_2S_2O_5$, brine, dried over anhydrous sodium sulfate, and concentrated to afford the brown solid. The solid was washed with Hexane to afford the title compound: HPLC retention time=3.52 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile), MS (ES) M+H expect=276.9, found=277.1.

Synthesis of 3-methyl-4-floro-5(trifluoromethyl)pyrazole

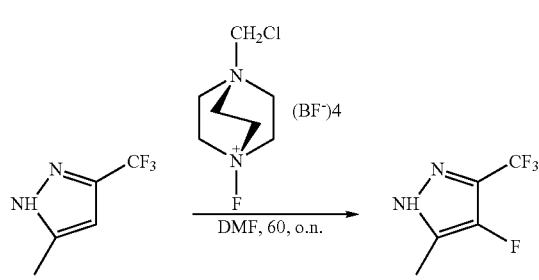

3-Methyl-5-(trifluoromethyl)pyrazole (0.30 g, 2 mmol), select-fluor reagent (3.54 g, 10 mmol) were mixtured in DMF and stirred at 60° C. overnight. EtOAc was added, the mixture was filtered, and the filtrate was washed with Sat. NaHCO₃, Brine, dried over Na₂SO₄, and concentrated to afford the product.

6-(4-Chloro-5-methyl-1H-pyrazol-3-yl)-pyridine-2-carboxylic acid ethyl ester

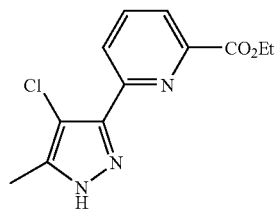

Following Protocol L, 6-(5-Methyl-1H-pyrazol-3-yl)-pyridine-2-carboxylic acid ethyl ester was treated with N-chlorosuccinimide to give the title compound.

Synthesis of 4-(4-Chloro-5-methyl-1H-pyrazol-3-yl)-pyrimidine

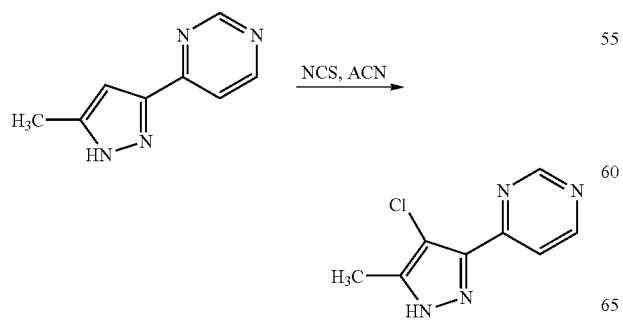

Following protocol L, 4-(5-Methyl-1H-pyrazol-3-yl)-pyrimidine was treated with N-chlorosuccinimide in acetonitrile to give the title compound.

Synthesis of 4-Chloro-3-iodo-5-methyl-1H-pyrazole

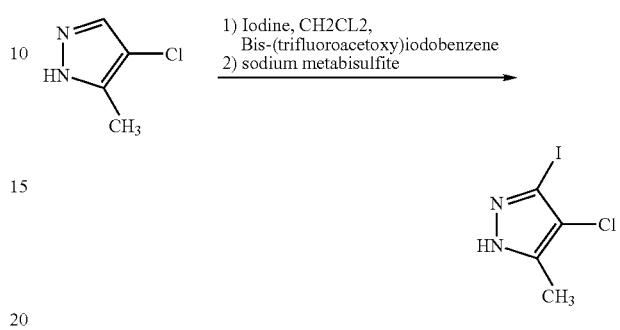

7.0 gm (60 mmol) of 4-Chloro-3-methylpyrazole, 34 gm (78 mmol) of Bis-(trifluoroacetoxy)iodobenzene, and 20 gm (78 mmol) of iodine were added to 350 mL dichloromethane in a flask with a large stirbar. After 14 hours, the mixture was partitioned between 3M sodium metabisulfite and hexane, and the phases were separated. The hexane phase was washed once each with 3M sodium metabisulfite and brine, dried over sodium sulfate, filtered, and concentrated. The residue was crystallized from hexane to give the title compound.

Synthesis of 4-(4-Bromo-5-methyl-2H-pyrazol-3-yl)-pyridine

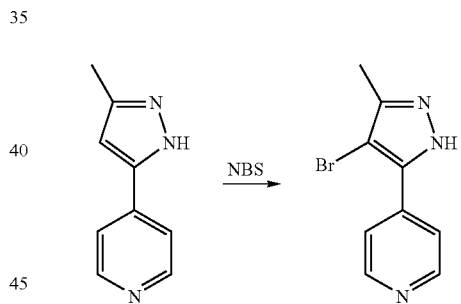

Following protocol X, 4-(5-methyl-2H-pyrazol-3-yl)-pyridine was treated with NBS in acetonitile to give the title compound.

Synthesis of 4-(4-Chloro-5-methyl-2H-pyrazol-3-yl)-pyridine

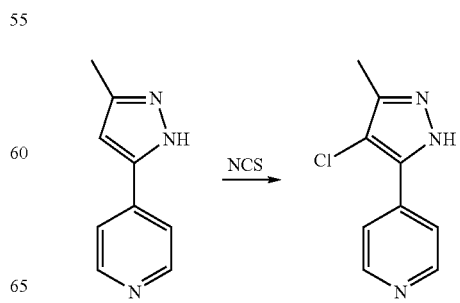

Following protocol X, 4-(5-methyl-2H-pyrazol-3-yl)-pyridine was treated with NCS in acetonitile to give the title compound.

Synthesis of 2-(4-Chloro-5-Methyl-1H-pyrazol-3-yl)-pyrimidine

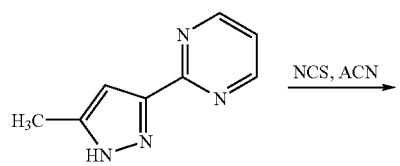

Following Protocol L, 2-(5-Methyl-1H-pyrazol-3-yl)-pyrimidine was treated with N-chlorosuccinimide at 60° C. for one hour. The reaction mixture was cooled to concentrated, and the residue was partitioned between ethyl acetate and water. The phases were separated, and the aqueous phase was back-extracted twice with ethyl acetate. The combined ethyl acetate phases were washed with 1M NaOH, brine, dried over $Na_2SO_4$, and concentrated. The residue was slurried in ether, and the solids were isolated by filtration to give the title compound.

Synthesis of 2-Methyl-5-(4-chloro-5-methyl-2H-pyrazol-3-yl)-pyridine

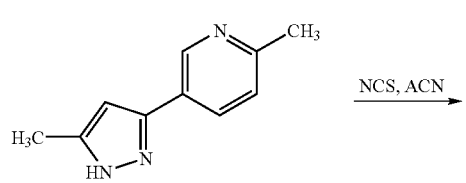

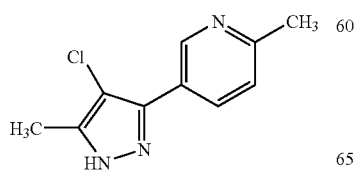

Following protocol L, 2-Methyl-5-(5-methyl-2H-pyrazol-3-yl)-pyridine was treated with N-chlorosuccinimide in acetonitrile to give the title compound.

4-Chloro-3,5-dipyridin-2-yl-pyrazol-1-yl

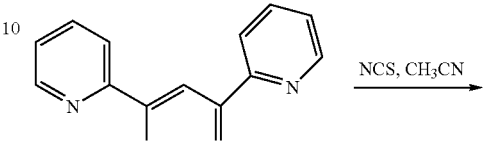

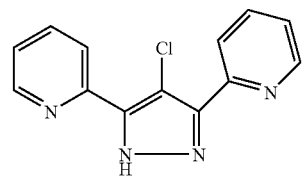

The above compound was synthesized following Protocol L using the commercially available dipyridylpyrazole.

2-Methyl-4-(4-chloro-5-methyl-1H-pyrazol-3-yl)-pyridine

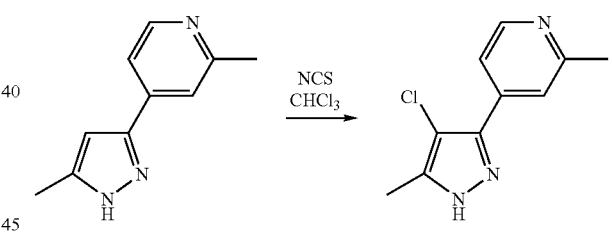

Following Protocol L, 2-Methyl-4-(5-methyl-1H-pyrazol-3-yl)-pyridine was treated with N-Chlorosuccinimide to give the title compound.

5-(4-Chloro-5-methyl-1H-pyrazol-3-yl)-pyridine-2-carboxylic acid ethyl ester

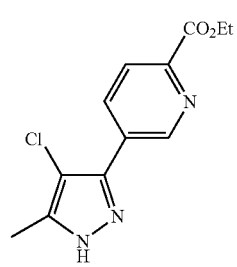

Following Protocol L, 5-(5-Methyl-1H-pyrazol-3-yl)-pyridine-2-carboxylic acid ethyl ester was treated with NCS to give the title compound.

(A=0.1% formic acid/5% acetonitrile/94.9% water, B=0.08% formic acid/99.9% acetonitrile). MS (ES) M+H expect=196.0, found=196.1.

Synthesis of 3-Bromo-4-chloro-5-methyl-1H-pyrazole

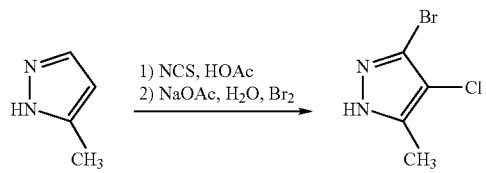

Synthesis of 3-methyl-4-amino-5(trifluoromethyl)pyrazole

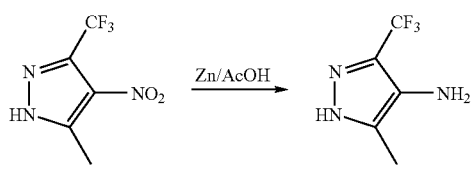

5.0 mL (61 mmol) of 3-methylpyrazole and 8.95 gm (67.1 mmol) of N-chlorosuccinimide in 50 mL of glacial acetic acid were heated at 60° C. for two hours in a sealed vessel. Following this, 5.5 gm (74 mmol) of sodium acetate, 40 mL of water, and 3.2 mL (61 mmol) of bromine were added, the vessel was sealed, and the dark mixture was heated at 100° C. for three hours. The light orange solution was cooled to ambient temperature, and 100 mL of water was added slowly. The solids were isolated by filtration, washed with water, and dried to give the title compound.

Following Protocol M, 3-Methyl-4-nitro-5(trifluoromethyl)pyrazole was treated with Zinc in acetic acid to afford the title compound: MS (ES) M+H expect=166.0, found=165.0.

Protocol M: General Procedure for Reduction of Nitropyrazoles

Protocol P: Couplings of Arylpiperazines with Pyrazolyl-Acetic Acid Derivatives—Compounds Prepared by HATU Mediated Coupling

2-(4-Bromo-5-methyl-3-trifluoromethyl-pyrazol-1-yl)-1-[4-(2,4-dichloro-5-methoxy-phenyl)-piperazin-1-yl]-ethanone

Synthesis of 3-methyl-4-nitro-5(trifluoromethyl)pyrazole

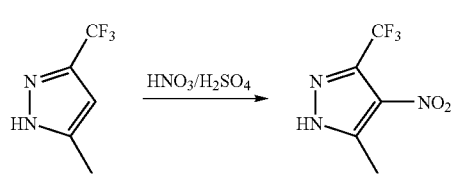

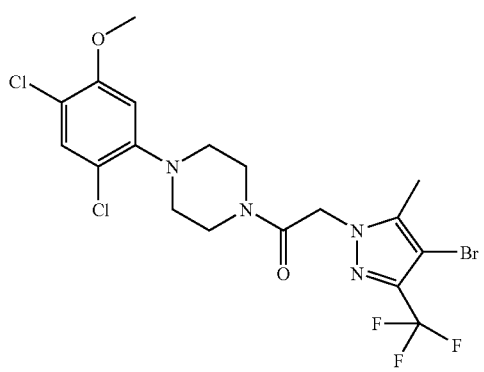

3-Methyl-5(trifluoromethyl)pyrazole (3.0 g, 20 mmol) was dissolved in 2 mL concentrated $H_2SO_4$ with vigorous stirring. 6 mL of nitric acid was added slowly into it. The reaction mixture was stirred at 60° C. overnight. The reaction mixture was cooled to room temperature, poured into 50 mL saturated $NaHCO_3$ in ice-bath, and the resulting mixture was extracted three times with ethyl acetate. The combined ethyl acetate layers were washed with brine, dried over anhydrous sodium sulfate, and concentrated to afford the title compound (3.9 g, yield: 100%). HPLC retention time=4.55 minutes (Agilent Zorbax SB-C18, 2.1×50 mm, 5μ, 35° C.) using a 4.5 minute gradient of 20% to 95% B with a 1.1 minute wash at 95% B Following Protocol P, 1-(2,4-Dichloro-5-methoxy-phenyl)-piperazine and (4-Bromo-5-methyl-3-trifluoromethyl-pyrazol-1-yl)-acetic acid were coupled using HATU to give the title compound: HPLC retention time=4.96 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-[4-(4-Chloro-2-fluoro-5-methoxy-phenyl)-piperazin-1-yl]-2-(4-chloro-5-methyl-3-trifluoromethyl-pyrazol-1-yl)-ethanone

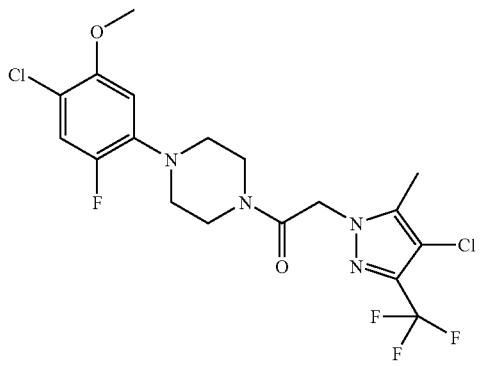

Following Protocol P, 1-(4-Chloro-2-fluoro-5-methoxy-phenyl)-piperazine and (4-Chloro-5-methyl-3-trifluoromethyl-pyrazol-1-yl)-acetic acid were coupled using HATU to give the title compound: HPLC retention time=7.38 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=469 (M+H).

2-(4-Bromo-5-methyl-3-trifluoromethyl-pyrazol-1-yl)-1-[(S)-4-(2,4-dichloro-5-methoxy-phenyl)-2-methyl-piperazin-1-yl]-ethanone

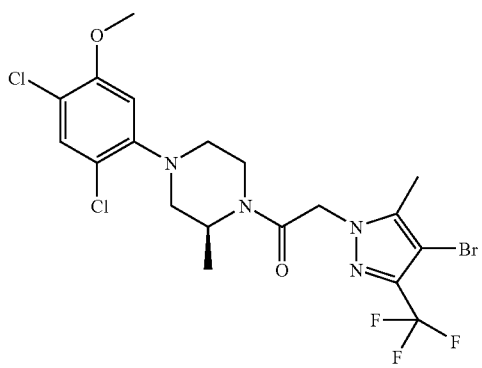

Following Protocol P, (S)-1-(2,4-Dichloro-5-methoxy-phenyl)-3-methyl-piperazine and (4-Bromo-5-methyl-3-trifluoromethyl-pyrazol-1-yl)-acetic acid were coupled using HATU to give the title compound: HPLC retention time=6.86 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)−=463 (M−Br).

2-(4-Bromo-5-methyl-3-trifluoromethyl-pyrazol-1-yl)-1-[(S)-4-(4-bromo-5-methoxy-phenyl)-2-methyl-piperazin-1-yl]-ethanone

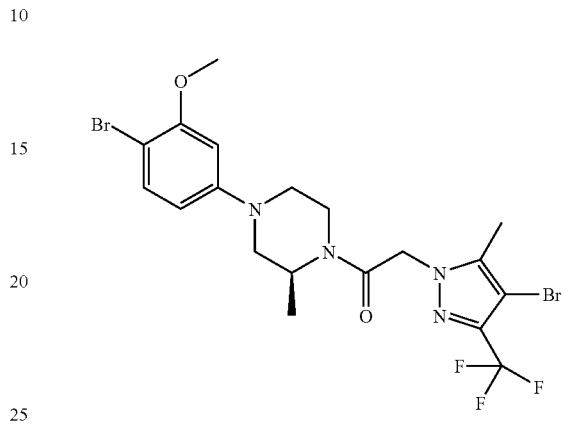

Following Protocol P, (S)-1-(4-Bromo-5-methoxy-phenyl)-3-methyl-piperazine and (4-Bromo-5-methyl-3-trifluoromethyl-pyrazol-1-yl)-acetic acid were coupled using HATU to give the title compound: HPLC retention time=7.32 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)−=473 (M−Br).

1-[4-(4-Chloro-3-methoxy-phenyl)-cis-2,3-dimethyl-piperazin-1-yl]-2-(4-chloro-5-methyl-3-trifluoromethyl-pyrazol-1-yl)-ethanone

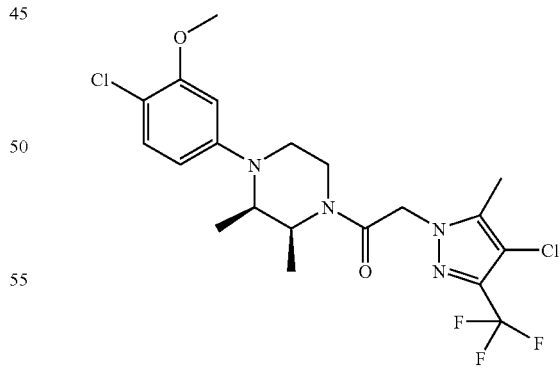

Following HATU mediated coupling Protocol P, 1-(4-Chloro-3-methoxy-phenyl)-2,3-cis-dimethyl-piperazine and (4-Chloro-5-methyl-3-trifluoromethyl-pyrazol-1-yl)-acetic acid were coupled to give the title compound: HPLC retention time=7.5 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile);

2-Chloro-5-{4-[2-(4-chloro-5-methyl-3-trifluoromethyl-pyrazol-1-yl)-acetyl]-piperazin-1-yl}-benzoic acid ethyl ester

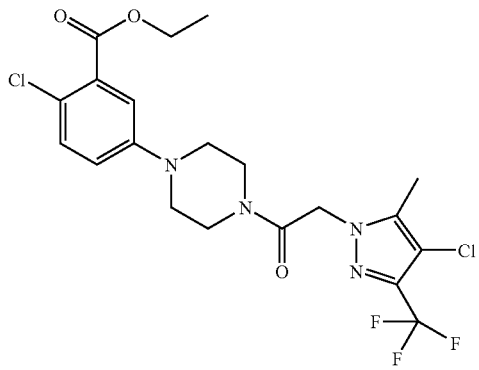

Following Protocol P, 2-Chloro-5-piperazin-1-yl-benzoic acid ethyl ester and (4-Chloro-5-methyl-3-trifluoromethyl-pyrazol-1-yl)-acetic acid were coupled using HATU to give the title compound: HPLC retention time=7.38 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

1-[4-(2-Bromo-4-chloro-5-methoxy-phenyl)-piperazin-1-yl]-2-(4-chloro-5-methyl-3-trifluoromethyl-pyrazol-1-yl)-ethanone

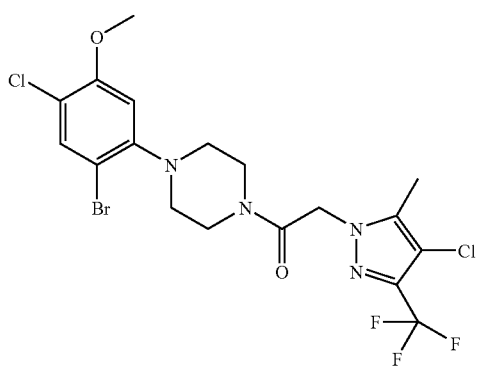

Following Protocol P, 1-(2-Bromo-4-chloro-5-methoxy-phenyl)-piperazine and (4-Chloro-5-methyl-3-trifluoromethyl-pyrazol-1-yl)-acetic acid were coupled using HATU to give the title compound: HPLC retention time=7.82 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

5-Chloro-2-{4-[2-(4-chloro-5-methyl-3-trifluoromethyl-pyrazol-1-yl)-acetyl]-piperazin-1-yl}-4-methoxy-benzoic acid methyl ester

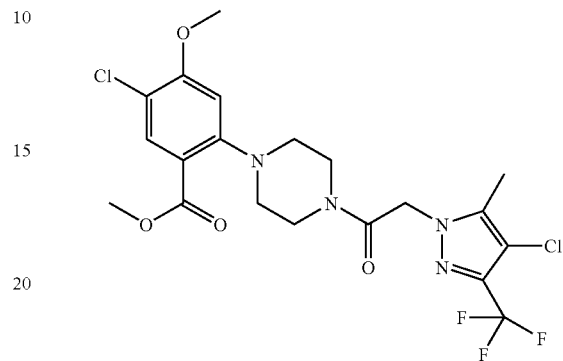

Following Protocol P, 5-Chloro-4-methoxy-2-piperazin-1-yl-benzoic acid methyl ester and (4-Chloro-5-methyl-3-trifluoromethyl-pyrazol-1-yl)-acetic acid were coupled using HATU to give the title compound: HPLC retention time=7.44 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)-=506.9 (M-H).

Synthesis of racemic 1-[4-(4-Chloro-3-methoxyphenyl)-2-trifluoromethylpiperazin-1-yl]-2-(4-chloro-5-methyl-3-trifluoromethylpyrazol-1-yl)ethanone

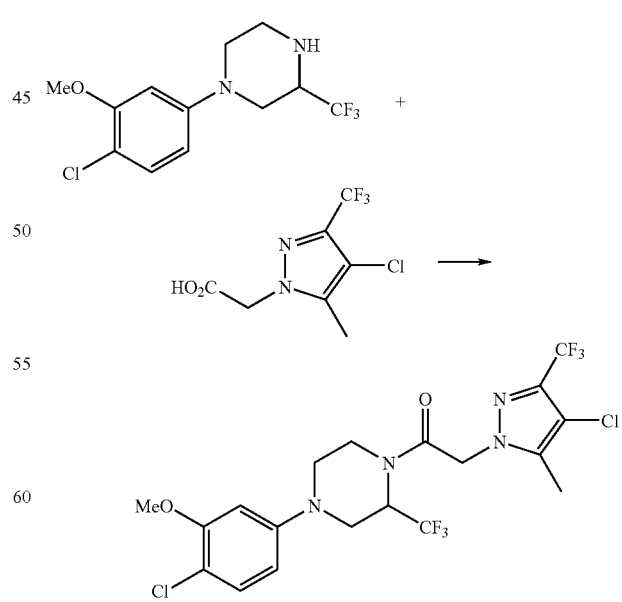

The title compound was obtained by following Protocol P: LCMS (ES): M+H 519.0; HPLC retention time=5.57 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)-cis-2,5-dimethylpiperazin-1-yl]-2-(4-chloro-5-methyl-3-trifluoromethylpyrazol-1-yl)ethanone

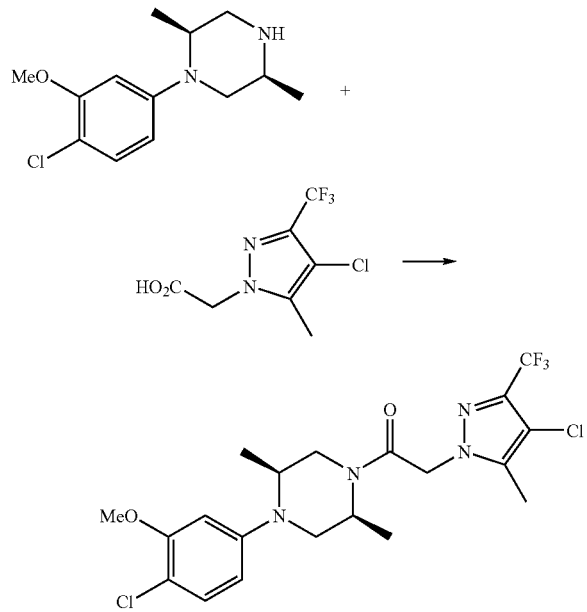

The title compound was obtained by following Protocol P: LCMS (ES): M+H 479.1; HPLC retention time=5.49 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of racemic 1-[4-(4-Chloro-3-methoxyphenyl)-trans-2,5-dimethylpiperazin-1-yl]-2-(4-chloro-5-methyl-3-trifluoromethylpyrazol-1-yl)ethanone

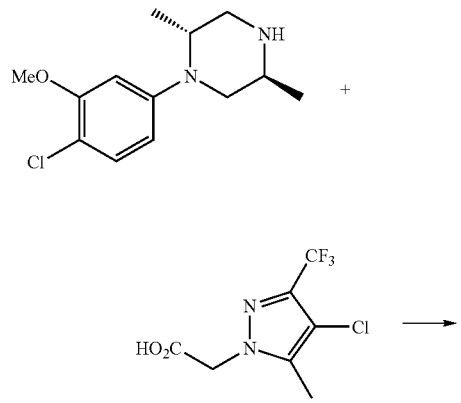

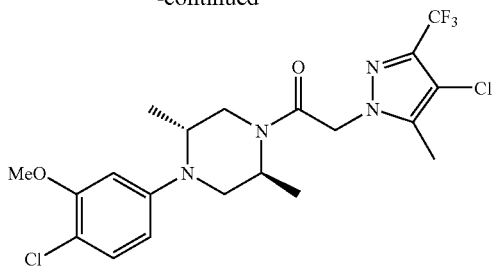

The title compound was obtained by following Protocol P: LCMS (ES): M+H 479.1; HPLC retention time=5.47 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(3-cyano-4-chloro-5-methyl-pyrazol-1-yl)-1-[4-(4-chloro-3-methoxy-phenyl)-[1,4]diazepan-1-yl]-ethanone

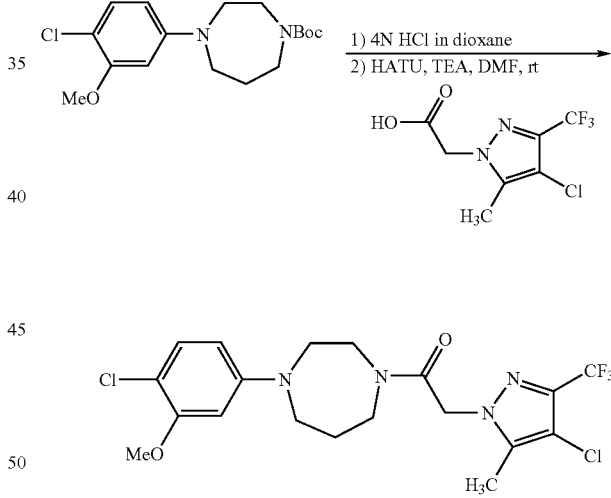

Step 1: A sample of 1-[4-(4-chloro-3-methoxy-phenyl)-[1,4]diazepane-1-carboxylic acid t-butyl ester (68 mg, 0.2 mmol, 1 equiv) was treated with 2 mL of 4N HCl in dioxane at room temperature for 2 hours and evaporated.

Step 2: To the solution of the residue in 1 mL of DMF were added (4-chloro-5-methyl-3-trifluomethyl-pyrazol-1-yl)-acetic acid (48 mg, 1 equiv), HATU (84 mg, 1.1 equiv), TEA (84 μL, 3 equiv) at room temperature overnight. The mixture was diluted with EtOAc and washed with saturated aqueous NaHCO$_3$ and brine. The organic layer was dried over Na$_2$SO$_4$, filtered, evaporated and subjected to reverse phase HPLC (acetonitrile-H$_2$O with 0.1% TFA as eluent) to yield the title compound: NMR signals from the major isomer are $^1$H NMR (400 MHz, CDCl$_3$) δ 7.33 (d, 1H), 6.76 (d, 1H), 6.60

(dd, 1H), 5.00 (s, 2H), 3.84 (s, 3H), 4.00-3.50 (m, 8H), 2.33 (m, 2H), 2.08 (s, 3H). LCMS observed for (M+H)⁺: 466.

4-Chloro-1-{2-[4-(4-chloro-3-methoxy-phenyl)-piperazin-1-yl]-2-oxo-ethyl}-5-methyl-1H-pyrazole-3-carboxylic acid methylamide

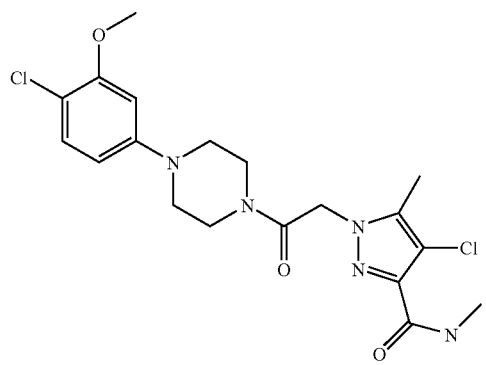

Following Protocol P, 4-Chloro-1-{2-[4-(4-chloro-3-methoxy-phenyl)-piperazin-1-yl]-2-oxo-ethyl}-5-methyl-1H-pyrazole-3-carboxylic acid and methylamine hydrochloride were coupled using HATU to give the title compound: HPLC retention time=4.78 minutes (Agilent Zorbax SB-C18, 2.1×50 mm, 5µ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=440.1 (M+H).

4-Chloro-1-{2-[4-(4-chloro-3-methoxy-phenyl)-piperazin-1-yl]-2-oxo-ethyl}-5-methyl-1H-pyrazole-3-carboxylic acid dimethylamide

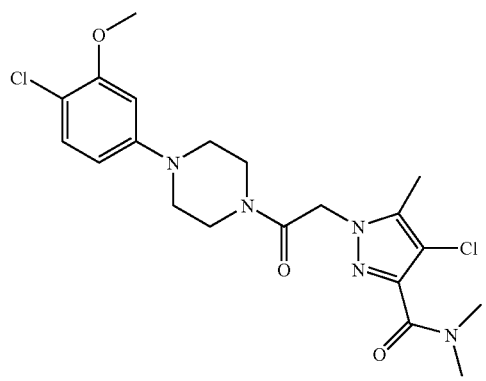

Following Protocol P, 4-Chloro-1-{2-[4-(4-chloro-3-methoxy-phenyl)-piperazin-1-yl]-2-oxo-ethyl}-5-methyl-1H-pyrazole-3-carboxylic acid and dimethylamine were coupled using HATU to give the title compound: HPLC retention time=4.899 minutes (Agilent Zorbax SB-C18, 2.1×50 mm, 5µ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=454.1 (M+H).

4-Chloro-1-{2-[4-(4-chloro-3-methoxy-phenyl)-piperazin-1-yl]-2-oxo-ethyl}-5-methyl-1H-pyrazole-3-carboxylic acid ethylamide

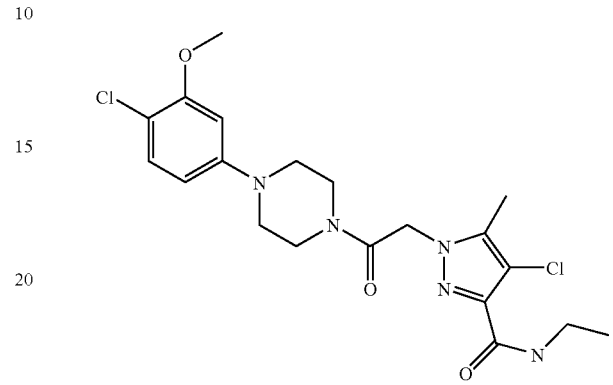

Following Protocol P, 4-Chloro-1-{2-[4-(4-chloro-3-methoxy-phenyl)-piperazin-1-yl]-2-oxo-ethyl}-5-methyl-1H-pyrazole-3-carboxylic acid and ethylamine were coupled using HATU to give the title compound: HPLC retention time=5.02 minutes (Agilent Zorbax SB-C18, 2.1×50 mm, 5µ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=454.1 (M+H).

Synthesis of 2-(4-Chloro-5-methyl-3-trifluoromethylpyrazol-1-yl)-1-[4-(2,4-dimethyl-phenyl)piperazin-1-yl]ethanone

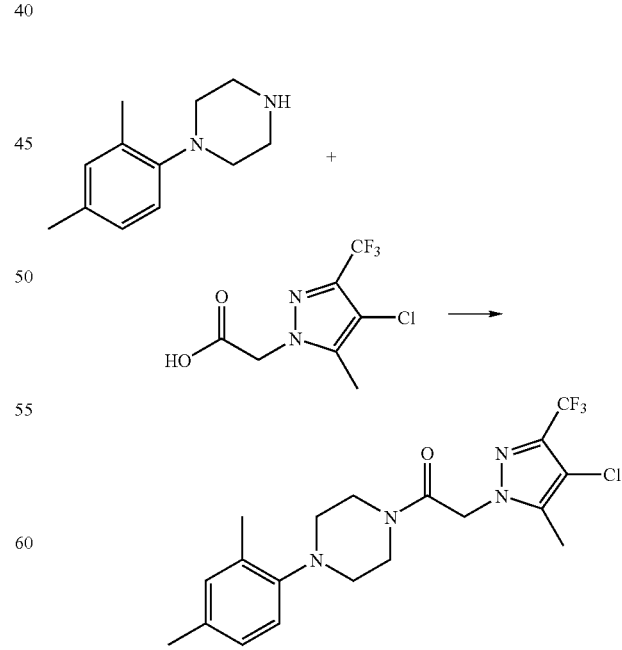

The title compound was obtained by following Protocol P: LCMS (ES): M+H 415.1; HPLC retention time=5.374 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-[4-(4-Chloro-3-methoxy-phenyl)-trans-2,5-dimethyl-piperazin-1-yl]-2-(4-chloro-5-methyl-3-pyridin-2-yl-pyrazol-1-yl)-ethanone

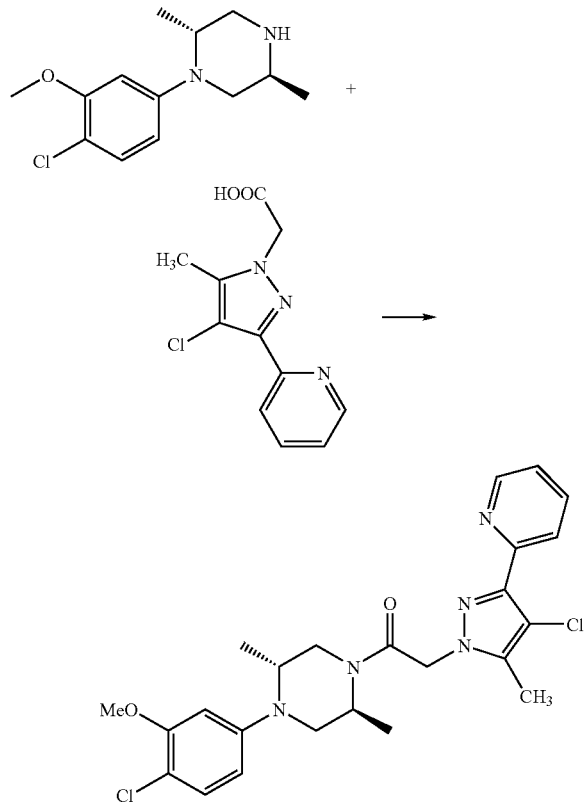

Following Protocol P, the title compound was prepared: $^1$H NMR (400 MHz, CDCl$_3$) δ 8.87-8.92 (m, 3H), 6.02-6.95 (s, 2H), 5.11 (s, 2H), 4.18 (q, 1H), 3.41 (q, 1H), 2.45 (s, 3H), 1.52 (t, 3H), 1.42 (d, 3H), 1.21 (d, 3H); LCMS (ES) M+H=488.4, RT 4.364 min (acetonitrile/H$_2$O 20-95% method).

1-[4-(4-Chloro-3-methoxyphenyl)piperazin-1-yl]-2-[4-chloro-5-methyl-3-(1-oxypyridin-4-yl)pyrazol-1-yl]ethanone

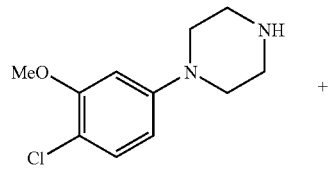

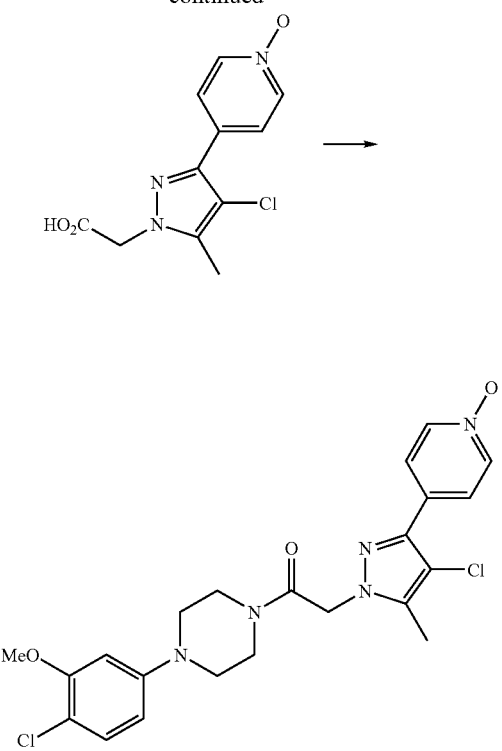

The title compound was obtained by following Protocol P: LCMS (ES): M+H 476.0; HPLC retention time=4.00 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)-2-(S)-methylpiperazin-1-yl]-2-[4-chloro-5-methyl-3-(1-oxypyridin-4-yl)pyrazol-1-yl]ethanone

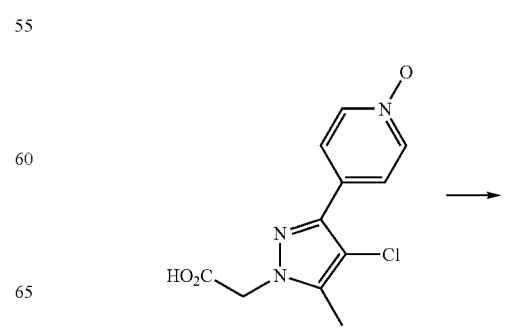

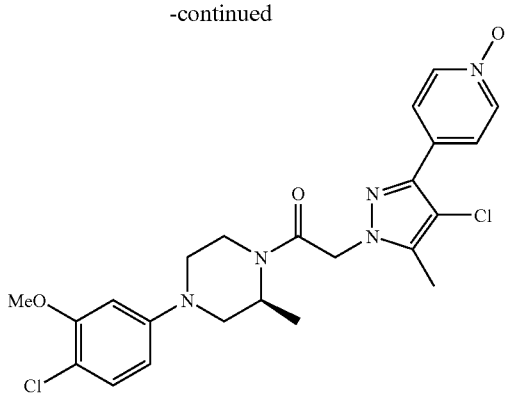

The title compound was obtained by following Protocol P: LCMS (ES): M+H 490.1; HPLC retention time=4.36 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-2-(S)-methyl-piperazin-1-yl]-2-[4-chloro-5-methyl-3-(1-oxy-pyridin-3-yl)-pyrazol-1-yl]-ethanone

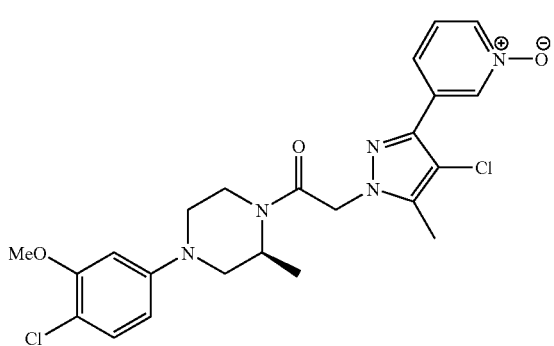

Following Protocol P, sodium [4-chloro-5-methyl-3-(1-oxy-pyridin-3-yl)-pyrazol-1-yl]-acetate and 1-(4-Chloro-3-methoxy-phenyl)-3-(S)-methyl-piperazine were coupled to give the title compound: MS (M+H⁺): 490.1; HPLC retention time=4.06 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-piperazin-1-yl]-2-[4-chloro-5-methyl-3-(1-oxy-pyridin-3-yl)-pyrazol-1-yl]-ethanone

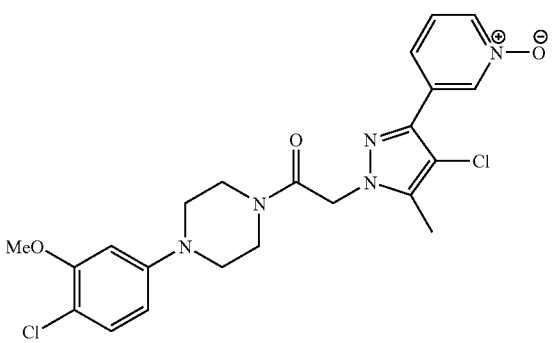

Following Protocol P, sodium [4-chloro-5-methyl-3-(1-oxy-pyridin-3-yl)-pyrazol-1-yl]-acetate and 1-(4-Chloro-3-methoxy-phenyl)-piperazine were coupled to give the title compound: MS (M+H⁺): 476.1; HPLC retention time=3.80 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-[4-(4-Chloro-3-methoxybenzyyl)piperazin-1-yl]-2-(4-chloro-5-methyl-3-trifluoromethylpyrazol-1-yl) ethanone

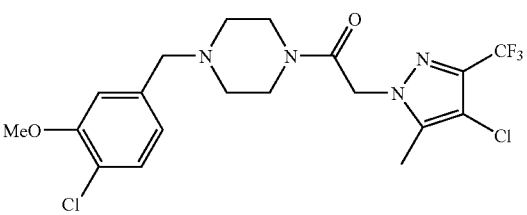

The title compound was obtained by following Protocol P: LCMS (ES) M+H: M+H=465.0; HPLC retention time=3.733 minutes (Agilent Zorbax SB-C18, 2.1×50 mm, 5μ, 35° C.) using a 4.5 minute gradient of 20% to 95% B with a 1.1

4-Chloro-1-{2-[4-(4-chloro-3-methoxy-phenyl)-piperazin-1-yl]-2-oxo-ethyl}-5-methyl-1H-pyrazole-3-carboxylic acid isopropylamide

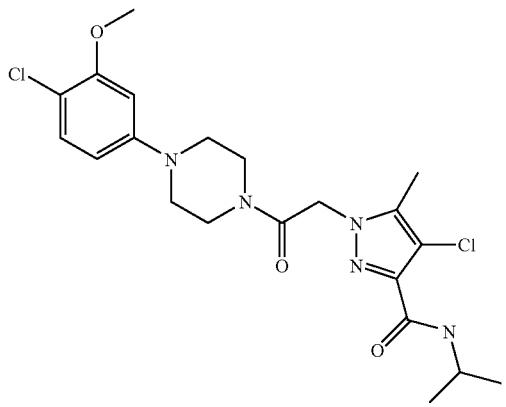

Following Protocol P, 4-Chloro-1-{2-[4-(4-chloro-3-methoxy-phenyl)-piperazin-1-yl]-2-oxo-ethyl}-5-methyl-1H-pyrazole-3-carboxylic acid and isopropylamine were coupled using HATU to give the title compound: HPLC retention time=5.23 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=468.1 (M+H).

1-[4-(4-Chloro-3-methoxy-phenyl)-2-pyrrolidin-1-ylmethyl-piperazin-1-yl]-2-(4-chloro-5-methyl-3-trifluoromethyl-pyrazol-1-yl)-ethanone

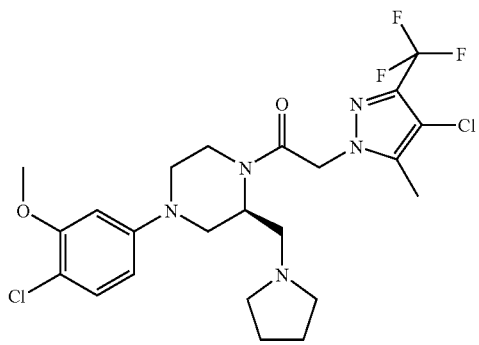

Approximately 0.28 mmol of 4-(4-Chloro-3-methoxy-phenyl)-2-pyrrolidin-1-ylmethyl-piperazine-1-carboxylic acid tert-butyl ester was dissolved in 1 mL of 1/1 dichloromethane and trifluoroacetic acid. After 30 minutes, the solution was concentrated to a residue. The crude residue was dissolved in 500 uL DMF, 82 mg of 4-chloro-3-trifluoromethyl-5-methylpyrazole-1-acetic acid (0.34 mmol), 293 uL of DIEA (1.7 mmol), and 128 mg of HATU (0.34 mmol) were added sequentially. The vial was stirred at room temperature for several hours, then placed in a 60° C. oil bath overnight. The crude mixture was purified by preparative HPLC. LC/MS(ES) (M+H) 534.5; HPLC retention time=6.47 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

1-[4-(4-Chloro-3-methoxy-phenyl)-2-morpholin-4-ylmethyl-piperazin-1-yl]-2-(4-chloro-5-methyl-3-trifluoromethyl-pyrazol-1-yl)-ethanone

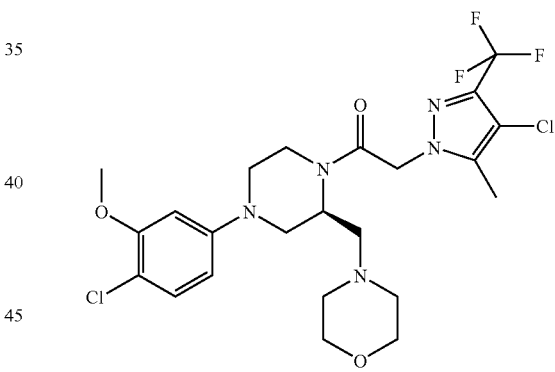

Approximately 0.28 mmol of 4-(4-Chloro-3-methoxy-phenyl)-2-morpholin-4-ylmethyl-piperazine-1-carboxylic acid tert-butyl ester was dissolved in 1 mL of 1/1 dichloromethane and trifluoroacetic acid. After 30 minutes, the solution was concentrated to a residue. The residue was dissolved in 500 uL DMF, and 82 mg 4-chloro-3-trifluoromethyl-5-methylpyrazole-1-acetic acid (0.34 mmol), 293 uL DIEA (1.7 mmol), and 128 mg HATU (0.34 mmol) were added sequentially. The vial was stirred at room temperature for several hours, then placed in a 60° C. oil bath overnight. The crude mixture was purified by preparative HPLC. LC/MS(ES) (M+H) 550.5; HPLC retention time=6.33 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

1-[4-(4-Chloro-3-methoxy-phenyl)-2-(4-methyl-piperazin-1-ylmethyl)-piperazin-1-yl]-2-(4-chloro-5-methyl-3-trifluoromethyl-pyrazol-1-yl)-ethanone

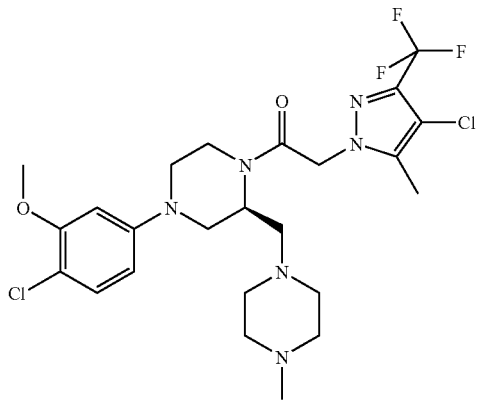

Approximately 0.28 mmol of 4-(4-Chloro-3-methoxy-phenyl)-2-(4-methyl-piperazin-1-ylmethyl)-piperazine-1-carboxylic acid tert-butyl ester was dissolved in 1 mL of 1/1 dichloromethane and trifluoroacetic acid. After 30 minutes, the solution was concentrated to a residue. The residue was dissolved in 500 uL DMF, and 82mg 4-chloro-3-trifluoromethyl-5-methylpyrazole-1-acetic acid (0.34 mmol), 293 uL DIEA (1.7 mmol), and 128 mg HATU (0.34 mmol) were added sequentially. The vial was stirred at room temperature for several hours, then placed in a 60° C. oil bath overnight. The crude mixture was purified by preparative HPLC. LC/MS(ES) (M+H)=563.5; HPLC retention time=7.25 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

1-[4-(4-Chloro-3-methoxy-phenyl)-piperazin-1-yl]-2-[4-chloro-5-methyl-3-(morpholine-4-carbonyl)-pyrazol-1-yl]-ethanone

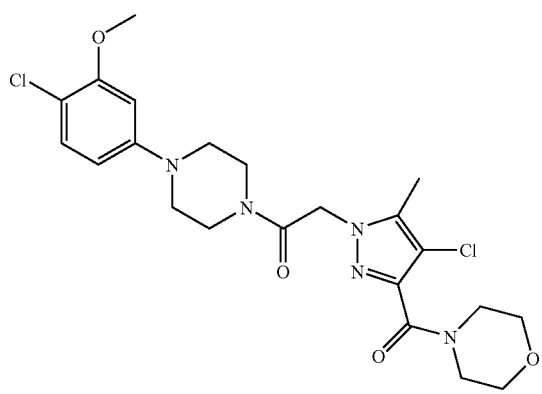

Following Protocol P, 4-Chloro-1-{2-[4-(4-chloro-3-methoxy-phenyl)-piperazin-1-yl]-2-oxo-ethyl}-5-methyl-1H-pyrazole-3-carboxylic acid and morpholine were coupled using HATU to give the title compound: HPLC retention time=4.90 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+ =496.1 (M+H).

Protocol S: Preparation of Chloroacetyl Arylpiperazines 4-chloromethylcarbonyl-1-(4-chloro-3-(2-fluoro) ethoxy-phenyl)-piperazine

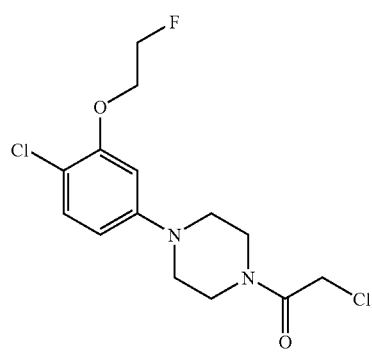

Following Protocol S, 1-(4-chloro-3-(2-fluoro)ethoxy-phenyl)-piperazine dihydrochloride (1.53 mmol, 1.0 eq), 1.0 g $K_2CO_3$ (7.5 mmol, 5.0 eq) were combined in a vial with 4 mL NMP. The vial was cooled in an ice water bath, then 197 uL chloroacetyl chloride (1.8 mmol, 1.2 eq) was added and the mixture allowed to stir at room temperature overnight. The material was purified by column chromatography to get 100 mg clean product.

4-chloromethylcarbonyl-1-(4-chloro-3-(2,2,2-trifluoro)ethoxy-phenyl)-piperazine

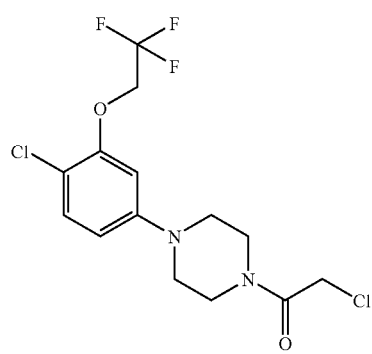

Following Protocol S, 1-(4-chloro-3-(2,2,2-trifluoro)ethoxy-phenyl)-piperazine dihydrochloride was reacted with chloroacetyl chloride to give the title compound.

4-chloromethylcarbonyl-1-(4-chloro-3-propoxy-phenyl)-piperazine

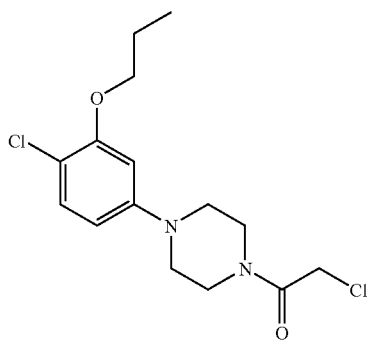

Following Protocol S, 1-(4-chloro-3-propoxy-phenyl)-piperazine dihydrochloride was reacted with chloroacetyl chloride to give the title compound.

Protocol T: K2CO3 Mediated Coupling Reaction of Chloroacetyl Arylpiperazines with Pyrazoles 1-[4-(4-Chloro-3-methoxy-phenyl)-piperazin-1-yl]-2-(4-chloro-5-methyl-3-pyridin-4-yl -pyrazol-1-yl)-ethanone

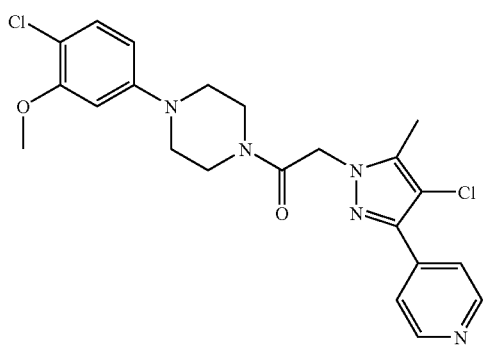

The title compound was prepared following Protocol T, using 1-(4-Chloro-3-methoxy-phenyl)-piperazine: HPLC retention time=5.57 minutes (Agilent Zorbax SB-C18, 2.1× 50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=460.1 (M+H).

Synthesis of 1-[4-(4-Chloro-3-methoxy-phenyl)-piperazin-1-yl]-2-(5-hydroxy-3-methyl -pyrazol-1-yl)-ethanone and 1-[4-(4-Chloro-3-methoxy-phenyl)-piperazin-1-yl]-2-(3-hydroxy-5-methyl-pyrazol-1-yl)-ethanone

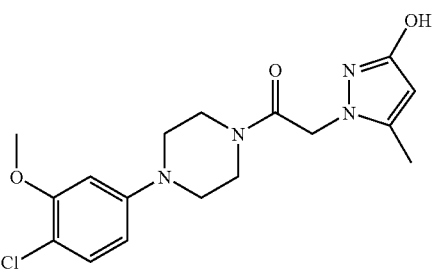

Title compounds were prepared following Protocol T, wherein (3-Methyl-5-(hydroxyl)pyrazole was used: 1-[4-(4-Chloro-3-methoxy-phenyl)-piperazin-1-yl]-2-(3-hydroxy-5-methyl-pyrazol-1-yl)-ethanone: HPLC retention time=2.89 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/ 94.9% water, B=0.08% formic acid/99.9% acetonitrile); MS (ES) M+H expect=365.1, found=365.4. 1-[4-(4-Chloro-3-methoxy-phenyl)-piperazin-1-yl]-2-(5-hydroxy-3-methyl-pyrazol-1-yl)-ethanone: HPLC retention time=3.33 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=365.1, found=365.4; $^1$H NMR (DMSO, 400 MHz)

7.20 (d, 1H), 70(s 1H), 6.52(d, 1H), 5.50 (s 1H), 4.84 (s, 2H), 3.83 (s, 3H), 3.5-3.6 (Par. Obsc.s, 4H), 3.1-3.3 (d, 4H), 2.15(s, 3H) ppm.

1-[4-(4-Chloro-3-methoxy-phenyl)-2-methyl-piperazin-1-yl]-2-[4-chloro-5-methyl-3-(4-methyl-pyridin-2-yl)-pyrazol-1-yl]-ethanone

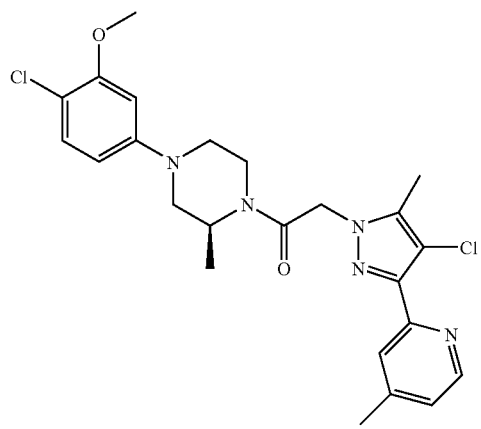

Following Protocol T, 2-Chloro-1-[4-(4-chloro-3-methoxy-phenyl)-2-(S)-methylpiperazin-1-yl]-ethanone and 2-(4-Chloro-5-methyl-1H-pyrazol-3-yl)-4-methyl-pyridine were combined to give the title compound: HPLC retention time=6.76 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile 194.9% water, B=0.08% formic acid/99.9% acetonitrile); (M/Z)+=488.1 (M+H).

4-(1-{2-[4-(4-Chloro-3-methoxy-phenyl)-2-(S)-methyl-piperazin-1-yl]-2-oxo-ethyl}-5-methyl-1H-pyrazol-3-yl)-pyridine-2-carbonitrile

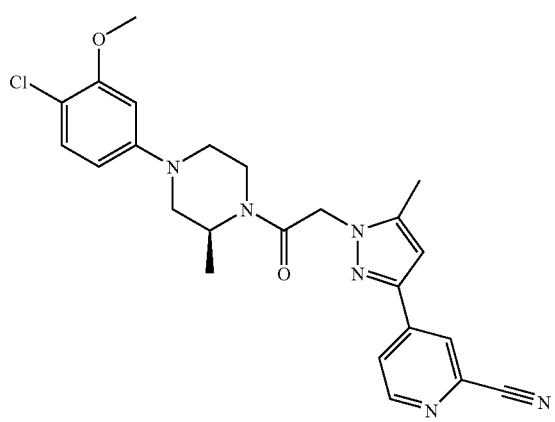

Following Protocol T, the title compound was prepared: HPLC retention time=6.90 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=465.3 (M+H).

4-(4-Chloro-1-{2-[4-(4-chloro-3-methoxy-phenyl)-piperazin-1-yl]-2-oxo-ethyl}-5-methyl-1H-pyrazol-3-yl)-pyridine-2-carbonitrile

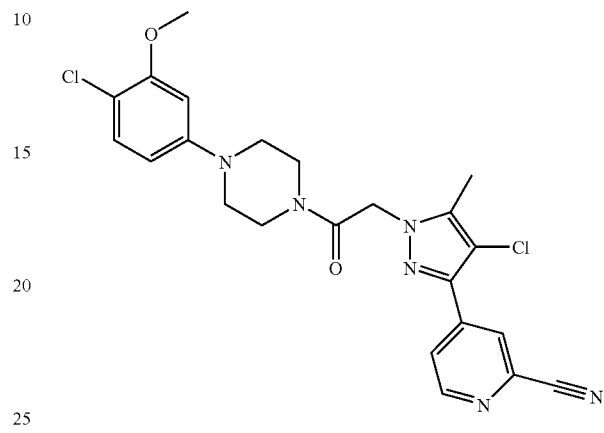

Following Protocol T, 2-Chloro-1-[4-(4-chloro-3-methoxy-phenyl)-piperazin-1-yl]-ethanone and 2-(4-Chloro-5-methyl-1H-pyrazol-3-yl)-4-methyl-pyridine were combined to give the title compound: HPLC retention time=7.14 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=486.2 (M+H).

4-(4-Chloro-1-{2-[4-(4-chloro-3-methoxy-phenyl)-2-methyl-piperazin-1-yl]-2-oxo-ethyl}-5-methyl-1H-pyrazol-3-yl)-pyridine-2-carbonitrile

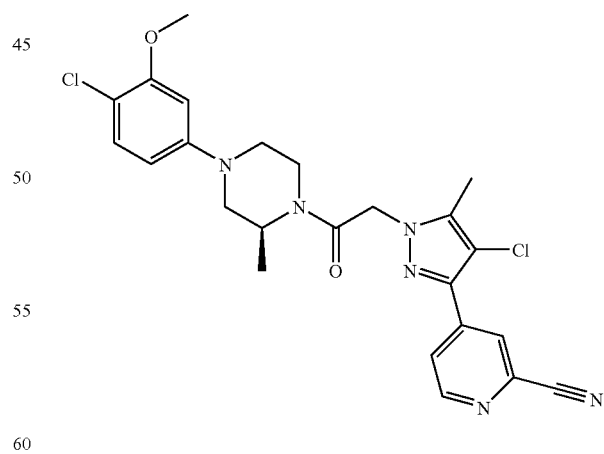

Following Protocol T, 2-Chloro-1-[4-(4-chloro-3-methoxy-phenyl)-2-(S)-methyl-piperazin-1-yl]-ethanone and 2-(4-Chloro-5-methyl-1H-pyrazol-3-yl)-4-methyl-pyridine were combined to give the title compound: HPLC retention time=7.42 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+= 499.2 (M+H).

1-{4-[4-Chloro-3-(2-fluoro-ethoxy)-phenyl]-piperazin-1-yl}-2-(4-chloro-5-methyl-3-pyridin-2-yl-pyrazol-1-yl)-ethanone

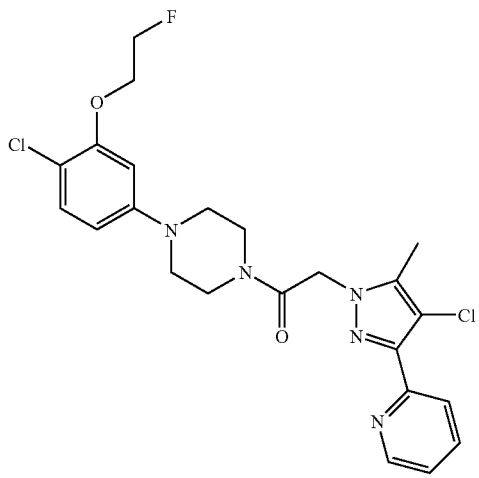

Following Protocol T, the title compound was prepared: LC/MS(ES) (M+H) 492.4; HPLC retention time=5.91 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile)

2-(4-Chloro-5-methyl-3-pyridin-2-yl-pyrazol-1-yl)-1-{4-[4-chloro-3-(2,2,2-trifluoro-ethoxy)-phenyl]-piperazin-1-yl}-ethanone

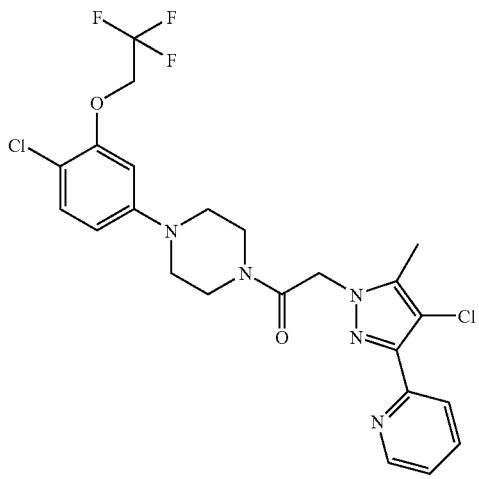

Following Protocol T, the title compound was prepared: LC/MS(ES) (M+H) 528.4; HPLC retention time=6.47 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

2-(4-Chloro-5-methyl-3-pyridin-2-yl-pyrazol-1-yl)-1-[4-(4-chloro-3-propoxy-phenyl)-piperazin-1-yl]-ethanone

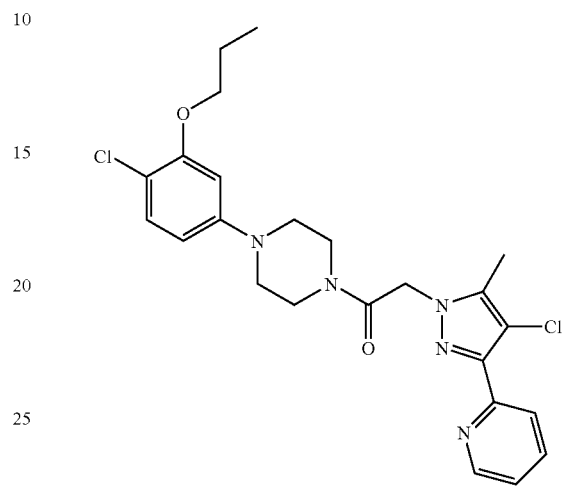

Following Protocol T, the title compound was prepared: LC/MS(ES) (M+H) 488.4; HPLC retention time=6.52 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

1-[4-(4-Chloro-3-methoxy-phenyl)-piperazin-1-yl]-2-(5-methyl-3-trifluoromethyl-pyrazol-1-yl)-ethanone

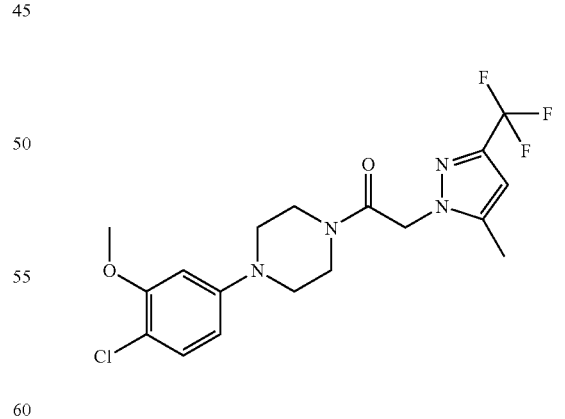

Following Protocol T, 2-Chloro-1-[4-(4-chloro-3-methoxy-phenyl)-piperazin-1-yl]-ethanone and 3-methyl-5-trifluoromethylpyrazole were coupled to give the title compound: HPLC retention time=7.18 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=417.2 (M+H).

1-[4-(4-Chloro-2-fluoro-5-methoxy-phenyl)-piperazin-1-yl]-2-(5-methyl-3-trifluoromethyl-pyrazol-1-yl)-ethanone

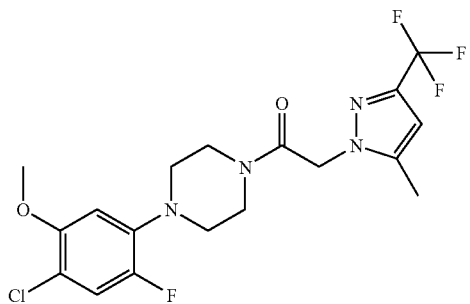

Following Protocol T, 2-Chloro-1-[4-(4-chloro-6-fluoro-3-methoxy-phenyl)-piperazin-1-yl]-ethanone and 3-methyl-5-trifluoromethylpyrazole were reacted to give the title compound: HPLC retention time=7.35 minutes (Agilent Zorbax SB-C 18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=435.2 (M+H).

2-(4-Chloro-3-hydroxymethyl-5-methyl-pyrazol-1-yl)-1-[4-(4-chloro-3-methoxy-phenyl)-piperazin-1-yl]-ethanone

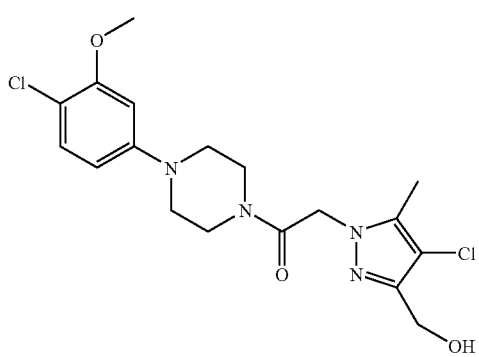

Following Protocol T, (4-Chloro-5-methyl-1H-pyrazol-3-yl)-methanol and 2-Chloro-1-[4-(4-chloro-3-methoxy-phenyl)-piperazin-1-yl]-ethanone were coupled to give the title compound: HPLC retention time=6.45 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=413.2 (M+H).

1-[4-(4-Chloro-3-methoxyphenyl)-2-(S)-methylpiperazin-1-yl]-2-(4-chloro-5-methyl-3-pyridin-4-ylpyrazol-1-yl)ethanone

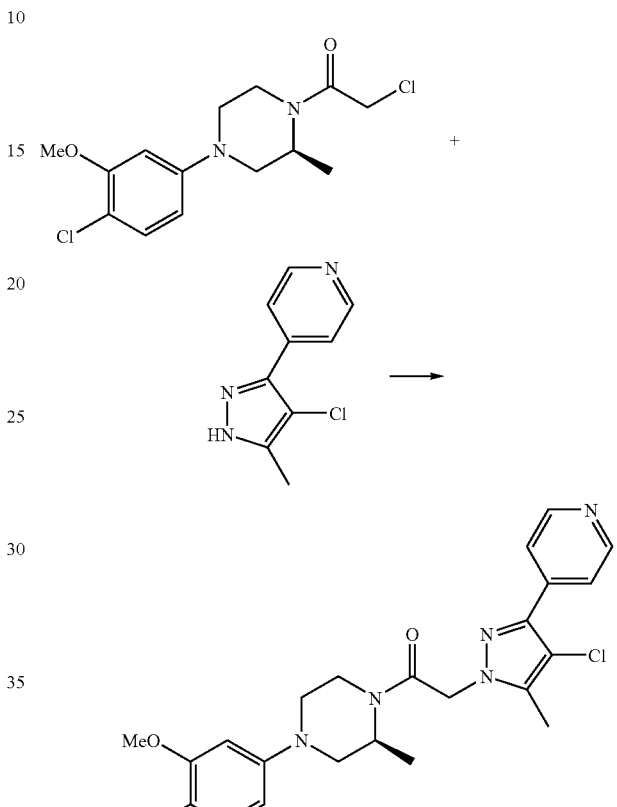

The title compound was obtained by following Protocol T: LCMS (ES): M+H 474.1; HPLC retention time=3.645 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

6-(4-Chloro-1-{2-[4-(4-chloro-3-methoxy-phenyl)-piperazin-1-yl]-2-oxo-ethyl}-5-methyl-1H-pyrazol-3-yl)-pyridine-2-carboxylic acid methylamide

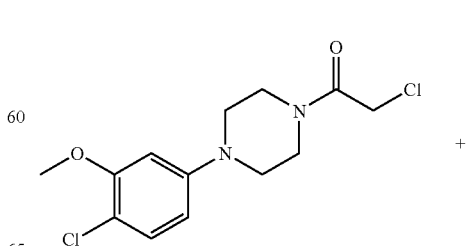

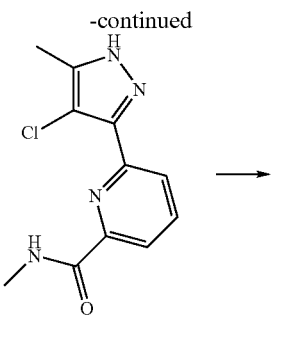

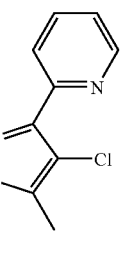

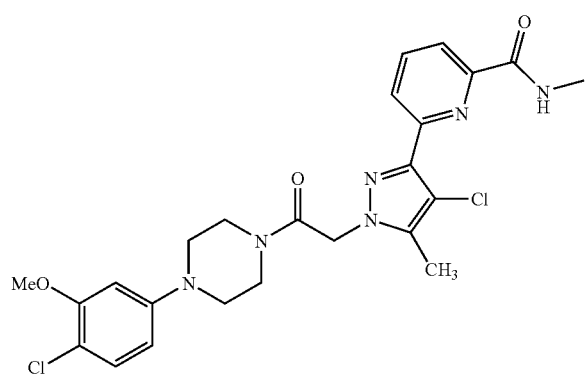

The title compound was made by following Protocol T: LCMS (ES) M+H=518.4; HPLC RT=4.308 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)piperazin-1-yl]-2-(4-chloro-5-methyl-3-pyridin-2-yl-pyrazol-1-yl)ethanone

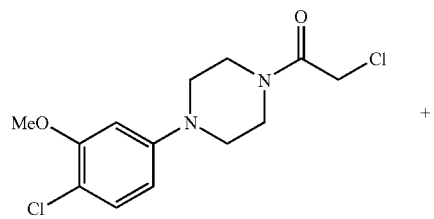

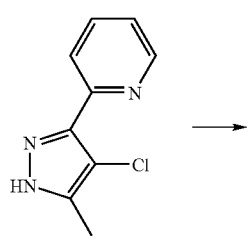

The title compound was obtained by following Protocol T: LCMS (ES): M+H 460.1; HPLC retention time=3.77 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

6-(4-Chloro-1-{2-[4-(4-chloro-3-methoxy-phenyl)-piperazin-1-yl]-2-oxo-ethyl}-5-methyl-1H-pyrazol-3-yl)-pyridine-2-carboxylic acid dimethylamide

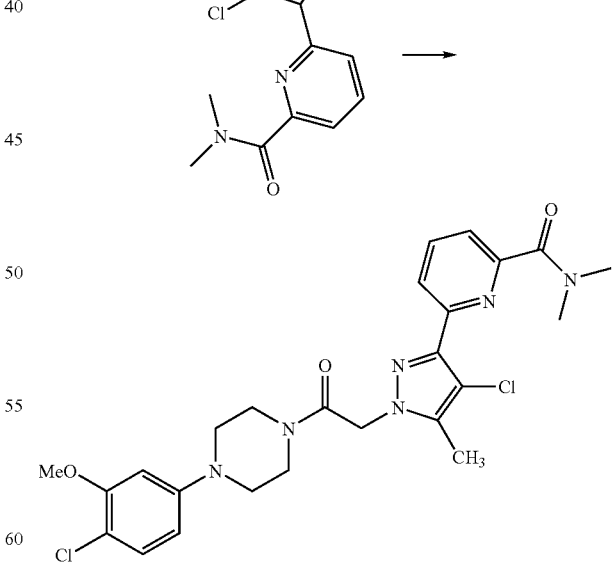

The title compound was made by following Protocol T: $^1$H NMR (400 MHz, CDCl$_3$) δδ 7.98-7.41 (m, 3H), 6.47 (m, 3H), 5.05 (s, 1H), 3.89 (q, 2H), 3.89 (s, 3H), 3.21-3.13 (dt, 2H), 2.34 (s, 3H), 2.18 (s, 3H), 1.63 (s, 1H); LCMS (ES) M+H=531.5; HPLC RT=4.113 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(3-methylsulfonyl-4-chloro-5-methyl-pyrazol-1-yl)-1-[4-(4-chloro-3-methoxy-phenyl)-2(S)-methyl-piperazin-1-yl]-ethanone

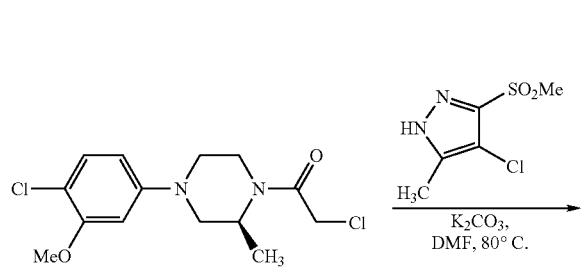

Following Protocol T, 2-chloro-1-[4-(4-chloro-3-methoxy-phenyl)-2(S)-methyl-piperazin-1-yl]-ethanone and 3-methylsulfonyl-4-chloro-5-methyl-pyrazol-1-yl were coupled to give the title compound: $^1$H NMR (400 MHz, CDCl$_3$) δ 7.30 (d, 1H), 7.18 (br, 1H), 6.80 (br, 1H), 6.05 (bt, 3H), 5.50 (br, 1H), 4.95 (br, 1H), 4.42 (br, 1H), 3.90 (s, 3H), 3.42 (br, 3H), 3.18 (s, 3H), 2.30 (s, 3H), 1.70 (d, 1.5H), 1.58 (d, 1.5H); LCMS observed for (M+H)$^+$: 475.

1-[4-(4-Chloro-3-methoxyphenyl)-2-(S)-methylpiperazin-1-yl]-2-(4-chloro-5-methyl-3-pyridin-2-ylpyrazol-1-yl)ethanone

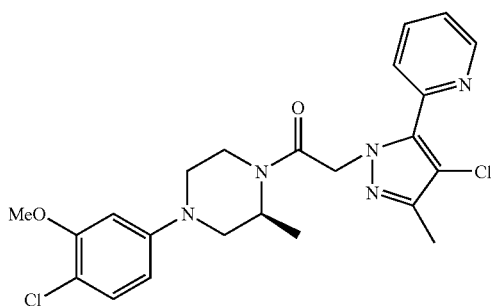

The title compound was prepared following Protocol T: LCMS (ES) M+H=474.1; HPLC retention time=4.95 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-2-fluoro-5-methoxyphenyl)piperazin-1-yl]-2-(4-chloro-5-methyl-3-pyridin-2-ylpyrazol-1-yl)ethanone

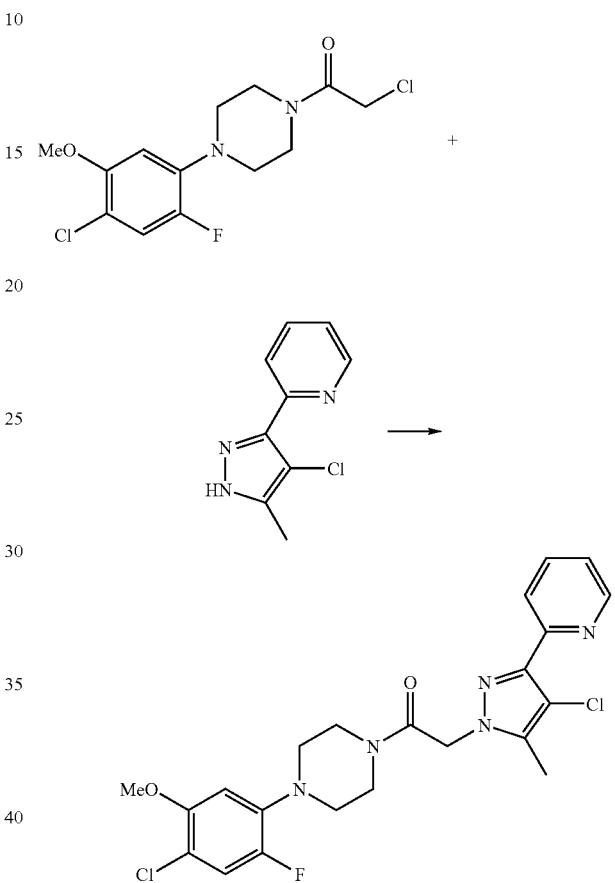

The title compound was obtained by following Protocol T: LCMS (ES): M+H 478.1; HPLC retention time=3.92 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)-2-methylpiperazin-1-yl]-2-[4-chloro-5-methyl-3-(6-methylpyridin-3-yl)pyrazol-1-yl]ethanone

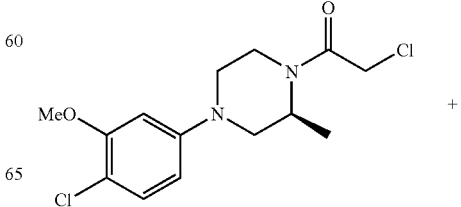

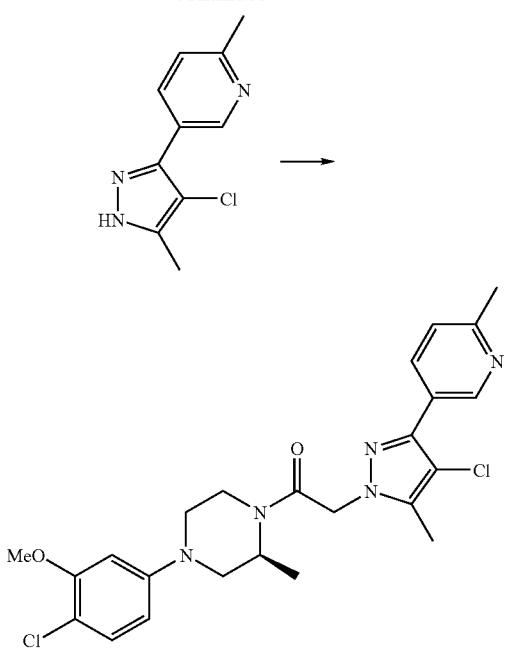

The title compound was obtained by following Protocol T: LCMS (ES): M+H 488.1; HPLC retention time=4.32 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-piperazin-1-yl]-2-(4-chloro-5-pyridin-2-yl-3-trifluoromethyl-pyrazol-1-yl)-ethanone and 1-[4-(4-Chloro-3-methoxy-phenyl)-piperazin-1-yl]-2-(4-chloro-3-pyridin-2-yl-5-trifluoromethyl-pyrazol-1-yl)-ethanone

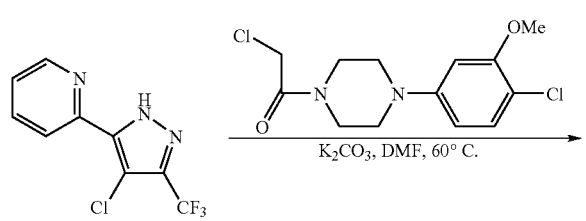

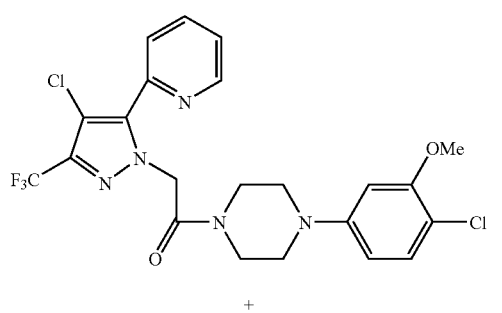

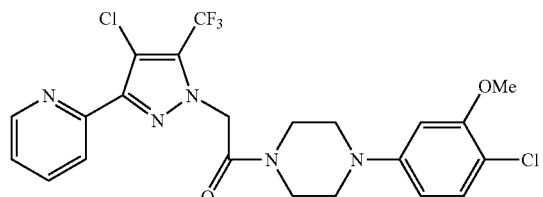

The above two isomers were synthesized by the same Protocol T. These isomers were purified by preparative TLC (50% EtOAc: n-Hexane).

1-(4-(4-Chloro-3-methoxyphenyl)-piperazin-1-yl)-2-(4-chloro-5-pyridin-2-yl-3-trifluoromethyl-pyrazol-1-yl)-ethanone (Major isomer): LC MS 514 (M+, 20-95 method, RT=4.99 min); $^1$H NMR (400 MHz, CDCl$_3$): δ 3.06 (t, J=4.7 Hz, 2H), 3.19 (t, J=4.7 Hz, 2H), 3.63 (apparent q, J=7.5 Hz, 4H), 3.87 (s, 3H), 5.63 (s, 2H), 6.39 (dd, J=2.6 & 8.8 Hz, 1H), 6.46 (d, J=2.6 Hz, 1H), 7.20 (d, J=8.8 Hz, 1H), 7.29-7.32 (m, 1H), 7.81 (dt, J=1.8 & 8.1 Hz, 1H), 7.92 (d, J=7.7 Hz, 1H), 8.60 (d, J=5.1 Hz, 1H).

1-(4-(4-Chloro-3-methoxyphenyl)-piperazin-1-yl)-2-(4-chloro-3-pyridin-2-yl-5-trifluoromethyl-pyrazol-1-yl)-ethanone (Minor isomer): LC MS 514 (M+, 20-95 method, RT=4.68 min); $^1$H NMR (400 MHz, CDCl$_3$): δ 3.06 (t, J=4.3 Hz, 2H), 3.21 (t, J=4.3 Hz, 2H), 3.60 (apparent q, J=6.5 Hz, 2H), 3.76 (apparent q, J=6.5 Hz, 2H) 3.85 (s, 3H), 5.24 (s, 2H), 6.39 (dd, J=2.6 & 8.8 Hz, 1H), 6.46 (d, J=2.6 Hz, 1H), 7.20 (d, J=8.8 Hz, 1H), 7.29-7.32 (m, 1H), 7.76 (dt, J=1.8 & 8.1 Hz, 1H), 7.98 (d, J=7.7 Hz, 1H), 8.74 (d, J=5.1 Hz, 1H).

Synthesis of 1-[4-(4-Chloro-3-methoxyphenyl)-2-(S)-methylpiperazin-1-yl]-2-(4-chloro-5-methyl-3-pyrimidin-4-ylpyrazol-1-yl)ethanone

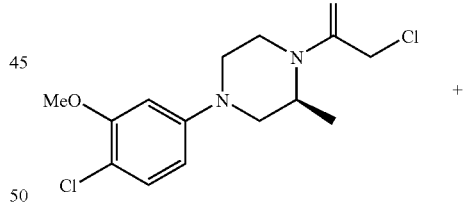

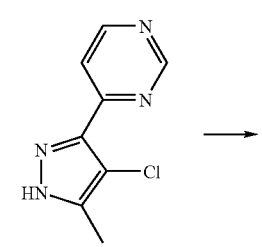

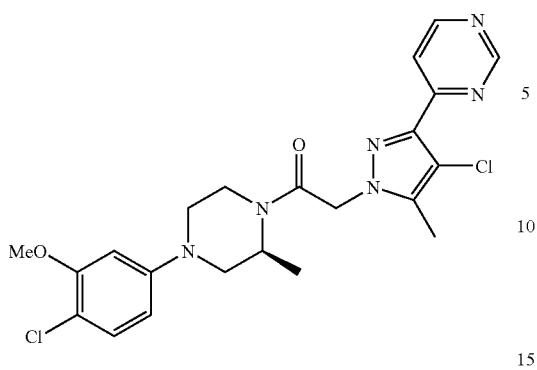

The title compound was obtained by following Protocol T: LCMS (ES): M+H 475.1; HPLC retention time=4.59 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-(4-(4-Chloro-3-methoxyphenyl)-2(S)-methylpiperazin-1-yl)-2-(4-chloro-5-pyridin-2-yl-3-trifluoromethyl-pyrazol-1-yl)-ethanone and 1-(4-(4-Chloro-3-methoxyphenyl)-2(S)-methylpiperazin-1-yl)-2-(4-chloro-3-pyridin-2-yl-5-trifluorometilyl-pyrazol-1-yl)-ethanone

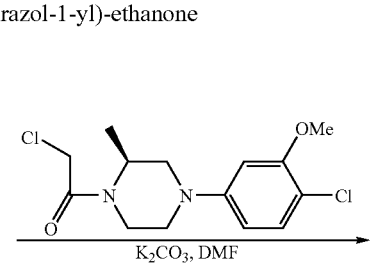

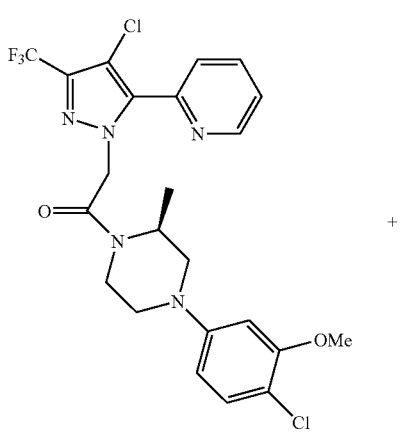

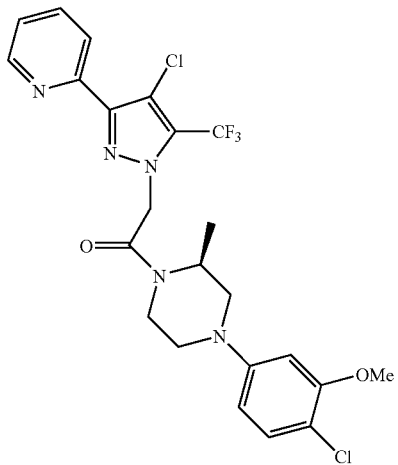

1-(4-(4-Chloro-3-methoxyphenyl)-2(S)-methylpiperazin-1-yl)-2-(4-chloro-5-pyridin-2-yl-3-trifluoromethyl-pyrazol-1-yl)ethanone: The above compound was synthesized by the same Protocol T: LCMS 528 (M⁺H); HPLC RT=5.29 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-(4-(4-Chloro-3-methoxyphenyl)-2(S)-methylpiperazin-1-yl)-2-(4-chloro-3-pyridin-2-yl-5-trifluoromethyl-pyrazol-1-yl)-ethanone: The above compound was synthesized by the same Protocol T: LCMS 528 (M⁺H); HPLC RT=4.95 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile)

Synthesis of 1-(4-(4-Chloro-2-fluoro-5-methoxyphenyl)-2(S)-methylpiperazin-1-yl)-2-(4-chloro-5-pyridin-2-yl-3-trifluoromethyl-pyrazol-1-yl)-ethanone and 1-(4-(4-Chloro-2-fluoro-5-methoxyphenyl)-2(S)-methylpiperazin-1-yl)-2-(4-chloro-3-pyridin-2-yl-5-trifluoromethyl-pyrazol-1-yl)-ethanone

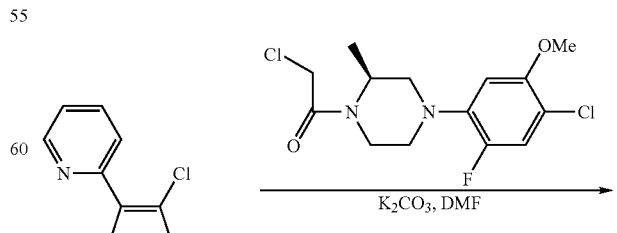

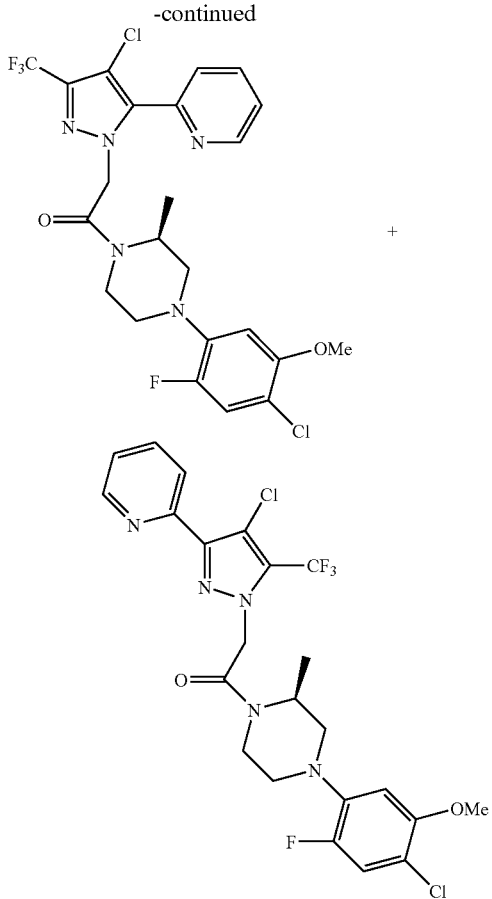

1-(4-(4-Chloro-2-fluoro-5-methoxyphenyl)-2(S)-methylpiperazin-1-yl)-2-(4-chloro-5-pyridin-2-yl-3-trifluoromethyl-pyrazol-1-yl)-ethanone: The above compound was synthesized by Protocol T: LC MS 546 (M⁺H); HPLC RT=5.52 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-(4-(4-Chloro-2-fluoro-5-methoxyphenyl)-2(S)-methylpiperazin-1-yl)-2-(4-chloro-3-pyridin-2-yl-5-trifluoromethyl-pyrazol-1-yl)ethanone: The above compound was synthesized by the same protocol XX. LC MS 546 (M⁺H); HPLC RT=5.19 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)-2-(S)-methylpiperazin-1-yl]-2-(4-chloro-5-methyl-3-pyrimidin-2-ylpyrazol-1-yl)ethanone

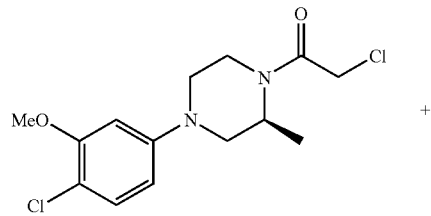

+

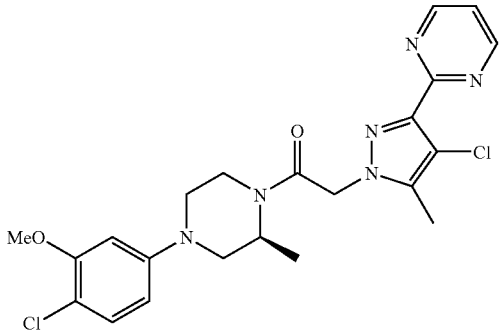

The title compound was obtained by following Protocol T: ¹H NMR: δ (400 MHz, CDCl₃) 8.95 (d, 2H), 7.60 (ddd, 1H), 7.39 (m, 1H), 6.52 (br, 2H), 5.28-4.77 (br, 2H), 4.47-4.18 (br, 2H), 3.89 (s, 3H), 3.78-2.73 (br, 5H), 2.36 (s, 3H), 1.53-0.78 (br, 3H); LCMS (ES): M+H 475.1; HPLC retention time=4.41 minutes (Agilent Zorbax SB-C 18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-piperazin-1-yl]-2-(4-fluoro-5-methyl-3-trifluoromethyl-pyrazol-1-yl)-ethanone

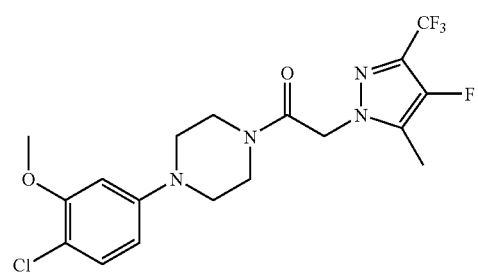

Title compound was prepared following Protocol T, wherein 1-(3-methoxyphenyl-4-chloro)piperazine-4-chloromethyl-keton and (3-Methyl-4-fluoro-5-(trifluoromethyl) pyrazole were used as the coupling components: HPLC retention time=4.69 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5%

6-(4-Chloro-1-{2-[4-(4-chloro-3-methoxy-phenyl)-piperazin-1-yl]-2-oxo-ethyl}-5-methyl-1H-pyrazol-3-yl)-pyridine-2-carbonitrile

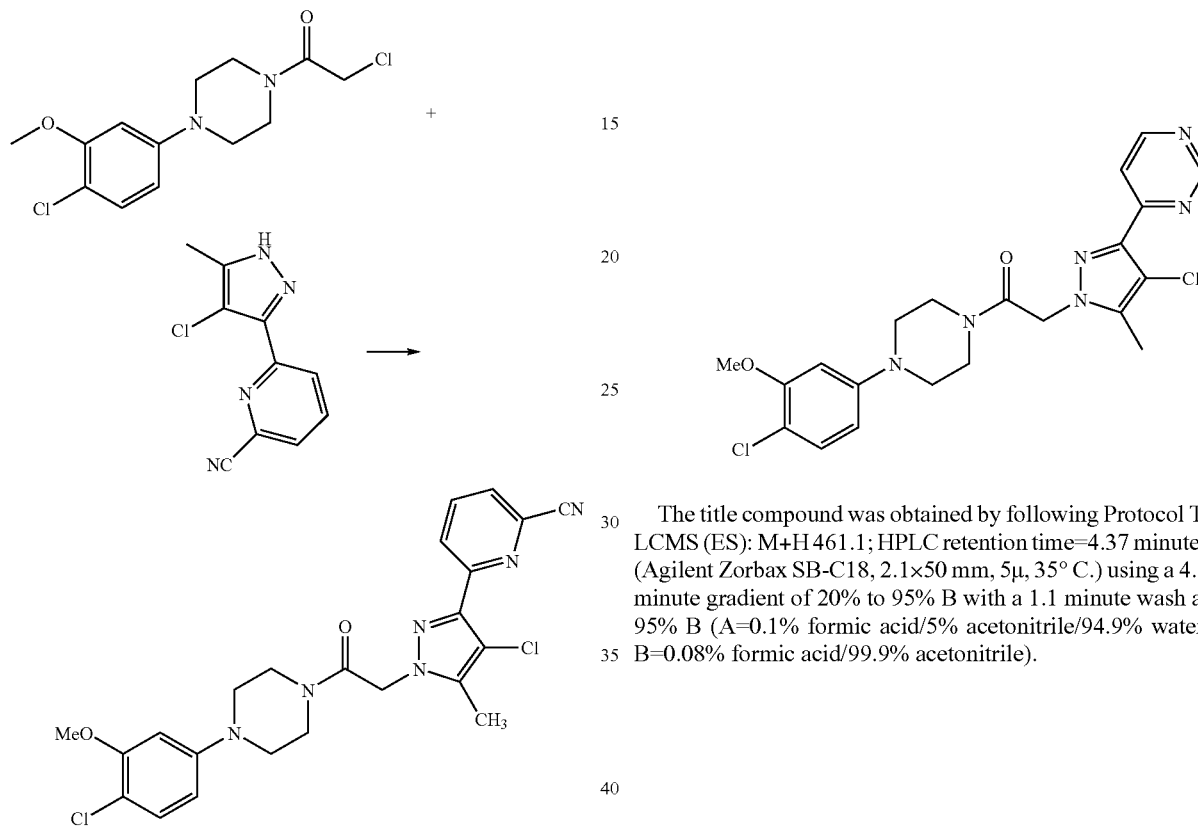

The title compound was made by following Protocol T: LCMS (ES) M+H=485.4; HPLC RT=6.859 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)piperazin-1-yl]-2-(4-chloro-5-methyl-3-pyrimidin-4-ylpyrazol-1-yl)ethanone

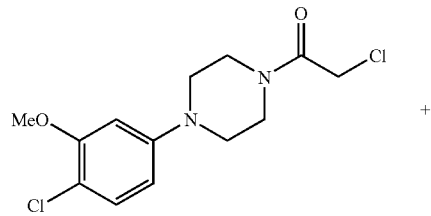 +

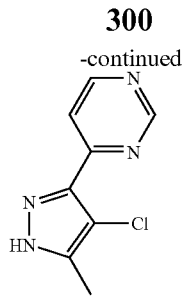 →

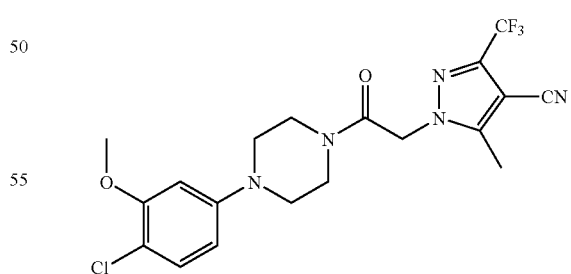

The title compound was obtained by following Protocol T: LCMS (ES): M+H 461.1; HPLC retention time=4.37 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-{2-[4-(4-Chloro-3-methoxy-phenyl)-piperazin-1-yl]-2-oxo-ethyl}-5methyl-3-trifluoromethyl-1H-pyrazole-4-carbonitrile Title compound was prepared following Protocol T, wherein 1-(3-methoxyphenyl-4-chloro)piperazine-4-chloromethyl-keton and (3-Methyl-4-cyano-5-(trifluoromethyl)pyrazole were used as the coupling components: HPLC retention time=4.59 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=442.1, found=442.4.

Synthesis of 1-[4-(4-Chloro-3-methoxy-phenyl)-piperazin-1-yl]-2-(4-iodo-5-methyl-3-trifluoromethyl-pyrazol-1-yl)-ethanone

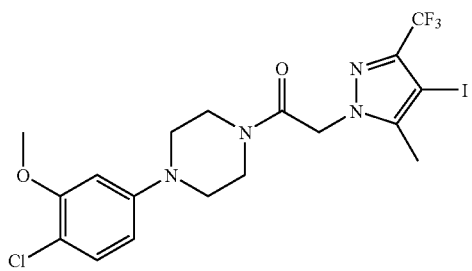

Title compound was prepared following Protocol T: HPLC retention time=4.89 minutes, (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=543.2, found=543.3.

Synthesis of N-(1-{2-[4-(4-Chloro-3-methoxy-phenyl)-piperazin-1-yl]-2-oxo-ethyl}-5-methyl-3-trifluoromethyl-1H-pyrazol-4-yl)-acetamide

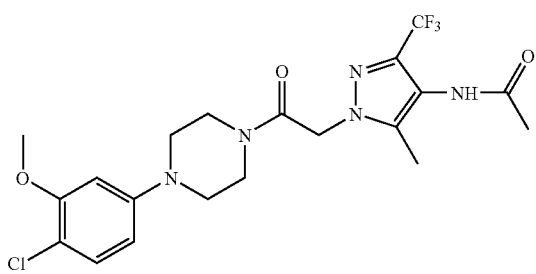

Title compound was prepared following Protocol T, wherein 1-(3-methoxyphenyl-4-chloro)piperazine-4-chloromethyl-keton and 3-Methyl-4-acetylamino-5-(trifluoromethyl)pyrazole were used as the coupling components: HPLC retention time=3.66 minutes, (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=474.1, found=474.4.

Synthesis of 2-(2-phenylimidazol-1-yl)-1-[4-(4-chloro-3-methoxy-phenyl)-piperazin-1-yl]-ethanone

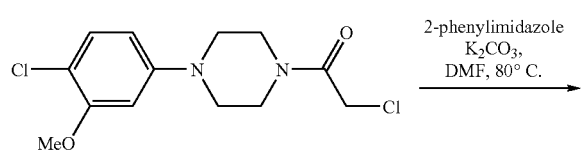

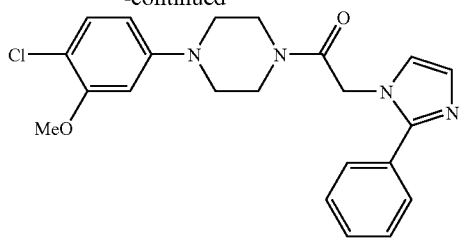

Following Protocol T, 2-Chloro-1-[4-(4-chloro-3-methoxy-phenyl)-piperazin-1-yl]-ethanone and 2-phenylimidazole were coupled to give the title compound: LCMS retention time: 2.86 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)$^+$: 411.

Synthesis of 2-Benzoimidazol-1-yl-1-[4-(4-chloro-3-methoxy-phenyl)-piperazin-1-yl]-ethanone

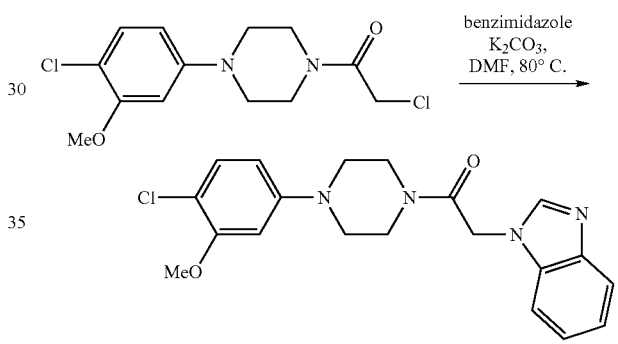

Following Protocol T, 2-Chloro-1-[4-(4-chloro-3-methoxy-phenyl)-piperazin-1-yl]-ethanone and benzimidazole were reacted to give the title compound: LCMS retention time: 2.57 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)$^+$: 385.

5-(4-Chloro-1-{2-[4-(4-chloro-3-methoxy-phenyl)-2-(S)-methyl-piperazin-1-yl]-2-oxo-ethyl}-5-methyl-1H-pyrazol-3-yl)-pyridine-2-carboxylic acid methylamide

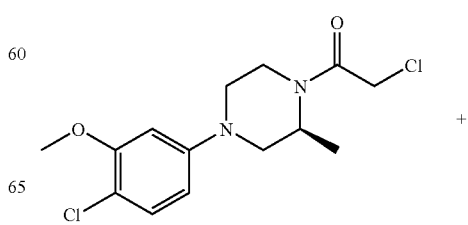

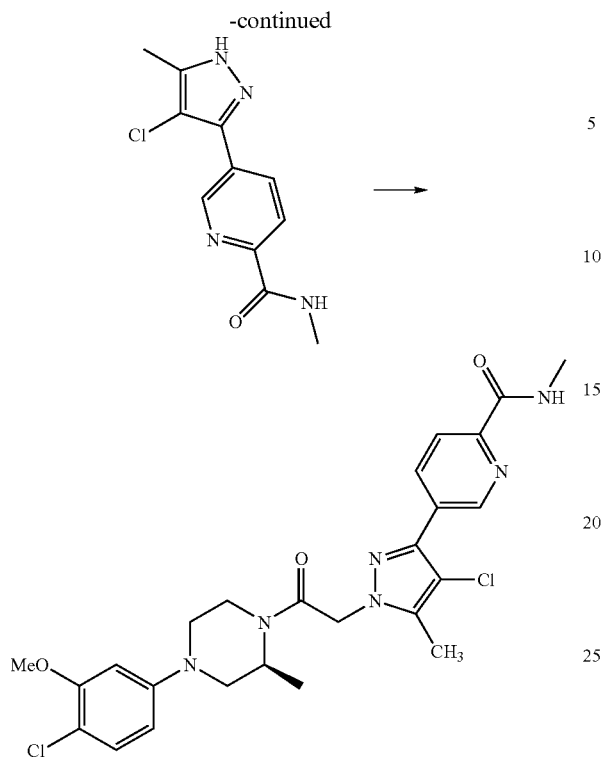

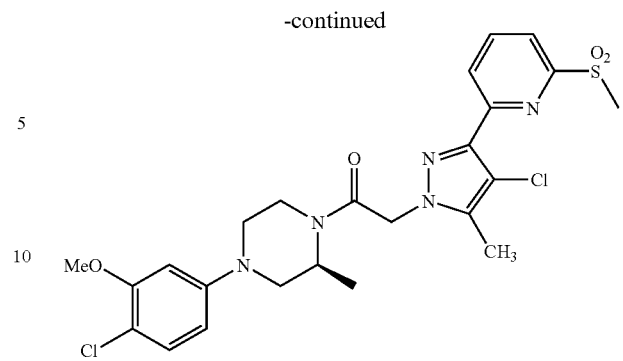

The title compound was made by following Protocol T: $^1$H NMR (400 MHz, CDCl$_3$) δδ 8.12-7.82 (m, 3H), 6.47 (m, 3H), 5.51 (s, 2H), 3.89 (s, 1H), 3.89 (s, 3H), 3.81(d, 2H), 3.79 (d, 2H), 3.36 (s, 3H), 3.18-3.13 (dt, 2H), 2.35 (s, 3H), 2.34(s, 3H), 1.60 (s, 1H); LCMS (ES) M+H=532.5; HPLC RT=4.582 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-2-fluoro-5-methoxyphenyl)piperazin-1-yl]-2-(4-chloro-5-methyl-3-pyrimidin-2-ylpyrazol-1-yl)ethanone

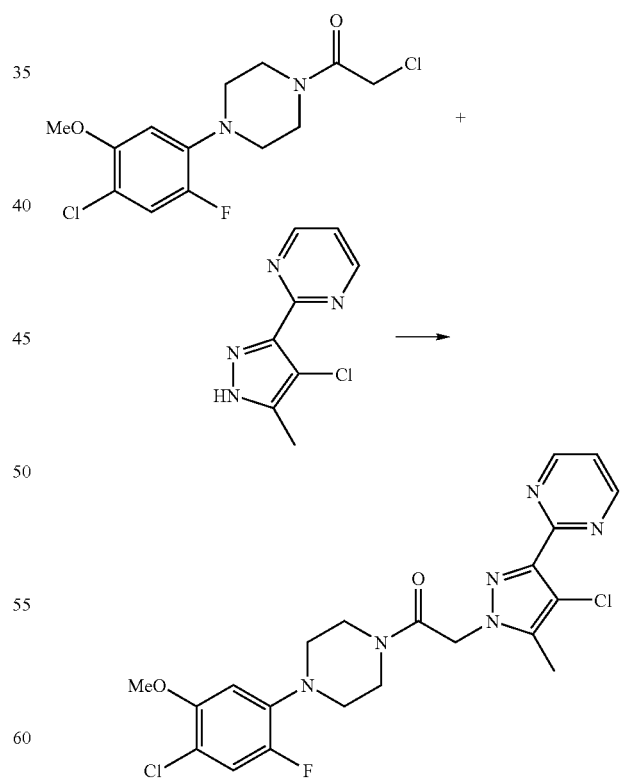

The title compound was made by following Protocol T: $^1$H NMR (400 MHz, CDCl$_3$): δ 9.21-8.12 (m, 3H), 6.47 (m, 3H), 4.64 (s, 2H), 3.81 (q, 2H), 3.89 (s, 1H), 3.89 (d, 2H), 3.79-3.32 (dt, 2H), 2.35 (s, 3H), 2.18 (s, 3H); LCMS (ES) M+H=531.5; HPLC RT=4.360 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-[4-Chloro-3-(6-methanesulfonyl-pyridin-2-yl)-5-methyl-pyrazol-1-yl]-1-[4-(4-chloro-3-methoxyphenyl)-2-(S)-methyl-piperazin-1-yl]-ethanone

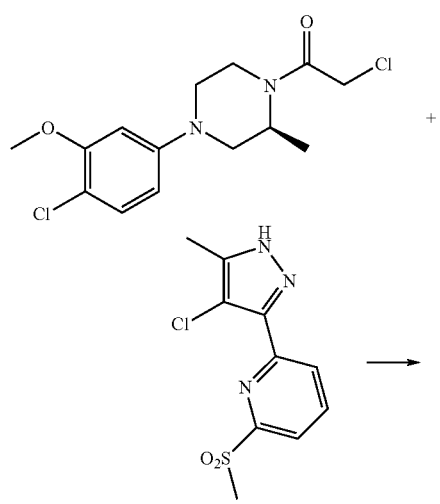

The title compound was obtained by following Protocol T: LCMS (ES): M+H 479.1; HPLC retention time=4.65 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-[4-Chloro-3-(6-chloro-pyridin-3-yl)-5-methyl-pyrazol-1-yl]-1-[4-(4-chloro-3-methoxy-phenyl)-2-(S)-methyl-piperazin-1-yl]-ethanone

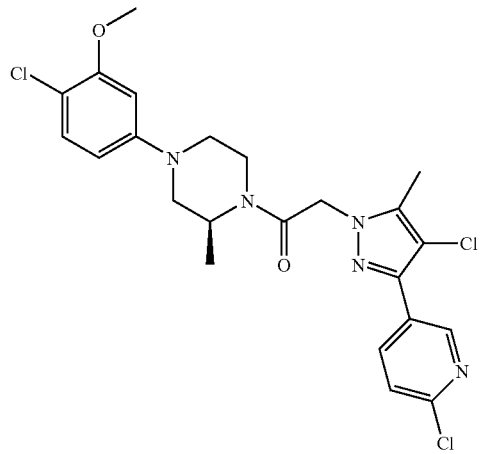

Following Protocol T, 2-Chloro-1-[4-(4-chloro-3-methoxy-phenyl)-2-(S)-methylpiperazin-1-yl]-ethanone and 2-Chloro-5-(4-chloro-5-methyl-1H-pyrazol-3-yl)-pyridine were coupled to give the title compound: HPLC retention time=7.83 minutes (Agilent Zorbax SB-C18, 2.1×50 mm, 5µ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)−= 506 (M−H).

4-Chloro-1-{2-[4-(4-chloro-3-methoxy-phenyl)-piperazin-1-yl]-2-oxo-ethyl}-5-methyl-1H-pyrazole-3-carboxylic acid ethyl ester

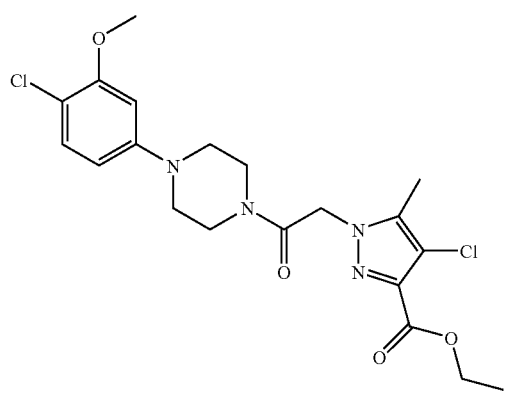

Following Protocol T, 2-Chloro-1-[4-(4-chloro-3-methoxy-phenyl)-piperazin-1-yl]-ethanone and 4-Chloro-5-methyl-1H-pyrazole-3-carboxylic acid ethyl ester were combined to give the title compound: HPLC retention time=7.14 minutes (Agilent Zorbax SB-C18, 2.1×50 mm, 5µ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=455.1 (M+H).

Synthesis of 1-[4-(4-Chloro-3-methoxyphenyl)piperazin-1-yl]-2-[4-chloro-5-methyl-3-(6-methylpyridin-2-yl)pyrazol-1-yl]ethanone

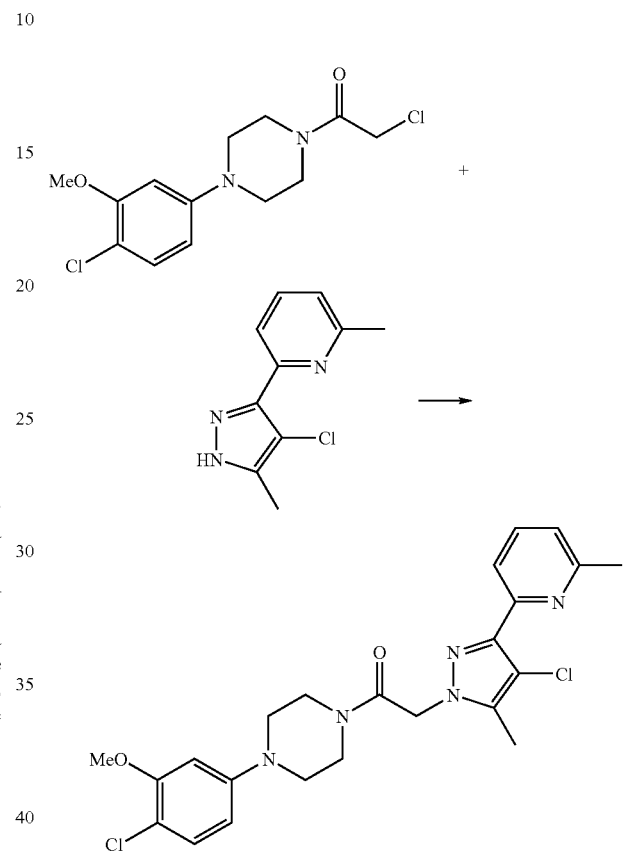

The title compound was obtained by following Protocol T: LCMS (ES): M+H 474.1; HPLC retention time=4.39 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)-2-(S)-methylpiperazin-1-yl]-2-[4-chloro-5-methyl-3-(6-methylpyridin-2-yl)pyrazol-1-yl]ethanone

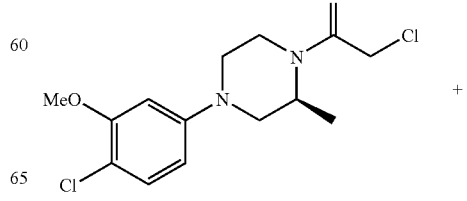

-continued

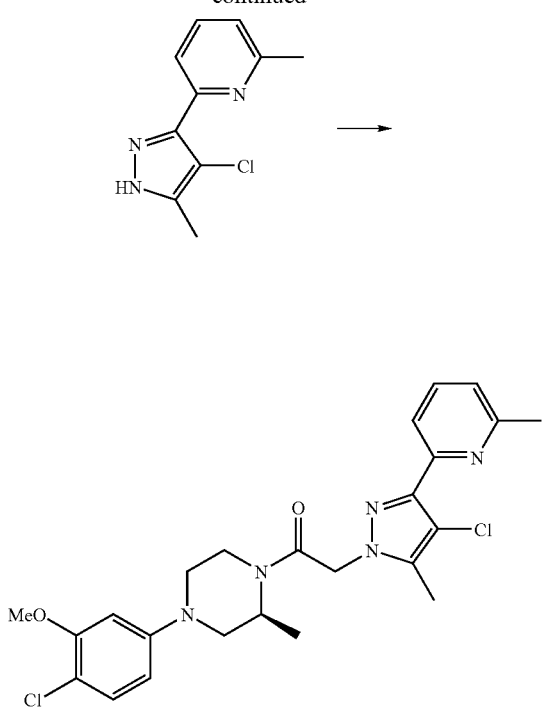

The title compound was obtained by following Protocol T: LCMS (ES): M+H 488.1; HPLC retention time=4.42 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-[4-Bromo-5-methyl-3-(6-methylpyridin-2-yl)pyrazol-1-yl]-1-[4-(4-chloro-3-methoxyphenyl)piperazin-1-yl]ethanone

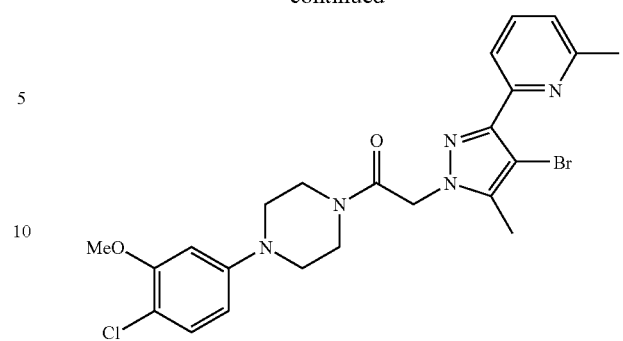

-continued

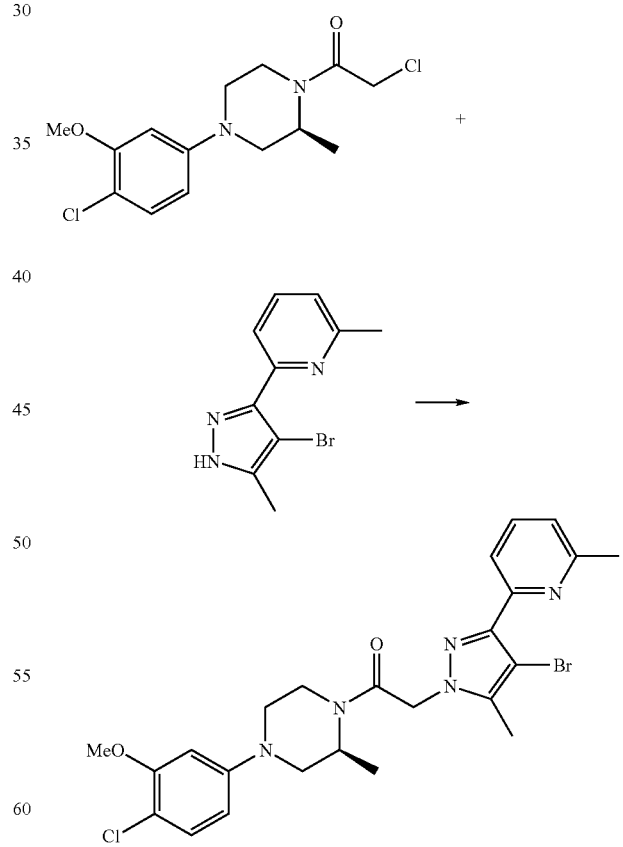

The title compound was obtained by following Protocol T: LCMS (ES): M+H 518.1; HPLC retention time=4.43 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-[4-Bromo-5-methyl-3-(6-methylpyridin-2-yl)pyrazol-1-yl]-1-[4-(4-chloro-3-methoxyphenyl)-2-(S)-methylpiperazin-1-yl]ethanone The title compound was obtained by following Protocol T: LCMS (ES): M+H 532.1; HPLC retention time=4.25 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)piperazin-1-yl]-2-[4-chloro-5-methyl-3-(2-methylpyridin-4-yl)pyrazol-1-yl]ethanone

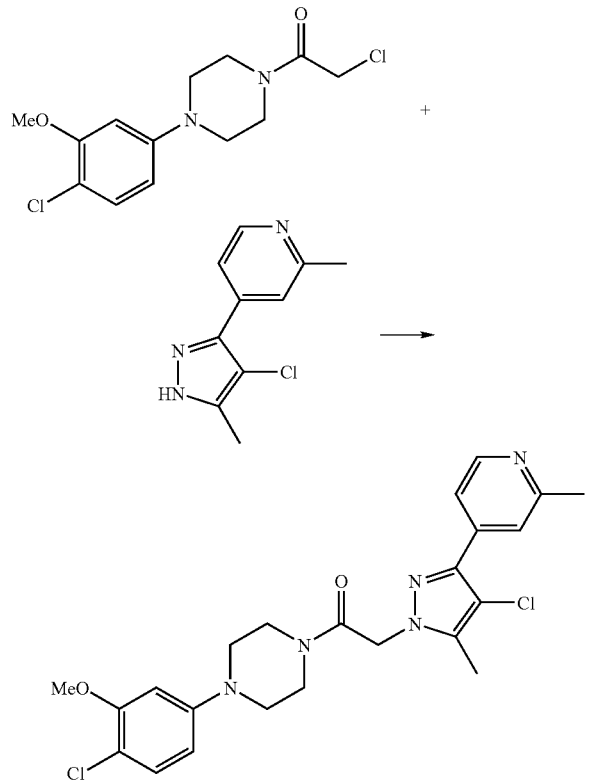

The title compound was obtained by following Protocol T: LCMS (ES): M+H 474.1; HPLC retention time=3.76 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)piperazin-1-yl]-2-[4-chloro-5-methyl-3-(6-trifluoromethylpyridin-2-yl)pyrazol-1-yl]ethanone

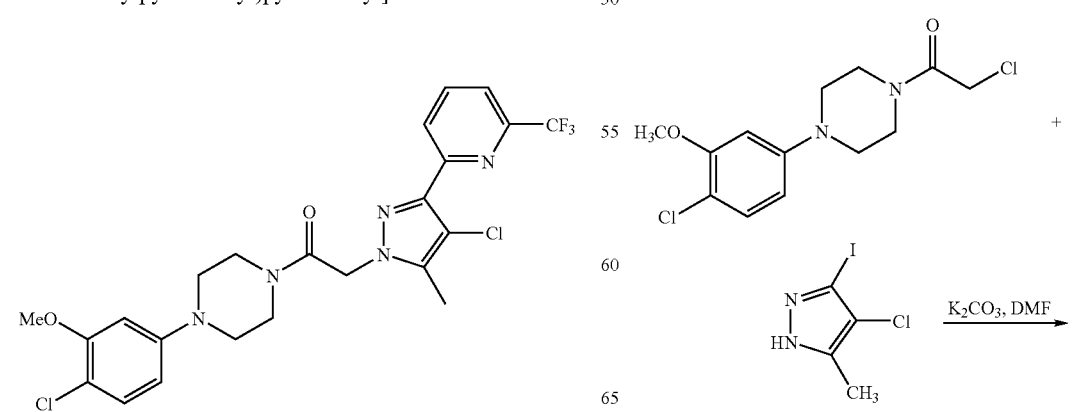

Following Protocol T, 2-(4-Chloro-5-methyl-1H-pyrazol-3-yl)-6-trifluoromethyl-pyridine and 2-Chloro-1-[4-(4-chloro-3-methoxy-phenyl)-piperazin-1-yl]-ethanone were combined to give the title compound: LCMS (ES): M+H 528.1; HPLC retention time=5.36 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-[4-(4-Chloro-2-fluoro-5-methoxy-phenyl)-2-(S)-methyl-piperazin-1-yl]-2-(4-chlor0-5-methyl-3-pyridin-2-yl-pyrazol-1-yl)-ethanone

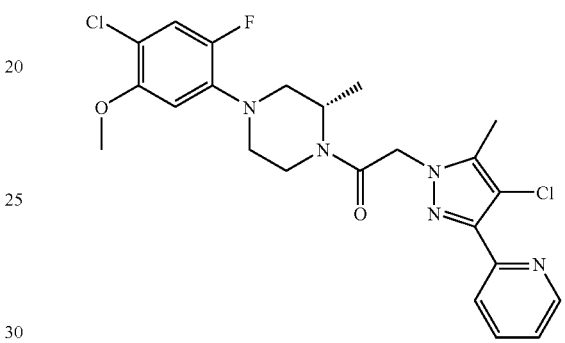

Following Protocol T, 2-Chloro-1-[4-(4-chloro-2-fluoro-5-methoxy-phenyl)-2-(S)-methyl-piperazin-1-yl]-ethanone and 2-(4-Chloro-5-methyl-1H-pyrazol-3-yl)-pyridine were combined to give the title compound: HPLC retention time=6.50 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+= 492.1 (M+H).

Synthesis of 2-(4-Chloro-3-iodo-5-methyl-pyrazol-1-yl)-1-[4-(4-chloro-3-methoxy-phenyl)-piperazin-1-yl]-ethanone

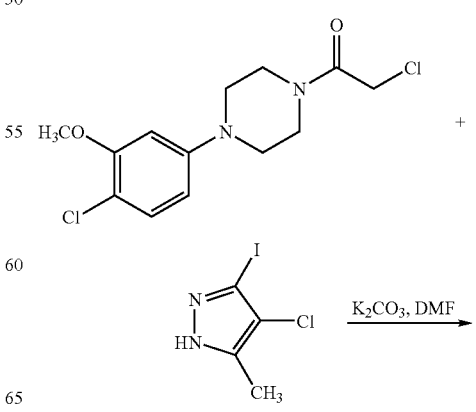

311
-continued

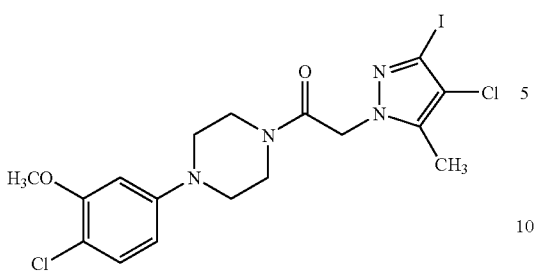

Following Protocol T, 2-(4-Chloro-5-methyl-1H-pyrazol-3-yl)-pyridine and 2-chloro-1-[4-(4-chloro-3-methoxyphenyl)-piperazin-1-yl]-ethanone were treated with potassium carbonate in N,N-dimethylformamide to yield the title compound: LCMS (ES) M+H=509.0; HPLC retention time=4.85 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-5-ethoxy-2-fluorophenyl)piperazin-1-yl]-2-(4-chloro-5-methyl-3-pyridin-2-ylpyrazol-1-yl)ethanone

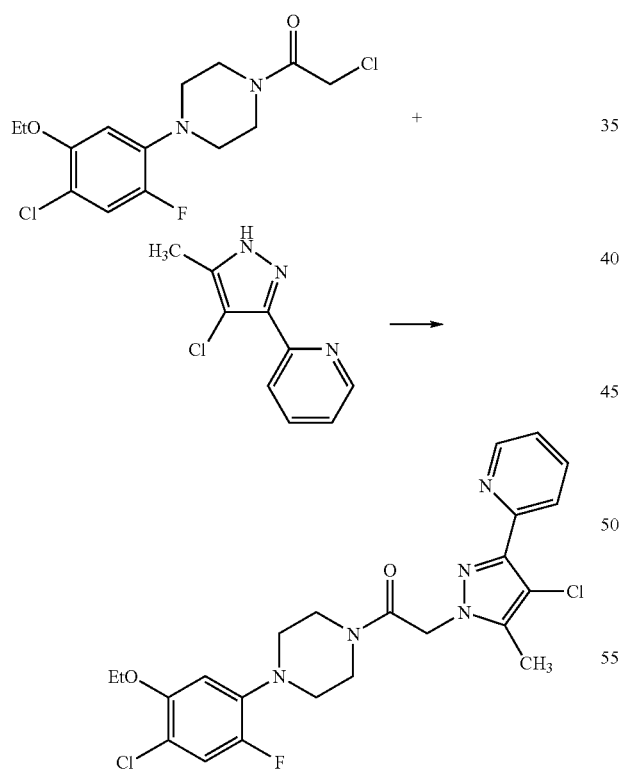

Following Protocol T, 2-(4-Chloro-5-methyl-1H-pyrazol-3-yl)-pyridine and 2-chloro-1-[4-(4-chloro-3-ethoxy-2-fluoro-phenyl)-piperazin-1-yl]-ethanone were treated with potassium carbonate in N,N-dimethylformamide to yield the title compound: $^1$H NMR (400 MHz, CDCl$_3$) δ 8.87-7.12 (m, 3H), 6.47 (d, 3H), 5.11 (s, 2H), 3.8 (q, 2H), 3.21-3.83 (dt, 2H),

312

2.35 (s, 3H). LCMS (ES) M+H=492.1, HPLC retention time=5.469 min (acetonitrile/H$_2$O 20-95% method).

Synthesis of 1-(4-(4-Chloro-3-methoxyphenyl)-piperazin-1-yl)-2-(3-trifluoromethyl)-5-(2-furyl)-pyrazol-1-yl)ethanone

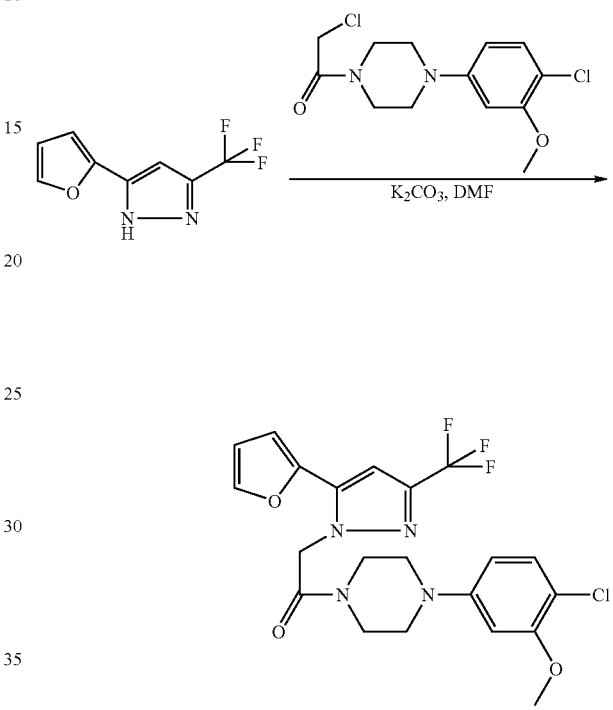

The above compound was synthesized following Protocol T: LCMS M+H=469; HPLC RT=4.81 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); $^1$H NMR (400 MHz, CDCl$_3$) δ 3.14-3.21 (m, 4H), 3.65-3.78 (m, 4H), 3.88 (s, 3H), 5.30 (s, 2H), 6.42 (dd, J=2.4 & 6.7 Hz, 1H), 6.48-6.50 (m, 2H), 6.70 (d, J=3.3 Hz, 1H), 6.75 (s, 1H), 7.21 (s, 1H), 7.46 (d, J=1.8 Hz, 1H).

Synthesis of 2-(4-Chloro-3,5-dipyridin-2-yl-pyrazol-1-yl)-1-(4-(4-chloro-3-methoxyphenyl)-piperazin-1-yl)ethanone

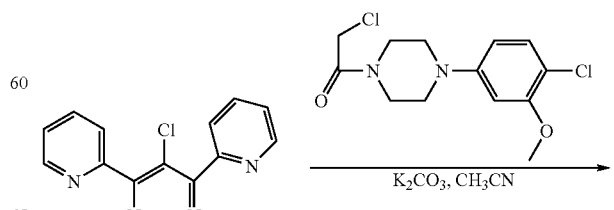

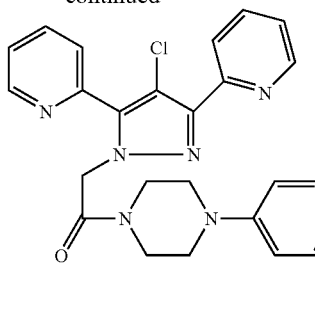

The above compound was synthesized following Protocol T: LCMS M+H=523; HPLC RT=4.29 minutes (Agilent Zorbax SB-C18, 2.1×50 mm, 5μ, 35° C.) using a 4.5 minute gradient of 20% to 95% B with a 1.1 minute wash at 95% B (A=0.1% folinic acid/5% acetonitrile/94.9% water, B=0.08% formic acid/99.9% acetonitrile); $^1$H NMR (400 MHz, DMSO-$d_6$): δ 3.10 (br, 2H), 3.25 (br, 2H), 3.51 (br, 2H), 3.68 (br, 2H), 3.87 (s, 3H), 5.65 (s, 2H), 6.52(dd, J=2.6 & 8.8 Hz, 1H), 6.71 (d, J=2.6 Hz, 1H). 7.23 (d, J=8.8 Hz, 1H) 6.48-6.50 (m, 2H), 6.70 (d, J=3.3 Hz, 1H), 6.75 (s, 1H), 7.21 (s, 1H), 7.46 (d, J=1.8 Hz, 1H), 7.43-7.50 (m, 2H), 7.90-7.94 (m, 2H), 8.01 (dt, J=1.8 & 7.7 Hz, 1H), 8.70-8.73 (m, 2H).

Synthesis of 2-(4-Chloro-3,5-dipyridin-2-yl-pyrazol-1-yl)-1-(4-(4-chloro-2-fluoro-5-methoxyphenyl)-2-(S)-methylpiperazin-1-yl)ethanone

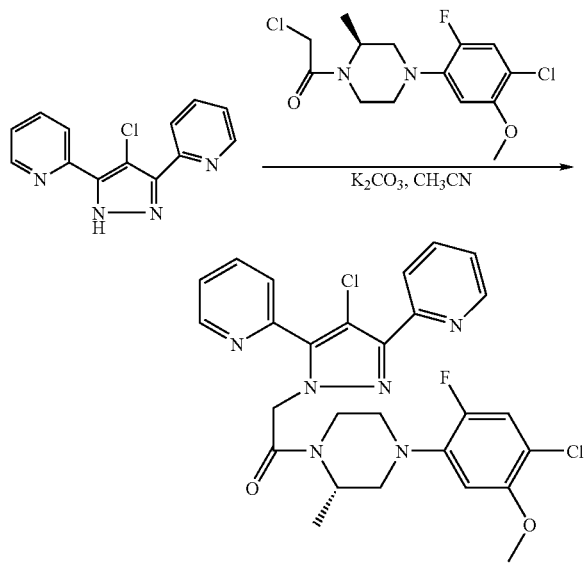

The above compound was synthesized following Protocol T: LCMS M+H=555; HPLC RT=4.77 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); $^1$H NMR (400 MHz, DMSO-$d_6$): δ 1.11 (d, J=6.3 Hz, 1.5H), 1.41 (d, J=6.5 Hz, 1.5H) 3.25 (br, 2H), 2.67-3.01 (m, 3H), 3.43-3.50 (m, 1H), 3.88 (s, 3H), 4.10-4.13 (m, 1H), 4.28 (br, 1H), 4.45(br, 1H), 5.60 (s, 1H), 5.68 (s, 1H), 6.74 (d, J=8 Hz, 1H), 7.38-7.56 (m, 3H), 7.90-7.97 (m, 2H), 8.02 (t, J=7.7 Hz, 1H), 8.71-8.75 (m, 2H).

Synthesis of 1-[4-(4-Chloro-3-ethoxyphenyl)-2-methylpiperazin-1-yl]-2-(4-chloro-5-methyl-3-pyridin-2-ylpyrazol-1-yl)ethanone

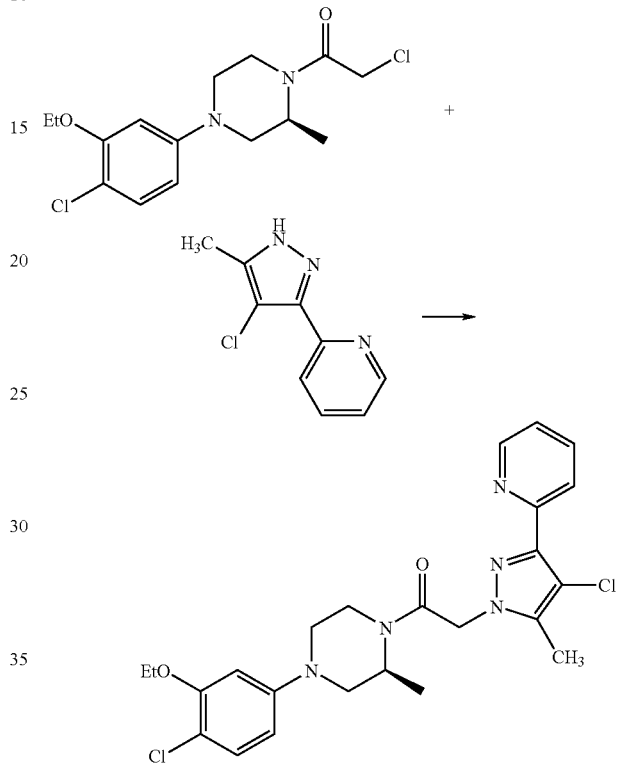

Following Protocol T, 2-(4-Chloro-5-methyl-1H-pyrazol-3-yl)-pyridine and 2-chloro-1-[4-(4-chloro-3-ethoxyphenyl)-2-(S)-methylpiperazin-1-yl]-ethanone were combined to yield the title compound: $^1$H NMR (400 MHz, CDCl$_3$) δ 8.87-7.12 (m, 3H), 6.47 (d, 3H), 5.11 (s, 2H), 3.8 (q, 2H), 3.21-3.83 (dt, 2H), 2.35 (s, 3H), 1.52 (d, 3H); LCMS (ES) M+H=488.1; HPLC RT=5.993 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 6-(4-Chloro-1-{2-[4-(4-chloro-3-ethoxyphenyl)piperazin-1-yl]-2-oxo-ethyl}-5-methyl-1H-pyrazol-3-yl)pyridine-2-carbonitrile

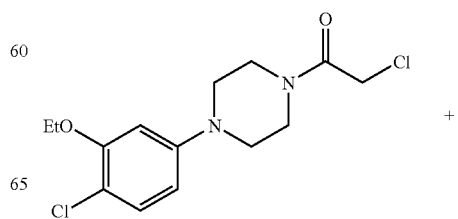

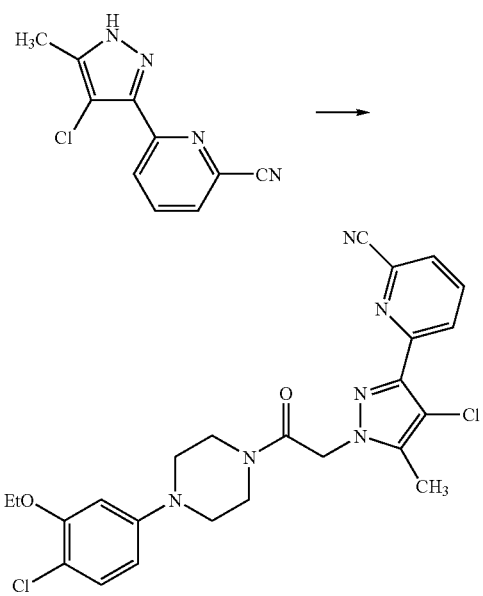

Following Protocol T, 2-(4-Chloro-5-methyl-1H-pyrazol-3-yl)-6-cyanopyridine and 2-chloro-1-[4-(4-chloro-3-ethoxyphenyl)-piperazin-1-yl]-ethanone were treated with potassium carbonate in N,N-dimethylformamide to yield the title compound: $^1$H NMR (400 MHz, CDCl$_3$) δ 8.87-8.92 (m, 3H), 6.57-6.45 (m, 3H), 5.11 (s, 2H), 4.18 (q, 2H), 3.21-3.68 (dt, 4H), 2.45 (s, 3H), 1.52 (t, 3H); LCMS (ES) M+H=499.2; HPLC RT=4.807 min. (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 6-(4-Chloro-1-{2-[4-(4-chloro-3-ethoxyphenyl)-2-(S)-methylpiperazin-1-yl]-2-oxo-ethyl}-5-methyl-1H-pyrazol-3-yl)pyridine-2-carbonitrile

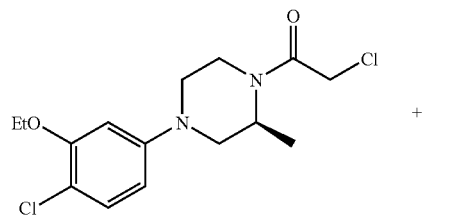

+

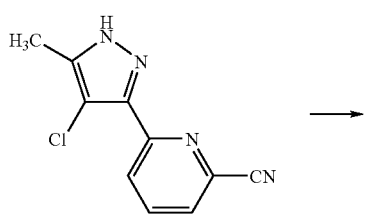

→

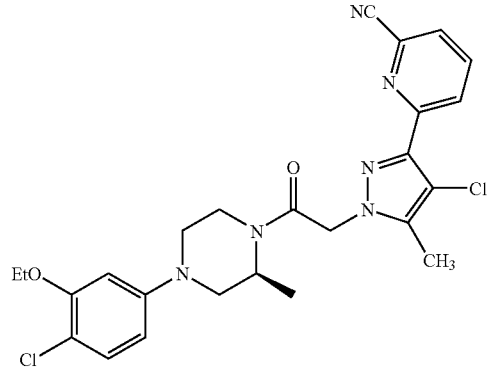

Following Protocol T, 2-(4-Chloro-5-methyl-1H-pyrazol-3-yl)-6-cyanopyridine and 2-chloro-1-[4-(4-chloro-3-ethoxyphenyl)-2-(S)-methylpiperazin-1-yl]-ethanone were treated with potassium carbonate in N,N-dimethylformamide to yield the title compound. $^1$H NMR (400 MHz, CDCl$_3$) δ 8.87-8.92 (m, 3H), 6.57-6.45 (m, 3H), 5.11 (s, 2H), 4.18 (q, 2H), 3.21-3.68 (dt, 4H), 2.45 (s, 3H), 1.52 (d, 3H), 1.40 (q, 1H); LCMS (ES) M+H=513.4; HPLC RT=5.192 min. (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-[4-chloro-1-{2-[4-(4-chloro-3-methoxy-phenyl)-piperazin-1-yl]-2-oxoethyl}-5-methyl-1H-pyrazol-3-yl)-isonicotinic acid ethyl ester

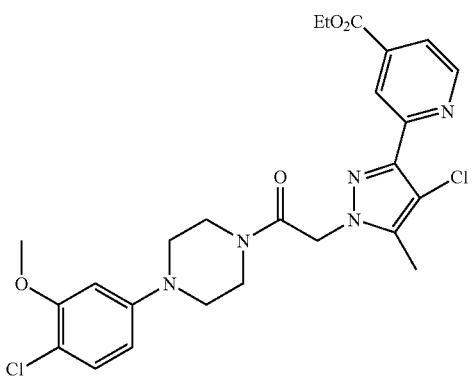

Title compound was prepared following Protocol T: HPLC retention time=5.9 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=532.14, found=532.2.

Synthesis of 2-[4-chloro-3-(6-methanesulfonyl-pyridin-2-yl)-5-methyl-pyrazol-1-yl]-1-[4-(4-chloro-3-methoxyphenyl)-piperazin-1-yl]-ethanone

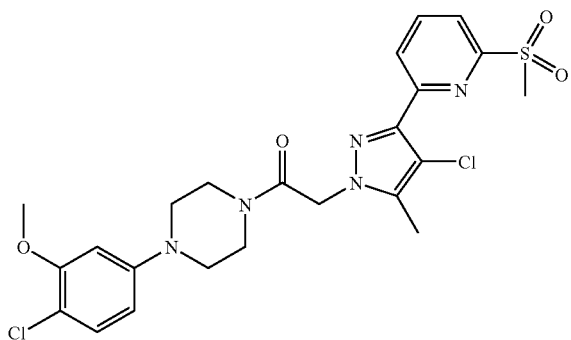

Title compound was prepared following Protocol T: HPLC retention time=5.55 minutes (Agilent Zorbax SB-C18, 2.1× 50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=538.1, found=538.1.

Synthesis of 1-[4-(4-chloro-3-methoxy-phenyl)-piperazin-1-yl]-2-(4-chloro-5-methyl-3-pyrimidin-2-yl-pyrazol-1-yl)-ethanone (Isomer I) and 1-[4-(4-chloro-3-methoxy-phenyl)-piperazin-1-yl]-2-(4-chloro-3-methyl-5-pyrimidin-2-yl-pyrazol-1-yl)-ethanone (Isomer II)

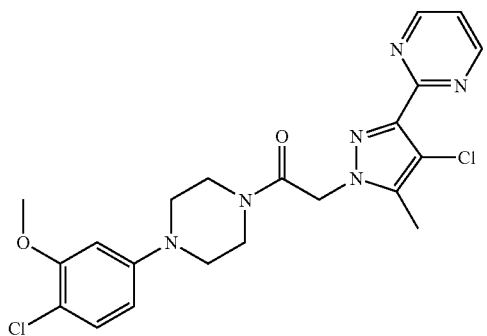

Title compounds were prepared following Protocol T: Isomer I: HPLC retention time=3.8 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile). MS(ES) M+H expect=461.1, found=461.3.

Isomer II: HPLC retention time=4.16 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile). MS (ES) M+H expect=461.1, found=461.3.

Synthesis of 1-[4-(4-chloro-3-ethoxy-phenyl)-piperazin-1-yl]-2-(4-chloro-5-methyl-3-pyrimidin-2-yl-pyrazol-1-yl)-ethanone (Isomer I) and 1-[4-(4-chloro-3-ethoxy-phenyl) -piperazin-1-yl]-2-(4-chloro-3-methyl-5-pyrimidin-2-yl-pyrazol-1-yl)-ethanone (Isomer II)

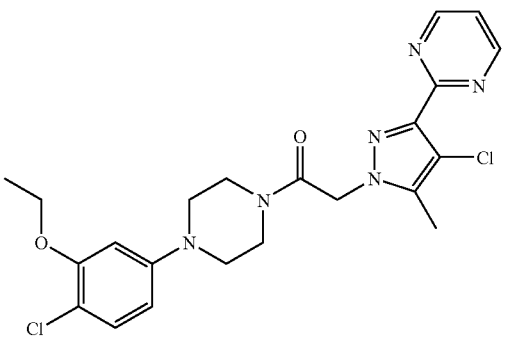

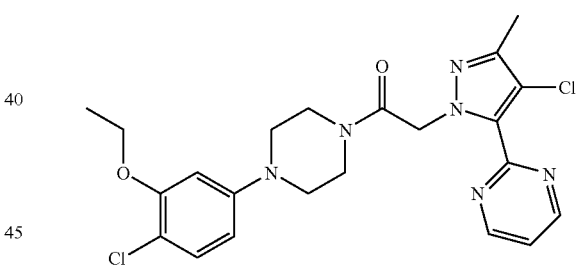

Title compounds were prepared following Protocol T: Isomer I: HPLC retention time=4.09 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS(ES) M+H expect=475.1, found=475.4; $^1$H NMR (CDCl3, 400 MHz) 8.88 (d, 2H), 7.31-7.25 (m, 4H), 6.64(s,1H), 6.52(d, 1H), 5.15 (s, 2H), 4.5-4.3, 4.08 (q, 2H), 3.83 (m, 4H), 3.25-3.19 (m, 4H), 2.37(s, 3H), 1.47 (t, 3H) ppm; NOESY shows co-relationship between α-H (5.1 ppm) and CH3-in pyrazole (2.4 ppm);

Isomer II: HPLC retention time=4.45 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile). MS (ES) M+H expect=475.1, found=475.4; $^1$H NMR (CDCl3, 400 MHz) 1H NMR (CDCl3, 400 MHz) 8.80 (d, 2H), 7.2 (m, 4H), 6.62 (s, 1H), 6.61 (d, 1H), 5.64 (s, 2H), 4.10 (d, 2H), 3.77-3.23

(d,d, 8H), 3.17(d, 4H), 2.34(s, 3H), 1.48 (t, 3H) ppm; NOESY shows no co-relationship between —H (5.64 ppm) and CH3- in pyrazole (2.34 ppm).

Synthesis of 1-[4-(4-chloro-3-ethoxy-phenyl)-2-methyl-piperazin-1-yl]-2-(4-chloro-5-methyl-3-pyrimidin-2-yl-pyrazol-1-yl)-ethanone (Isomer I) and 1-[4-(4-chloro-3-ethoxy-phenyl)-2-mthyl-piperazin-1-yl]-2-(4-chloro-3-methyl-5-pyrimidin-2-yl-pyrazol-1-yl)-ethanone (Isomer II)

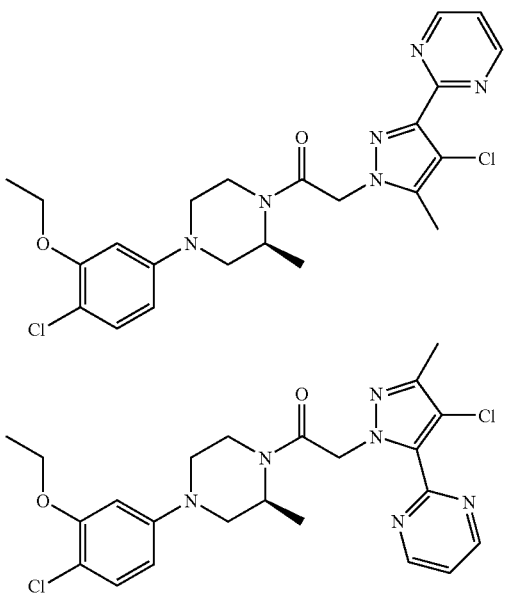

Title compounds were prepared following Protocol T: Isomer I: HPLC retention time=4.35 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile). MS(ES) M+H expect=489.2, found=489.4.

Isomer II: HPLC retention time=4.71 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile). MS (ES) M+H expect=461.1, found=489.4.

Synthesis of 1-[4-(4-chloro-1-{2-[4-(4-chloro-3-ethoxy-phenyl)-piperazin-1-yl]-2-oxo-ethyl}-5-methyl-1H-pyrazol-3-yl)-pyrimidine-2-carbonitrile

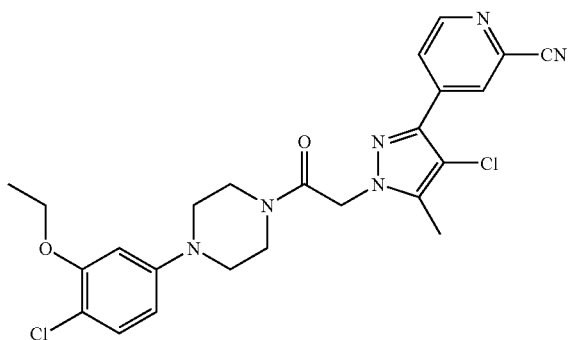

Title compound was prepared following Protocol T: HPLC retention time=4.94 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile). MS (ES) M+H expect=499.1, found=499.4.

Synthesis of 2-[4-chloro-3(1-hydroxy-1-methyl-ethyl)-5-methyl-pyrazol-1-yl]-1-[4-(3-methoxy-4-chloro-phenyl)-piperazin-1-yl]-ethanone (Isomer I) and 2-[4-chloro-5(1-hydroxy-1-methyl-ethyl)-3-methyl-pyrazol-1-yl]-1-[4-(3-methoxy-4-chloro-phenyl)-piperazin-1-yl]-ethanone (Isomer II)

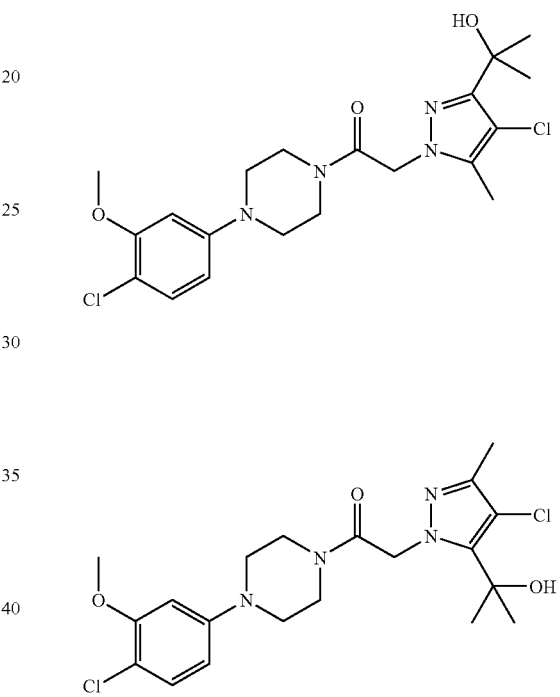

Following protocol T, 2-Chloro-1-[4-(4-chloro-3-methoxy-phenyl)-piperazin-1-yl]-ethanone and 2-(4-Chloro-5-methyl-1H-pyrazol-3-yl)-propan-2-ol were combined to give the title compounds. Isomer I: HPLC retention time=5.34 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=441.1, found=423.1(—H2O); $^1$H NMR (CDCl3, 400 MHz) 7.63 (s, 3H), 7.32(d 1H), 6.80(s, 1H), 6.65 (d 1H), 5.04 (s, 2H), 3.89 (m, 3H), 3.93-3.85 (Par. Obsc.m, 4H), 3.38 (t, 2H), 3.30 (t, 2H), 2.27(s, 2H), 1.63 (s, 6H) ppm; NOESY shows co-relationship between α-H (5.0 ppm) and CH3- in pyrazole (2.2 ppm).

Isomer II: HPLC retention time=5.5 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=441.1, found=423.1(—H2O); $^1$H NMR (CDCl3, 400 MHz) 9.6 (s, 1H), 7.25(d, 1H), 6.5 (s 1H), 6.45(d, 1H), 4.86 (s, 2H), 3.88 (s, 3H), 3.38 (m, 8H), 2.24(s, 3H), 1.82 (s, 6H) ppm;

NOESY shows no co-relationship between α-H (4.86 ppm) and CH3- in pyrazole (2.24 ppm).

Synthesis of 2-[4-chloro-3-isopropyl-5-methyl pyrazol-1-yl]-1-[4-(4-chloro-3-methoxy-phenyl)-piperazin-1-yl]ethanone

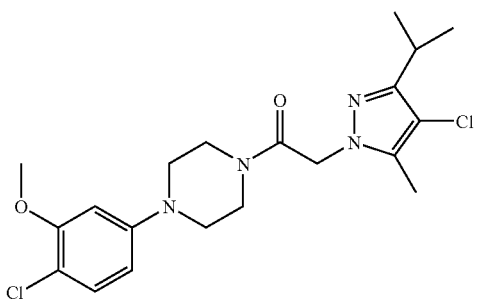

Title compound was prepared following Protocol T: HPLC retention time=6.0 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=425.1, found=425.1.

Synthesis of 1-4-(4-chloro-3-methoxyphenyl)-piperazin-1-yl)-2-(3,5-dipyridin-2-yl-pyrazol-1-yl)ethanone

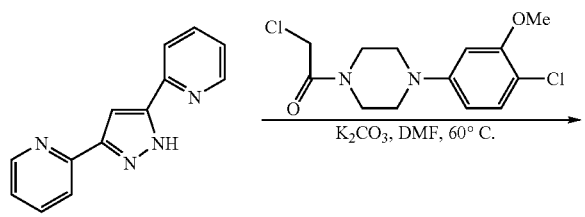

Following Protocol T, the title compound was prepared: LC MS 489 (M+, 20-95 method, RT=3.79 min); $^1$H NMR (400 MHz, CDCl$_3$): δ 3.13 (bs, 2H), 3.25 (bs, 2H), 3.74 (bs, 4H), 3.88 (s, 3H), 5.82 (s, 2H), 6.43 (dd, J=2.6 & 8.5 Hz, 1H), 6.48 (d, J=2.4 Hz, 1H), 7.17-7.24 (m, 3H), 7.37 (d, J=1.1 Hz, 1H), 7.68-7.76 (m, 3H), 7.97 (dd, J=0.7 & 7.3 Hz, 1H), 8.49-8.52 (m, 1H), 8.60-8.62 (m, 1H).

Synthesis of 6-(4-Chloro-1-{2-[4-(4-chloro-5-ethoxy-2-fluorophenyl)piperazin-1-yl]-2-oxo-ethyl}-5-methyl-1H-pyrazol-3-yl)pyridine-2-carbonitrile

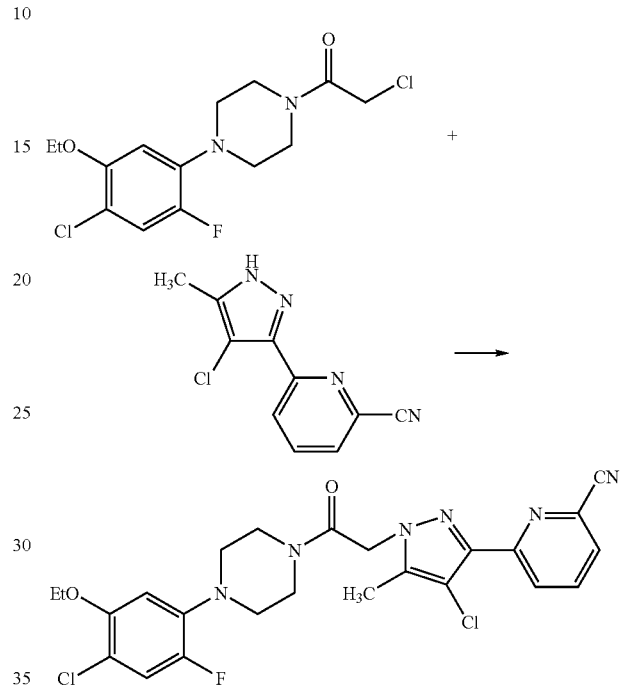

Following Protocol T, 2-(4-Chloro-5-methyl-1H-pyrazol-3-yl)-6-cyanopyridine and 2-chloro-1-[4-(4-chloro-3-ethoxy-2-fluorophenyl)-piperazin-1-yl]-ethanone were combined to yield the title compound: $^1$H NMR (400 MHz, CDCl$_3$) δ 8.87-8.92 (m, 3H), 6.02-6.95 (s, 2H), 5.11 (s, 2H), 4.18 (q, 2H), 3.21-3.68 (dt, 4H), 2.45 (s, 3H), 1.52 (t, 3H). LCMS (ES) M+H=517.4, RT=5.130 min (acetonitrile/H$_2$O 20-95% method).

Synthesis of 1-{2-[4-(4-Chloro-3-methoxy-phenyl)-2-methyl-piperazin-1-yl]-2-oxo-ethyl}-5-methyl-3-(5-methyl-isoxazol-3-yl)-1H-pyrazole-4-carboxylic acid ethyl ester

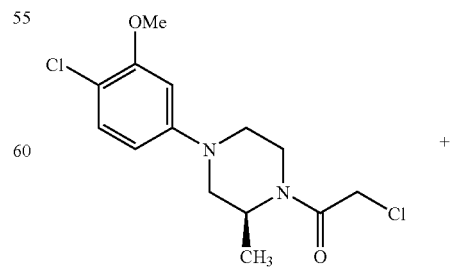

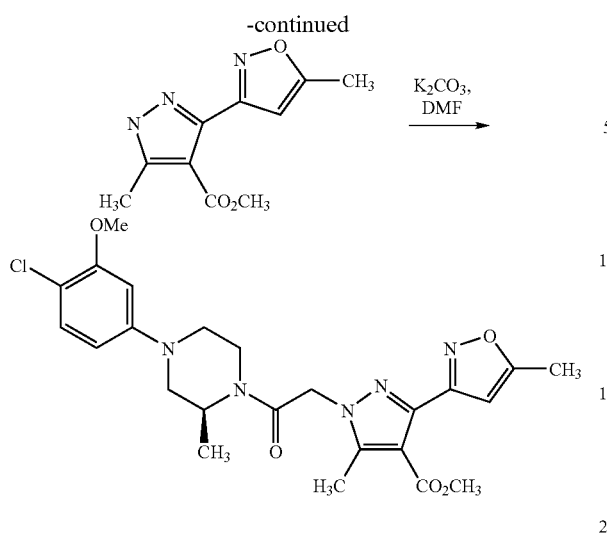

Following Protocol T, 5-Methyl-3-(5-methyl-isoxazol-3-yl)-1H-pyrazole-4-carboxylic acid ethyl ester and 2-Chloro-1-[4-(4-chloro-3-methoxy-phenyl)-2-(S)-methyl-piperazin-1-yl]-ethanone were combined to give the title compound: MS (M+H$^+$): 488.2; HPLC retention time=5.21 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(3-Bromoindazol-1-yl)-1-(4-(4-chloro-3-methoxyphenyl)-piperazin-1-yl)ethanone

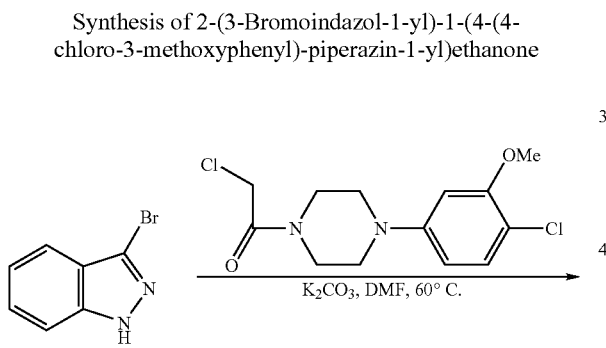

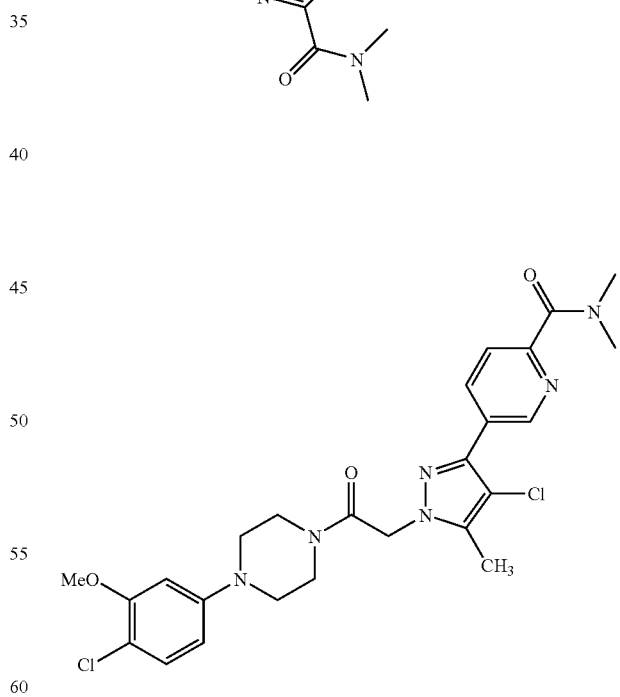

Following Protocol T, the title compound was prepared: LCMS M+H=464; HPLC RT=4.73 min. (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); $^1$H NMR (400 MHz, CDCl$_3$): δ 3.07 (apparent q, J=4.4 Hz, 4H), 3.75 (apparent q, J=4.4 Hz, 4H), 3.87 (s, 3H), 5.23 (s, 2H), 6.37 (dd, J=1.4 & 8.4 Hz, 1H), 6.48 (d, J=1.8 Hz, 1H), 7.18-7.24 (m, 2H), 7.42-7.45 (m, 2H), 7.59 (d, J=8.0 Hz, 1H).

5-(4-Chloro-1-{2-[4-(4-chloro-3-methoxy-phenyl)-piperazin-1-yl]-2-oxo-ethyl}-5-methyl-1H-pyrazol-3-yl)-pyridine-2-carboxylic acid dimethylamide

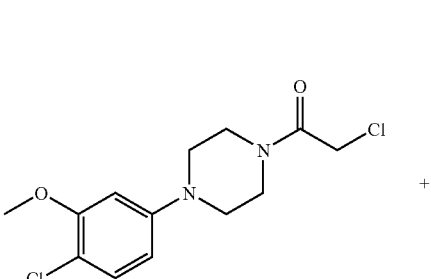

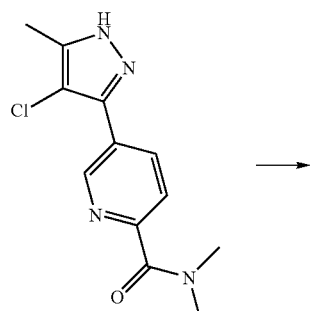

The title compound was made by following Protocol T: $^1$H NMR (400 MHz, CDCl$_3$) δ δ 9.21-8.12 (m, 3H), 6.47 (m, 3H), 4.48 (s, 2H), 3.8 (q, 2H), 3.89 (s, 1H), 3.79-3.32 (dt, 2H), 2.35 (s, 3H), 2.18 (s, 3H); LCMS (ES) M+H=532.4; HPLC RT=4.483 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

5-(4-Chloro-1-{2-[4-(4-chloro-3-methoxy-phenyl)-2-methyl-piperazin-1-yl]-2-oxo-ethyl}-5-methyl-1H-pyrazol-3-yl)-pyridine-2-carboxylic acid dimethylamide

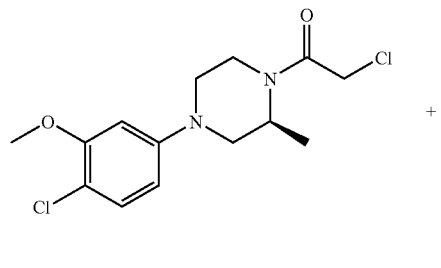

+

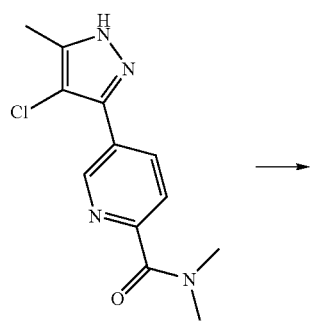

→

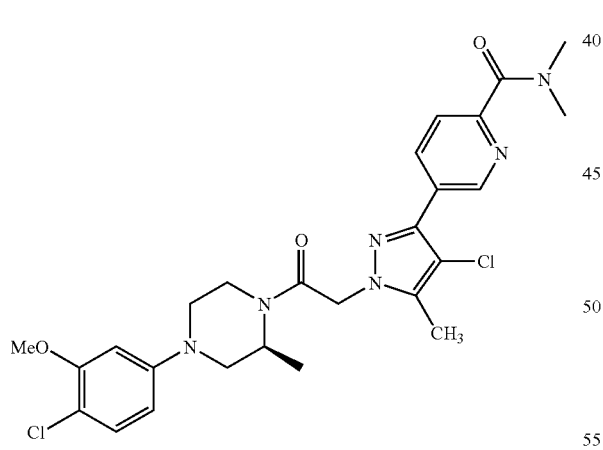

The title compound was made by following Protocol T: NMR (400 MHz, CDCl$_3$) δ δ 9.21-8.12 (m, 3H), 6.47 (m, 3H), 4.64 (s, 2H), 3.81 (q, 2H), 3.89 (s, 1H), 3.89 (d, 2H), 3.79-3.32 (dt, 2H), 2.35 (s, 3H), 2.18 (s, 3H); LCMS (ES) M+H=546.5; HPLC RT=6.887 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-2-methyl-piperazin-1-yl]-2-(4-chloro-5-methyl-3-pyridin-2-yl-pyrazol-1-yl)-ethanone

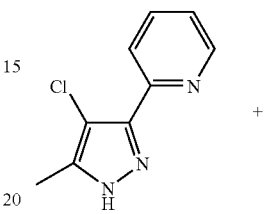

+

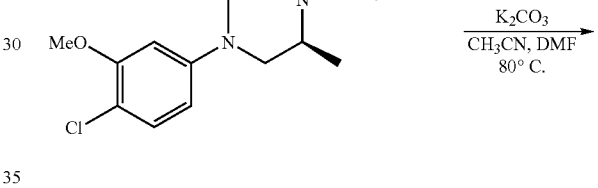

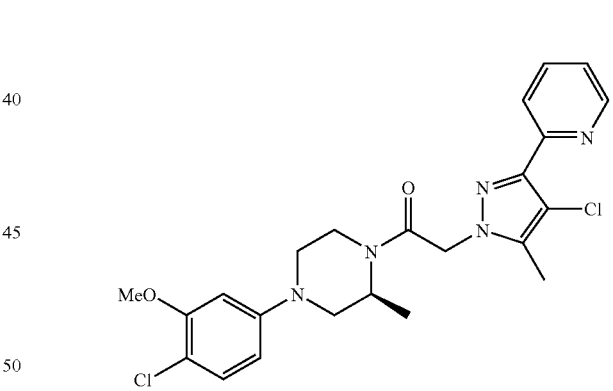

A mixture of 4-chloro-5-methyl-3-pyridylpyrazol (3.61 g, 18.7 mmol), phenylpiperazine-carbonylmethylchloride (5.75 g, 19.0 mmol) and K$_2$CO$_3$ (27.6 g, 200 mmol) in CH$_3$CN (50 mL) and DMF (5 mL) was heated to 80° C. for 2 hr. The mixture was filtered and evaporated in vacuo. The remaining residue of DMF was further removed by high vacuum overnight. Recrystallization in hot ethanol afforded the title compound as a white solid. The solid was dissolved in ethanol (200 mL) and hydrogen chloride in ether (2.0 M, 400 mL) was added slowly with stirring. The resulting precipitate was filtered to afford the title compound as a white solid. $^1$H NMR: δ (400 MHz, d-DMSO) major rotamer: 8.69 (br d, 1H), 8.15 (br, 1H), 8.07 (br d, 1H), 7.59 (br, d, 1H), 7.20 (d, 1H), 6.64 (br, 1H), 6.41 (br d, 1H), 5.55-5.18 (br m, 2H), 3.83 (s, 3H), 3.74-3.48 (br m, 4H), 3.18-2.59 (br m, 3H), 2.22 (s, 3H), 1.42-1.16 (br m, 3H). MS (M+H⁺): 474.1

1-[4-(4-Chloro-3-methoxy-phenyl)-2-(S)-methyl-piperazin-1-yl]-2-(4-chloro-5-methyl-3-pyridin-3-yl-pyrazol-1-yl)-ethanone

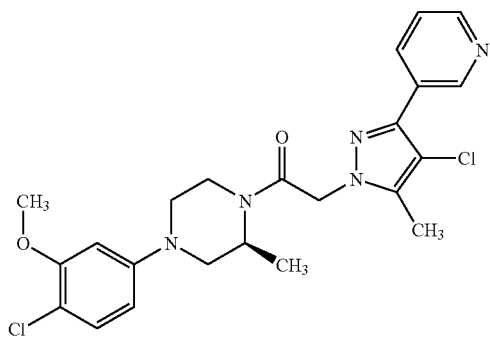

Following Protocol T, 3-(4-Chloro-5-methyl-1H-pyrazol-3-yl)-pyridine and 2-Chloro-1-[4-(4-chloro-3-methoxy-phenyl)-2-(S)-methyl-piperazin-1-yl]-ethanone were treated with potassium carbonate in N,N-dimethylformamide to give title compound: MS (M+H⁺): 474.1; HPLC retention time=3.96 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile);

1-[4-(4-Chloro-3-methoxy-phenyl)-piperazin-1-yl]-2-(4-chloro-5-methyl-3-pyridin-3-yl-pyrazol-1-yl)-ethanone

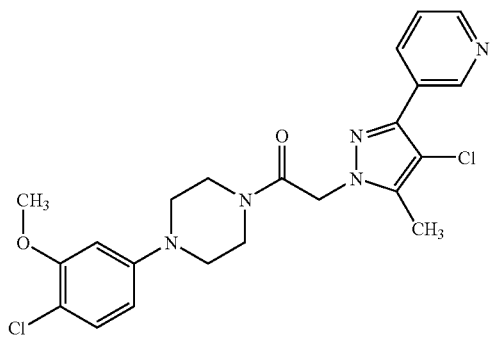

Following Protocol T, 3-(4-Chloro-5-methyl-1H-pyrazol-3-yl)-pyridine and 2-Chloro-1-[4-(4-chloro-3-methoxy-phenyl)-piperazin-1-yl]-ethanone were treated with potassium carbonate in N,N-dimethylformamide to give title compound: MS (M+H⁺): 460.1; HPLC retention time=3.59 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Protocol V: Preparation of Compounds Via Acid or Base-Mediated De-Protections

4-Chloro-1-{2-[4-(4-chloro-3-methoxy-phenyl)-piperazin-1-yl]-2-oxo-ethyl}-5-methyl-1H-pyrazole-3-carboxylic acid

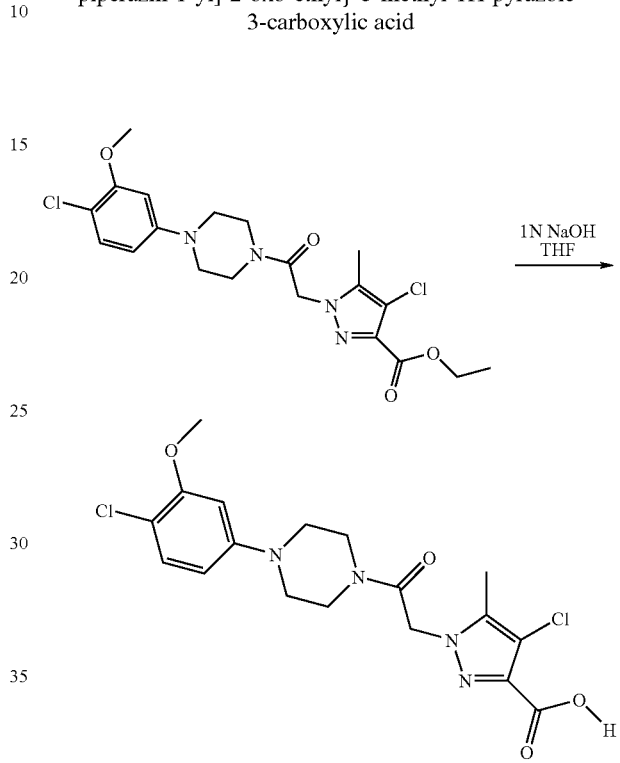

4-Chloro-1-{2-[4-(4-chloro-3-methoxy-phenyl)-piperazin-1-yl]-2-oxo-ethyl}-5-methyl-1H-pyrazole-3-carboxylic acid ethyl ester (100 mg) was dissolved in THF (7 ml) and 5 mL of 1N NaOH was added to the solution and the reaction mixture was stirred overnight. It was then acidified with 1N HCl and was the extracted with ethyl acetate. It was then dried and solvent removed to get a clean product: 1H NMR (CDCl3, 400 MHz) 7.18-7.22 (d, 1H), 6.74-6.76 (d, 1H), 6.54-6.58 (dd, 2H), 5.3 (s, 2H), 3.88 (s, 3H), 3.68-3.82 (m, 4H), 3.22-3.38 (m, 4H), 2.24 (s, 3H) ppm. MS (ES)M+H expected=427, found=427.

6-(4-Chloro-5-methyl-1H-pyrazol-3-yl)-pyridine-2-carboxylic acid amide

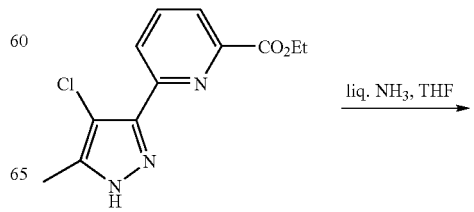

liq. NH₃, THF

329

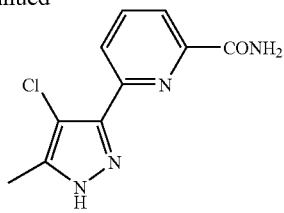

To Ethyl 6-(4-Chloro-5-methyl-1H-pyrazol-3-yl)-pyridine-2-carboxylate (1.0 gm, 0.78 mmol) in 10 mL of dry THF was added 10 mL of liquid ammonia. It was then heated to 60° C. for next 6 h, in which time the reaction was over and the solid product precipitated. The reaction was cooled and THF was rotavaped off to generate 0.5 gm of the title compound.

6-(4-Chloro-5-methyl-1H-pyrazol-3-yl)-pyridine-2-carbonitrile

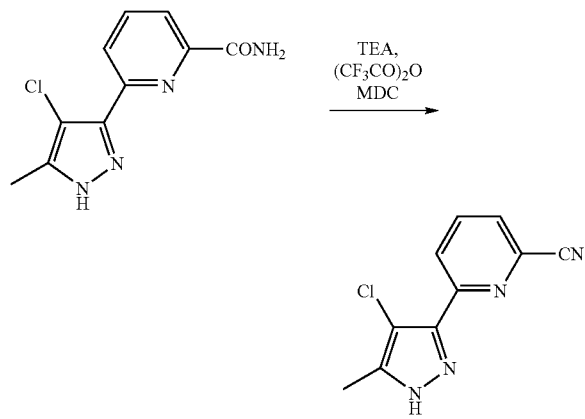

6-(4-Chloro-5-methyl-1H-pyrazol-3-yl)-pyridine-2-carboxylic acid amide (0.15 gm, 0.63 mmol) was dissolved in 5 mL of dry CH₂Cl₂, and 1 mL of TEA (7.29 mmol) was added to it. It was then cooled to 0° C. and was treated with (CF₃CO)₂O (0.2 ml, 0.952 mmol). The reaction mixture was slowly warmed to ambient temperature, and was then stirred for another 4 hours. The mixture was washed once each with 10% NaHCO₃, 5% citric acid, and finally with saturated brine. The methylene chloride phase was concentrated, and the residue was purified by chromatography to give the title compound.

6-(4-Chloro-5-methyl-1H-pyrazol-3-yl)-pyridine-2-carboxylic acid

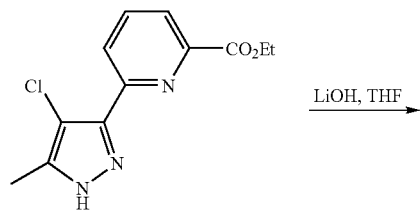

330

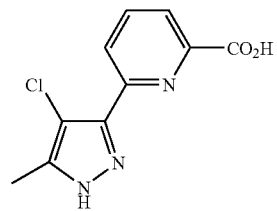

Ethyl 6-(4-Chloro-5-methyl-1H-pyrazol-3-yl)-pyridine-2-carboxylate (0.23 gm, 0.78 mmol) was dissolved in 5 mL of dry THF and 5 mL of water, and LiOH (0.3 gm) was added to it. After 6 hours, the THF was rotavaped off, and the residue was then acidified with citric acid. The resultant solids were isolated to give the title compound.

Protocol W: Preparation of Compounds Via Borohydride-Mediated Reductive Alkylation 1-(4-Chloro-3-methoxybenzyl)piperazine

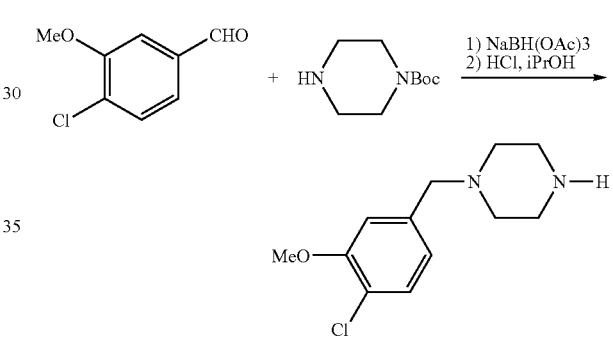

The title compound was obtained by following Protocol W, using 4-chloro-3-methoxybenzaldehyde and 1-Boc-piperazine, followed by N-Boc cleavage with HCl in isopropanol.

4-(4-Chloro-3-methoxy-phenyl)-2-formyl-piperazine-1-carboxylic acid tert-butyl ester

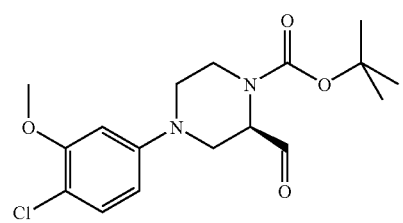

500 mg (1.40 mmol) of 4-(4-Chloro-3-methoxy-phenyl)-2-hydroxymethyl-piperazine-1-carboxylic acid tert-butyl ester was dissolved in 5 mL of dichloromethane, the solution was cooled to 0° C., and 7.3 mL (1.82 mmol) of 0.25M Des-Martin periodinane in dichloromethane was added slowly. After 2 hours, the mixture was washed with sat.

4-(4-Chloro-3-methoxy-phenyl)-2-pyrrolidin-1-ylmethyl-piperazine-1-carboxylic acid tert-butyl ester

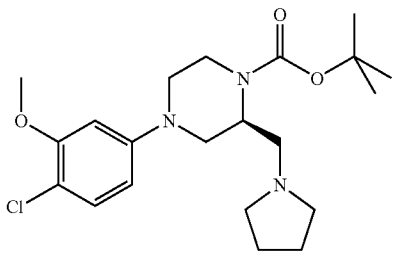

To approximately 0.28 mmol of 4-(4-Chloro-3-methoxy-phenyl)-2-formyl-piperazine-1-carboxylic acid tert-butyl ester in 2.4 mL of dichloromethane was added 0.5 mL methanol, 0.1 mL (1.1 mmol) of pyrrolidine, and 35 mg (0.56 mmol) of sodium cyanoborohydride. After 4 hours, the reaction was quenched with 50 microliters of acetic acid. One hour later, the mixture was washed with sat. sodium bicarbonate, brine, dried over sodium sulfate, and concentrated to a residue.

4-(4-Chloro-3-methoxy-phenyl)-2-morpholin-4-ylmethyl-piperazine-1-carboxylic acid tert-butyl ester

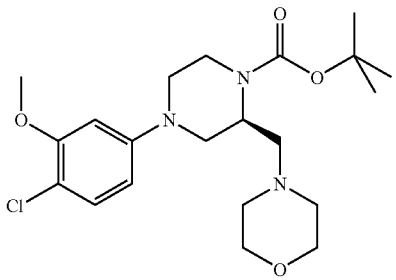

To approximately 0.28 mmol of 4-(4-Chloro-3-methoxy-phenyl)-2-formyl-piperazine-1-carboxylic acid tert-butyl ester in 2.4 mL of dichloromethane was added 0.5 mL methanol, 0.1 mL (1.1 mmol) of morpholine, and 35 mg (0.56 mmol) of sodium cyanoborohydride. After 4 hours, the reaction was quenched with 50 microliters of acetic acid. One hour later, the mixture was washed with sat. sodium bicarbonate, brine, dried over sodium sulfate, and concentrated to a residue.

4-(4-Chloro-3-methoxy-phenyl)-2-(4-methyl-piperazin-1-ylmethyl)-piperazine-1-carboxylic acid tert-butyl ester

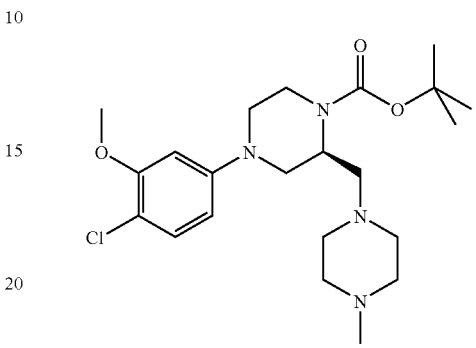

To approximately 0.28 mmol of 4-(4-Chloro-3-methoxy-phenyl)-2-formyl-piperazine-1-carboxylic acid tert-butyl ester in 2.4 mL of dichloromethane was added 0.5 mL methanol, 0.12 mL (1.1 mmol) of 1-methylpiperazine, and 35 mg (0.56 mmol) of sodium cyanoborohydride. After 4 hours, the reaction was quenched with 50 microliters of acetic acid. One hour later, the mixture was washed with sat. sodium bicarbonate, brine, dried over sodium sulfate, and concentrated to a residue.

Protocol X: Preparation of Compounds Via Acylation or Sulfonylation

N-(4-Chloro-1-{2-[4-(4-chloro-3-methoxy-phenyl)-piperazin-1-yl]-2-oxo-ethyl}-5-methyl-1H-pyrazol-3-yl)-methanesulfonamide

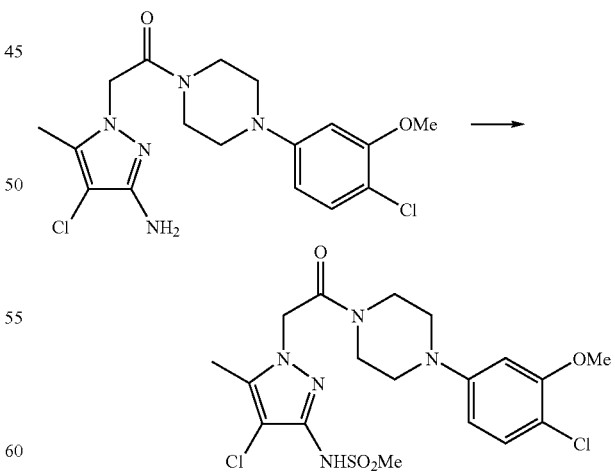

To 2-(3-Amino-4-chloro-5-methyl-pyrazol-1-yl)-1-[4-(4-chloro-3-methoxy-phenyl)-piperazin-1-yl]-ethanone (1.0 g) in dichloromethane (20 ml) was added triethylamine (0.7 ml) and MeSO$_2$Cl (0.19 ml), and the mixture was stirred for 5 hours at 0° C. The disulfonated compound formed was dissolved in methanol (10 ml) and NaOH (0.42 g in 5-mL water) was added and stirred at 60° C. for 2 hours. The methanol was removed under vacuum, water was added, and the pH was adjusted to acidic using citric acid. The solid compound was filtered and purified by chromatography to give the title compound Synthesis of
3-methyl-4-acetylamino-5(trifluoromethyl)pyrazole

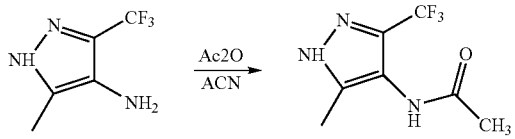

To 3-methyl-4-amino-5(trifluoromethyl)pyrazole (165 mg, 1 mmol) dissolved in ACN was added 0.1 mL acetic anhydride. A precipitate was formed after addition, and was isolated by filtration to give the title compound: HPLC retention time=0.36 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=208.1, found=208.2.

Protocol Y: Preparation of Compounds Via Alkylation

Synthesis of 2-(4-Chloro-5-methyl-1H-pyrazol-3-yl)-propan-2-ol

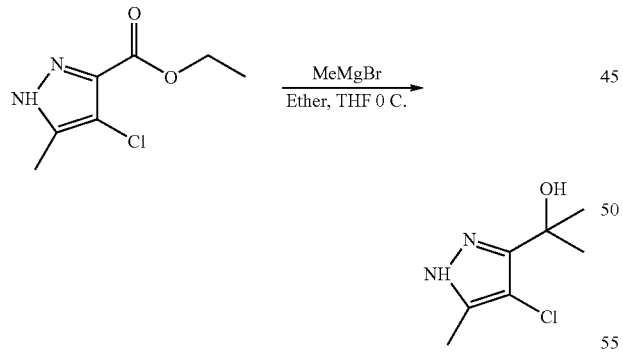

4-Chloro-5-methyl-1H-pyrazole-3-carboxylic acid ethyl ester (0.14 g, 0.8 mmol) was dissolved in 6 mL anhydrous THF, cooled to 0° C., and 3 mL (9.0 mmol) of 3M MeMgBr in ethyl ether was added drop wise. The reaction was then removed from the ice-bath, and was stirred at ambient temperature for one hour. The reaction mixture was poured into 1M phosphate buffer (pH=7), and the mixture was extracted with EtOAc. The phases were separated, and the ethyl acetate layer was washed with brine, dried over anhydrous sodium sulfate, and concentrated to afford the title compound: MS (ES) M-OH expect=157.1, found=157.1; $^1$H NMR (CDCL$_3$, 400 MHz) δ 2.25 (s, 3H), 1.64 (s, 6H) ppm.

Synthesis of
4-Chloro-3-isopropyl-5-methyl-1H-pyrazole

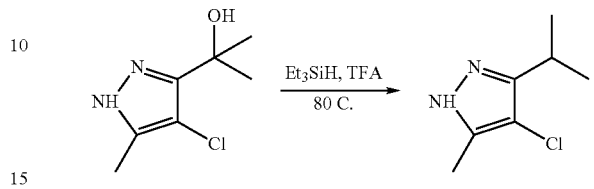

2-(4-Chloro-5-methyl-1H-pyrazol-3-yl)-propan-2-ol (52 mg, 0.3 mmol), 2 mL DCM, 1 mL triethylsilane and 0.1 mL TFA were added together and stirred at 80° C. overnight, then the solvent was removed in vacuo. The residue was dissolved in ethyl acetate, washed with saturated NaHCO$_3$, brine, dried over anhydrous sodium sulfate, and concentrated to afford the title compound. HPLC retention time=4.9 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=159.1, found=159.1.

Protocol AA: Synthesis of Tri-Substituted Pyrazoles Via Suzuki Coupling

2-[4-Chloro-3-(5-fluoro-2-methoxy-pyridin-4-yl)-5-methyl-pyrazol-1-yl]-1-[4-(4-chloro-3-methoxy-phenyl)-piperazin-1-yl]-ethanone

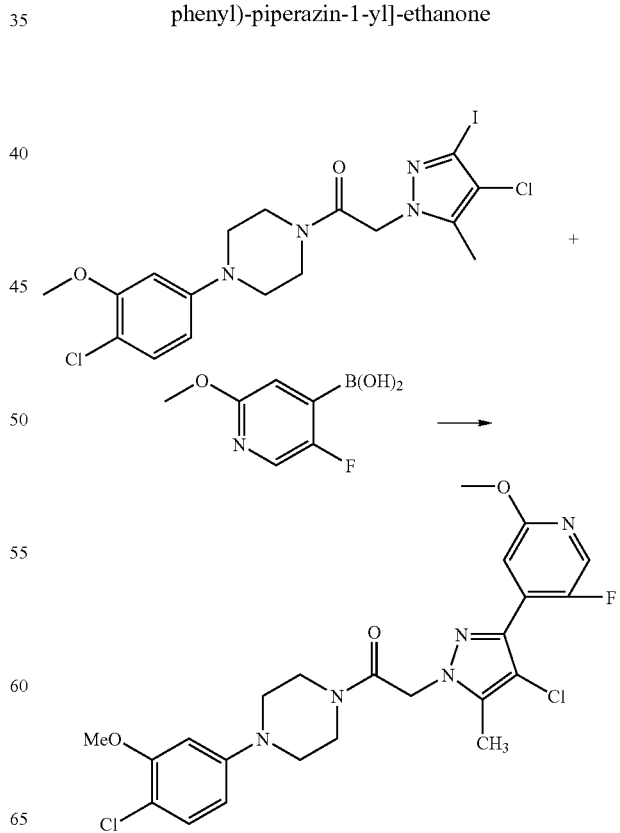

The title compound was made by following Protocol AA: LCMS (ES) M+H=509.3; HPLC RT=4.714 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-[4-Chloro-3-(3-methoxy-phenyl)-5-methyl-pyrazol-1-yl]-1-[4-(4-chloro-3-methoxy-phenyl)-piperazin-1-yl]-ethanone

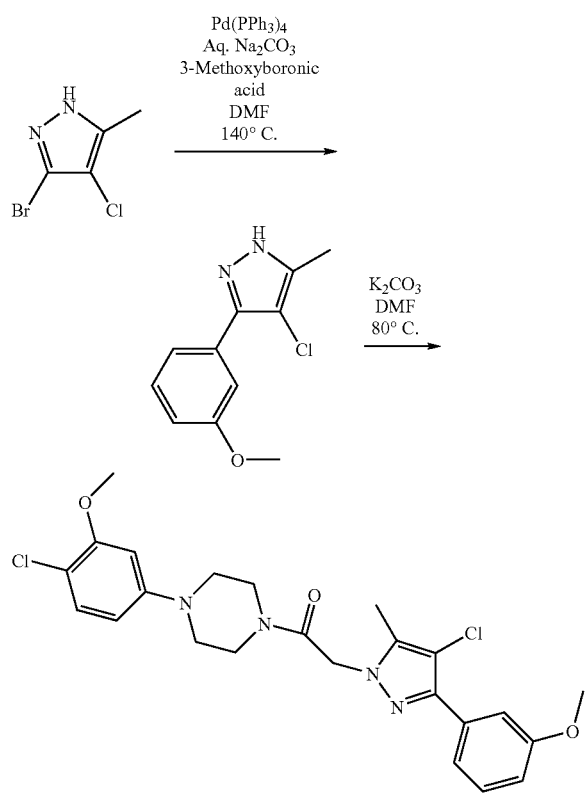

Step 1: 3-Methyl-4-chloro-5-bromopyrazol (222.5 mg) was dissolved in DMF (10 ml). To the mixture was added Pd(PPh₃)4 (44.6 mg), aq. Na₂CO₃ (306.16 in 2 mL of H₂O) and finally 3-methoxyphenylboronic acid (190 mg). The reaction mixture was heated in an oil bath at about 140° C. for 14 h. Once the starting material is all consumed it was then cooled and then the solid residue was filtered off. etOAc was added to the reaction mixture and was then washed with water to remove the DMF. The organic layer was then dried and solvent removed to get the crude product.

Step 2: The product was then dissolved in DMF (7 ml) and was treated with K₂CO₃ (123.2 mg) and 2-Chloro-1-[4-(4-chloro-3-methoxy-phenyl)-piperazin-1-yl]-ethanone A (278 mg). It was then heated at about 80° C. for 16 h and then cooled, quenched with water and extracted with ethyl acetate. The solvent was removed and the crude product was purified by chromatography to give the title compound: $R_f$: 0.7; ¹H NMR (CDCl₃, 400 MHz) 7.4-7.48 (2H, m), 7.28-7.34 (t, 1H), 7.2-7.22 (d, 1H), 6.86-6.91 (m, 1H), 6.4-6.48 (m, 2H), 5.0 (2H, s), 3.84 (s, 3H), 3.82 (s, 3H), 3.72-3.8 (m, 4H), 3.12-3.18 (m, 4H), 2.3 (s, 3H) ppm. ¹³CNMR (400 MHz, CDCl₃) δ 161, 160, 158, 152, 148, 140, 134, 130, 128, 120, 112, 111.5, 110, 109, 100, 58, 56, 54, 50.2, 50, 46, 42, 10.

2-(4-Chloro-3-furan-2-yl-5-methyl-pyrazol-1-yl)-1-[4-(4-chloro-3-methoxy-phenyl)-2-(S)-methyl-piperazin-1-yl]-ethanone

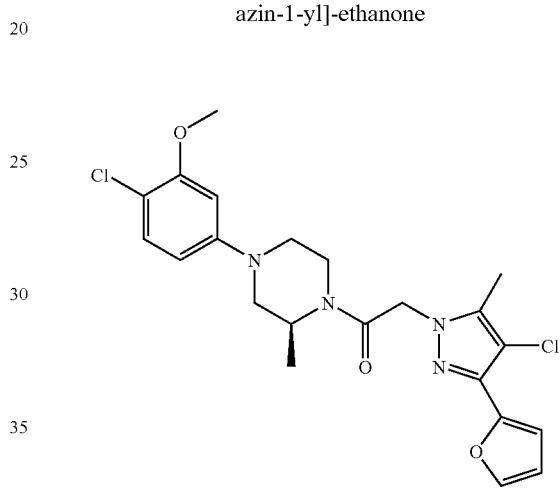

Following Protocol AA, 2-(3-Bromo-4-chloro-5-methyl-pyrazol-1-yl)-1-[4-(4-chloro-3-methoxy-phenyl)-2-(S)-methyl-piperazin-1-yl]-ethanone and furan-2-boronic acid were cross-coupled to give the title compound: HPLC retention time=7.42 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+ =463.2 (M+H).

Synthesis of 2-[4-Chloro-3-(2,4-difluoro-phenyl)-5-methyl-pyrazol-1-yl]-1-[4-(4-chloro-3-methoxy-phenyl)-2-(S)-methylpiperazin-1-yl]-ethanone

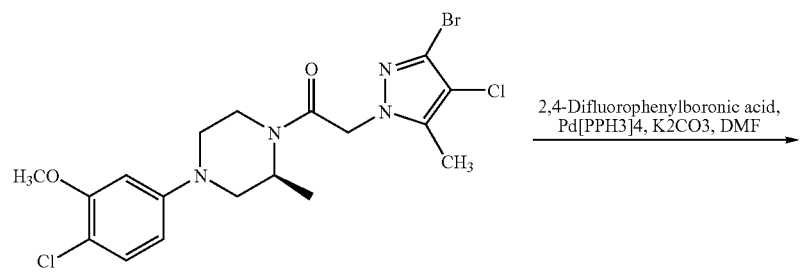

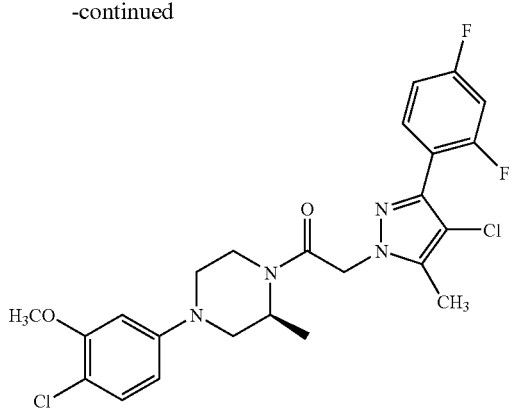

Following Protocol AA, 2,4-difluorophenylboronic acid and 2-(3-Bromo-4-chloro-5-methyl-pyrazol-1-yl)-1-[4-(4-chloro-3-methoxy-phenyl)-2-(S)-methyl-piperazin-1-yl]-ethanone were coupled to give the title compound. HPLC retention time=5.39 minutes (Agilent Zorbax SB-C18, 2.1× 50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-[4-Chloro-3-(3-fluoro-pyridin-4-yl)-5-methyl-pyrazol-1-yl]-1-[4-(4-chloro-3-methoxy-phenyl)-piperazin-1-yl]-ethanone

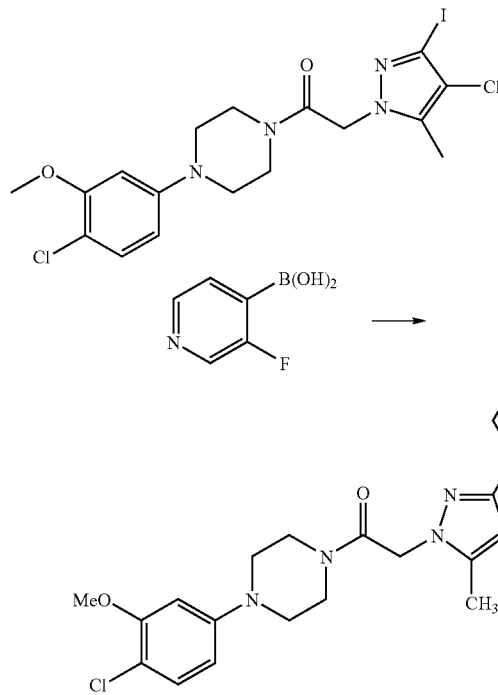

The title compound was made by following Suzuki Protocol AA: LCMS (ES) M+H=478.3; HPLC RT=4.724 min (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-[4-Chloro-3-(2-chloro-pyridin-3-yl)-5-methyl-pyrazol-1-yl]-1-[4-(4-chloro-3-methoxy-phenyl)-piperazin-1-yl]-ethanone

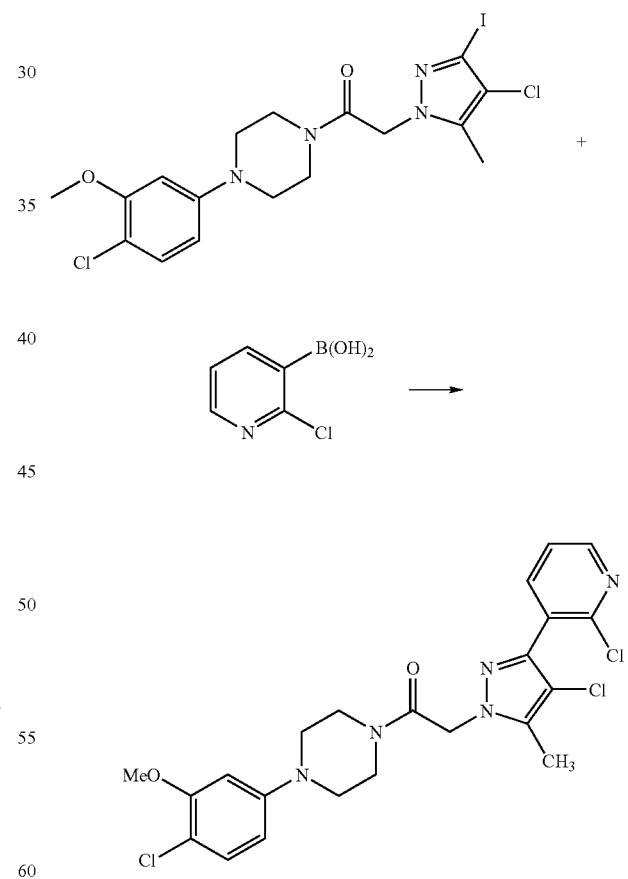

The title compound was made by following Suzuki Protocol AA: $^1$H NMR (400 MHz, CDCl$_3$) δ 8.87-7.12 (m, 3H), 6.47 (d, 3H), 4.64 (s, 2H), 3.89 (s, 1H), 3.21-3.83 (dt, 2H), 2.85 (s, 3H); LCMS (ES) M+H=494.4; HPLC RT=4.514 min (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-[4-Chloro-3-(2,4-dimethoxy-pyrimidin-5-yl)-5-methyl-pyrazol-1-yl]-1-[4-(4-chloro-3-methoxy-phenyl)-piperazin-1-yl]-ethanone

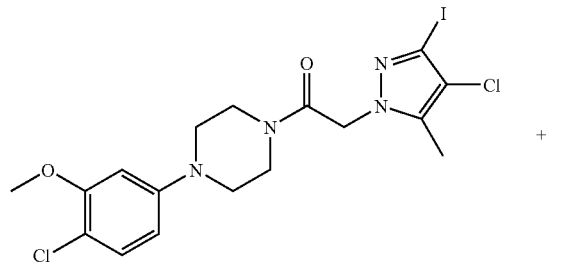

+

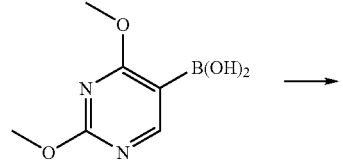

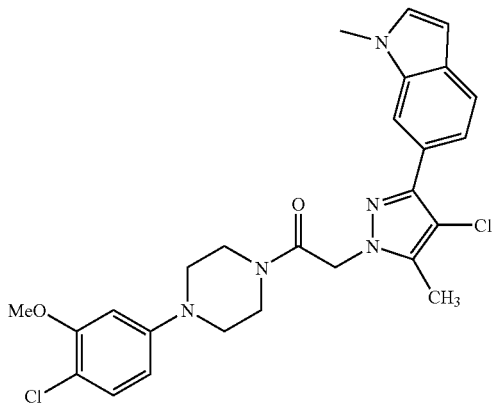

The title compound was made by following Suzuki Protocol AA: LCMS (ES) M+H=521.4; HPLC retention time=4.499 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-[4-(4-Chloro-3-methoxy-phenyl)-piperazin-1-yl]-2-[4-chloro-5-methyl-3-(1-methyl-1H-indol-6-yl)-pyrazol-1-yl]-ethanone

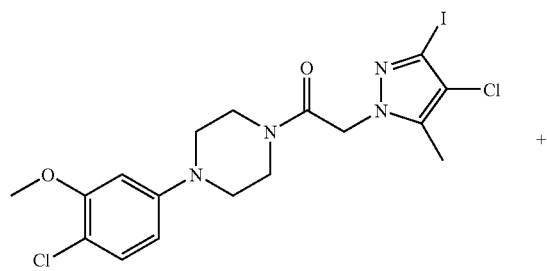

+

-continued

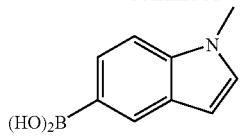

The title compound was made by following Suzuki Protocol AA: LCMS (ES) M+H=512.4; HPLC RT=5.038 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-[4-(4-Chloro-3-methoxy-phenyl)-piperazin-1-yl]-2-[4-chloro-5-methyl-3-(5-methyl-furan-2-yl)-pyrazol-1-yl]-ethanone

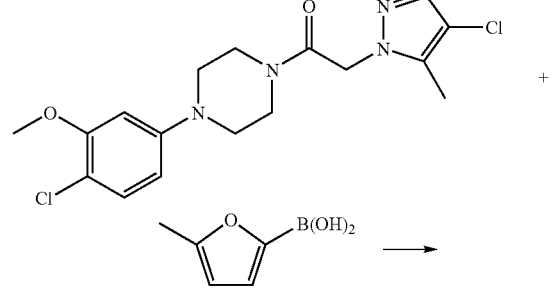

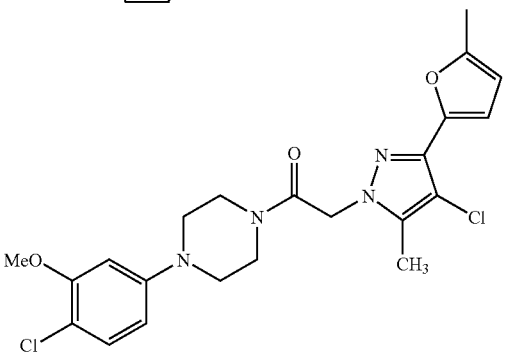

The title compound was made by following Suzuki Protocol AA: LCMS (ES) M+H=463.4; HPLC retention time=4.961 min (Agilent Zorbax SB-C18, 2.1×50 mm, 5μ, 35° C.) using a 4.5 minute gradient of 20% to 95% B with a

2-(4-Chloro-3-furan-3-yl-5-methyl-pyrazol-1-yl)-1-[4-(4-chloro-3-methoxy-phenyl)-2-(S)-methyl-piperazin-1-yl]-ethanone

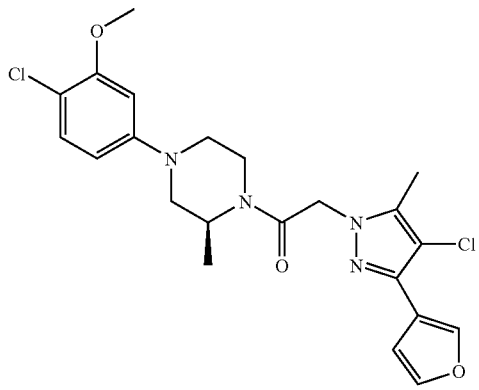

Following Suzuki Protocol AA, 2-(3-Bromo-4-chloro-5-methyl-pyrazol-1-yl)-1-[4-(4-chloro-3-methoxy-phenyl)-2-(S)-methyl-piperazin-1-yl]-ethanone and furan-3-boronic acid were cross-coupled to give the title compound: HPLC retention time=7.49 minutes (Agilent Zorbax SB-C18, 2.1× 50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=463.2 (M+H).

2-[4-Chloro-3-(4-fluoro-phenyl)-5-methyl-pyrazol-1-yl]-1-[4-(4-chloro-3-methoxy-phenyl)-piperazin-1-yl]-ethanone

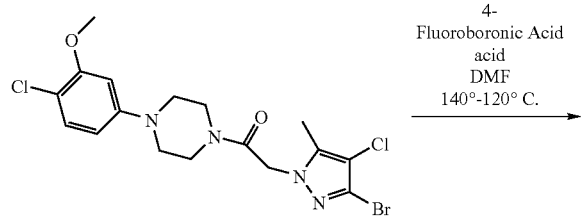

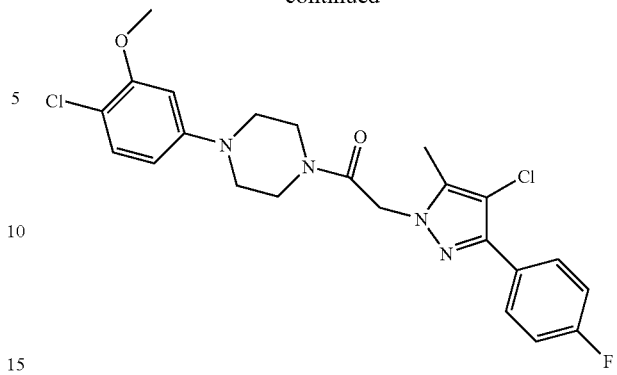

Following Protocol AA, 2-[4-Chloro-3-bromo-5-methyl-pyrazol-1-yl]-1-[4-(4-chloro-3-methoxy-phenyl)-piperazin-1-yl]-ethanone and 4-Fluoroboronic acid were cross-coupled to give the title compound: $R_f$=0.57; $^1$H NMR (CDCl$_3$, 400 MHz) 7.8-7.9 (2H, m), 7.2-7.22 (d, 1H), 7.05-7.12 (m, 2H), 6.4-6.48 (m, 2H), 5.0 (2H, s), 3.82 (s, 3H), 3.7-3.8 (m, 4H), 3.1-3.2 (m, 4H), 2.3 (s, 3H) ppm. $^{13}$CNMR (400 MHz, CDCl$_3$) δ 162, 160, 155, 152, 148, 140, 134, 130, 118, 112, 110, 109, 100, 58, 56, 54, 52, 46, 42, 10 ppm.

2-[4-Chloro-3-(2-fluoro-phenyl)-5-methyl-pyrazol-1-yl]-1-[4-(4-chloro-3-methoxy-phenyl)-piperazin-1-yl]-ethanone

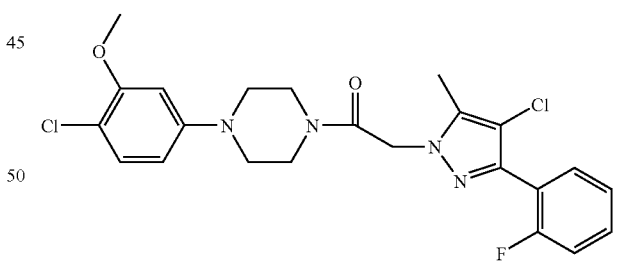

Following Protocol AA, 2-[4-Chloro-3-bromo-5-methyl-pyrazol-1-yl]-1-[4-(4-chloro-3-methoxy-phenyl)-piperazin-1-yl]-ethanone and 2-Fluoroboronic acid were coupled to give the title compound: $R_f$: 0.521; $^1$H NMR (CDCl$_3$, 400 MHz) 7.5-7.56 (1H, m), 7.32-7.38 (m, 1H), 7.1-7.21 (m, 3H), 7.12-7.22 (d, 1H), 6.4-6.48 (m, 2H), 5.0 (2H, s), 3.83 (s, 3H), 3.7-3.8 (m, 4H), 3.08-3.18 (m, 4H), 2.3 (s, 3H) ppm. $^{13}$CNMR (400 MHz, CDCl$_3$) δ 162, 160, 158, 155, 138, 131, 130, 124, 118, 112, 110, 109, 100, 58, 56, 54, 52, 46, 42, 10 ppm.

2-[4-Chloro-3-(3-fluoro-phenyl)-5-methyl-pyrazol-1-yl]-1-[4-(4-chloro-3-methoxy-phenyl)-piperazin-1-yl]-ethanone

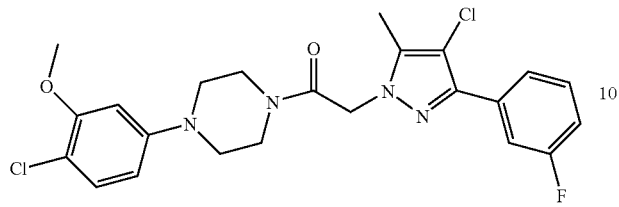

Following Protocol AA, 2-[4-Chloro-3-bromo-5-methyl-pyrazol-1-yl]-1-[4-(4-chloro-3-methoxy-phenyl)-piperazin-1-yl]-ethanone and 3-Fluoroboronic acid were coupled to give the title compound: $R_f$: 0.68; $^1$H NMR (CDCl$_3$, 400 MHz) 7.68-7.72 (1H, m), 7.58-7.62 (m, 1H), 7.32-7.38 (m, 1H), 7.18-7.22 (d, 1H), 6.98-7.04 (m, 1H), 6.38-6.48 (m, 2H), 4.98 (2H, s), 3.88 (s, 3H), 3.7-3.8 (m, 4H), 3.1-3.2 (m, 4H), 2.3 (s, 3H) ppm; $^{13}$CNMR (400 MHz, CDCl$_3$) δ 164, 156, 150, 144, 130, 129, 124, 118, 114-116 (m), 110, 100, 56, 52, 50, 49, 46, 42, 10 ppm.

2-[4-Chloro-3-(2,4-difluoro-phenyl)-5-methyl-pyrazol-1-yl]-1-[4-(4-chloro-3-methoxy-phenyl)-piperazin-1-yl]-ethanone

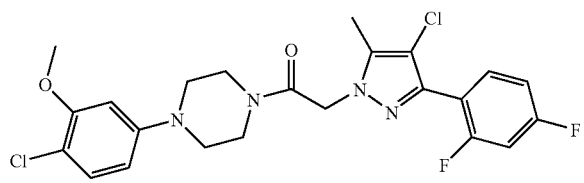

Following Protocol AA, 2-[4-Chloro-3-bromo-5-methyl-pyrazol-1-yl]-1-[4-(4-chloro-3-methoxy-phenyl)-piperazin-1-yl]-ethanone and 2,4-Difluoroboronic acid were cross-coupled to give the title compound: $R_f$: 0.7; $^1$H NMR (CDCl$_3$, 400 MHz) 7.48-7.56 (1H, m), 7.18-7.22 (d, 1H), 6.86-6.94 (m, 2H), 6.38-6.48 (m, 2H), 5.00 (2H, s), 3.88 (s, 3H), 3.68-3.8 (m, 4H), 3.1-3.2 (m, 4H), 2.3 (s, 3H) ppm; $^{13}$CNMR (400 MHz, CDCl$_3$) δ 164, 156, 150, 138, 132, 130, 122, 118, 114-116 (m), 102, 56, 52, 50, 49, 46, 42, 10 ppm.

1-[4-(4-Chloro-3-methoxy-phenyl)-piperazin-1-yl]-2-(4-chloro-5-methyl-3-pyrimidin-5-yl-pyrazol-1-yl)-ethanone

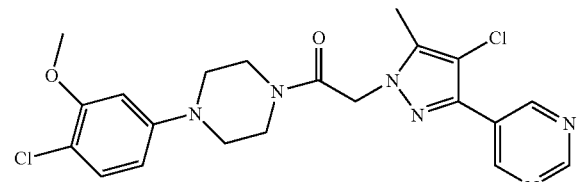

Following Protocol AA, 2-[4-Chloro-3-bromo-5-methyl-pyrazol-1-yl]-1-[4-(4-chloro-3-methoxy-phenyl)-piperazin-1-yl]-ethanone and 4-Pyrimidineboronic acid were cross-coupled to give the title compound: $R_f$: 0.7; $^1$H NMR (CDCl$_3$, 400 MHz) 9.15 (s, 1H), 9.23 (s, 2H), 7.2-7.25 (d, 1H), 6.38-6.48 (m, 2H), 5.02 (s, 2H), 3.88 (s, 3H), 3.72-3.82 (m, 4H), 3.12-3.22 (m, 4H), 2.32 (s, 3H) ppm; MS (ES)M+H expected=461, found=461.1.

2-(4-Chloro-3-furan-3-yl-5-methyl-pyrazol-1-yl)-1-[4-(4-chloro-3-methoxy-phenyl)-piperazin-1-yl]-ethanone

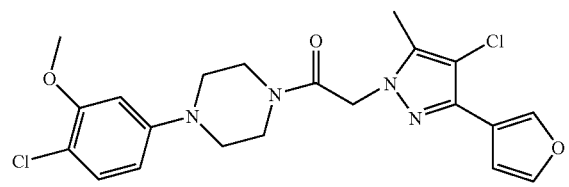

Following Protocol AA, 2-[4-Chloro-3-bromo-5-methyl-pyrazol-1-yl]-1-[4-(4-chloro-3-methoxy-phenyl)-piperazin-1-yl]-ethanone and 3-Furanboronic acid were cross-coupled to give the title compound: $R_f$: 0.7; $^1$H NMR (CDCl$_3$, 400 MHz) 8.00 (s, 1H), 7.42-7.44 (t, 1H), 7.18-7.22 (d, 1H), 6.82-6.84 (d, 2H), 6.38-6.48 (m, 2H), 4.84 (s, 2H), 3.88 (s, 3H), 3.68-3.8 (m, 4H), 3.1-3.2 (m, 4H), 2.3 (s, 3H) ppm; $^{13}$CNMR (400 MHz, CDCl$_3$) δ 164, 156, 151, 143, 141, 138, 130, 118, 116, 110, 111, 102, 56, 52, 50, 49, 46, 42, 10 ppm.

2-(4-Chloro-3-furan-2-yl-5-methyl-pyrazol-1-yl)-1-[4-(4-chloro-3-methoxy-phenyl)-piperazin-1-yl]-ethanone

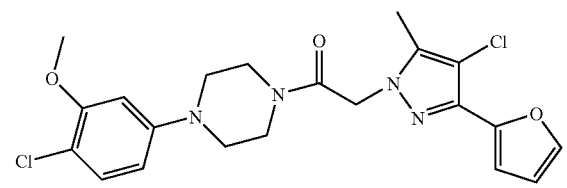

Following Protocol AA, 2-[4-Chloro-3-bromo-5-methyl-pyrazol-1-yl]-1-[4-(4-chloro-3-methoxy-phenyl)-piperazin-1-yl]-ethanone and 2-Furanboronic were cross-coupled to give the title compound: $R_f$: 0.7; $^1$H NMR (CDCl$_3$, 400 MHz) 7.48-7.52 (d, 1H), 7.18-7.22 (d, 1H), 6.91-6.92 (d, 1H), 6.38-6.48 (m, 3H), 5.00 (s, 2H), 3.88 (s, 3H), 3.68-3.78 (m, 4H), 3.1-3.2 (m, 4H), 2.3 (s, 3H) ppm; $^{13}$CNMR (400 MHz, CDCl₃) δ 164, 156, 151, 146, 142, 138, 130, 114, 111, 109, 108, 100, 56, 52, 50, 49, 46, 42, 10 ppm.

1-[4-(4-Chloro-3-methoxy-phenyl)-2-(S)-methyl-piperazin-1-yl]-2-(4-chloro-5-methyl-3-pyrimidin-5-yl-pyrazol-1-yl)-ethanone

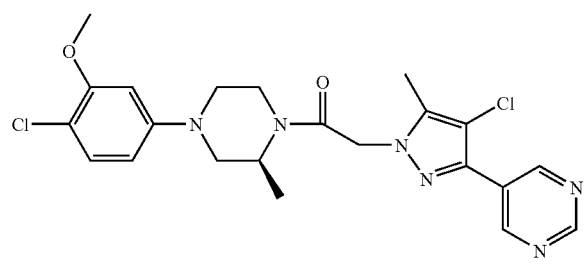

Following Protocol AA, 2-[4-Chloro-3-bromo-5-methyl-pyrazol-1-yl]-1-[4-(4-chloro-3-methoxy-phenyl)-2-methyl-piperazin-1-yl]-ethanone and 4-Pyrimidineboronic acid were cross-coupled to give the title compound: R$_f$: 0.7; ¹H NMR (CDCl₃, 400 MHz) 9.15 (s, 1H), 9.23 (s, 2H), 7.2-7.25 (d, 1H), 6.38-6.48 (m, 2H), 4.32-5.2 (m, 5H), 3.88 (s, 3H), 2.52-3.52 (m, 7H), 2.3-2.4 (s, 4H) ppm; MS (ES)M+H expected=475, found=475.1.

1-[4-(4-Chloro-3-methoxy-phenyl)-piperazin-1-yl]-2-(4-chloro-5-methyl-3-quinolin-3-yl-pyrazol-1-yl)-ethanone

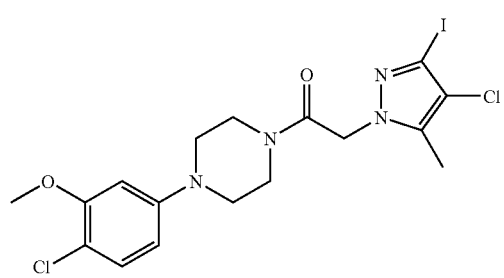

+

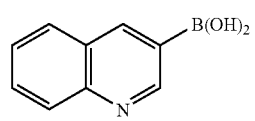

→

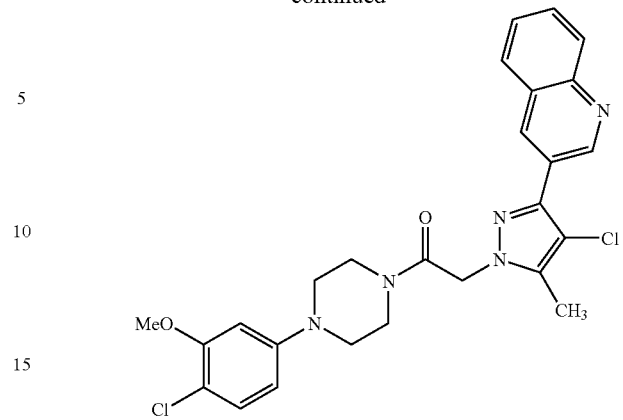

The title compound was made by following Suzuki Protocol AA: ¹H NMR (400 MHz, CDCl₃) δ 9.21-7.43 (m, 6H), 6.47 (d, 3H), 4.64 (s, 2H), 3.89 (s, 1H), 3.21-3.83 (dt, 2H), 2.85 (s, 3H); LCMS (ES) M+H=510.3, HPLC RT=4.718 min (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-2-fluoro-5-methoxyphenyl)piperazin-1-yl]-2-(4-chloro-3-furan-3-yl-5-methylpyrazol-1-yl)ethanone

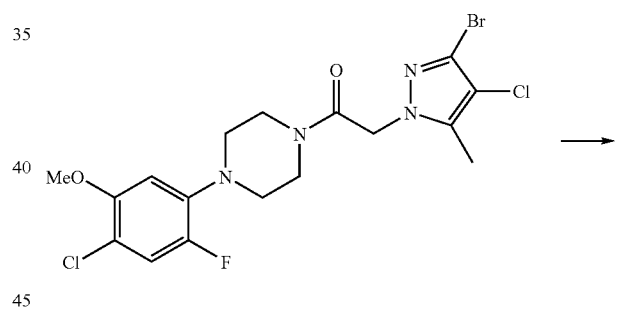

→

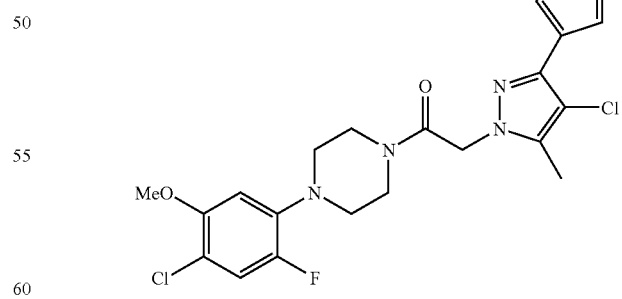

The title compound was obtained by following Protocol AA: LCMS (ES): M+H 467.1; HPLC retention time=4.98 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Protocol CC: One-Pot HATU Mediated Coupling and Azide Reduction Reactions 2-(5-Aminomethyl-4-chloro-3-trifluoromethyl-pyrazol-1-yl)-1-[4-(2,4-dichloro-5-methoxy-phenyl)-piperazin-1-yl]-ethanone

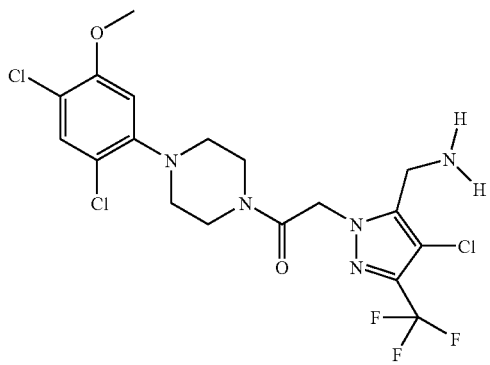

50 mg of 1-(2,4-Dichloro-5-methoxy-phenyl)-piperazine di-HCl (0.14 mmol, 1.0 eq), 48 mg of (5-Azidomethyl-4-chloro-3-trifluoromethyl-pyrazol-1-yl)-acetic acid (0.17 mmol, 1.2 eq), 100 uL of DIEA (0.57 mmol, 4.0 eq) and 65 mg of HATU (0.17 mmol, 1.2 eq) were combined in 250 uL DMF in a 4 mL vial. After four hours, 157 mg (0.7 mmol) of Stannous (II) chloride was added, and the vial was sealed and heated in a 60° C. oil bath overnight. The reaction was purified by preparative HPLC to give the title compound: HPLC retention time=5.01 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=496.7 (M+H).

2-(5-Aminomethyl-4-chloro-3-trifluoromethyl-pyrazol-1-yl)-1-[4-(4-bromo-3-methoxy-phenyl)-piperazin-1-yl]-ethanone

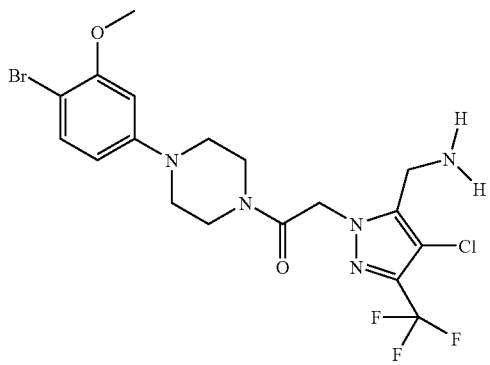

Following Protocol CC, 1-(4-Bromo-5-methoxy-phenyl)-piperazine di-HCl and (5-Azidomethyl-4-chloro-3-trifluoromethyl-pyrazol-1-yl)-acetic acid were coupled with HATU, and the crude product was reduced in situ with Stannous (II) chloride to give the title compound: HPLC retention time=5.46 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+=509.0 (M+H).

2-(5-Aminomethyl-4-chloro-3-trifluoromethyl-pyrazol-1-yl)-1-[4-(4-bromo-3-methoxy-phenyl)-2-methyl-piperazin-1-yl]-ethanone

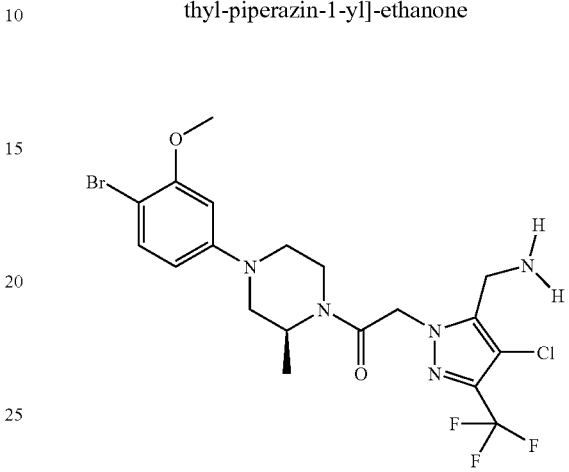

Following Protocol CC, (S)-1-(4-Bromo-3-methoxy-phenyl)-3-methyl-piperazine and (5-Azidomethyl-4-chloro-3-trifluoromethyl-pyrazol-1-yl)-acetic acid were coupled with HATU and the crude mixture was treated with Stannous (II) chloride to give the title compound: HPLC retention time=5.58 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)-=443.9 (M-Br).

2-(5-Aminomethyl-4-chloro-3-trifluoromethyl-pyrazol-1-yl)-1-[4-(4-chloro-2-fluoro-5-methoxy-phenyl)-piperazin-1-yl]-ethanone

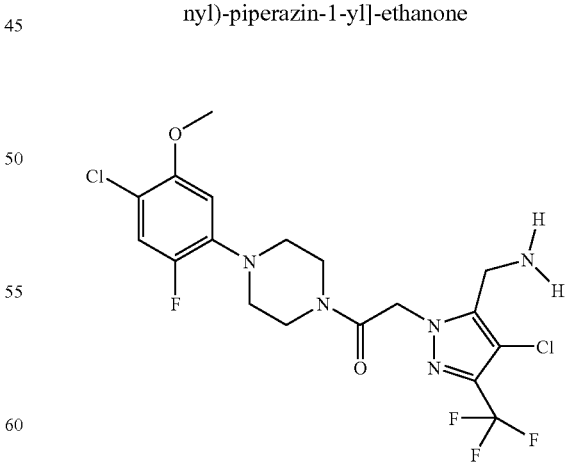

Following Protocol CC, 1-(4-Chloro-2-fluoro-5-methoxy-phenyl)-piperazine and (5-Azidomethyl-4-chloro-3-trifluoromethyl-pyrazol-1-yl)-acetic acid were coupled using HATU and the crude mixture was treated with Stannous (II)

chloride to give the title compound: HPLC retention time=5.84 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)+= 481.9 (M+H).

2-(5-Aminomethyl-4-chloro-3-trifluoromethyl-pyrazol-1-yl)-1-[4-(4-chloro-3-methoxy-phenyl)-2-(S)-methyl-piperazin-1-yl]-ethanone

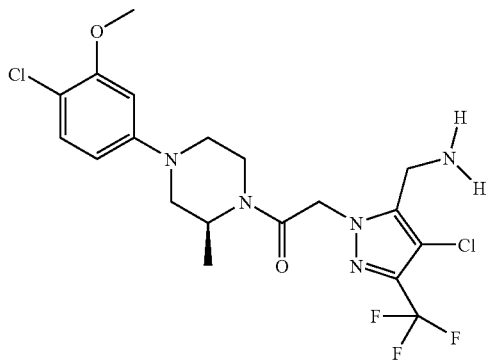

Following Protocol CC, (S)-1-(4-chloro-3-methoxy-phenyl)-3-methyl-piperazine and (5-Azidomethyl-4-chloro-3-trifluoromethyl-pyrazol-1-yl)-acetic acid were coupled using HATU, and the crude mixture was treated with Stannous (II) chloride to give the title compound: HPLC retention time=5.74 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile); (M/Z)= 487.8 (M+H).

Protocol DD: Preparation of Compounds Via Palladium and Copper Mediated Processes Synthesis of 2-(3-morpholino-4-chloro-5-methyl-pyrazol-1-yl)-1-[4-(4-chloro-3-methoxy-phenyl)-piperazin-1-yl]-ethanone

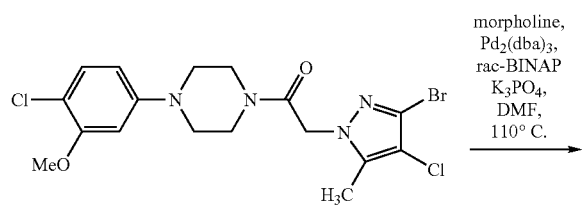

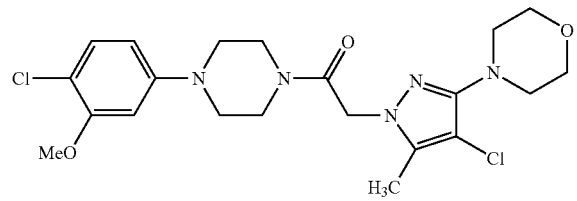

A mixture of 2-(3-bromo-4-chloro-5-methyl-pyrazol-1-yl)-1-[4-(4-chloro-3-methoxy-phenyl)-piperazin-1-yl]-ethanone (46 mg, 0.1 mmol, 1 equiv), morpholine (44 m g, 45 μL, 5 equiv), racemic-BINAP (20 mg, 0.3 equiv), Pd$_2$(dba)$_3$ (10 mg, 0.1 equiv) and K$_3$PO$_4$.H$_2$O (138 mg, 6 equiv) in 1 mL of DMF were heated at 110° C. overnight and then cooled to room temperature, taken up in a 1:1 mixture of methanol and EtOAc, filtered through a thin pad of celite and concentrated. The crude product was purified by reverse phase HPLC (acetonitrile-H$_2$O with 0.1% TFA as eluent) to yield 2-(3-morpholino-4-chloro-5-methyl-pyrazol-1-yl)-1-[4-(4-chloro-3-methoxy-phenyl)-piperazin-1-yl]-ethanone. $^1$H NMR (400 MHz, CDCl$_3$) δ 7.23 (d, 1H), 6.50 (d, 1H), 6.42 (dd, 1H), 4.95 (s, 1H), 3.90 (s, 3H), 3.78 (m, 8H), 3.20 (m, 8H), 2.30 (s, 3H). LCMS observed for (M+H)$^+$: 468.

Synthesis of 2-(4-chloro-5-methyl-pyrazol-1-yl)-1-[4-(4-chloro-3-methoxy-phenyl)-piperazin-1-yl]-ethanone

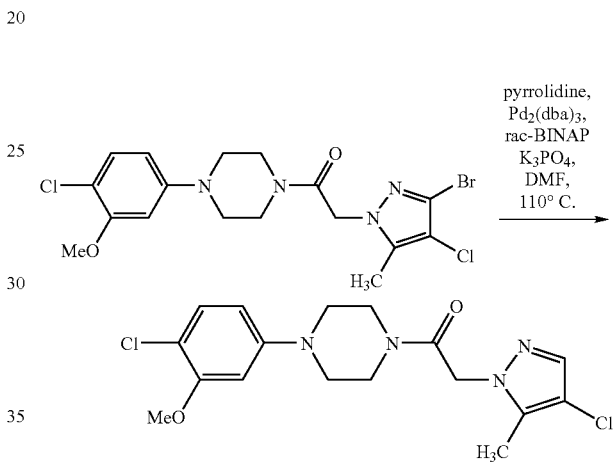

A mixture of 2-(3-bromo-4-chloro-5-methyl-pyrazol-1-yl)-1-[4-(4-chloro-3-methoxy-phenyl)-piperazin-1-yl]-ethanone (46 mg, 0.1 mmol, 1 equiv), pyrrolidine (42 mg, 42 μL, 5 equiv), racemic-BINAP (20 mg, 0.3 equiv), Pd$_2$(dba)$_3$ (10 mg, 0.1 equiv) and K$_3$PO$_4$.H$_2$O (138 mg, 6 equiv) in 1 mL of DMF were heated at 110° C. overnight and then cooled to room temperature, taken up in a 1:1 mixture of methanol and EtOAc, filtered through a thin pad of celite and concentrated. The crude product was purified by reverse phase HPLC (acetonitrile-H$_2$O with 0.1% TFA as eluent) to yield 2-(4-chloro-5-methyl-pyrazol-1-yl)-1-[4-(4-chloro-3-methoxy-phenyl)-piperazin-1-yl]-ethanone. $^1$H NMR (400 MHz, CDCl$_3$) δ 7.46 (s, 1H), 7.30 (d, 1H), 6.74 (d, 1H), 6.60 (dd, 1H), 5.08 (s, 1H), 3.90 (s, 3H), 3.88 (m, 2H), 3.80 (m, 2H), 3.34 (m, 2H), 3.25 (m, 2H), 2.20 (s, 3H). LCMS observed for (M+H)$^+$: 383.

Synthesis of 3-methyl-4-cyano-5(trifluoromethyl)pyrazole

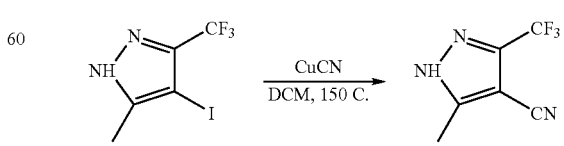

3-Methyl-4-iodo-5-(trifluoromethyl)pyrazole (0.28 g, 1 mmol) and Copper(I) cyanide (0.9 g, 10 mmol) were mixtured in 1 mL DMF and stirred at 150° C. for 1 hour. The reaction mixture were slowly poured into 30 mL heated EtOAc/MeOH under stirring, and this was filtered to remove the solid. The mixture was partitioned between EtOAc and Sat. NaHCO$_3$, and the phases were separated. The ethyl acetate phase was washed with Brine, dried over Na$_2$SO$_4$ and concentrated to afford the title product.

Synthesis of 1-[4-(4-Chloro-3-methoxy-phenyl)-piperazin-1-yl]-2-(4-methanesulfonyl-5-methyl-3-trifluoromethyl-pyrazol-1-yl)-ethanone

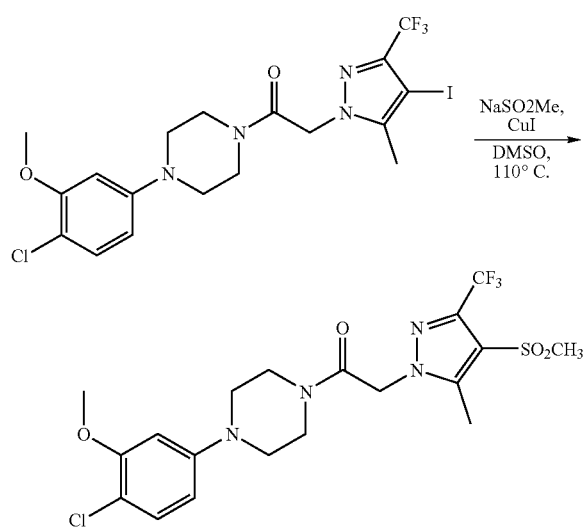

Title compounds were prepared by mixture 1-[4-(4-Chloro-3-methoxy-phenyl)-piperazin-1-yl]-2-(4-iodo-5-methyl-3-trifluoromethyl-pyrazol-1-yl)-ethanone (109 mg, 0.2 mmol), NaSO$_2$Me (61 mg, 0.6 mmol) and CuI (114 mg, 0.6 mmol) in DMSO (1 ml) at 110° C. for 3 hours. The crude reaction was purified by HPLC: HPLC retention time=4.21 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=495.1, found=495.4.

Synthesis of 3-methylsulfonyl-4-chloro-5-methyl-pyrazole

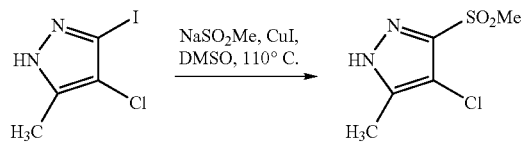

A mixture of 3-iodo-4-chloro-5-methyl-pyrazole (48 mg, 0.2 mmol, 1 equiv), NaSO$_2$Me (72 mg, 3 equiv) and CuI (114 mg, 3 equiv) in 1 mL of DMSO were heated at 110° C. for 3 h and then cooled to room temperature, taken up in a 1:1 mixture of methanol and EtOAc, filtered through a thin pad of celite and concentrated. The residue was dissolved in EtOAc and washed with water. The organic layer was dried over Na$_2$SO$_4$, filtered and concentrated. The crude product was used in the next step without purification.

Synthesis of 1-(4-chloro-1-{2-[4-(4-chloro-3-methoxy-phenyl)-piperazin-1-yl]-2-oxo-ethyl}-5-methyl-1H-pyrazol-3-yl)-pyrrolidin-2-one

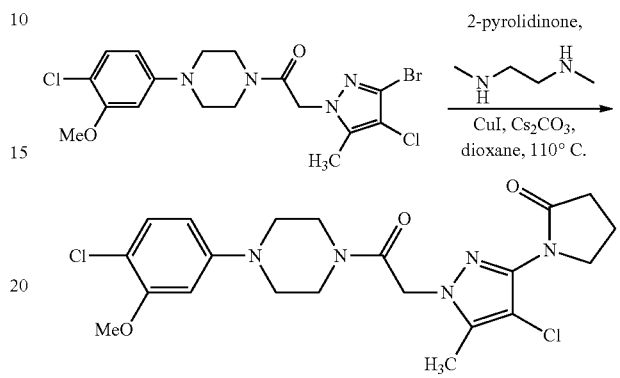

A mixture of 2-(3-bromo-4-chloro-5-methyl-pyrazol-1-yl)-1-[4-(4-chloro-3-methoxy-phenyl)-piperazin-1-yl]-ethanone (92 mg, 0.2 mmol, 1 equiv), 2-pyrolidinone (17 mg, 1 equiv), N,N-dimethylethylenediamine (5.3 mg, 0.3 equiv), CuI (12 mg, 0.3 equiv) and Cs$_2$CO$_3$ (130 mg, 2 equiv) in 1 mL of dioxane were heated at 110° C. overnight and then cooled to room temperature, taken up in a 1:1 mixture of methanol and EtOAc, filtered through a thin pad of celite and concentrated. The crude product was purified by reverse phase HPLC (acetonitrile-H$_2$O with 0.1% TFA as eluent) to yield 1-(4-chloro-1-{2-[4-(4-chloro-3-methoxy-phenyl)-piperazin-1-yl]-2-oxo-ethyl}-5-methyl-1H-pyrazol-3-yl)-pyrrolidin-2-one. $^1$H NMR (400 MHz, CDCl$_3$) δ 7.32 (d, 1H), 6.78 (d, 1H), 6.65 (dd, 1H), 4.93 (s, 2H), 3.90 (s, 3H), 3.88 (m, 6H), 3.35 (m, 2H), 3.28 (m, 2H), 2.60 (m, 2H), 3.30 (s, 3H), 2.24 (m, 2H). LCMS observed for (M+H)$^+$: 466.

Synthesis of 2-(3-methylsulfonyl-4-chloro-5-methyl-pyrazol-1-yl)-1-[4-(4-chloro-3-methoxy-phenyl)-piperazin-1-yl]-ethanone

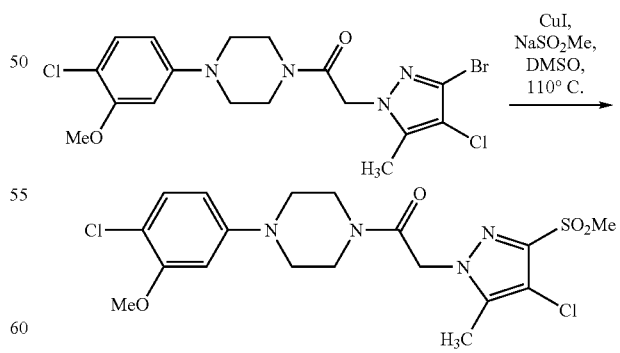

A mixture of 2-(3-bromo-4-chloro-5-methyl-pyrazol-1-yl)-1-[4-(4-chloro-3-methoxy-phenyl)-piperazin-1-yl]-ethanone (46 mg, 0.1 mmol, 1 equiv), NaSO$_2$Me (36 mg, 3 equiv) and CuI (57 mg, 3 equiv) in 1 mL of DMSO were heated at 110° C. overnight and then cooled to room temperature, taken up in a 1:1 mixture of methanol and EtOAc, filtered through a thin pad of celite and concentrated. The crude product was purified by reverse phase HPLC (acetonitrile-H₂O with 0.1% TFA as eluent) to yield 2-(3-methylsulfonyl-4-chloro-5-methyl-pyrazol-1-yl)-1-[4-(4-chloro-3-methoxy-phenyl)-piperazin-1-yl]-ethanone. ¹H NMR (400 MHz, CDCl₃) δ 7.38 (d, 1H), 6.82 (d, 1H), 6.70 (dd, 1H), 5.18 (s, 2H), 3.92 (m, 4H), 3.90 (s, 3H), 3.40 (m, 2H), 3.36 (m, 2H), 3.19 (s, 3H), 2.34 (s, 3H). LCMS observed for (M+H)⁺: 461.

Synthesis of 2-[4-chloro-3-(2-phenyl)imidazol-1-yl-5-methyl-pyrazol-1-yl]-1-[4-(4-chloro-3-methoxy-phenyl)-piperazin-1-yl]-ethanone

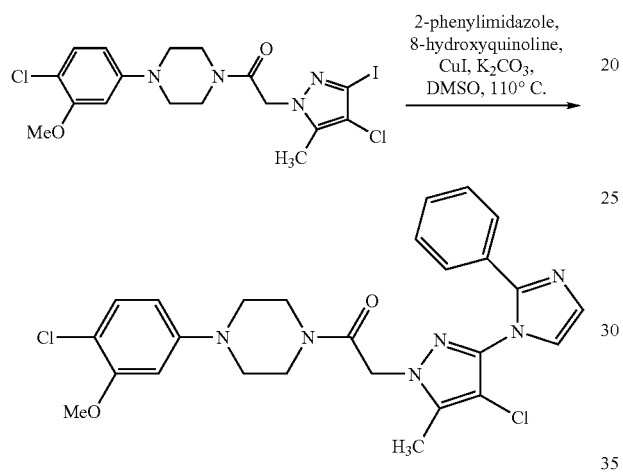

A mixture of 2-(3-iodo-4-chloro-5-methyl-pyrazol-1-yl)-1-[4-(4-chloro-3-methoxy-phenyl)-piperazin-1-yl]-ethanone (102 mg, 0.2 mmol, 1 equiv), 2-phenylimidazole (86 mg, 3 equiv), 8-hydroxyquinoline (5.8 mg, 0.2 equiv), CuI (7.6 mg, 0.2 equiv) and K₂CO₃ (42 mg, 1.5 equiv) in 1 mL of DMSO were heated at 110° C. over two nights and then cooled to room temperature, taken up in a 1:1 mixture of methanol and EtOAc, filtered through a thin pad of celite and concentrated. The crude product was purified by reverse phase HPLC to yield the title compound: LCMS Retention time: 4.04 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)⁺: 525.

Synthesis of 2-(4-chloro-3-[1,2,3]triazol-1-yl-5-methyl-pyrazol-1-yl)-1-[4-(4-chloro-3-methoxy-phenyl)-piperazin-1-yl]-ethanone

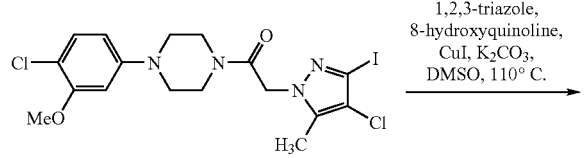

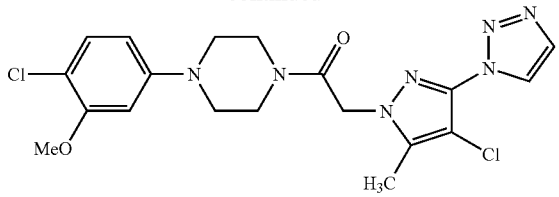

A mixture of 2-(3-iodo-4-chloro-5-methyl-pyrazol-1-yl)-1-[4-(4-chloro-3-methoxy-phenyl)-piperazin-1-yl]ethanone (102 mg, 0.2 mmol, 1 equiv), 1,2,3-triazole (42 mg, 3 equiv), 8-hydroxyquinoline (5.8 mg, 0.2 equiv), CuI (7.6 mg, 0.2 equiv) and K₂CO₃ (42 mg, 1.5 equiv) in 1 mL of DMSO were heated at 110° C. over two nights and then cooled to room temperature, taken up in a 1:1 mixture of methanol and EtOAc, filtered through a thin pad of celite and concentrated. The crude product was purified by reverse phase HPLC to yield the title compound: LCMS Retention time=3.93 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)⁺: 450.

Synthesis of 2-(3-cyano-4-chloro-5-methyl-pyrazol-1-yl)-1-[4-(4-chloro-3-methoxy-phenyl)-piperazin-1-yl]ethanone

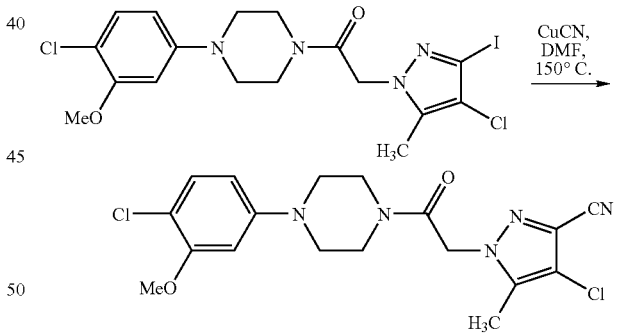

A mixture of 2-(3-iodo-4-chloro-5-methyl-pyrazol-1-yl)-1-[4-(4-chloro-3-methoxy-phenyl)-piperazin-1-yl]-ethanone (51 mg, 0.1 mmol, 1 equiv) and CuCN (180 mg, 20 equiv) in 1 mL of DMF were heated at 175° C. for 1 h and then cooled to room temperature, taken up in a 1:1 mixture of methanol and EtOAc, filtered through a thin pad of celite and concentrated. The crude product was purified by reverse phase HPLC (acetonitrile-H₂O with 0.1% TFA as eluent) to yield 2-(3-cyano-4-chloro-5-methyl-pyrazol-1-yl)-1-[4-(4-chloro-3-methoxy-phenyl)-piperazin-1-yl]-ethanone. ¹H NMR (400 MHz, CDCl₃) δ 7.30 (d, 1H), 6.65 (d, 1H), 6.56

(dd, 1H), 5.02 (s, 2H), 3.90 (s, 3H), 3.88 (m, 2H), 3.80 (m, 2H), 3.35(m, 2H), 3.28 (m, 2H), 2.32 (s, 3H).

Synthesis of 2-[4-chloro-3-(2-methylimidazol-1-yl)-5-methyl-pyrazol-1-yl]-1-[4-(4-chloro-3-methoxy-phenyl)-piperazin-1-yl]-ethanone

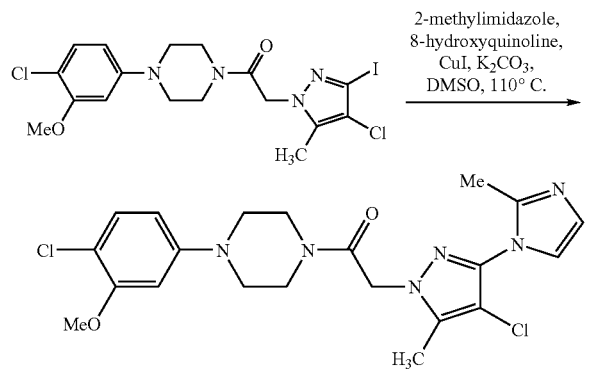

A mixture of 2-(3-iodo-4-chloro-5-methyl-pyrazol-1-yl)-1-[4-(4-chloro-3-methoxy-phenyl)-piperazin-1-yl]ethanone (102 mg, 0.2 mmol, 1 equiv), 2-methyl imidazole (32 m g, 2 equiv), 8-hydroxyquinoline (5.8 mg, 0.2 equiv), CuI (7.6 mg, 0.2 equiv) and $K_2CO_3$ (42 mg, 1.5 equiv) in 1 mL of DMSO were heated at 110° C. over two nights and then cooled to room temperature, taken up in a 1:1 mixture of methanol and EtOAc, filtered through a thin pad of celite and concentrated. The crude product was purified by reverse phase HPLC (acetonitrile-$H_2O$ with 0.1% TFA as eluent) to give the title compound: $^1$H NMR (400 MHz, $CDCl_3$) δ 8.92 (s, 1H), 7.66 (d, 1H), 7.40 (d, 1H), 7.28 (d, 1H), 7.21 (d, 1H), 6.53 (d, 1H), 6.42 (dd, 1H), 5.00 (s, 2H), 3.90 (s, 3H), 3.80 (m, 214), 3.71 (m, 2H), 3.28(m, 2H), 3.20 (m, 2H), 2.72 (s, 3H), 2.37 (s, 3H); LCMS observed for (M+H)$^+$: 463.

Synthesis of 2-[4-chloro-3-(4-methylimidazol-1-yl)-5-methyl-pyrazol-1-yl]-1-[4-(4-chloro-3-methoxy-phenyl)-piperazin-1-yl]-ethanone

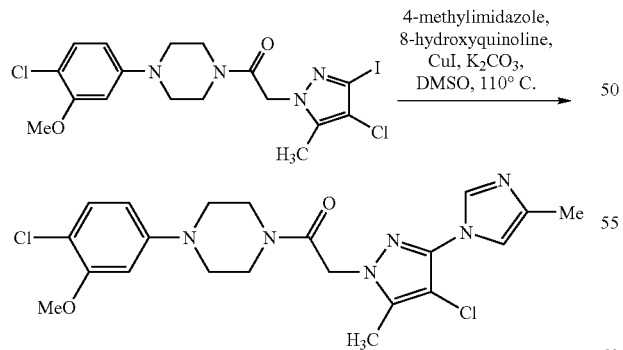

Following the same procedure as the previous example, 2-(3-iodo-4-chloro-5-methyl-pyrazol-1-yl)-1-[4-(4-chloro-3-methoxy-phenyl)-piperazin-1-yl]-ethanone and 4-methyl imidazole were coupled to give the title compound: $^1$H NMR (400 MHz, $CDCl_3$) δ 8.93 (s, 1H), 7.40 (s, 1H), 7.20 (d, 1H), 6.52 (d, 1H), 6.44 (dd, 1H), 5.00 (m, 2H), 3.90 (s, 3H), 3.80 (m, 2H), 3.73 (m, 2H), 3.28(m, 2H), 3.20 (m, 2H), 2.47 (s, 3H), 2.35 (m, 3H); LCMS observed for (M+H)$^+$: 463.

Synthesis of 2-(4-chloro-3-benzimidazol-1-yl-5-methyl-pyrazol-1-yl)-1-[4-(4-chloro-3-methoxy-phenyl)-piperazin-1-yl]-ethanone

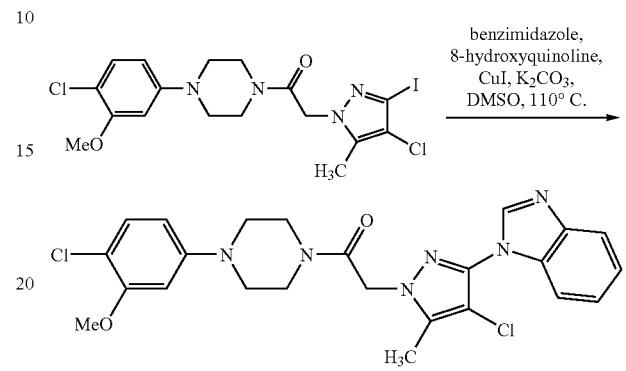

Following the same procedure as the previous example, 2-(3-iodo-4-chloro-5-methyl-pyrazol-1-yl)-1-[4-(4-chloro-3-methoxy-phenyl)-piperazin-1-yl]-ethanone and benzimidazole were coupled to give the title compound: $^1$H NMR (400 MHz, $CDCl_3$) δ 9.13 (s, 1H), 8.00 (m, 1H), 7.80 (m, 1H), 7.53 (m, 2H), 7.22 (d, 1H), 6.52 (d, 1H), 6.44 (dd, 1H), 5.06 (s, 21-1), 3.88 (s, 3H), 3.84 (m, 2H), 3.76 (m, 2H), 3.26(m, 2H), 3.22 (m, 2H), 2.40 (s, 3H); LCMS observed for (M+H)$^+$: 499.

Synthesis of 2-(4-chloro-3-pyrazol-1-yl-5-methyl-pyrazol-1-yl)-1-[4-(4-chloro-3-methoxy-phenyl)-piperazin-1-yl]-ethanone

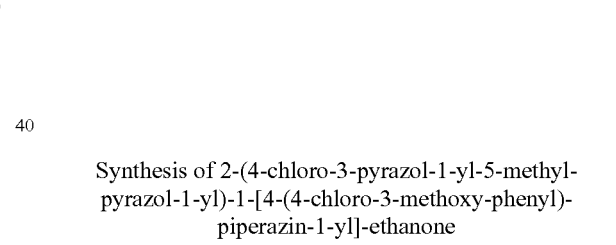

Following the same procedure as the previous example, 2-(3-iodo-4-chloro-5-methyl-pyrazol-1-yl)-1-[4-(4-chloro-3-methoxy-phenyl)-piperazin-1-yl]-ethanone and pyrazole were coupled to give the title compound: $^1$H NMR (400 MHz, $CDCl_3$) δ 8.00 (br, 1H), 7.63 (br, 2H), 7.40 (d, 1H), 7.18 (d, 1H), 6.42 (br, 1H), 5.40 (br, 2H), 4.40 (br, 2H), 4.24 (br, 2H), 3.90 (s, 3H), 3.55 (br, 2H), 3.36 (br, 2H), 2.36 (s, 3H); LCMS observed for (M+H)+: 449.

Synthesis of 2-[4-chloro-3-(3-methyl)-pyrazol-1-yl-5-methyl-pyrazol-1-yl]-1-[4-(4-chloro-3-methoxy-phenyl)-piperazin-1-yl]-ethanone

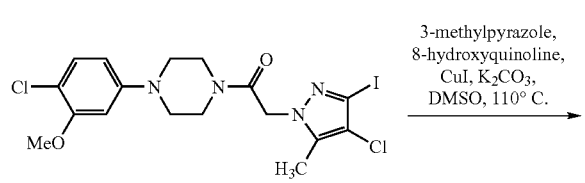

3-methylpyrazole, 8-hydroxyquinoline, CuI, K₂CO₃, DMSO, 110° C.

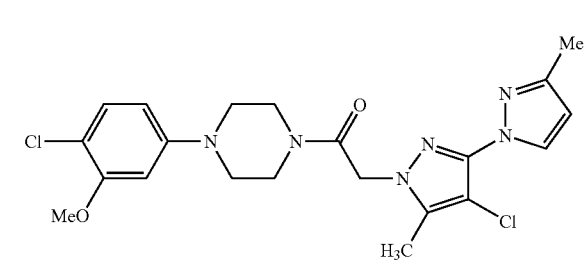

Following the previous example, 2-(3-iodo-4-chloro-5-methyl-pyrazol-1-yl)-1-[4-(4-chloro-3-methoxy-phenyl)-piperazin-1-yl]-ethanone and 3-methylpyrazole were coupled to give the title compound: $^1$H NMR (400 MHz, CDCl$_3$) δ 7.97 (d, 1H), 7.30 (d, 1H), 6.74 (d, 1H), 6.60 (dd, 1H), 6.24 (d, 1H), 5.00 (s, 2H), 3.82 (s, 3H), 3.80 (m, 4H), 3.33 (m, 2H), 3.24 (m, 2H), 2.37 (s, 3H), 2.30 (s, 3H); LCMS observed for (M+H)+: 463.

Synthesis of 2-[4-chloro-3-(3-trifluoromethyl)-pyrazol-1-yl-5-methyl-pyrazol-1-yl]-1-[4-(4-chloro-3-methoxy-phenyl)-piperazin-1-yl]-ethanone

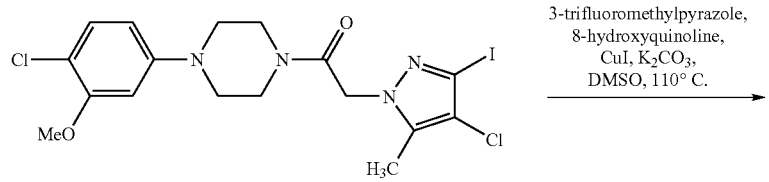

3-trifluoromethylpyrazole, 8-hydroxyquinoline, CuI, K₂CO₃, DMSO, 110° C.

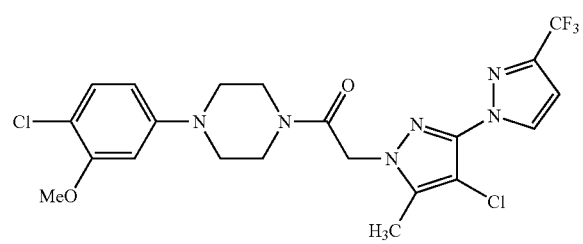

Following the previous example, 2-(3-iodo-4-chloro-5-methyl-pyrazol-1-yl)-1-[4-(4-chloro-3-methoxy-phenyl)-piperazin-1-yl]-ethanone and 3-trifluoromethylpyrazole were coupled to give the title compound: $^1$H NMR (400 MHz, CDCl$_3$) δ 8.08 (d, 1H), 7.30 (d, 1H), 6.73 (d, 1H), 6.70 (d, 1H), 6.60 (dd, 1H), 5.10 (s, 2H), 3.90 (s, 3H), 3.89 (m, 4H), 3.30 (m, 4H), 2.38 (s, 3H); LCMS observed for (M+H)+: 517.

Synthesis of 1-(4-Chloro-1-{2-[4-(4-chloro-3-methoxy-phenyl)-piperazin-1-yl]-2-oxo-ethyl}-5-methyl-1H-pyrazol-3-yl)-1H-pyridin-2-one

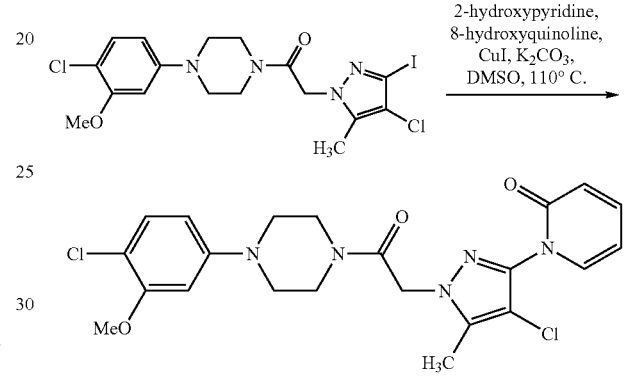

Following the previous example, 3-iodo-4-chloro-5-methyl-pyrazol-1-yl)-1-[4-(4-chloro-3-methoxy-phenyl)-piperazin-1-yl]ethanone and 2-hydroxypyridine were coupled to give the title compound: $^1$H NMR (400 MHz, CDCl$_3$) δ 8.19 (m, 1H), 7.74 (m, 1H), 7.22 (d, 1H), 7.06 (m, 2H), 6.60 (d, 2H), 6.48 (dd, 1H), 4.92 (s, 2H), 3.90 (s, 3H), 3.80 (m, 4H), 3.70 (m, 2H), 3.22 (m, 2H), 2.32 (s, 3H); LCMS observed for (M+H)+: 476.

359

Synthesis of 1-[4-(4-Chloro-3-hydroxy-phenyl)-piperazin-1-yl]-2-[4-chloro-5-methyl-3-(pyridin-2-yloxy)-pyrazol-1-yl]-ethanone

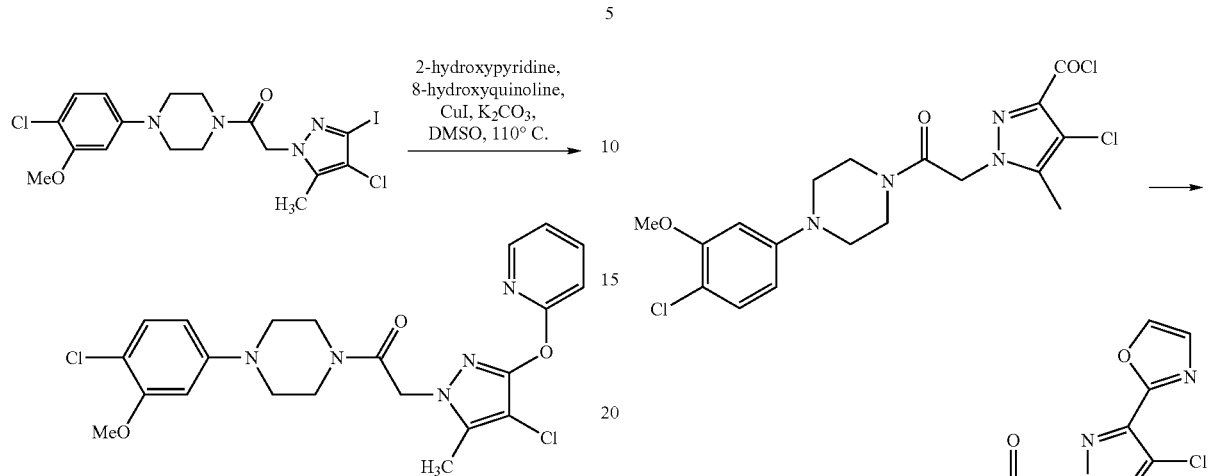

The title compound is also obtained from the previous reaction: $^1$H NMR (400 MHz, CDCl$_3$) δ 7.50-7.00 (m, 5H), 6.58 (d, 1H), 6.23 (d, 1H), 4.95 (s, 2H), 4.20-4.00 (m, 4H), 3.95 (s, 3H), 3.42 (m, 2H), 3.36 (m, 2H), 2.40 (s, 3H). LCMS observed for (M+H)$^+$: 476.

Protocol EE: General Procedure for the Synthesis of Oxazole Substitution on Pyrazol 4-Chloro-1-{2-[4-(4-chloro-3-methoxyphenyl)piperazin-1-yl]-2-oxethyl}-5-methyl-1H-pyrazole-3-carbonyl chloride

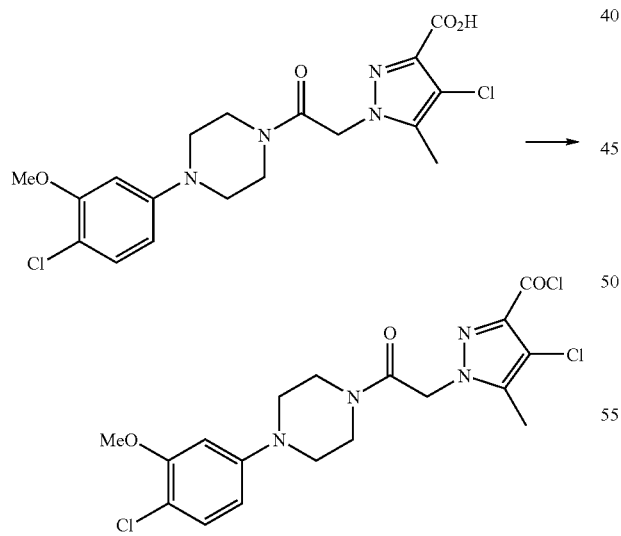

To a solution of 4-Bromo-1-{2-[4-(4-chloro-3-methoxyphenyl)-2-methylpiperazin-1-yl]-2-oxethyl}-5-methyl-1H-pyrazole-3-carboxylic acid obtained from last reaction in CH$_2$Cl$_2$ (1 mL) was added oxalyl chloride (1 mL). The reaction mixture was stirred at 60° C. for 12 h, cooled to room temperature and evaporated in vacuo to afford the title compound which was used as it was.

360

1-[4-(4-Chloro-3-methoxyphenyl)piperazin-1-yl]-2-(4-chloro-5-methyl-3-oxazol-2-yl-pyrazol-1-yl)ethanone

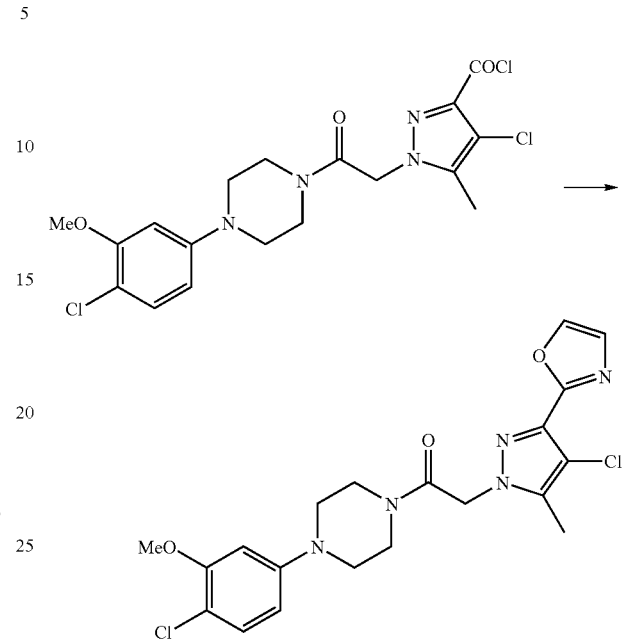

A mixture of 4-Chloro-1-{2-[4-(4-chloro-3-methoxyphenyl)piperazin-1-yl]-2-oxethyl}-5-methyl-1H-pyrazole-3-carbonyl chloride obtained from last reaction, 1,2,3-triazole (0.008 mL) and K$_2$CO$_3$ (41 mg) in tetramethylene sulfone (0.5 mL) was heated to 140° C. for 10 min and cooled to room temperature. The residue was purified on preparative HPLC to afford the title compound. $^1$H NMR: δ (400 MHz, CDCl$_3$) (400 MHz, CDCl$_3$) 7.71 (d, 1H), 7.29 (d, 1H), 7.22 (s, 1H), 6.48 (d, 1H), 6.44 (dd, 1H), 5.06 (s, 2H), 3.89 (s, 3H), 3.86 (m, 4H), 3.19 (m, 4H), 2.35 (s, 3H). LCMS (ES): M+H 450.1; HPLC retention time=4.45 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Protocol FF: General Procedure for the Synthesis of 1,3,4-oxadiazole Substitution on Pyrazol Synthesis of 1-[4-(4-Chloro-3-methoxyphenyl)piperazin-1-yl]-2-(4-chloro-5-methyl-3-[1,3,4]oxadiazol-2-yl-pyrazol-1-yl)ethanone

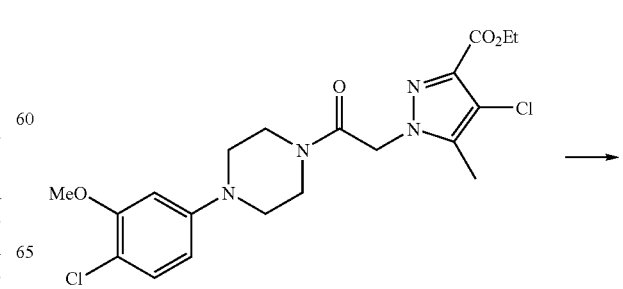

-continued

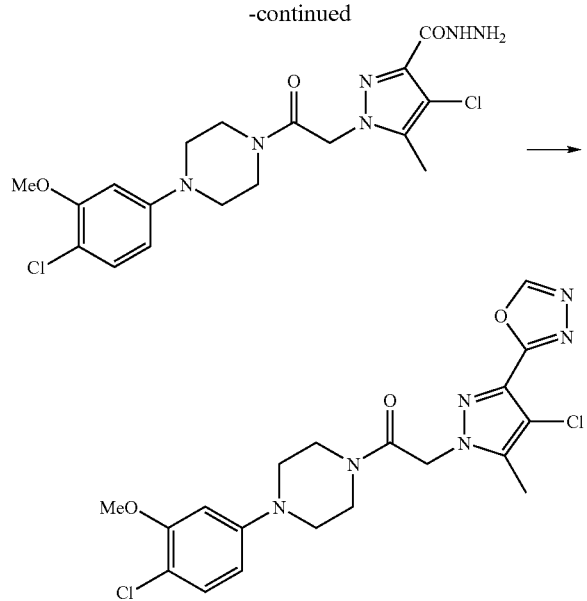

Step 1: To a solution of pyrazolecarboxylic ester (140 mg) in MeOH (20 mL) was added hydrazine hydrate (2 mL). The reaction mixture was stirred at 25° C. for 12 h and evaporated in vacuo to afford the corresponding hydrazide which was used as it was.

Step 2: The hydrazide was dissolved in trimethylorthoformate (30 mL), stirred and under a positive nitrogen flow heated to 80° C. for 3 h. The reaction mixture was cooled to room temperature and evaporated in vacuo. The residue was purified by preparative HPLC to afford the title compound: $^1$H NMR: δ (400 MHz, CDCl$_3$) 8.46 (s, 1H), 7.22 (d, 1H), 6.49 (s, 1H), 6.35 (dd, 1H), 5.09 (s, 2H), 3.89 (s, 3H), 3.76 (m, 4H), 3.20 (m, 4H), 2.36 (s, 3H). LCMS (ES): M+H 451.1; HPLC retention time=4.13 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)-2-(S)-methylpiperazin-1-yl]-2-(4-chloro-5-methyl-3-[1,3,4]oxadiazol-2-ylpyrazol-1-yl)ethanone

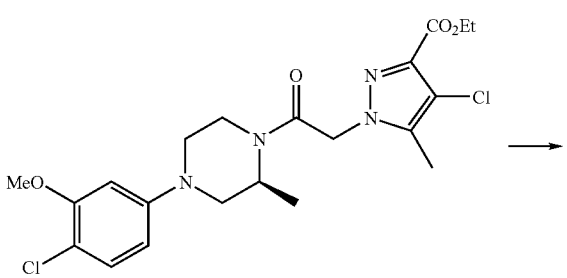

-continued

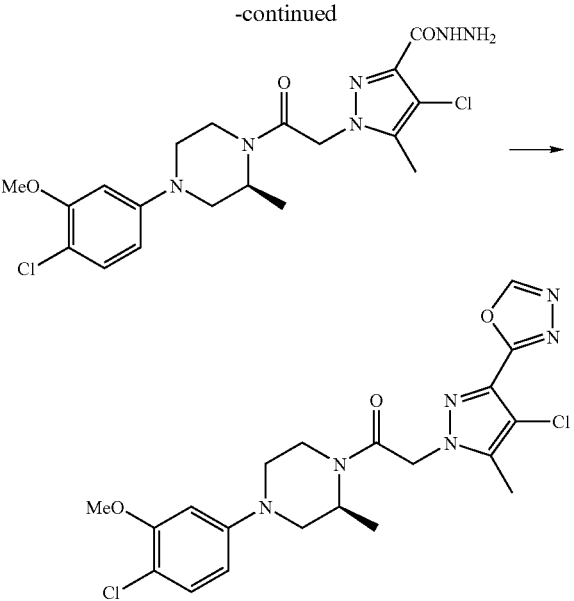

The title compound was obtained by following the same protocol as the previous example: LCMS (ES): M+H 465.1; HPLC retention time=5.02 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)piperazin-1-yl]-2-[4-chloro-5-methyl-3-(5-methyl-[1,3,4]oxadiazol-2-yl)pyrazol-1-yl]ethanone

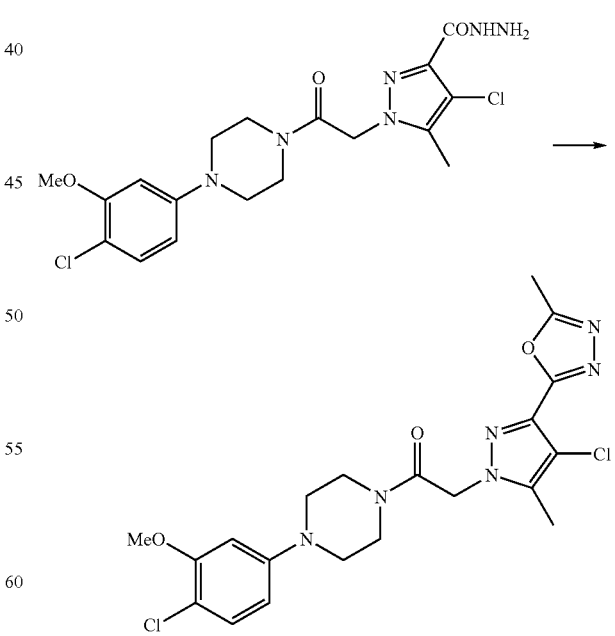

The title compound was obtained by following the same protocol as in the previous example, using trimethylorthoacetate: LCMS (ES): M+H 465.3; HPLC retention time=3.90 minutes (Agilent Zorbax SB-C18, 2.1×50 mm, 5μ, 35° C.)

Protocol GG: General Procedure for the Synthesis of Substituted Oxazoles on Pyrazoles Synthesis of 1-[4-(4-Chloro-3-methoxyphenyl)piperazin-1-yl]-2-[4-chloro-5-methyl-3-(4-methyloxazol-2-yl)pyrazol-1-yl]ethanone

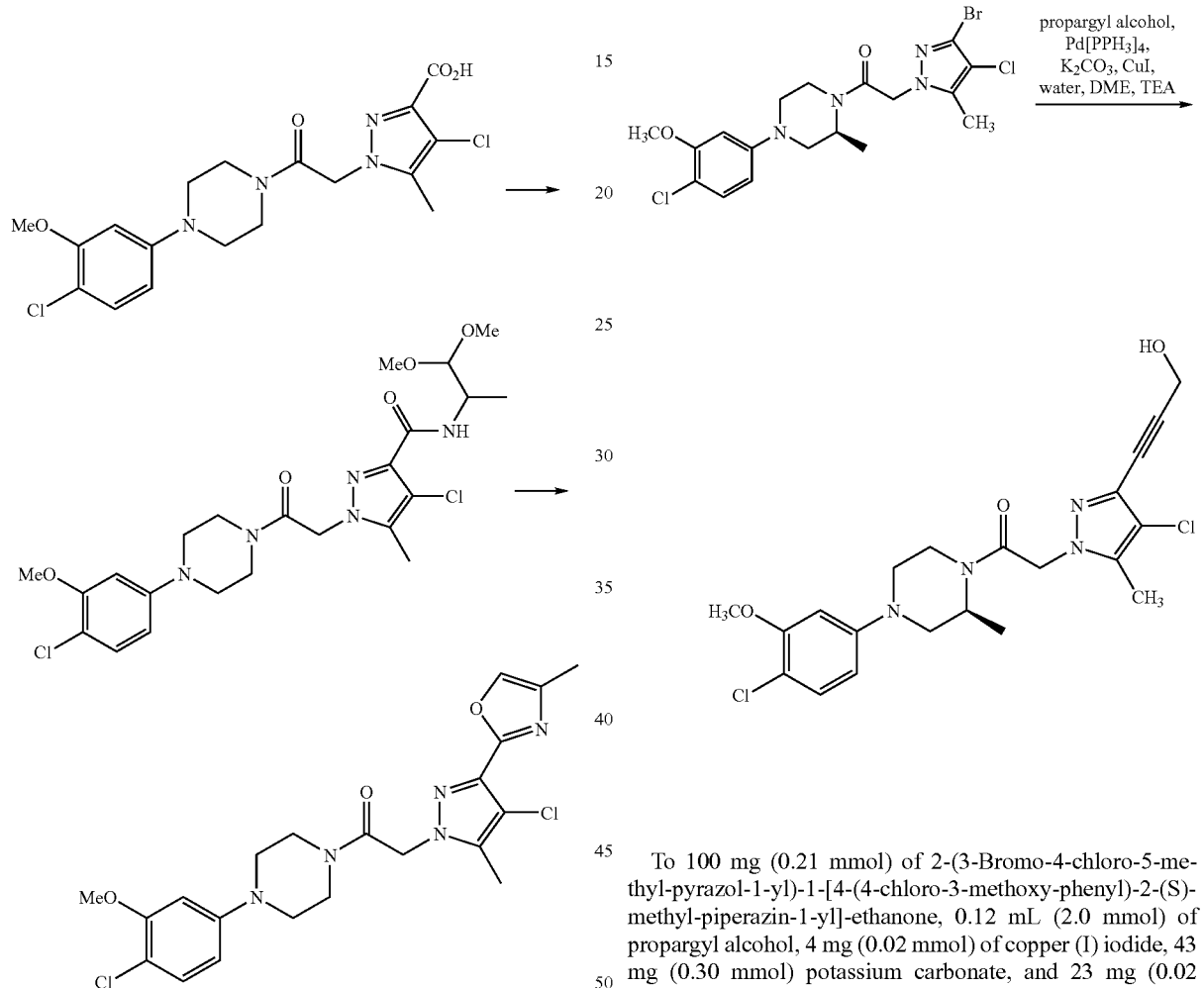

Step 1: The pyrazolcarboxylic acid was coupled with 2-aminopropaldehyde dimethylacetal by following Protocol P to afford the corresponding amide.

Step 2: The amide was dissolved in POCl$_3$ and heated to 90° C. for 24 h. The reaction mixture was cooled to room temperature and evaporated in vacuo. The residue was purified by preparative HPLC to afford the title compound: LCMS (ES): M+H 464.3; HPLC retention time=4.22 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Protocol HH: Sonagashira Coupling of Terminal Alkynes to 3-Halopyrazoles

Synthesis of 2-[4-Chloro-3-(3-hydroxy-prop-1-ynyl)-5-methyl-pyrazol-1-yl]-1-[4-(4-chloro-3-methoxy-phenyl)-2-(S)-methyl-piperazin-1-yl]-ethanone To 100 mg (0.21 mmol) of 2-(3-Bromo-4-chloro-5-methyl-pyrazol-1-yl)-1-[4-(4-chloro-3-methoxy-phenyl)-2-(S)-methyl-piperazin-1-yl]-ethanone, 0.12 mL (2.0 mmol) of propargyl alcohol, 4 mg (0.02 mmol) of copper (I) iodide, 43 mg (0.30 mmol) potassium carbonate, and 23 mg (0.02 mmol) of palladium (0) tetrakis-triphenylphosphine in 1.4 mL of 1,2-dimethoxyethane and 0.4 mL of water under a nitrogen atmosphere was added 0.2 mL of triethylamine, the vessel was sealed, and the mixture was heated at 135° C. for four hours. The mixture was cooled to ambient temperature, and was partitioned between ethyl acetate and water. The phases were separated, and the aqueous was back-extracted once with ethyl acetate. The combined ethyl acetate phases were washed once each with water, pH=7 1M phosphate buffer, and brine, dried over sodium sulfate, and concentrated. The residue was purified by chromatography to give the title compound: LCMS (ES) M+H=451.2; HPLC retention time=4.49 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-[4-Chloro-3-(3-hydroxy-prop-1-ynyl)-5-methyl-pyrazol-1-yl]-1-[4-(4-chloro-3-methoxy-phenyl)-piperazin-1-yl]-ethanone

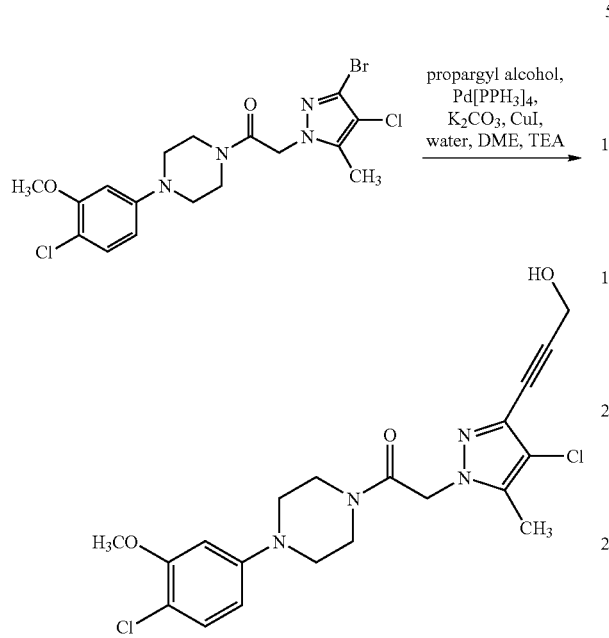

Following Protocol HH, 2-(3-Bromo-4-chloro-5-methyl-pyrazol-1-yl)-1-[4-(4-chloro-3-methoxy-phenyl)-piperazin-1-yl]-ethanone was cross-coupled with propargyl alcohol to give the title compound: LCMS (ES) M+H=437.1; HPLC retention time=4.24 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-3-ethynyl-5-methyl-pyrazol-1-yl)-1-(4-chloro-3-methoxyphenyl)-piperazin-1-yl)ethanone

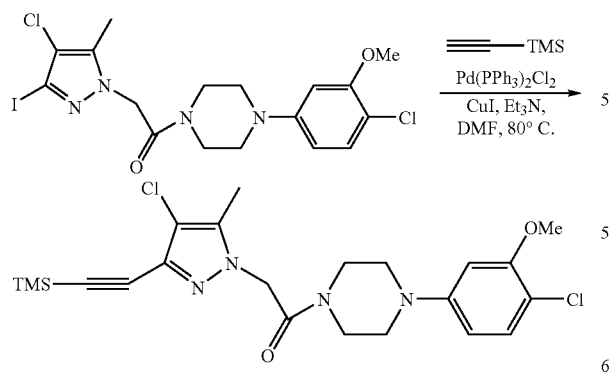

Following Protocol HH, TMSacetylene was cross-coupled to 2-(4-Chloro-3-iodo-5-methyl-pyrazol-1-yl)-1-[4-(4-chloro-3-methoxy-phenyl)-piperazin-1-yl]-ethanone to give the TMS-protected terminal alkyne: LC MS 479 (M+, 20-95 method, RT=5.43 min); $^1$H NMR (400 MHz, CDCl$_3$): δ 0.24 (s, 9H), 2.25 (s, 3H), 3.12 (apparent q, J=4.8 Hz, 4H), 3.68 (t, J=5.1 Hz, 2H), 3.74 (t, J=5.1 Hz, 2H), 3.87 (s, 3H), 4.92 (s, 2H), 6.40 (dd, J=2.5 & 8.8 Hz, 1H), 6.46 (d, J=2.5 Hz, 1H), 7.20 (d, J=8.4 Hz, 1H).

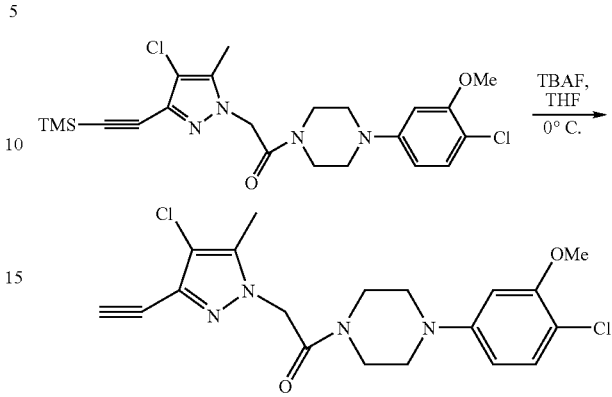

To a solution of the TMS protected alkyne from above (480 mg, 1 mmol) in THF (2 mL) at 0° C. under nitrogen atmosphere was added TBAF (1.4 mL, 1.4 mmol). After two hours, the reaction was quenched with saturated aq. NH$_4$Cl, and was extracted with Et$_2$O (4×20 mL). The combined ethereal layer was dried (Na$_2$SO$_4$) and concentrated. The residue was purified by chromatography to give the title compound: LC MS 407 (M+, 20-95 method, RT=4.42 min); $^1$H NMR (400 MHz, CDCl$_3$): δ 2.23 (s, 3H), 3.14-3.18 (m, 4H), 3.22 (s, 1H), 3.69 (t, J=4.8 Hz, 2H), 3.74 (t, J=5.1 Hz, 2H), 3.87 (s, 3H), 4.93 (s, 2H), 6.40-6.43 (m, 1H), 6.46 (d, J=2.6 Hz, 1H), 7.20 (d, J=8.3 Hz, 1H).

Protocol II: Preparation of Oxo-Pyridine Species

Synthesis of (4-Chloro-5-methyl-3-pyridin-3-yl-pyrazol-1-yl)-acetic acid ethyl ester

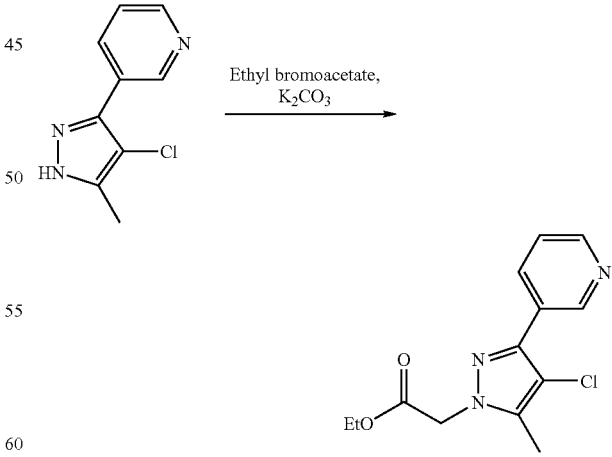

1.92 gm (9.95 mmol) of 3-(3-pyridyl)-4-chloro-5-methylpyrazole, 1.62 gm (11.75 mmol) potassium carbonate, and 1.51 gm (9.04 mmol) of ethyl bromoacetate were combined in 25 mL of dry N,N-dimethylformamide, and the mixture was heated at 85° C. for four hours. The mixture was then allowed to cool to ambient temperature, partitioned between 1M pH=7 phosphate buffer and ethyl acetate, and the phases were separated. The ethyl acetate phase was washed twice with water, once with brine, dried over Na₂SO₄, filtered, and concentrated in vacuo. The residue was purified by chromatography to give the title compound.

Synthesis of [4-Chloro-5-methyl-3-(1-oxy-pyridin-3-yl)-pyrazol-1-yl]-acetic acid ethyl ester

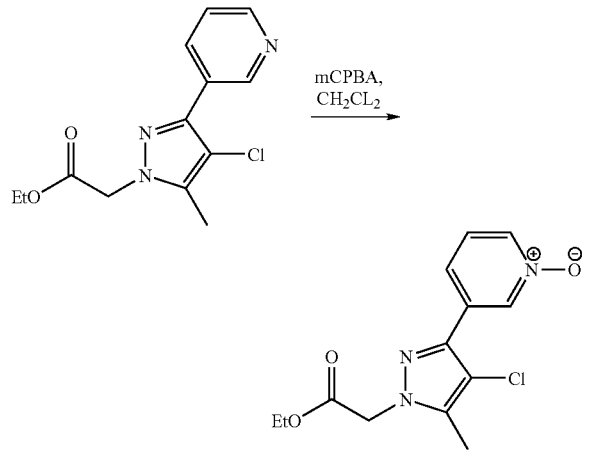

370 mg (1.32 mmol) of (4-Chloro-5-methyl-3-pyridin-3-yl-pyrazol-1-yl)-acetic acid ethyl ester was dissolved in 6 mL of dry dichloromethane, the solution was cooled to 0° C., and 320 mg (1.85 mmol) of approximately 77% meta-chloroperoxybenzoic acid was added. After 30 minutes, the flask was removed from the ice-water bath, and was allowed to warm to room temperature. After three hours, the reaction was partitioned between ethyl acetate and saturated sodium bicarbonate, and the phases were separated. The ethyl acetate phase was dried over Na₂SO₄, filtered, and concentrated in vacuo. The solids were isolated via filtration after trituration with ether to give the title compound.

Synthesis of Sodium [4-chloro-5-methyl-3-(1-oxy-pyridin-3-yl)-pyrazol-1-yl]-acetate

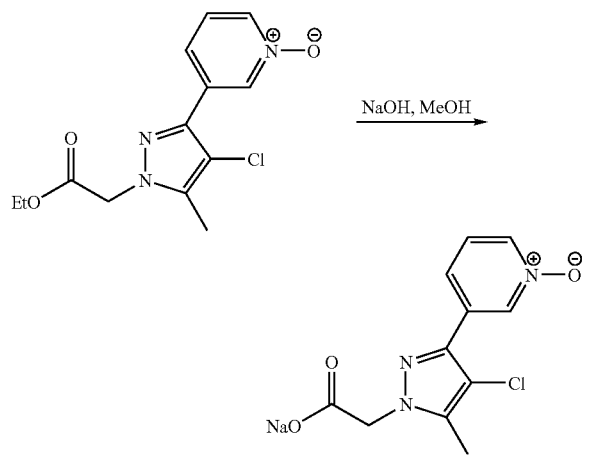

170 mg (0.58 mmol) of [4-Chloro-5-methyl-3-(1-oxy-pyridin-3-yl)-pyrazol-1-yl]-acetic acid ethyl ester and 46 mg (1.6 mmol) of sodium hydroxide were combined in 2.3 mL of dry methanol at 50° C. After 30 minutes the reaction was complete, and the flask was allowed to cool to room temperature. The slurry was diluted with ethyl acetate, and the solids were isolated by filtration to give the title compound.

[4-Chloro-5-methyl-3-(1-oxypyridin-4-yl)-pyrazol-1-yl]-acetic acid

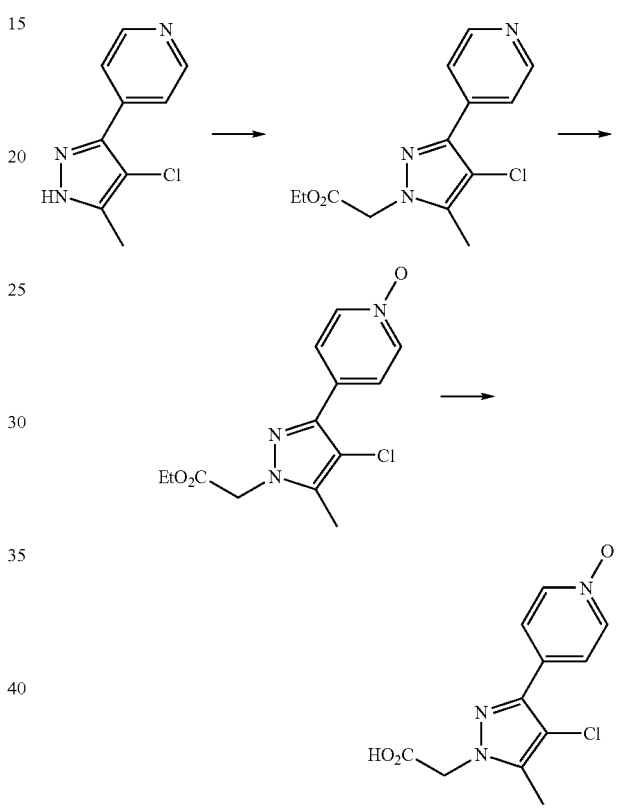

The title compound was obtained by following Protocol II.

Protocol JJ: Heteroaryl Substituted Pyrazoles Via Cycloaddition and Cyclization Reactions Synthesis of 2-(4-chloro-3-tetrazol-5-yl-5-methyl-pyrazol-1-yl)-1-[4-(4-chloro-3-methoxy-phenyl)-piperazin-1-yl]-ethanone

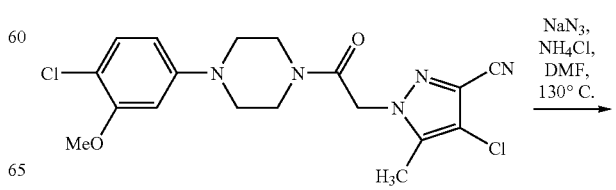

-continued

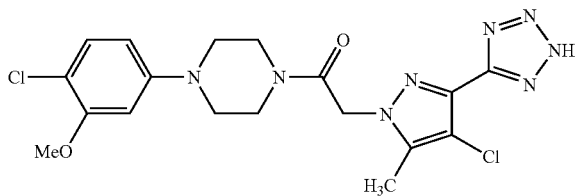

A mixture of 2-(3-cyano-4-chloro-5-methyl-pyrazol-1-yl)-1-[4-(4-chloro-3-methoxy-phenyl)-piperazin-1-yl]-ethanone (41 mg, 0.1 mmol, 1 equiv), NaN3 (130 mg, 2 equiv), and NH4Cl (110 mg, 2 equiv) in 1 mL of DMF were heated at 130° C. for 3 hours, and then cooled to room temperature. The crude product was purified by reverse phase HPLC (acetonitrile-H2O with 0.1% TFA as eluent) to yield the title compound: 1H NMR (400 MHz, CDCl3) δ 7.35 (d, 1H), 6.82 (d, 1H), 6.70 (dd, 1H), 5.12 (s, 2H), 3.90 (s, 3H), 3.88 (m, 4H), 3.50 (m, 2H), 3.34(m, 2H), 2.33 (s, 3H); LCMS observed for (M+H)+: 451.

Synthesis of 2-[4-chloro-5-methyl-3-[1,2,3]oxadiazol-3-yl-pyrazol-1-yl]-1-[4-(4-chloro-3-methoxy-phenyl)-piperazin-1-yl]-ethanone

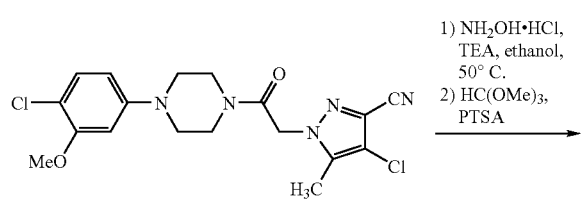

1) NH2OH·HCl, TEA, ethanol, 50° C.
2) HC(OMe)3, PTSA

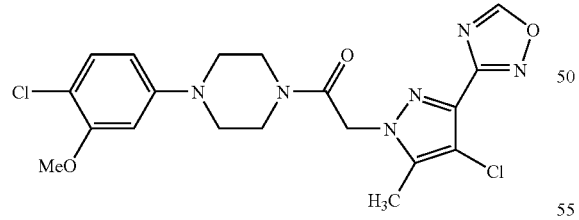

A mixture of 2-(3-cyano-4-chloro-5-methyl-pyrazol-1-yl)-1-[4-(4-chloro-3-methoxy-phenyl)-piperazin-1-yl]-ethanone (41 mg, 0.1 mmol, 1 equiv), NH2OH.HCl (35 mg, 5 equiv) and Et3N (140 µL, 10 equiv) in 1 mL of ethanol were heated at 50° C. for 2 hours and then cooled to room temperature. The white solid was collected, treated with trimethylformate (1 mL) and 1 crystal of PTSA at 50° C. for 2 hours. Reverse phase HPLC (acetonitrile-H2O with 0.1% TFA as eluent) gave the title compound: $^1$H NMR (400 MHz, CDCl3) δ 8.80 (s, 1H), 7.30 (d, 1H), 6.72 (d, 1H), 6.62 (dd, 1H), 5.18 (s, 2H), 3.90 (s, 3H), 3.92 (m, 2H), 3.80 (m, 2H), 3.38(m, 2H), 3.30 (m, 2H), 2.39 (s, 3H); LCMS observed for (M+H)+: 451.

Protocol KK: Synthesis of Compounds Using Negishi Coupling Reactions

Synthesis of 1-[4-(4-Chloro-3-methoxy-phenyl)-piperazin-1-yl]-2-[4-chloro-5-methyl-3-(1-methyl-1H-imidazol-2-yl)-pyrazol-1-yl]-ethanone

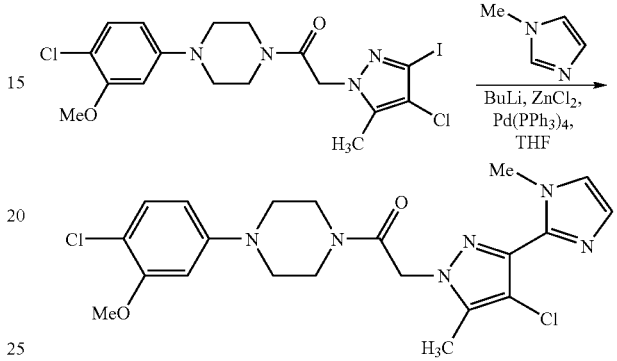

1-methylimidazole (48 mg, 1.5 equiv) in 10 mL of THF at −78° C. was treated with BuLi (2.5 M in hexanes, 0.28 mL, 1.5 equiv) for 1 h. ZnCl2 (1M in ether (1.8 mL, 4.5 equiv) was added and the mixture was stirred at 0° C. for 1 h. 2-(3-iodo-4-chloro-5-methyl-pyrazol-1-yl)-1-[4-(4-chloro-3-methoxy-phenyl)-piperazin-1-yl]-ethanone (204 mg, 0.4 mmol, 1 equiv) and Pd(PPh3)4 (46 mg, 0.1 equiv) were added sequentially. The resulting mixture was refluxed overnight, cooled to room temperature, quenched with water, extracted with EtOAc. The organic layer was purified by reverse phase HPLC to yield the title compound: LCMS Retention time: 3.3 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 463.

Protocol LL: Mannich Additions to Aromatic Rings

1-[4-(4-Chloro-5-methoxy-2-methylaminomethyl-phenyl)-piperazin-1-yl]-2-(4-chloro-5-methyl-3-trifluoromethyl-pyrazol-1-yl)-ethanone

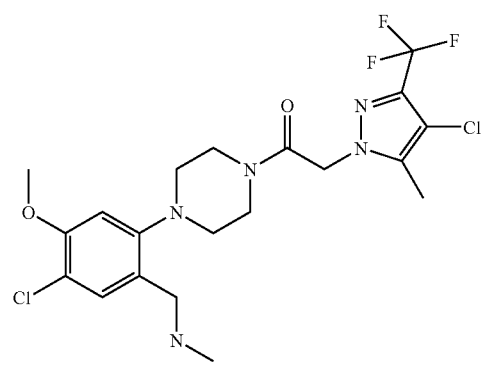

250 mg of 1-[4-(4-Chloro-5-methoxyphenyl)-piperazin-1-yl]-2-(4-chloro-5-methyl-3-trifluoromethyl-pyrazol-1-yl)- ethanone (0.55 mmol, 1.0 eq), 374 mg methylamine HCl (5.5 mmol, 10.0 eq), 414 uL 37% formaldehyde in H₂O (5.5 mmol, 10.0 eq), and 1 mL DME were combined in a 4 mL vial. The mixture was heated in a 60° C. oil bath overnight and purified by preparative HPLC: LC/MS(ES) (M+H) 494.4; HPLC retention time=5.71 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

Example 3

Protocols referred to within the following example are the protocols described within Example 3, unless otherwise indicated.

Protocol A: Metal Catalysed Arylation Reactions of Secondary Amines

Synthesis of 1-[4-(4-Chloro-3-methoxy-phenyl)-piperazin-1-yl]-2-(4-chloro-5-methyl-3-piperazin-1-yl-pyrazol-1-yl)-ethanone

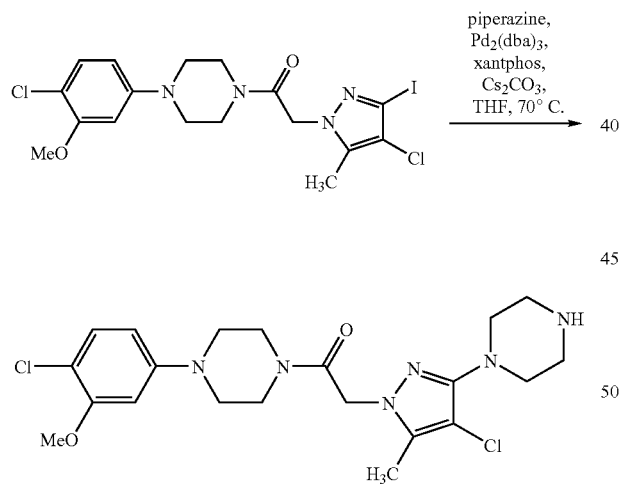

Following Protocol A from example 1, A mixture of 2-(3-iodo-4-chloro-5-methyl-pyrazol-1-yl)-1-[4-(4-chloro-3-methoxy-phenyl)-piperazin-1-yl]-ethanone (204 mg, 1 equiv), piperazine (430 mg, 10 equiv), Xantphos (40 mg, 0.3 equiv), Pd₂(dba)₃ (72 mg, 0.1 equiv) and Cs₂CO₃ (200 mg, 1.5 equiv) in 1 mL of THF were heated at 70° C. overnight and then cooled to room temperature, taken up in EtOAc, washed with water. The organic layer was purified by reverse phase HPLC (acetonitrile-H₂O with 0.1% TFA as eluent) to yield the title compound: LCMS Retention time: 3.07 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)⁺: 467.

Synthesis of 1-[4-(4-Chloro-3-methoxy-phenyl)-piperazin-1-yl]-2-(4-chloro-5-methyl-3-pyrrolidin-1-yl-pyrazol-1-yl)-ethanone

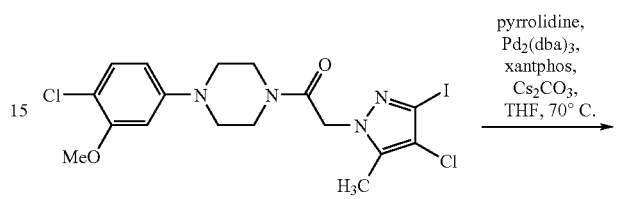

The title compound was prepared following a variation on Protocol A. LCMS retention time: 4.77 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)⁺: 452.

Synthesis of 1-[4-(4-Chloro-3-methoxy-phenyl)-piperazin-1-yl]-2-(4-chloro-5-methyl-4-piperidin-1-yl-pyrazol-1-yl)-ethanone

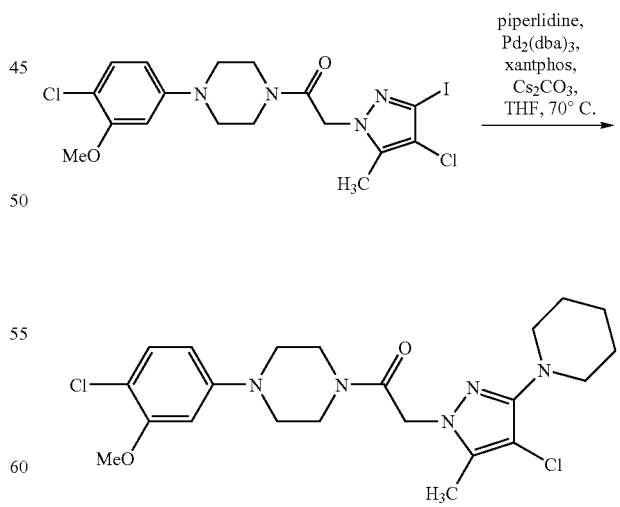

The title compound was prepared following a variation on Protocol A. LCMS retention time: 5.07 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 466.

Synthesis of 1-[4-(4-Chloro-3-methoxy-phenyl)-piperazin-1-yl]-2-[4-chloro-5-methyl-3-(4-methyl-piperazin-1-yl)-pyrazol-1-yl]-ethanone

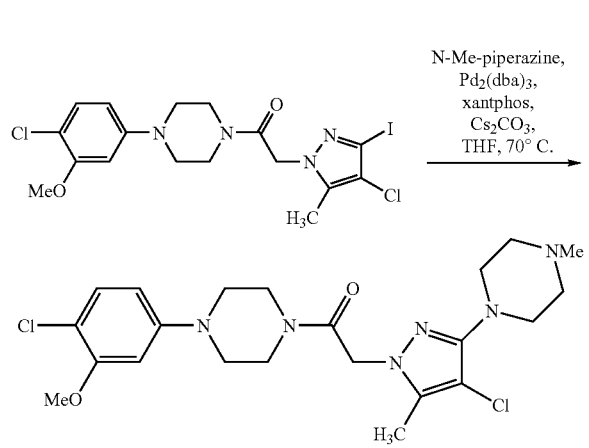

The title compound was prepared following a variation on Protocol A. LCMS retention time: 3.24 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 481.

Synthesis of 2-[4-Chloro-3-(1,1-dioxo-1lambda*6*-thiomorpholin-4-yl)-5-methyl-pyrazol-1-yl]-1-[4-(4-chloro-3-methoxy-phenyl)-piperazin-1-yl]-ethanone

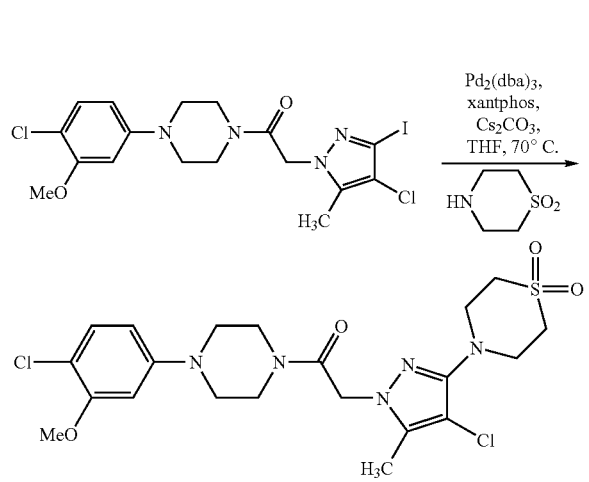

The title compound was prepared following a variation on Protocol A. LCMS retention time: 4.26 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 516.

Synthesis of 2-(4-Chloro-3-dimethylamino-5-methyl-pyrazol-1-yl)-1-[4-(4-chloro-3-methoxy-phenyl)-piperazin-1-yl]-ethanone

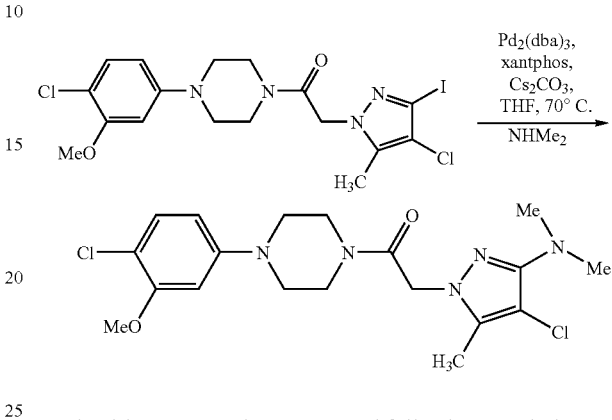

The title compound was prepared following a variation on Protocol A. LCMS retention time: 5.29 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 426.

Protocol I: General Procedure for the Synthesis of Pyrazoles Via Condensation of Hydrazines with β-Diketones Synthesis of 3-Trifluorometyl-1,4,6,7-tetrahydro-pyrazolo[4,3-c]pyridine-5-carboxylic acid tert-butyl ester

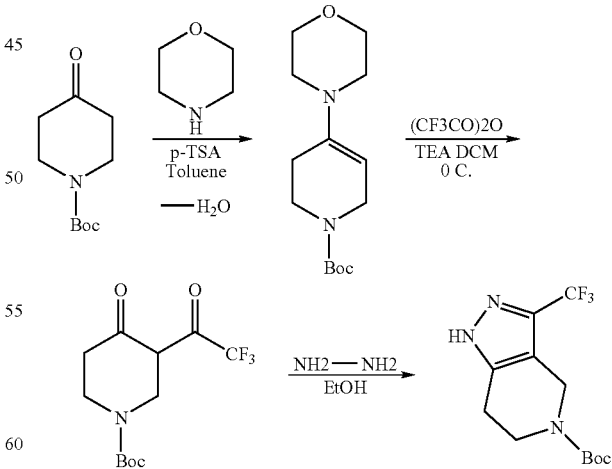

5 g 1-Boc-4-piperidone (25 mmol), 15 mg p-TSA, 25 ml benzene and 2.2 ml morphiline (25 mmol) were added in a 50 ml round bottle flask with Dean-Stark, headed to reflux overnight. After removing most of benzene by rotor-evaporator, 15 ml DCM was added, cold in ice-bath and added 0.35 ml TEA (25 mmol), 0.35 ml Trifluoroacetic anhydride (25 mmol) was added drop wise at 0 C. After addition, remove the ice-bath. The reaction mixture was stirred at room temperature overnight. The solvent was removed by rotor-evaporator. Dissolved the residues in anhydride EtOH, and 3 equivalent of hydrazine was added under ice-bath, then removed the ice-bath and stirred at room temperature overnight. The solvent was removed by rotor-evaporator. The compounds were purified by normal phase column (Column: 140 g silica gel, Running Buffer: 50% EtOAc/Hexane) to gave above title product, along with some Boc-deprotected product.

Protocol L: Chlorination or Bromination of Pyrazoles with N-Chlorosuccinimide (NCS) or N-Bromosuccinimide (NBS)

4-Chloro-3-trifluoromethyl-1H-pyrazole

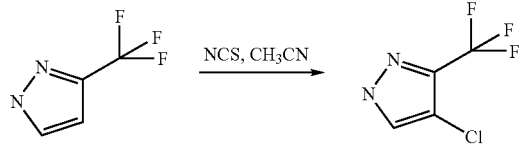

The above compound was prepared using same Protocol L from example 1.

4-Chloro-3-iodo-5-trifluoromethylpyrazole

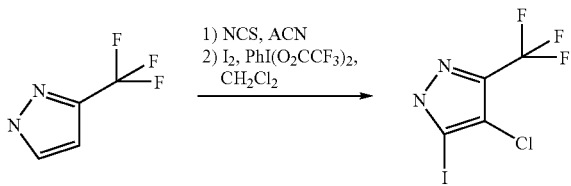

The above compound was prepared using same protocol as in the synthesis of 4-Chloro-3-Iodo-5-methylpyrazole.

3-Iodoindazole

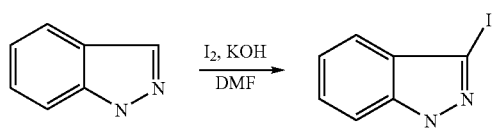

Iodine (8 g, 32 mmol), potassium hydroxide (3.36 g, 60 mmol) were successively added to a solution of indazole (1.88 g, 16 mmol) in DMF (30 mL) at room temperature Stirring continued for 1.5 h. Then, the reaction mixture was diluted with ether (100 mL), washed with saturated aqueous sodiumthio sulfite. The aqueous phase was back extracted with ether, the ethereal layer was washed with water, brine, dried ($MgSO_4$) and concentrated. The iodoindazole obtained in 95% yield and was pure enough for further reactions.

Protocol P: Couplings of Arylpiperazines with Pyrazolyl-Acetic Acid Derivatives—Compounds Prepared by HATU Mediated Coupling 2-(4-Chloro-5-(2-hydroxypropyl)-3-trifluoromethylpyrazol-1-yl)-1-(4-(4-chloro-3-methoxyphenyl)piperazin-1-yl)ethanone

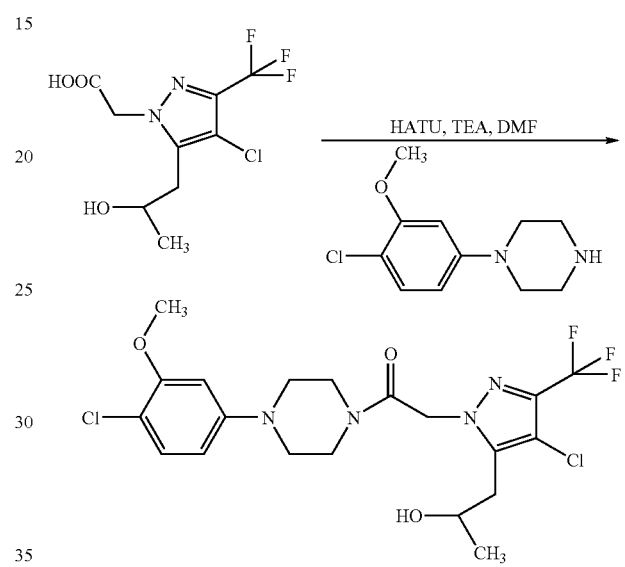

The above compound was synthesized using the same Protocol P in example 1, and the crude product was purified by HPLC. LC MS: m/z 495 (M+H), retention time=4.71 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-(4-(4-chloro-3-methoxyphenyl)-2(R)-piperazin-1-yl)-2-(4-Chloro-3-(1-hydroxy-3-pyrimidin-2-yl-pyrazol-1-yl)ethanone

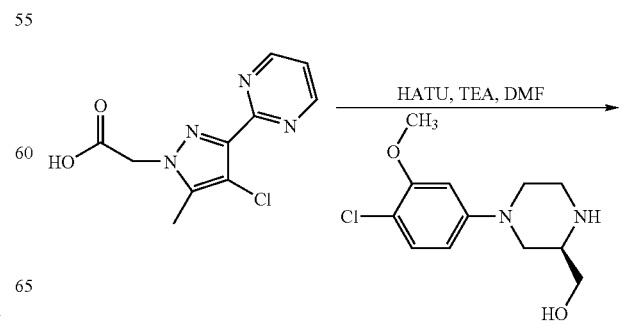

-continued

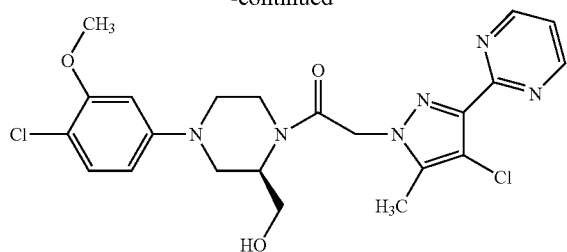

The above compound was synthesized following Protocol P, and the crude product was purified by PTLC using 70 ethyl acetate: 30% n-hexane as mobile phase. LC MS: m/z 491 (M+H), $R_f$=3.59 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-2-(R)-hydroxymethyl-piperazin-1-yl]-2-[4-chloro-5-methyl-3-(2-methyl-pyridin-4-yl)-pyrazol-1-yl]-ethanone

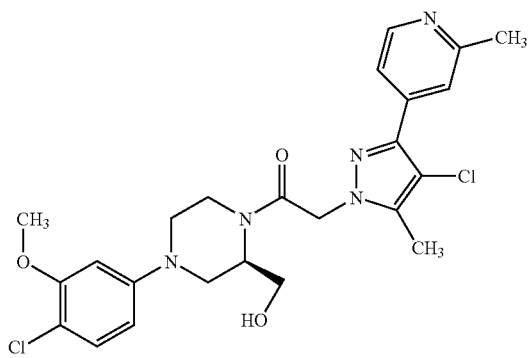

Title compounds were prepared following Protocol P, wherein 1-(3-methoxyphenyl-4-chloro)-3-(R)-hydroxymethyl piperazine and ([4-Chloro-5-methyl-3-(2-methyl-pyridin-4-yl)-pyrazol-1-yl]-acetic acid were used as the coupling components. Purified by HPLC (Column: Varian Dynamax 250×21.4 mm Microsorb 100-8 C18, Buffer A: 0.1% TFA/H₂O, Buffer B: 0.1% TFA/ACN, Gradient: B from 10% to 95% within 60 min, Flow: 20 ml/min) to give the title products as a white powder: HPLC retention time=4.94 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=504.1, found=504.1.

Synthesis of 1-[4-(4-Chloro-2-fluoro-5-methoxy-phenyl)-piperazin-1-yl]-2-(4-chloro-5-methyl-3-pyrimidin-2-yl-pyrazol-1-yl)-ethanone

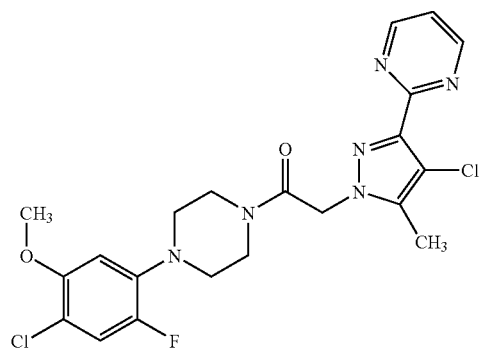

Title compound was prepared following Protocol P, wherein 1-(4-Chloro-2-fluoro-5-methoxy-phenyl)piperazine and [4-chloro-5-methyl-3-pyrimidin-2-yl-pyrazol-1-yl]-acetic acid were used as the coupling components. Purified by TLC (5% MeOH in DCM) to give the title compound as a white solid: HPLC retention time=3.41 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=479.1, found=479.1.

Synthesis of 1-[4-(4-Chloro-2-fluoro-5-methoxy-phenyl)-2-(S)-methyl-piperazin-1-yl]-2-[4-chloro-3-(1-hydroxy-1-methyl-ethyl)-5-methyl-pyrazol-1-yl]-ethanone

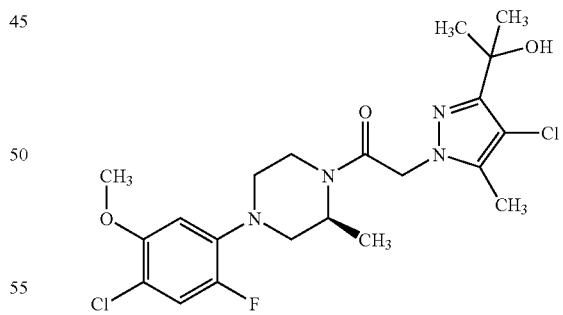

Title compound were prepared following Protocol P, wherein 1-(4-Chloro-2-fluoro-5-methoxy-phenyl)-3-(S)-methyl piperazine and [4-chloro-3-(1-hydroxy-1-methyl-ethyl)-5-methyl-pyrazol-1-yl]-acetic acid were used as the coupling components. Purified by HPLC (Column: Varian Dynamax 250×21.4 mm Microsorb100-8 C18, Buffer A: 0.1% TFA/H₂O, Buffer B: 0.1% TFA/ACN, Gradient: B from 25% to 95% within 60 min, Flow: 20 ml/min) to give the title compound: HPLC retention time=4.48 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=473.1, found=455.1 and 473.1.

Synthesis of 2-(4-Chloro-3-iodo-5-methyl-pyrazol-1-yl)-1-[4-(4-chloro-3-methoxy-phenyl)-2(S)-methyl-piperazin-1-yl]-ethanone

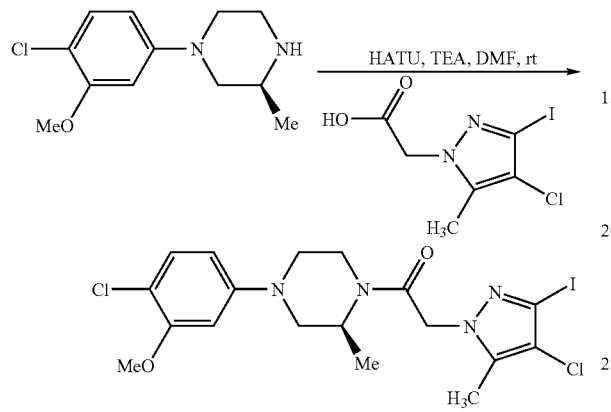

Following Protocol P, 1-(4-Chloro-3-methoxy-phenyl)-3-(S)-methyl-piperazine and (4-Chloro-3-iodo-5-methyl-pyrazol-1-yl)-acetic acid were coupled to give the title compound: LCMS Retention time: 5.20 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 523.

Synthesis of 1-[4-(4-Chloro-2-fluoro-5-methoxy-phenyl)-piperazin-1-yl]-2-(4-chloro-3-iodo-5-methyl-pyrazol-1-yl)-ethanone

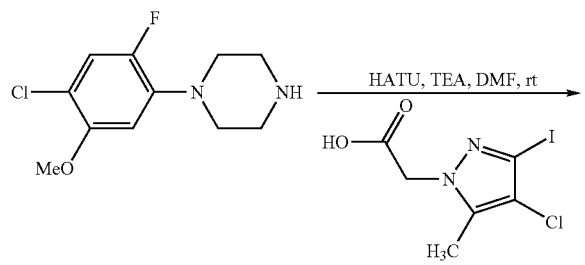

Following Protocol P, 1-(4-Chloro-2-fluoro-5-methoxyphenyl)-piperazine and (4-Chloro-3-iodo-5-methyl-pyrazol-1-yl)-acetic acid were coupled to give the title compound: LCMS Retention time: 5.13 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 527.

Synthesis of 1-[4-(4-Chloro-2-fluoro-5-methoxy-phenyl)-2(S)-methyl-piperazin-1-yl]-2-(4-chloro-3-iodo-5-methyl-pyrazol-1-yl)-ethanone

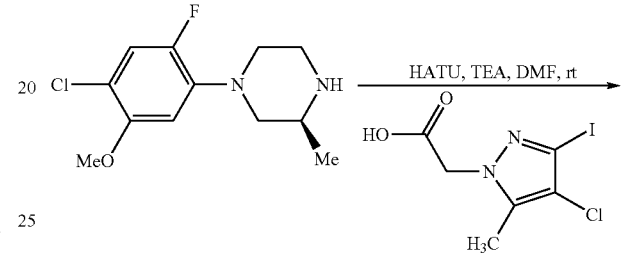

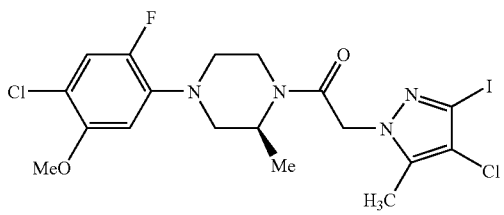

Following Protocol P, 1-(4-Chloro-2-fluoro-5-methoxyphenyl)-3-(S)-methyl-piperazine and (4-Chloro-3-iodo-5-methyl-pyrazol-1-yl)-acetic acid were coupled to give the title compound: LCMS Retention time: 5.23 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 541.

Synthesis of 1-[4-(4-Chloro-3-methoxyphenyl)-2-(S)-methylpiperazin-1-yl]-2-(4-chloro-5-methyl-3-oxazol-2-yl-pyrazol-1-yl)ethanone

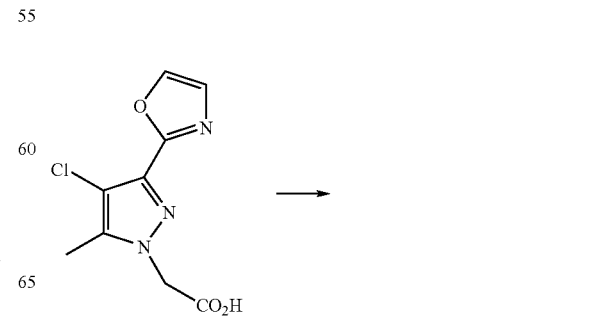

-continued

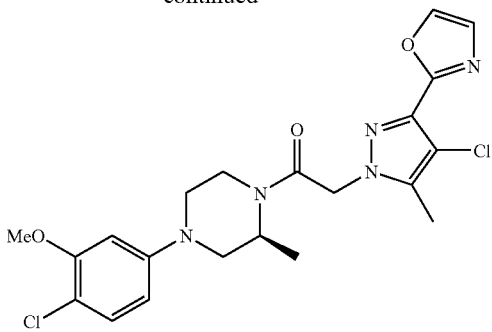

The title compound was obtained according to peptide coupling Protocol P. LCMS (ES) M+H 464.1; R$_f$ 4.40 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-Chloro-3-methoxyphenyl)-2-(R)-hydroxymethylpiperazin-1-yl]-2-(4-chloro-5-methyl-3-oxazol-2-ylpyrazol-1-yl)ethanone

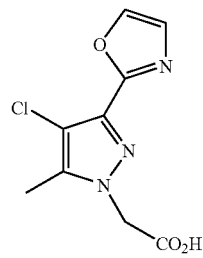

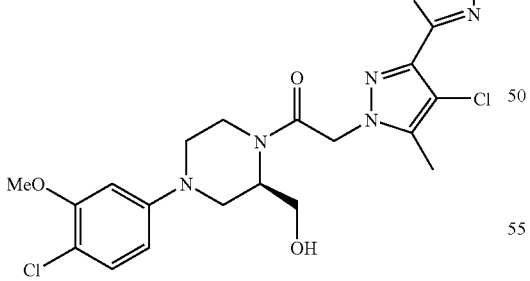

The title compound was obtained according to peptide coupling Protocol P. LCMS (ES) M+H 480.2; R$_f$ 3.95 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-[4-Chloro-5-methyl-3-(2-methyl-pyridin-4-yl)-pyrazol-1-yl]-1-[4-(2,4-difluoro-5-methoxy-phenyl)-piperazin-1-yl]-ethanone

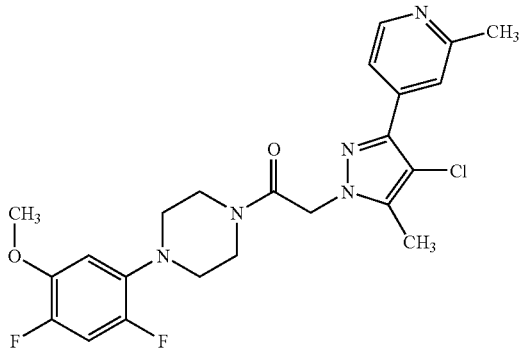

Title compound was prepared following Protocol P, wherein 2,4-difluoro-5-methoxy-phenyl)-piperazine and [4-Chloro-5-methyl-3-(2-methyl-pyridin-4-yl)-pyrazol-1-yl]-acetic acid were used as the coupling components. Purified by HPLC to give the title compound: HPLC retention time=3.3 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=476.1, found=476.1.

Synthesis of 2-[4-chloro-3(1,2-dihydroxy-1-methyl-ethyl)-5-methyl-pyrazol-1-yl]-1-[4-(3-methoxy-4-chloro-phenyl)-piperazin-1-yl]-ethanone

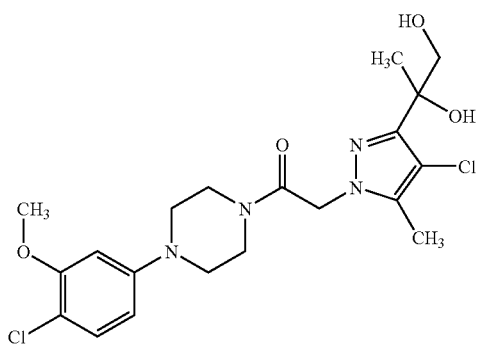

Title compounds were prepared following Protocol P, wherein 1-[4-(3-methoxy-4-chloro-phenyl)]-piperazin and 2-[4-chloro-3(1, 2-dihydroxy-1-methyl-ethyl)-5-methyl-pyrazol-1-yl]-acetic acid were used as the coupling components. Purified by HPLC (Column: Varian Dynamax 250× 21.4 mm Microsorb100-8 C18, Buffer A: 0.1% TFA/H$_2$O, Buffer B: 0.1% TFA/ACN, Gradient: B from 10% to 60% within 40 min, Flow: 20 ml/min) to give the title compound. HPLC retention time=3.41 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=457.1, found=439.1(—H$_2$O), 457.1.

Synthesis of 1-(4-(4-chloro-3-methoxyphenyl)piperazin-1-yl)-2-(4-Chloro-5-pyrazol-1-ylmethyl-3-trifluoromethyl pyrazol-1-yl)ethanone

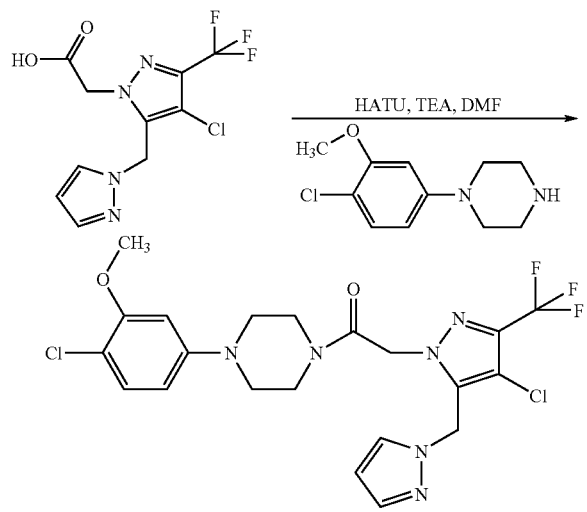

The above compound was synthesized using (4-Chloro-5-pyrazol-1-ylmethyl-3-trifluoromethyl-pyrazol-1-yl)-acetic acid, following Protocol P. The crude product was purified by PTLC using 70% ethyl acetate: 30% n-hexane as mobile phase: LC MS m/z 517 (M+H), R$_t$=5.47 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); 1H NMR (400 MHz, CDCl3): δ 3.17 (t, J=5.1 Hz, 2H), 3.23 (t, J=5.1 Hz, 2H) 3.64 (t, J=5.2 Hz, 2H), 3.77 (t, J=5.2 Hz, 2H), 3.89 (s, 3H), 5.32 (s, 2H), 5.38 (s, 2H), 6.28 (t, J=2.2 Hz, 1H), 6.43 (apparent dd, J=2.9 & 8.5 Hz, 1H), 6.49 (d, J=2.6 Hz, 1H), 7.22 (d, J=8.3 Hz, 1H), 7.47 (t, J=1.9 Hz, 1H).

Protocol T: K$_2$CO$_3$ Mediated Coupling Reaction of Chloroacetyl Arylpiperazines with Pyrazoles Synthesis of 2-(4-Chloro-5-(1-hydroxy-1-methylethyl)-3-trifluoromethylpyrazol-1-yl)-1-(4-(4-chloro-3-methoxyphenyl)piperazin-1-yl)ethanone

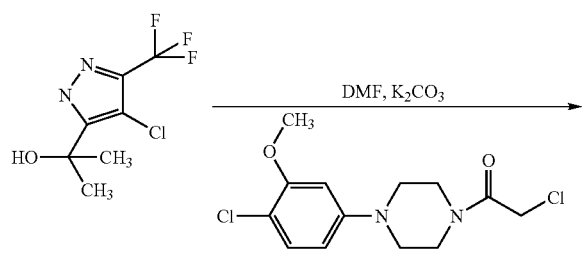

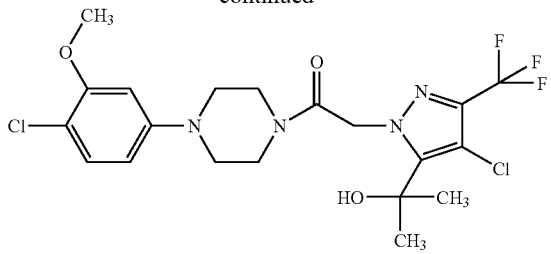

The above compound was synthesized using 2-(4-Chloro-5-trifluoromethyl-2H-pyrazol-3-yl)-propan-2-ol, following Protocol T from example 1, and the crude product was purified by HPLC. LC MS: m/z 495 (M+H), R$_t$=5.33 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

2-(4-Chloro-5-iodo-3-trifluoromethyl-pyrazol-1-yl)-1-[4-(4-chloro-3-methoxy-phenyl)-piperazin-1-yl]-ethanone

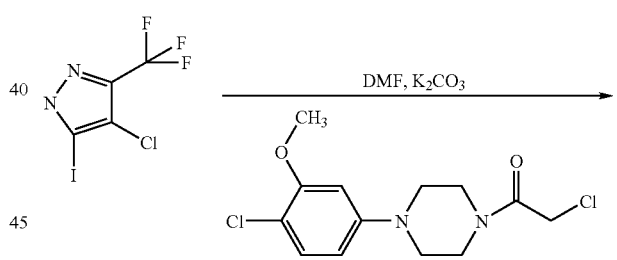

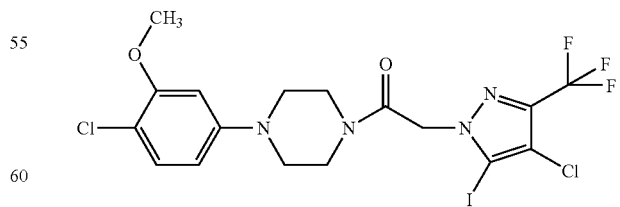

The above compound was prepared using 4-Chloro-5-iodo-3-trifluoromethyl-1-H-pyrazole, following Protocol T.

Synthesis of 1-[4-(4-Chloro-2-fluoro-5-methoxy-phenyl)-2-(S)-methyl-piperazin-1-yl]-2-(4-chloro-5-methyl-3-pyrimidin-2-yl-pyrazol-1-yl)-ethanone and 1-[4-(4-Chloro-2-fluoro-5-methoxy-phenyl)-2-(S)-methyl-piperazin-1-yl]-2-(S)-methyl-piperazin-1-yl]-2-(4-chloro-3-methyl-5-pyrimidin-2-yl-pyrazol-1-yl)ethanone

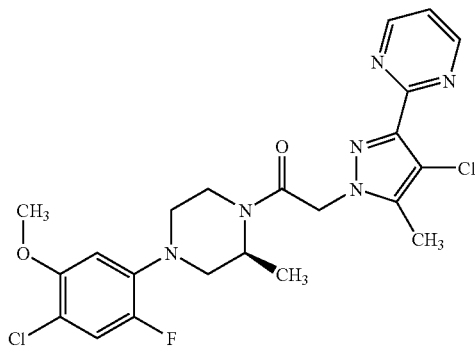

Isomer 1

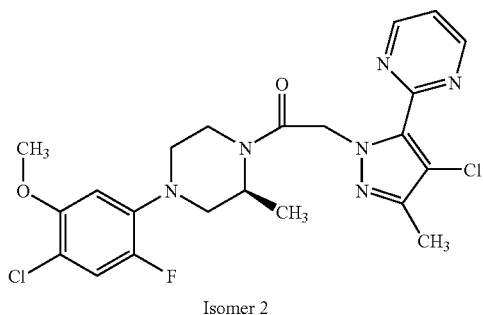

Isomer 2

Title compounds were prepared following Protocol T, wherein 2-Chloro-1-[4-(4-chloro-2-fluoro-5-methoxy-phenyl)-2-(S)-methyl-piperazin-1-yl]-ethanone and 4-chloro-5-methyl-3-pyrimidin-2-yl-pyrazol were used as the coupling components. Purified by HPLC (Column: Varian Dynamax 250×21.4 mm Microsorb100-8 C18, Buffer A: 0.1% TFA/H$_2$O, Buffer B: 0.1% TFA/ACN, Gradient: B from 10% to 95% within 60 min, Flow: 20 ml/min) to give above title products as white powders.

Isomer I: HPLC retention time=4.31 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=493.1, found=493.4.

Isomer II: HPLC retention time=4.66 minutes (same conditions as above); MS (ES) M+H expect=493.1, found=493.4.

Synthesis of 1-[4-(4-Chloro-3-methoxyphenyl)piperazin-1-yl]-2-(4-chloro-5-methyl-3-oxazol-5-ylpyrazol-1-yl)ethanone

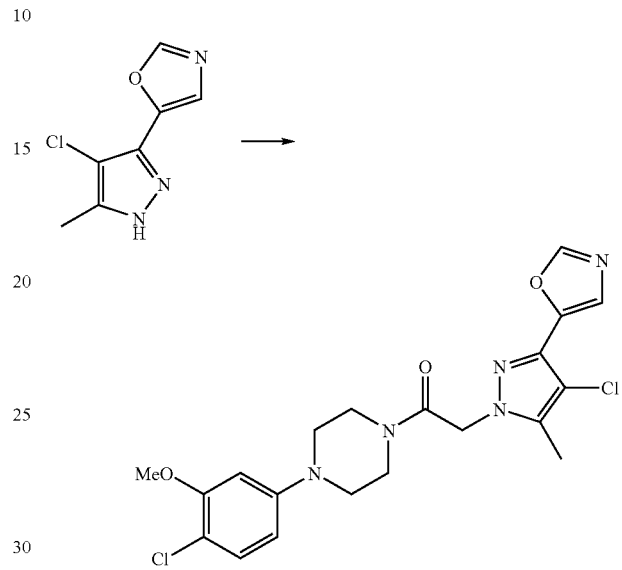

The title compound was synthesized according to Protocol T. LCMS (ES) M+H 450.1; R$_f$ 4.15 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(3-chloroindazol-1-yl)-1-(4-(4-chloro-3-methoxyphenyl)piperazin-1-yl)ethanone

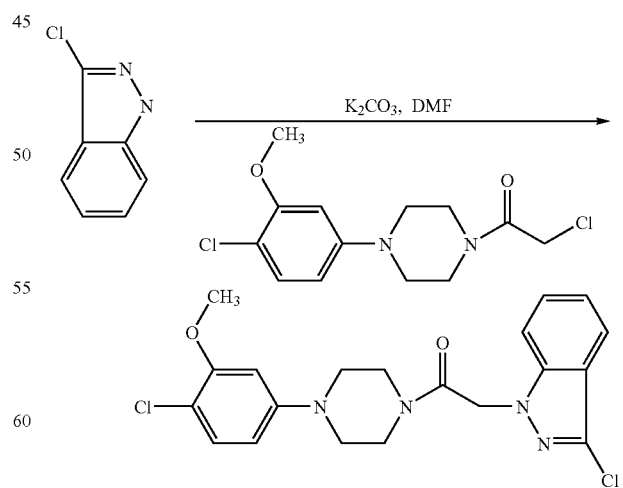

The above compound was synthesized following Protocol T: LCMS 419 (M+H), R$_f$=4.79 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-(4-(4-chlro-3-methoxyphenyl)piperzin-1-yl)-2-indazol-1-yl-ethanone and 1-(4-(4-chlro-3-methoxyphenyl)piperzin-1-yl)-2-indazol-2-yl-ethanone

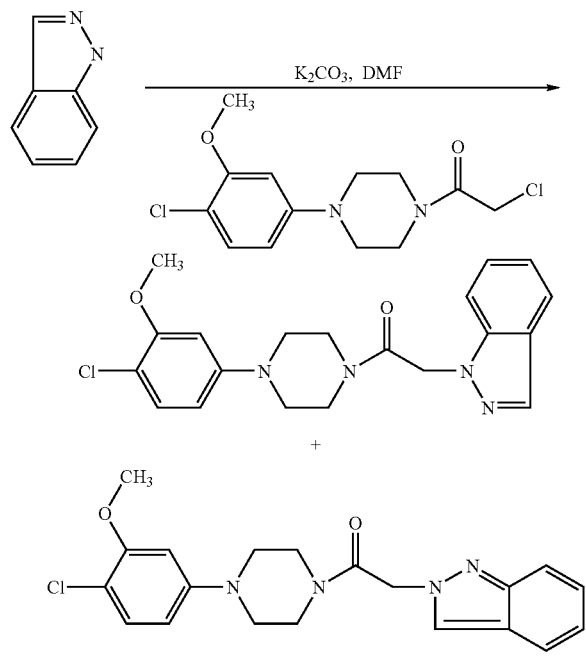

The above compounds were obtained following Protocol T.
N1-Isomer: LC MS 385 (M+H), R$_t$=4.22 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).
N2-Isomer: LC MS 385 (M+H), R$_t$=4.03 minutes (same method as above).

Synthesis of 1-[4-(4-Chloro-2-fluoro-5-methoxy-phenyl)-piperazin-1-yl]-2-[4-chloro-3-(1-hydroxy-1-methyl-ethyl)-5-methyl-pyrazol-1-yl]-ethanone

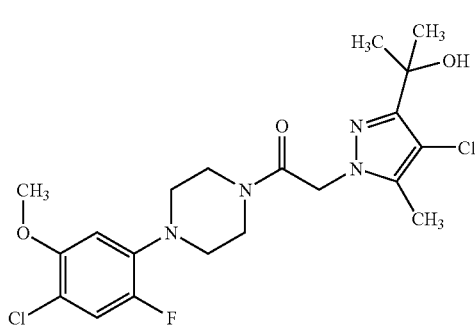

Title compound was prepared following Protocol T, wherein 1-(4-Chloro-2-fluoro-5-methoxy-phenyl)piperazin-4-chloromethyl-ketone and 4-chloro-3-(1-hydroxy-1-methyl-ethyl)-5-methyl-pyrazol were used as the coupling components. Purified by HPLC (Column: Varian Dynamax 250× 21.4 mm Microsorb100-8 C18, Buffer A: 0.1% TFA/H$_2$O, Buffer B: 0.1% TFA/ACN, Gradient: B from 25% to 70% within 40 min, Flow: 20 ml/min) to give the title compound: HPLC retention time=5.26 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=459.1, found=441.1 and 459.1.

Synthesis of 1-{2-[4-(4-Chloro-3-hydroxy-phenyl)-piperazin-1-yl]-2-oxo-ethyl}-3-trifluoromethyl-1,4,6,7-tetrahydro-pyrazolo[4,3-c]pyridine-5-carboxylic acid tert-butyl ester

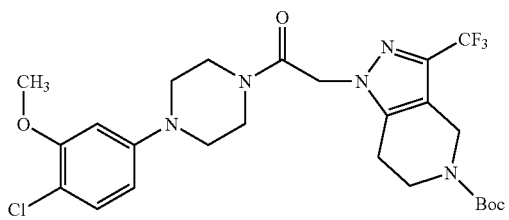

Title compound was prepared following Protocol T, wherein 1-(3-methoxyphenyl-4-chloro)piperazin-4-chloromethyl-ketone and 3-trifluoromethyl-1,4,6,7-tetrahydro-pyrazolo[4,3-c]pyridine-5-carboxylic acid tert-butyl ester were used as the coupling components. Purified by recrystallization with ACN/H$_2$O. HPLC retention time=5.17 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=558.2, found=502.2; $^1$H NMR (CDCl3, 400 MHz) 7.22 (d, 1H), 6.48(s, 1H), 6.43(d, 1H), 4.96 (s,2H), 4.50 (s, 2H), 3.83 (s, 3H), 3.65-3.80 (m, 6H), 3.12-3.22 (d, 4H), 2.73 (m, 2H), 1.48(s, 9H)ppm.

Synthesis of 1-[4-(2,4-difluoro-5-methoxy-phenyl)-piperazin-1-yl]-2-[4-chloro-3-(1-hydroxy-1-methyl-ethyl)-5-methyl-pyrazol-1-yl]-ethanone

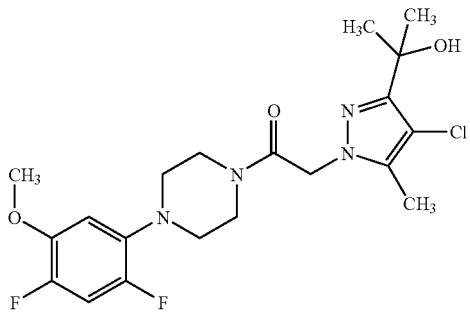

Title compound was prepared following Protocol T, wherein 1-(2,4-difluoro-5-methoxy-phenyl)piperazin-4-chloromethyl-ketone and 4-chloro-3-(1-hydroxy-1-methylethyl)-5-methyl-pyrazol were used as the coupling components. Purified by normal phase column (Column: 40 g silica gel, 20%-30% EtOAc/DCM), and recrystallization by ACN/Water to give the title products as a white solid: HPLC retention time=3.9 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=443.1, found=425.1(—$H_2O$) and 443.1.

Synthesis of 1-[4-(4-Chloro-3-methoxy-phenyl)-2-(S)-methyl-piperazin-1-yl]-2-(4-fluoro-5-methyl-3-pyridin-2-yl-pyrazol-1-yl)-ethanone

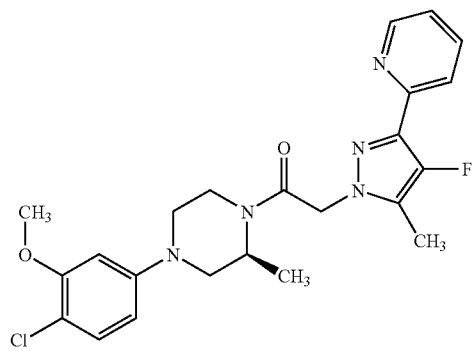

Title compound was prepared following Protocol T, wherein 1-(3-methoxyphenyl-4-chloro+3-methyl-piperazin-4-chloromethyl-ketone and 4-fluoro-5-methyl-3-pyridin-2-yl-pyrazol were used as the coupling components. Purified by HPLC to give the title compound: HPLC retention time=3.75 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=458.2, found=458.2.

Synthesis of 2-(3-iodoindazol-1-yl)-1-(4-(4-chloro-3-methoxyphenyl)piperazin-1-yl)ethanone

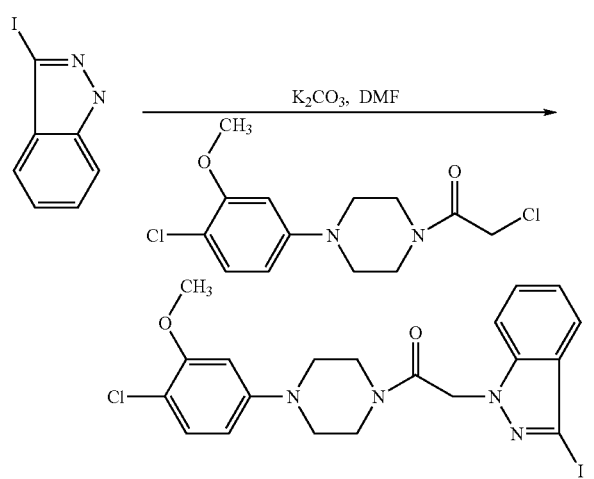

The above compound was synthesized following Protocol T: LC MS 511 (M+H); $R_t$=4.89 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-[4-chloro-3 (1-hydroxy-1-methyl-ethyl)-5-methyl-pyrazol-1-yl]-1-[4-(3-methoxy-4-chloro-phenyl)-2-methyl-piperazin-1-yl]-ethanone (Isomer I) and of 2-[4-chloro-5(1-hydroxy-1-methyl-ethyl)-3-methyl-pyrazol-1-yl]-1-[4-(3-methoxy-4-chloro-phenyl)-2-methyl-piperazin-1-yl]-ethanone (Isomer II)

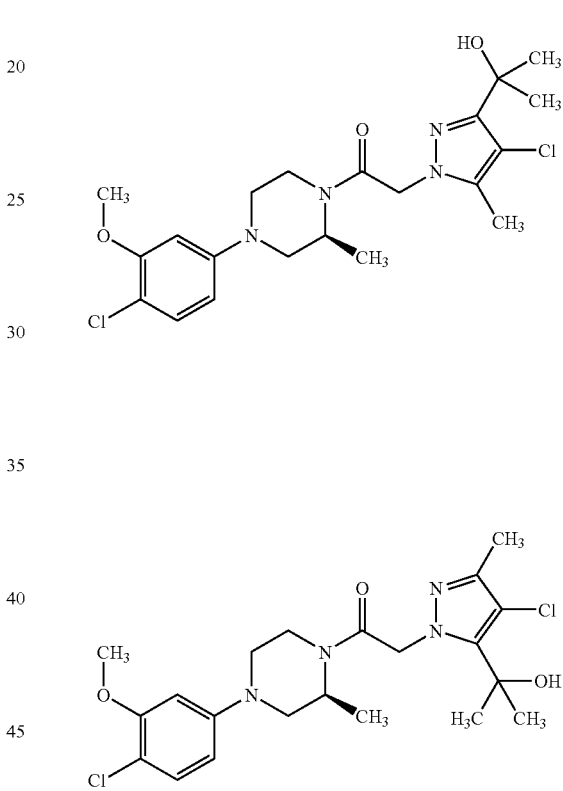

Title compounds were prepared following Protocol T, wherein 1-(3-methoxyphenyl-4-chloro) 2-methyl-piperazine-4-chloromethyl-ketone and 4-chloro-3 (1-hydroxy-1-methyl-ethyl)-5-methyl-pyrazol were used as the coupling components, purified by HPLC (Column: Varian Dynamax 250×21.4 mm Microsorb100-8 C18, Buffer A: 0.1% TFA/$H_2O$, Buffer B: 0.1% TFA/ACN, Gradient: B from 10% to 95% within 60 min, Flow: 20 ml/min) to give above 2 isomer products as a white powder.

Isomer I: HPLC retention time=4.28 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=455.1, found=437.1(—$H_2O$), 455.1.

Isomer II: HPLC retention time=4.54 minutes (same method as with isomer I); MS (ES) M+H expect=455.1, found=437.1(—H₂O), 455.1.

Protocol V: Preparation of Compounds Via Acid or Base-Mediated De-Protections

Synthesis of 1-[4-(4-Chloro-3-methoxy-phenyl)-piperazin-1-yl]-2-(3-trifluoromethyl-4,5,6,7-tetrahydro-pyrazolo[4,3-c]pyridin-1-yl)-ethanone

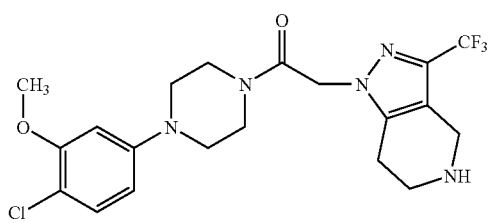

0.23 g of 1-{2-[4-(4-Chloro-3-hydroxy-phenyl)-piperazin-1-yl]-2-oxo-ethyl}-3-trifluoromethyl-1,4,6,7-tetrahydro-pyrazolo[4,3-c]pyridine-5-carboxylic acid tert-butyl ester was stirred with 2 ml 4N HCl/Dioxane at room temperature for 40 minutes. 20 ml Ethyl ether was added, and the resulting solid was collected and washed with ether. The compound was recrystallized with ACN/H₂O to give 0.2 g of the title compound: HPLC retention time=3.03 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=458.15, found=458.1.

Synthesis of lithium 5-chloro-2-{4-[2-(4-chloro-5-methyl-3-trifluoromethyl-pyrazol-1-yl)-acetyl]-piperazin-1-yl}-4-methoxy-benzoate

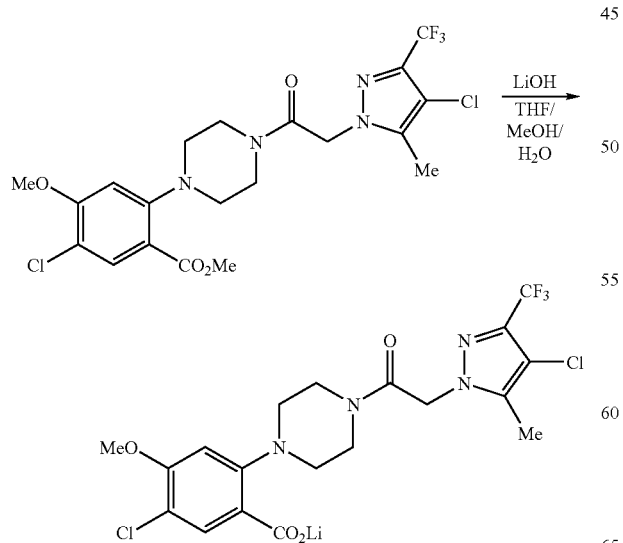

Following a variation of Protocol V, A 5 mL flask was charged with 5-chloro-2-{4-[2-(4-chloro-5-methyl-3-trifluoromethyl-pyrazol-1-yl)-acetyl]-piperazin-1-yl}-4-methoxy-benzoic acid methyl ester (43 mg, 0.084 mmol), 0.4 mL MeOH, 0.9 mL THF, and LiOH (0.42 mL, 0.25 M). After stirring 2 days, the solution was diluted with water and the volatile solvents were removed in vacuo, during which the lithium carboxylate precipitated. The solids were filtered and dried at reduced pressure to afford 36 mg (86%) of the target salt as a white solid: 1H NMR (400 MHz, CD3OD) δ 7.44 (s, 1H), 6.58 (s, 1H), 5.28 (s, 2H), 3.89 (s, 3H), 3.71-3.79 (m, 4H), 3.16-3.21 (m, 2H), 3.09-3.14 (m, 2H), 2.26 (s, 3H); MS (ES) M+H expect 495.1, found 495.1; HPLC (80:20-5:95 0.1% TFA/H₂O :0.08% TFA/MeCN) $R_t$=4.87 min.

Protocol X: Preparation of Compounds Via Acylation or Sulfonylation

Synthesis of 1-[4-(4-Chloro-3-methoxy-phenyl)-piperazin-1-yl]-2-(5-methanesulfonyl-3-trifluoromethyl-4,5,6,7-tetrahydro-pyrazolo[4,3-c]pyridin-1-yl)-ethanone

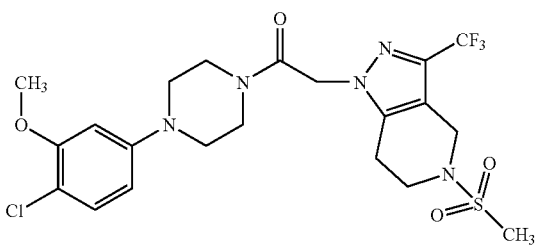

To a stirred solution of 70 mg (0.13 mmol) 1-[4-(4-Chloro-3-methoxy-phenyl)-piperazin-1-yl]-2-(3-trifluoromethyl-4,5,6,7-tetrahydro-pyrazolo[4,3-c]pyridin-1-yl)-ethanone in 2 ml DCM under ice-bath was added 0.046 ml TEA (0.33 mmol), following by 0.012 ml (0.15 mmol) Methanesulfonyl chloride. The reaction was stirred for 30 min in ice bath. More DCM was added after reaction, and the DCM layer was washed with Sat. NaHCO₃, Brine, dried over MgSO₄, and concentrated to give the title compound as a white solid: HPLC retention time=4.78 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=536.1, found=536.1.

393

N-(5-Chloro-2-{4-[2-(4-chloro-5-methyl-3-trifluoromethyl-pyrazol-1-yl)-acetyl]-piperazin-1-yl}-4-methoxy-benzyl)-N-methyl-methanesulfonamide

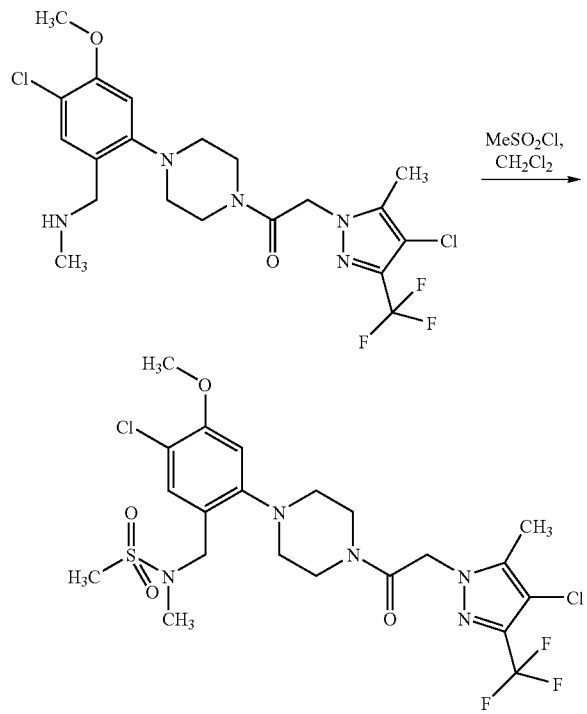

To 200 mg of 1-[4-(4-Chloro-5-methoxy-2-methylaminomethyl-phenyl)-piperazin-1-yl]-2-(4-chloro-5-methyl-3-trifluoromethyl-pyrazol-1-yl)-ethanone (0.42 mmol, 1.0 eq) and 126 uL triethylamine (0.90 mmol, 2.1 eq) in 1.4 mL dichloromethane in a 4 mL vial fitted was added a stir bar. The solution was cooled in an ice water bath and 34 uL methanesulfonylchloride (0.43 mmol, 1.05 eq) was added. The ice bath was removed and the solution was allowed to stir overnight. The crude product was purified by HPLC, and the product was treated with 4M HCl in p-dioxane to give the title compound: LC/MS(ES) (M+H)=572.1; retention time=7.32 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-piperazin-1-yl]-2-(4-chloro-5-acetylaminomethyl-3-trifluoromethyl-pyrazol-1-yl)-ethanone

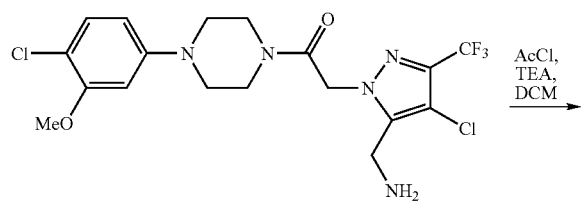

394

-continued

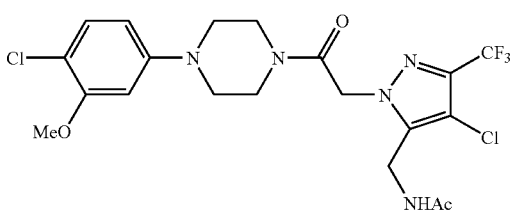

A mixture of 1-[4-(4-Chloro-3-methoxy-phenyl)-piperazin-1-yl]-2-(4-chloro-5-aminomethyl-3-trifluoromethyl-pyrazol-1-yl)-ethanone (50 mg, 1 equiv), acetyl chloride (13 mg, 1.5 equiv), and TEA (50 mg, 3 equiv) in 2 mL of DCM was stirred at room temperature for 1 h. Reverse phase HPLC (acetonitrile-H$_2$O with 0.1% TFA as eluent) gave the title compound: LCMS retention time: 4.60 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 508.

Synthesis of 1-[4-(4-Chloro-3-methoxy-phenyl)-piperazin-1-yl]-2-(4-chloro-5-methylsulfonylaminomethyl-3-trifluoromethyl-pyrazol-1-yl)-ethanone

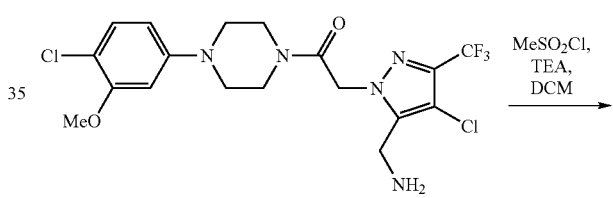

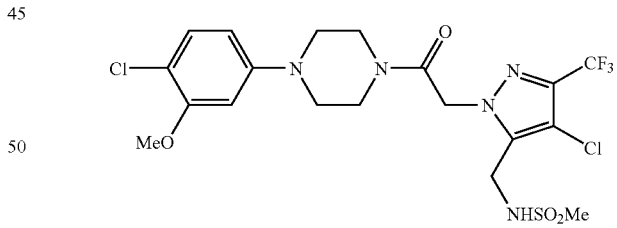

A mixture of 1-[4-(4-Chloro-3-methoxy-phenyl)-piperazin-1-yl]-2-(4-chloro-5-aminomethyl-3-trifluoromethyl-pyrazol-1-yl)-ethanone (50 mg, 1 equiv), MeSO2Cl (19 mg, 1.5 equiv), and TEA (50 mg, 3 equiv) in 2 mL of DCM was stirred at room temperature for 1 h. Reverse phase HPLC (acetonitrile-H$_2$O with 0.1% TFA as eluent) gave the title compound: LCMS retention time: 4.78 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 544.

Synthesis of (4-Chloro-2-{2-[4-(4-chloro-3-methoxy-phenyl)-piperazin-1-yl]-2-oxo-ethyl}-5-trifluoromethyl-2H-pyrazol-3-ylmethyl)-urea

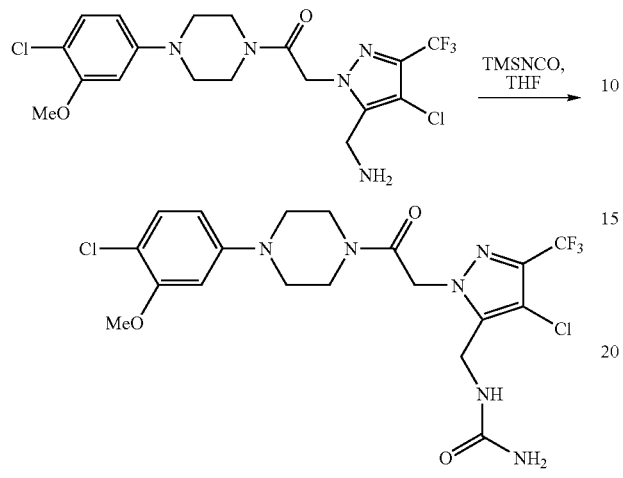

A mixture of 1-[4-(4-Chloro-3-methoxy-phenyl)-piperazin-1-yl]-2-(4-chloro-5-aminomethyl-3-trifluoromethyl-pyrazol-1-yl)-ethanone (50 mg, 1 equiv), TMSNCO (30 mg, 2.5 equiv in 2 mL of THF was stirred at room temperature for 1 h. Reverse phase HPLC (acetonitrile-H₂O with 0.1% TFA as eluent) gave the title compound: LCMS retention time: 4.26 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 509.

Protocol Y: Preparation of Compounds Via Alkylation

Synthesis of 2-(4-Chloro-5-methyl-1H-pyrazol-3-yl)-propan-2-ol

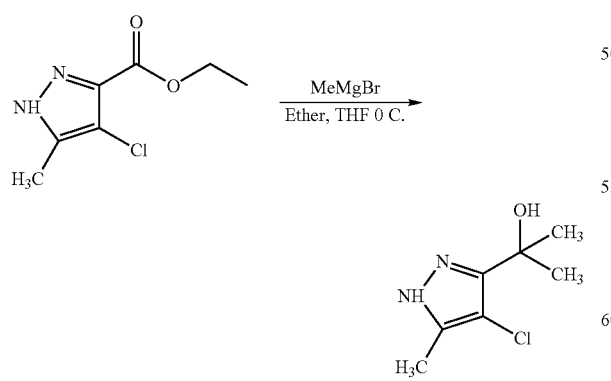

4-Chloro-5-methyl-1H-pyrazole-3-carboxylic acid ethyl ester (0.14 g, 0.8 mmol) was dissolved in 6 ml anhydrous THF, cooled to 0° C., and 3 ml (9.0 mmol) of 3M MeMgBr in ethyl ether was added drop wise. The reaction was then removed from the ice-bath, and was stirred at ambient temperature for one hour. The reaction mixture was poured into 1M phosphate buffer (pH=7), and the mixture was extracted with EtOAc. The phases were separated, and the ethyl acetate layer was washed with brine, dried over anhydrous sodium sulfate, and concentrated to afford the title compound: MS (ES) M-OH expect=157.1, found=157.1; 1H NMR (CDCL3, 400 MHz) δ 2.25 (s, 3H), 1.64 (s, 6H) ppm.

2-(4-Chloro-5-trifluoromethyl-2H-pyrazol-3-yl)-propan-2-ol

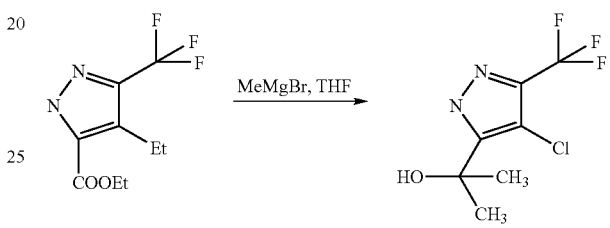

The above compound was synthesized following the same protocol as above using 4-Chloro-5-trifluoromethyl-1H-pyrazole-3-carboxylic acid ethyl ester.

(4-Chloro-5-pyrazol-1-ylmethyl-3-trifluoromethyl-pyrazol-1-yl)-acetic acid

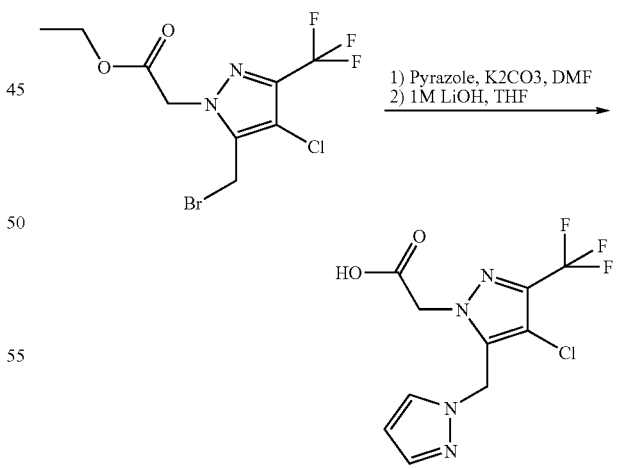

(5-Bromomethyl-4-chloro-3-trifluoromethyl-pyrazol-1-yl)-acetic acid ethyl ester was treated with an excess of pyrazole and potassium carbonate in DMF at 60° C., followed by treatment of the product with lithium hydroxide to give the title compound.

397

1-{4-[4-Chloro-2-(1-hydroxy-ethyl)-5-methoxy-phenyl]-piperazin-1-yl}-2-(4-chloro-5-methyl-3-trifluoromethyl-pyrazol-1-yl)-ethanone

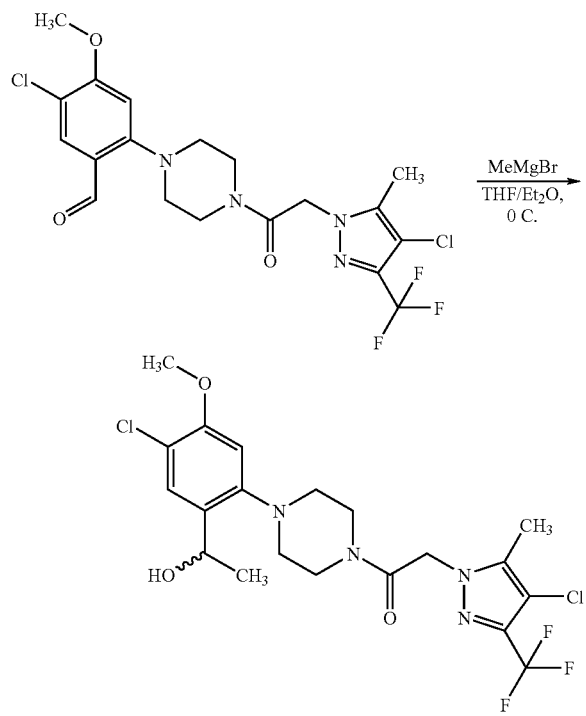

Prepared a slurry of 10 g of 5-Chloro-2-{4-[2-(4-chloro-5-methyl-3-trifluoromethyl-pyrazol-1-yl)-acetyl]-piperazin-1-yl}-4-methoxy-benzaldehyde (20.9 mmol, 1.0 eq) in 70 mL THF in a 250 mL 3-necked flask fitted with a stir bar, thermometer, and addition funnel fitted with an $N_2$ inlet. The mixture was cooled in an ice water bath to 3° C., then 7.3 mL of 3.0M MeMgBr in $Et_2O$ (21.9 mmol, 1.05 eq) was added dropwise. LC/MS showed reaction was only about 50% complete. Additional MeMgBr solution was added until the aldehyde was consumed (approx. 5 mL were needed). The reaction was quenched with a small amount of water, the solvents removed under vacuum, and the crude material purified by column chromatography to give the title compound: LC/MS (ES) (M+H) 495.1; retention time 5.41 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

Synthesis of 1-[4-(4-Chloro-3-methoxy-phenyl)-piperazin-1-yl]-2-[4-chloro-5-methyl-3-(2-methyl-2H-tetrazol-5-yl)-pyrazol-1-yl]-ethanone and 1-[4-(4-Chloro-3-methoxy-phenyl)-piperazin-1-yl]-2-[4-chloro-5-methyl-3-(2-methyl-1H-tetrazol-5-yl)-pyrazol-1-yl]-pyrazol-1-yl]-ethanone

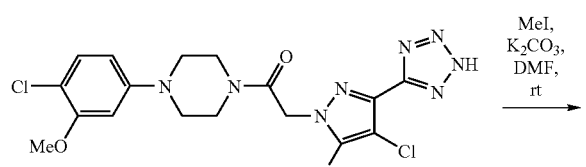

398

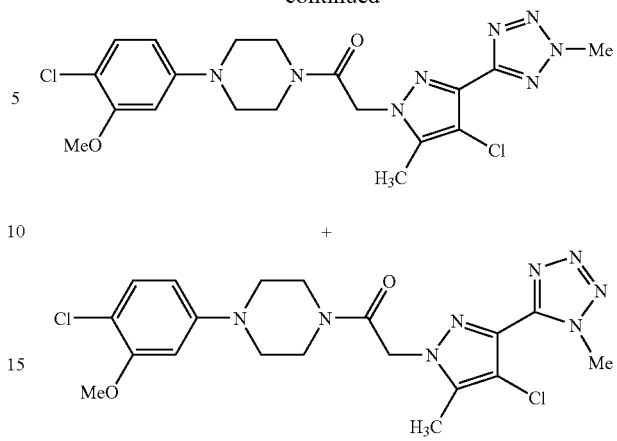

A mixture of 2-(4-chloro-3-tetrazol-5-yl-5-methyl-pyrazol-1-yl)-1-[4-(4-chloro-3-methoxy-phenyl)-piperazin-1-yl]-ethanone (9 mg, 1 equiv), MeI (3 μL, 5 equiv), and K2CO3 (20 mg, excess) in 1 mL of DMF were heated at room temperature for 3 days. The crude product was purified by reverse phase HPLC (acetonitrile-$H_2O$ with 0.1% TFA as eluent) to yield 1-[4-(4-Chloro-3-methoxy-phenyl)-piperazin-1-yl]-2-[4-chloro-5-methyl-3-(2-methyl-2H-tetrazol-5-yl)-pyrazol-1-yl]-ethanone. LCMS Retention time: 4.06 min. LCMS observed for (M+H)+: 465. From this reaction, 1-[4-(4-Chloro-3-methoxy-phenyl)-piperazin-1-yl]-2-[4-chloro-5-methyl-3-(2-methyl-1H-tetrazol-5-yl)-pyrazol-1-yl]-ethanone was also obtained. The two products co-eluted from HPLC and TLC. LCMS Retention time: 4.06 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile) for both isomers. LCMS observed for (M+H)+: 465 for both isomers.

Synthesis of 1-[4-(4-Chloro-3-methoxy-phenyl)-piperazin-1-yl]-2-(4-chloro-5-morpholin-4-ylmethyl-3-trifluoromethyl-pyrazol-1-yl)-ethanone

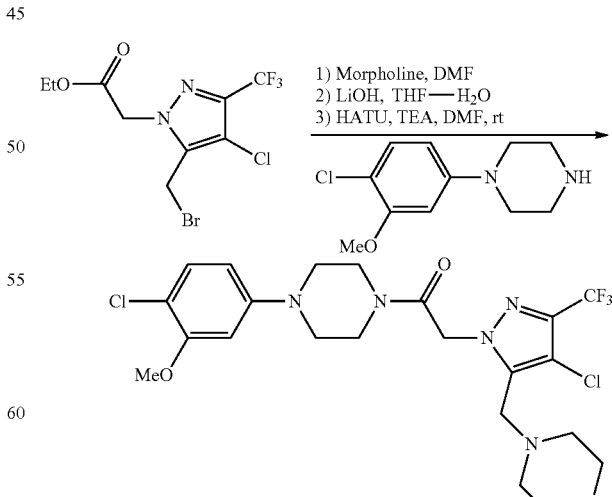

A mixture of (5-Bromomethyl-4-chloro-3-trifluoromethyl-pyrazol-1-yl)-acetic acid ethyl ester (350 mg, 1 equiv)

and morpholine (0.5 mL, 5 equiv) in 1 mL of DMF was stirred at room temperature overnight, diluted with ethyl acetate, washed with water. The organic layer was evaporated, diluted with 3 mL of THF and treated with 3 mL of 1N LiOH for 2 hours. Preparative reverse phase HPLC gave (4-Chloro-5-morpholin-4-ylmethyl-3-trifluoromethyl-pyrazol-1-yl)-acetic acid.

A mixture of 1-(4-Chloro-3-methoxy-phenyl)-piperazine (30 mg, 1 equiv), (4-Chloro-5-morpholin-4-ylmethyl-3-trifluoromethyl-pyrazol-1-yl)-acetic acid (44 mg, 1 equiv), HATU (42 mg, 1.1 equiv) and TEA (0.2 mL, 6 equiv) in 1 mL of DMF was stirred at room temperature for 12 hours. Dilution with EtOAc, followed by washing with saturated aqueous NaHCO$_3$ and reverse phase HPLC (acetonitrile-H$_2$O with 0.1% TFA as eluent) gave the title compound: LCMS retention time: 4.69 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 536.

Synthesis of 1-[4-(4-Chloro-3-methoxy-phenyl)-piperazin-1-yl]-2-(4-chloro-5-dimethylaminomethyl-3-trifluoromethyl-pyrazol-1-yl)-ethanone

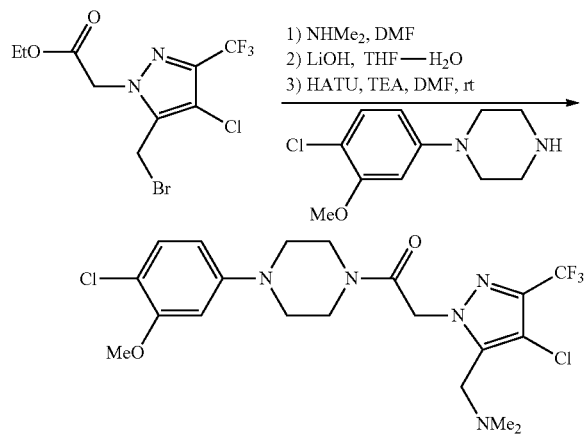

A mixture of (5-Bromomethyl-4-chloro-3-trifluoromethyl-pyrazol-1-yl)-acetic acid ethyl ester (350 mg, 1 equiv) and NHMe2 (2 M in THF, 2.5 mL, 5 equiv) in 1 mL of DMF was stirred at room temperature overnight, diluted with ethyl acetate, washed with water. The organic layer was evaporated, diluted with 3 mL of THF and treated with 3 mL of 1N LiOH for 2 hours. Preparative reverse phase HPLC gave (4-Chloro-5-dimethylaminomethyl-3-trifluoromethyl-pyrazol-1-yl)-acetic acid.

A mixture of 1-(4-Chloro-3-methoxy-phenyl)-piperazine (30 mg, 1 equiv), (4-Chloro-5-dimethylaminomethyl-3-trifluoromethyl-pyrazol-1-yl)-acetic acid (28 mg, 1 equiv), HATU (42 mg, 1.1 equiv) and TEA (0.2 mL, 6 equiv) in 1 mL of DMF was stirred at room temperature for 12 hours. Dilution with EtOAc, followed by washing with saturated aqueous NaHCO$_3$ and reverse phase HPLC (acetonitrile-H$_2$O with 0.1% TFA as eluent) gave the title compound: LCMS retention time: 3.42 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 494.

Synthesis of 1-[4-(4-Chloro-3-methoxy-phenyl)-piperazin-1-yl]-2-(4-chloro-5-methylsulfonylmethyl-3-trifluoromethyl-pyrazol-1-yl)-ethanone

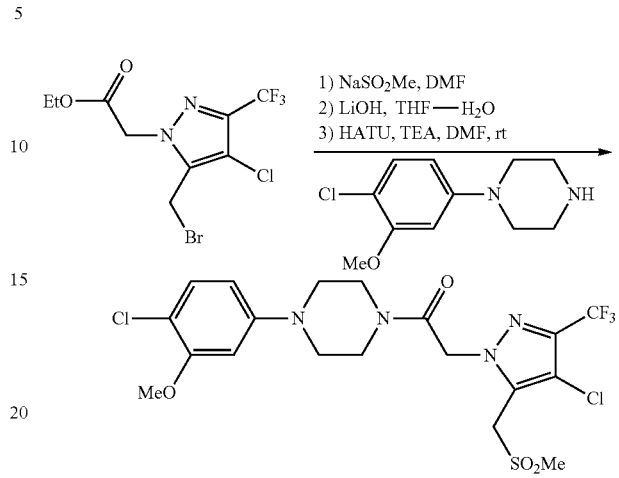

A mixture of (5-Bromomethyl-4-chloro-3-trifluoromethyl-pyrazol-1-yl)-acetic acid ethyl ester (350 mg, 1 equiv) and NaSO2Me (510 mg, 5 equiv) in 1 mL of DMF was stirred at room temperature overnight, diluted with ethyl acetate, washed with water. The organic layer was evaporated, diluted with 3 mL of THF and treated with 3 mL of 1N LiOH for 2 hours. Preparative reverse phase HPLC gave (4-Chloro-5-methylsulfonylmethyl-3-trifluoromethyl-pyrazol-1-yl)-acetic acid.

A mixture of 1-(4-Chloro-3-methoxy-phenyl)-piperazine (30 mg, 1 equiv), (4-Chloro-5-methylsulfonylmethyl-3-trifluoromethyl-pyrazol-1-yl)-acetic acid (32 mg, 1 equiv), HATU (42 mg, 1.1 equiv) and TEA (0.2 mL, 6 equiv) in 1 mL of DMF was stirred at room temperature for 12 hours. Dilution with EtOAc, followed by washing with saturated aqueous NaHCO$_3$ and reverse phase HPLC (acetonitrile-H$_2$O with 0.1% TFA as eluent) gave the title compound: LCMS retention time: 5.08 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 529.

Protocol Z: Preparation of Compounds Via Peroxyacid-Mediated N-Oxidation

Synthesis of 1-[4-(4-Chloro-3-methoxyphenyl)-4-oxypiperazin-1-yl]-2-(4-chloro-5-methyl-3-oxazol-2-ylpyrazol-1-yl)ethanone

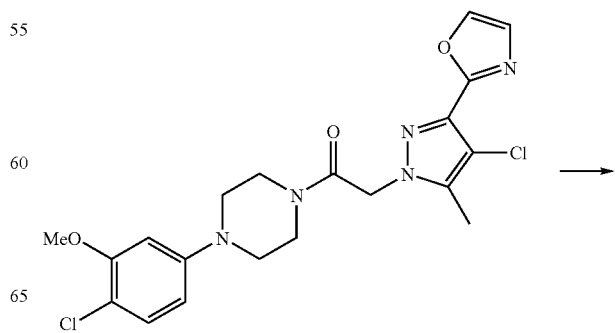

-continued

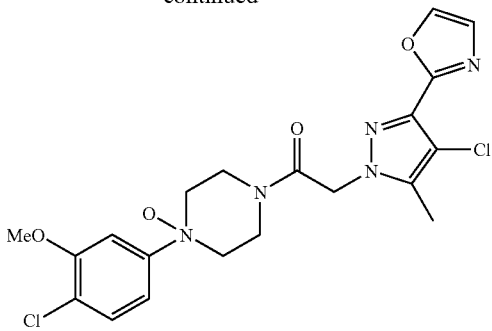

The title compound was synthesized according to Protocol Z, from example 1. LCMS (ES) M+H 466.1, $R_t$ 0.62 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Protocol DD: Preparation of Compounds Via Palladium and Copper Mediated Processes Synthesis of 2-(4-Chloro-5-methanesulfonyl-3-trifluoromethylpyrazol-1-yl)-1-(4-(4-chloro-3-methoxyphenyl)piperazin-1-yl)ethanone and 1-(4-(4-chloro-3-methoxyphenyl)piperazin-1-yl)-2-(4-Chloro-3-trifluoromethyl pyrazol-1-yl)ethanone

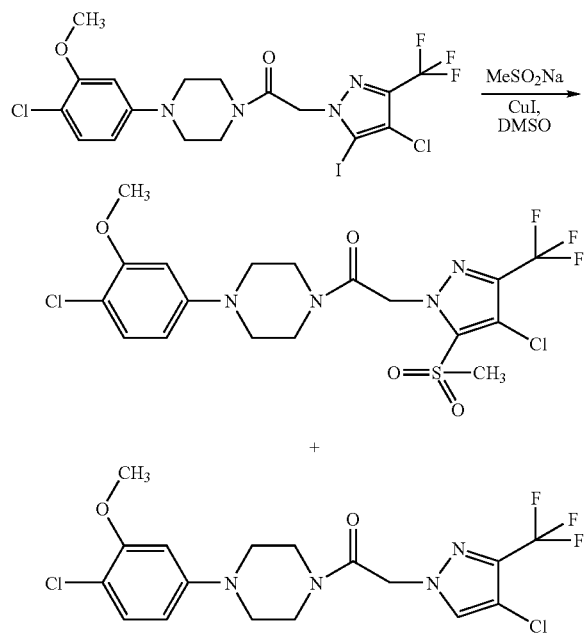

The above compounds were obtained following the copper-mediated processes in Protocol DD from example 2, and the reaction mixture was purified by PTLC using 50% ethyl acetate:50% n-hexane as mobile phase.

2-(4-Chloro-5-methanesulfonyl-3-trifluoromethylpyrazol-1-yl)-1-(4-(4-chloro-3-methoxyphenyl)piperazin-1-yl) ethanone: LC MS m/z 515 (M+H), $R_t$=5.34 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

1-(4-(4-chloro-3-methoxyphenyl)piperazin-1-yl)-2-(4-Chloro-3-trifluoromethyl pyrazol-1-yl)ethanone: LC MS m/z 437 (M+H), $R_t$=5.22 minutes (same method as above); 1H NMR (400 MHz, CDCl3): δ 3.15 (apparent quintet, J=5.1 Hz, 4H), 3.68 (apparent t, J=5.1 Hz, 2H), 3.78 (apparent t, J=5.1 Hz, 2H), 3.89 s, 3H), 5.03 (s, 2H), 6.42 (apparent dd, J=2.5 & 8.4 Hz, 1H), 6.48 (d, J=2.5 Hz, 1H), 7.22 (d, J=8.3 Hz, 1H), 7.64 (s, 1H).

Synthesis of 2-(3-phenylsulfonyl-4-chloro-5-methyl-pyrazol-1-yl)-1-[4-(4-chloro-3-methoxy-phenyl)-piperazin-1-yl]-ethanone

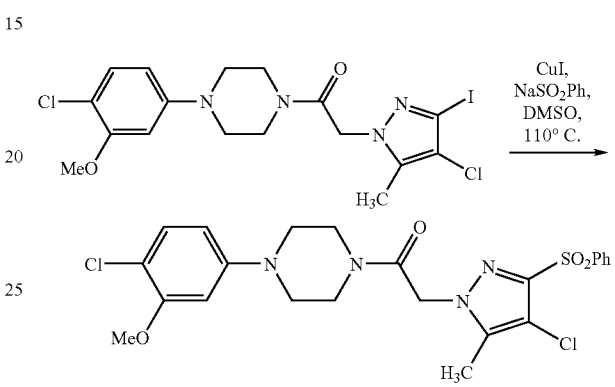

A mixture of 2-(4-Chloro-3-iodo-5-methyl-pyrazol-1-yl)-1-[4-(4-chloro-3-methoxy-phenyl)-2(S)-methyl-piperazin-1-yl]-ethanone (204 mg, 1 equiv), NaSO2Ph (200 mg, 3 equiv) and CuI (228 mg, 3 equiv) in 1 mL of DMSO were heated at 110° C. overnight and then cooled to room temperature, taken up in a 1:1 mixture of methanol and EtOAc, filtered through a thin pad of celite and concentrated. The crude product was purified by reverse phase HPLC (acetonitrile-H₂O with 0.1% TFA as eluent) to yield the title compound: LCMS Retention time: 4.95 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 523.

Synthesis of 2-(4-chloro-3-[1,2,4]triazol-1-yl-5-methyl-pyrazol-1-yl)-1-[4-(4-chloro-3-methoxy-phenyl)-piperazin-1-yl]-ethanone

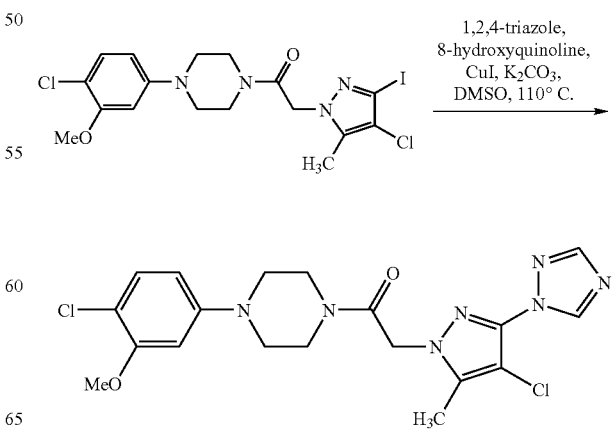

The title compound was prepared following a variation on Protocol DD. LCMS Retention time: 3.80 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 450.

1-[4-(4-Chloro-3-methoxy-phenyl)-2(S)-methyl-piperazin-1-yl]-2-(4-chloro-5-methyl-3-[1,2,3]triazol-1-yl-pyrazol-1-yl)-ethanone

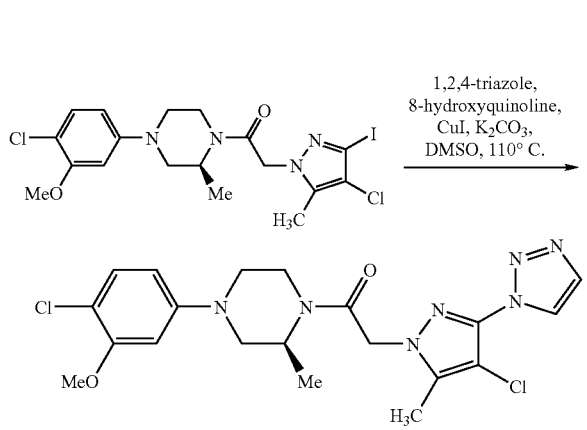

The title compound was prepared following a variation on Protocol DD. LCMS Retention time: 4.28 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 464.

1-[4-(4-Chloro-3-methoxy-phenyl)-2(S)-methyl-piperazin-1-yl]-2-(4-chloro-5-methyl-3-pyrazol-1-yl-pyrazol-1-yl)-ethanone

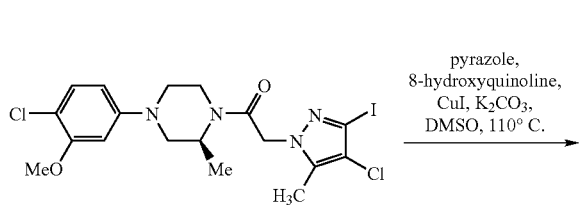

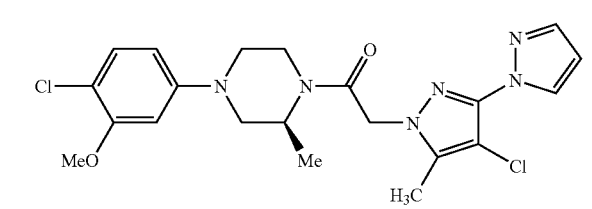

The title compound was prepared following a variation on Protocol DD. LCMS Retention time: 4.56 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 463.

2-(4'-Chloro-3,5'-dimethyl-[1,3']bipyrazolyl-1'-yl)-1-[4-(4-chloro-3-methoxy-phenyl)-2(S)-methyl-piperazin-1-yl]-ethanone

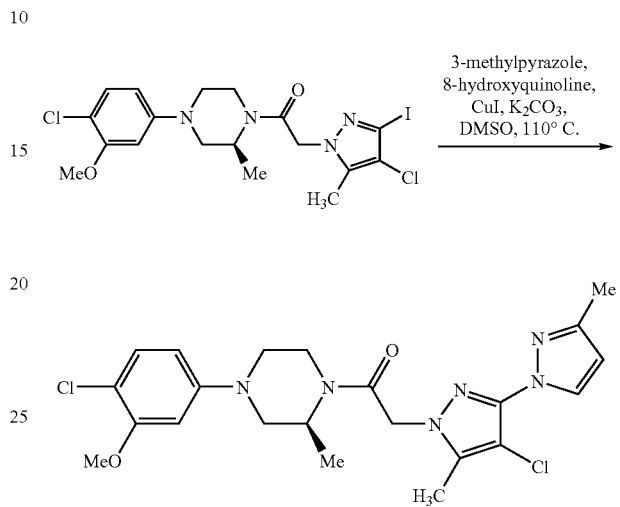

The title compound was prepared following a variation on Protocol DD. LCMS Retention time: 4.59 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 477.

1-[4-(4-Chloro-2-fluoro-5-methoxy-phenyl)-piper-azin-1-yl]-2-(4-chloro-5-methyl-3-[1,2,3]triazol-1-yl-pyrazol-1-yl)-ethanone

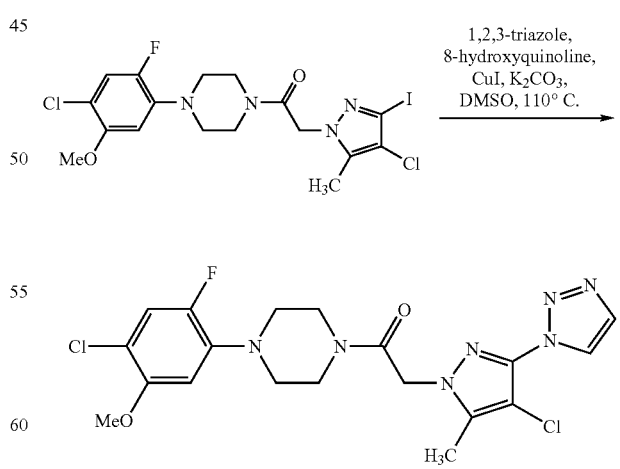

The title compound was prepared following a variation on Protocol DD. LCMS Retention time: 5.75 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 468.

1-[4-(4-Chloro-2-fluoro-5-methoxy-phenyl)-piperazin-1-yl]-2-(4-chloro-5-methyl-3-pyrazol-1-yl-pyrazol-1-yl)-ethanone

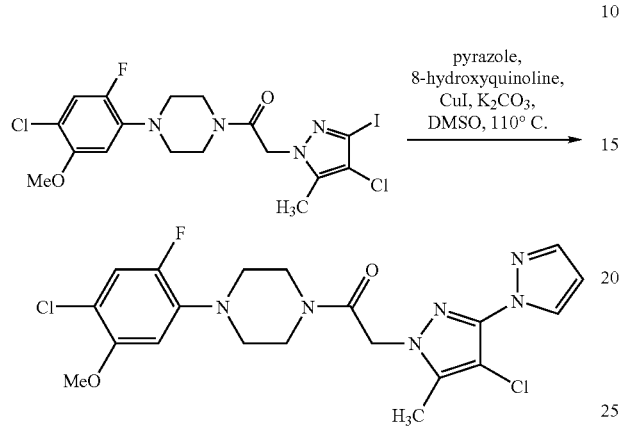

The title compound was prepared following a variation on Protocol DD. LCMS Retention time: 5.96 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 467.

2-(4'-Chloro-3,5'-dimethyl-[1,3']bipyrazolyl-1'-yl)-1-[4-(4-Chloro-2-fluoro-5-methoxy-phenyl)-piperazin-1-yl]-ethanone

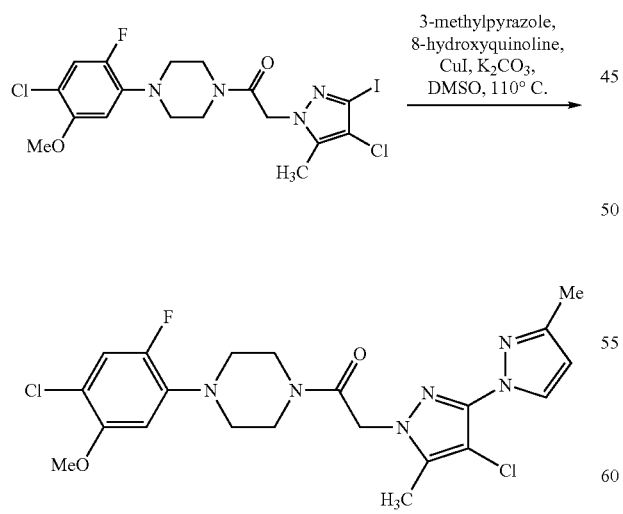

The title compound was prepared following a variation on Protocol DD. LCMS Retention time: 6.02 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 481.

Synthesis of 1-[4-(4-Chloro-2-fluoro-5-methoxy-phenyl)-piperazin-1-yl]-2-(4-chloro-3-cyano-5-methyl-pyrazol-1-yl)-ethanone

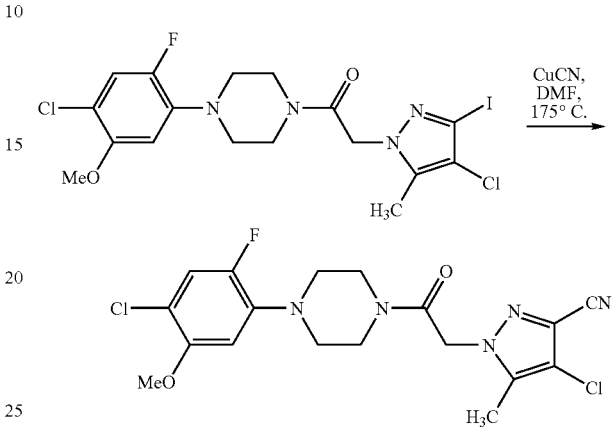

A mixture of 1-[4-(4-Chloro-2-fluoro-5-methoxy-phenyl)-piperazin-1-yl]-2-(4-chloro-3-iodo-5-methyl-pyrazol-1-yl)-ethanone (260 mg, 1 equiv) and CuCN (450 mg, 10 equiv) in 1 mL of DMF were heated at 175° C. for 1 h and then cooled to room temperature, taken up in a 1:1 mixture of methanol and EtOAc, filtered through a thin pad of celite and concentrated. The crude product was purified by reverse phase HPLC (acetonitrile-H₂O with 0.1% TFA as eluent) to yield the title compound: LCMS Retention time: 5.12 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 426.

Synthesis of 2-(3-b enzenesulfonyl-4-chloro-5-methyl-pyrazol-1-yl)-1-[4-(4-chloro-3-methoxy-phenyl)-2(S)-methyl-piperazin-1-yl]-ethanone

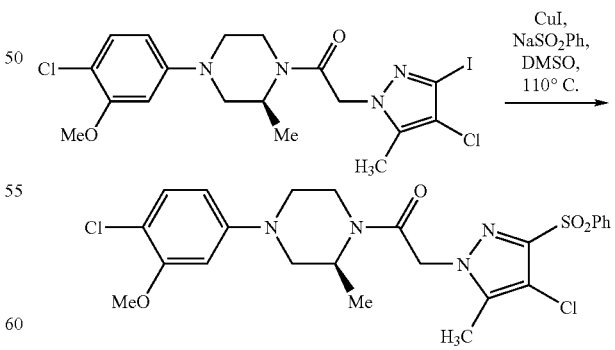

A mixture of 2-(3-iodo-4-chloro-5-methyl-pyrazol-1-yl)-1-[4-(4-chloro-3-methoxy-phenyl)-2-(S)-methylpiperazin-1-yl]-ethanone (204 mg, 1 equiv), NaSO2Ph (200 mg, 3 equiv) and CuI (228 mg, 3 equiv) in 1 mL of DMSO were heated at 110° C. overnight and then cooled to room temperature, taken up in a 1:1 mixture of methanol and EtOAc, filtered through a thin pad of celite and concentrated. The crude product was purified by reverse phase HPLC (acetonitrile-H₂O with 0.1% TFA as eluent) to yield the title compound: LCMS Retention time: 5.40 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 537.

Synthesis of 1-[4-(4-Chloro-2-fluoro-5-meth oxyphenyl)-piperazin-1-yl]-2-(4-chloro-3-methanesulfonyl-5-methyl-pyrazol-1-yl)-ethanone

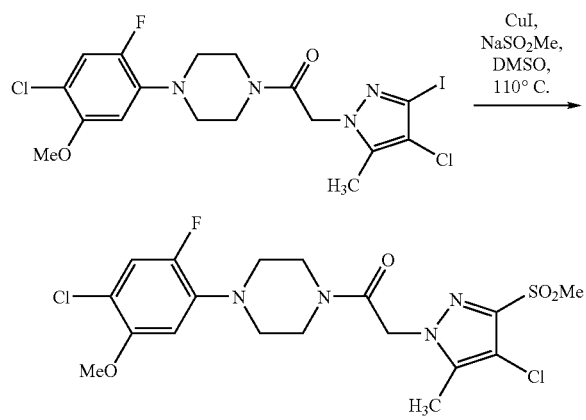

A mixture of 2-(3-iodo-4-chloro-5-methyl-pyrazol-1-yl)-1-[4-(4-Chloro-2-fluoro-5-methoxy-phenyl)-piperazin-1-yl]-ethanone (200 mg, 1 equiv), NaSO2Me (117 mg, 3 equiv) and CuI (217 mg, 3 equiv) in 1 mL of DMSO were heated at 110° C. overnight and then cooled to room temperature, taken up in a 1:1 mixture of methanol and EtOAc, filtered through a thin pad of celite and concentrated. The crude product was purified by reverse phase HPLC (acetonitrile-H₂O with 0.1% TFA as eluent) to yield the title compound: LCMS Retention time: 5.90 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 479.

Synthesis of 2-(3-cyano-4-chloro-5-methyl-pyrazol-1-yl)-1-[4-(4-chloro-3-methoxy-phenyl)-2(S)-methyl-piperazin-1-yl]-ethanone

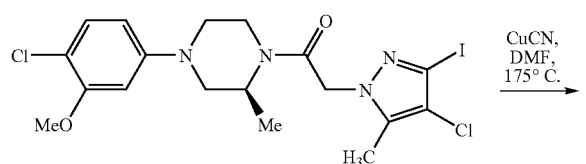

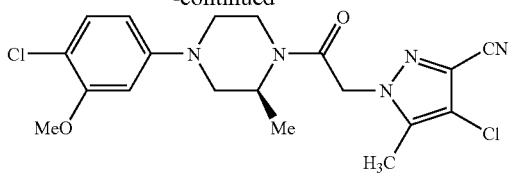

A mixture of 2-(3-iodo-4-chloro-5-methyl-pyrazol-1-yl)-1-[4-(4-chloro-3-methoxy-phenyl)-2-(S)-methylpiperazin-1-yl]-ethanone (260 mg, 1 equiv) and CuCN (450 mg, 10 equiv) in 1 mL of DMF were heated at 175° C. for 1 h and then cooled to room temperature, taken up in a 1:1 mixture of methanol and EtOAc, filtered through a thin pad of celite and concentrated. The crude product was purified by reverse phase HPLC (acetonitrile-H₂O with 0.1% TFA as eluent) to yield the title compound: LCMS Retention time: 5.96 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 422.

Synthesis of 1-(4-(4-chlro-3-methoxyphenyl)piperzin-1-yl)-2-(3-pyrazol-1-yl-indazol-1-yl)ethanone

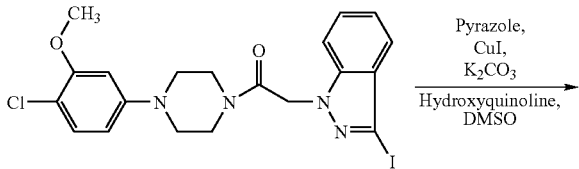

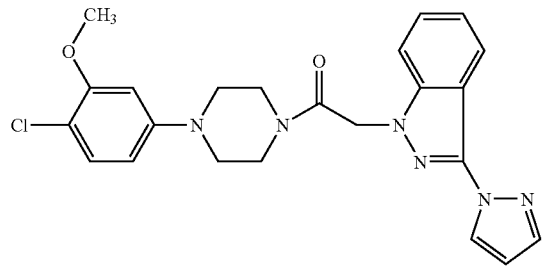

The above compound was synthesized following the copper-mediated amine arylation protocol DD, using 2-(3-iodo-indazol-1-yl)-1-(4-(4-chloro-3-methoxyphenyl)piperazin-1-yl)ethanone and pyrazole. LC MS 451 (M+H); retention time=5.89 minutes (Agilent Zorbax SB-C18, 2.1×50 mm, 5μ, 35° C.) using a 4.5 minute gradient of 20% to 95% B with a

Synthesis of 1-(4-(4-chlro-3-methoxyphenyl)piperzin-1-yl)-2-(3-methanesulfonyl-indazol-1-yl)ethanone

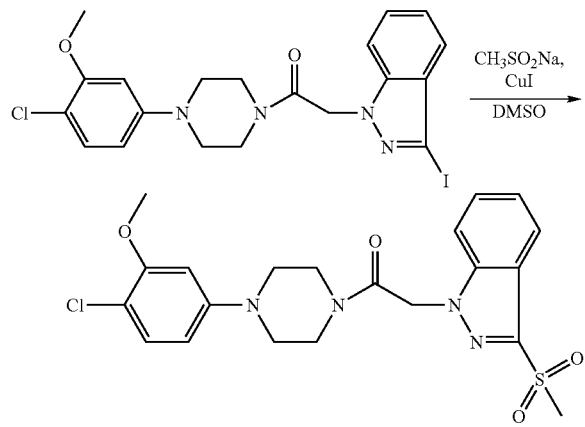

The above compound was synthesized using the copper-mediated variant of Protocol DD used to make sulfones. LC MS 463 (M+H), retention time=5.46 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Protocol EE: General Procedure for the Synthesis of Oxazole Substitution on Pyrazol

Synthesis of (5-Methyl-1H-pyrazol-3-yl)methanol

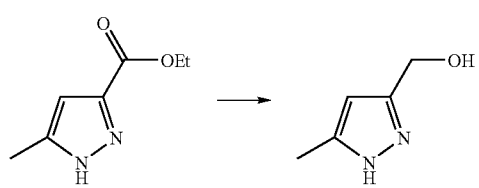

To a solution of the ester (308 mg) in CH$_2$Cl$_2$ (8 mL) and THF (10 mL) stirring at 0° C., a solution of lithium aluminum hydride (1 M in ether, 3.0 mL) was slowly added. The reaction mixture was stirred for an additional 30 min and was quenched by the addition of H$_2$O (0.1 mL), aqueous NaOH solution (10%, 0.2 mL) and H$_2$O (0.3 mL). The mixture was filtered and evaporated in vacuo to give the title compound.

Synthesis of (4-Chloro-5-methyl-1H-pyrazol-3-yl)methanol

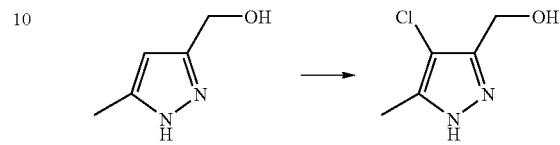

To a solution of the alcohol (1.32 g) in CH$_2$Cl$_2$ (30 mL) was added N-chlorosuccinimide (1.74 g). The reaction mixture was stirred at room temperature for overnight and aqueous NaOH solution (30 mL) was added. The organic layer was separated out and the aqueous layer was extracted with ethyl acetate (3×30 mL). The combined organic phase was dried (Na$_2$SO$_4$), filtered and evaporated in vacuo to give the title compound.

Synthesis of 4-Chloro-5-methyl-1H-pyrazole-3-carbaldehyde

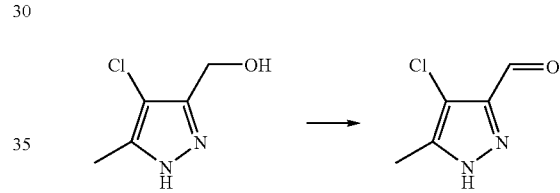

To a solution of the alcohol (14.6 mg) in dimethoxyethane (1 mL) was added MnO$_2$ (51 mg) in one portion. The reaction mixture was heated up to 110° C. for 3 h and cooled to room temperature. The mixture was filtered and the remaining solid was washed with hot ethanol (3 mL). The combined organic solution was evaporated in vacuo to give the title aldehyde.

Synthesis of 5-(4-Chloro-5-methyl-1H-pyrazol-3-yl)oxazole

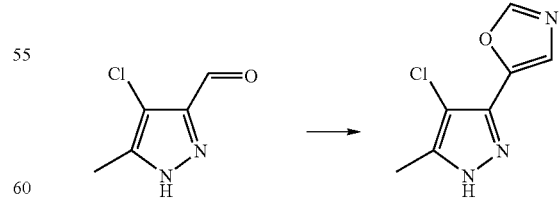

To a solution of the aldehyde (14 mg) in ethanol (1 mL) was added NaOEt (14 mg) and TosMic (20 mg). The reaction mixture was stirred at room temperature for 1 h and evaporated in vacuo. The mixture was dissolved in saturated aqueous NaHCO$_3$ solution (1 mL) and extracted with ethyl acetate (3×1 mL). The combined organic solution was dried and evaporated to give the title compound.

Protocol JJ: Heteroaryl Substituted Pyrazoles Via Cycloaddition and Cyclization Reactions Synthesis of 1-[4-(4-Chloro-3-methoxy-phenyl)-piperazin-1-yl]-2-[4-chloro-5-methyl-3-(5-methyl-[1,2,4]oxadiazol-3-yl)-pyrazol-1-yl]-ethanone

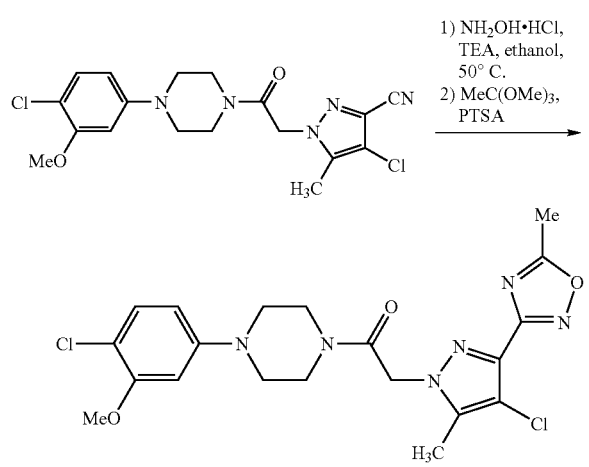

A mixture of 2-(3-cyano-4-chloro-5-methyl-pyrazol-1-yl)-1-[4-(4-chloro-3-methoxy-phenyl)-piperazin-1-yl]-ethanone (41 mg, 1 equiv), NH₂OH·HCl (35 mg, 5 equiv) and Et3N (140 µL, 10 equiv) in 1 mL of ethanol were heated at 50° C. for 2 hours and then cooled to room temperature. The white solid was collected, treated with trimethylorthoacetate (1 mL) and 1 crystal of PTSA at 50° C. for 2 hours. Reverse phase HPLC (acetonitrile-H₂O with 0.1% TFA as eluent) gave the title compound: LCMS Retention time: 4.26 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 465.

Synthesis of 1-[4-(4-Chloro-3-methoxy-phenyl)-2(S)-methyl-piperazin-1-yl]-2-(4-chloro-5-methyl-3-[1,2,4]oxadiazol-3-yl-pyrazol-1-yl)-ethanone

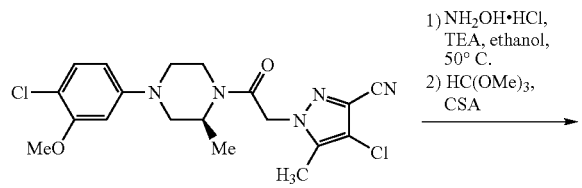

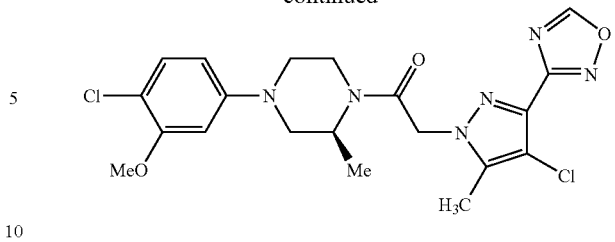

A mixture of 2-(3-cyano-4-chloro-5-methyl-pyrazol-1-yl)-1-[4-(4-chloro-3-methoxy-phenyl)-2-(S)-methyl-piperazin-1-yl]-ethanone (160 mg, 1 equiv), NH₂OH·HCl (79 mg, 3 equiv) and Et3N (264 µL, 5 equiv) in 1 mL of ethanol were heated at 50° C. for 2 hours and then cooled to room temperature. The white solid was collected, treated with trimethylorthoformate (1 mL) and 1 crystal of CSA at 50° C. for 2 hours. Reverse phase HPLC (acetonitrile-H₂O with 0.1% TFA as eluent) gave the title compound: LCMS Retention time: 5.24 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 465.

Synthesis of 1-[4-(4-Chloro-2-fluoro-5-methoxy-phenyl)-piperazin-1-yl]-2-(4-chloro-5-methyl-3-[1,2,4]oxadiazol-3-yl-pyrazol-1-yl)-ethanone

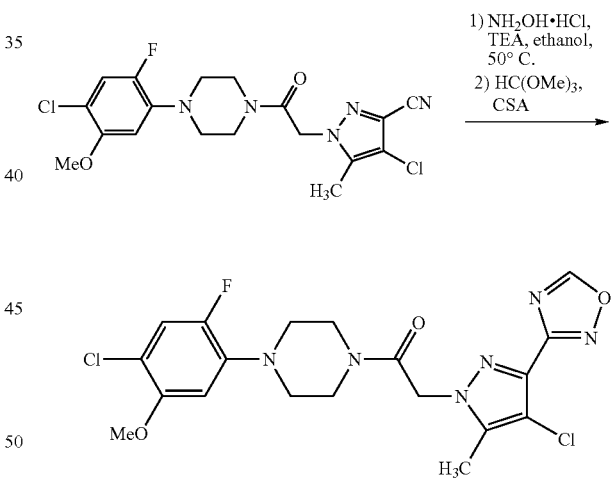

A mixture of 1-[4-(4-chloro-2-fluoro-5-methoxy-phenyl)-piperazin-1-yl]-2-(4-chloro-3-cyano-5-methyl-pyrazol-1-yl)-ethanone (165 mg, 1 equiv), NH₂OH·HCl (79 mg, 3 equiv) and Et3N (264 µL, 5 equiv) in 1 mL of ethanol were heated at 50° C. for 2 hours and then cooled to room temperature. The white solid was collected, treated with trimethylorthoformate (1 mL) and 1 crystal of CSA at 50° C. for 2 hours. Reverse phase HPLC (acetonitrile-H₂O with 0.1% TFA as eluent) gave the title compound: LCMS Retention time: 5.30 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); LCMS observed for (M+H)+: 469.

Protocol KK: Synthesis of Compounds Using Negishi Coupling Reactions

Synthesis of 1-(4-(4-chlro-3-methoxyphenyl)piperzin-1-yl)-2-(3-thiazol-2-yl-indazol-1-yl)ethanone

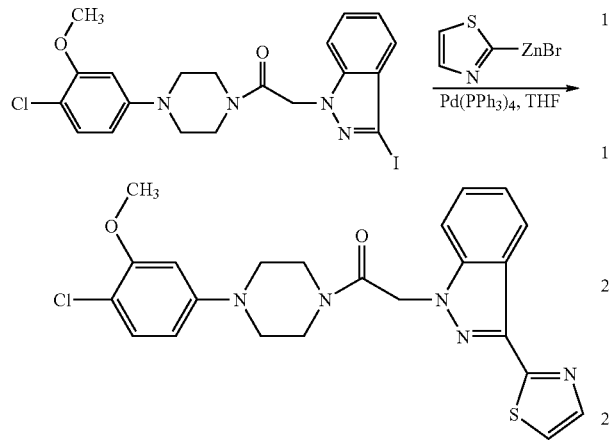

The above compound was synthesized following Protocol KK from example 2, using 1-[4-(4-Chloro-3methoxy-phenyl)-piperazin-1-yl]-2-(3-iodo-indazol-1-yl)-ethanone, to give the title compound: LC MS 462 (M+H), $R_f$=5.37 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); 1H NMR (400 MHz, CDCl3): δ 3.07 (apparent quintet, J=4.8 Hz, 4H), 3.75 (t, J=5.2 Hz, 2H), 3.81 (t, J=4.8 Hz, 2H), 3.86 (s, 3H), 5.34 (s, 2H), 6.37 (dd, J=2.6 & 8.4 Hz, 1H), 6.42 (d, J=2.5 Hz, 1H), 7.18 (d, J=8.5 Hz, 1H), 7.30-7.35 (m, 2H), 7.45-7.53 (m, 2H), 7.96 (d, J=3.0 Hz, 1H), 8.46-8.48 (m, 1H).

Synthesis of (4-Chloro-5-methyl-3-oxazol-2-ylpyrazol-1-yl)acetic acid tert-butyl ester

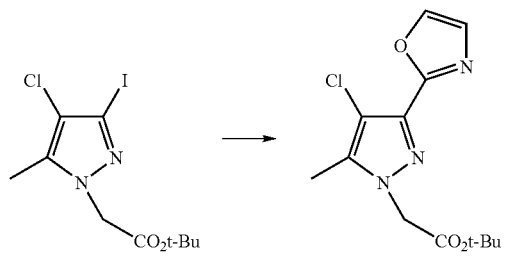

The title compound was obtained according to Nigishi Coupling Protocol KK.

Synthesis of (4-Chloro-5-methyl-3-oxazol-2-yl-pyrazol-1-yl)acetic acid

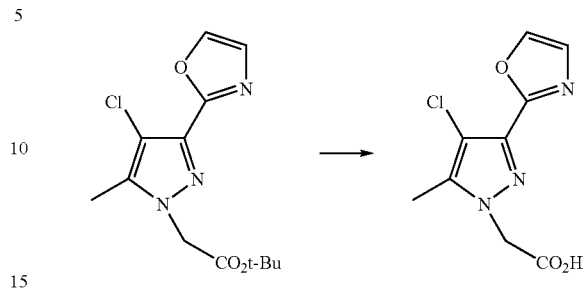

To a solution of the ester (144 mg) in CH$_2$Cl$_2$ (3 mL) was added trifluoroacetic acid (0.23 mL) and triethylsilane (1 mL). The reaction mixture was stirred at room temperature for 3 h and evaporated in vacuo to give the title compound.

Synthesis of 1-[4-(4-Chloro-3-methoxy-phenyl)-piperazin-1-yl]-2-(4-chloro-5-methyl-3-thiazol-2-yl-pyrazol-1-yl)ethanone

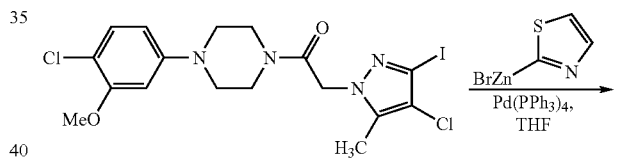

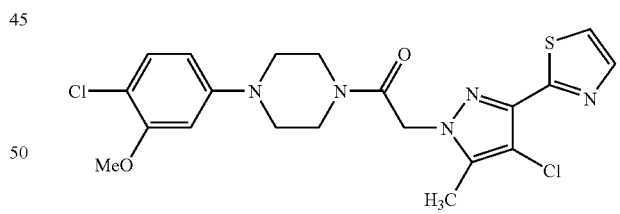

Following Protocol KK, A mixture of 2-(3-iodo-4-chloro-5-methyl-pyrazol-1-yl)-1-[4-(4-chloro-3-methoxy-phenyl)-piperazin-1-yl]-ethanone (204 mg, 0.4 mmol, 1 equiv), 2-thiazonyl Zinc bromide (0.5 M in THF, 1.6 mL, 2 equiv) and Pd(PPh3)4 (46 mg, 0.1 equiv) was refluxed overnight, cooled to room temperature, quenched with water, extracted with EtOAc. The organic layer was purified by reverse phase HPLC to yield the title compound: LCMS Retention time: 4.36 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/

94.9% water, B=0.08% formic acid/99.9% acetonitrile); LCMS observed for (M+H)+: 466.

of 20% to 95% B with a 2.5 minute wash at 95% B (A=0.1% formic acid/5% acetonitrile/94.9% water, B=0.08% formic acid/99.9% acetonitrile).

Protocol LL: Mannich Additions to Aromatic Rings

Synthesis of 5-Chloro-2-{4-[2-(4-chloro-5-methyl-3-trifluoromethyl-pyrazol-1-yl)-acetyl]-piperazin-1-yl}-4-methoxy-benzaldehyde

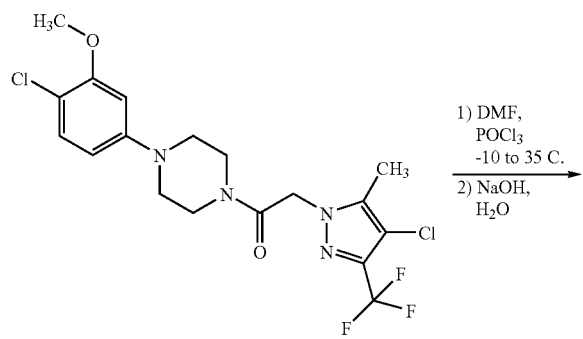

1-[4-(4-Chloro-2-hydroxymethyl-5-methoxy-phenyl)-piperazin-1-yl]-2-(4-chloro-5-methyl-3-trifluoromethyl-pyrazol-1-yl)-ethanone

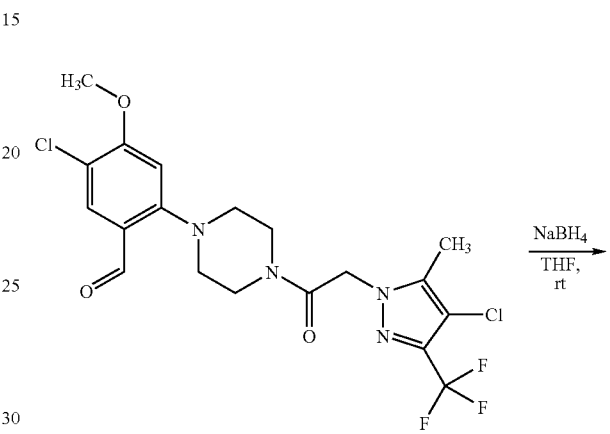

Took 7.6 g dry DMF (97.5 mmol, 4.4 eq) in a 250 mL 3-necked flask fitted with a stirring paddle, thermometer, and addition funnel fitted with an N2 inlet. The flask was cooled in a salt water bath until t~−10 C, then 2.3 mL POCl3 (24.4 mmol, 1.1 eq) was added in a slow stream over a five minute period. The mixture was allowed to stir for 15 min, then a solution of 10.0 g of 1-[4-(4-Chloro-3-methoxy-phenyl)-piperazin-1-yl]-2-(4-chloro-5-methyl-3-trifluoromethyl-pyrazol-1-yl)-ethanone (22.2 mmol, 1.0 eq) in 35 mL dry DMF was added dropwise over ½ hr period. The temperature was kept below 5° C. during the addition. The flask was then transferred to an oil bath and warmed to 35° C. After four hours, the solution was poured into 200 mL of vigorously stirring H₂O which resulted in a thick beige precipitate. The pH was adjusted to ~8 with 40% NaOH in H₂O, and the solid was collected by vacuum filtration, washed well with H₂O, then dried under vacuum to give the title compound: LC/MS (ES) (M+H) 479.0; retention time 7.24 minutes (Agilent Zorbax SB-C18, 2.1×50 mm, 5μ, 35° C.) using a 2.0 minute isocratic period of 20% B, followed by a 5.0 minute gradient Took 100 mg 5-Chloro-2-{4-[2-(4-chloro-5-methyl-3-trifluoromethyl-pyrazol-1-yl)-acetyl]-piperazin-1-yl}-4-methoxy-benzaldehyde (0.20 mmol, 1.0 eq) and 15.3 mg NaBH4 (0.40 mmol, 2.0 eq) in 500 uL THF in a 4 mL vial fitted with a stir bar. The vial was loosely capped and the mixture allowed to stir for 3 hours at room temperature. The reaction was quenched with a small amount of aqueous HCl, the resulting white precipitate was collected by vacuum filtration and dried under vacuum to give the title compound: LC/MS (ES) (M+H) 481.3, retention time=4.51 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

Protocol MM: Preparation of Compounds by Transformation of C—C and C—N Triple Bonds Synthesis of 2-(3-acetyl-4-chloro-5-methylpyrazol-1-yl)-1-(4-(4-chloro-3-methoxy phenyl)piperazin-1-yl)ethanone

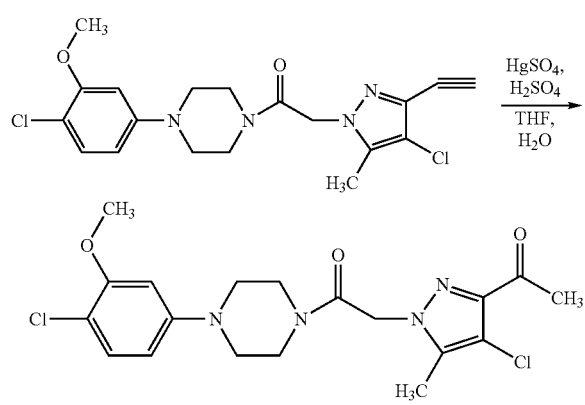

Mercuric sulfate (16 mg, 0.05 mmol) was added to a 0° C. stirred solution of 2-(4-Chloro-3-ethynyl-5-methyl-pyrazol-1-yl)-1-(4-chloro-3-methoxyphenyl)-piperazin-1-yl)ethanone (90 mg, 0.22 mmol) and conc. sulfuric acid (0.2 mL) in a mixture of THF:H$_2$O solvent (2 mL:1 mL). Stirring continued at r.t for 1 h, neutralized with saturated aqueous NaHCO$_3$, and extracted with ethyl acetate (3X 20 mL). The combined organic layer was washed with water, brine, dried (Na$_2$SO$_4$) and concentrated. The residue was purified by HPLC using 20-80% method to get 2-(3-Acetyl-4-Chloro-5methylpyrazol-1-yl)-1-(4-(4-chloro-3-methoxyphenyl)piperazin-1-yl)ethanone in pure form in 60% yield: LC MS: m/z 425 M$^{+H}$, R$_t$=4.33 min (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); $^1$H NMR (400 MHz, CDCl$_3$): δ 2.28 (s, 3H), 2.55 (s, 3H), 3.18 (apparent d, J=15.4 Hz, 4H), 3.73 (apparent d, J=15.6 Hz, 4H), 3.89 (s, 3H), 5.01 (s, 2H), 6.43 (apparent d, J=8.7 Hz, 1H), 6.49 (s, 1H), 7.21 (d, J=8.3 Hz, 1H).

Synthesis of 2-(4-Chloro-3-(1-hydroxyethyl)-5methylpyrazol-1-yl)-1-(4-(4-chloro-3-methoxy phenyl)piperazin-1-yl)ethanone

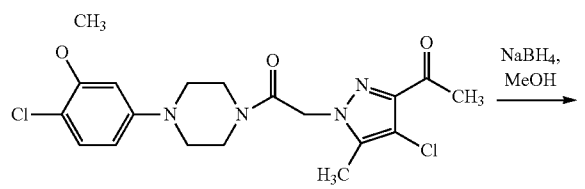

-continued

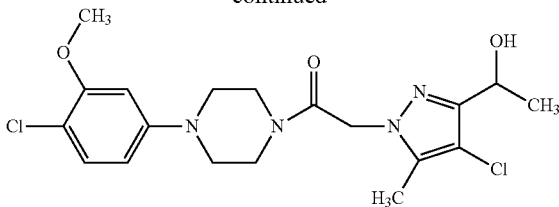

Sodium borohydride was added to a stirred solution of 2-(3-Acetyl-4-Chloro-5methylpyrazol-1-yl)-1-(4-(4-chloro-3-methoxyphenyl)piperazin-1-yl)ethanone (100 mg, 0.23 mmol) in methanol at 0° C. The reaction was pulled out of the ice/water bath, and stirring was continued for 2 hours. Then the reaction mixture was diluted with water and extracted with ethyl acetate. The combined organic layer was washed with water, brine, dried over Na2SO4 and concentrated. The residue was purified by HPLC using 20-80% method to get 2-(4-Chloro3-(1-hydroxyethyl)-5methylpyrazol-1-yl)-1-(4-(4-chloro-3-methoxy phenyl)piperazin-1-yl)ethanone: LC MS: m/z 427 M+H, R$_t$=3.91 minutes (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-[3-(2-Aminomethylpyridin-4-yl)-4-chloro-5-methylpyrazol-1-yl]-1-[4-(4-chloro-3-methoxyphenyl)piperazin-1-yl]ethanone

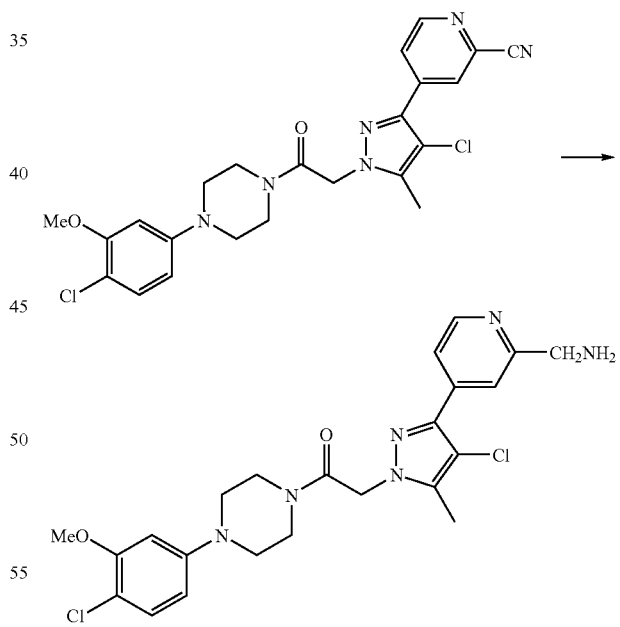

To a solution of 4-(4-Chloro-1-{2-[4-(4-chloro-3-methoxy-phenyl)-piperazin-1-yl]-2-oxo-ethyl}-5-methyl-1H-pyrazol-3-yl)-pyridine-2-carbonitrile (49 mg) in MeOH (1 mL) at 0° C. was added CoCl2.6H$_2$O (71 mg) and NaBH4 (114 mg). The reaction mixture was stirred at 0° C. for an additional 30 min and quenched by the addition of water (1 mL). The mixture was filtered and purified by preparative HPLC to give the title compound: LCMS (ES) M+H 489.1; R$_f$ 3.13 minutes (Agilent Zorbax SB-C18, 2.1×50 mm, 5µ, 35°

C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Protocol NN: Preparation of Compounds Using Nickel and Chromium-Mediated Reactions 2-[4-Chloro-5-(1-hydroxy-ethyl)-3-trifluoromethyl-pyrazol-1-yl]-1-[4-(4-chloro-3-methoxy-phenyl)-piperazin-1-yl]-ethanone

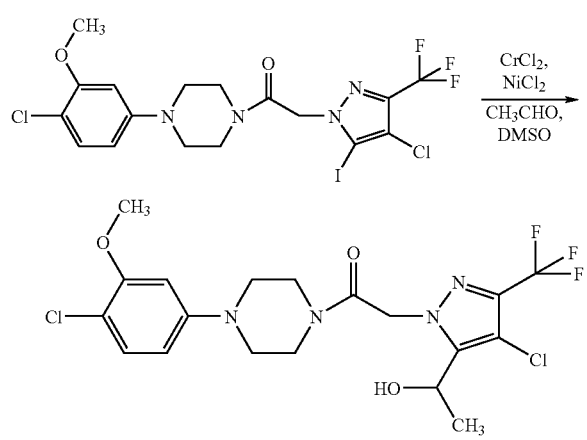

2-(4-Chloro-5-iodo-3-trifluoromethylpyrazol-1-yl)-1-(4-(4-chloro-3-methoxyphenyl)piperazin-1-yl)ethanone (100 mg, 0.18 mmol) was added to a 0° C. stirred solution of acetaldehyde (156 mg, 3.56 mmol) and chromous chloride (218 mg, 1.78 mmol) doped with 1% $NiCl_2$ (2 mg) in dry DMSO. The reaction was removed from the bath, and stirring continued for 2 hours. Then, the reaction mixture was diluted with saturated aqueous ammonium chloride and extracted with ethyl acetate (3X 20 mL). The combined organic layer was washed with water, brine, dried ($Na_2SO_4$) and concentrated. The residue was purified by HPLC to get the title compound in 55% yield. LC MS: m/z 481 (M+H), Retention time=4.68 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 2-(4-Chloro-5-(1-hydroxyphenylm-ethyl)-3-trifluoromethylpyrazol-1-yl)-1-(4-(4-chloro-3-methoxy phenyl)piperazin-1-yl)ethanone

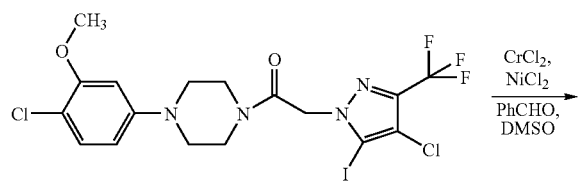

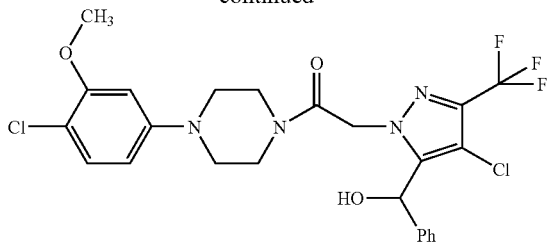

The title compound was synthesized using same as the above protocol. LC MS: m/z 543 (M+H), $R_t$=5.20 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); $^1$H NMR (400 MHz, $CDCl_3$): δ 3.08-3.20 (m, 4H), 3.40-3.45 (m, 1H), 3.51-3.58 (m, 1H), 3.75 (apparent t, J=5.1 Hz, 2H), 3.89 (s, 3H), 4.33 (d, J=16.1 Hz, 1H), 4.70 (d, J=6.6 Hz, 1H), 4.96 (d, J=16.1 Hz, 1H), 6.19 (apparent d, J=6.2 Hz, 1H), 6.40 (apparent dd, J=3.6 & 8.8 Hz, 1H), 6.46 (apparent d, J=2.6 Hz, 1H),7.20-7.40 (m, 5H).

Synthesis of 2-(5-Benzoyl-4-Chloro-3-trifluorometh-ylpyrazol-1-yl)-1-(4-(4-chloro-3-methoxy phenyl) piperazin-1-yl)ethanone

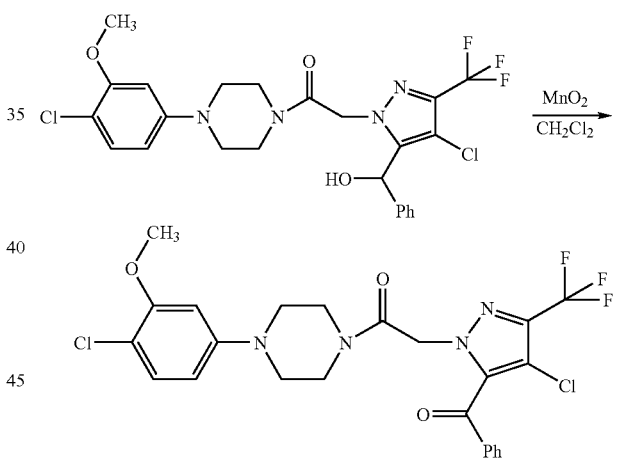

$MnO_2$ (20 mg) was added to a stirred solution of 2-(4-Chloro-5-(1-hydroxyphenylmethyl)-3-trifluoromethylpyra-zol-1-yl)-1-(4-(4-chloro-3-methoxy phenyl)piperazin-1-yl) ethanone (20 mg) in dry dichloromethane (1 mL) at ambient temperature under nitrogen. Stirring continued at same temperature for 24 hours. Then, the reaction mixture was diluted with acetone, passed through a short plug of $SiO_2$ column to remove inorganic impurities. The eluent was concentrated and the residue was purified by HPLC to get the title compound in 85% yield. LC MS: m/z 541 (M+H), 20-95 method, $R_t$=5.64 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); $^1$H NMR (400 MHz, $CDCl_3$): δ 3.07 (t, J=5.1 Hz, 2H), 3.21 (t, J=4.8 Hz, 2H), 3.60 (t, J=5.1 Hz, 2H), 3.65 (t, J=5.1 Hz, 2H), 3.89 (s, 3H), 5.44 (s, 2H), 4.33 (d, J=16.1 Hz, 1H), 4.70 (d, J=6.6 Hz, 1H), 6.40 (apparent dd, J=2.6 & 8.3 Hz, 1H), 6.46 (apparent d, J=3 Hz, 1H),7.20-7.22 (m, 1H), 7.50-7.54 (m, 2H), 7.63-7.67 (m, 1H), 7.89-7.91 (m, 2H).

Synthesis of [4-Chloro-5-(2-hydroxy-propyl)-3-trifluoromethyl-pyrazol-1-yl]-acetic acid

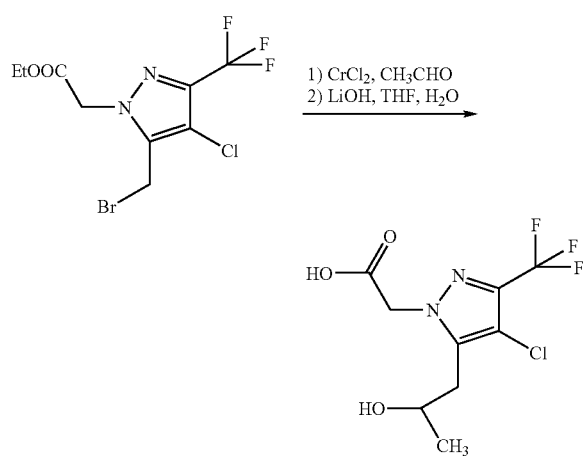

The above compound was synthesized via a two-step procedure. The first step follows the general chromous chloride-mediated Protocol NN, followed by basic hydrolysis of the ester to give the title compound.

Protocol OO: Reductive Amination on Aryl Aldehydes Using Borohydride Reagents

1-[4-(4-Chloro-2-dimethylaminomethyl-5-methoxyphenyl)-piperazin-1-yl]-2-(4-chloro-5-methyl-3-trifluoromethyl-pyrazol-1-yl)ethanone

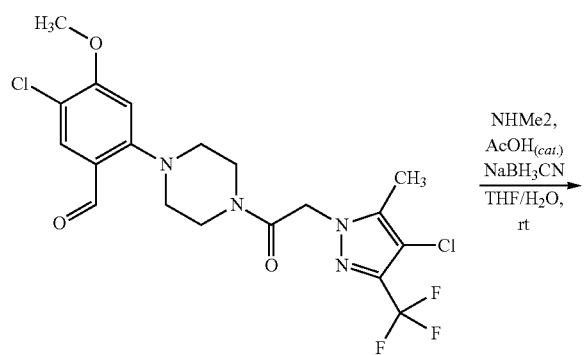

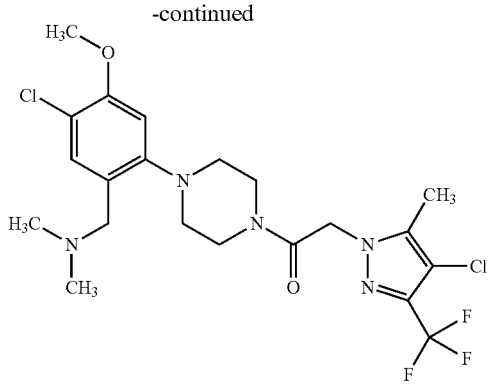

Took 200 mg of 5-Chloro-2-{4-[2-(4-chloro-5-methyl-3-trifluoromethyl-pyrazol-1-yl)-acetyl]-piperazin-1-yl}-4-methoxy-benzaldehyde (0.42 mmol, 1.0 eq), 5 uL AcOH (~0.08 mmol, 0.10 eq), 2.4 eq of dimethylamine as a 1M solution in methanol (1.0 mmol), and 1.0 mL of 1:1(v/v) THF:MeOH in 4 mL vials fitted with stir bars; the mixture was allowed to stir for ½ hr at room temperature, after which 79 mg NaBH3CN (1.26 mmol, 3.0 eq) was added. The vial was then loosely capped, and the stirring was allowed to continue overnight at room temperature. The crude product was purified by preparative HPLC, followed by treatment with 4M HCl in p-dioxane to give the title compound: LC/MS (ES) (M+H) 508.2; retention time 5.42 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

1-{4-[4-Chloro-2-(isopropylamino-methyl)-5-methoxy-phenyl]-piperazin-1-yl}-2-(4-chloro-5-methyl-3-trifluoromethyl-pyrazol-1-yl)-ethanone

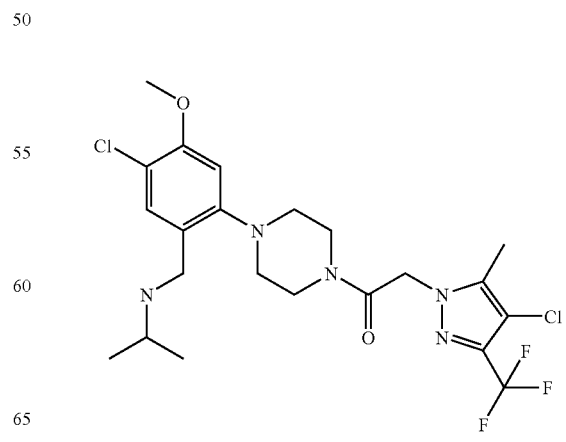

Following Protocol OO above, using isopropylamine, gave the title compound: LC/MS(ES) (M+H) 522.2, retention time 5.73 minutes using the same method as in the protocol above.

1-{4-[4-Chloro-2-(ethylamino-methyl)-5-methoxy-phenyl]-piperazin-1-yl}-2-(4-chloro-5-methyl-3-trifluoromethyl-pyrazol-1-yl)-ethanone

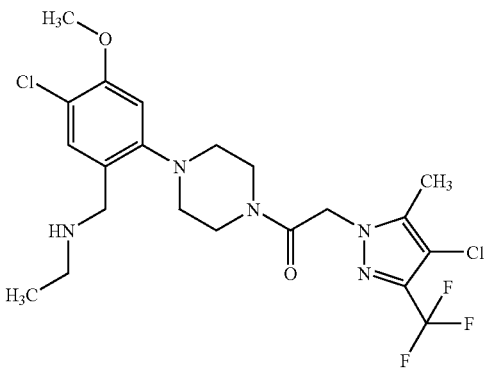

Following Protocol OO above, using ethylamine, gave the title compound: LC/MS(ES) (M+H) 508.2, retention time 5.73 minutes using the same method as in the protocol above.

1-[4-(4-Chloro-2-cyclopentylaminomethyl-5-methoxy-phenyl)-piperazin-1-yl]-2-(4-chloro-5-methyl-3-trifluoromethyl-pyrazol-1-yl)-ethanone

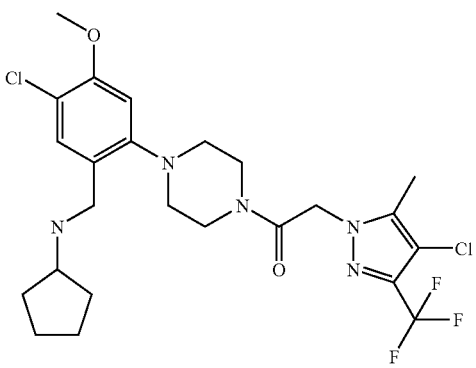

Following Protocol OO above, using aminocyclopentane, gave the title compound: LC/MS(ES) (M+H) 548.2, retention time 5.90 minutes using the same method as in the protocol above.

1-[4-(4-Chloro-5-methoxy-2-morpholin-4-ylmethyl-phenyl)-piperazin-1-yl]-2-(4-chloro-5-methyl-3-trifluoromethyl-pyrazol-1-yl)-ethanone

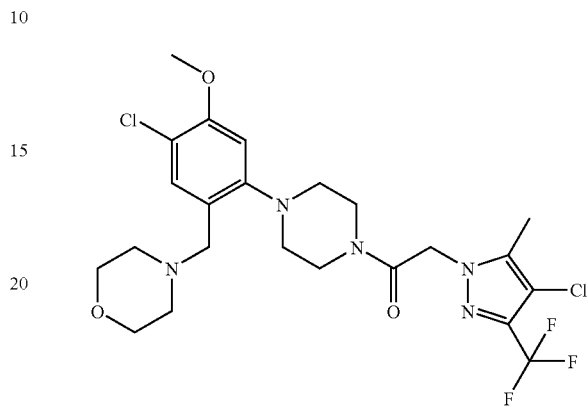

Following Protocol OO above, using morpholine, gave the title compound: LC/MS(ES) (M+H) 550.2, retention time 5.36 minutes using the same method as in the protocol above.

1-[4-(2-Acetyl-4-chloro-5-methoxy-phenyl)-piperazin-1-yl]-2-(4-chloro-5-methyl-3-trifluoromethyl-pyrazol-1-yl)-ethanone

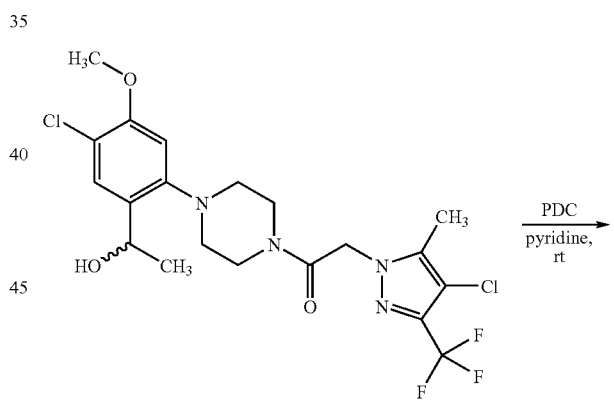

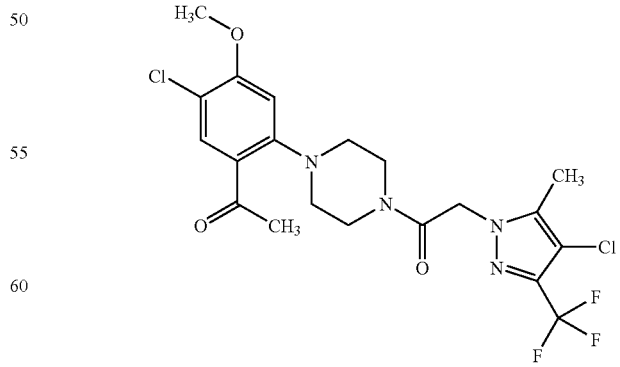

Took 8.0 g 1-{4-[4-Chloro-2-(1-hydroxy-ethyl)-5-methoxy-phenyl]-piperazin-1-yl}-2-(4-chloro-5-methyl-3-trifluoromethyl-pyrazol-1-yl)-ethanone (16.2 mmol, 1.0 eq) in 70 mL pyridine in a 200 mL round bottom flask fitted with a stir bar and N2 inlet. Added 9.1 g PDC (24.2 mmol, 1.5 eq) and stirred the mixture overnight at room temperature. The solvent was then removed under vacuum and the crude product purified by column chromatography (chloroform/hexane) to give the title compound: LC/MS(ES) (M+H) 493.1; retention time=4.90 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

Protocol PP: Reductive Amination on Aryl Ketones Using Borohydride Reagents

1-{4-[4-Chloro-5-methoxy-2-(1-methylamino-ethyl)-phenyl]-piperazin-1-yl}-2-(4-chloro-5-methyl-3-trifluoromethyl-pyrazol-1-yl)-ethanone

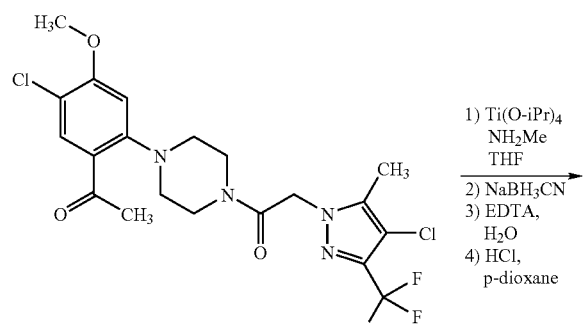

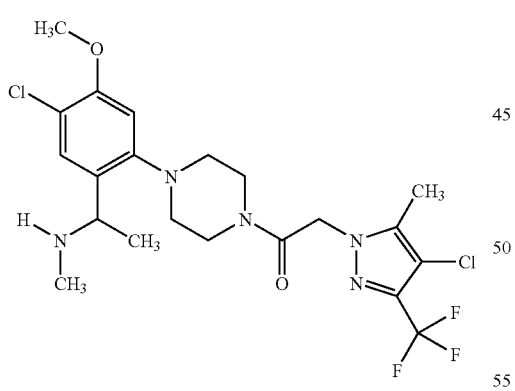

Took 100 mg 1-[4-(2-Acetyl-4-chloro-5-methoxy-phenyl)-piperazin-1-yl]-2-(4-chloro-5-methyl-3-trifluoromethyl-pyrazol-1-yl)-ethanone (0.20 mmol, 1.0 eq), 180 uL Ti(OiPr)4 (0.60 mmol, 3.0 eq), and 2.5 eq of methylamine (2M in THF) in 500 uL of THF in a 4 mL vial fitted with a stir bar. The mixture was stirred at room temperature for 3 hours, then 38 mg NaBH3CN (0.60 mmole, 3.0 eq) was added to the vial and the mixture was stirred overnight. The reaction was quenched with a small amount of aqueous HCl, and the resulting white precipitate was removed by vacuum filtration and discarded. The mother liquor was purified by HPLC. The product were then re-dissolved in methylene chloride, and washed with 0.5M aqueous EDTA. The organic phase was separated and dried under vacuum. The residue was treated with 4M HCl in p-dioxane to give the title product as a solid: LC/MS(ES) (M+H) 508.1, retention time=5.08 minutes (Agilent Zorbax SB-C18, 2.1×50 mm, 5μ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

1-{4-[4-Chloro-2-(1-dimethylamino-ethyl)-5-methoxy-phenyl]-piperazin-1-yl}-2-(4-chloro-5-methyl-3-trifluoromethyl-pyrazol-1-yl)-ethanone

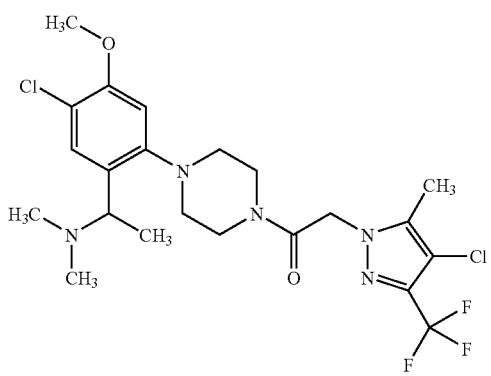

Following Protocol PP above, using dimethylamine, gave the title compound: LC/MS(ES) (M+H) 522.1, retention time 5.02 minutes using the same method as in the protocol above.

1-{4-[4-Chloro-5-methoxy-2-(1-ethylamino-ethyl)-phenyl]-piperazin-1-yl}-2-(4-chloro-5-methyl-3-trifluoromethyl-pyrazol-1-yl)-ethanone

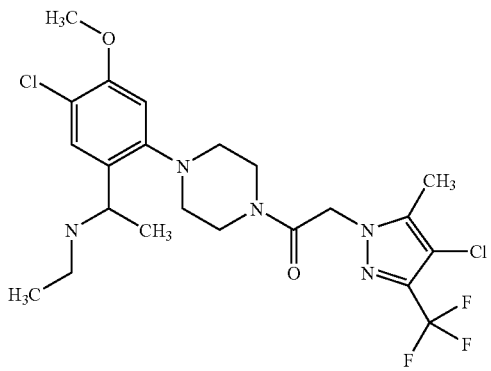

Following Protocol PP above, using ethylamine, gave the title compound: LC/MS(ES) (M+H) 522.1, retention time 4.96 minutes using the same method as in the protocol above.

1-{4-[4-Chloro-5-methoxy-2-(1-isopropylamino-ethyl)-phenyl]-piperazin-1-yl}-2-(4-chloro-5-methyl-3-trifluoromethyl-pyrazol-1-yl)-ethanone

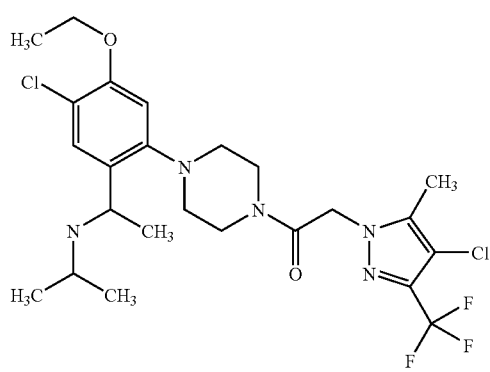

Following Protocol PP above, using isopropylamine, gave the title compound: LC/MS(ES) (M+H) 536.2, retention time 5.10 minutes using the same method as in the protocol above.

1-{4-[4-Chloro-5-methoxy-2-(1-cyclopentylamino-ethyl)-phenyl]-piperazin-1-yl}-2-(4-chloro-5-methyl-3-trifluoromethyl-pyrazol-1-yl)-ethanone

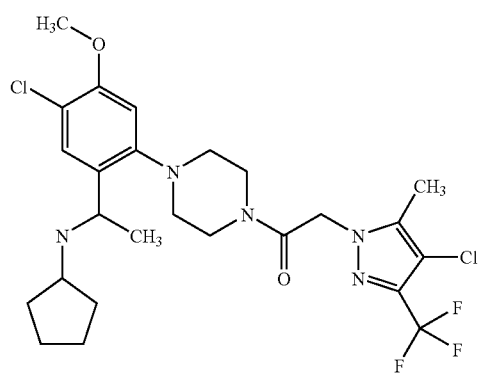

Following Protocol PP above, using cyclopentylamine, gave the title compound: LC/MS(ES) (M+H) 562.2, retention time 5.19 minutes using the same method as in the protocol above.

1-{4-[4-Chloro-5-methoxy-2-(1-pyrrolidin-1-yl-ethyl)-phenyl]-piperazin-1-yl}-2-(4-chloro-5-methyl-3-trifluoromethyl-pyrazol-1-yl)-ethanone

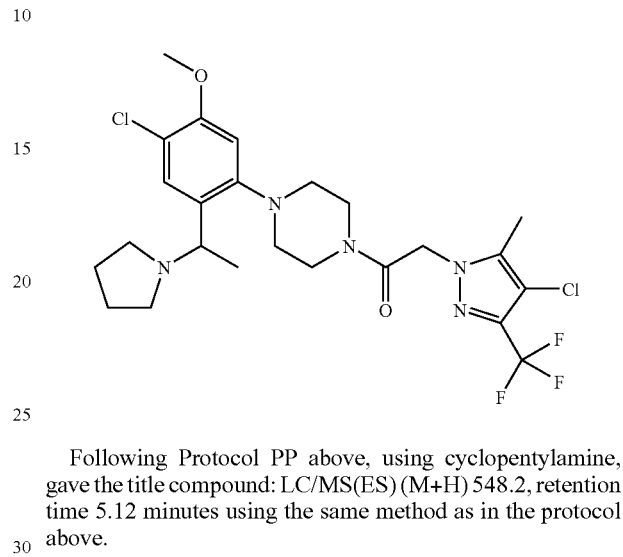

Following Protocol PP above, using cyclopentylamine, gave the title compound: LC/MS(ES) (M+H) 548.2, retention time 5.12 minutes using the same method as in the protocol above.

Protocol QQ: General Preparation of Oxime Derivatives from Aryl Aldehydes and Ketones

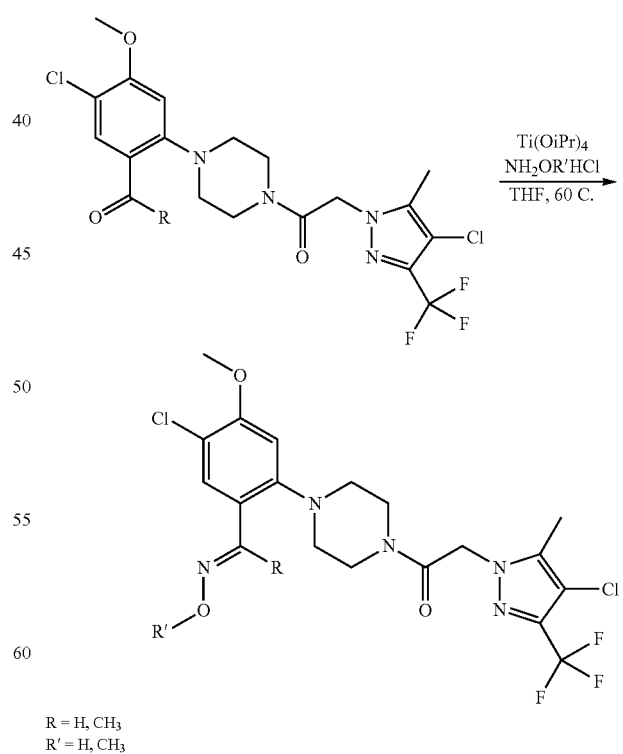

R = H, CH$_3$
R' = H, CH$_3$

Took 100 mg of the appropriate carbonyl compound (0.20 mmol, 1.0 eq), 90 uL Ti(OiPr)4 (0.30 mmol, 1.5 eq), and 5.0 eq of the appropriate hydroxylamine HCl in 500 uL THF in 4 mL vials fitted with stir bars: the mixtures were allowed to stir overnight at 60 C. The reactions were quenched with a small amount of conc. HCl and purified by preparative HPLC. The free bases were prepared by dissolving the products in DCM and extraction with aqueous K2CO3, after which the organic phases were separated and dried under vacuum. The products were analyzed by LCMS using the following method: (Agilent Zorbax SB-C18, 2.1×50 mm, 5µ, 35° C.) using a 2.0 minute isocratic period of 20% B, followed by a 5.0 minute gradient of 20% to 95% B with a 2.5 minute wash at 95% B (A=0.1% formic acid/5% acetonitrile/94.9% water, B=0.08% formic acid/99.9% acetonitrile).

5-Chloro-2-{4-[2-(4-chloro-5-methyl-3-trifluoromethyl-pyrazol-1-yl)-acetyl]-piperazin-1-yl}-4-methoxy-benzaldehyde oxime

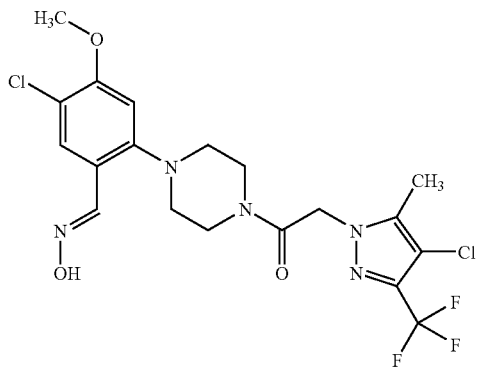

Following Protocol QQ, using 5-Chloro-2-{4-[2-(4-chloro-5-methyl-3-trifluoromethyl-pyrazol-1-yl)-acetyl]-piperazin-1-yl}-4-methoxy-benzaldehyde and hydroxylamine, gave the title compound as a mixture of cis and trans isomers: LC/MS(ES) (M+H) 494.1, retention time=4.70 minutes.

5-Chloro-2-{4-[2-(4-chloro-5-methyl-3-trifluoromethyl-pyrazol-1-yl)-acetyl]-piperazin-1-yl}-4-methoxy-benzaldehyde O-methyl-oxime

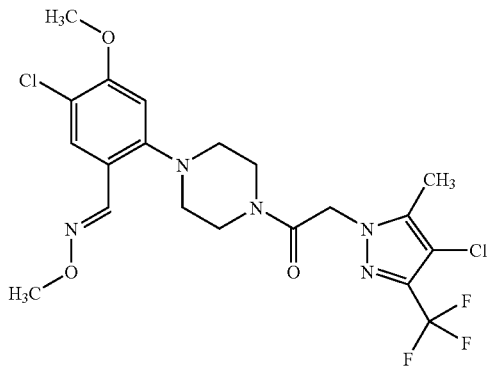

Following Protocol QQ, using 5-Chloro-2-{4-[2-(4-chloro-5-methyl-3-trifluoromethyl-pyrazol-1-yl)-acetyl]-piperazin-1-yl}-4-methoxy-benzaldehyde and O-methylhydroxylamine, gave the title compound as a mixture of cis and trans isomers: LC/MS(ES) (M+H) 508.1, retention time=4.67 minutes.

1-{4-[4-Chloro-2-(1-(Z)-hydroxyimino-ethyl)-5-methoxy-phenyl]-piperazin-1-yl}-2-(4-chloro-5-methyl-3-trifluoromethyl-pyrazol-1-yl)-ethanone

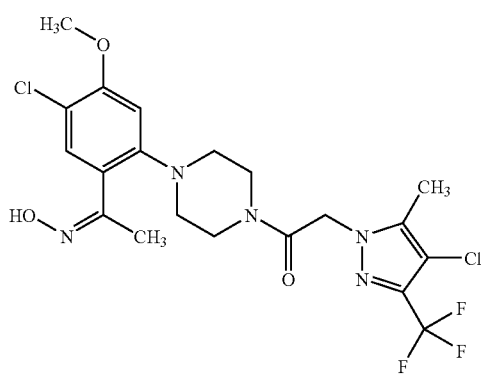

Following Protocol QQ, using 1-[4-(2-Acetyl-4-chloro-5-methoxy-phenyl)-piperazin-1-yl]-2-(4-chloro-5-methyl-3-trifluoromethyl-pyrazol-1-yl)-ethanone and hydroxylamine, gave the title compound: LC/MS(ES) (M+H) 508.1, retention time=4.73 minutes.

1-{4-[4-Chloro-2-(1-(E)-hydroxyimino-ethyl)-5-methoxy-phenyl]-piperazin-1-yl}-2-(4-chloro-5-methyl-3-trifluoromethyl-pyrazol-1-yl)-ethanone

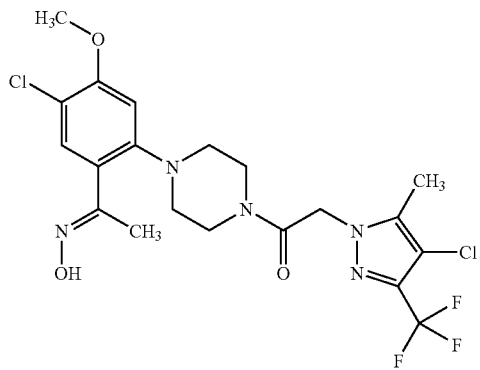

Following Protocol QQ, using 1-[4-(2-Acetyl-4-chloro-5-methoxy-phenyl)-piperazin-1-yl]-2-(4-chloro-5-methyl-3trifluoromethyl-pyrazol-1-yl)-ethanone and hydroxylamine, gave the title compound: LC/MS(ES) (M+H) 508.1, retention time=4.67 minutes. -

1-{4-[4-Chloro-5-methoxy-2-(1-(Z)-methoxyimino-ethyl)-phenyl]-piperazin-1-yl}-2-(4-chloro-5-methyl-3-trifluoromethyl-pyrazol-1-yl)-ethanone

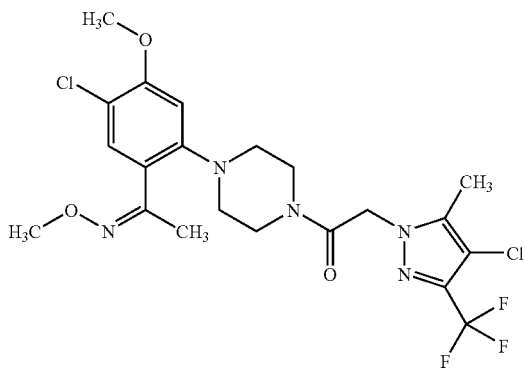

Following Protocol QQ, using 1-[4-(2-Acetyl-4-chloro-5-methoxy-phenyl)-piperazin-1-yl]-2-(4-chloro-5-methyl-3-trifluoromethyl-pyrazol-1-yl)-ethanone and O-Methylhydroxylamine, gave the title compound: LC/MS(ES) (M+H) 522.1, retention time=5.27 minutes.

1-{4-[4-Chloro-5-methoxy-2-(1-(E)-methoxyimino-ethyl)-phenyl]-piperazin-1-yl}-2-(4-chloro-5-methyl-3-trifluoromethyl-pyrazol-1-yl)-ethanone

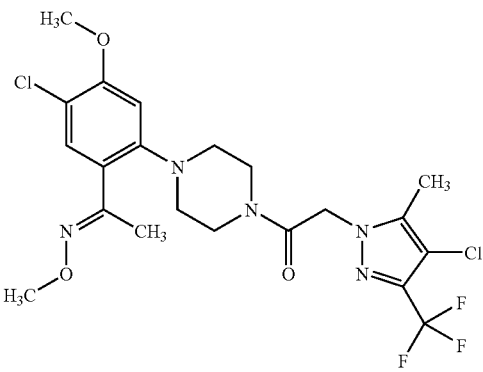

Following Protocol QQ, using 1-[4-(2-Acetyl-4-chloro-5-methoxy-phenyl)-piperazin-1-yl]-2-(4-chloro-5-methyl-3-trifluoromethyl-pyrazol-1-yl)-ethanone and O-Methylhydroxylamine, gave the title compound: LC/MS(ES) (M+H) 522.1, retention time=5.42 minutes.

Protocol RR: General Protocol for Addition of Organometallic Reagents to Aldehydes, Followed by Deprotection and Bop-Mediated Coupling

Synthesis of 1-[4-(4-chloro-3-methoxy-phenyl)-2-(1-hydroxy-ethyl)-piperazin-1-yl]-2-(4-chloro-5-methyl-3-trifluoromethyl-pyrazol-1-yl)-ethanone

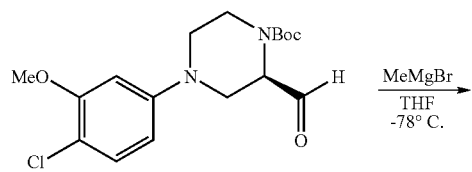

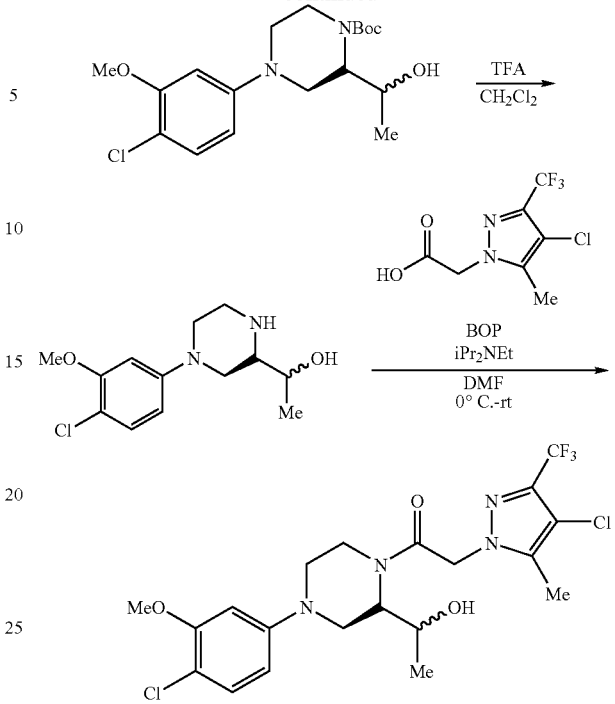

To a rapidly stirring solution of 4-(4-chloro-3-methoxy-phenyl)-2-formyl-piperazine-1-carboxylic acid tert-butyl ester (120 mg, 0.338 mmol) in 2.5 mL THF at −78° C. was added MeMgBr (0.17 mL, 3.0 M) dropwise. The homogeneous mixture was stirred 1 h at −78° C., removed from the cold bath, and then quenched with saturated ammonium chloride. The resultant solution was partitioned between ethyl acetate and saturated sodium bicarbonate, the organic phase separated, and the aqueous phase extracted with ethyl acetate (3×25 mL). The combined organics were dried with sodium sulfate and concentrated in vacuo to afford 120 mg of the hydroxylethyl piperazine. The crude product (110 mg, 0.296 mmol) was dissolved in 2.3 mL methylene chloride, lowered to 0° C., and TFA (0.228 mL, 2.96 mmol) was added dropwise. The reaction was stirred 15 min at 0° C., removed from the ice bath, and stirred a further 265 min at room temperature. The resultant solution was concentrated under reduced pressure to afford the deprotected amine as a dark foam. A 10 mL flask was subsequently charged with the crude amine salt, (4-chloro-5-methyl-3-trifluoromethyl-pyrazol-1-yl)-acetic acid (86 mg, 0.355 mmol), diisopropylethyl amine (0.226 mL, 1.30 mmol), and DMF (4 mL). The solution was lowered to 0° C. and BOP (157 mg, 0.355 mmol) was added in one portion. The reaction was stirred 10 min at 0° C., raised to room temperature, and stirred a further 3 h. The resultant solution was diluted with ether, quenched with saturated ammonium chloride, partitioned with sodium bicarbonate and ethyl acetate, and the aqueous layer extracted with ethyl acetate (4×35 mL). The combined organics were diluted with 30 mL hexanes, washed with saturated sodium bicarbonate (2×30 mL), dried with sodium sulfate, and concentrated in vacuo. The crude product (168 mg) was purified by column chromatography (30:70 EtOAc:hexanes) to afford 39 mg of the title compound: MS (ES) M+H expect 495.1, found 495.0; HPLC $R_t$=5.05 minutes, using the following method: (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 1-[4-(4-chloro-3-methoxy-phenyl)-2-(1-hydroxy-2-methyl-propyl)-piperazin-1-yl]-2-(4-chloro-5-methyl-3-trifluoromethyl-pyrazol-1-yl)-ethanone

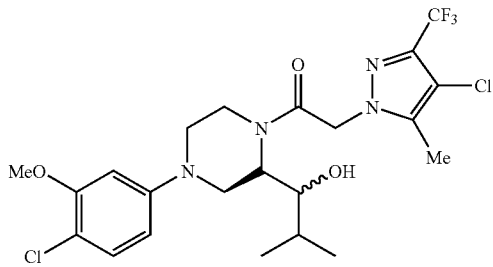

Following the sequence of steps in Protocol RR, using iso-Propylmagnesium chloride as the organometallic reagent, afforded the title compound: MS (ES) M+H expect 523.1, found 523.1; HPLC $R_t$=5.59 min.

Synthesis of 1-[4-(4-chloro-3-methoxy-phenyl)-2-(hydroxy-phenyl-methyl)-piperazin-1-yl]-2-(4-chloro-5-methyl-3-trifluoromethyl-pyrazol-1-yl)-ethanone

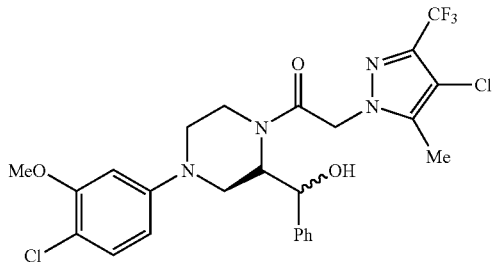

Following the sequence of steps in Protocol RR, using phenylmagnesium bromide as the organometallic reagent, afforded the title compound: MS (ES) M+H expect 557.1, found 557.1; HPLC $R_t$=5.59 min.

Synthesis of 1-[4-(4-chloro-3-methoxy-phenyl)-2-(1-hydroxy-2-phenyl-ethyl)-piperazin-1-yl]-2-(4-chloro-5-methyl-3-trifluoromethyl-pyrazol-1-yl)-ethanone

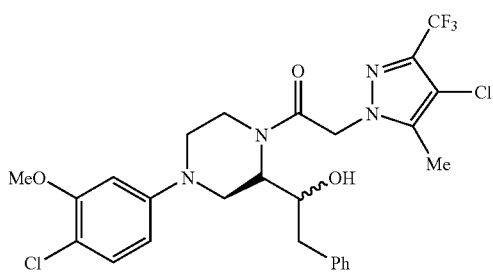

Following the sequence of steps in Protocol RR, using benzylmagnesium chloride as the organometallic reagent, afforded the title compound: MS (ES) M+H expect 571.1, found 571.1; HPLC $R_t$=5.61 min.

Synthesis of (5-chloro-2-{4-[2-(4-chloro-5-methyl-3-trifluoromethyl-pyrazol-1-yl)-acetyl]-piperazin-1-yl}-4-methoxy-phenyl)-hydroxy-acetonitrile

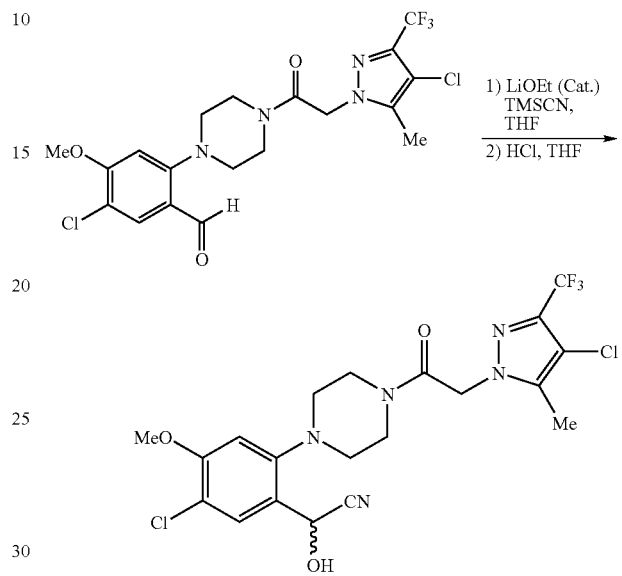

Step 1: To a solution of ethanol (0.018 mL, 0.313 mmol) in 25 mL THF at 0° C. was added n-BuLi (0.125 mL, 0.313 mmol) dropwise. The solution was stirred 10 min, followed by the addition of trimethylsilyl cyanide (0.625 mL, 4.70 mmol). The reaction was stirred a further 10 min and 5-chloro-2-{4-[2-(4-chloro-5-methyl-3-trifluoromethyl-pyrazol-1-yl)-acetyl]-piperazin-1-yl}-4-ethoxy-benzaldehyde (1.50 g, 3.13 mmol) was added in one portion. The resultant solution was removed from the ice bath, stirred 2.75 h, and then quenched with saturated ammonium bicarbonate. The aqueous layer was subsequently extracted with ethyl acetate (3×40 mL), the combined organics dried with sodium sulfate, and the solvent removed in vacuo to afford 1.78 g (98%) of the crude TMS cyanohydrin which was used directly in the next step.

Step 2: A 50 mL flask was charged with the crude TMS cyanohydrin, 3.1 mL 10% HCl, 10 mL water, and 10 mL THF. The resultant solution was stirred vigorously for 90 min, followed by dilution with ethyl acetate and quenching with saturated sodium bicarbonate. The mixture was stirred 5 min, the organic layer separated, and the aqueous layer extracted with ethyl acetate (3×30 mL). The combined organics were dried with sodium sulfate and concentrated in vacuo to generate 1.32 g of the crude cyanohydrin, contaminated with approximately 10% of the corresponding 6-benzaldehyde. The crude product was recrystallized (EtOAc/CH2Cl2/hexanes) to afford 780 mg (50%) of the desired cyanohydrin containing <5% of the aldehyde side-product: $^1$H NMR (400 MHz, CDCl$_3$) δ 7.42 (s, 1H), 6.81 (s, 1H), 5.52 (s, 1H), 5.00 (s, 2H), 3.80 (s, 3H), 3.65-3.83 (m, 4H), 3.02-3.20 (m, 2H), 2.85-2.98 (m, 2H), 2.60 (s, 3H); MS (ES) M+H expect 506.1, found 506.1; HPLC $R_t$=4.68 min.

Synthesis of (5-chloro-2-{4-[2-(4-chloro-5-methyl-3-trifluoromethyl-pyrazol-1-yl)-acetyl]-piperazin-1-yl}-4-methoxy-phenyl)-oxo-acetonitrile

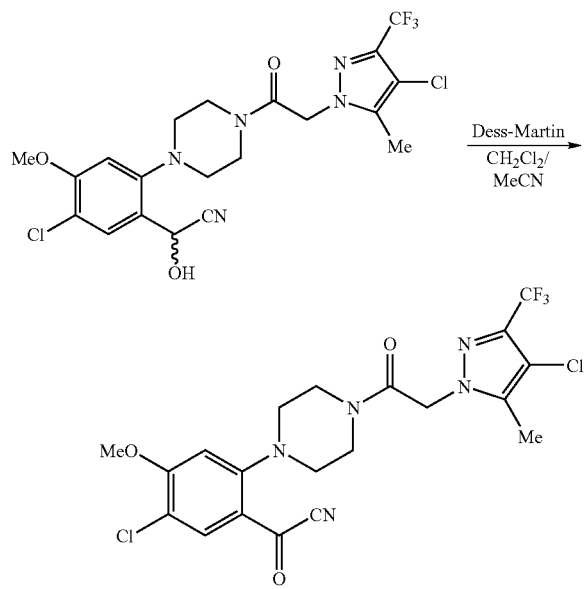

(5-chloro-2-{4-[2-(4-chloro-5-methyl-3-trifluoromethyl-pyrazol-1-yl)-acetyl]-piperazin-1-yl}-4-methoxy-phenyl)-hydroxy-acetonitrile (650 mg, 1.28 mmol) was dissolved in 1 mL MeCN, diluted with 8 mL methylene chloride, and the Dess-Martin Periodinane (5.7 mL, 0.25 M) was added dropwise (due to the poor solubility of the recrystallized starting material in methylene chloride, the cyanohydrin was dissolved in THF and then the solvent removed at reduced pressure to reveal a foam that was soluble in MeCN). Upon stirring 3 h, the reaction was quenched with saturated sodium thiosulfate and stirred 10 min. The resulting solution was partitioned between ethyl acetate and sodium bicarbonate, the organic layer separated, and the aqueous layer extracted with ethyl acetate (3×40 mL). The combined organics were dried over sodium sulfate and evaporated in vacuo to afford 550 mg (85%) of the desired acyl cyanide, contaminated with approximately 10% of the 6-benzaldehyde, which was used directly in the next step.

Protocol SS: Formation of Amide Bonds Via Reaction of Acylcyanides with Amines

Synthesis of 5-chloro-4-methoxy-2-{4-[2-(5-methyl-4-phenyl-3-trifluoromethyl-pyrazol-1-yl)-acetyl]-piperazin-1-yl}-benzamide

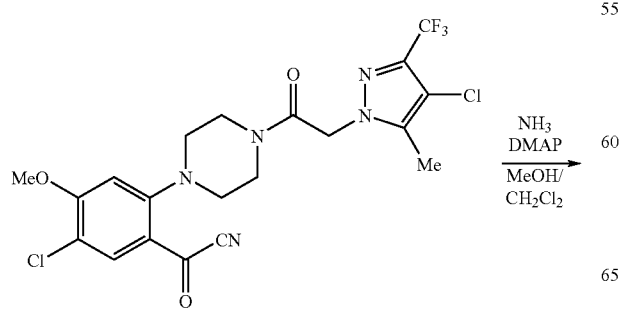

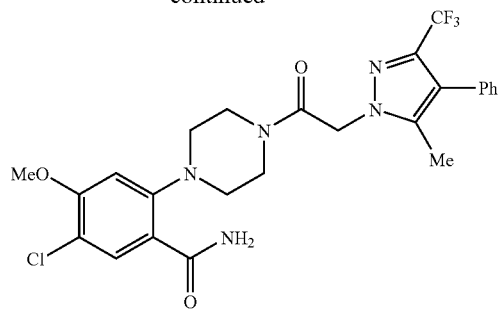

A 4 mL scintillation vial was charged with (5-chloro-2-{4-[2-(4-chloro-5-methyl-3-trifluoromethyl-pyrazol-1-yl)-acetyl]-piperazin-1-yl}-4-methoxy-phenyl)-oxo-acetonitrile (82 mg, 0.163 mmol), a catalytic quantity of dimethylaminopyridine, ammonia (0.813 mL, 2.0 M in MeOH), and methylene chloride (0.8 mL). The resultant solution was stirred 5 h, concentrated in vacuo, and purified by reverse phase HPLC to afford the title compound: MS (ES) M+H expect 494.1, found 494.1; HPLC $R_t$=4.26 minutes, using the following method: (Agilent Zorbax SB-C18, 2.1×50 mm, 5µ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile).

Synthesis of 5-chloro-2-{4-[2-(4-chloro-5-methyl-3-trifluoromethyl-pyrazol-1-yl)-acetyl]-piperazin-1-yl}-4-methoxy-N-methyl-benzamide

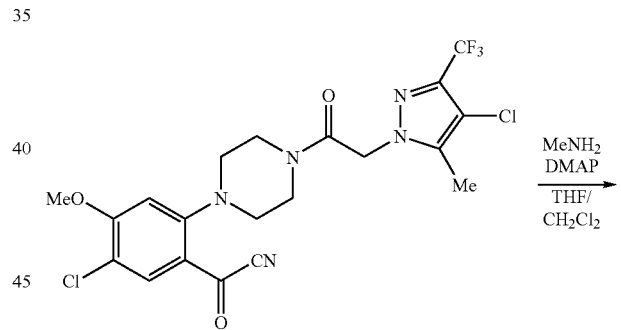

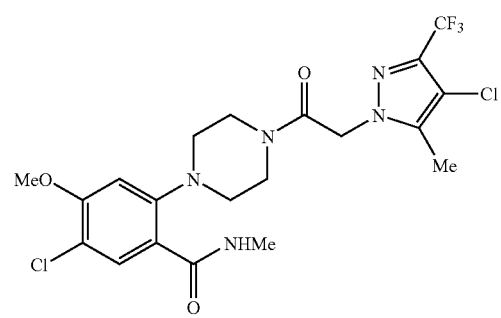

Following Protocol SS, using methylamine, gave the title compound: MS (ES) M+H expect 508.1, found 508.1; HPLC $R_t$=4.44 min.

Synthesis of 5-chloro-2-{4-[2-(4-chloro-5-methyl-3-trifluoromethyl-pyrazol-1-yl)-acetyl]-piperazin-1-yl}-4-methoxy-N,N-dimethyl-benzamide

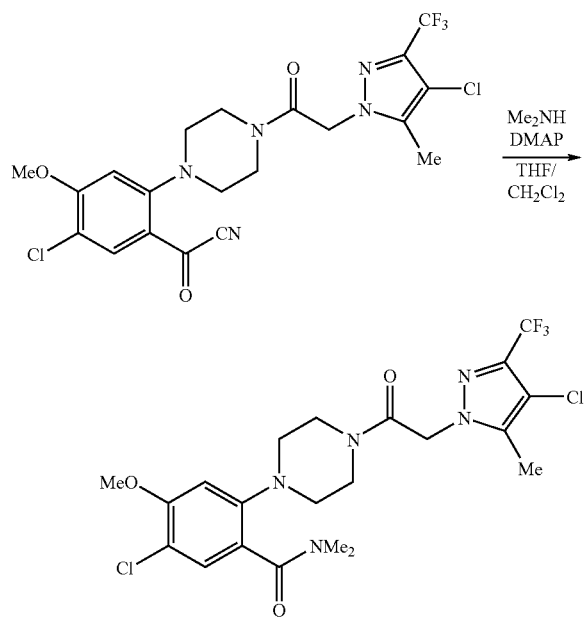

Following Protocol SS, using dimethylamine, gave the title compound: MS (ES) M+H expect 522.1, found 522.1; HPLC $R_t$=4.46 min.

Synthesis of 5-chloro-2-{4-[2-(4-chloro-5-methyl-3-trifluoromethyl-pyrazol-1-yl)-acetyl]-piperazin-1-yl}-N-ethyl-4-methoxy-benzamide

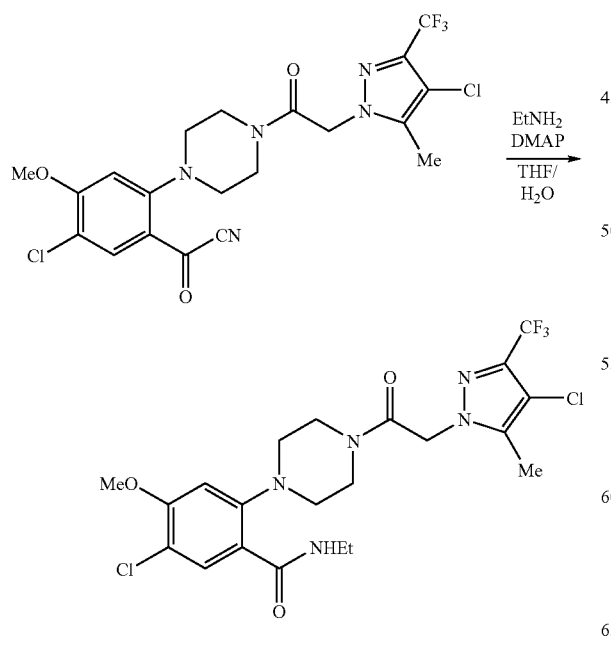

Following Protocol SS, using ethylamine, gave the title compound: MS (ES) M+H expect 522.1, found 522.1; HPLC $R_t$=4.66 min.

Synthesis of 1-{4-[4-chloro-5-methoxy-2-(pyrrolidine-1-carbonyl)-phenyl]-piperazin-1-yl}-2-(5-methyl-4-phenyl-3-trifluoromethyl-pyrazol-1-yl)-ethanone

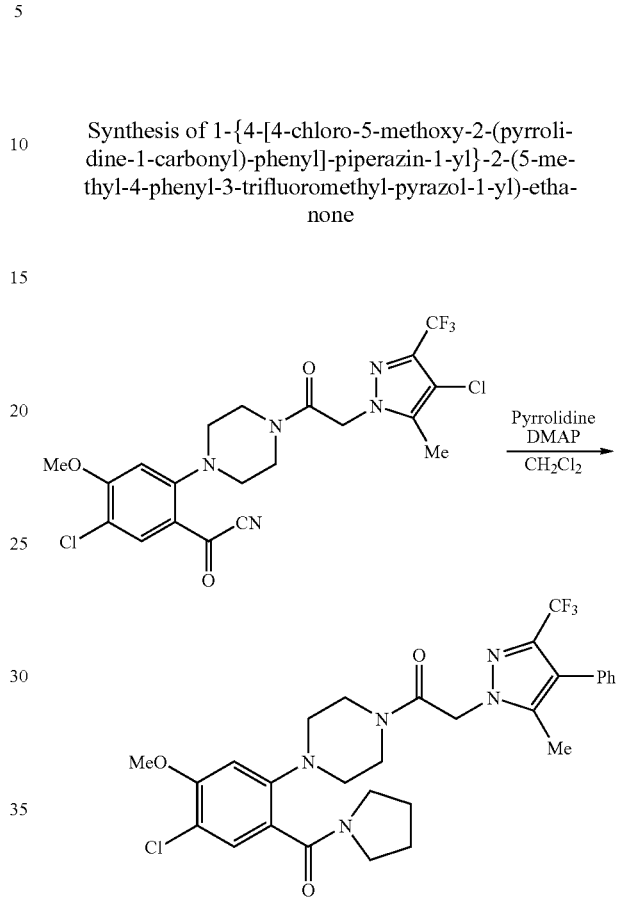

Following Protocol SS, using pyrrolidine, gave the title compound: MS (ES) M+H expect 548.1, found 548.1; HPLC $R_t$=4.64 min.

Synthesis of 1-{4-[4-chloro-5-methoxy-2-(morpholine-4-carbonyl)-phenyl]-piperazin-1-yl}-2-(4-chloro-5-methyl-3-trifluoromethyl-pyrazol-1-yl)-ethanone

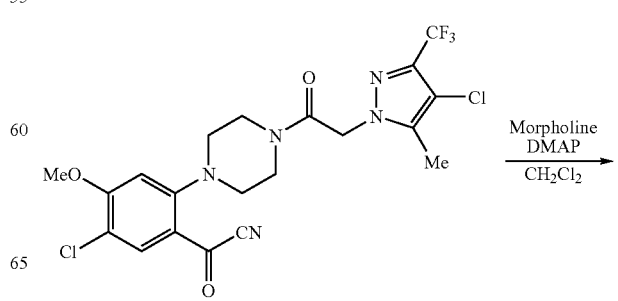

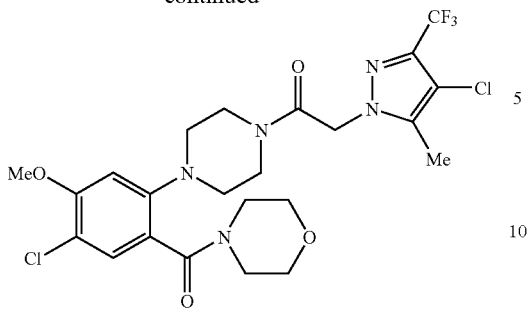

Following Protocol SS, using morpholine, gave the title compound: MS (ES) M+H expect 564.1, found 564.1; HPLC $R_t$=4.42 min.

Synthesis of 5-chloro-2-{4-[2-(4-chloro-5-methyl-3-trifluoromethyl-pyrazol-1-yl)-acetyl]-piperazin-1-yl}-4-methoxy-N-(2-methoxy-ethyl)-benzamide

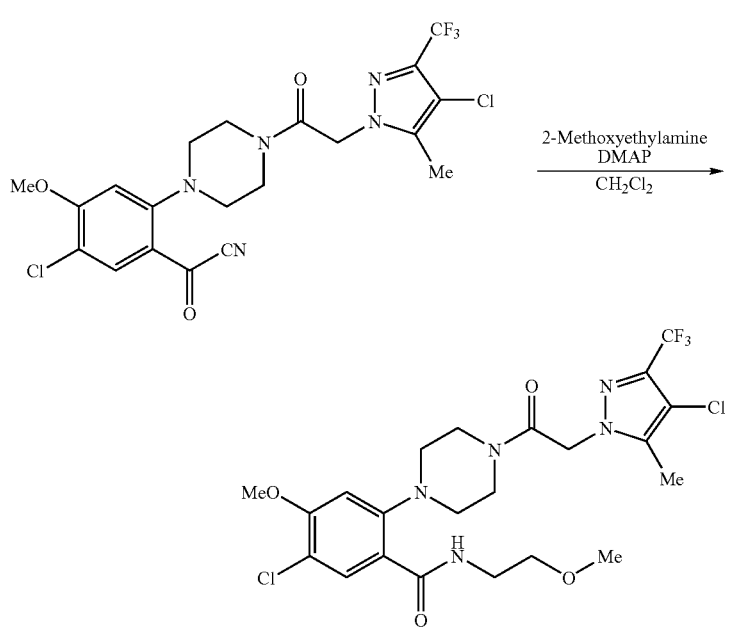

Following Protocol SS, using 2-methoxylethylamine, gave the title compound: MS (ES) M+H expect 552.1, found 552.1; HPLC $R_t$=4.66 min.

Synthesis of 5-chloro-2-{4-[2-(4-chloro-5-methyl-3-trifluoromethyl-pyrazol-1-yl)-acetyl]-piperazin-1-yl}-4-methoxy-N-(2-morpholin-4-yl-ethyl)-benzamide

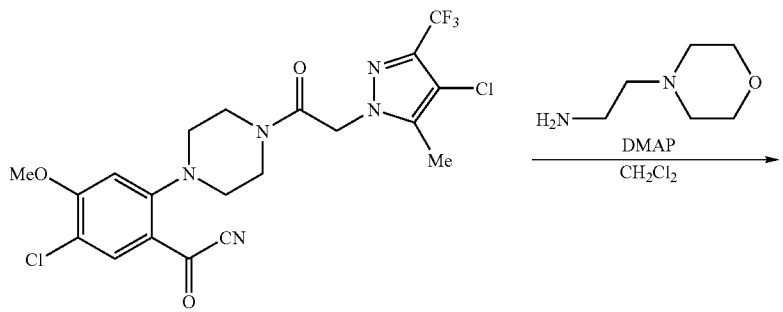

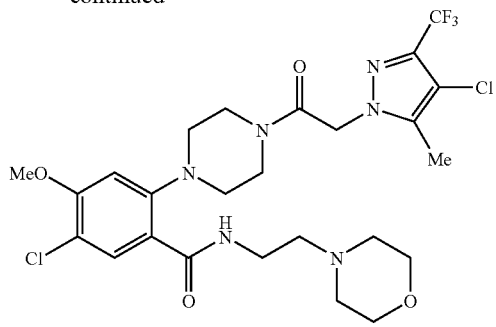

Following Protocol SS, using 2-N-Morpholino-ethylamine, gave the title compound: MS (ES) M+H expect 607.2, found 607.2; HPLC $R_t$=3.47 min.

Synthesis of 1-{4-[4-chloro-5-methoxy-2-(4-pyrimidin-2-yl-piperazine-1-carbonyl)-phenyl]-piperazin-1-yl}-2-(4-chloro-5-methyl-3-trifluoromethyl-pyrazol-1-yl)-ethanone

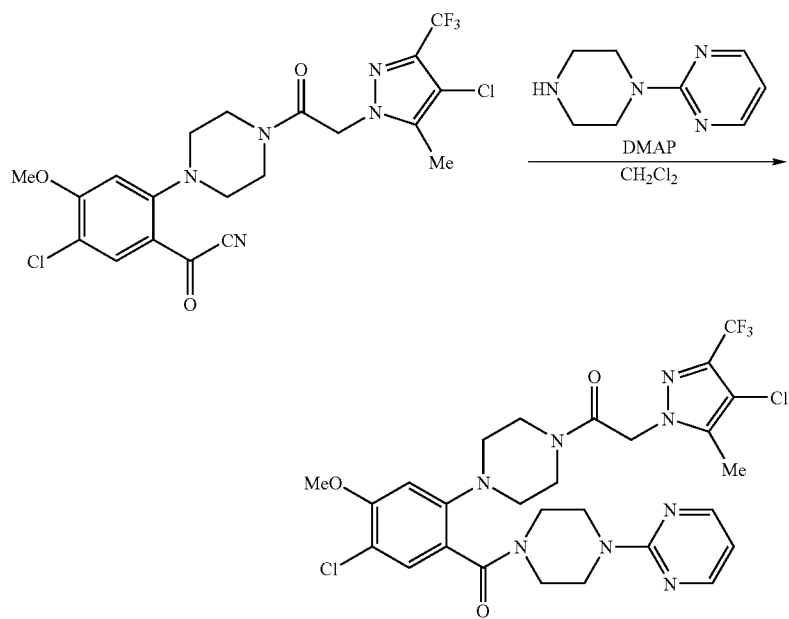

Following Protocol SS, using 1-(2-pyridyl)piperazine, gave the title compound: MS (ES) M+H expect 641.2, found 641.1; HPLC $R_t$=4.77 min.

Synthesis of 5-chloro-2-{4-[2-(4-chloro-5-methyl-3-trifluoromethyl-pyrazol-1-yl)-acetyl]-piperazin-1-yl}-4-methoxy-N-(2-pyridin-2-yl-ethyl)-benzamide

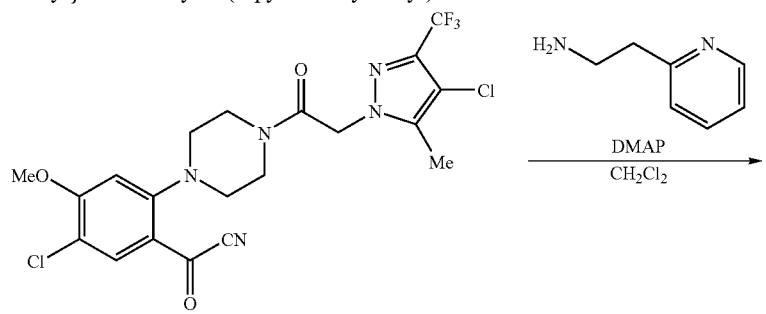

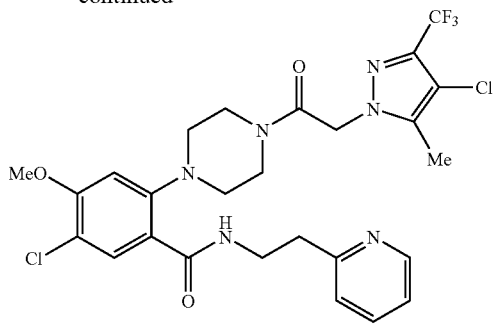

Following Protocol SS, using 2-(2-aminoethyl)pyridine, gave the title compound: MS (ES) M+H expect 599.2, found 599.1; HPLC $R_t$=3.75 min.

Synthesis of 1-{4-[4-chloro-5-methoxy-2-(4-pyridin-4-yl-piperazine-1-carbonyl)-phenyl]-piperazin-1-yl}-2-(4-chloro-5-methyl-3-trifluoromethyl-pyrazol-1-yl)-ethanone

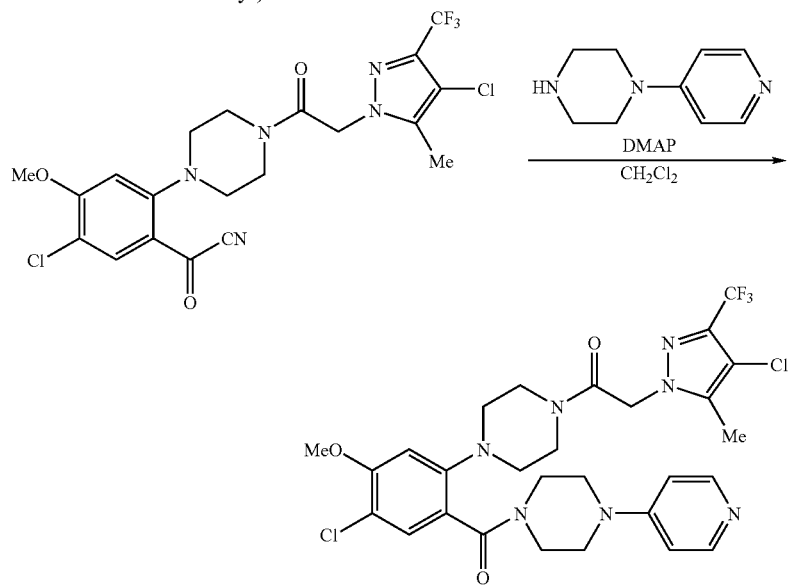

Following Protocol SS, using 1-(4-pyridyl)piperazine, gave the title compound: MS (ES) M+H expect 640.2, found 640.1; HPLC $R_t$=3.61 min.

Synthesis of 5-chloro-2-{4-[2-(4-chloro-5-methyl-3-trifluoromethyl-pyrazol-1-yl)-acetyl]-piperazin-1-yl}-N-(3-imidazol-1-yl-propyl)-4-methoxy-benzamide

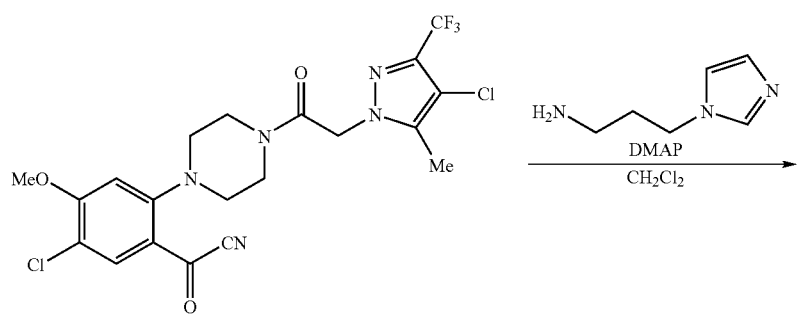

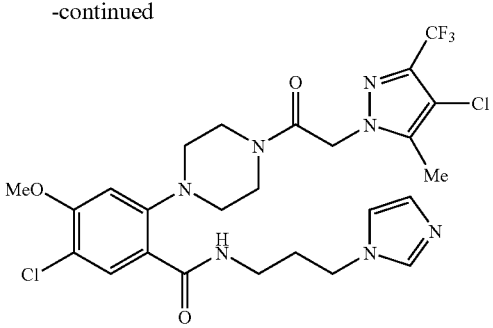

Following Protocol SS, using 1-(3-aminopropyl)imidazole, gave the title compound: MS (ES) M+H expect 602.2, found 602.1; HPLC R$_f$=3.41 min.

Synthesis of 5-chloro-2-{4-[2-(4-chloro-5-methyl-3-trifluoromethyl-pyrazol-1-yl)-acetyl]-piperazin-1-yl}-4-methoxy-benzoic acid methyl ester

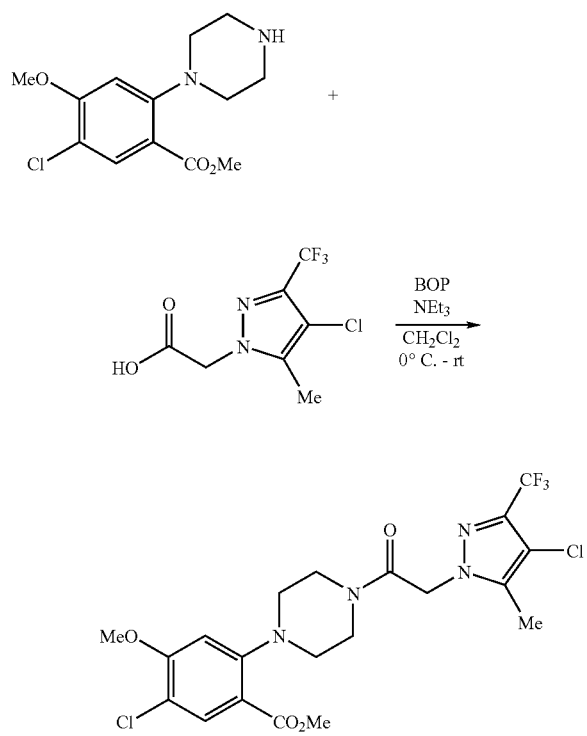

Following a variant of Protocol P, a solution of 5-chloro-4-methoxy-2-piperazin-1-yl-benzoic acid methyl ester (183 mg, 0.642 mmol), (4-chloro-5-methyl-3-trifluoromethyl-pyrazol-1-yl)-acetic acid (218 mg, 0.899 mmol), and triethylamine (0.45 mL, 3.21 mmol) in methylene chloride (5 mL) at 0° C. was added BOP (397 mg, 0.899 mmol) in one portion. After stirring 15 min at 0° C. and then 165 min at room temperature, the solvent was removed in vacuo. The resultant residue was partitioned between ether and saturated sodium bicarbonate, and the aqueous layer extracted with ether (3×25 mL) and ethyl acetate (3×25 mL). The combined organics were dried with Na$_2$SO4, concentrated in vacuo, and the resultant crude product was purified via silica gel chromatography (30:70 EtOAc:hexanes) to afford 188 mg (57% yield) of the target amide as a white solid.

Synthesis of 4-(4-chloro-3-methoxy-phenyl)-2-(R)-formyl-piperazine-1-carboxylic acid tert-butyl ester

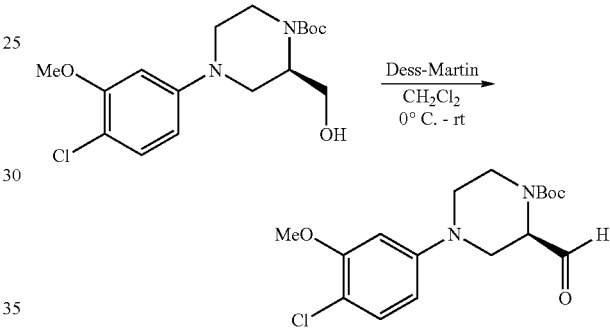

To a solution of 4-(4-chloro-3-methoxy-phenyl)-2-(R)-hydroxymethyl-piperazine-1-carboxylic acid tert-butyl ester (1.10 g, 2.08 mmol) in methylene chloride (30 mL) at 0° C. was added the Dess-Martin Periodinane (16 mL, 0.25 M) dropwise. The resultant solution was stirred 1 h at 0° C., 1 h at room temperature, and then quenched with saturated sodium thiosulfate and saturated sodium bicarbonate. The aqueous layer was subsequently extracted with ethyl acetate (3×30 mL), the combined organics dried with sodium sulfate, and the solvent removed in vacuo. The residue was purified via column chromatography to afford 498 mg (46%) of the desired aldehyde.

Protocol TT: Synthesis of Compounds Via Epoxide Formation and Ring-Opening Reactions Synthesis of (4-Chloro-3-isopropenyl-5-methyl-pyrazol-1-yl)-acetic acid ethyl ester

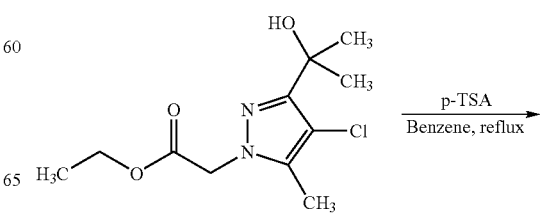

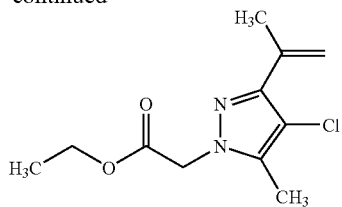

1.3 g [4-Chloro-3-(1-hydroxy-1-methyl-ethyl)-5-methyl-pyrazol-1-yl]-acetic acid ethyl ester and 15 ml Benzene with catalytic amount of p-TSA was reflux with a Dean-Stark overnight. Washed with water, dry over MgSO$_4$ and removed the solvent. Purified by normal phase column (Column: 25 g silica gel, 0%-10% EtOAc/Hexane) to give 0.4 g above title product. HPLC retention time=5.3 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M+H expect=243.1, found=243.1. $^1$H NMR (CDCl3, 400 MHz) 5.80 (d, 1H), 5.25(m, 1H), 4.81 (s, 2H), 4.2 (q, 2H), 2.21 (s, 3H), 2.13(m, 3H)ppm, 1.57 (s, 2H), 1.29(t, 3H) ppm.

Synthesis of [4-Chloro-3-(1,2-dihydroxy-1-methyl-ethyl)-5-methyl-pyrazol-1-yl]-acetic acid

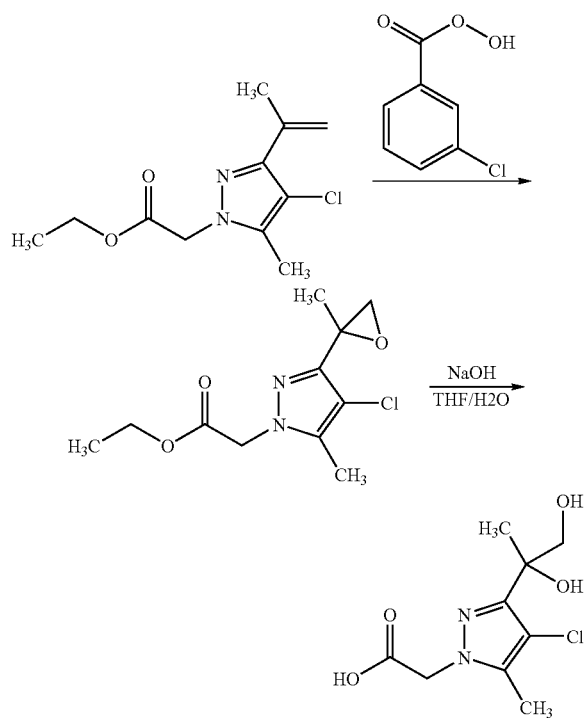

To 0.4 g (4-Chloro-3-isopropenyl-5-methyl-pyrazol-1-yl)-acetic acid ethyl ester dissolved in DCM, 1.3 eq of 3-Chloro-peroxybenzoic acid was added at ambient temperature. After 3 hours, 1.3 eq. of NaHCO$_3$ was added. After stirring 2 more hours, more DCM was added, the mixture was washed with Sat. NaHCO$_3$, Brine, and dried over MgSO$_4$. After filtration, removed solvent in vacuo to give 0.5 g of the crude epoxide.

The crude epoxide, 3 ml THF, 1 ml MeOH and 0.6 ml 1 N NaOH were combined, and stirred overnight. The mixture was neutralized to PH 5-6, most of the solvent was removed in vacuo, and the residue was partitioned between water and ethyl acetate, and the phases were separated. The aqueous phase was lyophilized to give the title compound: HPLC retention time=0.35 minutes (Agilent Zorbax SB-C18, 2.1×50 mm, 5μ, 35° C.) using a 4.5 minute gradient of 20% to 95% B with a 1.1 minute wash at 95% B (A=0.1% formic acid/5% acetonitrile/94.9% water, B=0.08% formic acid/99.9% acetonitrile); MS (ES) M−H expect=247.1, found=246.9.

Example 4

This example illustrates the activity associated with representative compounds of the invention.

Materials and Methods

A. Cells

1. CCR1 Expressing Cells a) THP-1 Cells

THP-1 cells were obtained from ATCC (TIB-202) and cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, 0.05% 2-mercaptoethanol and 10% FBS. Cells were grown under 5% $CO_2$/95% air, 100% humidity at 37° C. and sub-cultured twice weekly at 1:5 (cells were cultured at a density range of $2\times10^5$ to $2\times10^6$ cells/mL) and harvested at $1\times10^6$ cells/mL. THP-1 cells express CCR1 and can be used in CCR1 binding and functional assays.

b) Isolated Human Monocytes

Monocytes were isolated from human buffy coats using the Miltenyi bead isolation system (Miltenyi, Auburn, Calif.). Briefly, following a Ficoll gradient separation to isolate peripheral blood mononuclear cells, cells were washed with PBS and the red blood cells lysed using standard procedures. Remaining cells were labeled with anti-CD14 antibodies coupled to magnetic beads (Miltenyi Biotech, Auburn, Calif.). Labeled cells were passed through AutoMACS (Miltenyi, Auburn, Calif.) and positive fraction collected. Monocytes express CCR1 and can be used in CCR1 binding and functional assays.

B. Assays

1. Inhibition of CCR1 Ligand Binding

CCR1 expressing cells were centrifuged and resuspended in assay buffer (20 mM HEPES pH 7.1, 140 mM NaCl, 1 mM $CaCl_2$, 5 mM $MgCl_2$, and with 0.2% bovine serum albumin) to a concentration of $5\times10^6$ cells/mL for THP-1 cells and $5\times10^5$ for monocytes. Binding assays were set up as follows. 0.1 mL of cells ($5\times10^5$ THP-1 cells/well or $5\times10^4$ monocytes) was added to the assay plates containing the compounds, giving a final concentration of ~2-10 μM each compound for screening (or part of a dose response for compound $IC_{50}$ determinations). Then 0.1 mL of $^{125}$I labeled MIP-1α (obtained from Perkin Elmer Life Sciences, Boston, Mass.) or 0.1 mL of $^{125}$I labeled CCL15/leukotactin (obtained as a custom radiolabeling by Perkin Elmer Life Sciences, Boston, Mass.) diluted in assay buffer to a final concentration of ~50 pM, yielding ~30,000 cpm per well, was added (using $^{125}$I labeled MIP-1α with THP-1 cells and $^{125}$I labeled CCL15/leukotactin with monocytes), the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 μl; Microscint 20, Packard Instruments) was added to each well, the plates were sealed and radioactivity measured in a Topcount scintillation counter (Packard Instruments). Control wells containing either diluent only (for total counts) or excess MIP-1α or MIP-1β (1 μg/mL, for non-specific binding) were used to calculate the percent of total inhibition for compound. The computer program Prism from GraphPad, Inc. (San Diego, Calif.) was used to calculate $IC_{50}$ values. $IC_{50}$ values are those concentrations required to reduce the binding of labeled MIP-1α to the receptor by 50%. (For further descriptions of ligand binding and other functional assays, see Dairaghi, et al., *J. Biol. Chem.* 274:21569-21574 (1999), Penfold, et al., Proc. Natl. Acad. Sci. USA. 96:9839-9844 (1999), and Dairaghi, et al, *J. Biol. Chem.* 272:28206-28209 (1997)).

2. Calcium Mobilization

To detect the release of intracellular stores of calcium, cells (THP-1 or monocytes) were incubated with 3 μM of INDO-1AM dye (Molecular Probes; Eugene, Oreg.) in cell media for 45 minutes at room temperature and washed with phosphate buffered saline (PBS). After INDO-1AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing $10^6$ cells in 2 mL of flux buffer. The chemokine ligands may be used over a range from 1 to 100 nM. The emission ratio was plotted over time (typically 2-3 minutes). Candidate ligand blocking compounds (up to 10 μM) were added at 10 seconds, followed by chemokines at 60 seconds (i.e., MIP-1α; R&D Systems; Minneapolis, Minn.) and control chemokine (i.e., SDF-1α; R&D Systems; Minneapolis, Minn.) at 150 seconds.

3. Chemotaxis Assays

Chemotaxis assays were performed using 5 ſm pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 mediated migration. Other chemokines (i.e., SDF-1α; R&D Systems; Minneapolis, Minn.) are used as specificity controls. The lower chamber was loaded with 29 μl of chemokine (i.e., 0.1 nM CCL15/Leukotactin) and varying amounts of compound; the top chamber contained 100,000 THP-1 or monocyte cells in 20 μl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

Identification of Inhibitors of CCR1

A. Assay

To evaluate small organic molecules that prevent the receptor CCR1 from binding ligand, an assay was employed that detected radioactive ligand (i.e, MIP-1α or CCL15/Leukotactin) binding to cells expressing CCR1 on the cell surface (for example, THP-1 cells or isolated human monocytes). For compounds that inhibited binding, whether competitive or not, fewer radioactive counts are observed when compared to uninhibited controls.

THP-1 cells and monocytes lack other chemokine receptors that bind the same set of chemokine ligands as CCR1 (i.e., MIP-1α, MPIF-1, Leukotactin, etc.). Equal numbers of cells were added to each well in the plate. The cells were then incubated with radiolabeled MIP-1α. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

% inhibitition=(1−[(sample cpm)−(nonspecific cpm)]/[total cpm)−(nonspecific cpm)]×100.

B. Inhibitors from a Compound Library Identified using CCR1 Expressing Cells

In a screen of a set of compounds, the normalized standard deviation was 17%, indicating that inhibitory activity of 34% or more was significant; again, a 40% threshold was used. These pooled compound plates yielded 39 wells that exhibited greater than 40% inhibition of MIP-1α binding. When screened a second time as pooled compound plates, 14 of these wells decreased ligand by greater than 40%. To determine which of the compounds in each well inhibited CCR1 ligation of MIP-1α, the pools were deconvoluted by testing each of the compounds individually for inhibitory activity in the assay. Because some compounds may act together to inhibit binding and deconvolution assays only tested compounds individually, compounds that were effective in combination but not singly were not found in this experiment. Testing the compounds singly identified inhibitory candidates:

C. Inhibitor from Compound Library Identified Using CCR1-Expressing Cells

CCX-105 was identified from the compound screening effort.

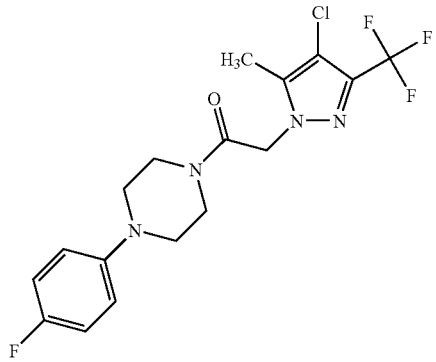

1. Dose Response Curves

To ascertain a candidate compound's affinity for CCR1 as well as confirm its ability to inhibit ligand binding, inhibitory activity was titered over a $1\times10^{-10}$ to $1\times10^{-4}$ M range of compound concentrations. In the assay, the amount of compound was varied; while cell number and ligand concentration were held constant. Compound CCX-105 was titered and found to be a potent inhibitor of CCR1 specific chemokine binding (see Table, for compound 1.001).

2. CCR1 Functional Assays

CCR1 is a seven transmembrane, G-protein linked receptor. A hallmark of signaling cascades induced by the ligation of some such receptors is the pulse-like release of calcium ions from intracellular stores. Calcium mobilization assays were performed to determine if the candidate CCR1 inhibitory compounds were able to also block aspects of CCR1 signaling. Candidate compounds able to inhibit ligand binding and signaling with an enhanced specificity over other chemokine and non-chemokine receptors were desired.

Calcium ion release in response to CCR1 chemokine ligands (i.e., MIP-1α, MPIF-1, Leukotactin, etc.) was measured using the calcium indicator INDO-1. THP-1 cells or monocytes were loaded with INDO-1/AM and assayed for calcium release in response to CCR1 chemokine ligand (i.e., MIP-1α) addition. To control for specificity, non-CCR1 ligands, specifically bradykinin, was added, which also signals via a seven transmembrane receptor. Without compound, a pulse of fluorescent signal will be seen upon MIP-1α addition. If a compound specifically inhibits CCR1-MIP-1α signaling, then little or no signal pulse will be seen upon MIP-1α addition, but a pulse will be observed upon bradykinin addition. However, if a compound non-specifically inhibits signaling, then no pulse will be seen upon both MIP-1α and bradykinin addition.

As shown below, CCX-105 was able to significantly and specifically inhibit signaling from CCR1.

TABLE 2

Inhibition of calcium signaling

| Compound | MIP-1α[1] | Bradykinin[1] | Comments |
|---|---|---|---|
| CCX-105 | − | + | Specific inhibition |

[1]+, pulse observed,
−, no pulse observed,
n.s., non-specific signal (see main text)

One of the primary functions of chemokines is their ability to mediate the migration of chemokine receptor-expressing cells, such as white blood cells. To confirm that CCX-105 inhibited not only CCR1 specific binding and signaling (at least as determined by calcium mobilization assays), but also CCR1 mediated migration, a chemotaxis assay was employed. THP-1 myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were place in the top compartment of a microwell migration chamber, while MIP-1α (or other potent CCR1 chemokine ligand) and increasing concentrations of CCX-105 or other candidate compound was loaded in the lower chamber. In the absence of inhibitor, cells will migrate to the lower chamber in response to the chemokine agonist; if a compound inhibited CCR1 function, then the majority of cells will remain in the upper chamber. To ascertain a candidate compound's affinity for CCR1 as well as to confirm its ability to inhibit CCR1 mediated cell migration, inhibitory activity was titered over a $1 \times 10^{-10}$ to $1 \times 10^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate $IC_{50}$ values. $IC_{50}$ values are those compound concentrations required to inhibit the number of cells responding to a CCR1 agonist by 50%.

3. In Vivo Efficacy

Rabbit Model of Destructive Joint Inflammation

A study was conducted to evaluate the effects of CCX-105 on inhibiting the inflammatory response of rabbits to an intra-articular injection of the bacterial membrane component lipopolysaccharide (LPS). This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., J. Immunol. 169(11):6435-6444 (2002)).

In a rabbit LPS study conducted essentially as described in Podolin, et al. ibid., female New Zealand rabbits (approximately 2 kilograms) were treated intra-articularly in one knee with LPS (10 ng) together with either vehicle only (phosphate buffered saline with 1% DMSO) or with addition of CCX-105 (dose 1=50 μM or dose 2=100 μM) in a total volume of 1.0 mL. Sixteen hours after the LPS injection, knees were lavaged and cells counts performed. Beneficial effects of treatment were determined by histopathologic evaluation of synovial inflammation. The following inflammation scores were used for the histopathologic evaluation: 1—minimal, 2—mild, 3—moderate, 4—moderate-marked. As shown below, CCX-105 was able to significantly and specifically inhibit the inflammatory response in this in vivo assay.

TABLE 3

CCX-105 efficacy in a rabbit model of destructive joint inflammation

| | synovium inflammation score |
|---|---|
| Vehicle | 3 |
| CCX-105 (dose 1) | 2 |
| CCX-105 (dose 2) | 1 |

Evaluation of Compound 1.028 in a Rat Model of Collagen Induced Arthritis

A 17 day developing type II collagen arthritis study was conducted to evaluate the effects of compound 1.028 on arthritis induced clinical ankle swelling. Rat collagen arthritis is an experimental model of polyarthritis that has been widely used for preclinical testing of numerous anti-arthritic agents (see Trentham, et al., J. Exp. Med. 146(3):857-868 (1977), Bendele, et al., Toxicologic Pathol. 27:134-142 (1999), Bendele, et al., Arthritis Rheum. 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) were anesthetized with isoflurane and injected with Freund's Incomplete Adjuvant containing 2 mg/mL bovine type II collagen at the base of the tail and two sites on the back on days 0 and 6 of this 17 day study. Compound 1.028 was dosed daily in a sub-cutaneous manner from day 0 till day 17 at a dose of 25 mg/kg and a volume of 1 mL/kg in the following vehicle (20% N,N-dimethylacetamide, 75% corn oil, 5% Tween-80). Caliper measurements of the ankle joint diameter were taken, and reducing joint swelling was taken as a measure of efficacy. As shown below, compound 1.028 was able to significantly and specifically inhibit the arthritis induced ankle swelling in this in vivo assay.

TABLE 4

Efficacy of compound 1.028 in a rat collagen induced arthritis assay

| | change in joint diameter day9-day17 |
|---|---|
| Vehicle | 15.7% +/− 2.0% |
| Normal | 0% +/− 0.3% |
| Compound 1.028 | 9.1% +/− 1.8% |

In the table below, structures and activity are provided for representative compounds described herein. Activity is provided as follows for either or both of the chemotaxis assay and/or binding assay, described above: +, $IC_{50} > 12.5$ μM; ++, 2500 nM < $IC_{50}$ < 12.5 μM; +++, 500 nM < $IC_{50}$ < 2500 nM; and ++++, $IC_{50}$ < 500 n.

TABLE 5

Structure

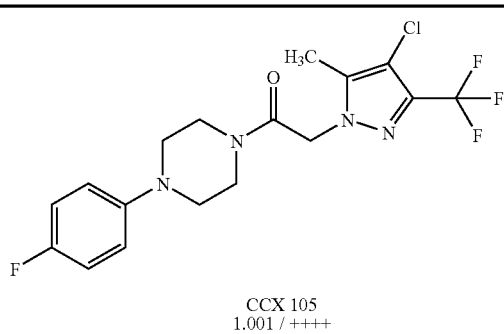

CCX 105
1.001 / ++++

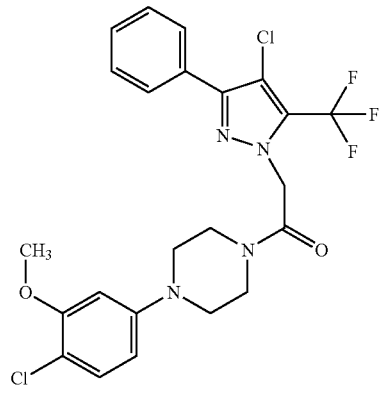

1.002 / ++++

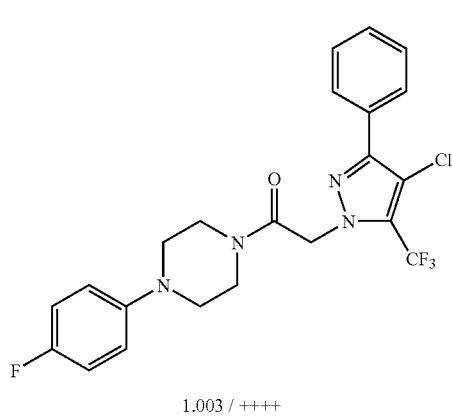

1.003 / ++++

TABLE 5-continued

Structure

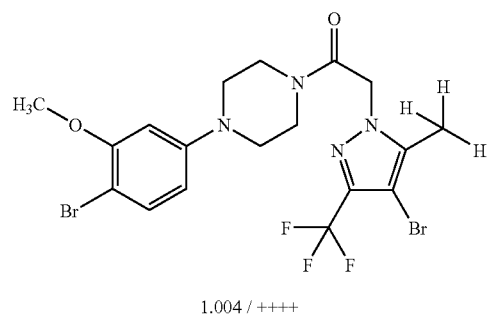

1.004 / ++++

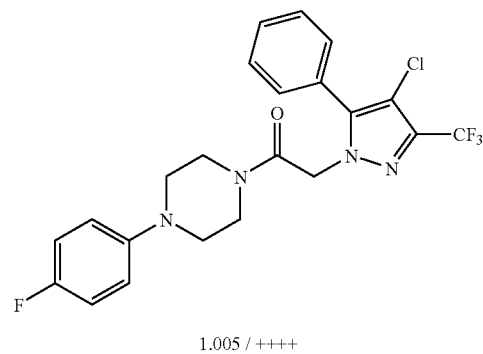

1.005 / ++++

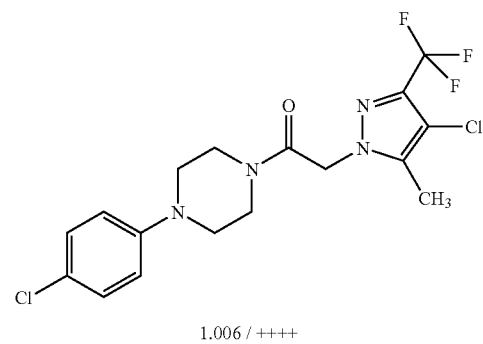

1.006 / ++++

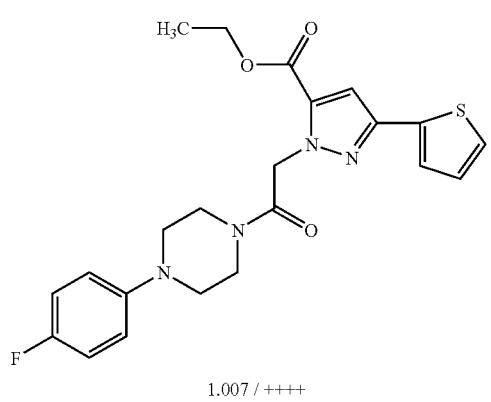

1.007 / ++++

TABLE 5-continued
Structure
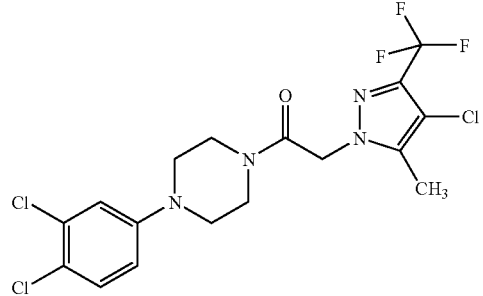
1.008 / ++++
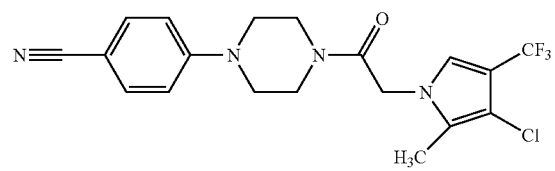
1.009 / ++++
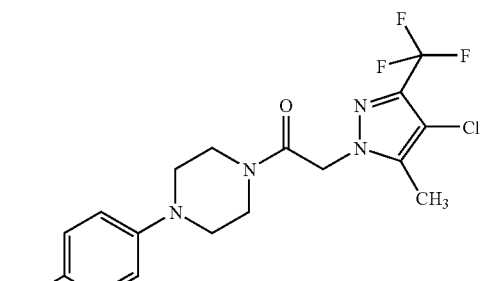
1.010 / ++++
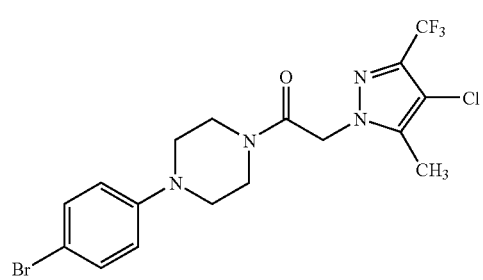
1.011 / ++++
TABLE 5-continued
Structure
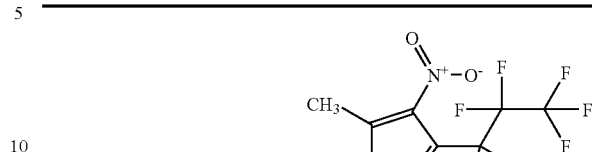
1.012 / ++++
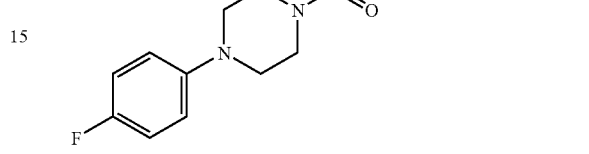
1.013 / ++++
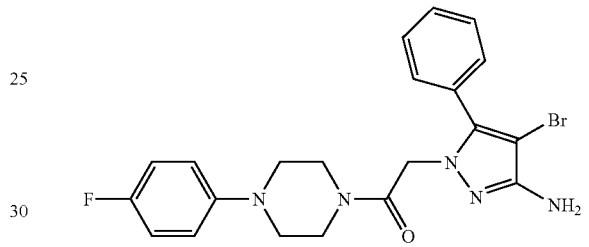
1.014 / +++
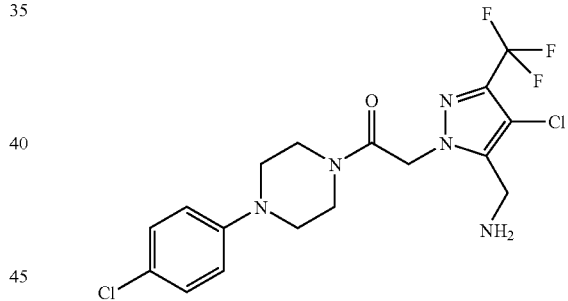
1.015 / ++++

TABLE 5-continued
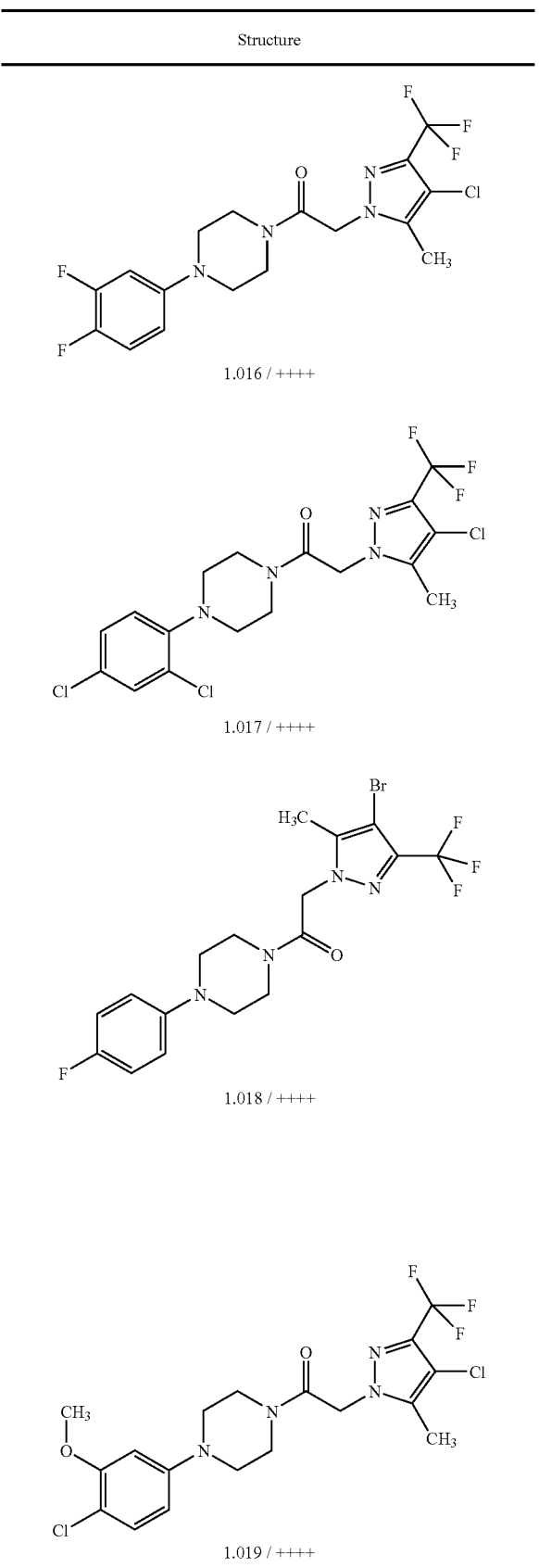
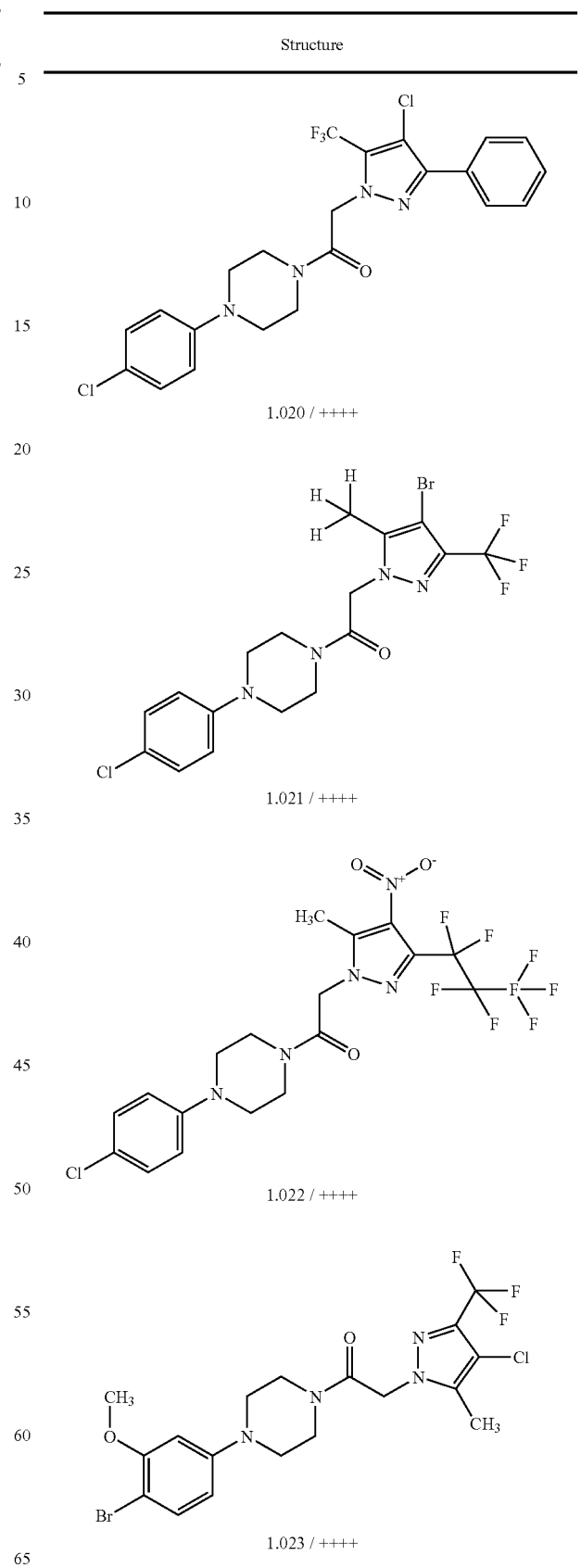

TABLE 5-continued
| Structure |
|---|
| 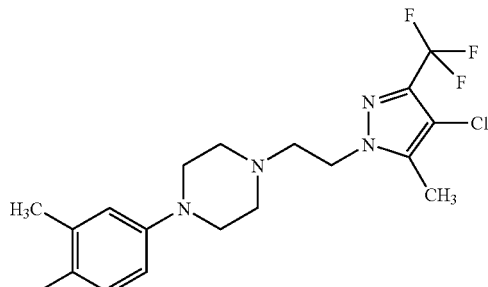 |
| 1.024 / ++++ |
| 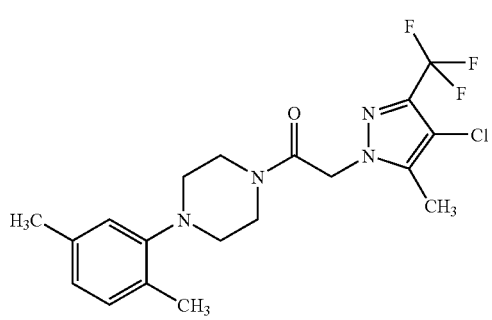 |
| 1.025 / ++++ |
| 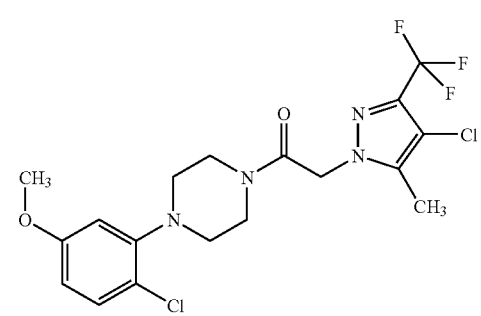 |
| 1.026 / ++++ |
| 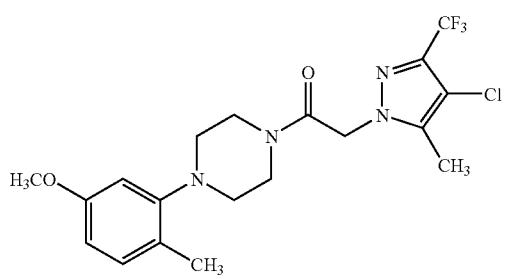 |
| 1.027 / ++++ |
TABLE 5-continued
| Structure |
|---|
| 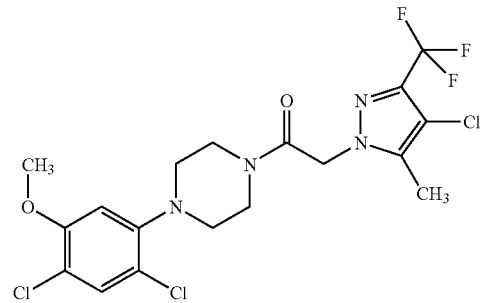 |
| 1.028 / ++++ |
| 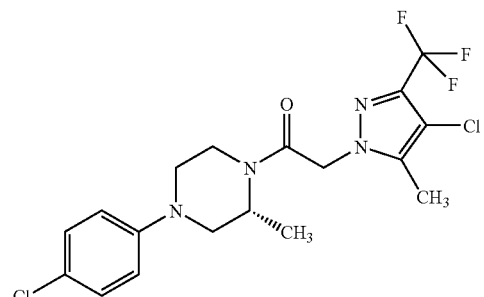 |
| 1.029 / ++++ |
| 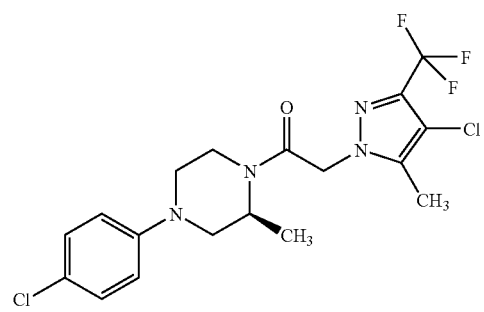 |
| 1.030 / ++++ |
| 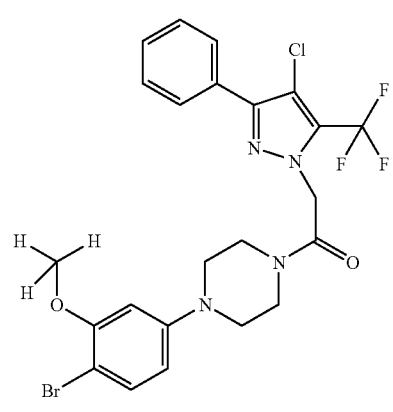 |
| 1.031 / ++++ |

TABLE 5-continued
| Structure |
|---|
| 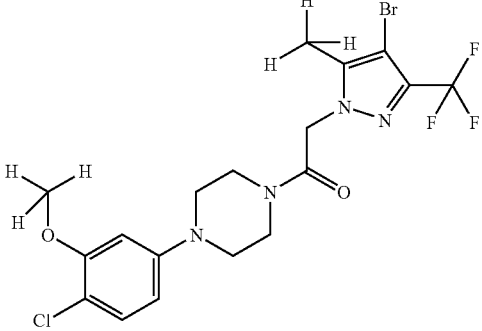 1.032 / ++++ |
| 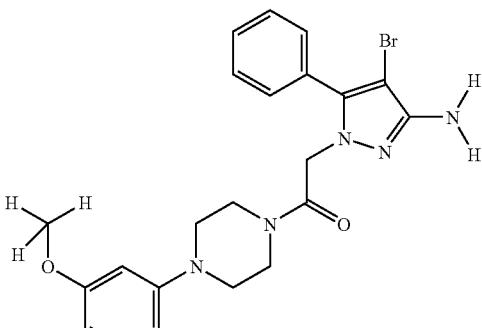 1.033 / ++++ |
| 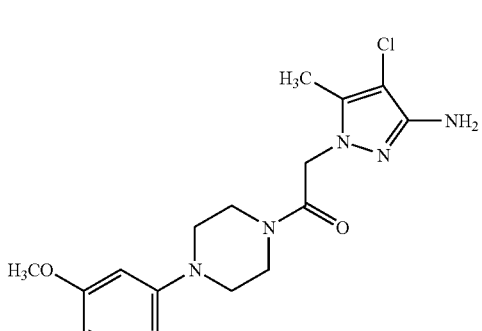 1.034 / ++++ |
| 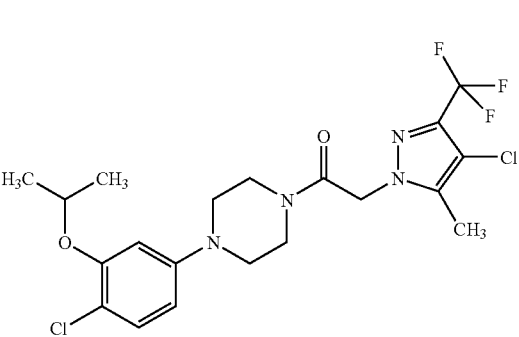 1.035 / ++++ |
TABLE 5-continued
| Structure |
|---|
| 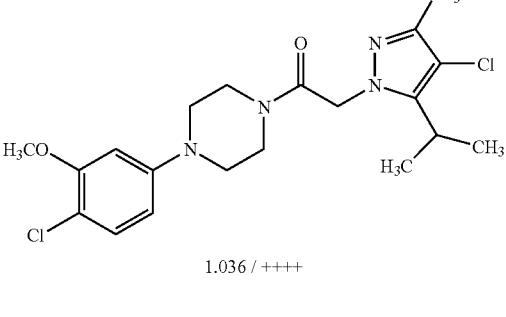 1.036 / ++++ |
| 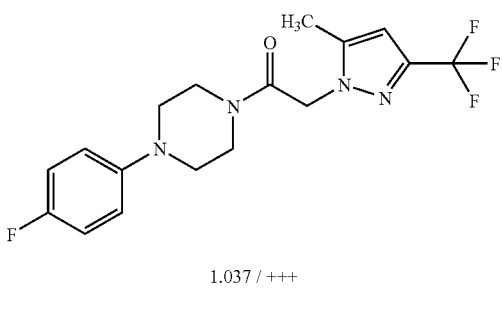 1.037 / +++ |
| 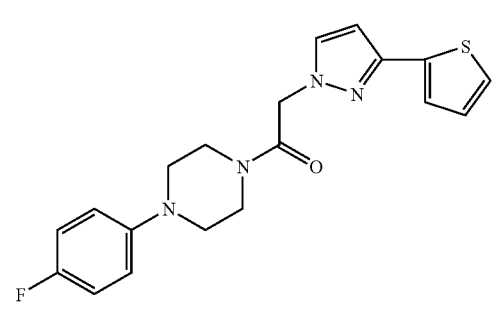 1.038 / +++ |
| 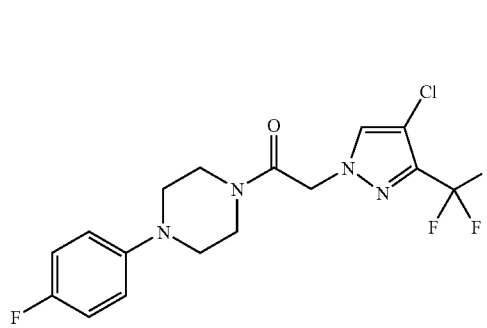 1.039 / +++ |

TABLE 5-continued
Structure
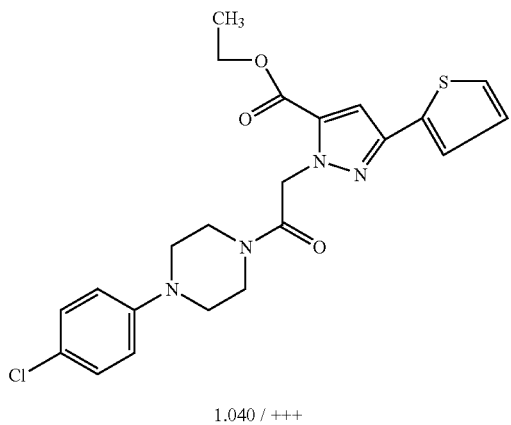
1.040 / +++
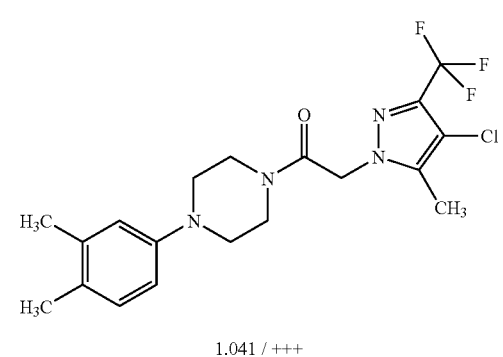
1.041 / +++
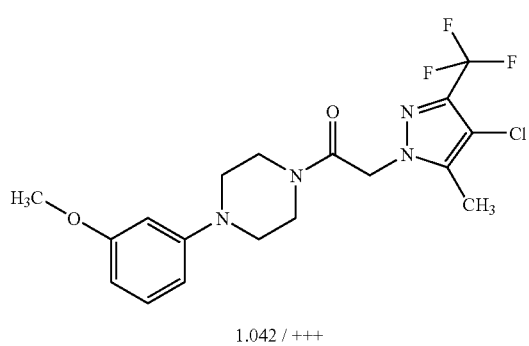
1.042 / +++
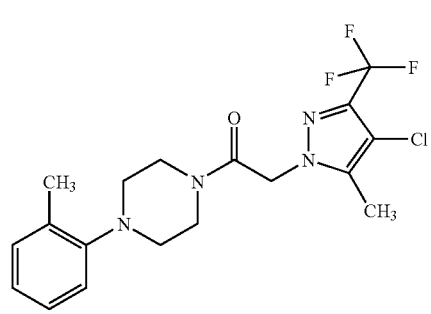
1.043 / +++
TABLE 5-continued
Structure
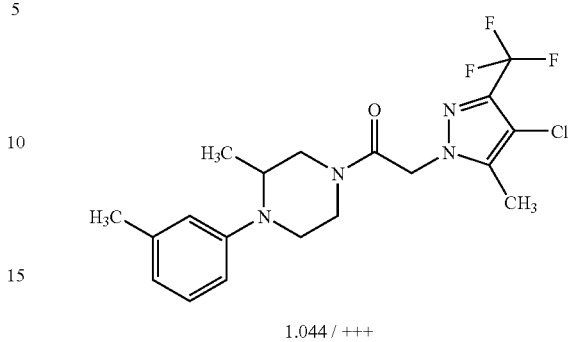
1.044 / +++
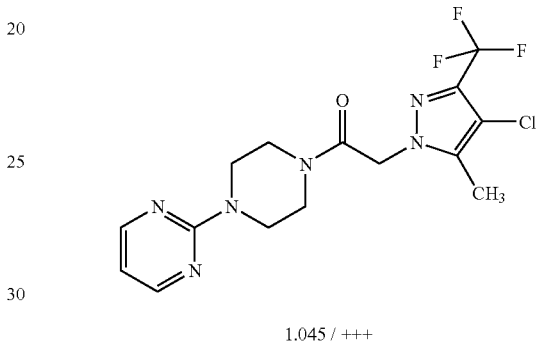
1.045 / +++
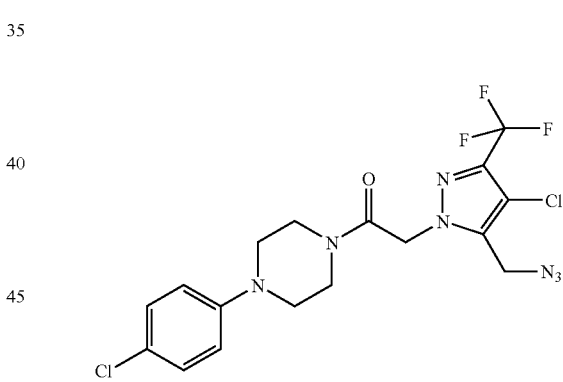
1.046 / +++
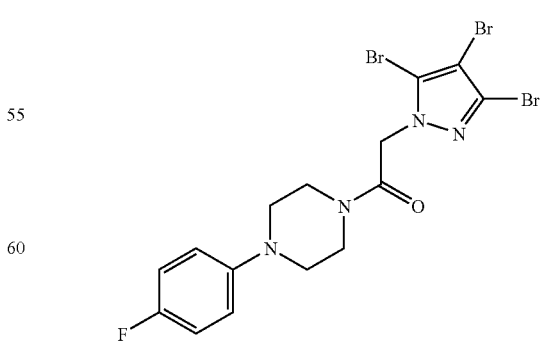
1.047 / +++

TABLE 5-continued
Structure
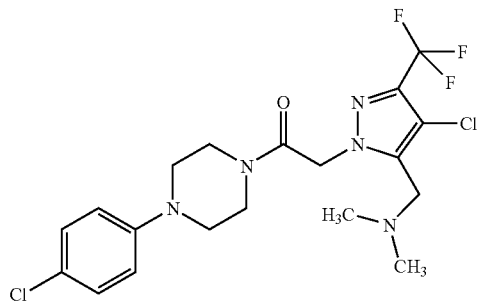
1.048 / +++
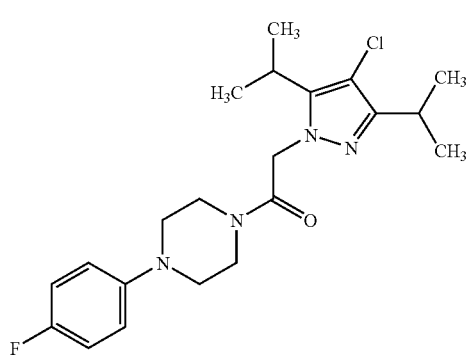
1.049 / +++
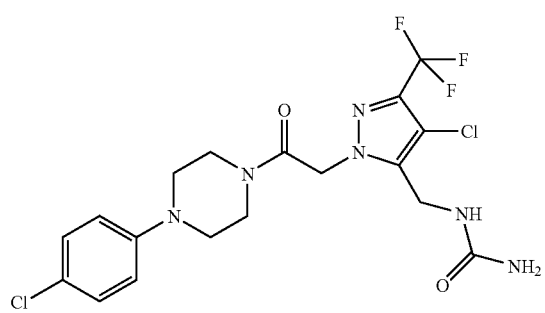
1.050 / +++
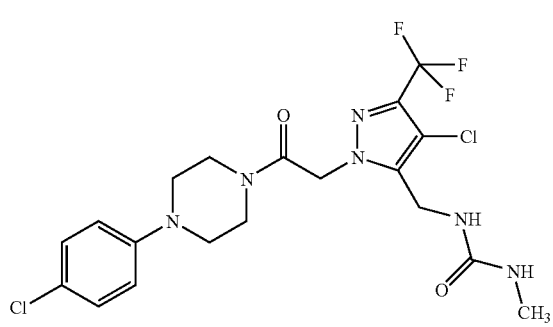
1.051 / +++
TABLE 5-continued
Structure
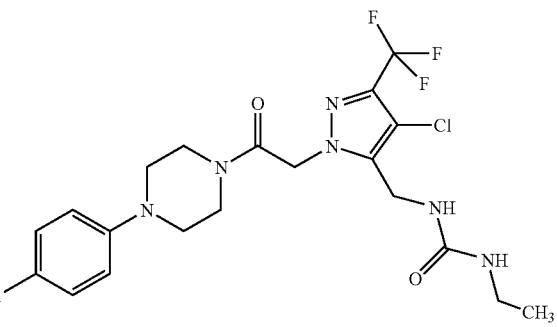
1.052 / +++
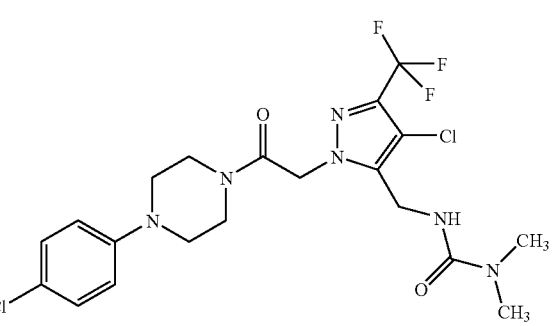
1.053 / +++
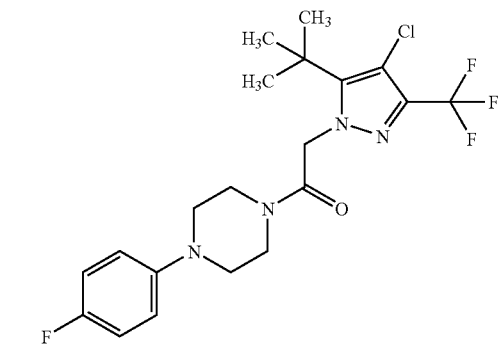
1.054 / +++
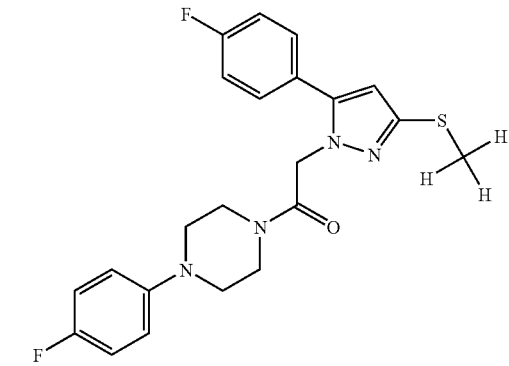
1.055 / +++

TABLE 5-continued
Structure
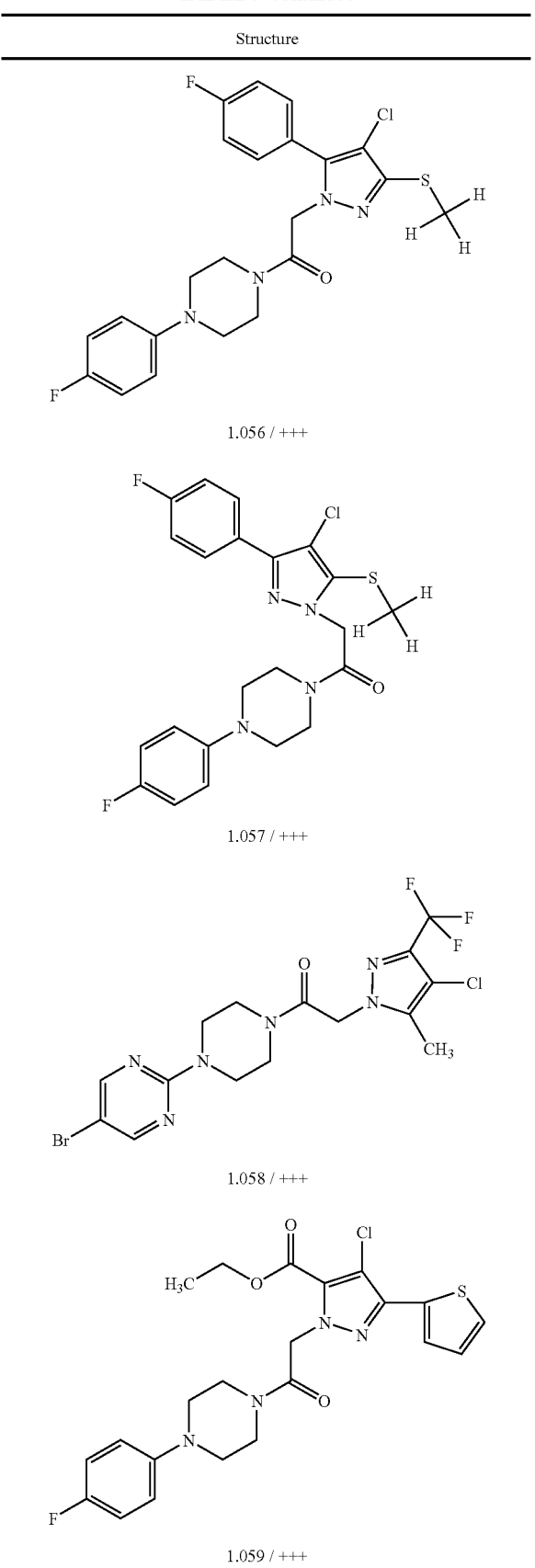
1.056 / +++
1.057 / +++
1.058 / +++
1.059 / +++
TABLE 5-continued
Structure
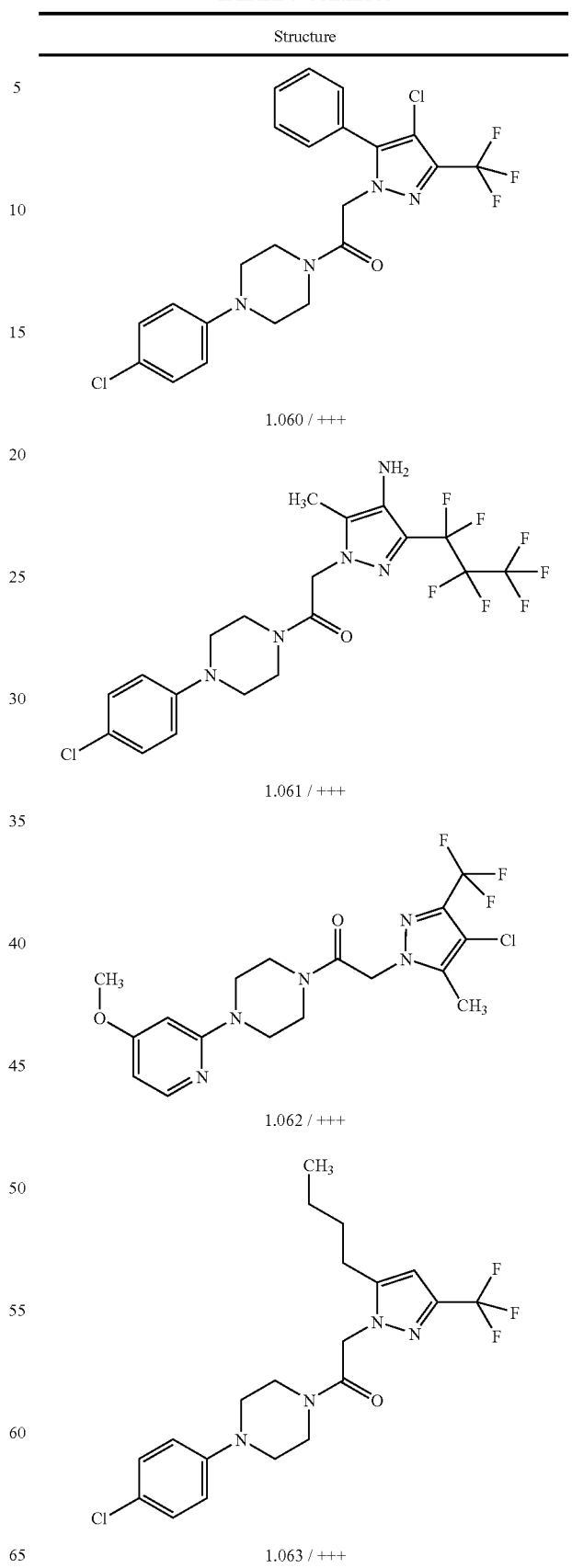
1.060 / +++
1.061 / +++
1.062 / +++
1.063 / +++

TABLE 5-continued
Structure
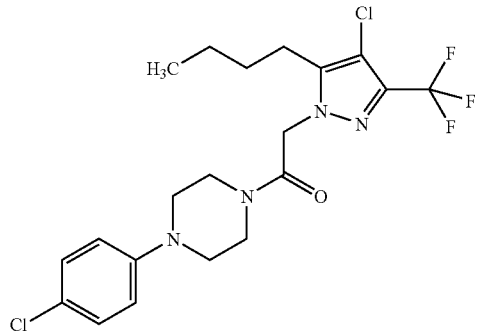
1.064 / +++
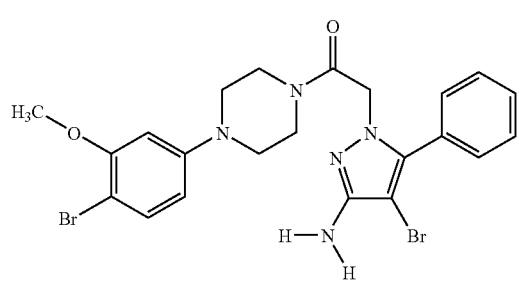
1.065 / +++
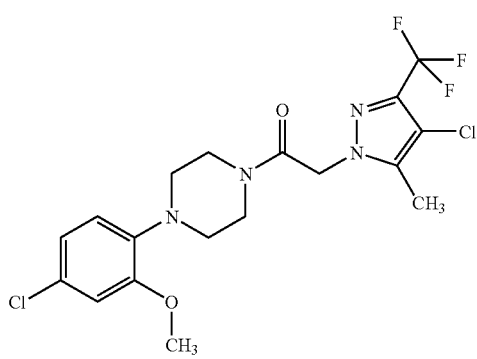
1.066 / +++
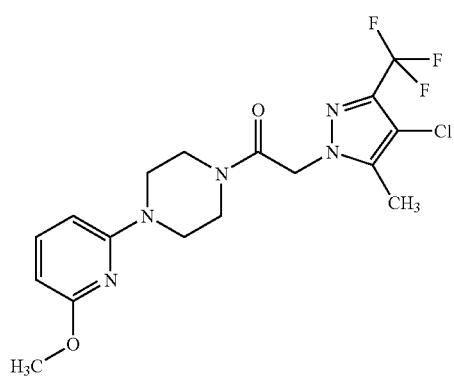
1.067 / +++
TABLE 5-continued
Structure
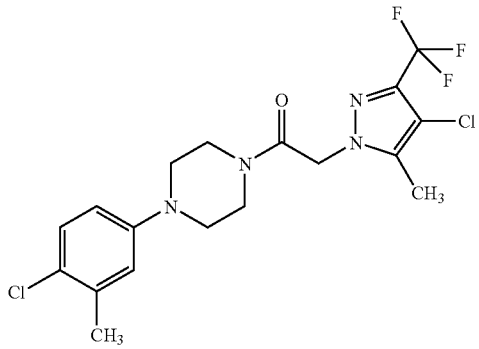
1.068 / ++++
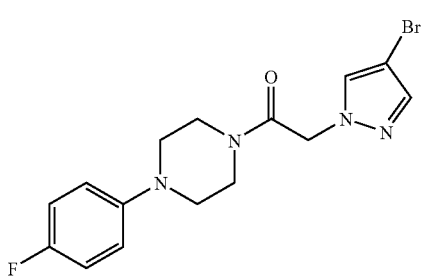
1.069 / ++
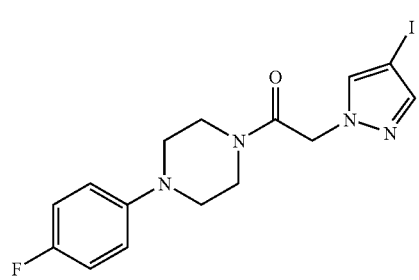
1.070 / ++
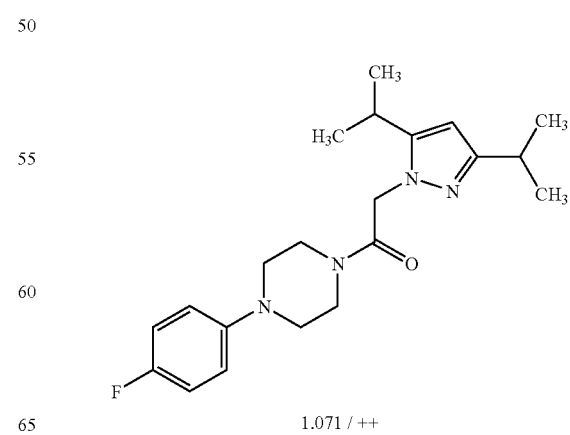
1.071 / ++

TABLE 5-continued

Structure 1.072 / ++

1.073 / ++

1.074 / ++

1.075 / ++

1.076 / ++

1.077 / ++

1.078 / ++

TABLE 5-continued

| Structure |
|---|
| 1.079 / ++ |
| 1.080 / ++ |
| 1.081 / ++ |
| 1.082 / ++ |

TABLE 5-continued

| Structure |
|---|
| 1.083 / ++ |
| 1.084 / ++ |
| 1.085 / ++ |
| 1.086 / ++ |

TABLE 5-continued

| Structure | |
|---|---|
| 1.087 / ++ | 1.091 / ++ |
| 1.088 / ++ | 1.092 / ++ |
| 1.089 / ++ | 1.093 / ++ |
| 1.090 / ++ | 1.094 / ++ |

TABLE 5-continued
| Structure |
|---|
| 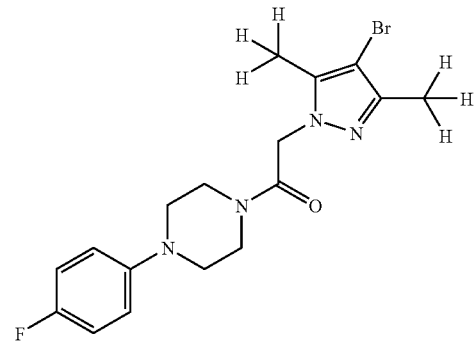 |
| 1.095 / ++ |
| 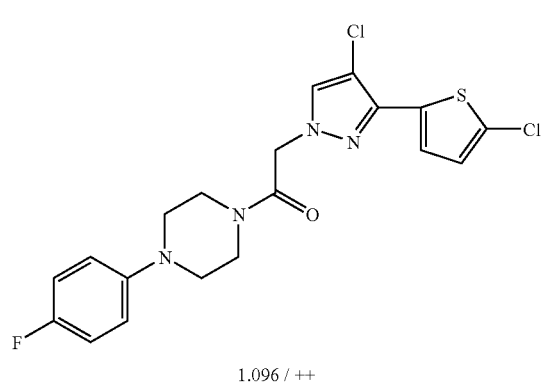 |
| 1.096 / ++ |
| 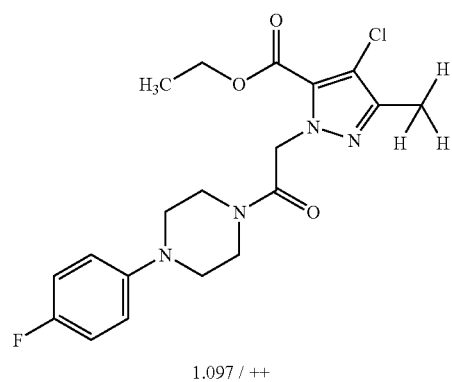 |
| 1.097 / ++ |
| 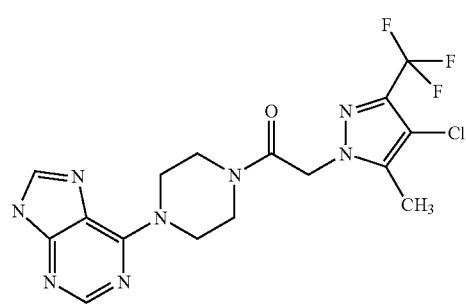 |
| 1.098 / ++ |
TABLE 5-continued
| Structure |
|---|
| 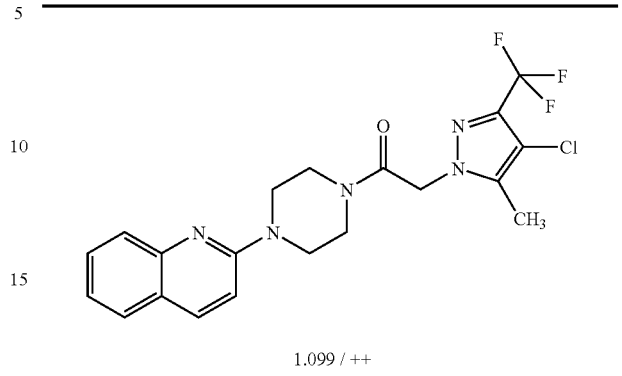 |
| 1.099 / ++ |
| 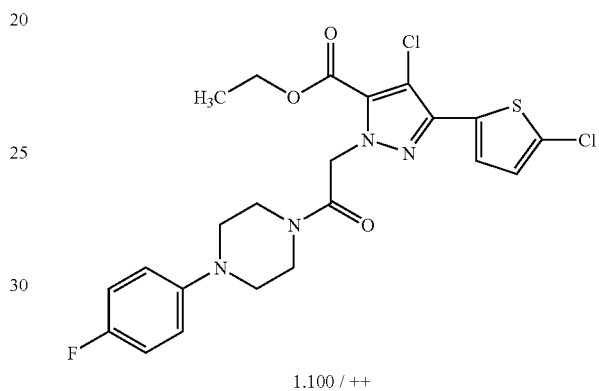 |
| 1.100 / ++ |
| 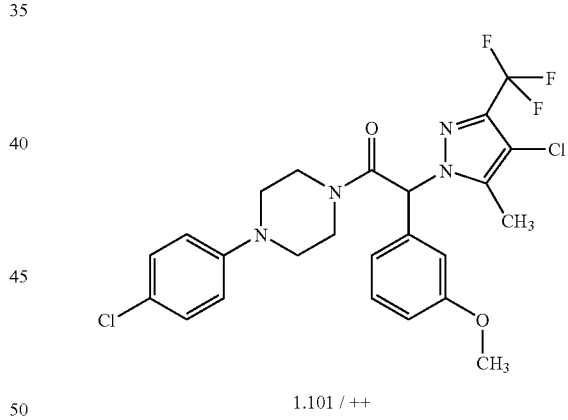 |
| 1.101 / ++ |
| 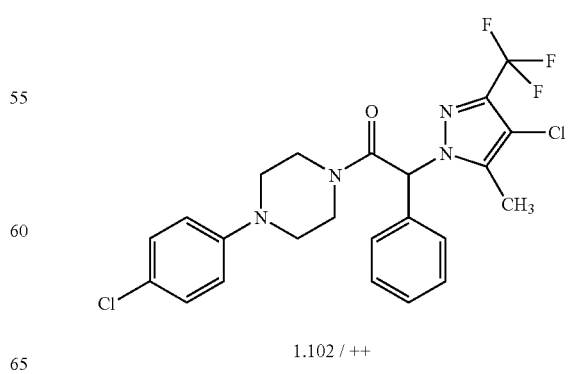 |
| 1.102 / ++ |

TABLE 5-continued
| Structure | | Structure |
|---|---|---|
| 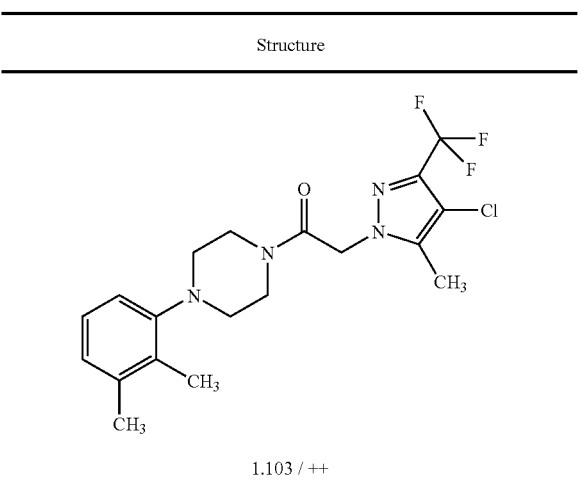 1.103 / ++ | | 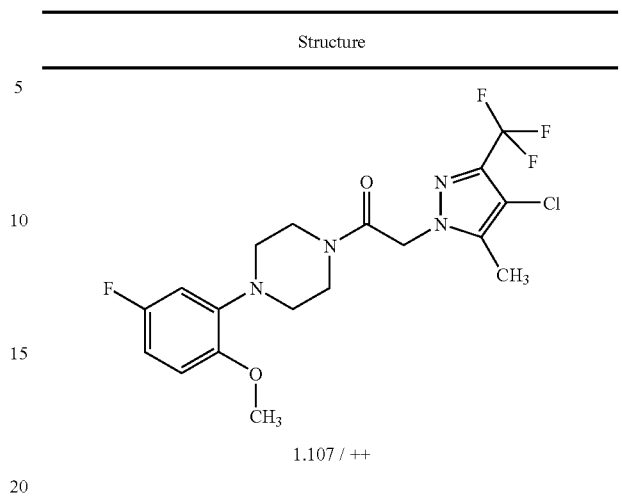 1.107 / ++ |
| 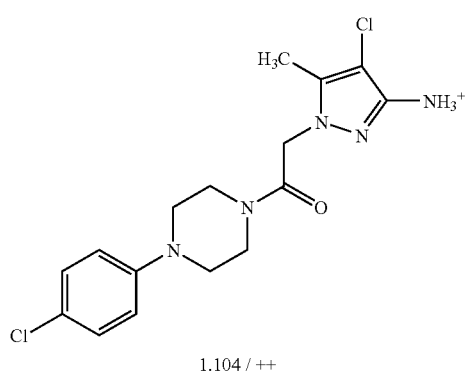 1.104 / ++ | | 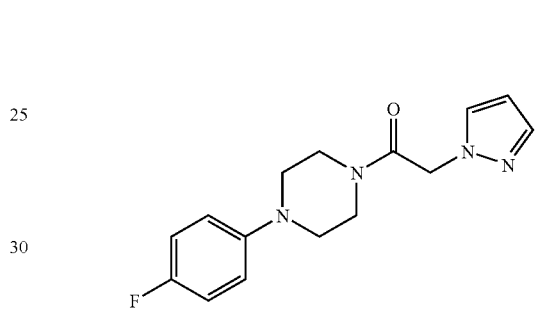 1.108 / + |
| 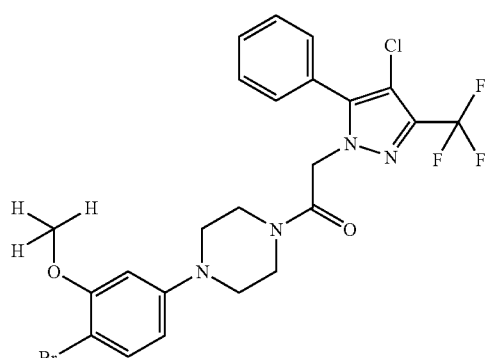 1.105 / ++ | | 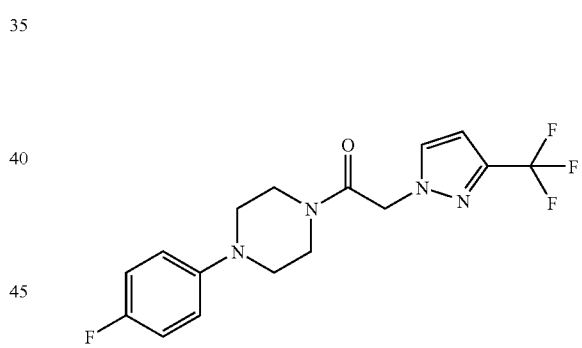 1.109 / + |
| 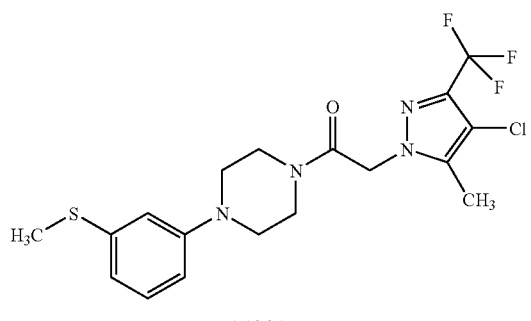 1.106 / ++ | | 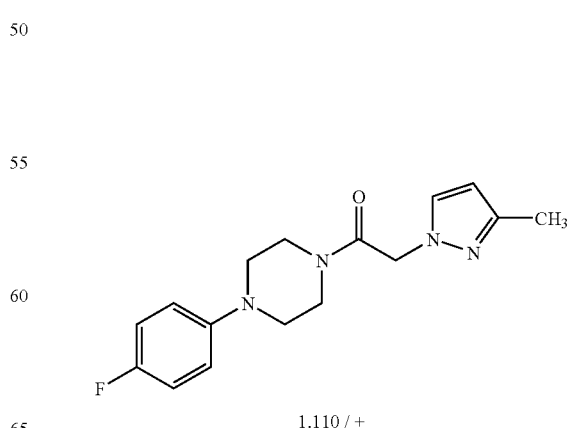 1.110 / + |

TABLE 5-continued
| Structure |
|---|
| 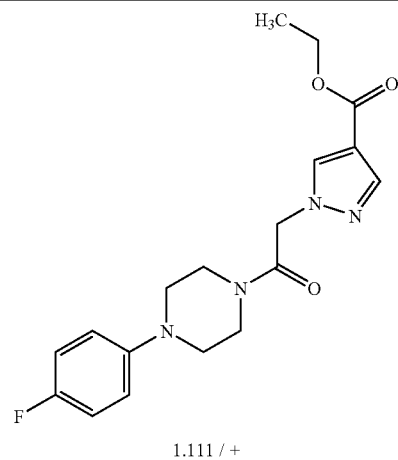
1.111 / + |
| 1.112 / + |
| 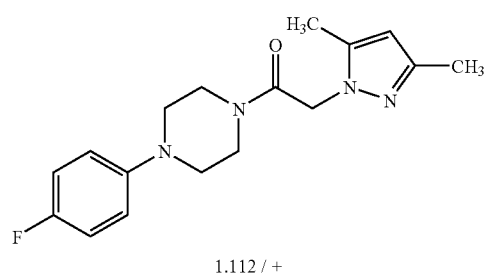
1.112 / + |
| 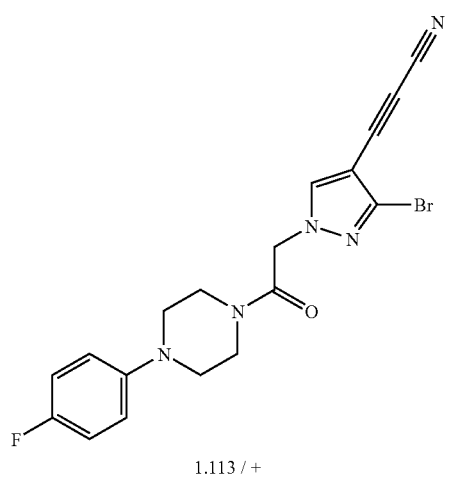
1.113 / + |
| 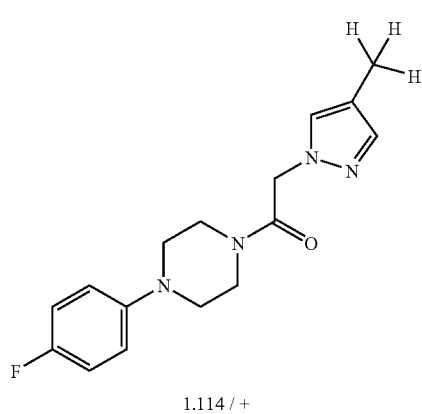
1.114 / + |
TABLE 5-continued
| Structure |
|---|
| 1.115 / + |
| 1.116 / + |
| 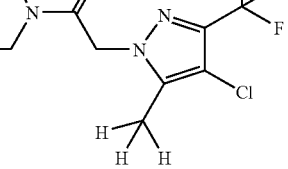
1.117 / + |
| 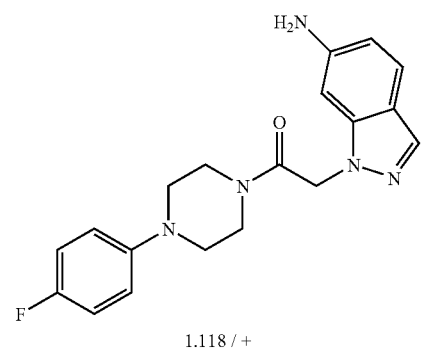
1.118 / + |

TABLE 5-continued

| Structure | |
|---|---|
| 1.119 / + | |
| 1.120 / + | |
| 1.121 / + | |
| 1.122 / + | |
| 1.123 / + | |
| 1.124 / +++ | |
| 1.125 / + | |
| 1.126 / + | |
| 1.127 / + | |
| 1.128 / + | |

TABLE 5-continued
Structure
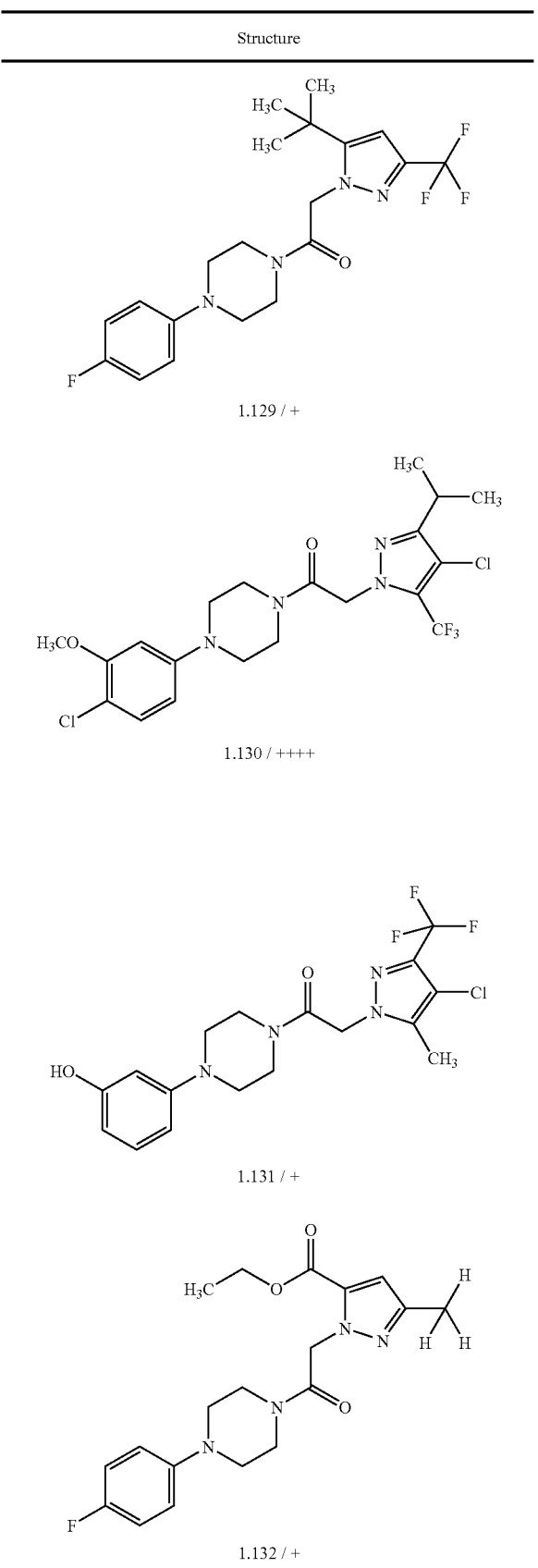
1.129 / +
1.130 / ++++
1.131 / +
1.132 / +
TABLE 5-continued
Structure
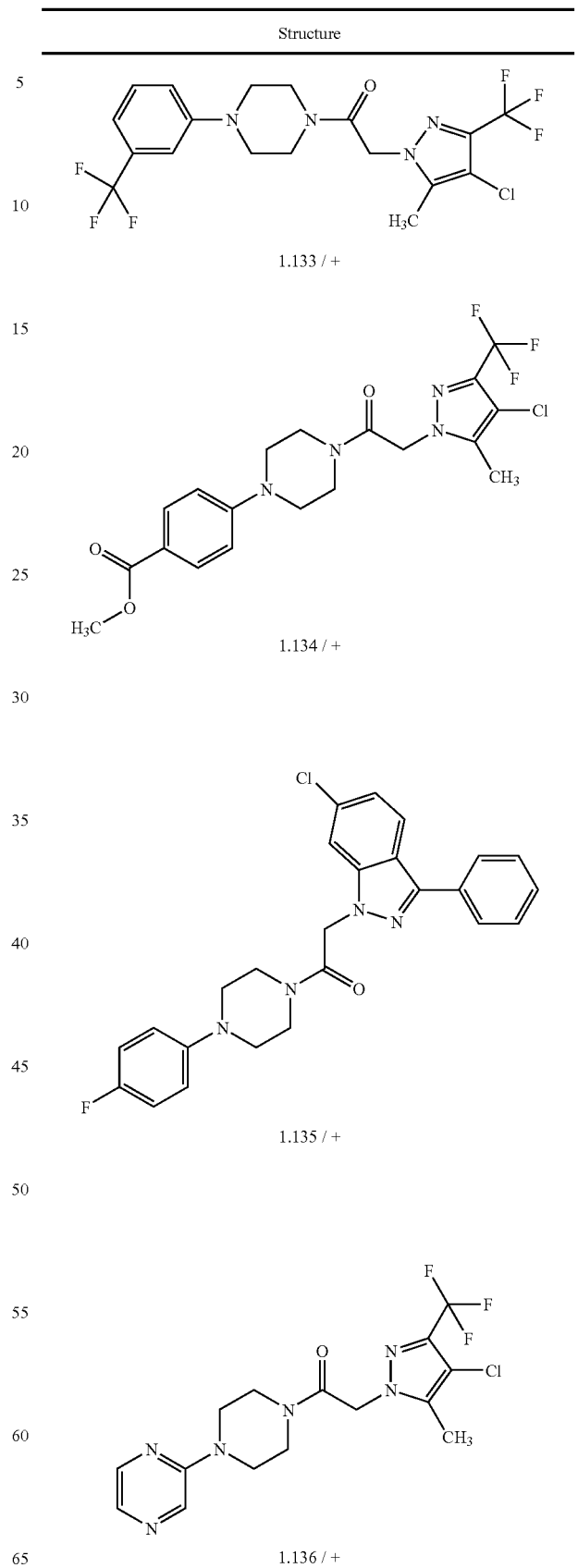
1.133 / +
1.134 / +
1.135 / +
1.136 / +

TABLE 5-continued
Structure
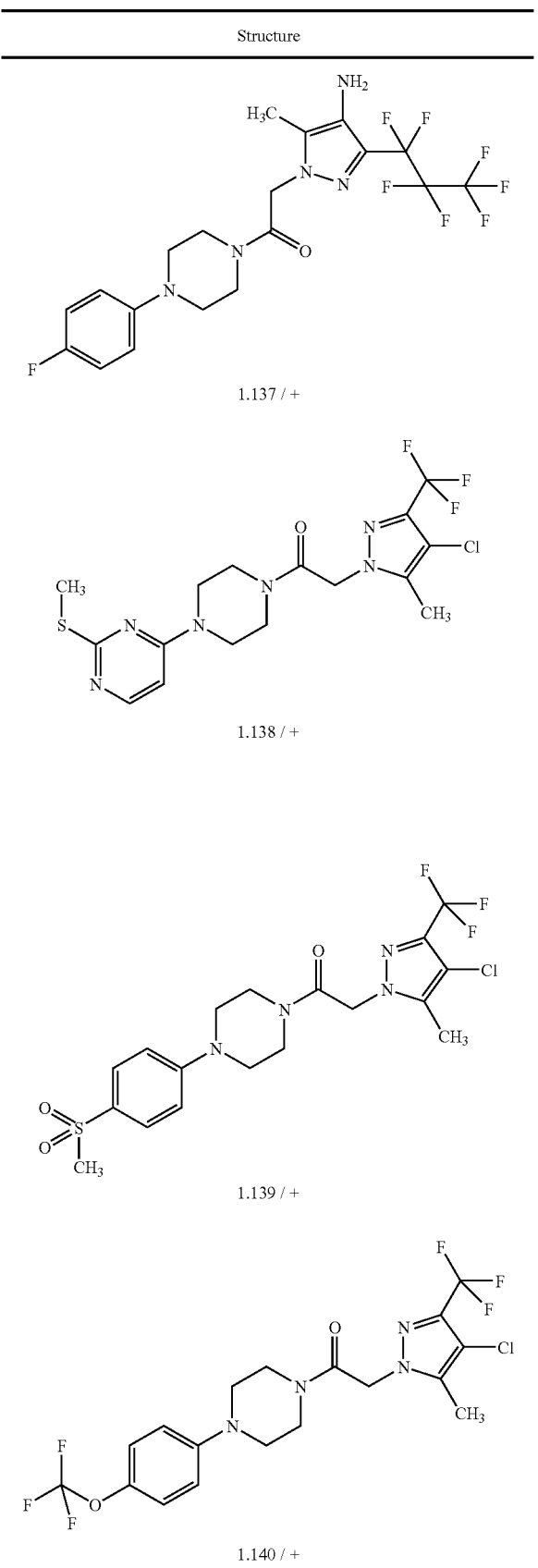
1.137 / +
1.138 / +
1.139 / +
1.140 / +
TABLE 5-continued
Structure
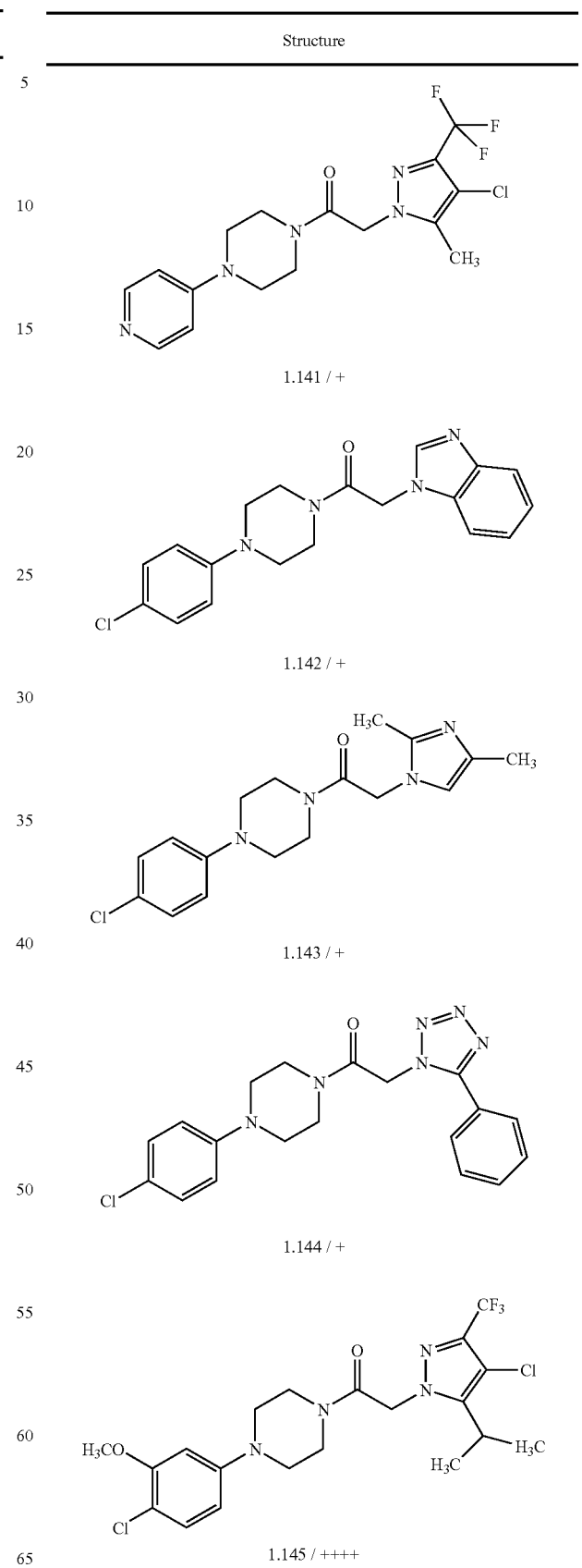
1.141 / +
1.142 / +
1.143 / +
1.144 / +
1.145 / ++++

TABLE 5-continued

| Structure | |
|---|---|
| (structure 1.146) | 1.146 / + |
| (structure 1.147) | 1.147 / + |
| (structure 1.148) | 1.148 / + |
| (structure 1.149) | 1.149 / + |
| (structure 1.150) | 1.150 / ++++ |
| (structure 1.151) | 1.151 / ++++ |
| (structure 1.152) | 1.152 / ++++ |
| (structure 1.153) | 1.153 / ++++ |
| (structure 1.154) | 1.154 / ++++ |

TABLE 5-continued
Structure
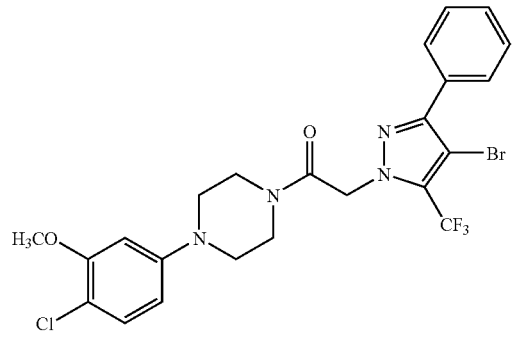
1.155 / ++++
1.156 / ++
1.157 / ++++
1.158 / ++++
TABLE 5-continued
Structure
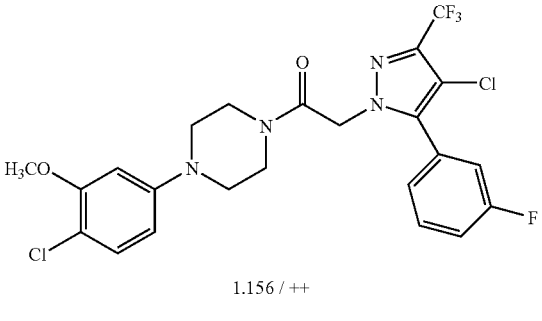
1.159 / +++
1.160 / ++++
1.161 / +++
1.162 / ++++
1.163 / ++++

TABLE 5-continued
Structure
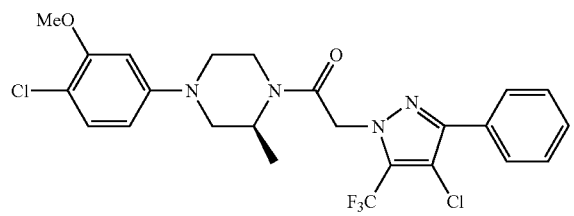
1.164 / ++++
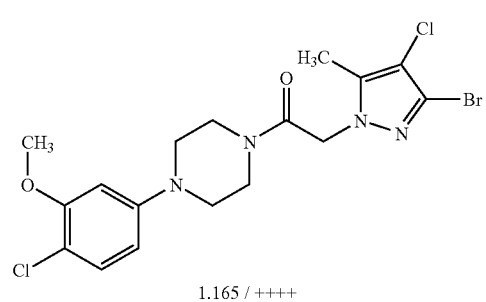
1.165 / ++++
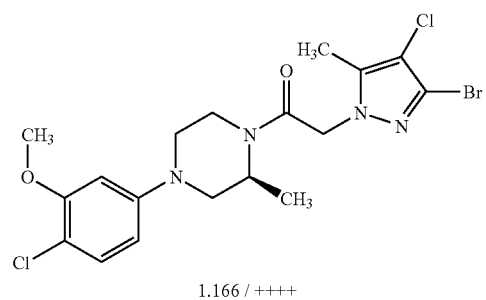
1.166 / ++++
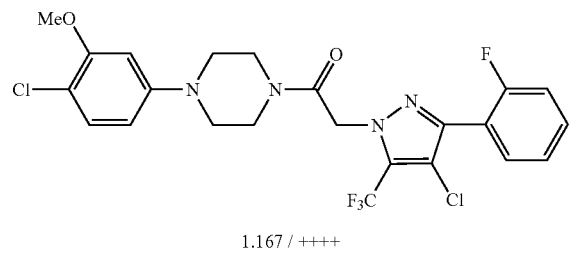
1.167 / ++++
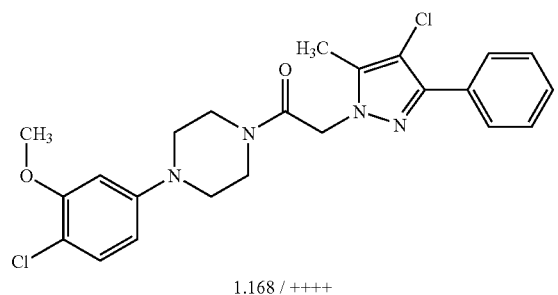
1.168 / ++++
TABLE 5-continued
Structure
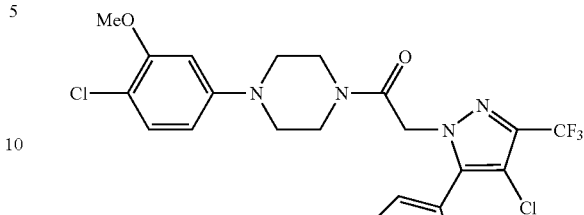
1.169 / ++++
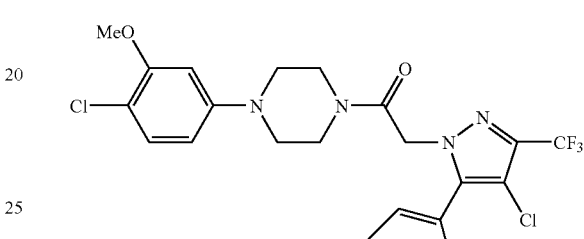
1.170 / +++
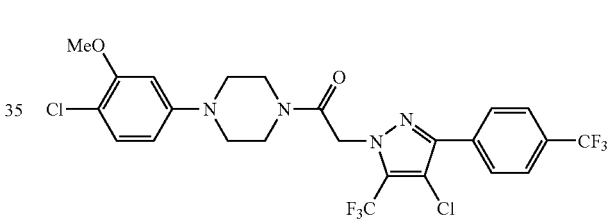
1.171 / ++++
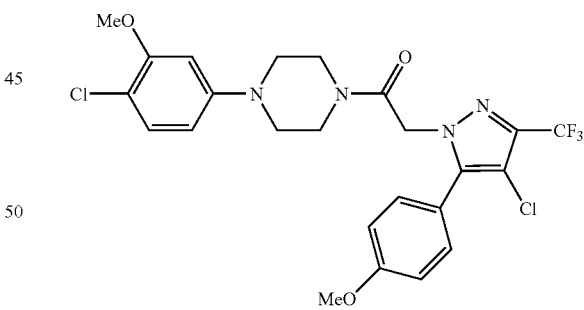
1.172 / +++
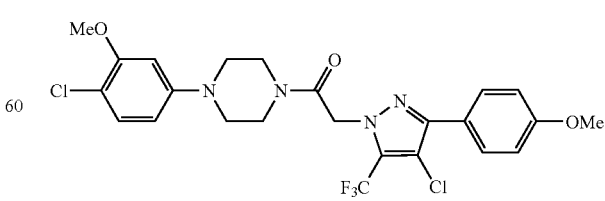
1.173 / ++++

TABLE 5-continued

Structure 1.174 / ++++

1.175 / ++++

1.176 / ++++

1.177 / ++++

1.178 / ++++

1.179 / ++++

1.180 / ++++

1.181 / ++++

1.182 / ++++

1.183 / ++++

1.184 / ++++

TABLE 5-continued

Structure 1.185 / ++++

1.186 / +

1.187 / +

1.188 / / +

1.189 / ++++

1.190 / ++++

1.191 / ++++

1.192 / / ++

TABLE 5-continued
Structure
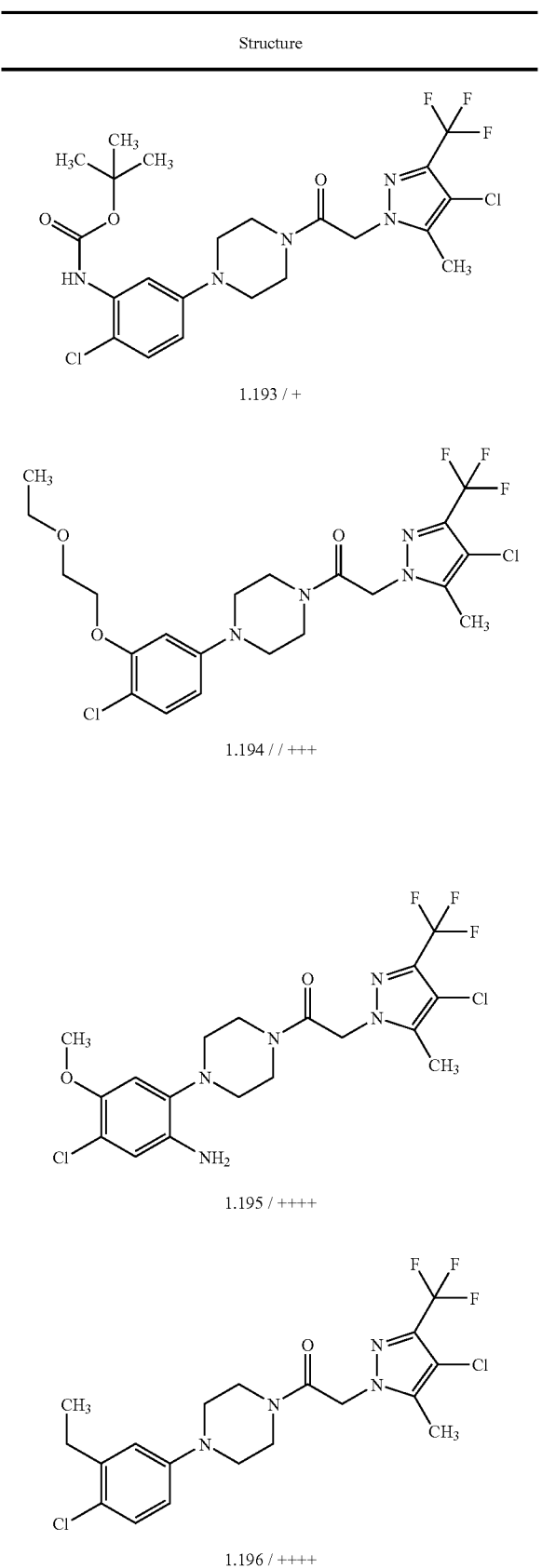
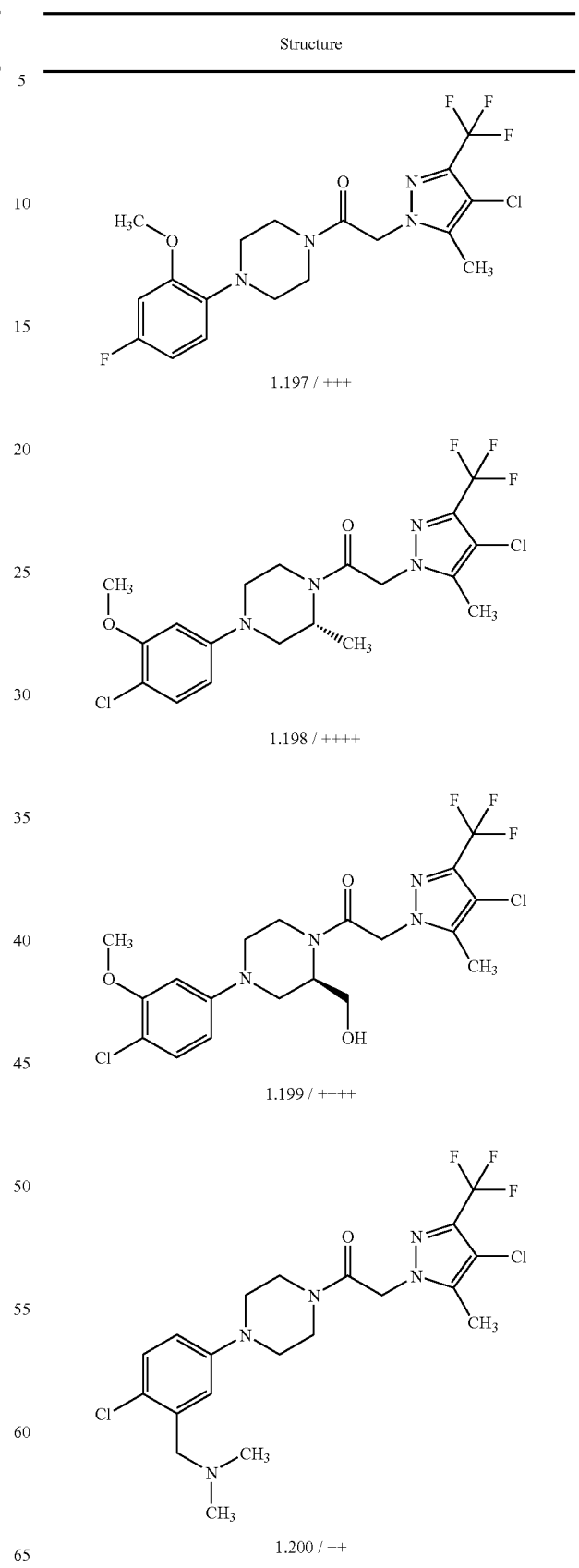

TABLE 5-continued
Structure
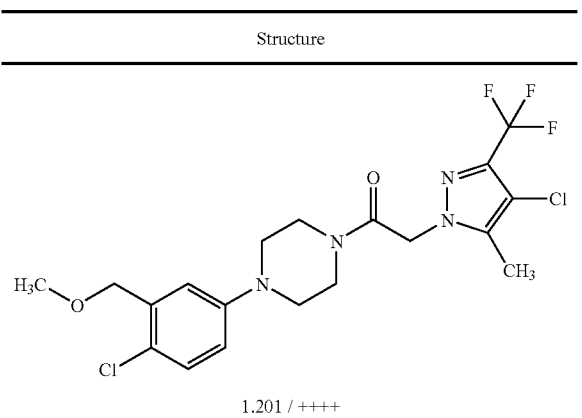
1.201 / ++++
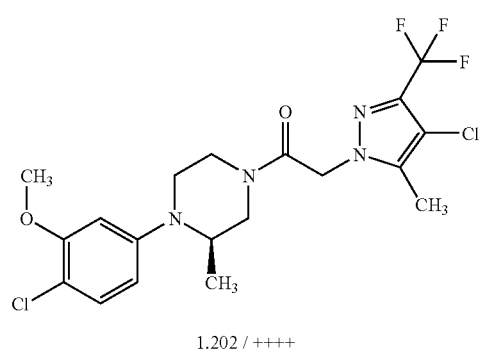
1.202 / ++++
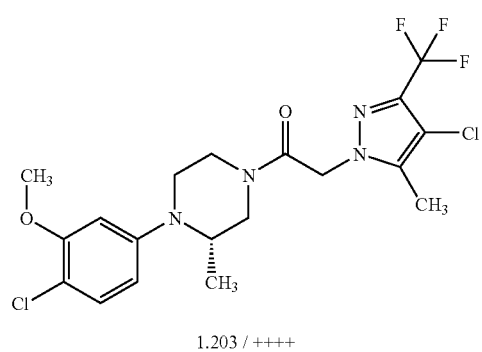
1.203 / ++++
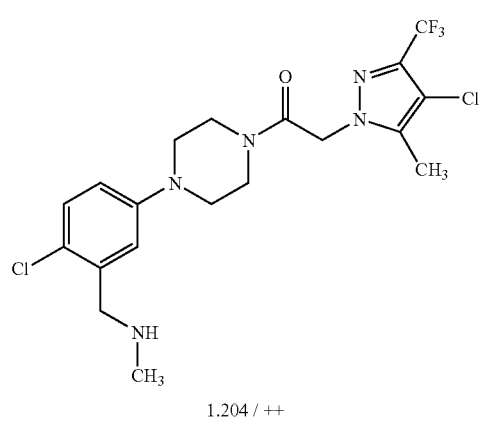
1.204 / ++
TABLE 5-continued
Structure
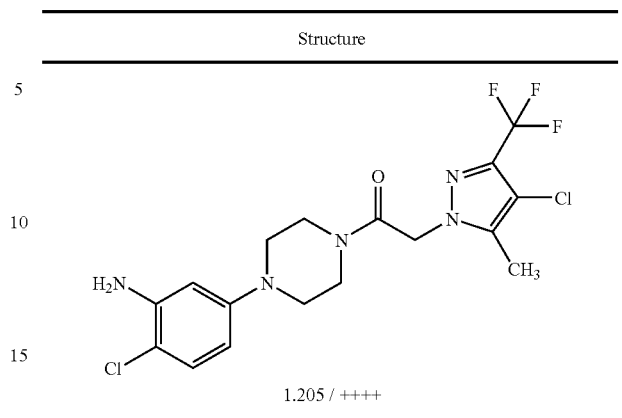
1.205 / ++++
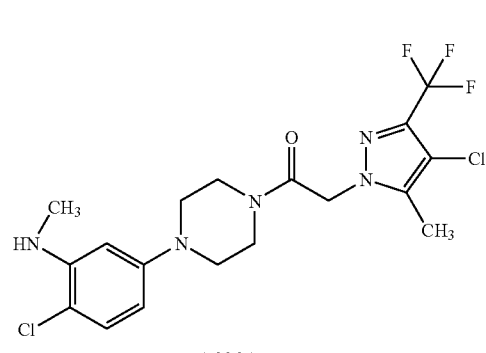
1.206 / ++++
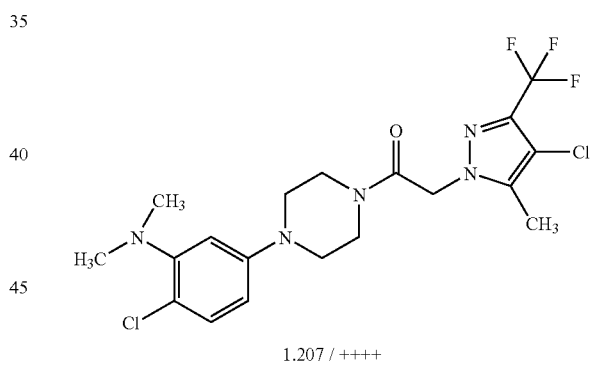
1.207 / ++++
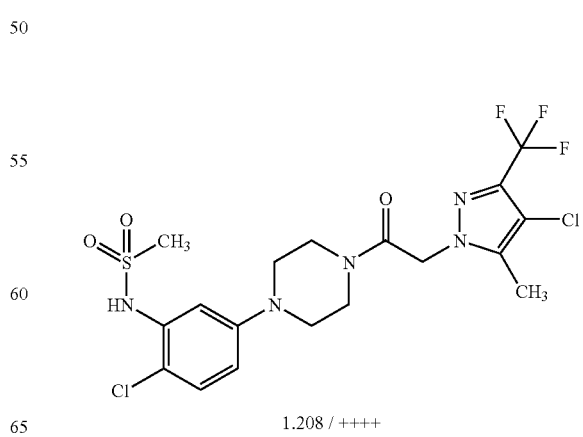
1.208 / ++++

TABLE 5-continued
Structure
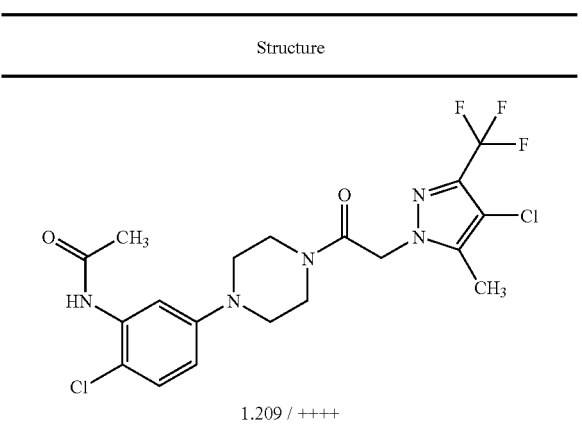
1.209 / ++++
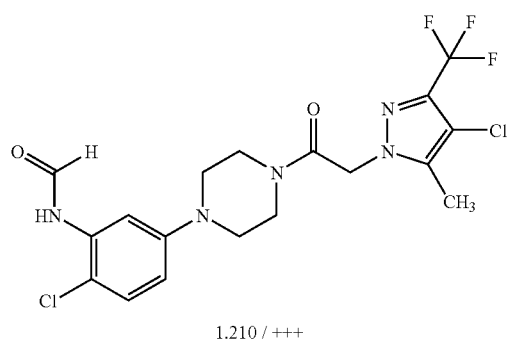
1.210 / +++
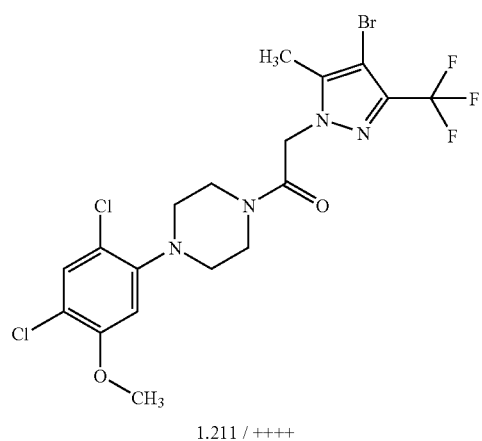
1.211 / ++++
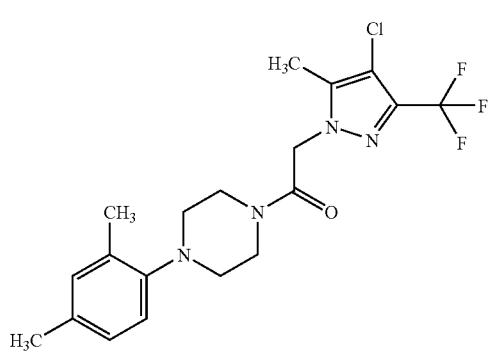
1.212 / ++
TABLE 5-continued
Structure
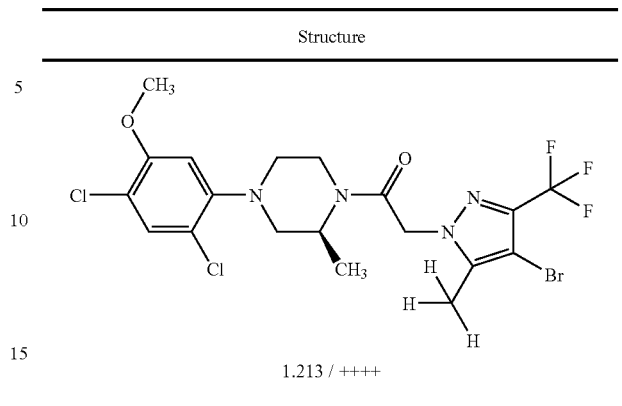
1.213 / ++++
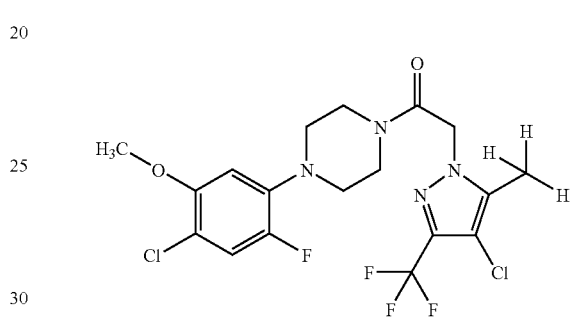
1.214 / ++++
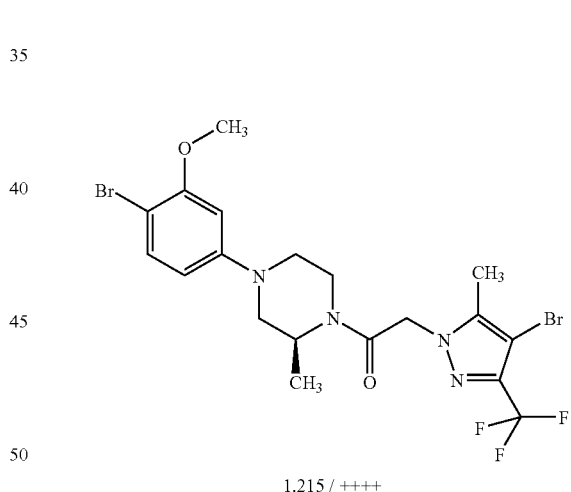
1.215 / ++++
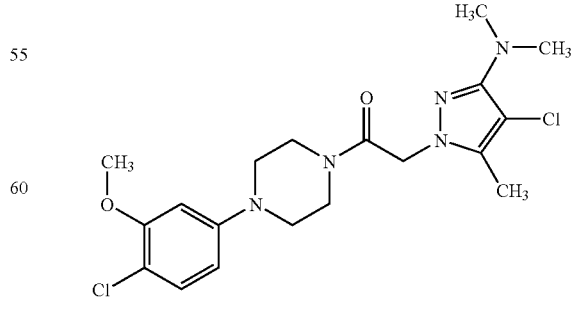
1.216 / ++++

TABLE 5-continued
Structure
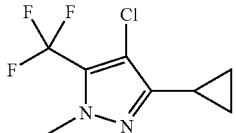
1.217 / ++++
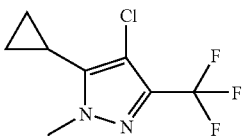
1.218 / ++++
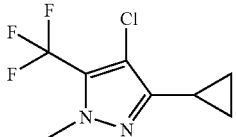
1.219 / ++++
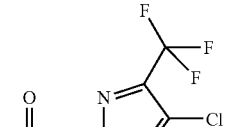
1.220 / ++++
TABLE 5-continued
Structure
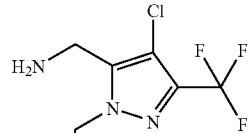
1.221 / +++
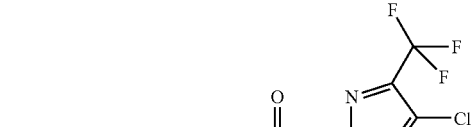
1.222 / ++++
1.223 / ++++
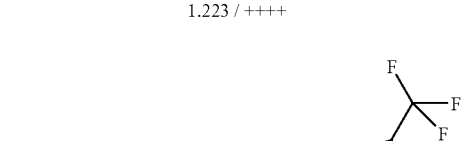
1.224 / ++++

TABLE 5-continued

Structure 1.225 / +++

1.226 / ++++

1.227 / ++++

1.128 / ++++

TABLE 5-continued

Structure 1.229 / ++++

1.230 / ++++

1.231 / ++++

1.232 / ++++

1.233 / ++++

TABLE 5-continued
| Structure |
|---|
| 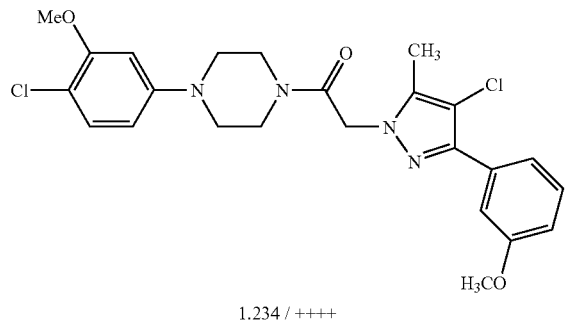 1.234 / ++++ |
| 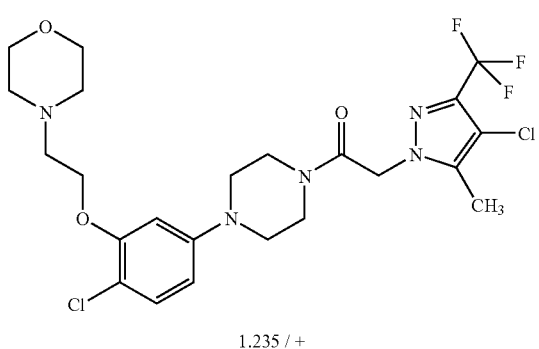 1.235 / + |
| 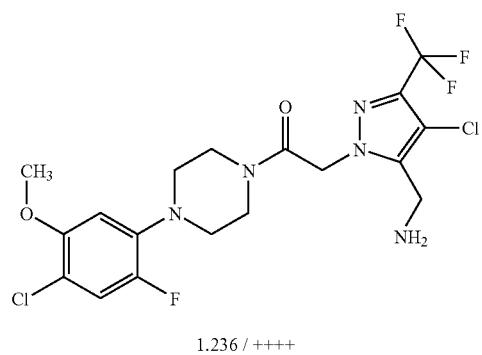 1.236 / ++++ |
| 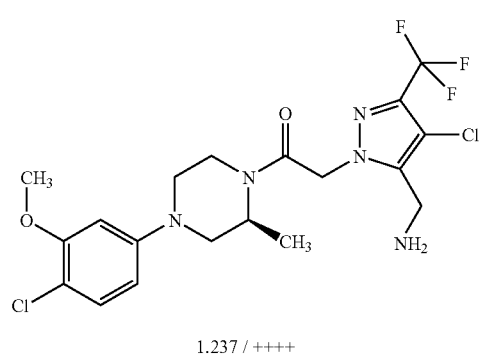 1.237 / ++++ |
TABLE 5-continued
| Structure |
|---|
| 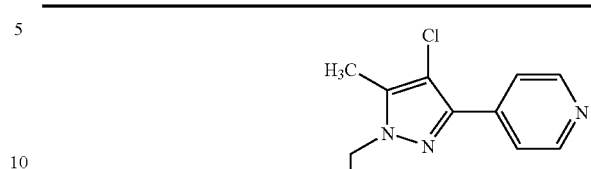 1.238 / ++++ |
| 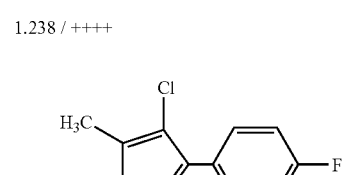 1.239 / ++++ |
| 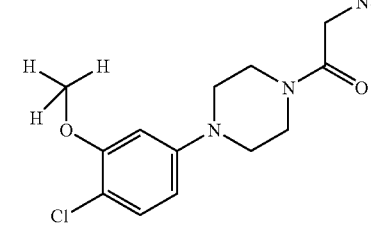 1.240 / ++++ |
| 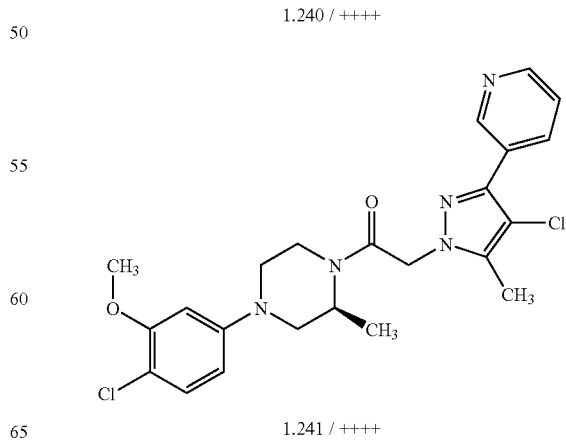 1.241 / ++++ |

TABLE 5-continued
| Structure |
|---|
| 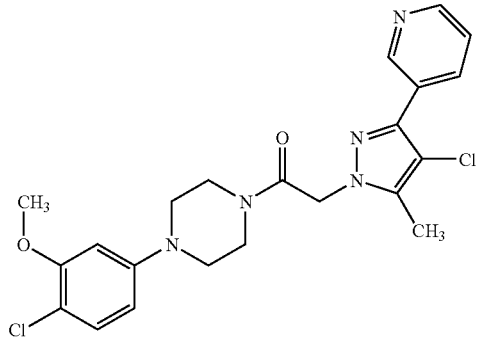<br>1.242 / ++++ |
| 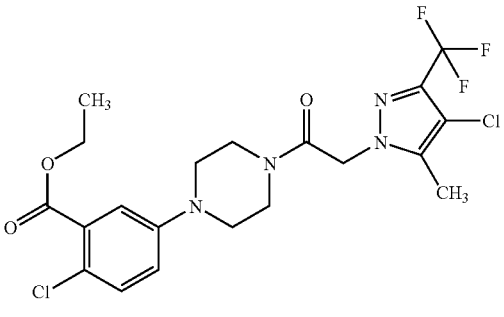<br>1.243 / +++ |
| 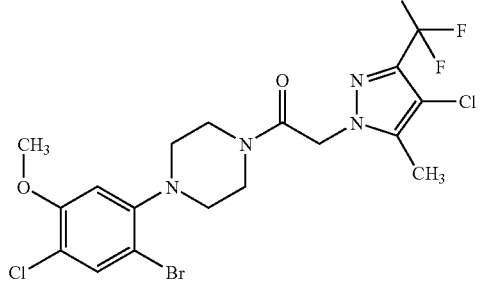<br>1.244 / ++++ |
| 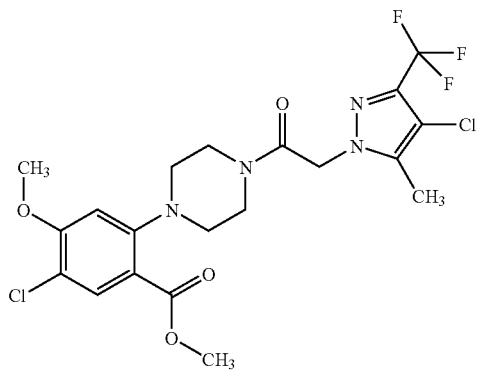<br>1.245 / ++++ |
TABLE 5-continued
| Structure |
|---|
| 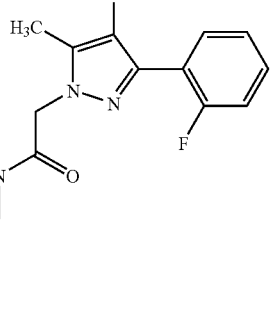<br>1.246 / ++++ |
| 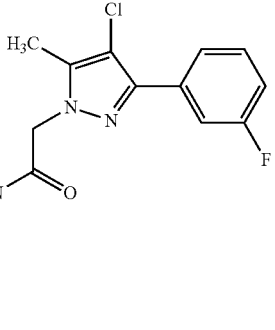<br>1.247 / ++++ |
| 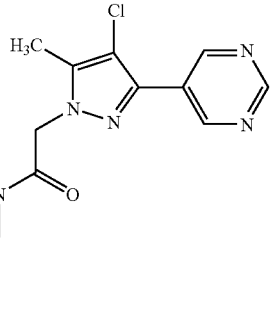<br>1.248 / ++++ |
| 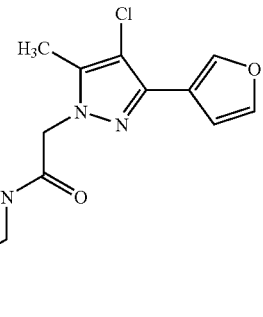<br>1.249 / ++++ |

TABLE 5-continued
Structure
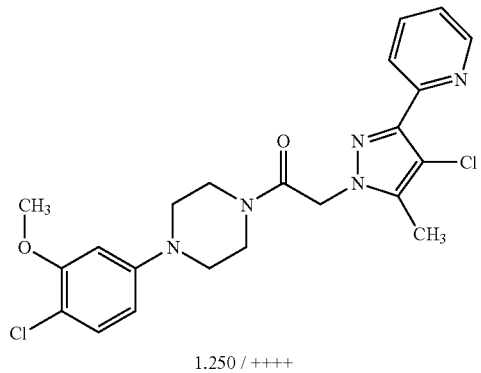
1.250 / ++++
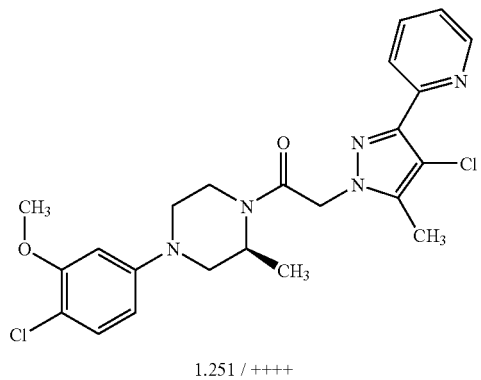
1.251 / ++++
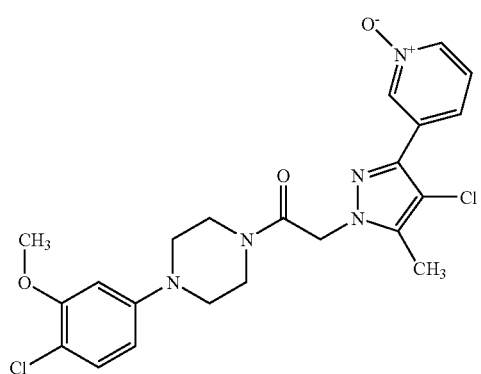
1.252 / ++++
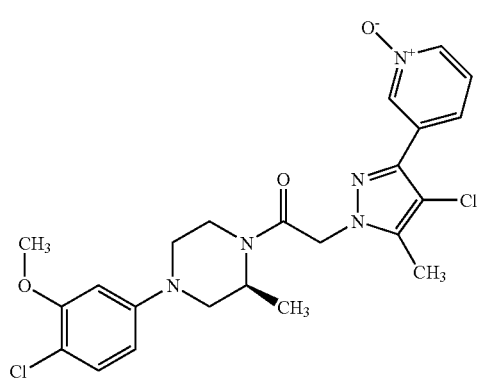
1.253 / ++++
TABLE 5-continued
Structure
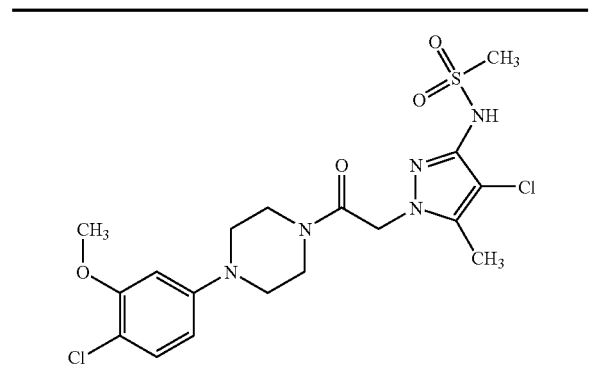
1.254 / ++++
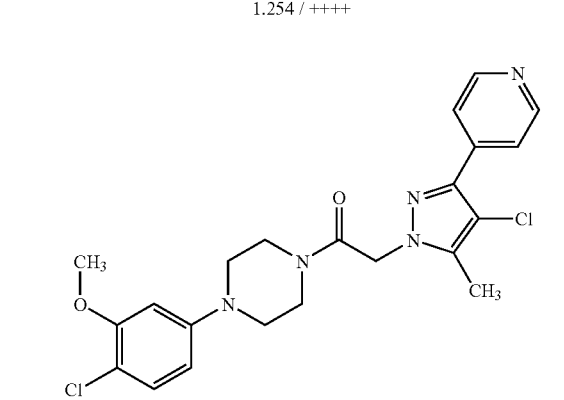
1.255 / ++++
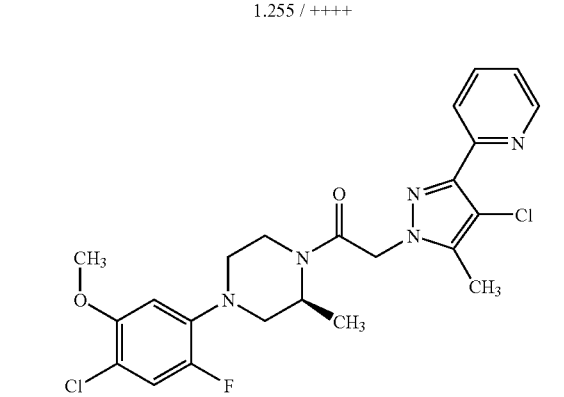
1.256 / ++++
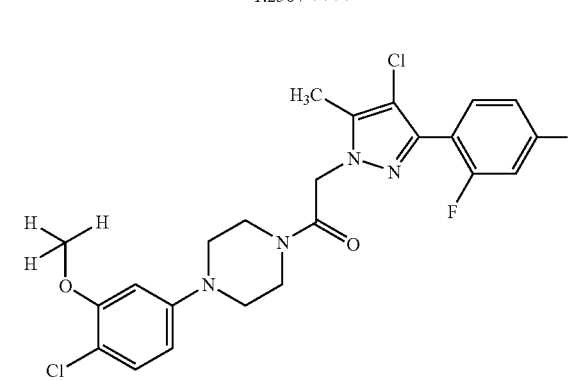
1.257 / ++++

TABLE 5-continued

Structure 1.258 / ++++

1.259 / ++++

1.260 / ++++

1.261 / ++++

TABLE 5-continued

Structure 1.262 / ++++

1.263 / ++++

1.264 / ++++

1.265 / ++++

TABLE 5-continued
Structure
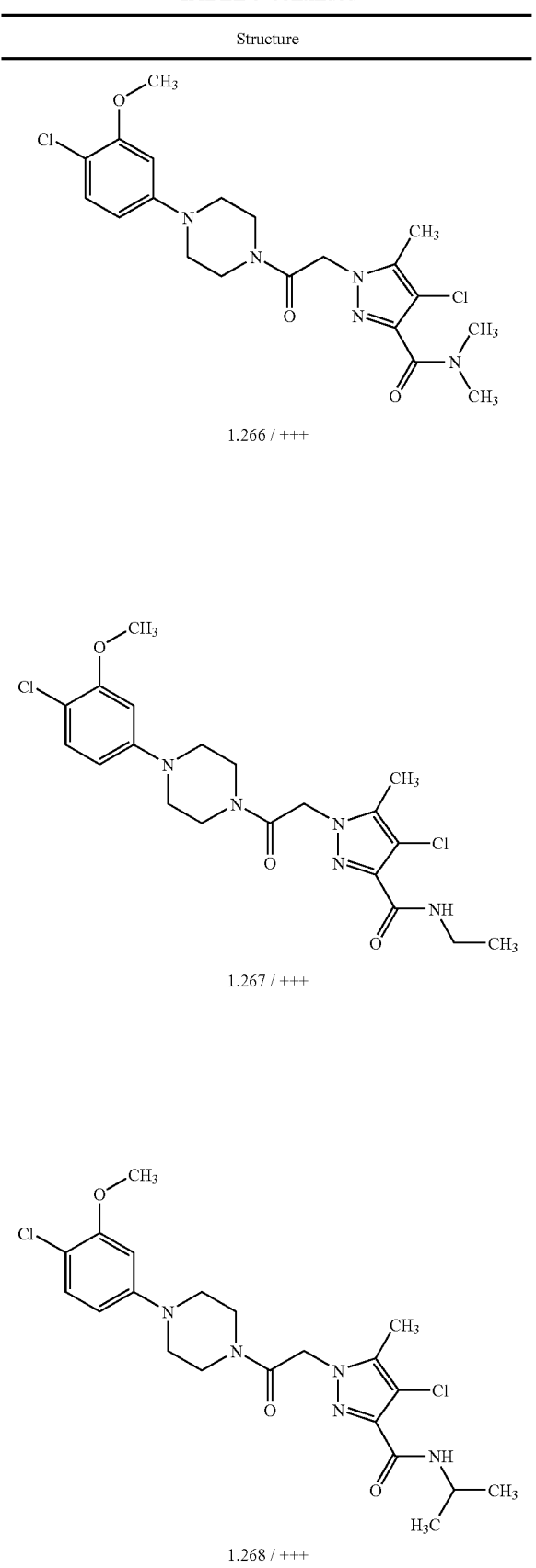
1.266 / +++
1.267 / +++
1.268 / +++
TABLE 5-continued
Structure
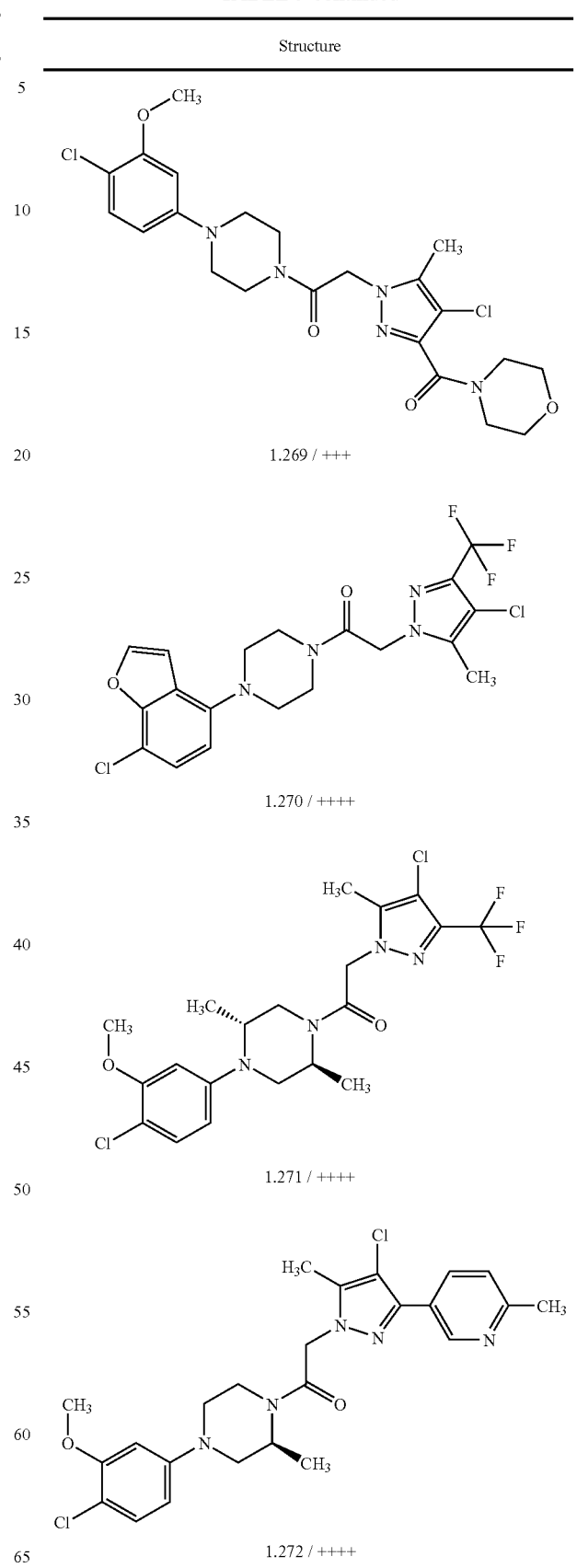
1.269 / +++
1.270 / ++++
1.271 / ++++
1.272 / ++++

TABLE 5-continued
Structure
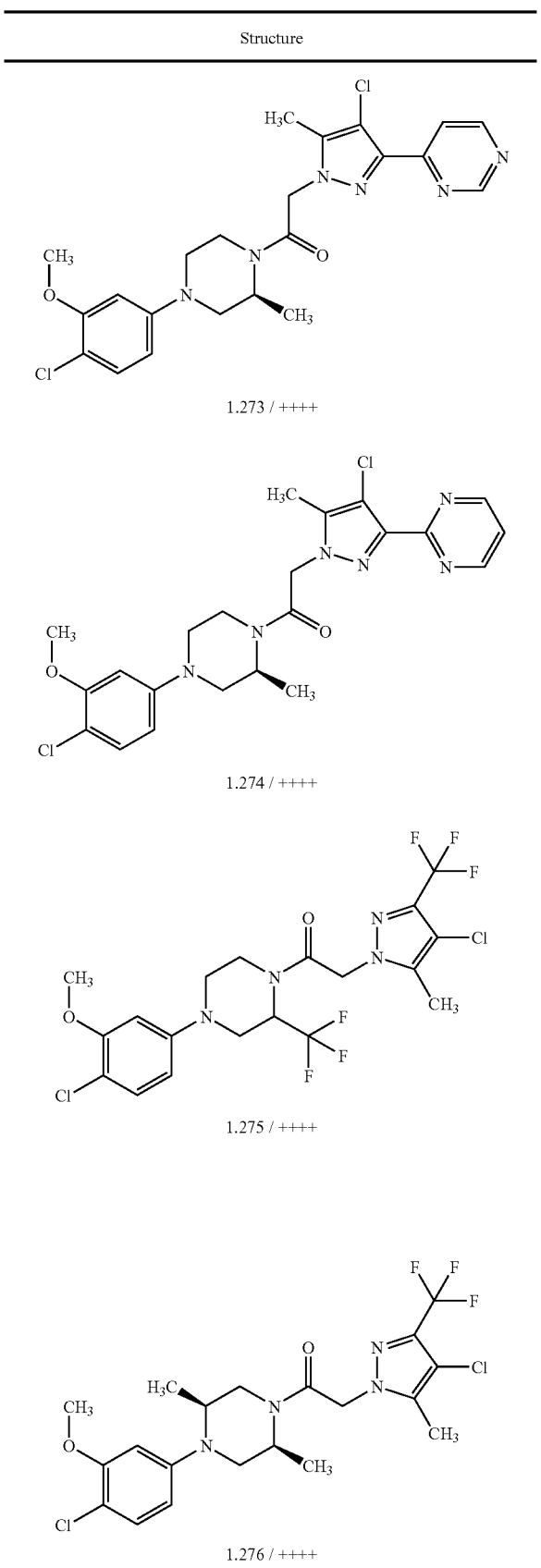
1.273 / ++++
1.274 / ++++
1.275 / ++++
1.276 / ++++
TABLE 5-continued
Structure
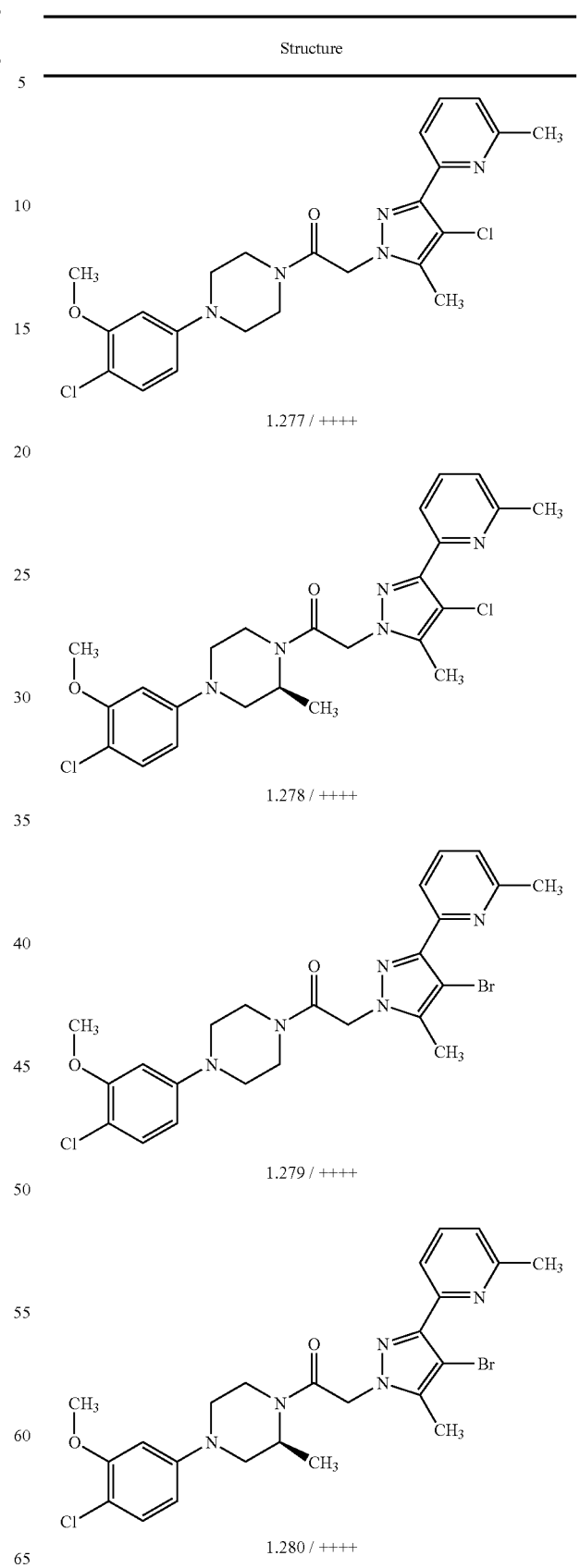
1.277 / ++++
1.278 / ++++
1.279 / ++++
1.280 / ++++

TABLE 5-continued

| Structure |
|---|
| 1.281 / ++++ |
| 1.282 / ++++ |
| 1.283 / ++++ |
| 1.284 / ++++ |
| 1.285 / ++++ |
| 1.286 / ++++ |
| 1.287 / ++++ |
| 1.288 / ++++ |

TABLE 5-continued
Structure
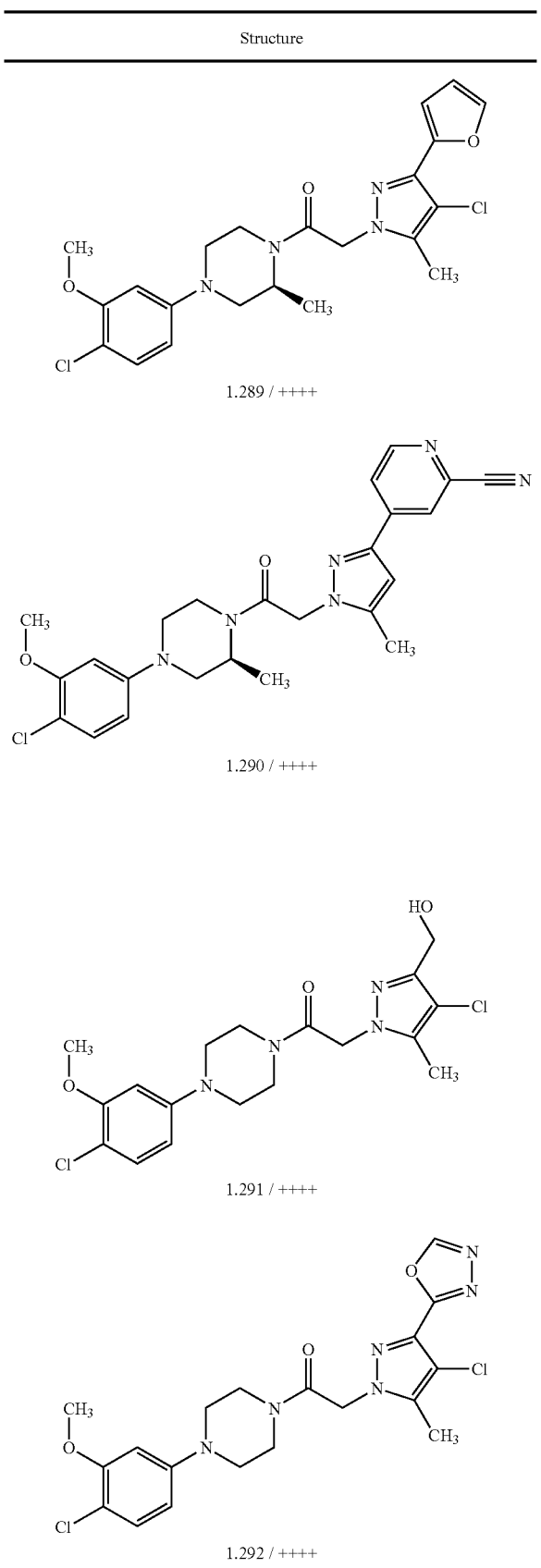
1.289 / ++++
1.290 / ++++
1.291 / ++++
1.292 / ++++
TABLE 5-continued
Structure
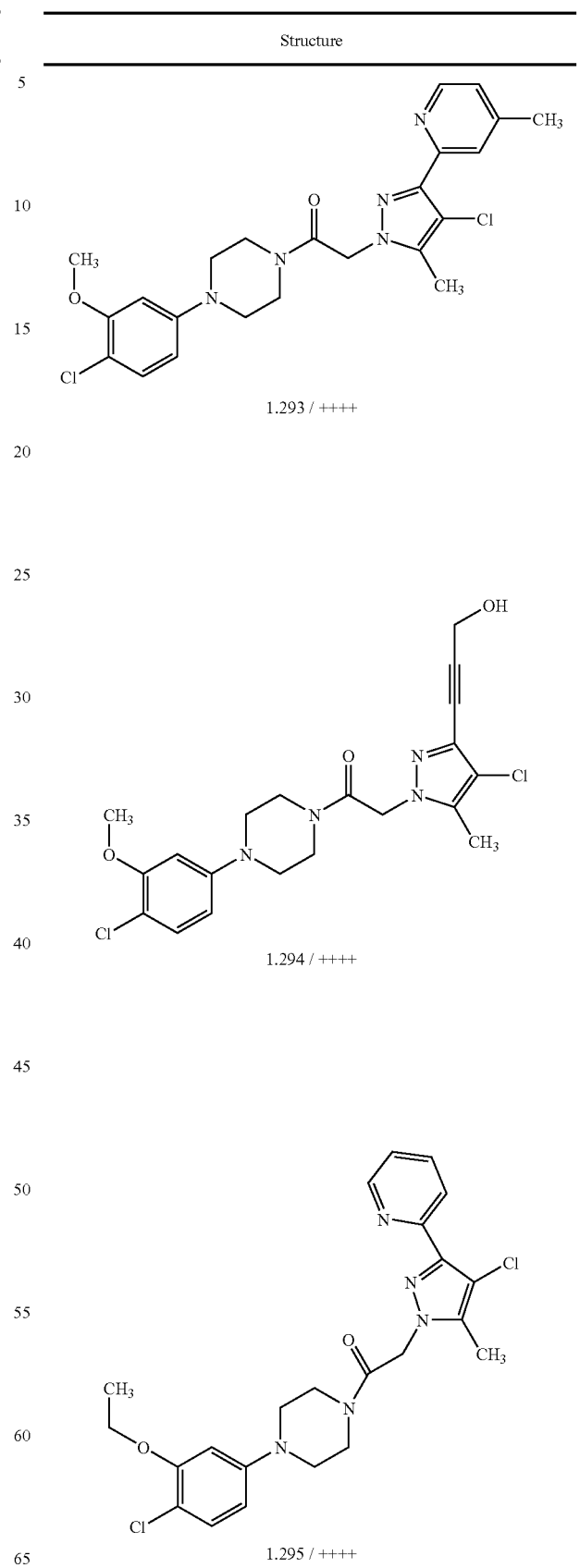
1.293 / ++++
1.294 / ++++
1.295 / ++++

TABLE 5-continued

| Structure |
|---|
| 1.296 / ++++ |
| 1.297 / ++++ |
| 1.298 / ++++ |
| 1.299 / ++++ |
| 1.300 / ++++ |
| 1.301 / ++++ |
| 1.302 / ++++ |
| 1.303 / ++++ |

TABLE 5-continued

| Structure |
|---|
| 1.304 / ++++ |
| 1.305 / ++++ |
| 1.306 / ++++ |
| 1.307 / ++++ |
| 1.308 / ++++ |
| 1.309 / ++++ |
| 1.310 / ++++ |

TABLE 5-continued

| Structure |
|---|
| 1.311 / ++++ |
| 1.312 / ++++ |
| 1.313 / ++++ |
| 1.314 / ++++ |
| 1.315 / ++++ |
| 1.316 / ++++ |
| 1.317 / ++++ |
| 1.318 / ++++ |

TABLE 5-continued
Structure
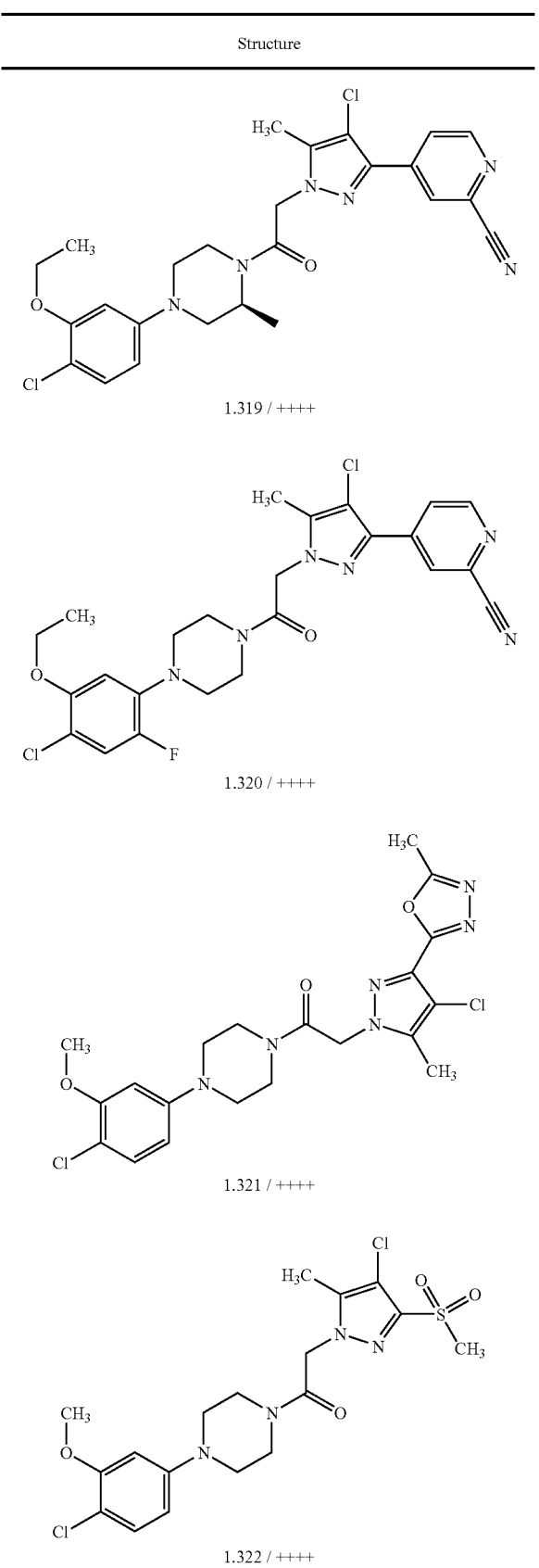
1.319 / ++++
1.320 / ++++
1.321 / ++++
1.322 / ++++
TABLE 5-continued
Structure
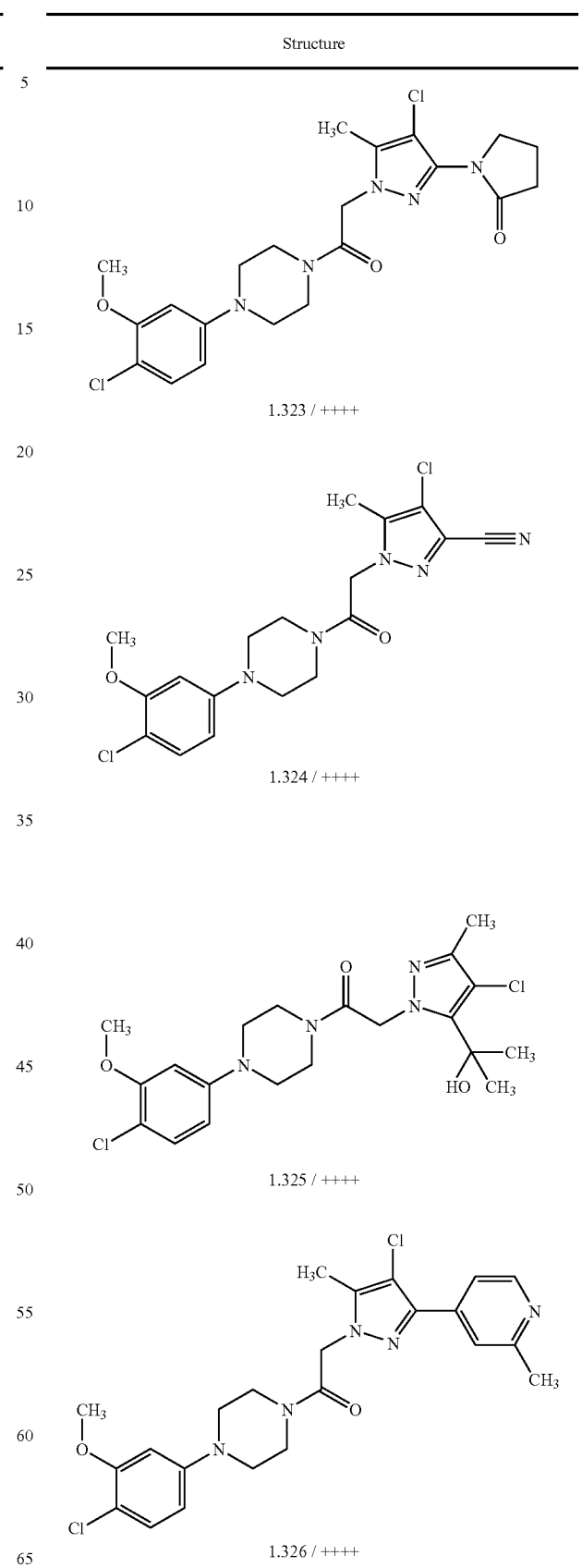
1.323 / ++++
1.324 / ++++
1.325 / ++++
1.326 / ++++

TABLE 5-continued
Structure
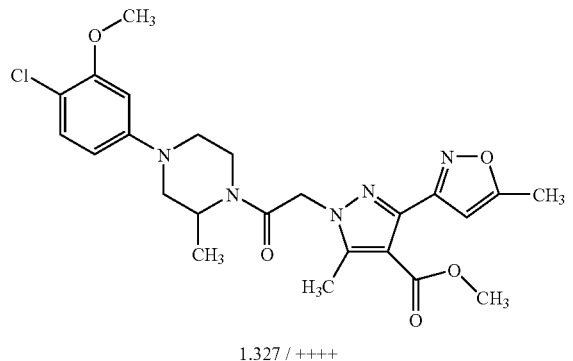
1.327 / ++++
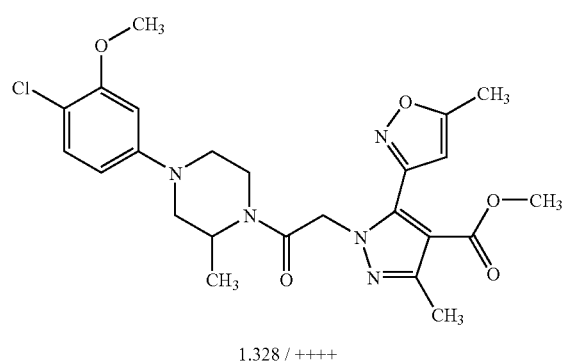
1.328 / ++++
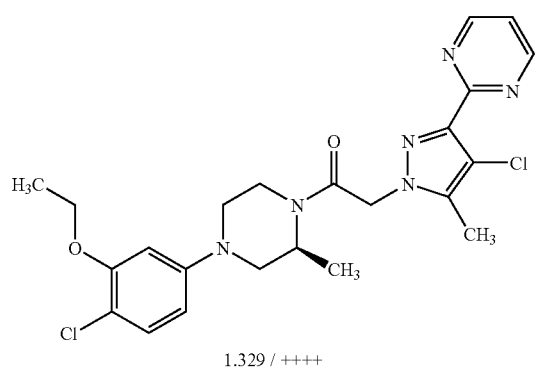
1.329 / ++++
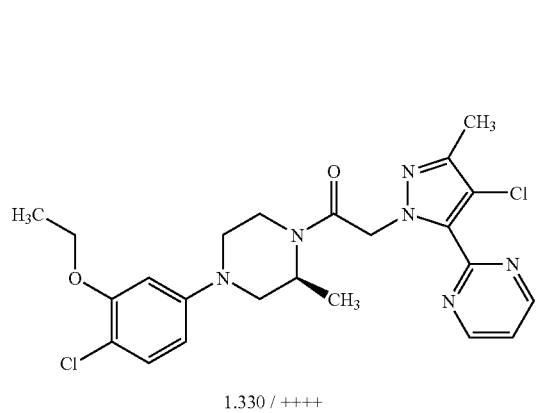
1.330 / ++++
TABLE 5-continued
Structure
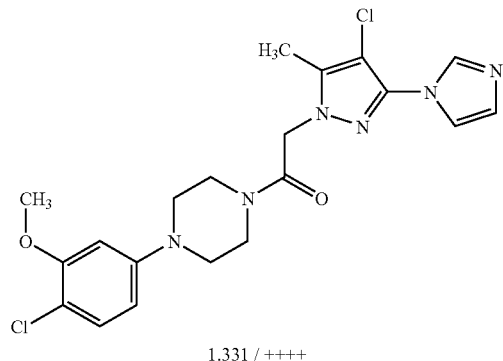
1.331 / ++++
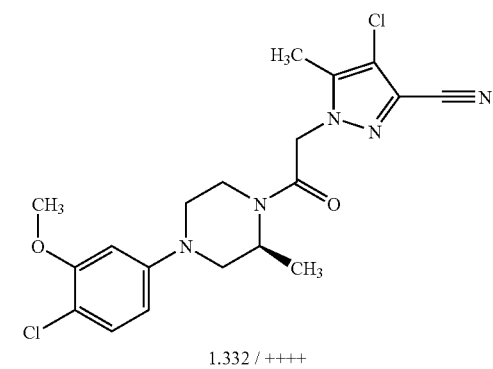
1.332 / ++++
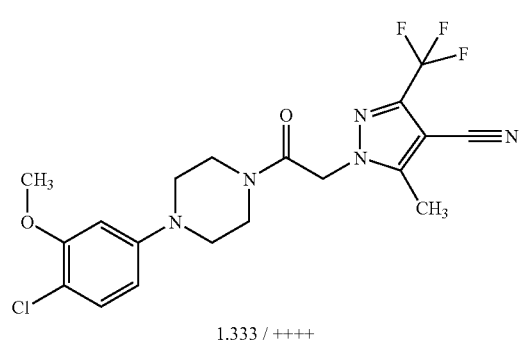
1.333 / ++++
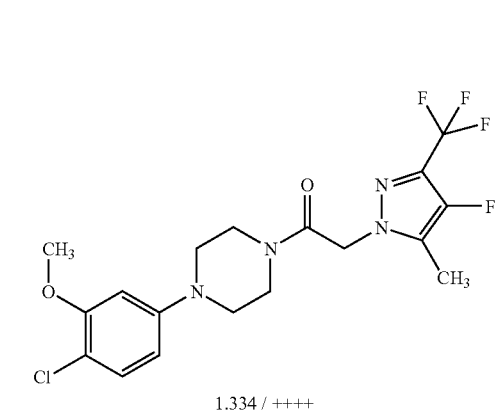
1.334 / ++++

TABLE 5-continued

Structure 1.335 / ++++

1.336 / +++

1.337 / ++

1.338 / ++++

1.339 / ++++

1.340 / ++++

1.341 / ++++

1.342 / ++++

TABLE 5-continued

| Structure |
|---|
| (1.343 / ++++) |
| (1.344 / ++++) |
| (1.345 / ++++) |
| (1.346 / ++++) |
| (1.347 / ++++) |
| (1.348 / ++++) |
| (1.349 / ++++) |
| (1.350 / +++) |

TABLE 5-continued
Structure
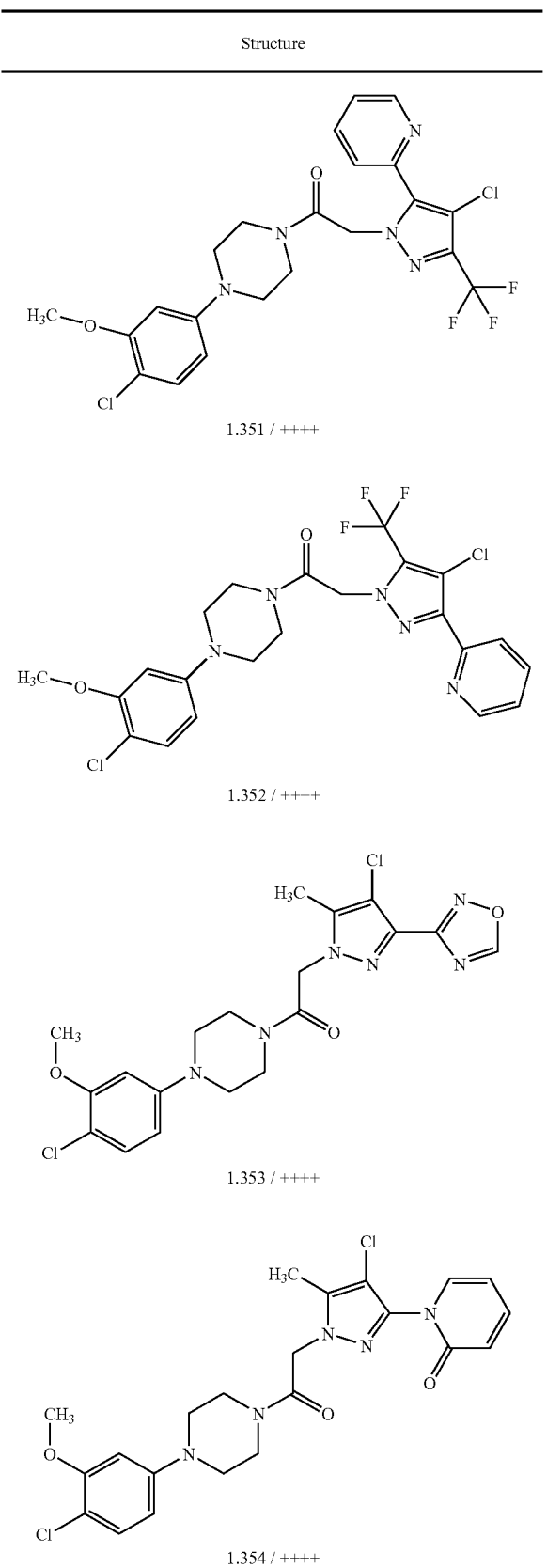
1.351 / ++++
1.352 / ++++
1.353 / ++++
1.354 / ++++
TABLE 5-continued
Structure
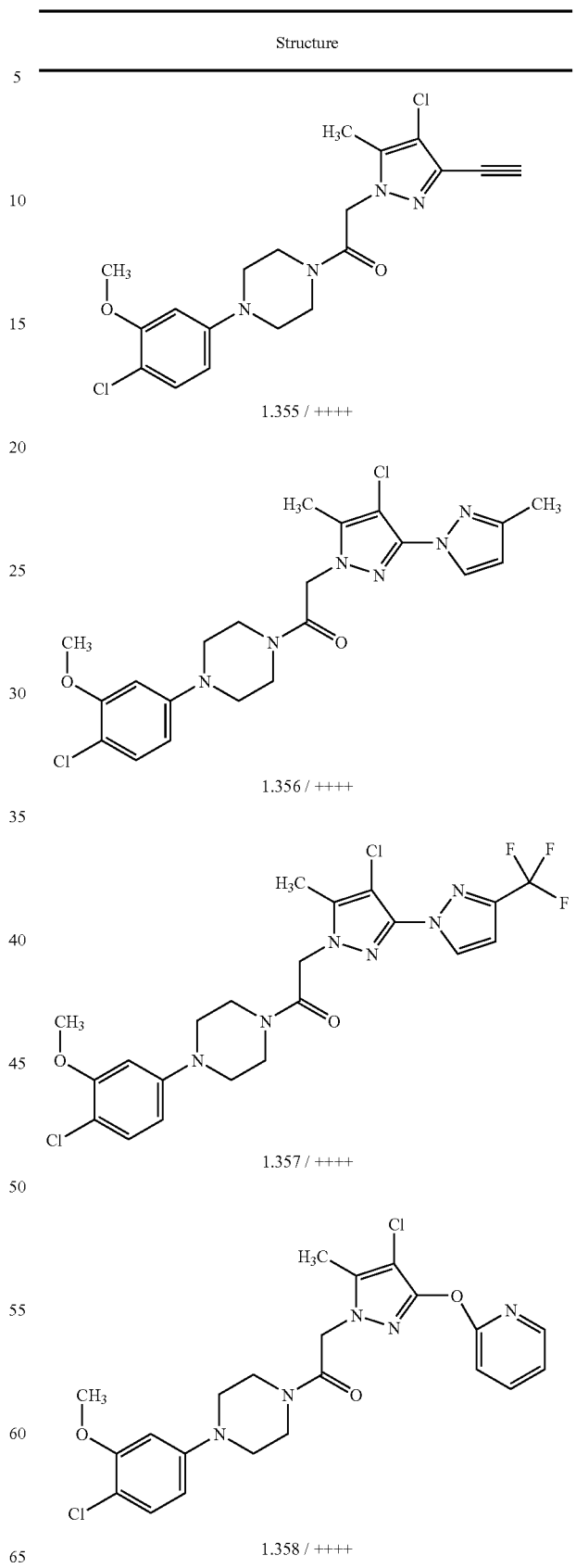
1.355 / ++++
1.356 / ++++
1.357 / ++++
1.358 / ++++

TABLE 5-continued
| Structure |
|---|
| 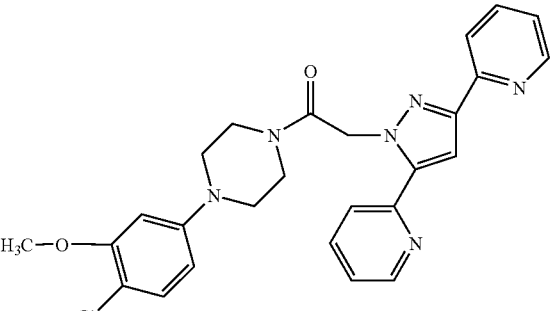 1.359 / +++ |
| 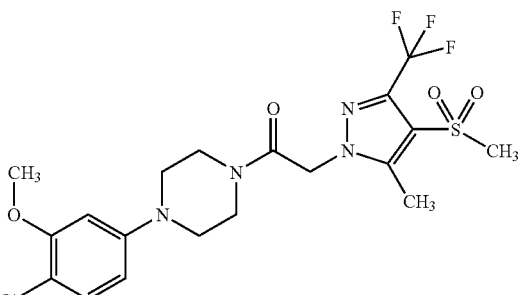 1.360 / ++++ |
| 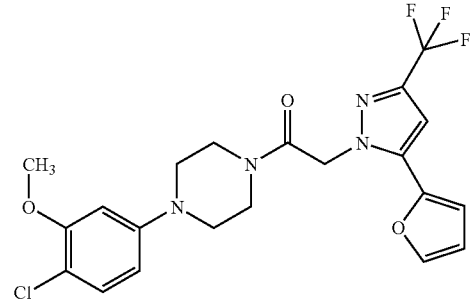 1.361 / ++++ |
| 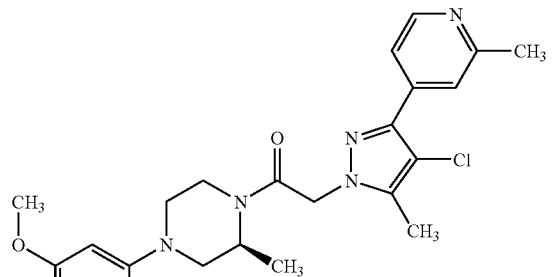 1.362 / ++++ |
TABLE 5-continued
| Structure |
|---|
| 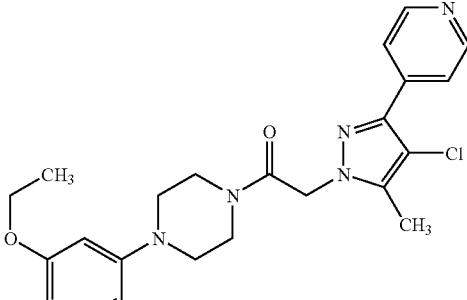 1.363 / ++++ |
| 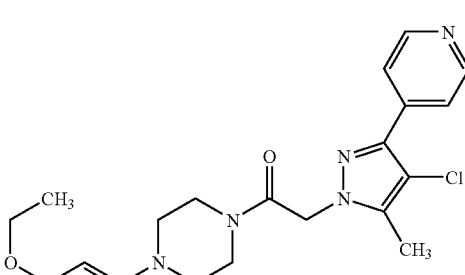 1.364 / ++++ |
| 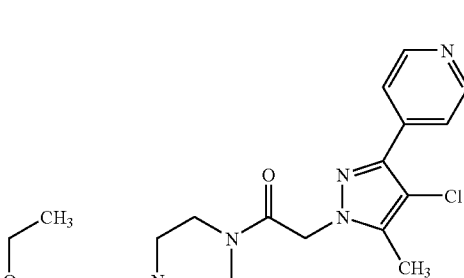 1.365 / ++++ |
| 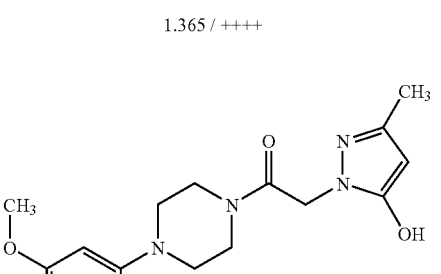 1.366 / ++++ |

TABLE 5-continued

| Structure |
|---|
| 1.367 / ++++ |
| 1.368 / ++++ |
| 1.369 / ++++ |

TABLE 5-continued

| Structure |
|---|
| 1.370 / |
| 1.371 / ++++ |
| 1.372 / ++++ |
| 1.373 / ++++ |

TABLE 5-continued
Structure
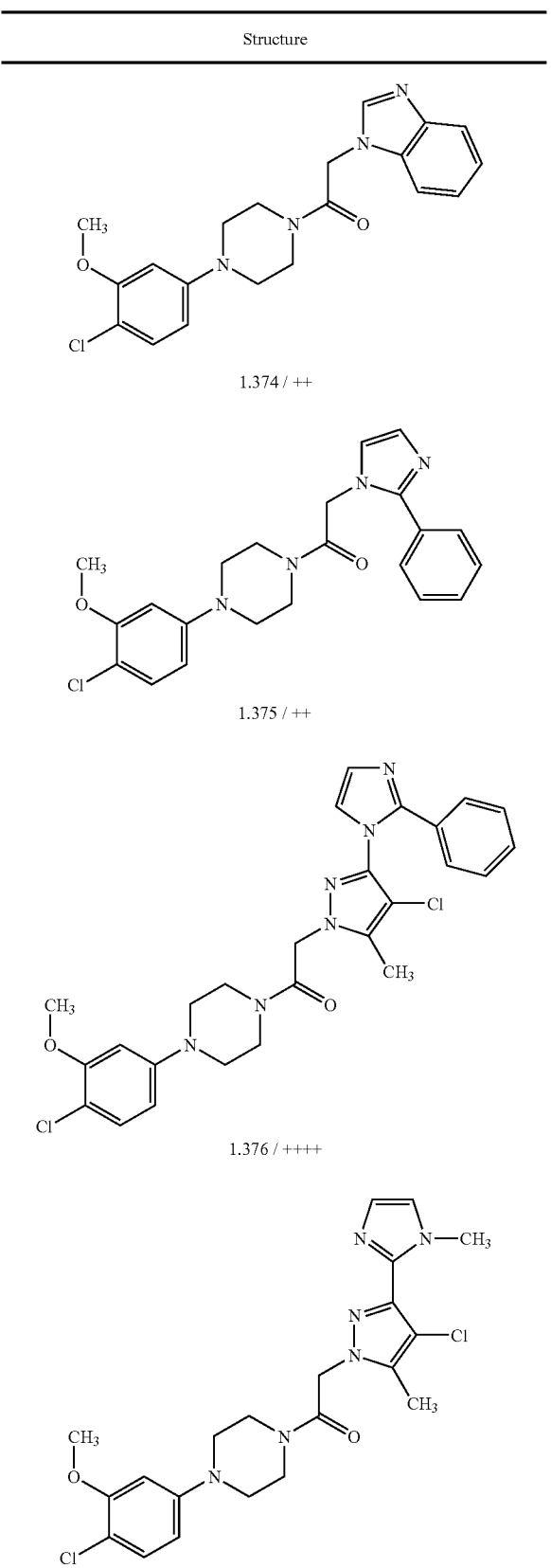
1.374 / ++
1.375 / ++
1.376 / ++++
1.377 / ++++
TABLE 5-continued
Structure
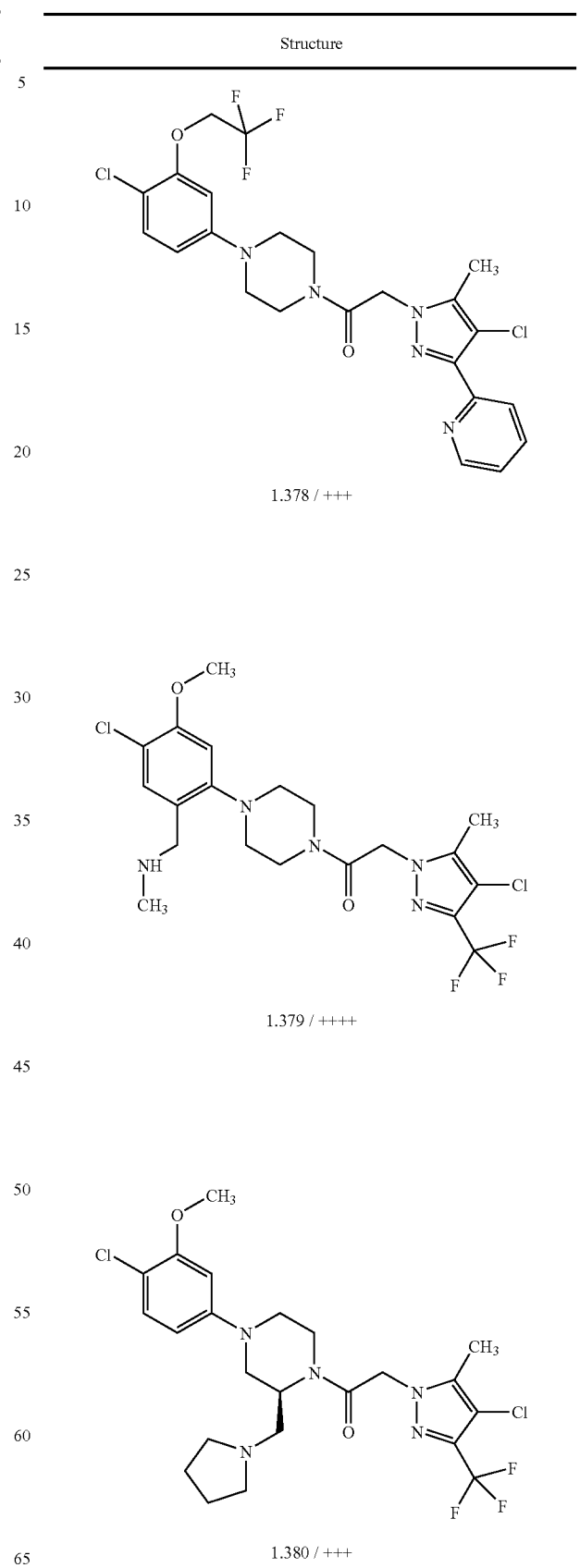
1.378 / +++
1.379 / ++++
1.380 / +++

TABLE 5-continued
| Structure | Structure |
|---|---|
| 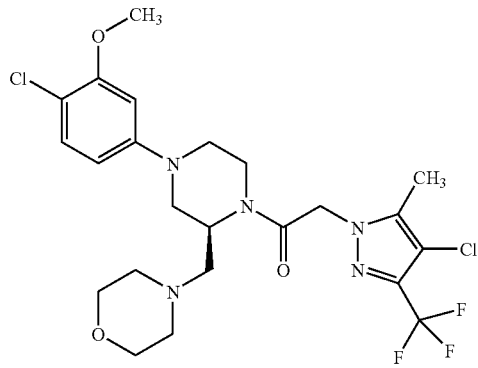<br>1.381 / +++ | 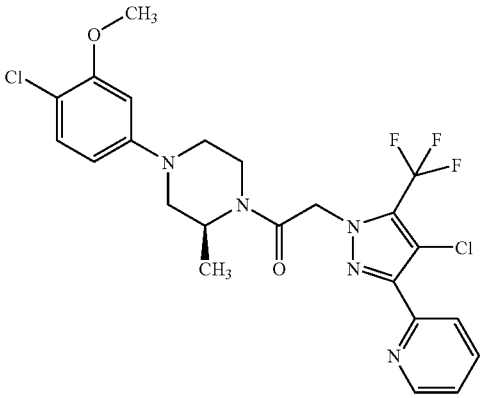<br>1.384 / ++++ |
| 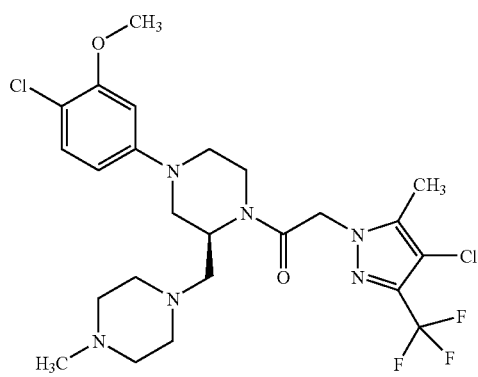<br>1.382 / ++ | 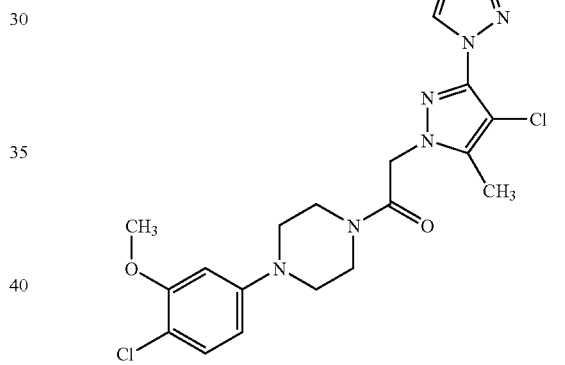<br>1.385 / ++++ |
| 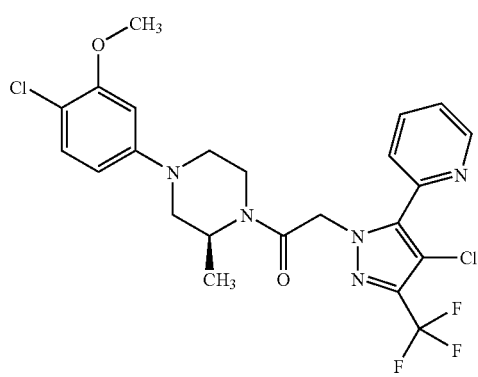<br>1.383 / ++++ | 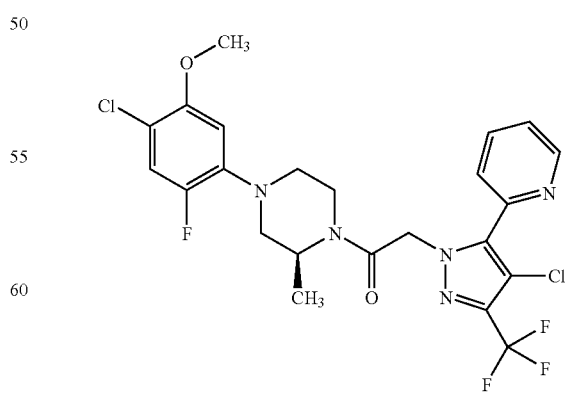<br>1.386 / ++++ |

TABLE 5-continued
Structure
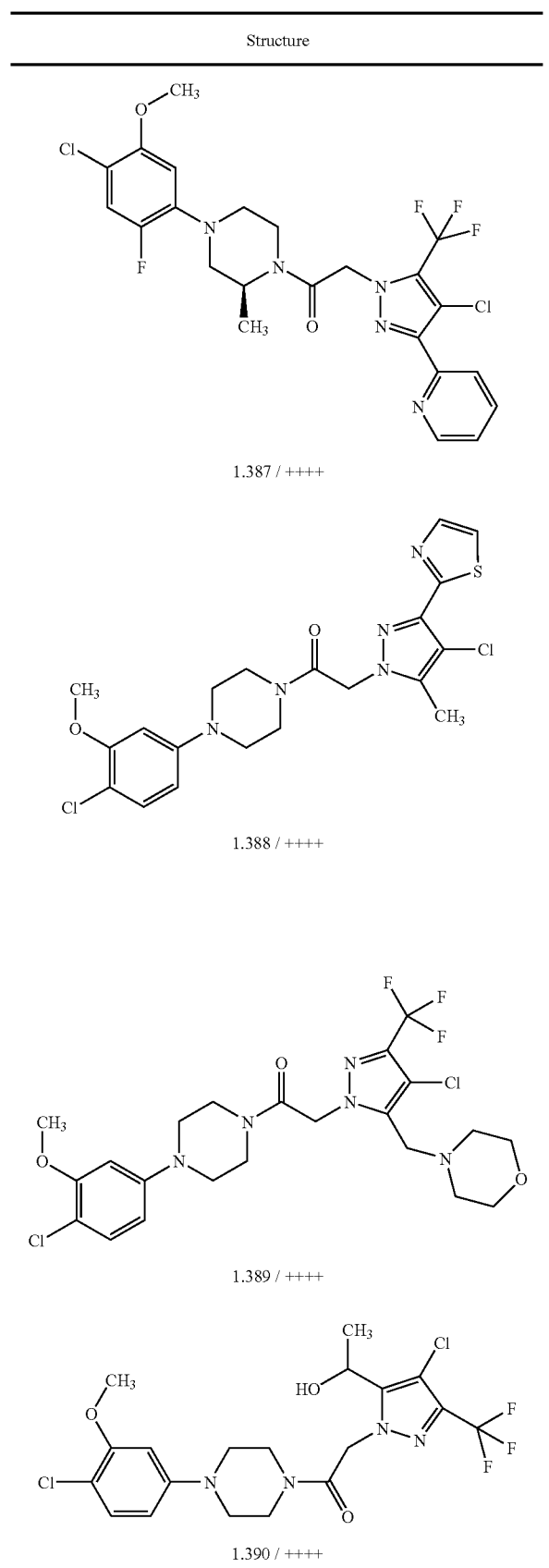
1.387 / ++++
1.388 / ++++
1.389 / ++++
1.390 / ++++
TABLE 5-continued
Structure
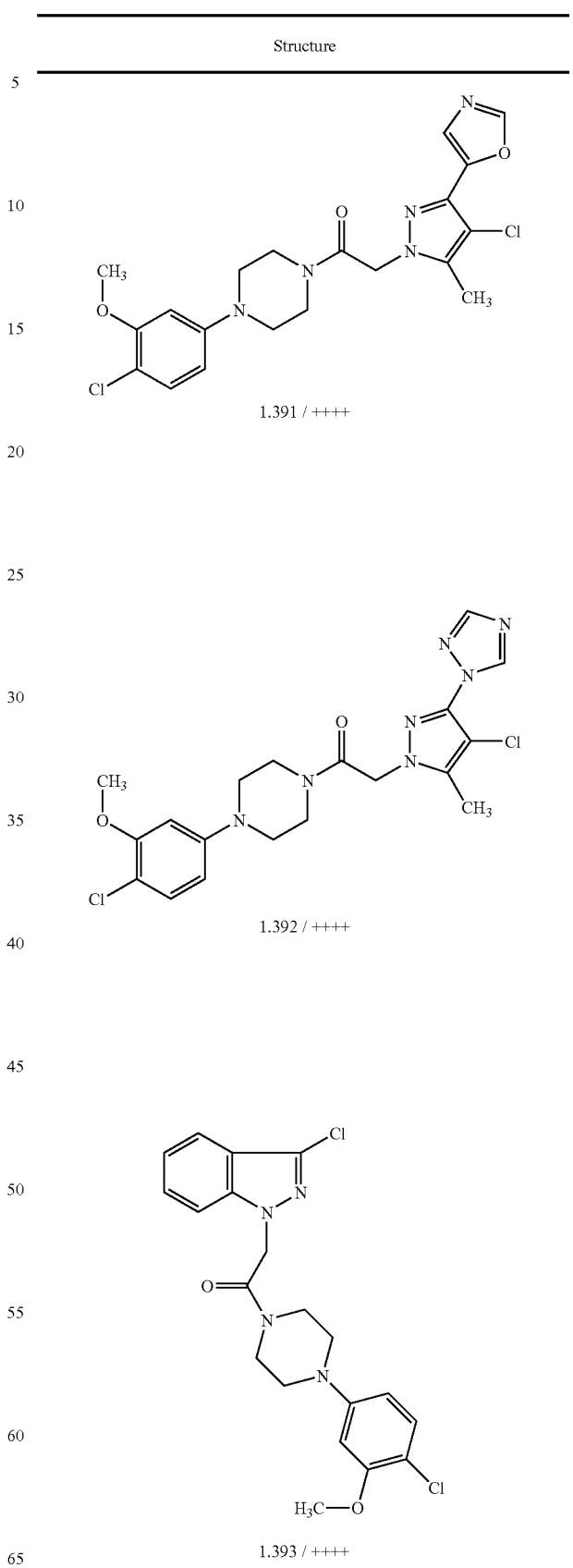
1.391 / ++++
1.392 / ++++
1.393 / ++++

TABLE 5-continued

| Structure |
|---|
| 1.394 / ++++ |
| 1.395 / ++++ |
| 1.396 / ++++ |
| 1.397 / ++++ |
| 1.398 / ++++ |
| 1.399 / ++++ |

TABLE 5-continued

| Structure |
|---|
| 1.400 / +++ |
| 1.401 / ++++ |
| 1.402 / ++++ |
| 1.403 / ++++ |
| 1.404 / ++++ |
| 1.405 / ++++ |
| 1.406 / ++++ |
| 1.407 / ++++ |

TABLE 5-continued
Structure
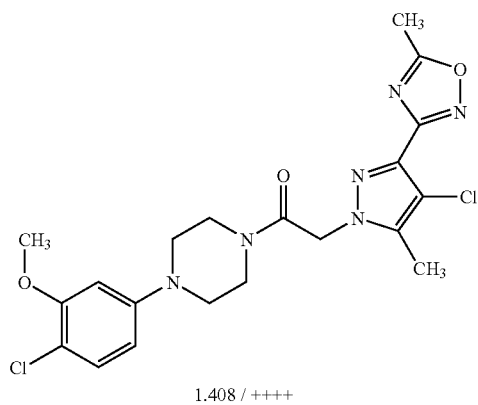
1.408 / ++++
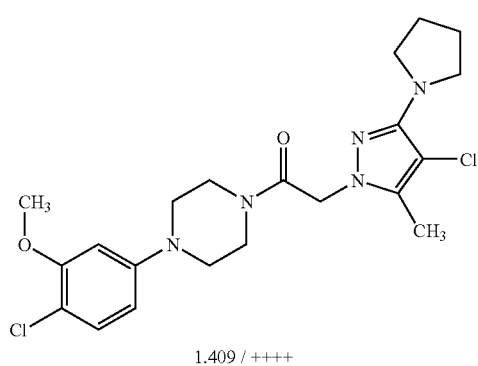
1.409 / ++++
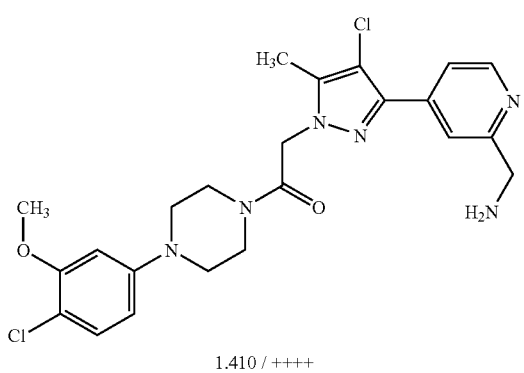
1.410 / ++++
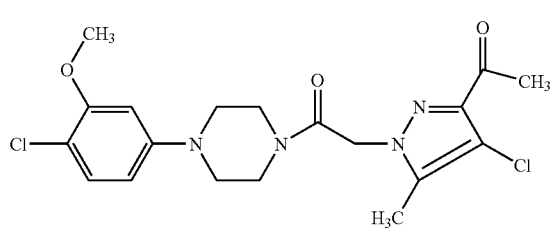
1.411 / ++++
TABLE 5-continued
Structure
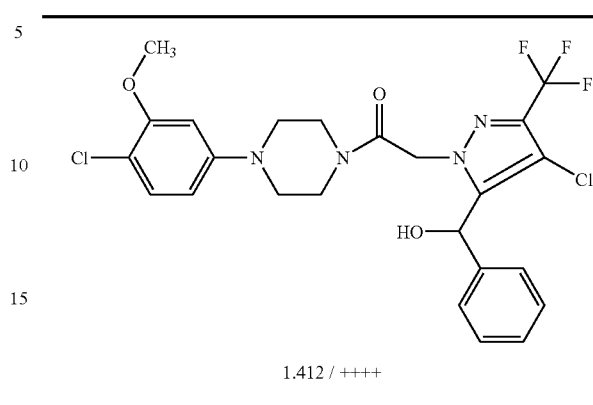
1.412 / ++++
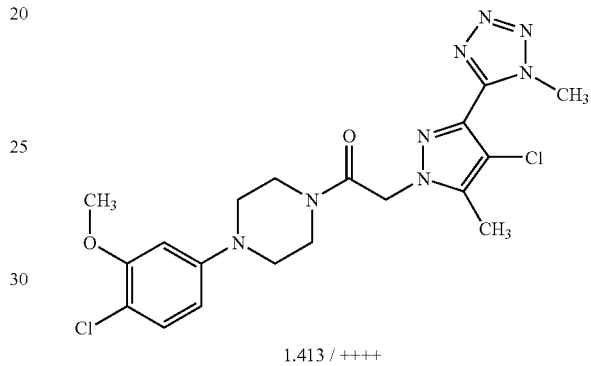
1.413 / ++++
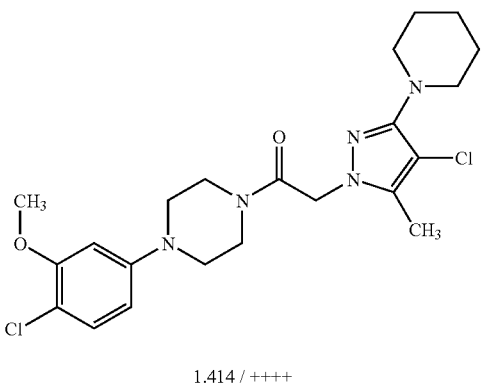
1.414 / ++++
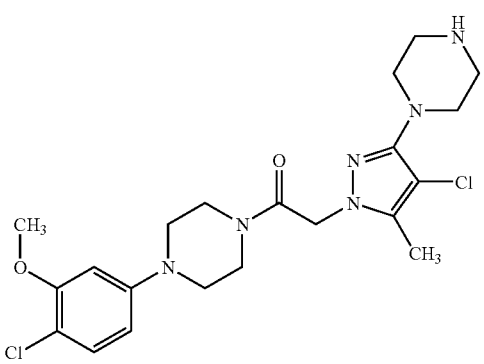
1.415 / ++

TABLE 5-continued
Structure
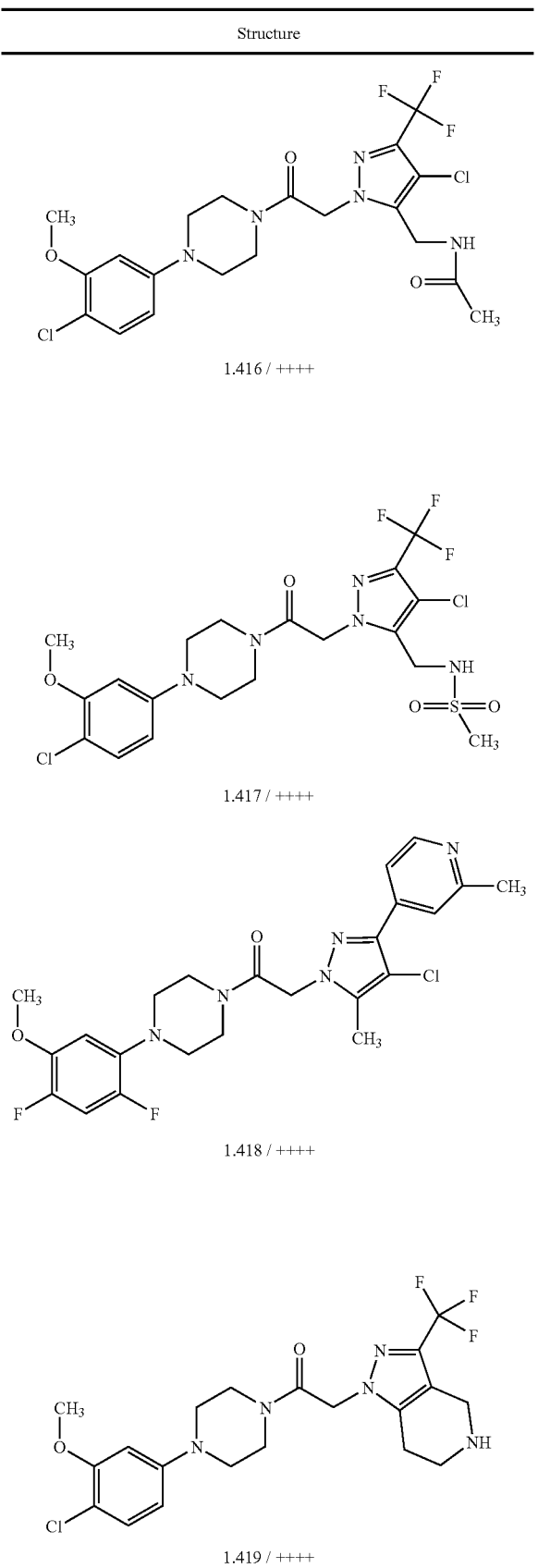
1.416 / ++++
1.417 / ++++
1.418 / ++++
1.419 / ++++
TABLE 5-continued
Structure
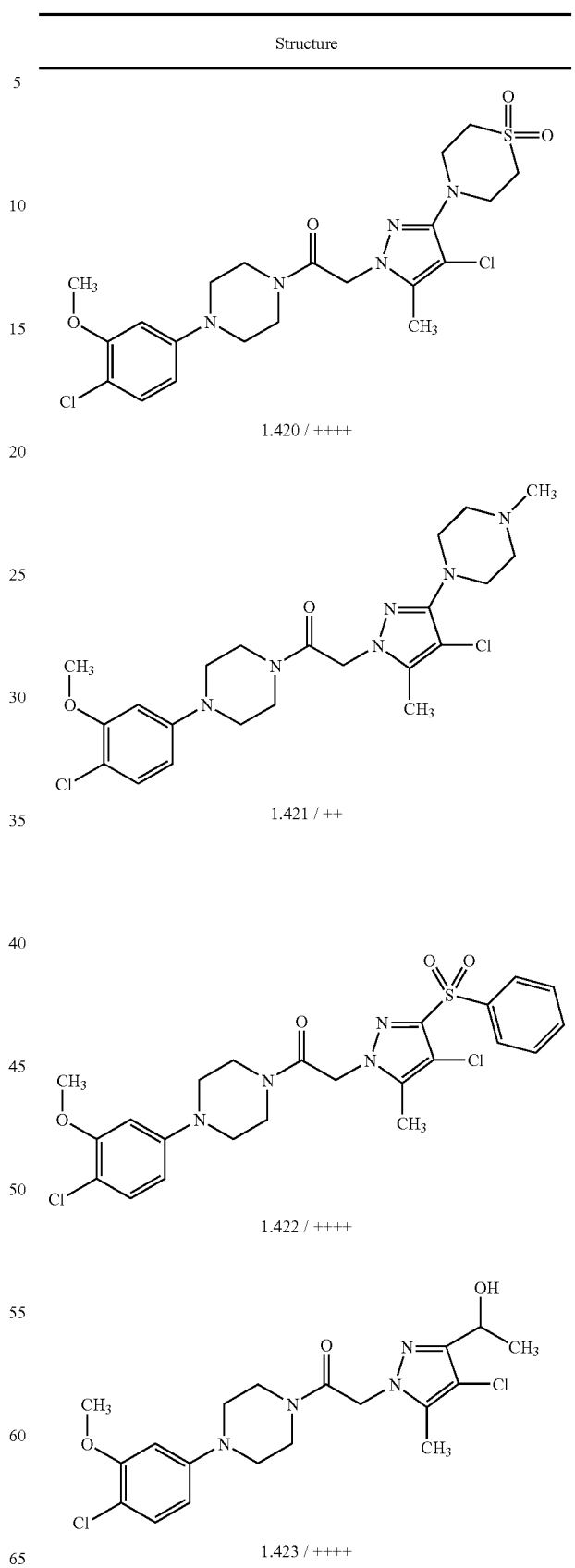
1.420 / ++++
1.421 / ++
1.422 / ++++
1.423 / ++++

TABLE 5-continued
| Structure |
|---|
| 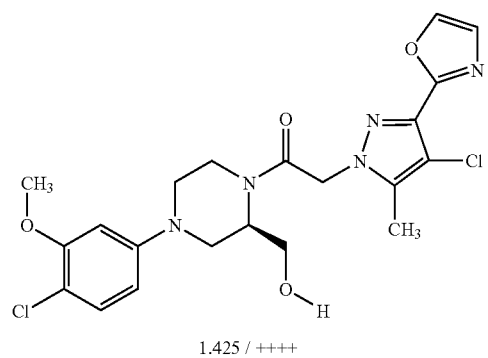
1.424 / ++++ |
| 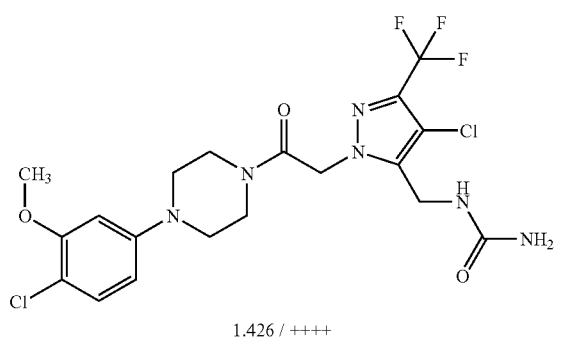
1.425 / ++++ |
| 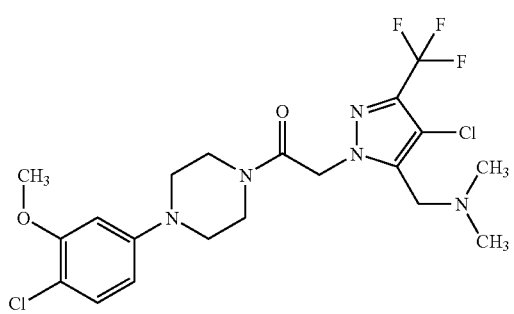
1.426 / ++++ |
| 1.427 / ++++ |
TABLE 5-continued
| Structure |
|---|
| 1.428 / ++++ |
| 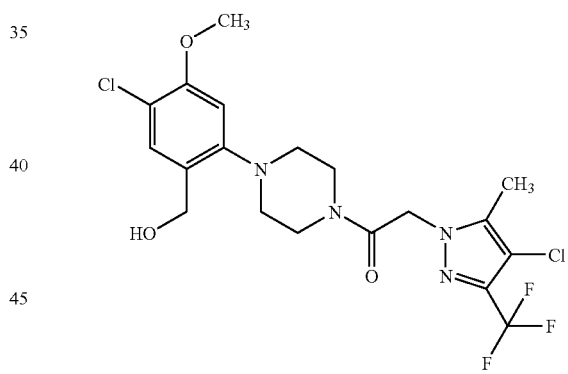
1.429 / ++++ |
| 1.430 / ++++ |
| 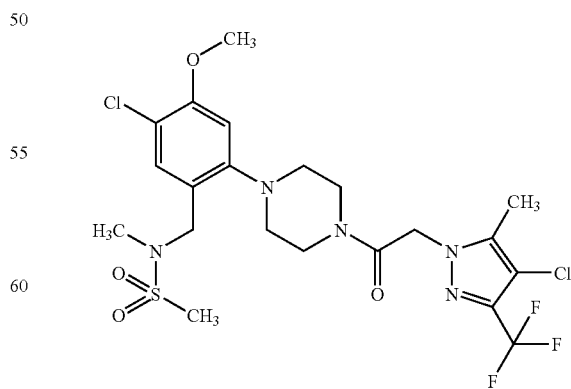
1.431 / ++++ |

TABLE 5-continued

| Structure |
|---|
| 1.432 / ++++ |
| 1.433 / ++++ |
| 1.435 / ++++ |
| 1.435 / ++++ |
| 1.436 / ++++ |
| 1.437 / ++++ |
| 1.438 / ++++ |
| 1.439 / ++++ |
| 1.440 / ++++ |

TABLE 5-continued
Structure
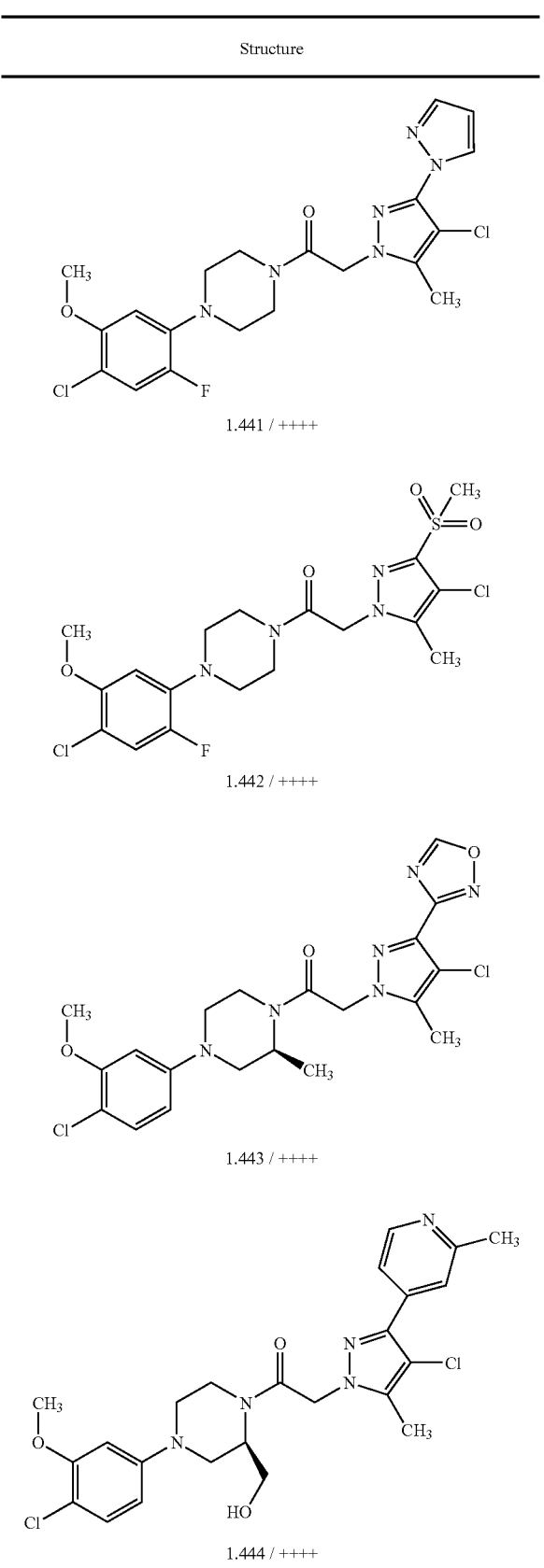
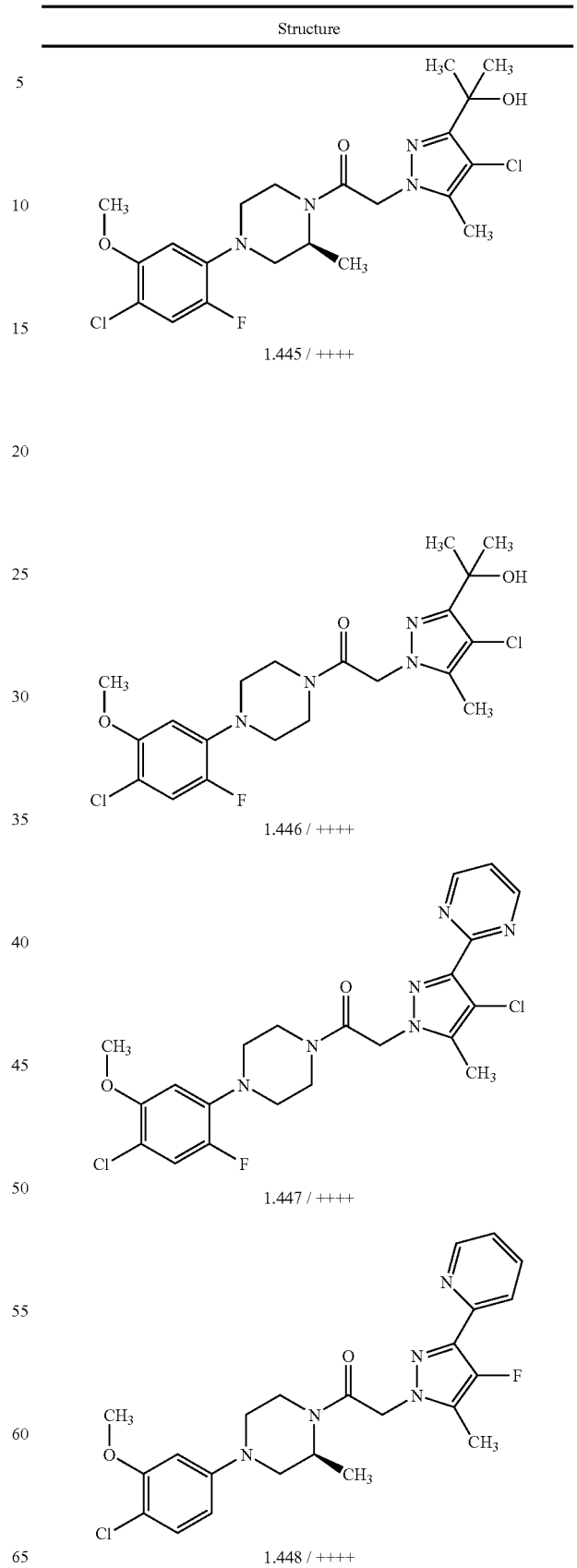

TABLE 5-continued

Structure 1.449 / ++++

1.450 / +++

1.451 / ++++

1.452 / +++

1.453 / +++

1.454 / ++++

1.455 / ++++

TABLE 5-continued
Structure
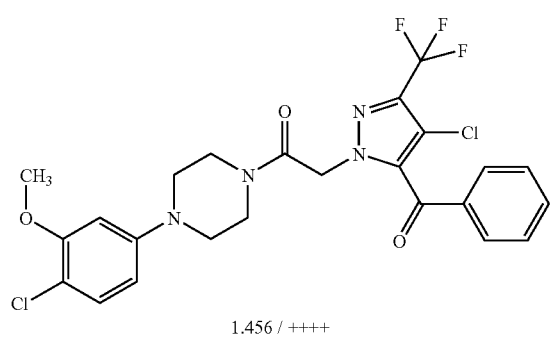
1.456 / ++++
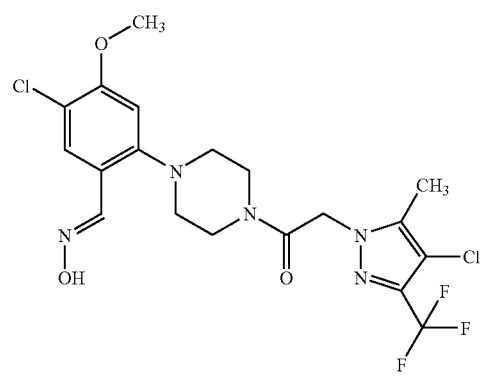
1.457 / ++++
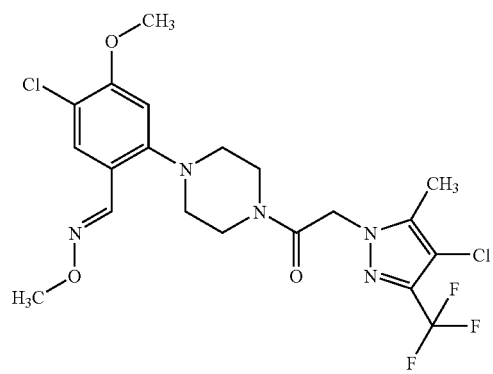
1.458 / ++++
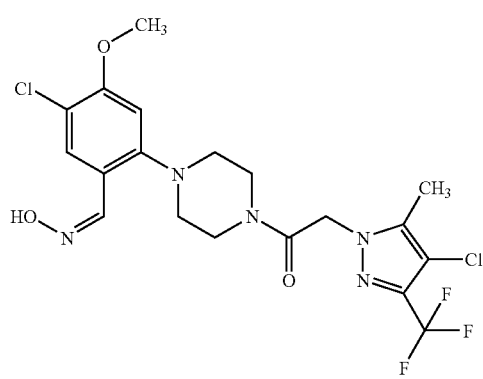
1.459 / ++++
TABLE 5-continued
Structure
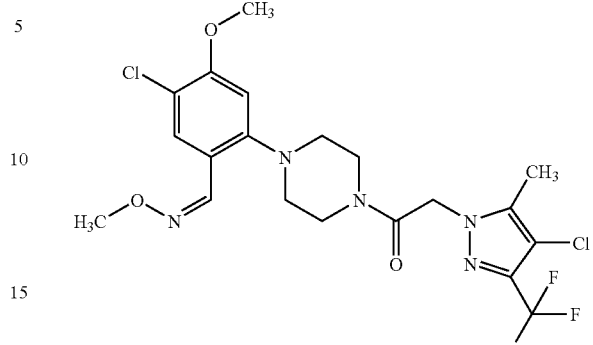
1.460 / ++++
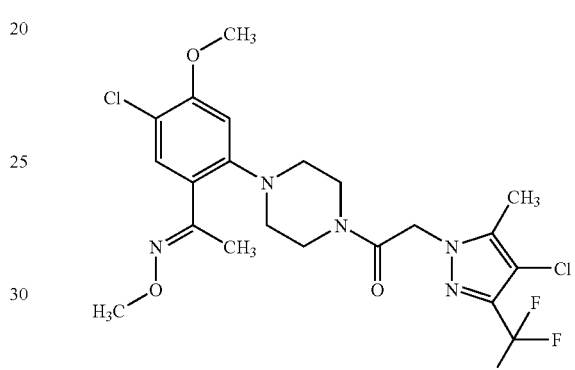
1.461 / ++++
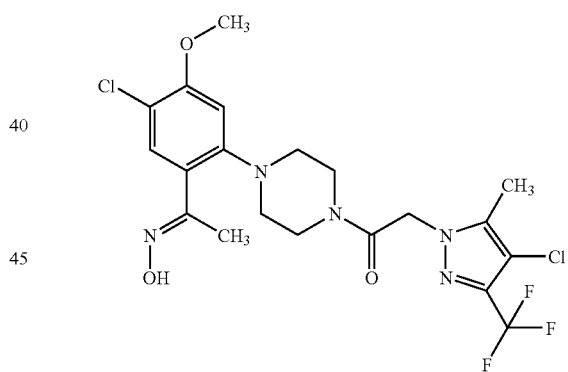
1.462 / ++++
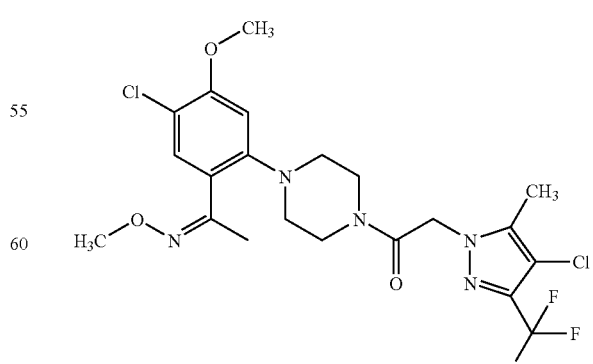
1.463 / ++++

TABLE 5-continued
Structure
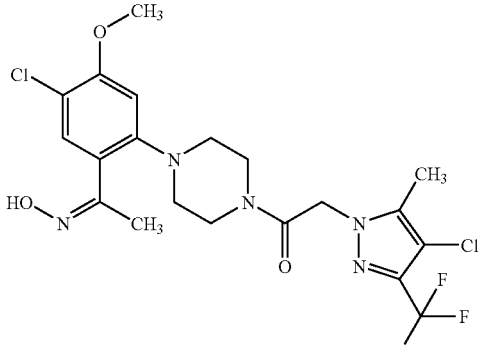
1.464 / ++++
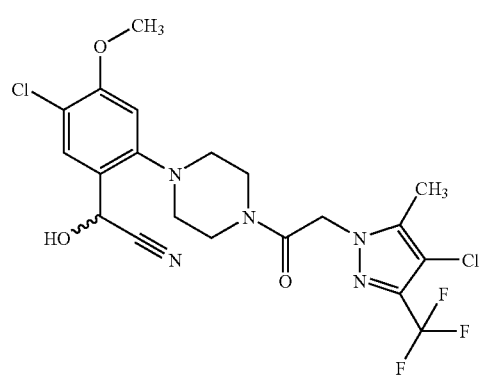
1.465 / ++++
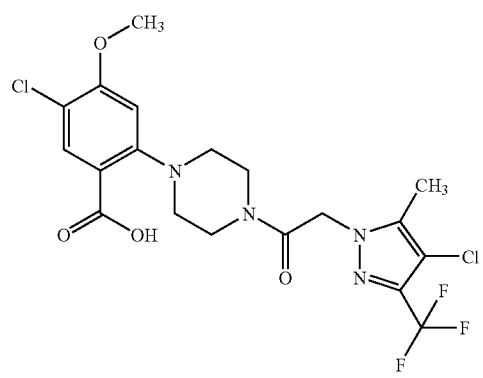
1.466 / ++++
TABLE 5-continued
Structure
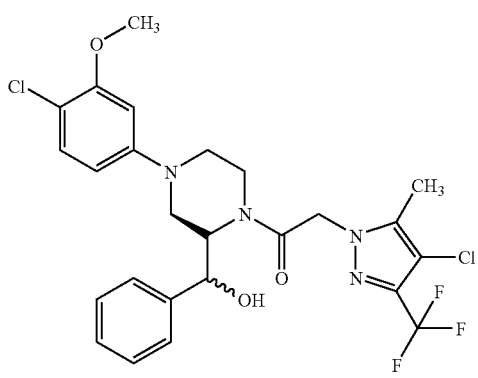
1.467 / ++++
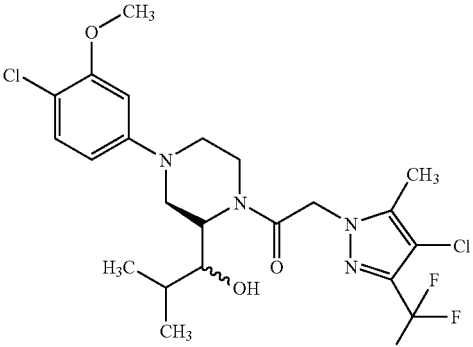
1.468 / ++++
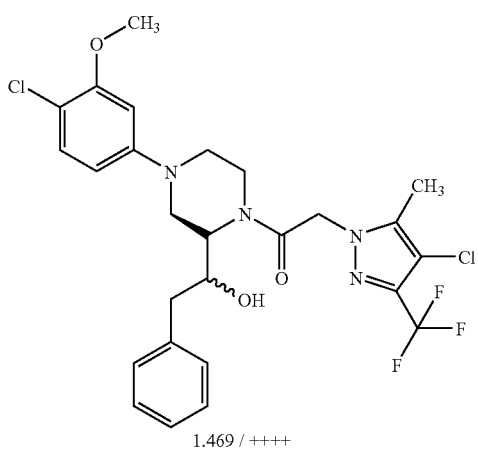
1.469 / ++++

TABLE 5-continued

Structure

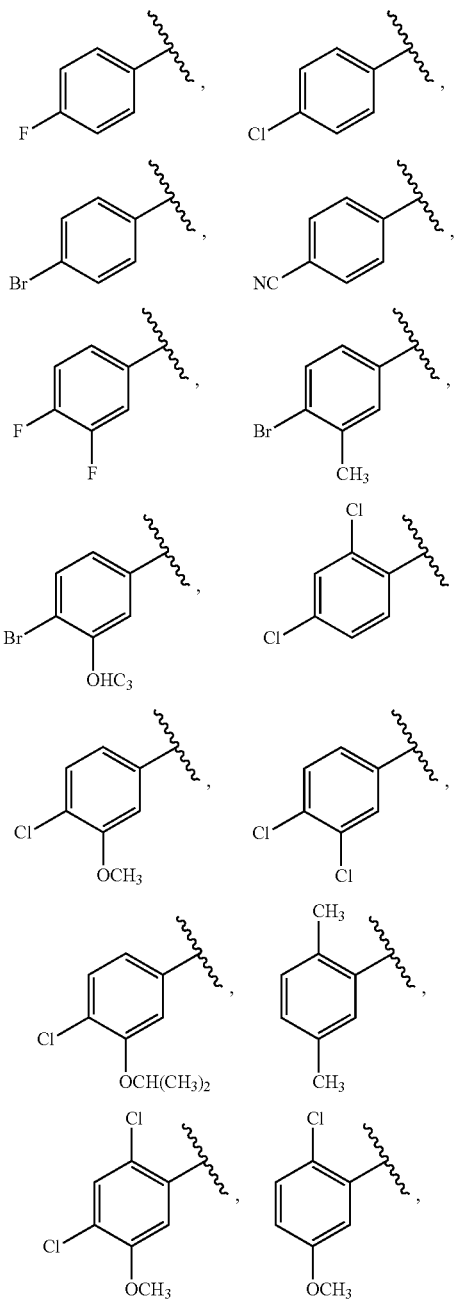

1.470 / ++++

1.471 / ++++

1.472 / ++++

1.473 / ++++

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A compound having the formula:

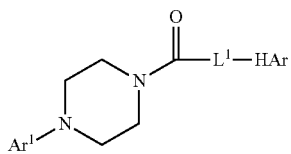

or a pharmaceutically acceptable salt thereof, wherein $Ar^1$ is selected from the group consisting of

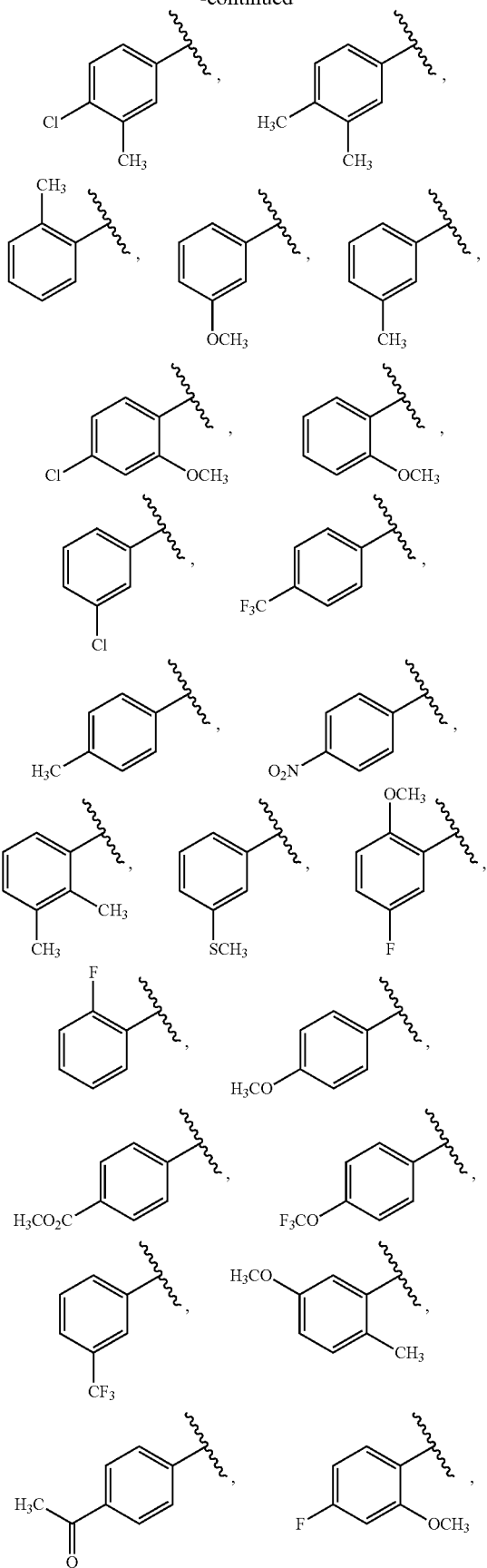

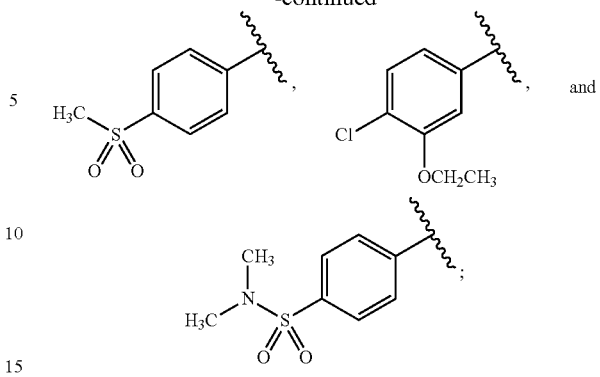

HAr is a heteroaryl group selected from the group consisting of triazolyl and tetrazolyl, each of which is linked through a ring member nitrogen heteroatom to the remainder of the molecule and is substituted with from one to five $R^3$ substituents independently selected from the group consisting of halogen, phenyl, thienyl, —$OR^f$, —$CO_2R^f$, —$COR^f$, —$CONR^fR^g$, —$NO_2$, —$R^h$, —$CN$, —$SR^f$, —$S(O)R^h$, —$S(O)_2R^h$ and —$NR^fR^g$, wherein $R^f$ and $R^g$ are each independently selected from the group consisting of H, $C_{1-8}$ alkyl, $C_{3-6}$ cycloalkyl and $C_{1-8}$ haloalkyl, and each $R^h$ is independently selected from the group consisting of $C_{1-8}$ alkyl, $C_{3-6}$ cycloalkyl and $C_{1-8}$ haloalkyl; and $L^1$ is a $CH_2$ group.

2. A pharmaceutical composition comprising a pharmaceutically acceptable excipient and a compound of claim 1.

3. A compound that is

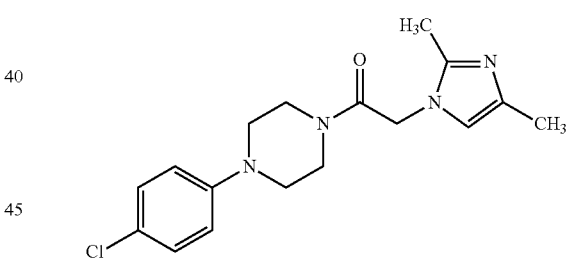

or a pharmaceutically acceptable salt thereof.

4. A compound of claim 1 that is

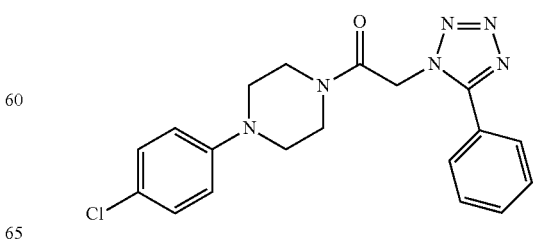

or a pharmaceutically acceptable salt thereof.

5. A compound of claim 1 that is

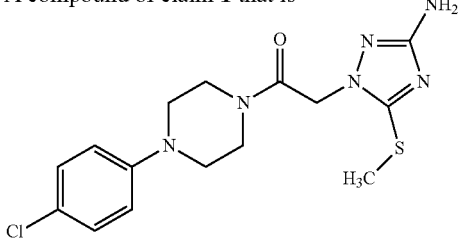

or a pharmaceutically acceptable salt thereof.

6. A pharmaceutical composition comprising a pharmaceutically acceptable excipient and a compound of claim 3.

7. A pharmaceutical composition comprising a pharmaceutically acceptable excipient and a compound of claim 4.

8. A pharmaceutical composition comprising a pharmaceutically acceptable excipient and a compound of claim 5.

* * * * *